US009816079B2

(12) United States Patent
Davis

(10) Patent No.: US 9,816,079 B2
(45) Date of Patent: Nov. 14, 2017

(54) VARIANT THIOESTERASES AND METHODS OF USE

(71) Applicant: TerraVia Holdings, Inc., South San Francisco, CA (US)

(72) Inventor: David Davis, San Bruno, CA (US)

(73) Assignee: TerraVia Holdings, Inc., South San Francisco, CA (US)

( * ) Notice: Subject to any disclaimer, the term of this patent is extended or adjusted under 35 U.S.C. 154(b) by 645 days.

(21) Appl. No.: 14/167,908

(22) Filed: Jan. 29, 2014

(65) Prior Publication Data

US 2014/0234920 A1 Aug. 21, 2014

Related U.S. Application Data

(63) Continuation-in-part of application No. 13/797,733, filed on Mar. 12, 2013, now Pat. No. 9,567,615.

(60) Provisional application No. 61/758,223, filed on Jan. 29, 2013.

(51) Int. Cl.

| | |
|---|---|
| ***C12N 9/16*** | (2006.01) |
| ***C12N 15/82*** | (2006.01) |
| ***C12P 7/64*** | (2006.01) |

(52) U.S. Cl.

CPC ........... *C12N 9/16* (2013.01); *C12N 15/8247* (2013.01); *C12P 7/6463* (2013.01); *C12Y 301/02014* (2013.01)

(58) Field of Classification Search

None

See application file for complete search history.

(56) References Cited

U.S. PATENT DOCUMENTS

| | | | |
|---|---|---|---|
| 4,049,724 | A | 9/1977 | Sheng et al. |
| 4,288,378 | A | 9/1981 | Japikse et al. |
| 4,335,156 | A | 6/1982 | Kogan et al. |
| 4,584,139 | A | 4/1986 | Gray et al. |
| 4,603,188 | A | 7/1986 | Kusakawa et al. |
| 4,683,202 | A | 7/1987 | Mullis |
| 4,798,793 | A | 1/1989 | Eigtved |
| 4,940,835 | A | 7/1990 | Shah et al. |
| 4,940,845 | A | 7/1990 | Hirota et al. |
| 4,945,050 | A | 7/1990 | Sanford et al. |
| 4,992,189 | A | 2/1991 | Chen et al. |
| 5,080,848 | A | 1/1992 | Strauss et al. |
| 5,091,116 | A | 2/1992 | Krishnamurthy et al. |
| 5,156,963 | A | 10/1992 | Eigtved |
| 5,233,099 | A | 8/1993 | Tabata |
| 5,233,100 | A | 8/1993 | Tabata et al. |
| 5,258,197 | A | 11/1993 | Wheeler et al. |
| 5,268,192 | A | 12/1993 | Zook et al. |
| 5,298,421 | A | 3/1994 | Davies et al. |
| 5,298,637 | A | 3/1994 | Cooper |
| 5,304,481 | A | 4/1994 | Davies et al. |
| 5,304,664 | A | 4/1994 | Peppmoller et al. |
| 5,342,768 | A | 8/1994 | Pedersen et al. |
| 5,344,771 | A | 9/1994 | Davies et al. |
| 5,346,724 | A | 9/1994 | Ohgake et al. |
| 5,380,894 | A | 1/1995 | Burg et al. |
| 5,391,383 | A | 2/1995 | Sullivan et al. |
| 5,427,704 | A | 6/1995 | Lawate |
| 5,434,278 | A | 7/1995 | Pelloso et al. |
| 5,451,332 | A | 9/1995 | Lawate |
| 5,455,167 | A | 10/1995 | Voelker et al. |
| 5,458,795 | A | 10/1995 | Lawate |
| 5,475,160 | A | 12/1995 | Singleton et al. |
| 5,506,201 | A | 4/1996 | McDermott et al. |
| 5,512,482 | A | 4/1996 | Voelker et al. |
| 5,567,359 | A | 10/1996 | Cassidy et al. |
| 5,576,027 | A | 11/1996 | Friedman et al. |
| 5,639,790 | A | 6/1997 | Voelker et al. |
| 5,654,495 | A | 8/1997 | Voelker et al. |
| 5,667,997 | A | 9/1997 | Voelker et al. |
| 5,674,385 | A | 10/1997 | Ivaschenko et al. |
| 5,686,131 | A | 11/1997 | Sato et al. |
| 5,693,507 | A | 12/1997 | Daniell et al. |
| 5,723,761 | A | 3/1998 | Voelker et al. |
| 5,776,741 | A | 7/1998 | Pedersen et al. |
| 5,807,893 | A | 9/1998 | Voelker et al. |
| 5,833,999 | A | 11/1998 | Trinh et al. |
| 5,850,022 | A | 12/1998 | Dehesh et al. |
| 5,885,440 | A | 3/1999 | Hoehn et al. |

(Continued)

FOREIGN PATENT DOCUMENTS

| | | |
|---|---|---|
| CN | 102 586 350 A | 7/2012 |
| EP | 1 605 048 A1 | 12/2005 |

(Continued)

OTHER PUBLICATIONS

Dubois et al 2007 (Eur. J. Lipid Sci Technol. 109: p. 710-732).*

U.S. Appl. No. 14/808,361, filed Jul. 24, 2015, Davis et al.

U.S. Office Action, dated Jul. 16, 2015, issued in U.S. Appl. No. 13/797,733.

U.S. Office Action, dated Jul. 22, 2015, issued in U.S. Appl. No. 13/837,996.

PCT International Search Report and Written Opinion dated Jun. 24, 2014 issued in PCT/US2014/013676.

PCT International Preliminary Report on Patentability and Written Opinion dated Aug. 13, 2015 issued in PCT/US2014/013676.

(Continued)

*Primary Examiner* — Matthew Keogh

(74) *Attorney, Agent, or Firm* — Weaver Austin Villeneuve & Sampson LLP

(57) ABSTRACT

The present invention relates to variant thioesterases and their use in plants, e.g., to increase enzymatic activity and to promote increased production of mid-chain length fatty acids (e.g., 8 to 14 carbons) and at desired ratios. Further disclosed herein are methods of manufacturing renewable chemicals through the manufacture of novel triglyceride oils followed by chemical modification of the oils. Oils containing fatty acid chain lengths of C8, C10, C12 or C14 are also disclosed and are useful as feedstocks in the methods described herein.

18 Claims, 76 Drawing Sheets

(56) References Cited

U.S. PATENT DOCUMENTS

| | | | |
|---|---|---|---|
| 5,888,947 | A | 3/1999 | Lambert et al. |
| 5,928,696 | A | 7/1999 | Best et al. |
| 5,942,479 | A | 8/1999 | Frankenbach et al. |
| 5,945,585 | A | 8/1999 | Hitz et al. |
| 6,020,509 | A | 2/2000 | Weerasooriya et al. |
| 6,022,577 | A | 2/2000 | Chrysam et al. |
| 6,027,900 | A | 2/2000 | Allnutt et al. |
| 6,051,539 | A | 4/2000 | Kodali et al. |
| 6,057,375 | A | 5/2000 | Wollenweber et al. |
| 6,080,853 | A | 6/2000 | Corrigan et al. |
| 6,086,903 | A | 7/2000 | Trinh et al. |
| 6,113,971 | A | 9/2000 | Elmaleh |
| 6,140,302 | A | 10/2000 | Lueder et al. |
| 6,150,512 | A | 11/2000 | Yuan |
| 6,217,746 | B1 | 4/2001 | Thakkar et al. |
| 6,268,517 | B1 | 7/2001 | Filler et al. |
| 6,278,006 | B1 | 8/2001 | Kodali et al. |
| 6,320,101 | B1 | 11/2001 | Kaplan et al. |
| 6,331,664 | B1 | 12/2001 | Rubin-Wilson et al. |
| 6,342,208 | B1 | 1/2002 | Hyldgaard et al. |
| 6,380,410 | B1 | 4/2002 | Oftring et al. |
| 6,391,815 | B1 | 5/2002 | Weston et al. |
| 6,395,965 | B1 | 5/2002 | Xia |
| 6,398,707 | B1 | 6/2002 | Wu et al. |
| 6,407,044 | B2 | 6/2002 | Dixon |
| 6,465,642 | B1 | 10/2002 | Kenneally et al. |
| 6,468,955 | B1 | 10/2002 | Smets et al. |
| 6,538,169 | B1 | 3/2003 | Pittman et al. |
| 6,590,113 | B1 | 7/2003 | Sleeter |
| 6,596,155 | B1 | 7/2003 | Gates et al. |
| 6,596,768 | B2 | 7/2003 | Block et al. |
| 6,630,066 | B2 | 10/2003 | Cash et al. |
| 6,680,426 | B2 | 1/2004 | Daniell et al. |
| 6,692,730 | B2 | 2/2004 | Perron et al. |
| 6,750,048 | B2 | 6/2004 | Ruecker et al. |
| 6,770,104 | B2 | 8/2004 | Murphy |
| 6,808,737 | B2 | 10/2004 | Ullanoormadam |
| 6,869,597 | B2 | 3/2005 | Arnaud |
| 6,881,873 | B2 | 4/2005 | Gillespie et al. |
| 6,924,333 | B2 | 8/2005 | Bloom et al. |
| 6,946,430 | B2 | 9/2005 | Sakai et al. |
| 6,977,322 | B2 | 12/2005 | Gillespie |
| 7,041,866 | B1 | 5/2006 | Gillespie |
| 7,053,267 | B2 | 5/2006 | Knauf et al. |
| 7,081,567 | B2 | 7/2006 | Xue et al. |
| 7,115,173 | B2 | 10/2006 | Caswell et al. |
| 7,115,760 | B2 | 10/2006 | Sparso et al. |
| 7,118,773 | B2 | 10/2006 | Floeter et al. |
| 7,135,290 | B2 | 11/2006 | Dillon |
| 7,135,620 | B2 | 11/2006 | Daniell et al. |
| 7,196,124 | B2 | 3/2007 | Parker et al. |
| 7,232,935 | B2 | 6/2007 | Jakkula et al. |
| 7,238,277 | B2 | 7/2007 | Dahlberg et al. |
| 7,262,158 | B1 | 8/2007 | Lukenbach et al. |
| 7,264,886 | B2 | 9/2007 | Cui et al. |
| 7,268,276 | B2 | 9/2007 | Ruezinsky et al. |
| 7,288,278 | B2 | 10/2007 | Mellerup et al. |
| 7,288,685 | B2 | 10/2007 | Marker |
| 7,588,931 | B2 | 9/2009 | Damude et al. |
| 7,622,570 | B2 | 11/2009 | Oswald et al. |
| 8,029,579 | B2 | 10/2011 | Knuth et al. |
| 8,530,207 | B2 | 9/2013 | Watts et al. |
| 9,290,749 | B2 | 3/2016 | Rudenko et al. |
| 9,567,615 | B2 | 2/2017 | Davis |
| 2002/0178467 | A1 | 11/2002 | Dehesh |
| 2003/0097686 | A1 | 5/2003 | Knauf et al. |
| 2003/0145350 | A1 | 7/2003 | Spener et al. |
| 2005/0005333 | A1 | 1/2005 | Ruezinsky et al. |
| 2005/0102716 | A1 | 5/2005 | Venkatramesh et al. |
| 2005/0262588 | A1 | 11/2005 | Dehesh et al. |
| 2007/0175091 | A1 | 8/2007 | Danzer et al. |
| 2007/0261138 | A1 | 11/2007 | Graham et al. |
| 2009/0176272 | A1 | 7/2009 | Champagne et al. |
| 2009/0317878 | A1 | 12/2009 | Champagne et al. |
| 2010/0058651 | A1 | 3/2010 | Knuth et al. |
| 2010/0105955 | A1 | 4/2010 | Alibhai et al. |
| 2010/0154293 | A1 | 6/2010 | Hom et al. |
| 2011/0072714 | A1 | 3/2011 | Gaertner et al. |
| 2011/0145944 | A1 | 6/2011 | Laga et al. |
| 2011/0250659 | A1 | 10/2011 | Roberts et al. |
| 2011/0293785 | A1 | 12/2011 | Franklin et al. |
| 2012/0009636 | A1 | 1/2012 | Berry et al. |
| 2012/0283460 | A1 | 11/2012 | Franklin et al. |
| 2012/0288930 | A1 | 11/2012 | Trimbur et al. |
| 2013/0031678 | A1 | 1/2013 | Zheng et al. |
| 2013/0034887 | A1 | 2/2013 | Franklin et al. |
| 2014/0215654 | A1 | 7/2014 | Davis |
| 2014/0275586 | A1 | 9/2014 | Rudenko et al. |
| 2014/0288320 | A1 | 9/2014 | Rudenko et al. |
| 2016/0032332 | A1 | 2/2016 | Davis et al. |
| 2016/0083758 | A1 | 3/2016 | Casolari et al. |
| 2016/0251685 | A1 | 9/2016 | Rudenko et al. |

FOREIGN PATENT DOCUMENTS

| | | | |
|---|---|---|---|
| EP | 1 640 437 | A1 | 3/2006 |
| EP | 1 681 337 | A1 | 7/2006 |
| EP | 1 741 767 | A1 | 1/2007 |
| EP | 1 741 768 | A1 | 1/2007 |
| EP | 1 795 576 | A1 | 6/2007 |
| EP | 1 682 466 | A1 | 11/2008 |
| WO | WO 89/01032 | A1 | 2/1989 |
| WO | WO 92/11373 | A1 | 7/1992 |
| WO | WO 92/20636 | A1 | 11/1992 |
| WO | WO 94/10288 | A2 | 5/1994 |
| WO | WO 95/13390 | A2 | 5/1995 |
| WO | WO 96/23892 | A2 | 8/1996 |
| WO | WO 98/55633 | A1 | 12/1998 |
| WO | WO 00/61740 | A1 | 10/2000 |
| WO | WO 00/66750 | A2 | 11/2000 |
| WO | WO 02/08403 | A2 | 1/2002 |
| WO | WO 2005/047216 | A1 | 5/2005 |
| WO | WO 2006/055322 | A2 | 5/2006 |
| WO | WO 2007/106903 | A2 | 9/2007 |
| WO | WO 2008/002643 | A2 | 1/2008 |
| WO | WO 2008/151149 | A2 | 12/2008 |
| WO | WO 2010/019813 | A2 | 2/2010 |
| WO | WO 2010/063031 | A2 | 6/2010 |
| WO | WO 2010/063032 | A2 | 6/2010 |
| WO | WO 2010/120939 | A2 | 10/2010 |
| WO | WO 2011/003034 | A2 | 1/2011 |
| WO | WO 2011/008565 | A1 | 1/2011 |
| WO | WO 2011/127069 | A1 | 10/2011 |
| WO | WO 2011/150410 | A2 | 12/2011 |
| WO | WO 2011/150411 | A1 | 12/2011 |
| WO | WO 2012/061647 | A2 | 5/2012 |
| WO | WO 2012/106560 | A1 | 8/2012 |
| WO | WO 2012/154626 | A1 | 11/2012 |
| WO | WO 2013/158938 | A1 | 10/2013 |
| WO | WO 2014/120829 | A1 | 8/2014 |
| WO | WO 2014/151904 | A1 | 9/2014 |
| WO | WO 2015/051319 | A2 | 4/2015 |
| WO | PCT/US2015/42044 | | 7/2015 |
| WO | WO 2016/014968 | A1 | 1/2016 |
| WO | WO 2016/044779 | A2 | 3/2016 |

OTHER PUBLICATIONS

Database Geneseq [Online] (Jun. 6, 2000) "Bay C18:1 preferring acyl-ACP thioesterase protein from clone 3A-17.", retrieved from EBI accession No. GSP:AAY80558 Database accession No. AAY80558; and Database Geneseq [Online] (Jun. 6, 2000) "Bay C18:1 preferring acyl-ACP thioesterase protein.", retrieved from EBI accession No. GSP:AAY80559 Database accession No. AAY80559.

Database Geneseq [Online] (Nov. 2, 1995) "Camphor thioesterase.", retrieved from EBI accession No. GSP:AAR74148 Database accession No. AAR74148.

Database Geneseq [Online] (Oct. 26, 1996) "Cuphea C14:0-ACP thioesterase.", retrieved from EBI accession No. GSP:AAW02081 Database accession No. AAW02081.

(56) References Cited

OTHER PUBLICATIONS

Database Geneseq [Online] (Aug. 5, 2010) "U. californica fatty acyl-ACP thioesterase protein (without PTS), SEQ:139.", retrieved from EBI accession No. GSP:AYC84249 Database accession No. AYC84249.
PCT Invitation to Pay Additional Fees and, Where Applicable, Protest Fee dated Jun. 18, 2014 issued in PCT/US2014/026644.
PCT International Search Report and Written Opinion dated Aug. 29, 2014 issued in PCT/US2014/026644.
PCT International Preliminary Report on Patentability dated Sep. 24, 2015 issued in PCT/US2014/026644.
Genbank Accession No. U17097, Umbellularia californica UC FatB2 (FatB) mRNA, complete cds., Jun. 1, 1995, 2pp.
Genbank: Accession No. U39834.1, Cuphea hookeriana 8:0- and 10:0-ACP specific thioesterase (FatB2) mRNA, complete cds, May 21, 2014, 2pp.
Genbank Accession No. AAC49001, UC FatB2 (FatB) Umbellularica californica, May 30, 1995, 2pp.
Apt et al., (1996) "Stable nuclear transformation of the diatom *Phaeodactylum tricornutum," Molecular and General Genetics*, 252:572-579.
Barnes et al., (2005) "Contribution of 5'- and 3'-untranslated regions of plastid mRNAs to the expression of *Chlamydomonas reinhardtii* chloroplast genes," *Mol Gen Genomics*274:625-636.
Blatti et al., (Sep. 2012) "Manipulating Fatty Acid Biosynthesis in Microalgae for Biofuel through Protein-Protein Interactions," *PLoS ONE* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in Arabidopsis Dethonstrates an Essential Role of Saturated Fatty Acids in Plant Growth," *The Plant Cell* 15:1020-1033.
Boynton et al., (1988) "Chloroplast Transformation in *Chlamydomonas* with High Velocity Microprojectiles," *Science*, 240(4858):1534-1538.
Chasan, (Mar. 1995) "Engineering Fatty Acids—The Long and Short of It," *Plant Cell*, 7:235-237.
Chen et al., (1988) "Recognition of prokaryotic transcription terminators by spinach chloroplast RNA polymerase," *Nucleic Acids Research*,16(17):8411-8431.
Chen et al., (2001) "Highly efficient expression of rabbit neutrophil peptide-1 gene in *Chlorella ellipsoidea* cells," *Current Genetics*, 39(5):365-370.
Chow et al., (1999) "Electrotransformation of *Chlorella vulgaris," Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon," Plasmid*,30(2):90-105.
Cobley et al., (2002) "CpeR is an activator required for expression of the phycoerythrin operon (cpeBA) in the cyanobacterium Fremyella diplosiphon and is encoded in the phycoerythrin linker-polypeptide operon (cpeCDESTR)," *Molecular Microbiololgy*,44(6):1517-1531.
Comai et al., (Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263(29):15104-15109.
Courchesne, Noémie Manuelle Dorval el al., (2009) "Enhancement of lipid production using biochemical, genetic and transcription factor engineering approaches," *Journal of Biotechnology*, 141(1):31-41.
Davies et al., (1992) "Expression of the arylsulfatase gene from the $\beta_2$-tubulin promoter in *Chlamydomonas reinhardtii," Nucleic Acids Res.*, 20(12):2959-2965.
Dawson et al., (1997) "Stable Transformation of *Chlorella*: Rescue of Nitrate Reductase-Deficient Mutants with the Nitrate Reductase Gene," *Current Microbiol.*, 35(6):356-362.
Debuchy et al., (1989) "The argininosuccinate lyase gene of *Chlamydomonas reinhardtii*: an important tool for nuclear transformation and for correlating the genetic and molecular maps of the ARG7 locus," *EMBO Journal*, 8(10):2803-2809.
Dehesh et al. (1996) "Production of high levels of 8:0 and 10:0 fatty acids in transgenic canola by overexpression of Ch FatB2, a thioesterase cDNA from *Cuphea hookeriana," The Plant Journal*, 9(2):167-172.
Dehesh et al., (1998) "KAS IV: a 3-ketoacyl-ACP synthase from *Cuphea* sp. is a medium chain specific condensing enzyme," *The Plant Journal*, 15:383-390.
Deshnium et al., (1995) "Transformation of *Synechococcus* with a gene for choline oxidase enhances tolerance to salt stress," *Plant Mol. Biol.*,29(5):897-907.
Dörmann et al., (Jan. 1995) "Cloning and Expression in *Escherichia coli* of a Novel Thioesterase from *Arabidopsis thaliana* Specific for Long-Chain Acyl-Acyl Carrier Proteins," *Archives of Biochemistry and Biophysics*, 316(1):612-618.
Eccleston et al., (1996) "Medium-chain fatty Acid biosynthesis and utilization in *Brassica napus* plants expressing lauroyl-acyl carrier protein thioesterase," *Planta*, 198:46-53.
El-Sheekh et al., (1999) "Stable transformation of the intact cells of *Chlorella kessleri* with high velocity microprojectiles," *Biologia Plantarium*, 42:(2):209-216.
Facciotti et al., (1998) "Molecular dissection of the plant acyl-acyl carrier protein thioesterases," *European Journal of Lipid Science and Technology*, 100(Nr. 4-5, S.):167-172.
Facciotti et al., (Jun. 1999) "Improved stearate phenotype in transgenic canola expressing a modified acyl-acyl carrier protein thioesterase," *Nat Biotechnol.*, 17(6):593-597.
Falciatore et al., (May 1999) "Transformation of Nonselectable Reporter Genes in Marine Diatoms," *Mar. Biotechnol.*, 1(3):239-251.
Frenz et al., (1989) "Hydrocarbon recovery by extraction with a biocompatible solvent from free and immobilized cultures of *Botryococcus braunii," Enzyme Microb. Technol.*, 11:717-724.
Fromm et al., (Sep. 1985) "Expression of genes transferred into monocot and dicot plant cells by electroporation," *Proc. Natl. Acad. Sci. USA*, 82:5824 5828.
Ginalski et al., (2003) "Detection of reliable and unexpected protein fold predictions using 3D-Jury," *Nucleic Acids Research*,31(13):3291-3292.
Giuffrida et al., (2004) "Formation and Hydrolysis of Triacylglycerol and Sterol Epoxides: Role of Unsaturated Triacylglycerol Peroxyl Radicals," *Free Radical Biology and & Medicine*, 37(1):104-114.
Gruber et al., (1991) "*Escherichia coli-Anacystis nidulans* Plasmid Shuttle Vectors Containing the $P_L$ Promoter from Bacteriophage Lambda," *Current Micro.* 22:15-19.
Gruber et al., (1996) "Expression of the *Volvox* gene encoding nitrate reductase: Mutation-dependent activation of cryptic splice sites and intron-enhanced gene expression from a cDNA," *Plant Molecular Biology*, 31(1):1-12.
Guo et al. (Jun. 22, 2004) "Protein tolerance to random amino acid change," *Proc. Natl. Acad. Sci. USA*, 101(25):9205-9210.
Hall et al., (1993) "Expression of a foreign gene in *Chlamydomonas reinhardtii," Gene*, 124:75-81.
Hallmann et al., (Nov. 1994) "Reporter genes and highly regulated promoters as tools for transformation experiments in *Volvox carteri," Proc. Natl. Acad. Sci. USA*, 91:11562-11566.
Hanley-Bowdoin et al., (Feb. 1987) "Chloroplast promoters," *TIBS*, 12:67-70.
Hawkins et al., (1999) "Expression of Human Growth Hormone by the Eukaryotic Alga, *Chlorella," Current Microbiology*, 38:335-341.
Heise et al., (1994) "Factors Controlling Medium-Chain Fatty Acid Synthesis in Plastids From *Cuphea* Embryos," *Prog. Lipid Res.*, 33(1/2):87-95.
Hejazi et al., (Apr. 2004) "Milking of microalgae," *TRENDS in Biotechnology*, 22(4):189-194.
Hillen et al., (1982) "Hydrocracking of the Oils of *Botryococcus braunii* to Transport Fuels," *Biotechnology and Bioengineering*, XXIV:193-205.

(56) References Cited

OTHER PUBLICATIONS

Hitz et al., (1994) "Cloning of a Higher-Plant Plastid ω-6 Fatty Acid Desaturase cDNA and Its Expression in a Cyanobacterium," *Plant Physiol.*,105(2):635-641.
Huang et al. (2006) "Expression of mercuric reductase from *Bacillus megaterium* MB1 in eukaryotic microalga *Chlorella* sp. DT: an approach for mercury phytoremediation," *Appl. Microbiol. Biotechnol.* 72:197-205.
Inoue et al., (1993) "Analysis of Oil Derived From Liquefaction of *Botryococcus braunii," Biomass Bioenergy*, 6(4):269-274).
Isbell et al., (Feb. 1994) "Acid-Catalyzed Condensation of Oleic Acid into Estolides and Polyestolides," *JAOCS*, 71(2):169-174.
Jakobiak et al. (Dec. 2004) "The Bacterial Paromomycin Resistance Gene, aphH, as a Dominant Selectable Marker in *Volvox carteri," Protist*,155(4):381-393.
Jarvis et al. (1991) "Transient expression of firefly luciferase in protoplasts of the green alga *Chlorella ellipsoidea," Current Genetics*, 19:317-321.
Jha et al., (2006) "Cloning and functional expression of an acyl-ACP thioesterase FatB type from *Diploknema* (*Madhuca*) *butyracea* seeds in *Escherichia coli," Plant Physiology and Biochemistry*, 44:645-655.
Jiang et al., (Apr. 2005) "The Actin Gene Promoter-driven bar as a Dominant Selectable Marker for Nuclear Transformation of Dunaliella salina," *Acta Genetica Sinica*, 32(4):424-433.
Jones et al., (Mar. 1995) "Palmitoyl-Acyl Carrier Protein (ACP) Thioesterase and the Evolutionary Origin of Plant Acyl-ACP Thioesterases," *The Plant Cell*, 7:359-371.
Kalscheuer et al., (1999) "Establishment of a gene transfer system for *Rhodococcus opacus* PD630 based on electroporation and its application for recombinant biosynthesis of poly(3-hydroxyalkanoic acids)," *Applied and Environmental Microbiology*, 52:508-515.
Kang et al., (Jul. 2000) "The Regulation Activity of Chlorella Virus Gene 5' Upstream Sequence in *Escherichia coli* and Eucaryotic Algae," [English Abstract] *Chinese Journal of Biotechnology*, 16(4):6 pages.
Kang et al., (2004) "Genetic diversity in chlorella viruses flanking*kcv*, a gene that encodes a potassium ion channel protein," *Virology*, 326(1):150-159.
Kawasaki et al., (2004) "Immediate early genes expressed in chlorovirus infections," *Virology*,318(1):214-223.
Kim et al., (2002) Stable Integration and Functional Expression of Flounder Growth Hormone Gene in Transformed Microalga, *Chlorella ellipsoidea, Mar. Biotechnol.*, 4(1):63-73.
Kindle, (Feb. 1990) "High-frequency nuclear transformation of *Chlamydomonas reinhardtii," Proc. Natl. Acad. Sci. USA*, 87(3):1228-1232.
Klein et al., (1987) "High-velocity microprojectiles for delivering nucleic acids into living cells," *Nature* London 327(7):70-73.
Knauf, (Feb. 1987) "The application of genetic engineering to oilseed crops," *TIBTECH*, 5:40-47.
Knutzon et al., (Jul. 1999) "Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels," *Plant Physiology*, 120:739-746.
Kojima et al., (1999) "Growth and Hydrocarbon Production of Microalga *Botryococcus braunii* in Bubble Column Photobioreactors," *Journal of Bioscience and Bioengineering*, 87(6):811-815.
Koksharova et al., (Feb. 2002) "Genetic tools for cyanobacteria," *Appl Microbiol Biotechnol* 58(2):123-137.
Krebbers et al., (1982) "The maize chloroplast genes for the β and ϵ subunits of the photosynthetic coupling factor $CF_1$ are fused," *Nucleic Acids Research*, 10(16):4985-5002.
La Scala et al., (Jan. 2002) "The Effect of Fatty Acid Composition on the Acrylation Kinetics of Epoxidized Triacylglycerols", *Journal of the American Oil Chemists' Society*, 79(1):59-63.
Lapidot et al., (May 2002) "Stable Chloroplast Transformation of the Unicellular Red Alga *Porphyridium* Species," *Plant Physiol.*, 129(1):7-12.
Larson et al., (2002) "Acyl CoA profilesof transgenic plants that accumulate medium-chain fatty acids indicate inefficient storage lipid synthesis in developing oilseeds," *The Plant Journal*, 32(4):519-527.
Lumbreras et al., (1998) "Efficient foreign gene expression in *Chlamydomonas reinhardtii* mediated by an endogenous intron," *Plant Journal*, 14(4):441-447.
Manuell et al., (2007) "Robust expression of a bioactive mammalian protein in *Chlamydomonas* chloroplast," *Plant Biotechnol Journal*, 5:402-412.
Kang et al., (2004) "Genetic diversity in chlorella viruses flanking kcv, a gene that encodes a potassium ion channel protein," *Virology*, 326(1):150-159.
Mayer et al., (Jan. 3, 2007) "Identification of amino acid residues involved in substrate specificity of plant acyl-ACP thioesterases using a bioinformatics-guided approach," *BMC Plant Biology*, 7(1):1-11 pages.
Mayfield et al., (Jan. 21, 2003) "Expression and assembly of a fully active antibody in algae," *Proc. Natl. Acad. Sci. USA*, 100(2):438-442.
Mekhedov et al., (Feb. 2000) "Toward a Functional Catalog of the Plant Genome. A Survey of Genes for Lipid Biosynthesis," *Plant Physiology*, 122:389-401.
Mendes et al. (2003) "Supercritical carbon dioxide extraction of compounds with pharmaceutical importance from microalgae," *Inorganica Chimica Acta*, 356:328-334.
Metzger et al., (Jun. 2003) "Lycopanerols I-L, Four New Tetraterpenoid Ethers from *Botryococcus braunii," J Nat. Prod.* 66(6):772-778.
Metzger et al., (2005) "*Botryococcus braunii*: a rich source for hydrocarbons and related ether lipids," *Appl Microbiol Biotechnol* 66:486-496.
Miao et al., (2004) "High yield bio-oil production from fast pyrolysis by metabolic controlling of *Chlorella protothecoides," Journal of Biotechnology*, 110:85-93.
Miao et al., (2006) "Biodiesel production from heterotrophic microalgal oil," *Biosource Technology*, 97:841-846.
Minowa et al., (1995) "Oil production from algal cells of *Dunaliella tertiolecta* by direct thermochemical liquefaction," *Fuel*, 74(12):1735-1738.
Mitra et al., (Oct. 14, 1994) "A Chlorella Virus Gene Promoter Functions as a Strong Promoter Both in Plants and Bacteria," *Biochemical Biophysical Research Communication*, 204(1):187-194.
Mitra et al., (Oct. 1994) "The *Chlorella* virus adenine methyltransferase gene promoter is a strong promoter in plants," *Plant Mol. Biol.*, 26(1):85-93.
Moreno-Pérez et al., (2012) "Reduced expression of FatA thioesterases in Arabidopsis affects the oil content and fatty acid composition of the seeds," *Planta*, 235:629-639.
Mullet et al., (1985) "Multiple transcripts for higher plant rbcL and atpB genes and localization of the transcription initiation site of the rbcL gene," *Plant Molecular Biology*, 4:39-54.
Oda et al., (2000) "Degradation of Polylactide by Commercial Proteases," *Journal of Polymers and the Environment*, 8(1):29-32.
Onai et al., (2004) "Natural transformation of the thermophilic cyanobacterium *Thermosynechococcus elongatus* BP-1: a simple and effcient method for gene transfer," *Mol Genet Genomics*, 271(1):50-59.
Park et al., (2005) "Isolation and Characterization of Chlorella Virus from Fresh Water in Korea and Application in Chlorella Transformation System," *The Plant Patholology Journal*, 21(1):13-20.
Pröschold et al., (Aug. 2005) "Portrait of a species: *Chlamydomonas reinhardtii," Genetics*,170:1601-1610.
Radakovits et al., (Apr. 2010) "Genetic Engineering of Algae for Enhanced Biofuel Production," *Eukaryotic Cell*, 9(4):486-501.
Rao et al., (2006) "Antioxidant Activity of *Botryococcus braunii* Extract Elucidated in Vitro Models," *J. Agric. Food Chem.*, 54(13):4593-4599.
Rehm et al., (2001)"Heterologous expression of the acyl-acyl carrier protein thioesterase gene from the plant *Umbellularia californica* mediates polyhydroxyalkanoate biosynthesis in recombinant *Escherichia coli," Appl Microbiol Biotechnol*, 55:205-209.

(56) References Cited

OTHER PUBLICATIONS

Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi:10.1186/1471-2164-12-148.
Rosenberg, Julian N. et al., (2008) "A green light for engineered algae: redirecting metabolism to fuel a biotechnology revolution," *Current Opinion in Biotechnology*, 19(5):430-436.
Salas et al., (2002) "Characterization of substrate specificity of plant FatA and FatB acyl-ACP thioesterases," *Archives of Biochemistry and Biophysics*, 403:25-34.
Sanford, (Dec. 1988) "The biolistic process," *Trends in Biotech.* 6:299-302.
Sawayama et al. (1999) Possibility of renewable energy production and $CO_2$ mitigation by thermochemical liquefaction of microalgae *Biomass and Bioenergy*, 17:33-39.
Schreier et al., (1985) "The use of nuclear-encoded sequences to direct the light-regulated synthesis and transport of a foreign protein into plant chloroplasts," *EMBO J.* 4(1):25-32.
Schultz et al., (Apr. 2005) "A common core of secondary structure of the internal transcribed spacer 2 (ITS2) throughout the Eukaryota," *RNA*, 11(4):361-364.
Schütt et al., (1998) "The role of acyl carrier protein isoforms from *Cuphea lanceolata* seeds in the de-novo biosynthesis of medium-chain fatty acids," *Publication, Planta*, 205:263-268.
Shao et al., (2002) "Cloning and expression of metallothionein mutant α-KKS-α in *Anabaena* sp. PCC 7120," *Marine Pollution Bulletin*,45(1-12):163-167.
Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Department of Energy's Office of Fuels Development, Prepared by *National Renewable Energy Laboratory*, NREL/TP-580-24190, 328 pages.
Stemmer et al., (1995) "Single-step assembly of a gene and entire plasmid from large numbers of oligodeoxyribonucleotides," *Gene*, 164(1):49-53.
Tan et al., (Aug. 2005) "Establishment of a Micro-Particle Bombardment Transformation System for *Dunaliella salina," The Journal of Microbiology*, 43(4):361-365.
Tang et al., (Aug. 1995) "Insertion Mutagenesis of *Chlamydomonas reinhardtii* by Electroporation and Heterologous DNA," *Biochemistry and Molecular Biology International*, 36(5):1025-1035.
Tyystjärvi et al., (2005) "Mathematical modelling of the light response curve of photoinhibition of Photosystem II," *Photosynthesis Research*, 84(1-3):21-27.
Vázquez-Bermúdez et al., (Jan. 2000) "Uptake of 2-Oxoglutarate in *Synechococcus* Strains Transformed with the *Escherichia coli kgtP* Gene," *Journal of Bacteriology*, 182(1):211-215.
Vázquez-Bermúdez et al., (2003) "Carbon supply and 2-oxoglutarate e¡ ects on expression of nitrate reductase and nitrogen-regulated genes in *Synechococcus* sp. strain PCC 7942," *FEMS Microbiology Letters*, 221(2):155-159.
Voelker, (1996) "Plant Acyl-ACP Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds," *Plant Physiol.*, 114:669-677.
Voetz et al., (1994) "Three Different cDNAs Encoding Acyl Carrier Proteins from *Cuphea lanceolata," Plant Physiol.*, 106:785-786.
Walker et al., (2005) "Characterisation of the *Dunaliella tertiolecta RbcS* genes and their promoter activity in *Chlamydomonas reinhardtii," Plant Cell Rep.* 23(10-11):727-735.
Westphal et al., (Mar. 27, 2001) "Vippl deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5):1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of *Chlorella* spp. isolates using ribosomal DNA sequences," *Bot. Bull. Acad. Sin.*42:115-121.
Yu et al., (2011) "Modifications of the metabolic pathways of lipid and triacylglycerol production in microalgae," *Microbial Cell Factories*, 10:91 [Retrieved from the Internet Jul. 24, 2012: <URL:http://www.microbialcellfactories.com/content/10/1/91>], 11 pages.
Yuan et al., (Nov. 1995) "Modification of the substrate specificity of an acyl-acyl carrier protein thioesterase by protein engineering," *Proc. Natl. Acad. Sci. USA*, 92:10639-10643.
Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.
Zurawski et al., (1981) "The structure of the gene for the large subunit of ribulose 1,5-bisphosphate carboxylase from spinach chloroplast DNA," *Nucleic Acids Res.* 9(14):3251-3270.
Zurawski et al., (Dec. 1982) "Nucleotide sequence of the gene for the $M_r$ 32,000 thylakoid membrane protein from *Spinacia oleracea* and *Nicotiana debneyi* predicts a totally conserved primary translation product of $M_r$ 38,950," *Proc. Natl. Acad. Sci. USA*, 79:7699-7703.
U.S. Final Office Action, dated Dec. 14, 2015, issued in U.S. Appl. No. 13/797,733.
U.S. Office Action, dated Jul. 26, 2016, issued in U.S. Appl. No. 13/797,733.
U.S. Notice of Allowance, dated Sep. 21, 2016, issued in U.S. Appl. No. 13/797,733.
U.S. Notice of Allowance, dated Nov. 17, 2015, issued in U.S. Appl. No. 13/837,996.
U.S. Office Action (Requirement for Restriction/Election), dated Jul. 12, 2016, issued in U.S. Appl. No. 14/209,931.
U.S. Office Action, dated Jan. 26, 2017, issued in U.S. Appl. No. 14/209,931.
U.S. Notice of Allowance, dated May 15, 2017, issued in U.S. Appl. No. 14/209,931.
U.S. Office Action, dated Jan. 19, 2017, issued in U.S. Appl. No. 14/808,361.
U.S. Notice of Allowance, dated Apr. 28, 2017, issued in U.S. Appl. No. 14/808,361.
U.S. Office Action (Requirement for Restriction/Election), dated Jun. 8, 2017, issued in U.S. Appl. No. 14/858,527.
European Examination Report dated Oct. 25, 2016 issued in EP 14 706 996.7.
Mexican Office Action [no translation] dated Sep. 21, 2015 issued in MX/a/2015/009730.
European Partial Supplementary Search Report (Communication pursuant to Rule 164(1)EPC) dated Jul. 6, 2016 issued in EP 14 76 9502.7.
European Extended Search Report dated Oct. 13, 2016 issued in EP 14 76 9502.7.
PCT International Search Report and Written Opinion dated Dec. 22, 2015 issued in PCT/US2015/042044.
PCT International Preliminary Report on Patentability dated Feb. 2, 2017 issued in PCT/US2015/042044.
Database UniProt [Online] (Jul. 24, 2013) "SubName: Full =FatB type acyl-ACP thioesterase-3 {EC0:0000313:EMBL:AGG79285.

(56) References Cited

OTHER PUBLICATIONS

1},” retrieved on Nov. 10, 2015 from EBI accession No. UNIPROT:R4J2L6, Database accession No. R4J2L6 sequence, 1 page.
Database UniProt [Online] (Jul. 9, 2014) “SubName: Full=Uncharacterized protein {EC0:0000313:EMBL:KCW58039. 1},” retrieved on Nov. 16, 2015 from EBI accession No. UNIPROT:A0A059AWB4, Database accession No. A0A059AWB4 sequence, 1 page.
PCT Invitation to Pay Additional Fees and, Where Applicable, Protest Fee dated Jan. 13, 2016 issued in PCT/US2015/051042.
PCT International Search Report and Written Opinion dated Mar. 31, 2016 issued in PCT/US2015/051042.
Hill et al.,(1998) “Functional Analysis of Conserved Histidines in ADP-Glucose Pyrophosphorylase from *Escherichia coli*,” Biochem. Biophys. Res. Comm., 244(2):573-577.
Mittendorf et al., (1999) “Polyhydroxyalkanoate synthesis in transgenic plants as a new tool to study carbon flow through β-oxidation,” The Plant Journal, 20(1):45-55.
Tjellström et al., (Feb. 20, 2013) “Disruption of plastid acyl:acyl carrier protein synthetases increases medium chain fatty acid accumulation in seeds of transgenic Arabidopsis,” FEBS Letters,587(7):936-942.
U.S. Notice of Allowance, dated Jun. 14, 2017, issued in U.S. Appl. No. 14/209,931.

* cited by examiner gctcttcgccgccgccactcctgctcgagcgcgcccgcgcgtgcgccgccagcgccttggc
cttttcgccgcgctcgtgcgcgtcgctgatgtccatcaccaggtccatgaggtctgccttg
cgccggctgagccactgcttcgtccgggcggccaagaggagcatgagggaggactcctggt
ccagggtcctgacgtggtcgcggctctgggagcgggccagcatcatctggctctgccgcac
cgaggccgcctccaactggtcctccagcagccgcagtcgccgccgaccctggcagaggaag
acaggtgaggggtgtatgaattgtacagaacaaccacgagccttgtctaggcagaatccct
accagtcatggctttacctggatgacggcctgcgaacagctgtccagcgaccctcgctgcc
gccgcttctcccgcacgcttctttccagcaccgtgatggcgcgagccagcgccgcacgctg
gcgctgcgcttcgccgatctgaggacagtcggggaactctgatcagtctaaaccccccttgc
gcgttagtgttgccatcctttgcagaccggtgagagccgacttgttgtgcgccacccccca
caccacctcctcccagaccaattctgtcacctttttggcgaaggcatcggcctcggcctgc
agagaggacagcagtgcccagccgctggggttggcggatgcacgctcaggtaccctttct
tgcgctatgacacttccagcaaaaggtagggcgggctgcgagacggcttcccggcgctgca
tgcaacaccgatgatgcttcgacccccccgaagctccttcggggctgcatgggcgctccgat
gccgctccagggcgagcgctgtttaaatagccaggcccccgattgcaaagacattatagcg
agctaccaaagccatattcaaacacctagatcactaccacttctacacaggccactcgagc
ttgtgatcgcactccgctaagggggcgcctcttcctcttcgtttcagtcacaacccgcaaa
cggcgcgcc*ATGctgctgcaggccttcctgttcctgctggccggcttcgccgccaagatca*
*gcgcctccatgacgaacgagacgtccgaccgccccctggtgcacttcacccccaacaaggg*
*ctggatgaacgaccccaacggcctgtggtacgacgagaaggacgccaagtggcacctgtac*
*ttccagtacaacccgaacgacaccgtctgggggacgcccttgttctggggccacgccacgt*
*ccgacgacctgaccaactgggaggaccagcccatcgccatcgccccgaagcgcaacgactc*
*cggcgccttctccggctccatggtggtggactacaacaacacctccggcttcttcaacgac*
*accatcgacccgcgccagcgctgcgtggccatctggacctacaacaccccggagtccgagg*
*agcagtacatctcctacagcctggacggcggctacaccttcaccgagtaccagaagaaccc*
*cgtgctggccgccaactccacccagttccgcgacccgaaggtcttctggtacgagccctcc*
*cagaagtggatcatgaccgcggccaagtcccaggactacaagatcgagatctactcctccg*
*acgacctgaagtcctggaagctggagtccgcgttcgccaacgagggcttcctcggctacca*
*gtacgagtgccccggcctgatcgaggtccccaccgagcaggaccccagcaagtcctactgg*
*gtgatgttcatctccatcaaccccggcgccccggccggcggctccttcaaccagtacttcg*
*tcggcagcttcaacggcacccacttcgaggccttcgacaaccagtcccgcgtggtggactt*
*cggcaaggactactacgccctgcagaccttcttcaacaccgacccgacctacgggagcgcc*
*ctgggcatcgcgtgggcctccaactgggagtactccgccttcgtgcccaccaacccctggc*
*gctcctccatgtccctcgtgcgcaagttctccctcaacaccgagtaccaggccaacccgga*
*gacggagctgatcaacctgaaggccgagccgatcctgaacatcagcaacgccggcccctgg*
*agccggttcgccaccaacaccacgttgacgaaggccaacagctacaacgtcgacctgtcca*
*acagcaccggcaccctggagttcgagctggtgtacgccgtcaacaccacccagacgatctc*
*caagtccgtgttcgcggacctctccctctggttcaagggcctggaggaccccgaggagtac*

*Fig. 3A* ctccgcatgggcttcgaggtgtccgcgtcctccttcttcctggaccgcgggaacagcaagg
tgaagttcgtgaaggagaacccctacttcaccaaccgcatgagcgtgaacaaccagccctt
caagagcgagaacgacctgtcctactacaaggtgtacggcttgctggaccagaacatcctg
gagctgtacttcaacgacggcgacgtcgtgtccaccaacacctacttcatgaccaccggga
acgccctgggctccgtgaacatgacgacggggtggacaacctgttctacatcgacaagtt
ccaggtgcgcgaggtcaagTGAcaattggcagcagcagctcggatagtatcgacacactct
ggacgctggtcgtgtgatggactgttgccgccacacttgctgccttgacctgtgaatatcc
ctgccgcttttatcaaacagcctcagtgtgtttgatcttgtgtgtacgcgcttttgcgagt
tgctagctgcttgtgctatttgcgaataccacccccagcatccccttccctcgtttcatat
cgcttgcatcccaaccgcaacttatctacgctgtcctgctatccctcagcgctgctcctgc
tcctgctcactgcccctcgcacagccttggtttgggctccgcctgtattctcctggtactg
caacctgtaaaccagcactgcaatgctgatgcacgggaagtagtgggatgggaacacaaat
ggaggatcccgcgtctcgaacagagcgcgcagaggaacgctgaaggtctcgcctctgtcgc
acctcagcgcggcatacaccacaataaccacctgacgaatgcgcttggttcttcgtccatt
agcgaagcgtccggttcacacacgtgccacgttggcgaggtggcaggtgacaatgatcggt
ggagctgatggtcgaaacgttcacagcctagggatatcgaattcGGCCGACAGGACGCGCG
TCAAAGGTGCTGGTCGTGTATGCCCTGGCCGGCAGGTCGTTGCTGCTGCTGGTTAGTGATT
CCGCAACCCTGATTTTGGCGTCTTATTTTGGCGTGGCAAACGCTGGCGCCCGCGAGCCGGG
CCGGCGGCGATGCGGTGCCCCACGGCTGCCGGAATCCAAGGGAGGCAAGAGCGCCCGGGTC
AGTTGAAGGGCTTTACGCGCAAGGTACAGCCGCTCCTGCAAGGCTGCGTGGTGGAATTGGA
CGTGCAGGTCCTGCTGAAGTTCCTCCACCGCCTCACCAGCGGACAAAGCACCGGTGTATCA
GGTCCGTGTCATCCACTCTAAAGAGCTCGACTACGACCTACTGATGGCCCTAGATTCTTCA
TCAAAAACGCCTGAGACACTTGCCCAGGATTGAAACTCCCTGAAGGGACCACCAGGGGCCC
TGAGTTGTTCCTTCCCCCCGTGGCGAGCTGCCAGCCAGGCTGTACCTGTGATCGAGGCTGG
CGGGAAAATAGGCTTCGTGTGCTCAGGTCATGGGAGGTGCAGGACAGCTCATGAAACGCCA
ACAATCGCACAATTCATGTCAAGCTAATCAGCTATTTCCTCTTCACGAGCTGTAATTGTCC
CAAAATTCTGGTCTACCGGGGGTGATCCTTCGTGTACGGGCCCTTCCCTCAACCCTAGGTA
TGCGCGCATGCGGTCGCCGCGCAACTCGCGCGAGGGCCGAGGGTTTGGGACGGGCCGTCCC
GAAATGCAGTTGCACCCGGATGCGTGGCACCTTTTTTGCGATAATTTATGCAATGGACTGC
TCTGCAAAATTCTGGCTCTGTCGCCAACCCTAGGATCAGCGGCGTAGGATTTCGTAATCAT
TCGTCCTGATGGGGAGCTACCGACTACCCTAATATCAGCCCGACTGCCTGACGCCAGCGTC
CACTTTTGTGCACACATTCCATTCGTGCCCAAGACATTTCATTGTGGTGCGAAGCGTCCCC
AGTTACGCTCACCTGTTTCCCGACCTCCTTACTGTTCTGTCGACAGAGCGGGCCCACAGGC
CGGTCGCAGCCactagtAACAATGGCCACCGCATCCACTTTCTCGGCGTTCAATGCCCGCT
GCGGCGACCTGCGTCGCTCGGCGGGCTCCGGGCCCCGGCGCCCAGCGAGGCCCCTCCCCGT
GCGCGggcgcgccCCCGACTGGTCCATGCTGTTCGCCGTGATCACCACCATCTTCTCCGCC
GCCGAGAAGCAGTGGACCAACCTGGAGTGGAAGCCCAAGCCCAACCCCCCCCAGCTGCTGG

Fig. 3B

*ACGACCACTTCGGCCCCCACGGCCTGGTGTTCCGCCGCACCTTCGCCATCCGCAGCTACGA*
*GGTGGGCCCCGACCGCTCCACCAGCATCGTGGCCGTGATGAACCACCTGCAGGAGGCCGCC*
*CTGAACCACGCCAAGTCCGTGGGCATCCTGGGCGACGGCTTCGGCACCACCCTGGAGATGT*
*CCAAGCGCGACCTGATCTGGGTGGTGAAGCGCACCCACGTGGCCGTGGAGCGCTACCCCGC*
*C*TGGGGCGACACCGTGGAGGTGGAGTGCTGGATCGGCGCCAGCGGCAACAACGGCATGCGC
CGCGACTTCCTGGTGCGCGACTGCAAGACCGGCGAGATCCTGACCCGCTGCACCTCCCTGA
GCGTGCTGATGAACACCCGCACCCGCCGCCTGAGCACCATCCCCGACGAGGTGCGCGGCGA
GATCGGCCCCGCCTTCATCGACAACGTGGCCGTGAAGGACGACGAGATCAAGAAGCTGCAG
AAGCTGAACGACTCCACCGCCGACTACATCCAGGGCGGCCTGACCCCCCGCTGGAACGACC
TGGACGTGAACCAGCACGTGAACAACCTGAAGTACGTGGCCTGGGTGTTCGAGACCGTGCC
CGACAGCATCTTCGAGTCCCACCACATCAGCTCCTTCACCCTGGAGTACCGCCGCGAGTGC
ACCCGCGACTCCGTGCTGCGCAGCCTGACCACCGTGAGCGGCGGCAGCTCCGAGGCCGGCC
TGGTGTGCGACCACCTGCTGCAGCTGGAGGGCGGCAGCGAGGTGCTGCGCGCCCGCACCGA
GTGGCGCCCCAAGCTGACCGACTCCTTCCGCGGCATCAGCGTGATCCCCGCCGAGCCCCGC
GTGatggactacaaggaccacgacggcgactacaaggaccacgacatcgactacaaggacg
acgacgacaagtgactcgaggcagcagcagctcggatagtatcgacacactctggacgctg
gtcgtgtgatggactgttgccgccacacttgctgccttgacctgtgaatatccctgccgct
tttatcaaacagcctcagtgtgtttgatcttgtgtgtacgcgcttttgcgagttgctagct
gcttgtgctatttgcgaataccacccccagcatccccttccctcgtttcatatcgcttgca
tcccaaccgcaacttatctacgctgtcctgctatccctcagcgctgctcctgctcctgctc
actgcccctcgcacagccttggtttgggctccgcctgtattctcctggtactgcaacctgt
aaaccagcactgcaatgctgatgcacgggaagtagtgggatgggaacacaaatggaaagct
tgagctcttgttttccagaaggagttgctccttgagcctttcattctcagcctcgataacc
tccaaagccgctctaattgtggaggggttcgaatttaaaagcttggaatgttggttcgtg
cgtctggaacaagcccagacttgttgctcactgggaaaaggaccatcagctccaaaaact
tgccgctcaaaccgcgtacctctgctttcgcgcaatctgccctgttgaaatcgccaccaca
ttcatattgtgacgcttgagcagtctgtaattgcctcagaatgtggaatcatctgcccccct
gtgcgagcccatgccaggcatgtcgcgggcgaggacacccgccactcgtacagcagaccat
tatgctacctcacaatagttcataacagtgaccatatttctcgaagctccccaacgagcac
ctccatgctctgagtggccaccccccggccctggtgcttgcggagggcaggtcaaccggca
tggggctaccgaaatccccgaccggatcccaccacccccgcgatgggaagaatctctcccc
gggatgtgggcccaccaccagcacaacctgctggcccaggcgagcgtcaaaccataccaca
caaatatccttggcatcggccctgaattccttctgccgctctgctacccggtgcttctgtc
cgaagcaggggttgctagggatcgctccgagtccgcaaacccttgtcgcgtggcggggctt
gttcgagcttgaagagc

*Fig. 3C*

CCCGACTGGTCCATGCTGTTCGCCGTGATCACCACCATCTTCAGCGCCGCCGAGAAGCAGT
GGACCAACCTGGAGTGGAAGCCCAAGCCCAAGCTGCCCCAGCTGCTGGACGACCACTTCGG
CCTGCACGGCCTGGTGTTCCGCCGCACCTTCGCCATCCGCTCCTACGAGGTGGGCCCCGAC
CGCAGCACCTCCATCCTGGCCGTGATGAACCACATGCAGGAGGCCACCCTGAACCACGCCA
AGAGCGTGGGCATCCTGGGCGACGGCTTCGGCACCACCCTGGAGATGTCCAAGCGCGACCT
GATGTGGGTGGTGCGCCGCACCCACGTGGCCGTGGAGCGCTACCCCACC*TGGGGCGACACC*
*GTGGAGGTGGAGTGCTGGGTGGGCGCCTCCGGCAACAACGGCCGCCGCCACGACTTCCTGG*
*TGCGCGACTGCAAGACCGGCGAGATCCTGACCCGCTGCACCTCCCTGAGCGTGATGATGAA*
*CACCCGCACCCGCCGCCTGAGCAAGATCCCCGAGGAGGTGCGCGGCGAGATCGGCCCCGCC*
*TTCATCGACAACGTGGCCGTGAAGGACGAGGAGATCAAGAAGCCCCAGAAGCTGAACGACT*
*CCACCGCCGACTACATCCAGGGCGGCCTGACCCCCCGCTGGAACGACCTGGACATCAACCA*
*GCACGTGAACAACATCAAGTACGTGGACTGGATCCTGGAGACCGTGCCCGACAGCATCTTC*
*GAGAGCCACCACATCTCCTCCTTCACCATCGAGTACCGCCGCGAGTGCACCATGGACAGCG*
*TGCTGCAGTCCCTGACCACCGTGAGCGGCGGCTCCTCCGAGGCCGGCCTGGTGTGCGAGCA*
*CCTGCTGCAGCTGGAGGGCGGCAGCGAGGTGCTGCGCGCCAAGACCGAGTGGCGCCCCAAG*
*CTGACCGACTCCTTCCGCGGCATCAGCGTGATCCCCGCCGAGTCCAGCGTG*

Fig. 4

*CCCGACTGGTCCATGCTGTTCGCCGTGATCACCACCATCTTCTCCGCCGCCGAGAAGCAGT*
*GGACCAACCTGGAGTGGAAGCCCAAGCCCAACCCCCCCAGCTGCTGGACGACCACTTCGG*
*CCCCCACGGCCTGGTGTTCCGCCGCACCTTCGCCATCCGCAGCTACGAGGTGGGCCCCGAC*
*CGCTCCACCAGCATCGTGGCCGTGATGAACCACCTGCAGGAGGCCGCCCTGAACCACGCCA*
*AGTCCGTGGGCATCCTGGGCGACGGCTTCGGCACCACCCTGGAGATGTCCAAGCGCGACCT*
*GATC*TGGGTGGTGCGCCGCACCCACGTGGCCGTGGAGCGCTACCCCACCTGGGGCGACACC
GTGGAGGTGGAGTGCTGGATCGGCGCCAGCGGCAACAACGGCATGCGCCGCGACTTCCTGG
TGCGCGACTGCAAGACCGGCGAGATCCTGACCCGCTGCACCTCCCTGAGCGTGCTGATGAA
CACCCGCACCCGCCGCCTGAGCACCATCCCCGACGAGGTGCGCGGCGAGATCGGCCCCGCC
TTCATCGACAACGTGGCCGTGAAGGACGACGAGATCAAGAAGCTGCAGAAGCTGAACGACT
CCACCGCCGACTACATCCAGGGCGGCCTGACCCCCCGCTGGAACGACCTGGACGTGAACCA
GCACGTGAACAACCTGAAGTACGTGGCCTGGGTGTTCGAGACCGTGCCCGACAGCATCTTC
GAGTCCCACCACATCAGCTCCTTCACCCTGGAGTACCGCCGCGAGTGCACCCGCGACTCCG
TGCTGCGCAGCCTGACCACCGTGAGCGGCGGCAGCTCCGAGGCCGGCCTGGTGTGCGACCA
CCTGCTGCAGCTGGAGGGCGGCAGCGAGGTGCTGCGCGCCCGCACCGAGTGGCGCCCCAAG
CTGACCGACTCCTTCCGCGGCATCAGCGTGATCCCCGCCGAGCCCCGCGTG

*Fig. 5*

*CCCGACTGGTCCATGCTGTTCGCCGTGATCACCACCATCTTCTCCGCCGCCGAGAAGCAGT*
*GGACCAACCTGGAGTGGAAGCCCAAGCCCAACCCCCCCCAGCTGCTGGACGACCACTTCGG*
*CCCCCACGGCCTGGTGTTCCGCCGCACCTTCGCCATCCGCAGCTACGAGGTGGGCCCCGAC*
*CGCTCCACC*TCCATCCTGGCCGTGATGAACCACATGCAGGAGGCCACCCTGAACCACGCCA
AGAGCGTGGGCATCCTGGGCGACGGCTTCGGCACCACCCTGGAGATGTCCAAGCGCGACCT
GATGTGGGTGGTGCGCCGCACCCACGTGGCCGTGGAGCGCTACCCCACCTGGGGCGACACC
GTGGAGGTGGAGTGCTGGATCGGCGCCAGCGGCAACAACGGCATGCGCCGCGACTTCCTGG
TGCGCGACTGCAAGACCGGCGAGATCCTGACCCGCTGCACCTCCCTGAGCGTGCTGATGAA
CACCCGCACCCGCCGCCTGAGCACCATCCCCGACGAGGTGCGCGGCGAGATCGGCCCCGCC
TTCATCGACAACGTGGCCGTGAAGGACGACGAGATCAAGAAGCTGCAGAAGCTGAACGACT
CCACCGCCGACTACATCCAGGGCGGCCTGACCCCCCGCTGGAACGACCTGGACGTGAACCA
GCACGTGAACAACCTGAAGTACGTGGCCTGGGTGTTCGAGACCGTGCCCGACAGCATCTTC
GAGTCCCACCACATCAGCTCCTTCACCCTGGAGTACCGCCGCGAGTGCACCCGCGACTCCG
TGCTGCGCAGCCTGACCACCGTGAGCGGCGGCAGCTCCGAGGCCGGCCTGGTGTGCGACCA
CCTGCTGCAGCTGGAGGGCGGCAGCGAGGTGCTGCGCGCCCGCACCGAGTGGCGCCCCAAG
CTGACCGACTCCTTCCGCGGCATCAGCGTGATCCCCGCCGAGCCCCGCGTG

*Fig. 6*

*CCCGACTGGTCCATGCTGTTCGCCGTGATCACCACCATCTTCTCCGCCGCCGAGAAGCAGT*
*GGACCAACCTGGAGTGGAAGCCCAAGCCC*AAGCTGCCCCAGCTGCTGGACGACCACTTCGG
CCTGCACGGCCTGGTGTTCCGCCGCACCTTCGCCATCCGCTCCTACGAGGTGGGCCCCGAC
CGCAGCACCTCCATCCTGGCCGTGATGAACCACATGCAGGAGGCCACCCTGAACCACGCCA
AGAGCGTGGGCATCCTGGGCGACGGCTTCGGCACCACCCTGGAGATGTCCAAGCGCGACCT
GATGTGGGTGGTGCGCCGCACCCACGTGGCCGTGGAGCGCTACCCCACCTGGGGCGACACC
GTGGAGGTGGAGTGCTGGATCGGCGCCAGCGGCAACAACGGCATGCGCCGCGACTTCCTGG
TGCGCGACTGCAAGACCGGCGAGATCCTGACCCGCTGCACCTCCCTGAGCGTGCTGATGAA
CACCCGCACCCGCCGCCTGAGCACCATCCCCGACGAGGTGCGCGGCGAGATCGGCCCCGCC
TTCATCGACAACGTGGCCGTGAAGGACGACGAGATCAAGAAGCTGCAGAAGCTGAACGACT
CCACCGCCGACTACATCCAGGGCGGCCTGACCCCCCGCTGGAACGACCTGGACGTGAACCA
GCACGTGAACAACCTGAAGTACGTGGCCTGGGTGTTCGAGACCGTGCCCGACAGCATCTTC
GAGTCCCACCACATCAGCTCCTTCACCCTGGAGTACCGCCGCGAGTGCACCCGCGACTCCG
TGCTGCGCAGCCTGACCACCGTGAGCGGCGGCAGCTCCGAGGCCGGCCTGGTGTGCGACCA
CCTGCTGCAGCTGGAGGGCGGCAGCGAGGTGCTGCGCGCCCGCACCGAGTGGCGCCCCAAG
CTGACCGACTCCTTCCGCGGCATCAGCGTGATCCCCGCCGAGCCCCGCGTG

*Fig. 7*

*CCCGACTGGTCCATGCTGTTCGCCGTGATCACCACCATCTTCTCCGCCGCCGAGAAGCAGT*
*GGACCAACCTGGAGTGGAAGCCCAAGCCC*AAGCTGCCCCAGCTGCTGGACGACCACTTCGG
CCTGCACGGCCTGGTGTTCCGCCGCACCTTCGCCATCCGCTCCTACGAGGTGGCCCCGAC
CGCAGCACC*AGCATCGTGGCCGTGATGAACCACCTGCAGGAGGCCGCCCTGAACCACGCCA*
*AGTCCGTGGGCATCCTGGGCGACGGCTTCGGCACCACCCTGGAGATGTCCAAGCGCGACCT*
*GATCT*GGGTGGTGCGCCGCACCCACGTGGCCGTGGAGCGCTACCCCACCTGGGGCGACACC
GTGGAGGTGGAGTGCTGGATCGGCGCCAGCGGCAACAACGGCATGCGCCGCGACTTCCTGG
TGCGCGACTGCAAGACCGGCGAGATCCTGACCCGCTGCACCTCCCTGAGCGTGCTGATGAA
CACCCGCACCCGCCGCCTGAGCACCATCCCCGACGAGGTGCGCGGCGAGATCGGCCCCGCC
TTCATCGACAACGTGGCCGTGAAGGACGACGAGATCAAGAAGCTGCAGAAGCTGAACGACT
CCACCGCCGACTACATCCAGGGCGGCCTGACCCCCCGCTGGAACGACCTGGACGTGAACCA
GCACGTGAACAACCTGAAGTACGTGGCCTGGGTGTTCGAGACCGTGCCCGACAGCATCTTC
GAGTCCCACCACATCAGCTCCTTCACCCTGGAGTACCGCCGCGAGTGCACCCGCGACTCCG
TGCTGCGCAGCCTGACCACCGTGAGCGGCGGCAGCTCCGAGGCCGGCCTGGTGTGCGACCA
CCTGCTGCAGCTGGAGGGCGGCAGCGAGGTGCTGCGCGCCCGCACCGAGTGGCGCCCCAAG
CTGACCGACTCCTTCCGCGGCATCAGCGTGATCCCCGCCGAGCCCCGCGTG

*Fig. 8* gctcttcgccgccgccactcctgctcgagcgcgcccgcgcgtgcgccgccagcgccttggc
cttttcgccgcgctcgtgcgcgtcgctgatgtccatcaccaggtccatgaggtctgccttg
cgccggctgagccactgcttcgtccgggcggccaagaggagcatgagggaggactcctggt
ccagggtcctgacgtggtcgcggctctgggagcgggccagcatcatctggctctgccgcac
cgaggccgcctccaactggtcctccagcagccgcagtcgccgccgaccctggcagaggaag
acaggtgaggggtgtatgaattgtacagaacaaccacgagccttgtctaggcagaatccct
accagtcatggctttacctggatgacggcctgcgaacagctgtccagcgaccctcgctgcc
gccgcttctcccgcacgcttctttccagcaccgtgatggcgcgagccagcgccgcacgctg
gcgctgcgcttcgccgatctgaggacagtcggggaactctgatcagtctaaccccccttgc
gcgttagtgttgccatcctttgcagaccggtgagagccgacttgttgtgcgccacccccca
caccacctcctcccagaccaattctgtcacctttttggcgaaggcatcggcctcggcctgc
agagaggacagcagtgcccagccgctgggggttggcggatgcacgctcaggtaccctttct
tgcgctatgacacttccagcaaaaggtagggcgggctgcgagacggcttcccggcgctgca
tgcaacaccgatgatgcttcgacccccccgaagctccttcggggctgcatgggcgctccgat
gccgctccagggcgagcgctgtttaaatagccaggcccccgattgcaaagacattatagcg
agctaccaaagccatattcaaacacctagatcactaccacttctacacaggccactcgagc
ttgtgatcgcactccgctaagggggcgcctcttcctcttcgtttcagtcacaacccgcaaa
cggcgcgcc*ATGctgctgcaggccttcctgttcctgctggccggcttcgccgccaagatca*
*gcgcctccatgacgaacgagacgtccgaccgccccctggtgcacttcacccccaacaaggg*
*ctggatgaacgaccccaacggcctgtggtacgacgagaaggacgccaagtggcacctgtac*
*ttccagtacaacccgaacgacaccgtctgggggacgcccttgttctggggccacgccacgt*
*ccgacgacctgaccaactgggaggaccagcccatcgccatcgccccgaagcgcaacgactc*
*cggcgccttctccggctccatggtggtggactacaacaacacctccggcttcttcaacgac*
*accatcgacccgcgccagcgctgcgtggccatctggacctacaacaccccggagtccgagg*
*agcagtacatctcctacagcctggacggcggctacaccttcaccgagtaccagaagaaccc*
*cgtgctggccgccaactccacccagttccgcgacccgaaggtcttctggtacgagccctcc*
*cagaagtggatcatgaccgcggccaagtcccaggactacaagatcgagatctactcctccg*
*acgacctgaagtcctggaagctggagtccgcgttcgccaacgagggcttcctcggctacca*
*gtacgagtgccccggcctgatcgaggtccccaccgagcaggaccccagcaagtcctactgg*
*gtgatgttcatctccatcaaccccggcgccccggccggcggctccttcaaccagtacttcg*
*tcggcagcttcaacggcacccacttcgaggccttcgacaaccagtcccgcgtggtggactt*
*cggcaaggactactacgccctgcagaccttcttcaacaccgacccgacctacgggagcgcc*
*ctgggcatcgcgtgggcctccaactgggagtactccgccttcgtgcccaccaacccctggc*
*gctcctccatgtccctcgtgcgcaagttctccctcaacaccgagtaccaggccaacccgga*
*gacggagctgatcaacctgaaggccgagccgatcctgaacatcagcaacgccggcccctgg*
*agccggttcgccaccaacaccacgttgacgaaggccaacagctacaacgtcgacctgtcca*
*acagcaccggcaccctggagttcgagctggtgtacgccgtcaacaccacccagacgatctc*
*caagtccgtgttcgcggacctctccctctggttcaagggcctggaggaccccgaggagtac*

Fig. 14A ctccgcatgggcttcgaggtgtccgcgtcctccttcttcctggaccgcgggaacagcaagg
tgaagttcgtgaaggagaacccctacttcaccaaccgcatgagcgtgaacaaccagccctt
caagagcgagaacgacctgtcctactacaaggtgtacggcttgctggaccagaacatcctg
gagctgtacttcaacgacggcgacgtcgtgtccaccaacacctacttcatgaccaccggga
acgccctgggctccgtgaacatgacgacgggggtggacaacctgttctacatcgacaagtt
ccaggtgcgcgaggtcaagTGAcaattggcagcagcagctcggatagtatcgacacactct
ggacgctggtcgtgtgatggactgttgccgccacacttgctgccttgacctgtgaatatcc
ctgccgcttttatcaaacagcctcagtgtgtttgatcttgtgtgtacgcgcttttgcgagt
tgctagctgcttgtgctatttgcgaataccacccccagcatccccttccctcgtttcatat
cgcttgcatcccaaccgcaacttatctacgctgtcctgctatccctcagcgctgctcctgc
tcctgctcactgcccctcgcacagccttggtttgggctccgcctgtattctcctggtactg
caacctgtaaaccagcactgcaatgctgatgcacgggaagtagtgggatgggaacacaaat
ggaggatcccgcgtctcgaacagagcgcgcagaggaacgctgaaggtctcgcctctgtcgc
acctcagcgcggcatacaccacaataaccacctgacgaatgcgcttggttcttcgtccatt
agcgaagcgtccggttcacacacgtgccacgttggcgaggtggcaggtgacaatgatcggt
ggagctgatggtcgaaacgttcacagcctagggatatcgaattcGGCCGACAGGACGCGCG
TCAAAGGTGCTGGTCGTGTATGCCCTGGCCGGCAGGTCGTTGCTGCTGCTGGTTAGTGATT
CCGCAACCCTGATTTTGGCGTCTTATTTTGGCGTGGCAAACGCTGGCGCCCGCGAGCCGGG
CCGGCGGCGATGCGGTGCCCCACGGCTGCCGGAATCCAAGGGAGGCAAGAGCGCCCGGGTC
AGTTGAAGGGCTTTACGCGCAAGGTACAGCCGCTCCTGCAAGGCTGCGTGGTGGAATTGGA
CGTGCAGGTCCTGCTGAAGTTCCTCCACCGCCTCACCAGCGGACAAAGCACCGGTGTATCA
GGTCCGTGTCATCCACTCTAAAGAGCTCGACTACGACCTACTGATGGCCCTAGATTCTTCA
TCAAAAACGCCTGAGACACTTGCCCAGGATTGAAACTCCCTGAAGGGACCACCAGGGGCCC
TGAGTTGTTCCTTCCCCCCGTGGCGAGCTGCCAGCCAGGCTGTACCTGTGATCGAGGCTGG
CGGGAAAATAGGCTTCGTGTGCTCAGGTCATGGGAGGTGCAGGACAGCTCATGAAACGCCA
ACAATCGCACAATTCATGTCAAGCTAATCAGCTATTTCCTCTTCACGAGCTGTAATTGTCC
CAAAATTCTGGTCTACCGGGGGTGATCCTTCGTGTACGGGCCCTTCCCTCAACCCTAGGTA
TGCGCGCATGCGGTCGCCGCGCAACTCGCGCGAGGGCCGAGGGTTTGGGACGGGCCGTCCC
GAAATGCAGTTGCACCCGGATGCGTGGCACCTTTTTTGCGATAATTTATGCAATGGACTGC
TCTGCAAAATTCTGGCTCTGTCGCCAACCCTAGGATCAGCGGCGTAGGATTTCGTAATCAT
TCGTCCTGATGGGGAGCTACCGACTACCCTAATATCAGCCCGACTGCCTGACGCCAGCGTC
CACTTTTGTGCACACATTCCATTCGTGCCCAAGACATTTCATTGTGGTGCGAAGCGTCCCC
AGTTACGCTCACCTGTTTCCCGACCTCCTTACTGTTCTGTCGACAGAGCGGGCCCACAGGC
CGGTCGCAGCCactagtAACAATGGCCACCGCATCCACTTTCTCGGCGTTCAATGCCCGCT
GCGGCGACCTGCGTCGCTCGGCGGGCTCCGGGCCCCGGCGCCCAGCGAGGCCCCTCCCCGT
GCGCGCTGCCATCGCCAGCGAGGTCCCCGTGGCCACCACCTCCCCCCGGCCCGACTGGTCC
ATGCTGTTCGCCGTGATCACCACCATCTTCAGCGCCGCCGAGAAGCAGTGGACCAACCTGG

Fig. 14B

AGTGGAAGCCCAAGCCCAAGCTGCCCCAGCTGCTGGACGACCACTTCGGCCTGCACGGCCT
GGTGTTCCGCCGCACCTTCGCCATCCGCTCCTACGAGGTGGGCCCCGACCGCAGCACCTCC
ATCCTGGCCGTGATGAACCACATGCAGGAGGCCACCCTGAACCACGCCAAGAGCGTGGGCA
TCCTGGGCGACGGCTTCGGCACCACCCTGGAGATGTCCAAGCGCGACCTGATGTGGGTGGT
GCGCCGCACCCACGTGGCCGTGGAGCGCTACCCCACCTGGGGCGACACCGTGGAGGTGGAG
TGCTGGATCGGCGCCAGCGGCAACAACGGCATGCGCCGCGACTTCCTGGTGCGCGACTGCA
AGACCGGCGAGATCCTGACCCGCTGCACCTCCCTGAGCGTGCTGATGAACACCCGCACCCG
CCGCCTGAGCACCATCCCCGACGAGGTGCGCGGCGAGATCGGCCCCGCCTTCATCGACAAC
GTGGCCGTGAAGGACGACGAGATCAAGAAGCTGCAGAAGCTGAACGACTCCACCGCCGACT
ACATCCAGGGCGGCCTGACCCCCCGCTGGAACGACCTGGACGTGAACCAGCACGTGAACAA
CCTGAAGTACGTGGCCTGGGTGTTCGAGACCGTGCCCGACAGCATCTTCGAGTCCCACCAC
ATCAGCTCCTTCACCCTGGAGTACCGCCGCGAGTGCACCCGCGACTCCGTGCTGCGCAGCC
TGACCACCGTGAGCGGCGGCAGCTCCGAGGCCGGCCTGGTGTGCGACCACCTGCTGCAGCT
GGAGGGCGGCAGCGAGGTGCTGCGCGCCCGCACCGAGTGGCGCCCCAAGCTGACCGACTCC
TTCCGCGGCATCAGCGTGATCCCCGCCGAGCCCCGCGTGatggactacaaggaccacgacg
gcgactacaaggaccacgacatcgactacaaggacgacgacgacaagtgactcgaggcagc
agcagctcggatagtatcgacacactctggacgctggtcgtgtgatggactgttgccgcca
cacttgctgccttgacctgtgaatatccctgccgcttttatcaaacagcctcagtgtgttt
gatcttgtgtgtacgcgcttttgcgagttgctagctgcttgtgctatttgcgaataccacc
cccagcatccccttccctcgtttcatatcgcttgcatcccaaccgcaacttatctacgctg
tcctgctatccctcagcgctgctcctgctcctgctcactgcccctcgcacagccttggttt
gggctccgcctgtattctcctggtactgcaacctgtaaaccagcactgcaatgctgatgca
cgggaagtagtgggatgggaacacaaatggaaagcttgagctcttgttttccagaaggagt
tgctccttgagcctttcattctcagcctcgataacctccaaagccgctctaattgtggagg
gggttcgaatttaaaagcttggaatgttggttcgtgcgtctggaacaagcccagacttgtt
gctcactgggaaaaggaccatcagctccaaaaaacttgccgctcaaaccgcgtacctctgc
tttcgcgcaatctgccctgttgaaatcgccaccacattcatattgtgacgcttgagcagtc
tgtaattgcctcagaatgtggaatcatctgccccctgtgcgagcccatgccaggcatgtcg
cgggcgaggacacccgccactcgtacagcagaccattatgctacctcacaatagttcataa
cagtgaccatatttctcgaagctccccaacgagcacctccatgctctgagtggccaccccc
cggccctggtgcttgcggagggcaggtcaaccggcatggggctaccgaaatccccgaccgg
atcccaccacccccgcgatgggaagaatctctccccgggatgtgggcccaccaccagcaca
acctgctggcccaggcgagcgtcaaaccataccacacaaatatccttggcatcggccctga
attccttctgccgctctgctacccggtgcttctgtccgaagcaggggttgctagggatcgc
tccgagtccgcaaacccttgtcgcgtggcggggcttgttcgagcttgaagagc

*Fig. 14C*

*AGCCTGAAGCGCCTG*CCCGACTGGTCCATGCTGTTCGCCGTGATCACCACCATCTTCAGCG
CCGCCGAGAAGCAGTGGACCAACCTGGAGTGGAAGCCCAAGCCCAAGCTGCCCCAGCTGCT
GGACGACCACTTCGGCCTGCACGGCCTGGTGTTCCGCCGCACCTTCGCCATCCGCTCCTAC
GAGGTGGGCCCCGACCGCAGCACCTCCATCCTGGCCGTGATGAACCACATGCAGGAGGCCA
CCCTGAACCACGCCAAGAGCGTGGGCATCCTGGGCGACGGCTTCGGCACCACCCTGGAGAT
GTCCAAGCGCGACCTGATGTGGGTGGTGCGCCGCACCCACGTGGCCGTGGAGCGCTACCCC
ACCTGGGGCGACACCGTGGAGGTGGAGTGCTGGATCGGCGCCAGCGGCAACAACGGCATGC
GCCGCGACTTCCTGGTGCGCGACTGCAAGACCGGCGAGATCCTGACCCGCTGCACCTCCCT
GAGCGTGCTGATGAACACCCGCACCCGCCGCCTGAGCACCATCCCCGACGAGGTGCGCGGC
GAGATCGGCCCCGCCTTCATCGACAACGTGGCCGTGAAGGACGACGAGATCAAGAAGCTGC
AGAAGCTGAACGACTCCACCGCCGACTACATCCAGGGCGGCCTGACCCCCCGCTGGAACGA
CCTGGACGTGAACCAGCACGTGAACAACCTGAAGTACGTGGCCTGGGTGTTCGAGACCGTG
CCCGACAGCATCTTCGAGTCCCACCACATCAGCTCCTTCACCCTGGAGTACCGCCGCGAGT
GCACCCGCGACTCCGTGCTGCGCAGCCTGACCACCGTGAGCGGCGGCAGCTCCGAGGCCGG
CCTGGTGTGCGACCACCTGCTGCAGCTGGAGGGCGGCAGCGAGGTGCTGCGCGCCCGCACC
GAGTGGCGCCCCAAGCTGACCGACTCCTTCCGCGGCATCAGCGTGATCCCCGCCGAGCCCC
GCGTG

*Fig. 15*

*ATCAACGGCACCAAGTTCAGCTACACCGAGAGCCTGAAGCGCCTG*CCCGACTGGTCCATGC
TGTTCGCCGTGATCACCACCATCTTCAGCGCCGCCGAGAAGCAGTGGACCAACCTGGAGTG
GAAGCCCAAGCCCAAGCTGCCCCAGCTGCTGGACGACCACTTCGGCCTGCACGGCCTGGTG
TTCCGCCGCACCTTCGCCATCCGCTCCTACGAGGTGGGCCCCGACCGCAGCACCTCCATCC
TGGCCGTGATGAACCACATGCAGGAGGCCACCCTGAACCACGCCAAGAGCGTGGGCATCCT
GGGCGACGGCTTCGGCACCACCCTGGAGATGTCCAAGCGCGACCTGATGTGGGTGGTGCGC
CGCACCCACGTGGCCGTGGAGCGCTACCCCACCTGGGGCGACACCGTGGAGGTGGAGTGCT
GGATCGGCGCCAGCGGCAACAACGGCATGCGCCGCGACTTCCTGGTGCGCGACTGCAAGAC
CGGCGAGATCCTGACCCGCTGCACCTCCCTGAGCGTGCTGATGAACACCCGCACCCGCCGC
CTGAGCACCATCCCCGACGAGGTGCGCGGCGAGATCGGCCCCGCCTTCATCGACAACGTGG
CCGTGAAGGACGACGAGATCAAGAAGCTGCAGAAGCTGAACGACTCCACCGCCGACTACAT
CCAGGGCGGCCTGACCCCCCGCTGGAACGACCTGGACGTGAACCAGCACGTGAACAACCTG
AAGTACGTGGCCTGGGTGTTCGAGACCGTGCCCGACAGCATCTTCGAGTCCCACCACATCA
GCTCCTTCACCCTGGAGTACCGCCGCGAGTGCACCCGCGACTCCGTGCTGCGCAGCCTGAC
CACCGTGAGCGGCGGCAGCTCCGAGGCCGGCCTGGTGTGCGACCACCTGCTGCAGCTGGAG
GGCGGCAGCGAGGTGCTGCGCGCCCGCACCGAGTGGCGCCCCAAGCTGACCGACTCCTTCC
GCGGCATCAGCGTGATCCCCGCCGAGCCCCGCGTG

*Fig. 16*

*AGCCTGAAGCGCCTG*CCCGACTGGTCCATGCTGTTCGCCGTGATCACCACCATCTTCTCCG
CCGCCGAGAAGCAGTGGACCAACCTGGAGTGGAAGCCCAAGCCCAACCCCCCCCAGCTGCT
GGACGACCACTTCGGCCCCCACGGCCTGGTGTTCCGCCGCACCTTCGCCATCCGCAGCTAC
GAGGTGGGCCCCGACCGCTCCACCAGCATCGTGGCCGTGATGAACCACCTGCAGGAGGCCG
CCCTGAACCACGCCAAGTCCGTGGGCATCCTGGGCGACGGCTTCGGCACCACCCTGGAGAT
GTCCAAGCGCGACCTGATCTGGGTGGTGAAGCGCACCCACGTGGCCGTGGAGCGCTACCCC
GCCTGGGGCGACACCGTGGAGGTGGAGTGCTGGGTGGGCGCCTCCGGCAACAACGGCCGCC
GCCACGACTTCCTGGTGCGCGACTGCAAGACCGGCGAGATCCTGACCCGCTGCACCTCCCT
GAGCGTGATGATGAACACCCGCACCCGCCGCCTGAGCAAGATCCCCGAGGAGGTGCGCGGC
GAGATCGGCCCCGCCTTCATCGACAACGTGGCCGTGAAGGACGAGGAGATCAAGAAGCCCC
AGAAGCTGAACGACTCCACCGCCGACTACATCCAGGGCGGCCTGACCCCCCGCTGGAACGA
CCTGGACATCAACCAGCACGTGAACAACATCAAGTACGTGGACTGGATCCTGGAGACCGTG
CCCGACAGCATCTTCGAGAGCCACCACATCTCCTCCTTCACCATCGAGTACCGCCGCGAGT
GCACCATGGACAGCGTGCTGCAGTCCCTGACCACCGTGAGCGGCGGCTCCTCCGAGGCCGG
CCTGGTGTGCGAGCACCTGCTGCAGCTGGAGGGCGGCAGCGAGGTGCTGCGCGCCAAGACC
GAGTGGCGCCCCAAGCTGACCGACTCCTTCCGCGGCATCAGCGTGATCCCCGCCGAGTCCA
GCGTG

*Fig. 18*

*AGCCTGAAGAAGCTG*CCCGACTGGTCCATGCTGTTCGCCGTGATCACCACCATCTTCTCCG
CCGCCGAGAAGCAGTGGACCAACCTGGAGTGGAAGCCCAAGCCCAACCCCCCCCAGCTGCT
GGACGACCACTTCGGCCCCCACGGCCTGGTGTTCCGCCGCACCTTCGCCATCCGCAGCTAC
GAGGTGGGCCCCGACCGCTCCACCAGCATCGTGGCCGTGATGAACCACCTGCAGGAGGCCG
CCCTGAACCACGCCAAGTCCGTGGGCATCCTGGGCGACGGCTTCGGCACCACCCTGGAGAT
GTCCAAGCGCGACCTGATCTGGGTGGTGAAGCGCACCCACGTGGCCGTGGAGCGCTACCCC
GCCTGGGGCGACACCGTGGAGGTGGAGTGCTGGGTGGGCGCCTCCGGCAACAACGGCCGCC
GCCACGACTTCCTGGTGCGCGACTGCAAGACCGGCGAGATCCTGACCCGCTGCACCTCCCT
GAGCGTGATGATGAACACCCGCACCCGCCGCCTGAGCAAGATCCCCGAGGAGGTGCGCGGC
GAGATCGGCCCCGCCTTCATCGACAACGTGGCCGTGAAGGACGAGGAGATCAAGAAGCCCC
AGAAGCTGAACGACTCCACCGCCGACTACATCCAGGGCGGCCTGACCCCCCGCTGGAACGA
CCTGGACATCAACCAGCACGTGAACAACATCAAGTACGTGGACTGGATCCTGGAGACCGTG
CCCGACAGCATCTTCGAGAGCCACCACATCTCCTCCTTCACCATCGAGTACCGCCGCGAGT
GCACCATGGACAGCGTGCTGCAGTCCCTGACCACCGTGAGCGGCGGCTCCTCCGAGGCCGG
CCTGGTGTGCGAGCACCTGCTGCAGCTGGAGGGCGGCAGCGAGGTGCTGCGCGCCAAGACC
GAGTGGCGCCCCAAGCTGACCGACTCCTTCCGCGGCATCAGCGTGATCCCCGCCGAGTCCA
GCGTG

*Fig. 19*

*GCGCACCCCAAGGCGAACGGCAGCGCGGTGTCGCTGAAGTCGGGCTCCCTGGAGACCCAGG*

*AGGACAAGACGAGCAGCTCGTCCCCCCCCCCCGCACGTTCATCAACCAGCTGCCCGTGTG*

*G*AGCATGCTGCTGTCGGCGGTGACCACGGTCTTCGGCGTGGCCGAGAAGCAGTGGCCCATG

CTGGACCGCAAGTCCAAGCGCCCCGACATGCTGGTCGAGCCCCTGGGCGTGGACCGCATCG

TCTACGACGGCGTGAGCTTCCGCCAGTCGTTCTCCATCCGCAGCTACGAGATCGGCGCCGA

CCGCACCGCCTCGATCGAGACGCTGATGAACATGTTCCAGGAGACCTCCCTGAACCACTGC

AAGATCATCGGCCTGCTGAACGACGGCTTCGGCCGCACGCCCGAGATGTGCAAGCGCGACC

TGATCTGGGTCGTGACCAAGATGCAGATCGAGGTGAACCGCTACCCCACGTGGGGCGACAC

CATCGAGGTCAACACGTGGGTGAGCGCCTCGGGCAAGCACGGCATGGGCCGCGACTGGCTG

ATCTCCGACTGCCACACCGGCGAGATCCTGATCCGCGCGACGAGCGTCTGGGCGATGATGA

ACCAGAAGACCCGCCGCCTGTCGAAGATCCCCTACGAGGTGCGCCAGGAGATCGAGCCCCA

GTTCGTCGACTCCGCCCCCGTGATCGTGGACGACCGCAAGTTCCACAAGCTGGACCTGAAG

ACGGGCGACAGCATCTGCAACGGCCTGACCCCCCGCTGGACGGACCTGGACGTGAACCAGC

ACGTCAACAACGTGAAGTACATCGGCTGGATCCTGCAGTCGGTCCCCACCGAGGTGTTCGA

GACGCAGGAGCTGTGCGGCCTGACCCTGGAGTACCGCCGCGAGTGCGGCCGCGACTCCGTG

CTGGAGAGCGTCACGGCCATGGACCCCTCGAAGGAGGGCGACCGCTCCCTGTACCAGCACC

TGCTGCGCCTGGAGGACGGCGCGGACATCGTGAAGGGCCGCACCGAGTGGCGCCCCAAGAA

CGCCGGCGCCAAGGGCGCCATCCTGACGGGCAAGACCAGCAACGGCAACTCGATCTCCTGA

*Fig. 21*

*GCGCACCCCAAGGCGAACGGCAGCGCGGTGTCGCTGAAGTCGGGCTCCCTGGAGACCCAGG*
*AGGACAAGACGAGCAGCTCGTCCCCCCCCCCCCGCACGTTCATCAACCAGCTGCCCGTGTG*
*G*AGCATGCTGCTGTCGGCGGTGACCACGGTCTTCGGCGTGGCCGAGAAGCAGTGGCCCATG
CTGGACCGCAAGTCCAAGCGCCCCGACATGCTGGTCGAGCCCCTGGGCGTGGACCGCATCG
TCTACGACGGCGTGAGCTTCCGCCAGTCGTTCTCCATCCGCAGCTACGAGATCGGCGCCGA
CCGCACCGCCTCGATCGAGACGCTGATGAACATGTTCCAGGAGACCTCCCTGAACCACTGC
AAGATCATCGGCCTGCTGAACGACGGCTTCGGCCGCACGCCCGAGATGTGCAAGCGCGACC
TGATCTGGGTCGTGACCAAGATGCAGATCGAGGTGAACCGCTACCCCACGTGGGGCGACAC
CATCGAGGTCAACACGTGGGTGAGCGCCTCGGGCAAGCACGGCATGGGCCGCGACTGGCTG
ATCTCCGACTGCCACACCGGCGAGATCCTGATCCGCGCGACGAGCGTCTGGGCGATGATGA
ACCAGAAGACCCGCCGCCTGTCGAAGATCCCCTACGAGGTGCGCCAGGAGATCGAGCCCCA
GTTCGTCGACTCCGCCCCCGTGATCGTGGACGACCGCAAGTTCCACAAGCTGGACCTGAAG
ACGGGCGACAGCATCTGCAACGGCCTGACCCCCCGCTGGACGGACCTGGACGTGAACCAGC
ACGTCAACAACGTGAAGTACATCGGCTGGATCCTGCAGTCGGTCCCCACCGAGGTGTTCGA
GACGCAGGAGCTGTGCGGCCTGACCCTGGAGTACCGCCGCGAGTGCGGCCGCGACTCCGTG
CTGGAGAGCGTCACGGCCATGGACCCCTCGAAGGAGGGCGACCGCTCCCTGTACCAGCACC
TGCTGCGCCTGGAGGACGGCGCGGACATCGTGAAGGGCCGCACCGAGTGGCGCCCCAAGAA
CGCCGGCGCCAAGGGCGCCATCCTGACGGGCAAGACCAGCAACGGCAACTCGATCTCCatg
gactacaaggaccacgacggcgactacaaggaccacgacatcgactacaaggacgacgacg
acaagtga

*Fig. 22*

*CCCCCCAAGCTGAACGGCTCCAACGTGGGCCTGGTGAAGTCCTCCCAGATCGTGAAGAAGG*

*GCGACGACACCACCTCCCCCCCCGCCCGCACCTTCATCAAC*CAGCTGCCCGACTGGAGCAT

GCTGCTGGCCGCGATCACCACCCTGTTCCTGGCGGCCGAGAAGCAGTGGATGATGCTGGAC

TGGAAGCCCAAGCGCCCCGACATGCTGGTGGACCCCTTCGGCCTGGGCCGCTTCGTGCAGG

ACGGCCTGGTGTTCCGCAACAACTTCAGCATCCGCAGCTACGAGATCGGCGCGGACCGCAC

CGCCAGCATCGAGACCCTGATGAACCACCTGCAGGAGACCGCCCTGAACCACGTGAAGAGT

GTGGGCCTGCTGGAGGACGGCCTGGGCAGCACCCGCGAGATGAGCCTGCGCAACCTGATCT

GGGTGGTGACCAAGATGCAGGTGGCGGTGGACCGCTACCCCACCTGGGGCGACGAGGTGCA

GGTGAGCAGCTGGGCGACCGCCATCGGCAAGAACGGCATGCGCCGCGAGTGGATCGTGACC

GACTTCCGCACCGGCGAGACCCTGCTGCGCGCCACCAGCGTGTGGGTGATGATGAACAAGC

TGACCCGCCGCATCAGCAAGATCCCCGAGGAGGTGTGGCACGAGATCGGCCCCAGCTTCAT

CGACGCGCCCCCCCTGCCCACCGTGGAGGACGACGGCCGCAAGCTGACCCGCTTCGACGAG

AGCAGCGCCGACTTCATCCGCAAGGGCCTGACCCCCCGCTGGAGCGACCTGGACATCAACC

AGCACGTGAACAACGTGAAGTACATCGGCTGGCTGCTGGAGAGCGCGCCCCCCGAGATCCA

CGAGAGCCACGAGATCGCCAGCCTGACCCTGGAGTACCGCCGCGAGTGCGGCCGCGACAGC

GTGCTGAACAGCGCCACCAAGGTGAGCGACAGCAGCCAGCTGGGCAAGAGCGCCGTGGAGT

GCAACCACCTGGTGCGCCTGCAGAACGGCGGCGAGATCGTGAAGGGCCGCACCGTGTGGCG

CCCCAAGCGCCCCCTGTACAACGACGGCGCCGTGGTGGACGTGCCCGCCAAGACCAGCTGA

*Fig. 24*

*CCCCCCAAGCTGAACGGCTCCAACGTGGGCCTGGTGAAGTCCTCCCAGATCGTGAAGAAGG*
*GCGACGACACCACCTCCCCCCCCGCCCGCACCTTCATCAAC*CAGCTGCCCGACTGGAGCAT
GCTGCTGGCCGCGATCACCACCCTGTTCCTGGCGGCCGAGAAGCAGTGGATGATGCTGGAC
TGGAAGCCCAAGCGCCCCGACATGCTGGTGGACCCCTTCGGCCTGGGCCGCTTCGTGCAGG
ACGGCCTGGTGTTCCGCAACAACTTCAGCATCCGCAGCTACGAGATCGGCGCGGACCGCAC
CGCCAGCATCGAGACCCTGATGAACCACCTGCAGGAGACCGCCCTGAACCACGTGAAGAGT
GTGGGCCTGCTGGAGGACGGCCTGGGCAGCACCCGCGAGATGAGCCTGCGCAACCTGATCT
GGGTGGTGACCAAGATGCAGGTGGCGGTGGACCGCTACCCCACCTGGGGCGACGAGGTGCA
GGTGAGCAGCTGGGCGACCGCCATCGGCAAGAACGGCATGCGCCGCGAGTGGATCGTGACC
GACTTCCGCACCGGCGAGACCCTGCTGCGCGCCACCAGCGTGTGGGTGATGATGAACAAGC
TGACCCGCCGCATCAGCAAGATCCCCGAGGAGGTGTGGCACGAGATCGGCCCCAGCTTCAT
CGACGCGCCCCCCCTGCCCACCGTGGAGGACGACGGCCGCAAGCTGACCCGCTTCGACGAG
AGCAGCGCCGACTTCATCCGCAAGGGCCTGACCCCCCGCTGGAGCGACCTGGACATCAACC
AGCACGTGAACAACGTGAAGTACATCGGCTGGCTGCTGGAGAGCGCGCCCCCCGAGATCCA
CGAGAGCCACGAGATCGCCAGCCTGACCCTGGAGTACCGCCGCGAGTGCGGCCGCGACAGC
GTGCTGAACAGCGCCACCAAGGTGAGCGACAGCAGCCAGCTGGGCAAGAGCGCCGTGGAGT
GCAACCACCTGGTGCGCCTGCAGAACGGCGGCGAGATCGTGAAGGGCCGCACCGTGTGGCG
CCCCAAGCGCCCCCTGTACAACGACGGCGCCGTGGTGGACGTGCCCGCCAAGACCAGCatg
gactacaaggaccacgacggcgactacaaggaccacgacatcgactacaaggacgacgacg
acaagtga

*Fig. 25*

ATGGCCACCGCATCCACTTTCTCGGCGTTCAATGCCCGCTGCGGCGACCTGCGTCGCTCGG
CGGGCTCCGGGCCCCGGCGCCCAGCGAGGCCCCTCCCCGTGCGCGGGCGCGCCCCCGACTG
GTCCATGCTGTTCGCCGTGATCACCACCATCTTCTCCGCCGCCGAGAAGCAGTGGACCAAC
CTGGAGTGGAAGCCCAAGCCCAACCCCCCCCAGCTGCTGGACGACCACTTCGGCCCCCACG
GCCTGGTGTTCCGCCGCACCTTCGCCATCCGCAGCTACGAGGTGGGCCCCGACCGCTCCAC
CAGCATCGTGGCCGTGATGAACCACCTGCAGGAGGCCGCCCTGAACCACGCCAAGTCCGTG
GGCATCCTGGGCGACGGCTTCGGCACCACCCTGGAGATGTCCAAGCGCGACCTGATCTGGG
TGGTGCGCCGCACCCACGTGGCCGTGGAGCGCTACCCCACCTGGGGCGACACCGTGGAGGT
GGAGTGCTGGATCGGCGCCAGCGGCAACAACGGCATGCGCCGCGACTTCCTGGTGCGCGAC
TGCAAGACCGGCGAGATCCTGACCCGCTGCACCTCCCTGAGCGTGCTGATGAACACCCGCA
CCCGCCGCCTGAGCACCATCCCCGACGAGGTGCGCGGCGAGATCGGCCCCGCCTTCATCGA
CAACGTGGCCGTGAAGGACGACGAGATCAAGAAGCTGCAGAAGCTGAACGACTCCACCGCC
GACTACATCCAGGGCGGCCTGACCCCCCGCTGGAACGACCTGGACGTGAACCAGCACGTGA
ACAACCTGAAGTACGTGGCCTGGGTGTTCGAGACCGTGCCCGACAGCATCTTCGAGTCCCA
CCACATCAGCTCCTTCACCCTGGAGTACCGCCGCGAGTGCACCCGCGACTCCGTGCTGCGC
AGCCTGACCACCGTGAGCGGCGGCAGCTCCGAGGCCGGCCTGGTGTGCGACCACCTGCTGC
AGCTGGAGGGCGGCAGCGAGGTGCTGCGCGCCCGCACCGAGTGGCGCCCCAAGCTGACCGA
CTCCTTCCGCGGCATCAGCGTGATCCCCGCCGAGCCCCGCGTG

*Fig. 27*

ATGGCCACCGCATCCACTTTCTCGGCGTTCAATGCCCGCTGCGGCGACCTGCGTCGCTCGG

CGGGCTCCGGGCCCCGGCGCCCAGCGAGGCCCCTCCCCGTGCGCGCTGCCATCGCCAGCGA

GGTCCCCGTGGCCACCACCTCCCCCCGG*agcctgaagcgcctg*CCCGACTGGTCCATGCTG

TTCGCCGTGATCACCACCATCTTCTCCGCCGCCGAGAAGCAGTGGACCAACCTGGAGTGGA

AGCCCAAGCCCAACCCCCCCCAGCTGCTGGACGACCACTTCGGCCCCCACGGCCTGGTGTT

CCGCCGCACCTTCGCCATCCGCAGCTACGAGGTGGGCCCCGACCGCTCCACCAGCATCGTG

GCCGTGATGAACCACCTGCAGGAGGCCGCCCTGAACCACGCCAAGTCCGTGGGCATCCTGG

GCGACGGCTTCGGCACCACCCTGGAGATGTCCAAGCGCGACCTGATCTGGGTGGTGCGCCG

CACCCACGTGGCCGTGGAGCGCTACCCCACCTGGGGCGACACCGTGGAGGTGGAGTGCTGG

ATCGGCGCCAGCGGCAACAACGGCATGCGCCGCGACTTCCTGGTGCGCGACTGCAAGACCG

GCGAGATCCTGACCCGCTGCACCTCCCTGAGCGTGCTGATGAACACCCGCACCCGCCGCCT

GAGCACCATCCCCGACGAGGTGCGCGGCGAGATCGGCCCCGCCTTCATCGACAACGTGGCC

GTGAAGGACGACGAGATCAAGAAGCTGCAGAAGCTGAACGACTCCACCGCCGACTACATCC

AGGGCGGCCTGACCCCCCGCTGGAACGACCTGGACGTGAACCAGCACGTGAACAACCTGAA

GTACGTGGCCTGGGTGTTCGAGACCGTGCCCGACAGCATCTTCGAGTCCCACCACATCAGC

TCCTTCACCCTGGAGTACCGCCGCGAGTGCACCCGCGACTCCGTGCTGCGCAGCCTGACCA

CCGTGAGCGGCGGCAGCTCCGAGGCCGGCCTGGTGTGCGACCACCTGCTGCAGCTGGAGGG

CGGCAGCGAGGTGCTGCGCGCCCGCACCGAGTGGCGCCCCAAGCTGACCGACTCCTTCCGC

GGCATCAGCGTGATCCCCGCCGAGCCCCGCGTG

*Fig. 28*

CpalFATB2 (C14) extended to AHPK -/+ FLAG Tag (psZ2479 and psZ2480)

UaFATB1 (C10-C16) extended to PPKL -/+ FLAG Tag (psZ2477 and psZ2478)

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgcc*CCCAAG*
*GCCAACGGCAGCGCCGTGAGCCTGAAGTCCGGCAGCCTGAACACCCTGGAGGACCCCCCCA*
*GCAGCCCCCCCCCCCGCACCTTCCTGAAC*CAGCTGCCCGACTGGAGCCGCCTGCTGACCGC
CATCACCACCGTGTTCGTGAAGTCCAAGCGCCCCGACATGCACGACCGCAAGTCCAAGCGC
CCCGACATGCTGGTGGACAGCTTCGGCCTGGAGTCCACCGTGCAGGACGGCCTGGTGTTCC
GCCAGTCCTTCTCCATCCGCTCCTACGAGATCGGCACCGACCGCACCGCCAGCATCGAGAC
CCTGATGAACCACCTGCAGGAGACCTCCCTGAACCACTGCAAGAGCACCGGCATCCTGCTG
GACGGCTTCGGCCGCACCCTGGAGATGTGCAAGCGCGACCTGATCTGGGTGGTGATTAAGA
TGCAGATCAAG*GTGAACCGCTACCCCACCTGGGGCGACACCGTGGAGATCAACAGCTGGTT*
*CAGCCAGAGCGGCAAGATCGGCATGGGCCGCGAGTGGCTGATCAGCGACTGCAACACCGGC*
*GAGATCCTGGTGCGCGCCACCAGCGCCTGGGCCATGATGAACCAGAAGACCCGCCGCTTCA*
*GCAAGCTGCCCTGCGAGGTGCGCCAGGAGATCGCCCCCCACTTCGTGGACGCCCCCCCCGT*
*GATCGAGGACAACGACCGCAAGCTGCACAAGTTCGACGTGAAGACCGGCGACAGCATCTGC*
*AAGGGCCTGACCCCCGGCTGGAACGACTTCGACGTGAACCAGCACGTGAGCAACGTGAAGT*
*ACATCGGCTGGATTCTGGAGAGCATGCCCACCGAGGTGCTGGAGACCCAGGAGCTGTGCAG*
*CCTGACCCTGGAGTACCGCCGCGAGTGCGGCCGCGAGAGCGTGGTGGAGAGCGTGACCAGC*
*ATGAACCCCAGCAAGGTGGGCGACCGCAGCCAGTACCAGCACCTGCTGCGCCTGGAGGACG*
*GCGCCGACATCATGAAGGGCCGCACCGAGTGGCGCCCCAAGAACGCCGGCACCAACCGCGC*
*CATCAGCACC*atggactacaaggaccacgacggcgactacaaggaccacgacatcgactac
aaggacgacgacgacaagtga

*Fig. 31*

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgcc*CCCAAG*
*GCCAACGGCAGCGCCGTGAGCCTGAAGTCCGGCAGCCTGAACACCCTGGAGGACCCCCCA*
*GCAGCCCCCCCCCCCGCACCTTCCTGAACCAGCTGCCCGACTGGAGCCGCCTGCGCACCGC*
*CATCACCACCGTGTTCGTGGCCGCCGAGAAGCAGTTCACCCGCCTGGACCGCAAGAGCAAG*
*CGCCCCGACATGCTGGTGGACTGGTTCGGCAGCGAGACCATCGTGCAGGACGGCCTGGTGT*
*TCCGCGAGCGCTTCAGCATCCGCAGCTACGAGATCGGCGCCGACCGCACCGCC*AGCATCGA
GACCCTGATGAACCACCTGCAGGAGACCTCCCTGAACCACTGCAAGAGCACCGGCATCCTG
CTGGACGGCTTCGGCCGCACCCTGGAGATGTGCAAGCGCGACCTGATCTGGGTGGTGATTA
AGATGCAGATCAAG*GTGAACCGCTACCCCACCTGGGGCGACACCGTGGAGATCAACAGCTG*
*GTTCAGCCAGAGCGGCAAGATCGGCATGGGCCGCGAGTGGCTGATCAGCGACTGCAACACC*
*GGCGAGATCCTGGTGCGCGCCACCAGCGCCTGGGCCATGATGAACCAGAAGACCCGCCGCT*
*TCAGCAAGCTGCCCTGCGAGGTGCGCCAGGAGATCGCCCCCCACTTCGTGGACGCCCCCCC*
*CGTGATCGAGGACAACGACCGCAAGCTGCACAAGTTCGACGTGAAGACCGGCGACAGCATC*
*TGCAAGGGCCTGACCCCCGGCTGGAACGACTTCGACGTGAACCAGCACGTGAGCAACGTGA*
*AGTACATCGGCTGGATTCTGGAGAGCATGCCCACCGAGGTGCTGGAGACCCAGGAGCTGTG*
*CAGCCTGACCCTGGAGTACCGCCGCGAGTGCGGCCGCGAGAGCGTGGTGGAGAGCGTGACC*
*AGCATGAACCCCAGCAAGGTGGGCGACCGCAGCCAGTACCAGCACCTGCTGCGCCTGGAGG*
*ACGGCGCCGACATCATGAAGGGCCGCACCGAGTGGCGCCCCAAGAACGCCGGCACCAACCG*
*CGCCATCAGCACC*atggactacaaggaccacgacggcgactacaaggaccacgacatcgac
tacaaggacgacgacgacaagtga

*Fig. 32*

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgcc*CCCAAG*
*GCCAACGGCAGCGCCGTGAGCCTGAAGTCCGGCAGCCTGAACACCCTGGAGGACCCCCCA*
*GCAGCCCCCCCCCCCGCACCTTCCTGAAC*CAGCTGCCCGACTGGAGCCGCCTGCTGACCGC
CATCACCACCGTGTTCGTGAAGTCCAAGCGCCCCGACATGCACGACCGCAAGTCCAAGCGC
CCCGACATGCTGGTGGACAGCTTCGGCCTGGAGTCCACCGTGCAGGACGGCCTGGTGTTCC
GCCAGTCCTTCTCCATCCGCTCCTACGAGATCGGCACCGACCGCACCGCC*AGCATCGAGAC*
*CCTGATGAACCACCTGCAGGACACCAGCCTGAACCACTGCAAGAGCGTGGGCCTGCTGAAC*
*GACGGCTTCGGCCGCACCCCCGAGATGTGCACCCGCGACCTGATCTGGGTGCTGACCAAGA*
*TGCAGATCGTGGTGAACCGCTACCCCACCTGGGGCGACACCGTGGAGATCAACAGCTGGTT*
*CAGCCAGAGCGGCAAGATCGGCATGGGCCGCGAGTGGCTGATCAGCGACTGCAACACCGGC*
*GAGATCCTGGTGCGCGCCACCAGCGCCTGGGCCATGATGAACCAGAAGACCCGCCGCTTCA*
*GCAAGCTGCCCTGCGAGGTGCGCCAGGAGATCGCCCCCCACTTCGTGGACGCCCCCCCCGT*
*GATCGAGGACAACGACCGCAAGCTGCACAAGTTCGACGTGAAGACCGGCGACAGCATCTGC*
*AAGGGCCTGACCCCCGGCTGGAACGACTTCGACGTGAACCAGCACGTGAGCAACGTGAAGT*
*ACATCGGCTGGATTCTGGAGAGCATGCCCACCGAGGTGCTGGAGACCCAGGAGCTGTGCAG*
*CCTGACCCTGGAGTACCGCCGCGAGTGCGGCCGCGAGAGCGTGGTGGAGAGCGTGACCAGC*
*ATGAACCCCAGCAAGGTGGGCGACCGCAGCCAGTACCAGCACCTGCTGCGCCTGGAGGACG*
*GCGCCGACATCATGAAGGGCCGCACCGAGTGGCGCCCCAAGAACGCCGGCACCAACCGCGC*
*CATCAGCACC*atggactacaaggaccacgacggcgactacaaggaccacgacatcgactac
aaggacgacgacgacaagtga

Fig. 33

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgccCCCAAG
GCCAACGGCTCCGCCGTGAGCCTGAAGAGCGGCAGCCTGAACACCCAGGAGGACACCTCCT
CCAGCCCCCCCCCCCGCACCTTCCTGCACCAGCTGCCCGACTGGAGCCGCCTGCTGACCGC
CATCACCACCGTGTTCGTGAAGTCCAAGCGCCCCGACATGCACGACCGCAAGTCCAAGCGC
CCCGACATGCTGGTGGACAGCTTCGGCCTGGAGTCCACCGTGCAGGACGGCCTGGTGTTCC
GCCAGTCCTTCTCCATCCGCTCCTACGAGATCGGCACCGACCGCACCGCCAGCATCGAGAC
CCTGATGAACCACCTGCAGGAGACCTCCCTGAACCACTGCAAGAGCACCGGCATCCTGCTG
GACGGCTTCGGCCGCACCCTGGAGATGTGCAAGCGCGACCTGATCTGGGTGGTGATTAAGA
TGCAGATCAAG*GTGAACCGCTACCCCACCTGGGGCGACACCGTGGAGATCAACAGCTGGTT*
*CAGCCAGAGCGGCAAGATCGGCATGGCCGCGAGTGGCTGATCAGCGACTGCAACACCGGC*
*GAGATCCTGGTGCGCGCCACCAGCGCCTGGGCCATGATGAACCAGAAGACCCGCCGCTTCA*
*GCAAGCTGCCCTGCGAGGTGCGCCAGGAGATCGCCCCCCACTTCGTGGACGCCCCCCCCGT*
*GATCGAGGACAACGACCGCAAGCTGCACAAGTTCGACGTGAAGACCGGCGACAGCATCTGC*
*AAGGGCCTGACCCCCGGCTGGAACGACTTCGACGTGAACCAGCACGTGAGCAACGTGAAGT*
*ACATCGGCTGGATTCTGGAGAGCATGCCCACCGAGGTGCTGGAGACCCAGGAGCTGTGCAG*
*CCTGACCCTGGAGTACCGCCGCGAGTGCGGCCGCGAGAGCGTGGTGGAGAGCGTGACCAGC*
*ATGAACCCCAGCAAGGTGGGCGACCGCAGCCAGTACCAGCACCTGCTGCGCCTGGAGGACG*
*GCGCCGACATCATGAAGGGCCGCACCGAGTGGCGCCCCAAGAACGCCGGCACCAACCGCGC*
*CATCAGCACC*atggactacaaggaccacgacggcgactacaaggaccacgacatcgactac
aaggacgacgacgacaagtga

*Fig. 34*

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgccCCCAAG
GCCAACGGCTCCGCCGTGAGCCTGAAGAGCGGCAGCCTGAACACCCAGGAGGACACCTCCT
CCAGCCCCCCCCCCCGCACCTTCCTGCACCAGCTGCCCGACTGGAGCCGCCTGCTGACCGC
CATCACCACCGTGTTCGTGAAGTCCAAGCGCCCCGACATGCACGACCGCAAGTCCAAGCGC
CCCGACATGCTGGTGGACAGCTTCGGCCTGGAGTCCACCGTGCAGGACGGCCTGGTGTTCC
GCCAGTCCTTCTCCATCCGCTCCTACGAGATCGGCACCGACCGCACCGCCAGCATCGAGAC
CCTGATGAACCACCTGCAGGAGACCTCCCTGAACCACTGCAAGAGCACCGGCATCCTGCTG
GACGGCTTCGGCCGCACCCTGGAGATGTGCAAGCGCGACCTGATCTGGGTGGTGATCAAGA
TGCAGATCAAGGTGAACCGCTACCCCGCCTGGGGCGACACCGTGGAGATCAACACCCGCTT
CAGCCGCCTGGGCAAGATCGGCATGGGCCGCGACTGGCTGATCTCCGACTGCAACACCGGC
GAGATCCTGGTGCGCGCCACCAGCGCCTACGCCATGATGAACCAGAAGACCCGCCGCCTGT
CCAAGCTGCCCTACGAGGTGCACCAGGAGATCGTGCCCCTGTTCGTGGACAGCCCCGTGAT
CGAGGACTCCGACCTGAAGGTGCACAAGTTCAAGGTGAAGACCGGCGACAGCATCCAGAAG
GGCCTGACCCCCGGCTGGAACGACCTGGACGTGAACCAGCACGTGTCCAACGTGAAGTACA
TCGGCTGGATCCTGGAGAGCATGCCCACCGAGGTGCTGGAGACCCAGGAGCTGTGCTCCCT
GGCCCTGGAGTACCGCCGCGAGTGCGGCCGCGACTCCGTGCTGGAGAGCGTGACCGCCATG
GACCCCAGCAAGGTGGGCGTGCGCTCCCAGTACCAGCACCTGCTGCGCCTGGAGGACGGCA
CCGCCATCGTGAACGGCGCCACCGAGTGGCGCCCCAAGAACGCCGGCGCCAACGGCGCCAT
CTCCACCGGCAAGACCAGCAACGGCAACTCCGTGTCCatggactacaaggaccacgacggc
gactacaaggaccacgacatcgactacaaggacgacgacgacaagtga

*Fig. 35*

ATGGTGGTGGCCGCCGCCGCCAGCAGCGCCTTCTTCCCCGTGCCCGCCCCCCGCCCCACCC
CCAAGCCCGGCAAGTTCGGCAACTGGCCCAGCAGCCTGAGCCAGCCCTTCAAGCCCAAGAG
CAACCCCAACGGCCGCTTCCAGGTGAAGGCCAACGTGAGCCCCCACgggcgcgcc*CCCAAG*
*GCCAACGGCAGCGCCGTGAGCCTGAAGTCCGGCAGCCTGAACACCCTGGAGGACCCCCCCA*
*GCAGCCCCCCCCCCCGCACCTTCCTGAACCAGCTGCCCGACTGGAGCCGCCTGCGCACCGC*
*CATCACCACCGTGTTCGTGGCCGCCGAGAAGCAGTTCACCCGCCTGGACCGCAAGAGCAAG*
*CGCCCCGACATGCTGGTGGACTGGTTCGGCAGCGAGACCATCGTGCAGGACGGCCTGGTGT*
*TCCGCGAGCGCTTCAGCATCCGCAGCTACGAGATCGGCGCCGACCGCACCGCCAGCATCGA*
*GACCCTGATGAACCACCTGCAGGACACCAGCCTGAACCACTGCAAGAGCGTGGGCCTGCTG*
*AACGACGGCTTCGGCCGCACCCCCGAGATGTGCACCCGCGACCTGATCTGGGTGCTGACCA*
*AGATGCAGATCGTGGTGAACCGCTACCCCACCTGGGGCGACACCGTGGAGATCAACAGCTG*
*GTTCAGCCAGAGCGGCAAGATCGGCATGGGCCGCGAGTGGCTGATCAGCGACTGCAACACC*
*GGCGAGATCCTGGTGCGCGCCACCAGCGCCTGGGCCATGATGAACCAGAAGACCCGCCGCT*
*TCAGCAAGCTGCCCTGCGAGGTGCGCCAGGAGATCGCCCCCCACTTCGTGGACGCCCCCCC*
*CGTGATCGAGGACAACGACCGCAAGCTGCACAAGTTCGACGTGAAGACCGGCGACAGCATC*
*TGCAAGGGCCTGACCCCCGGCTGGAACGACTTCGACGTGAACCAGCACGTGAGCAACGTGA*
*AGTACATCGGCTGGATTCTGGAGAGCATGCCCACCGAGGTGCTGGAGACCCAGGAGCTGTG*
*CAGCCTGACCCTGGAGTACCGCCGCGAGTGCGGCCGCGAGAGCGTGGTGGAGAGCGTGACC*
*AGCATGAACCCCAGCAAGGTGGGCGACCGCAGCCAGTACCAGCACCTGCTGCGCCTGGAGG*
*ACGGCGCCGACATCATGAAGGGCCGCACCGAGTGGCGCCCCAAGAACGCCGGCACCAACCG*
*CGCCATCAGCACC*gactacaaggacgacgacgacaagtga

*Fig. 36*

FA profiles from day3 lipid; matched Western samples

| Sample ID | C8:0 | C10:0 | C12:0 | C14:0 |
|---|---|---|---|---|
| Strain C pH7 | 0.00 | 0.01 | 0.00 | 1.30 |
| Strain C ; T467, D1558-6 | 0.00 | 0.07 | 0.32 | 1.71 |
| Strain C ; T467, D1558-8 | 0.00 | 0.20 | 0.99 | 2.61 |
| Strain C ; T467, D1558-10 | 0.00 | 0.13 | 0.64 | 2.18 |
| Strain C ; T467, D1558-11 | 0.00 | 0.06 | 0.28 | 1.67 |
| Strain C ; T467, D1558-12 | 0.00 | 0.08 | 0.31 | 1.70 |
| Strain C ; T467, D1559-2 (D1559 ChimeraB) | 0.00 | 2.59 | 5.33 | 8.62 |
| Strain C T467, D1559-4 (D1559 ChimeraB) | 0.00 | 0.93 | 2.13 | 4.72 |
| Strain C T467, D1559-8 (D1559 ChimeraB) | 0.00 | 0.93 | 2.09 | 4.68 |
| Strain C T467, D1559-9 (D1559 ChimeraB) | 0.00 | 1.25 | 2.97 | 5.27 |
| Strain C ; T467, D1559-10 (D1559 ChimeraB) | 0.00 | 3.07 | 5.83 | 8.89 |
| Strain C ; T467, D1560-1 | 0.00 | 0.26 | 2.88 | 3.51 |
| Strain C ; T467, D1560-2 | 0.00 | 0.11 | 0.92 | 1.99 |
| Strain C ; T467, D1560-7 | 0.00 | 0.23 | 2.23 | 2.89 |
| Strain C ; T467, D1560-8 | 0.00 | 0.04 | 0.37 | 1.61 |
| Strain C ; T467, D1560-17 | 0.00 | 0.89 | 8.21 | 6.49 |
| Strain C ; T467, D1561-1 | 0.00 | 0.11 | 0.57 | 2.26 |
| Strain C ; T467, D1561-5 | 0.00 | 0.18 | 1.03 | 2.90 |
| Strain C ; T467, D1561-6 | 0.00 | 0.15 | 0.67 | 2.14 |
| Strain C ; T467, D1561-9 | 0.00 | 0.15 | 0.83 | 2.52 |
| Strain C ; T467, D1561-13 | 0.00 | 0.18 | 0.78 | 2.24 |
| Strain C ; T467, D1562-1 | 1.90 | 11.29 | 0.28 | 1.52 |
| Strain C ; T467, D1562-7 | 11.94 | 25.41 | 0.45 | 1.18 |
| Strain C ; T467, D1562-10 | 2.06 | 9.87 | 0.20 | 1.18 |
| Strain C ; T467, D1562-12 | 2.60 | 10.33 | 0.23 | 1.77 |
| Strain C ; T467, D1562-16 | 1.66 | 9.11 | 0.20 | 1.37 |
| D447-13 - Strain G | 4.48 | 14.88 | 0.28 | 1.24 |
| D447-34 - Strain H | 1.67 | 12.51 | 0.43 | 1.86 |
| D965.60 - Strain J | 0.01 | 3.27 | 21.92 | 12.86 |
| D965.70 - Strain I | 0.02 | 3.21 | 19.69 | 11.42 |

*Fig. 39B*

| | | | | | | | | | | | | | | | | | | | | | | | | |
|---|---|---|---|---|---|---|---|---|---|---|---|---|---|---|---|---|---|---|---|---|---|---|---|---|
| D3042 | S | I | E | T | L | M | N | H | L | Q | E | T | S | L | N | H | C | K | S | T | G | I | L | L | D G F G R T T L E M C K R D L I |
| D1058 | S | I | L | A | V | M | N | H | L | Q | E | A | T | L | N | H | A | K | S | V | G | I | L | G | D G F G T T L E M S K R D L M |
| D1432 | S | I | V | A | V | M | N | H | L | Q | E | A | A | L | N | H | A | K | S | V | G | I | L | G | D G F G T T L E M S K R D L I |
| D1777 | S | I | V | A | V | M | N | H | L | Q | E | A | A | L | N | H | A | K | S | V | G | I | L | G | D G F G T T L E M S K R D L I |

Homology model of *Uc* FATB2 threaded onto 2OWN
(Putative oleoyl thioesterase from Lactobacillus plantarum)

B

Homology model of *Uc* FATB2 threaded onto 2OWN
(Putative oleoyl thioesterase from Lactobacillus plantarum)

Homology model of *Uc* FATB2 threaded onto 2OWN
(Putative oleoyl thioesterase from Lactobacillus plantarum)

Homology model of *Uc* FATB2 threaded onto 2OWN
(Putative oleoyl thioesterase from Lactobacillus plantarum)

Homology model of *Uc* FATB2 threaded onto 2OWN
(Putative oleoyl thioesterase from Lactobacillus plantarum)

Homology model of *Uc* FATB2 threaded onto 2OWN
(Putative oleoyl thioesterase from Lactobacillus plantarum)

Homology model of *Uc* FATB2 threaded onto 2OWN
(Putative oleoyl thioesterase from Lactobacillus plantarum)

matastfsafnarcgdlrrsagsgprrparplpvrgraSSLSPSFKPKSIPNGGFQVKAND
SAHPKANGSAVSLKSGSLNTQEDTSSSPPPRTFLHQLPDWSRLLTAITTVFVKSKRPDMHD
RKSKRPDMLVDSFGLESTVQDGLVFRQSFSIRSYEIGTDRTASIETLMNHLQETSLNHCKS
TGILLDGFGRTLEMCKRDLIWVVIKMQIKVNRYPAWGDTVEINTRFSRLGKIGMGRDWLIS
DCNTGEILVRATSAYAMMNQKTRRLSKLPYEVHQEIVPLFVDSPVIEDSDLKVHKFKVKTG
DSIQKGLTPGWNDLDVNQHVSNVKYIGWILESMPTEVLETQELCSLALEYRRECGRDSVLE
SVTAMDPSKVGVRSQYQHLLRLEDGTAIVNGATEWRPKNAGANGAISTGKTSNGNSVSMDY
KDHDGDYKDHDIDYKDDDDK

*Fig. 49*

SEQUENCE LISTING

<160> NUMBER OF SEQ ID NOS: 246

<210> SEQ ID NO 1
<211> LENGTH: 6666
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggtgt atgaattgta cagaacaacc acgagccttg tctaggcaga 360
atccctacca gtcatggctt tacctggatg acggcctgcg aacagctgtc cagcgaccct 420

```
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaacgg cgcgccatgc tgctgcaggc cttcctgttc ctgctggccg   1080
gcttcgccgc caagatcagc gcctccatga cgaacgagac gtccgaccgc cccctggtgc   1140
acttcacccc caacaagggc tggatgaacg accccaacgg cctgtggtac gacgagaagg   1200
acgccaagtg gcacctgtac ttccagtaca acccgaacga caccgtctgg gggacgccct   1260
tgttctgggg ccacgccacg tccgacgacc tgaccaactg ggaggaccag cccatcgcca   1320
tcgccccgaa gcgcaacgac tccggcgcct tctccggctc catggtggtg gactacaaca   1380
acacctccgg cttcttcaac gacaccatcg acccgcgcca gcgctgcgtg gccatctgga   1440
cctacaacac cccggagtcc gaggagcagt acatctccta cagcctggac ggcggctaca   1500
ccttcaccga gtaccagaag aaccccgtgc tggccgccaa ctccacccag ttccgcgacc   1560
cgaaggtctt ctggtacgag ccctcccaga agtggatcat gaccgcggcc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtcccca   1740
ccgagcagga ccccagcaag tcctactggg tgatgttcat ctccatcaac cccggcgccc   1800
cggccggcgg ctccttcaac cagtacttcg tcggcagctt caacggcacc cacttcgagg   1860
ccttcgacaa ccagtcccgc gtggtggact tcggcaagga ctactacgcc ctgcagacct   1920
tcttcaacac cgacccgacc tacgggagcg ccctgggcat cgcgtgggcc tccaactggg   1980
agtactccgc cttcgtgccc accaacccct ggcgctcctc catgtccctc gtgcgcaagt   2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accacccaga cgatctccaa gtccgtgttc gcggacctct   2280
ccctctggtt caagggcctg gaggaccccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca accagccctt caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg ggctccgtga   2580
acatgacgac gggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
```

-continued

```
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg gaacacaaat ggaggatccc   3060
gcgtctcgaa cagagcgcgc agaggaacgc tgaaggtctc gcctctgtcg cacctcagcg   3120
cggcatacac cacaataacc acctgacgaa tgcgcttggt tcttcgtcca ttagcgaagc   3180
gtccggttca cacacgtgcc acgttggcga ggtggcaggt gacaatgatc ggtggagctg   3240
atggtcgaaa cgttcacagc ctagggatat cgaattcggc cgacaggacg cgcgtcaaag   3300
gtgctggtcg tgtatgccct ggccggcagg tcgttgctgc tgctggttag tgattccgca   3360
accctgattt tggcgtctta ttttggcgtg gcaaacgctg gcgcccgcga gccgggccgg   3420
cggcgatgcg gtgccccacg gctgccggaa tccaagggag gcaagagcgc ccgggtcagt   3480
tgaagggctt tacgcgcaag gtacagccgc tcctgcaagg ctgcgtggtg gaattggacg   3540
tgcaggtcct gctgaagttc ctccaccgcc tcaccagcgg acaaagcacc ggtgtatcag   3600
gtccgtgtca tccactctaa agagctcgac tacgacctac tgatggccct agattcttca   3660
tcaaaaacgc ctgagacact tgcccaggat tgaaactccc tgaagggacc accaggggcc   3720
ctgagttgtt ccttcccccc gtggcgagct gccagccagg ctgtacctgt gatcgaggct   3780
ggcgggaaaa taggcttcgt gtgctcaggt catgggaggt gcaggacagc tcatgaaacg   3840
ccaacaatcg cacaattcat gtcaagctaa tcagctattt cctcttcacg agctgtaatt   3900
gtcccaaaat tctggtctac cgggggtgat ccttcgtgta cgggcccttc cctcaaccct   3960
aggtatgcgc gcatgcggtc gccgcgcaac tcgcgcgagg gccgagggtt tgggacgggc   4020
cgtcccgaaa tgcagttgca cccggatgcg tggcaccttt tttgcgataa tttatgcaat   4080
ggactgctct gcaaaattct ggctctgtcg ccaaccctag gatcagcggc gtaggatttc   4140
gtaatcattc gtcctgatgg ggagctaccg actaccctaa tatcagcccg actgcctgac   4200
gccagcgtcc acttttgtgc acacattcca ttcgtgccca agacatttca ttgtggtgcg   4260
aagcgtcccc agttacgctc acctgtttcc cgacctcctt actgttctgt cgacagagcg   4320
ggcccacagg ccggtcgcag ccactagtaa caatggccac cgcatccact ttctcggcgt   4380
tcaatgcccg ctgcggcgac ctgcgtcgct cggcgggctc cgggccccgg cgcccagcga   4440
ggcccctccc cgtgcgcggg cgcgccccg actggtccat gctgttcgcc gtgatcacca    4500
ccatcttctc cgccgccgag aagcagtgga ccaacctgga gtggaagccc aagcccaacc   4560
ccccccagct gctggacgac cacttcggcc cccacggcct ggtgttccgc cgcaccttcg   4620
ccatccgcag ctacgaggtg ggccccgacc gctccaccag catcgtggcc gtgatgaacc   4680
acctgcagga ggccgccctg aaccacgcca agtccgtggg catcctgggc gacggcttcg   4740
gcaccaccct ggagatgtcc aagcgcgacc tgatctgggt ggtgaagcgc acccacgtgg   4800
ccgtggagcg ctaccccgcc tggggcgaca ccgtggaggt ggagtgctgg atcggcgcca   4860
gcggcaacaa cggcatgcgc cgcgacttcc tggtgcgcga ctgcaagacc ggcgagatcc   4920
tgacccgctg cacctccctg agcgtgctga tgaacacccg cacccgccgc ctgagcacca   4980
tccccgacga ggtgcgcggc gagatcggcc ccgccttcat cgacaacgtg gccgtgaagg   5040
acgacgagat caagaagctg cagaagctga acgactccac cgccgactac atccagggcg   5100
gcctgacccc ccgctggaac gacctggacg tgaaccagca cgtgaacaac ctgaagtacg   5160
```

tggcctgggt gttcgagacc gtgcccgaca gcatcttcga gtcccaccac atcagctcct 5220
tcaccctgga gtaccgccgc gagtgcaccc gcgactccgt gctgcgcagc ctgaccaccg 5280
tgagcggcgg cagctccgag gccggcctgg tgtgcgacca cctgctgcag ctggagggcg 5340
gcagcgaggt gctgcgcgcc cgcaccgagt ggcgccccaa gctgaccgac tccttccgcg 5400
gcatcagcgt gatccccgcc gagccccgcg tgatggacta caaggaccac gacggcgact 5460
acaaggacca cgacatcgac tacaaggacg acgacgacaa gtgactcgag gcagcagcag 5520
ctcggatagt atcgacacac tctggacgct ggtcgtgtga tggactgttg ccgccacact 5580
tgctgccttg acctgtgaat atccctgccg cttttatcaa acagcctcag tgtgtttgat 5640
cttgtgtgta cgcgcttttg cgagttgcta gctgcttgtg ctatttgcga ataccacccc 5700
cagcatcccc ttccctcgtt tcatatcgct tgcatcccaa ccgcaactta tctacgctgt 5760
cctgctatcc ctcagcgctg ctcctgctcc tgctcactgc ccctcgcaca gccttggttt 5820
gggctccgcc tgtattctcc tggtactgca acctgtaaac cagcactgca atgctgatgc 5880
acgggaagta gtgggatggg aacacaaatg gaaagcttga gctcttgttt tccagaagga 5940
gttgctcctt gagcctttca ttctcagcct cgataacctc caaagccgct ctaattgtgg 6000
agggggttcg aatttaaaag cttggaatgt tggttcgtgc gtctggaaca agcccagact 6060
tgttgctcac tgggaaaagg accatcagct ccaaaaaact tgccgctcaa accgcgtacc 6120
tctgctttcg cgcaatctgc cctgttgaaa tcgccaccac attcatattg tgacgcttga 6180
gcagtctgta attgcctcag aatgtggaat catctgcccc ctgtgcgagc ccatgccagg 6240
catgtcgcgg gcgaggacac ccgccactcg tacagcagac cattatgcta cctcacaata 6300
gttcataaca gtgaccatat ttctcgaagc tccccaacga gcacctccat gctctgagtg 6360
gccacccccc ggccctggtg cttgcggagg gcaggtcaac cggcatgggg ctaccgaaat 6420
ccccgaccgg atcccaccac ccccgcgatg ggaagaatct ctccccggga tgtgggccca 6480
ccaccagcac aacctgctgg cccaggcgag cgtcaaacca taccacacaa atatccttgg 6540
catcggccct gaattccttc tgccgctctg ctacccggtg cttctgtccg aagcaggggt 6600
tgctagggat cgctccgagt ccgcaaaccc ttgtcgcgtg gcggggcttg ttcgagcttg 6660
aagagc 6666

<210> SEQ ID NO 2
<211> LENGTH: 1080
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
atggccaccg catccacttt ctcggcgttc aatgcccgct gcggcgacct gcgtcgctcg 60
gcgggctccg ggccccggcg cccagcgagg cccctccccg tgcgcgggcg cgccccccgac 120 tggtccatgc tgttcgccgt gatcaccacc atcttctccg ccgccgagaa gcagtggacc 180
aacctggagt ggaagcccaa gcccaacccc ccccagctgc tggacgacca cttcggcccc 240
cacggcctgg tgttccgccg caccttcgcc atccgcagct acgaggtggg ccccgaccgc 300
tccaccagca tcgtggccgt gatgaaccac ctgcaggagg ccgccctgaa ccacgccaag 360
tccgtgggca tcctgggcga cggcttcggc accaccctgg agatgtccaa gcgcgacctg 420
atctgggtgg tgaagcgcac ccacgtggcc gtggagcgct accccgcctg gggcgacacc 480

```
gtggaggtgg agtgctggat cggcgccagc ggcaacaacg gcatgcgccg cgacttcctg    540

gtgcgcgact gcaagaccgg cgagatcctg acccgctgca cctccctgag cgtgctgatg    600

aacacccgca cccgccgcct gagcaccatc cccgacgagg tgcgcggcga gatcggcccc    660

gccttcatcg acaacgtggc cgtgaaggac gacgagatca agaagctgca gaagctgaac    720

gactccaccg ccgactacat ccagggcggc ctgacccccc gctggaacga cctggacgtg    780

aaccagcacg tgaacaacct gaagtacgtg gcctgggtgt tcgagaccgt gcccgacagc    840

atcttcgagt cccaccacat cagctccttc accctggagt accgccgcga gtgcacccgc    900

gactccgtgc tgcgcagcct gaccaccgtg agcggcggca gctccgaggc cggcctggtg    960

tgcgaccacc tgctgcagct ggagggcggc agcgaggtgc tgcgcgcccg caccgagtgg   1020

cgccccaagc tgaccgactc cttccgcggc atcagcgtga tccccgccga gccccgcgtg   1080


<210> SEQ ID NO 3
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Pro Asp Trp Ser Met Leu Phe Ala Val Ile
        35                  40                  45

Thr Thr Ile Phe Ser Ala Ala Glu Lys Gln Trp Thr Asn Leu Glu Trp
    50                  55                  60

Lys Pro Lys Pro Asn Pro Pro Gln Leu Leu Asp Asp His Phe Gly Pro
65                  70                  75                  80

His Gly Leu Val Phe Arg Arg Thr Phe Ala Ile Arg Ser Tyr Glu Val
                85                  90                  95

Gly Pro Asp Arg Ser Thr Ser Ile Val Ala Val Met Asn His Leu Gln
            100                 105                 110

Glu Ala Ala Leu Asn His Ala Lys Ser Val Gly Ile Leu Gly Asp Gly
        115                 120                 125

Phe Gly Thr Thr Leu Glu Met Ser Lys Arg Asp Leu Ile Trp Val Val
    130                 135                 140

Lys Arg Thr His Val Ala Val Glu Arg Tyr Pro Ala Trp Gly Asp Thr
145                 150                 155                 160

Val Glu Val Glu Cys Trp Ile Gly Ala Ser Gly Asn Asn Gly Met Arg
                165                 170                 175

Arg Asp Phe Leu Val Arg Asp Cys Lys Thr Gly Glu Ile Leu Thr Arg
            180                 185                 190

Cys Thr Ser Leu Ser Val Leu Met Asn Thr Arg Thr Arg Arg Leu Ser
        195                 200                 205

Thr Ile Pro Asp Glu Val Arg Gly Glu Ile Gly Pro Ala Phe Ile Asp
    210                 215                 220

Asn Val Ala Val Lys Asp Asp Glu Ile Lys Lys Leu Gln Lys Leu Asn
225                 230                 235                 240

Asp Ser Thr Ala Asp Tyr Ile Gln Gly Gly Leu Thr Pro Arg Trp Asn
                245                 250                 255
```

```
Asp Leu Asp Val Asn Gln His Val Asn Asn Leu Lys Tyr Val Ala Trp
            260                 265                 270

Val Phe Glu Thr Val Pro Asp Ser Ile Phe Glu Ser His His Ile Ser
        275                 280                 285

Ser Phe Thr Leu Glu Tyr Arg Arg Glu Cys Thr Arg Asp Ser Val Leu
    290                 295                 300

Arg Ser Leu Thr Thr Val Ser Gly Gly Ser Ser Glu Ala Gly Leu Val
305                 310                 315                 320

Cys Asp His Leu Leu Gln Leu Glu Gly Gly Ser Glu Val Leu Arg Ala
                325                 330                 335

Arg Thr Glu Trp Arg Pro Lys Leu Thr Asp Ser Phe Arg Gly Ile Ser
            340                 345                 350

Val Ile Pro Ala Glu Pro Arg Val
        355                 360


<210> SEQ ID NO 4
<211> LENGTH: 966
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

cccgactggt ccatgctgtt cgccgtgatc accaccatct tctccgccgc cgagaagcag      60

tggaccaacc tggagtggaa gcccaagccc aacccccccc agctgctgga cgaccacttc     120

ggcccccacg gcctggtgtt ccgccgcacc ttcgccatcc gcagctacga ggtgggcccc     180

gaccgctcca ccagcatcgt ggccgtgatg aaccacctgc aggaggccgc cctgaaccac     240

gccaagtccg tgggcatcct gggcgacggc ttcggcacca ccctggagat gtccaagcgc     300

gacctgatct gggtggtgaa gcgcacccac gtggccgtgg agcgctaccc cgcctggggc     360

gacaccgtgg aggtggagtg ctggatcggc gccagcggca acaacggcat gcgccgcgac     420

ttcctggtgc gcgactgcaa gaccggcgag atcctgaccc gctgcacctc cctgagcgtg     480

ctgatgaaca cccgcacccg ccgcctgagc accatccccg acgaggtgcg cggcgagatc     540

ggccccgcct tcatcgacaa cgtggccgtg aaggacgacg agatcaagaa gctgcagaag     600

ctgaacgact ccaccgccga ctacatccag ggcggcctga ccccccgctg gaacgacctg     660

gacgtgaacc agcacgtgaa caacctgaag tacgtggcct gggtgttcga gaccgtgccc     720

gacagcatct tcgagtccca ccacatcagc tccttcaccc tggagtaccg ccgcgagtgc     780

acccgcgact ccgtgctgcg cagcctgacc accgtgagcg gcggcagctc cgaggccggc     840

ctggtgtgcg accacctgct gcagctggag ggcggcagcg aggtgctgcg cgcccgcacc     900

gagtggcgcc ccaagctgac cgactccttc cgcggcatca gcgtgatccc cgccgagccc     960

cgcgtg                                                                966


<210> SEQ ID NO 5
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Asp Trp Ser Met Leu Phe Ala Val Ile Thr Thr Ile Phe Ser Ala
```

-continued

```
1               5                   10                  15

Ala Glu Lys Gln Trp Thr Asn Leu Glu Trp Lys Pro Lys Pro Asn Pro
            20                  25                  30

Pro Gln Leu Leu Asp Asp His Phe Gly Pro His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Val Ala Val Met Asn His Leu Gln Glu Ala Ala Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Ile Trp Val Val Lys Arg Thr His Val Ala
            100                 105                 110

Val Glu Arg Tyr Pro Ala Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

<210> SEQ ID NO 6
<211> LENGTH: 966
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
cccgactggt ccatgctgtt cgccgtgatc accaccatct tcagcgccgc cgagaagcag     60

tggaccaacc tggagtggaa gcccaagccc aagctgcccc agctgctgga cgaccacttc    120

ggcctgcacg gcctggtgtt ccgccgcacc ttcgccatcc gctcctacga ggtgggcccc    180

gaccgcagca cctccatcct ggccgtgatg aaccacatgc aggaggccac cctgaaccac    240
```

gccaagagcg tgggcatcct gggcgacggc ttcggcacca ccctggagat gtccaagcgc 300
gacctgatgt gggtggtgcg ccgcacccac gtggccgtgg agcgctaccc cacctggggc 360
gacaccgtgg aggtggagtg ctgggtgggc gcctccggca acaacggccg ccgccacgac 420
ttcctggtgc gcgactgcaa gaccggcgag atcctgaccc gctgcacctc cctgagcgtg 480
atgatgaaca cccgcacccg ccgcctgagc aagatccccg aggaggtgcg cggcgagatc 540
ggccccgcct tcatcgacaa cgtggccgtg aaggacgagg agatcaagaa gccccagaag 600
ctgaacgact ccaccgccga ctacatccag ggcggcctga ccccccgctg gaacgacctg 660
gacatcaacc agcacgtgaa caacatcaag tacgtggact ggatcctgga gaccgtgccc 720
gacagcatct tcgagagcca ccacatctcc tccttcacca tcgagtaccg ccgcgagtgc 780
accatggaca gcgtgctgca gtccctgacc accgtgagcg gcggctcctc cgaggccggc 840
ctggtgtgcg agcacctgct gcagctggag ggcggcagcg aggtgctgcg cgccaagacc 900
gagtggcgcc ccaagctgac cgactccttc cgcggcatca gcgtgatccc cgccgagtcc 960
agcgtg 966

<210> SEQ ID NO 7
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Lys Leu
            20                  25                  30

Pro Gln Leu Leu Asp Asp His Phe Gly Leu His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Leu Ala Val Met Asn His Met Gln Glu Ala Thr Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Met Trp Val Val Arg Arg Thr His Val Ala
            100                 105                 110

Val Glu Arg Tyr Pro Thr Trp Gly Asp Thr Val Glu Val Glu Cys Trp
        115                 120                 125

Val Gly Ala Ser Gly Asn Asn Gly Arg Arg His Asp Phe Leu Val Arg
    130                 135                 140

Asp Cys Lys Thr Gly Glu Ile Leu Thr Arg Cys Thr Ser Leu Ser Val
145                 150                 155                 160

Met Met Asn Thr Arg Thr Arg Arg Leu Ser Lys Ile Pro Glu Glu Val
                165                 170                 175

Arg Gly Glu Ile Gly Pro Ala Phe Ile Asp Asn Val Ala Val Lys Asp
            180                 185                 190

Glu Glu Ile Lys Lys Pro Gln Lys Leu Asn Asp Ser Thr Ala Asp Tyr
        195                 200                 205

Ile Gln Gly Gly Leu Thr Pro Arg Trp Asn Asp Leu Asp Ile Asn Gln
    210                 215                 220
```

His Val Asn Asn Ile Lys Tyr Val Asp Trp Ile Leu Glu Thr Val Pro
225 230 235 240

Asp Ser Ile Phe Glu Ser His His Ile Ser Ser Phe Thr Ile Glu Tyr
245 250 255

Arg Arg Glu Cys Thr Met Asp Ser Val Leu Gln Ser Leu Thr Thr Val
260 265 270

Ser Gly Gly Ser Ser Glu Ala Gly Leu Val Cys Glu His Leu Leu Gln
275 280 285

Leu Glu Gly Gly Ser Glu Val Leu Arg Ala Lys Thr Glu Trp Arg Pro
290 295 300

Lys Leu Thr Asp Ser Phe Arg Gly Ile Ser Val Ile Pro Ala Glu Ser
305 310 315 320

Ser Val

<210> SEQ ID NO 8
<211> LENGTH: 966
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
cccgactggt ccatgctgtt cgccgtgatc accaccatct tctccgccgc cgagaagcag 60
tggaccaacc tggagtggaa gcccaagccc aacccccccc agctgctgga cgaccacttc 120
ggcccccacg gcctggtgtt ccgccgcacc ttcgccatcc gcagctacga ggtgggcccc 180
gaccgctcca ccagcatcgt ggccgtgatg aaccacctgc aggaggccgc cctgaaccac 240
gccaagtccg tgggcatcct gggcgacggc ttcggcacca ccctggagat gtccaagcgc 300
gacctgatct gggtggtgcg ccgcacccac gtggccgtgg agcgctaccc cacctggggc 360
gacaccgtgg aggtggagtg ctggatcggc gccagcggca acaacggcat gcgccgcgac 420
ttcctggtgc gcgactgcaa gaccggcgag atcctgaccc gctgcacctc cctgagcgtg 480
ctgatgaaca cccgcacccg ccgcctgagc accatccccg acgaggtgcg cggcgagatc 540
ggccccgcct tcatcgacaa cgtggccgtg aaggacgacg agatcaagaa gctgcagaag 600
ctgaacgact ccaccgccga ctacatccag ggcggcctga ccccccgctg gaacgacctg 660
gacgtgaacc agcacgtgaa caacctgaag tacgtggcct gggtgttcga gaccgtgccc 720
gacagcatct tcgagtccca ccacatcagc tccttcaccc tggagtaccg ccgcgagtgc 780
acccgcgact ccgtgctgcg cagcctgacc accgtgagcg gcggcagctc cgaggccggc 840
ctggtgtgcg accacctgct gcagctggag ggcggcagcg aggtgctgcg cgcccgcacc 900
gagtggcgcc ccaagctgac cgactccttc cgcggcatca gcgtgatccc cgccgagccc 960
cgcgtg 966

<210> SEQ ID NO 9
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Pro Asp Trp Ser Met Leu Phe Ala Val Ile Thr Thr Ile Phe Ser Ala
1 5 10 15

```
Ala Glu Lys Gln Trp Thr Asn Leu Glu Trp Lys Pro Lys Pro Asn Pro
            20                  25                  30

Pro Gln Leu Leu Asp Asp His Phe Gly Pro His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Val Ala Val Met Asn His Leu Gln Glu Ala Ala Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Ile Trp Val Val Arg Arg Thr His Val Ala
            100                 105                 110

Val Glu Arg Tyr Pro Thr Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

<210> SEQ ID NO 10
<211> LENGTH: 966
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
cccgactggt ccatgctgtt cgccgtgatc accaccatct tctccgccgc cgagaagcag     60

tggaccaacc tggagtggaa gcccaagccc aacccccccc agctgctgga cgaccacttc    120

ggcccccacg gcctggtgtt ccgccgcacc ttcgccatcc gcagctacga ggtgggcccc    180

gaccgctcca cctccatcct ggccgtgatg aaccacatgc aggaggccac cctgaaccac    240
```

-continued gccaagagcg tgggcatcct gggcgacggc ttcggcacca ccctggagat gtccaagcgc 300
gacctgatgt gggtggtgcg ccgcacccac gtggccgtgg agcgctaccc cacctggggc 360
gacaccgtgg aggtggagtg ctggatcggc gccagcggca acaacggcat gcgccgcgac 420
ttcctggtgc gcgactgcaa gaccggcgag atcctgaccc gctgcacctc cctgagcgtg 480
ctgatgaaca cccgcacccg ccgcctgagc accatccccg acgaggtgcg cggcgagatc 540
ggccccgcct tcatcgacaa cgtggccgtg aaggacgacg agatcaagaa gctgcagaag 600
ctgaacgact ccaccgccga ctacatccag ggcggcctga ccccccgctg gaacgacctg 660
gacgtgaacc agcacgtgaa caacctgaag tacgtggcct gggtgttcga gaccgtgccc 720
gacagcatct tcgagtccca ccacatcagc tccttcaccc tggagtaccg ccgcgagtgc 780
acccgcgact ccgtgctgcg cagcctgacc accgtgagcg gcggcagctc cgaggccggc 840
ctggtgtgcg accacctgct gcagctggag ggcggcagcg aggtgctgcg cgcccgcacc 900
gagtggcgcc ccaagctgac cgactccttc cgcggcatca gcgtgatccc cgccgagccc 960
cgcgtg 966

<210> SEQ ID NO 11
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Pro Asp Trp Ser Met Leu Phe Ala Val Ile Thr Thr Ile Phe Ser Ala
1 5 10 15

Ala Glu Lys Gln Trp Thr Asn Leu Glu Trp Lys Pro Lys Pro Asn Pro
20 25 30

Pro Gln Leu Leu Asp Asp His Phe Gly Pro His Gly Leu Val Phe Arg
35 40 45

Arg Thr Phe Ala Ile Arg Ser Tyr Glu Val Gly Pro Asp Arg Ser Thr
50 55 60

Ser Ile Leu Ala Val Met Asn His Met Gln Glu Ala Thr Leu Asn His
65 70 75 80

Ala Lys Ser Val Gly Ile Leu Gly Asp Gly Phe Gly Thr Thr Leu Glu
85 90 95

Met Ser Lys Arg Asp Leu Met Trp Val Val Arg Arg Thr His Val Ala
100 105 110

Val Glu Arg Tyr Pro Thr Trp Gly Asp Thr Val Glu Val Glu Cys Trp
115 120 125

Ile Gly Ala Ser Gly Asn Asn Gly Met Arg Arg Asp Phe Leu Val Arg
130 135 140

Asp Cys Lys Thr Gly Glu Ile Leu Thr Arg Cys Thr Ser Leu Ser Val
145 150 155 160

Leu Met Asn Thr Arg Thr Arg Arg Leu Ser Thr Ile Pro Asp Glu Val
165 170 175

Arg Gly Glu Ile Gly Pro Ala Phe Ile Asp Asn Val Ala Val Lys Asp
180 185 190

Asp Glu Ile Lys Lys Leu Gln Lys Leu Asn Asp Ser Thr Ala Asp Tyr
195 200 205

Ile Gln Gly Gly Leu Thr Pro Arg Trp Asn Asp Leu Asp Val Asn Gln
210 215 220

```
His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

```
<210> SEQ ID NO 12
<211> LENGTH: 966
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

cccgactggt ccatgctgtt cgccgtgatc accaccatct tctccgccgc cgagaagcag     60

tggaccaacc tggagtggaa gcccaagccc aagctgcccc agctgctgga cgaccacttc    120

ggcctgcacg gcctggtgtt ccgccgcacc ttcgccatcc gctcctacga ggtgggcccc    180

gaccgcagca cctccatcct ggccgtgatg aaccacatgc aggaggccac cctgaaccac    240

gccaagagcg tgggcatcct gggcgacggc ttcggcacca ccctggagat gtccaagcgc    300

gacctgatgt gggtggtgcg ccgcacccac gtggccgtgg agcgctaccc cacctggggc    360

gacaccgtgg aggtggagtg ctggatcggc gccagcggca acaacggcat gcgccgcgac    420

ttcctggtgc gcgactgcaa gaccggcgag atcctgaccc gctgcacctc cctgagcgtg    480

ctgatgaaca cccgcacccg ccgcctgagc accatccccg acgaggtgcg cggcgagatc    540

ggccccgcct tcatcgacaa cgtggccgtg aaggacgacg agatcaagaa gctgcagaag    600

ctgaacgact ccaccgccga ctacatccag ggcggcctga ccccccgctg gaacgacctg    660

gacgtgaacc agcacgtgaa caacctgaag tacgtggcct gggtgttcga gaccgtgccc    720

gacagcatct tcgagtccca ccacatcagc tccttcaccc tggagtaccg ccgcgagtgc    780

acccgcgact ccgtgctgcg cagcctgacc accgtgagcg gcggcagctc cgaggccggc    840

ctggtgtgcg accacctgct gcagctggag ggcggcagcg aggtgctgcg cgcccgcacc    900

gagtggcgcc ccaagctgac cgactccttc cgcggcatca gcgtgatccc cgccgagccc    960

cgcgtg                                                               966
```

```
<210> SEQ ID NO 13
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Asp Trp Ser Met Leu Phe Ala Val Ile Thr Thr Ile Phe Ser Ala
1               5                   10                  15
```

-continued

```
Ala Glu Lys Gln Trp Thr Asn Leu Glu Trp Lys Pro Lys Pro Lys Leu
            20                  25                  30

Pro Gln Leu Leu Asp Asp His Phe Gly Leu His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Leu Ala Val Met Asn His Met Gln Glu Ala Thr Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Met Trp Val Val Arg Arg Thr His Val Ala
            100                 105                 110

Val Glu Arg Tyr Pro Thr Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

<210> SEQ ID NO 14
<211> LENGTH: 966
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
cccgactggt ccatgctgtt cgccgtgatc accaccatct tctccgccgc cgagaagcag      60

tggaccaacc tggagtggaa gcccaagccc aagctgcccc agctgctgga cgaccacttc     120

ggcctgcacg gcctggtgtt ccgccgcacc ttcgccatcc gctcctacga ggtgggcccc     180

gaccgcagca ccagcatcgt ggccgtgatg aaccacctgc aggaggccgc cctgaaccac     240

gccaagtccg tgggcatcct gggcgacggc ttcggcacca ccctggagat gtccaagcgc     300
```

```
gacctgatct gggtggtgcg ccgcacccac gtggccgtgg agcgctaccc cacctggggc    360

gacaccgtgg aggtggagtg ctggatcggc gccagcggca acaacggcat gcgccgcgac    420

ttcctggtgc gcgactgcaa gaccggcgag atcctgaccc gctgcacctc cctgagcgtg    480

ctgatgaaca cccgcacccg ccgcctgagc accatccccg acgaggtgcg cggcgagatc    540

ggccccgcct tcatcgacaa cgtggccgtg aaggacgacg agatcaagaa gctgcagaag    600

ctgaacgact ccaccgccga ctacatccag ggcggcctga ccccccgctg gaacgacctg    660

gacgtgaacc agcacgtgaa caacctgaag tacgtggcct gggtgttcga gaccgtgccc    720

gacagcatct tcgagtccca ccacatcagc tccttcaccc tggagtaccg ccgcgagtgc    780

acccgcgact ccgtgctgcg cagcctgacc accgtgagcg gcggcagctc cgaggccggc    840

ctggtgtgcg accacctgct gcagctggag ggcggcagcg aggtgctgcg cgcccgcacc    900

gagtggcgcc ccaagctgac cgactccttc cgcggcatca gcgtgatccc cgccgagccc    960

cgcgtg                                                               966
```

<210> SEQ ID NO 15
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Lys Leu
            20                  25                  30

Pro Gln Leu Leu Asp Asp His Phe Gly Leu His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Val Ala Val Met Asn His Leu Gln Glu Ala Ala Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Ile Trp Val Val Arg Arg Thr His Val Ala
            100                 105                 110

Val Glu Arg Tyr Pro Thr Trp Gly Asp Thr Val Glu Val Glu Cys Trp
        115                 120                 125

Ile Gly Ala Ser Gly Asn Asn Gly Met Arg Arg Asp Phe Leu Val Arg
    130                 135                 140

Asp Cys Lys Thr Gly Glu Ile Leu Thr Arg Cys Thr Ser Leu Ser Val
145                 150                 155                 160

Leu Met Asn Thr Arg Thr Arg Arg Leu Ser Thr Ile Pro Asp Glu Val
                165                 170                 175

Arg Gly Glu Ile Gly Pro Ala Phe Ile Asp Asn Val Ala Val Lys Asp
            180                 185                 190

Asp Glu Ile Lys Lys Leu Gln Lys Leu Asn Asp Ser Thr Ala Asp Tyr
        195                 200                 205

Ile Gln Gly Gly Leu Thr Pro Arg Trp Asn Asp Leu Asp Val Asn Gln
    210                 215                 220

His Val Asn Asn Leu Lys Tyr Val Ala Trp Val Phe Glu Thr Val Pro
```

-continued

```
225                 230                 235                 240

Asp Ser Ile Phe Glu Ser His His Ile Ser Ser Phe Thr Leu Glu Tyr
                245                 250                 255

Arg Arg Glu Cys Thr Arg Asp Ser Val Leu Arg Ser Leu Thr Thr Val
            260                 265                 270

Ser Gly Gly Ser Ser Glu Ala Gly Leu Val Cys Asp His Leu Leu Gln
        275                 280                 285

Leu Glu Gly Gly Ser Glu Val Leu Arg Ala Arg Thr Glu Trp Arg Pro
    290                 295                 300

Lys Leu Thr Asp Ser Phe Arg Gly Ile Ser Val Ile Pro Ala Glu Pro
305                 310                 315                 320

Arg Val
```

<210> SEQ ID NO 16
<211> LENGTH: 6702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggtgt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaacgg cgcgccatgc tgctgcaggc cttcctgttc ctgctggccg   1080

gcttcgccgc caagatcagc gcctccatga cgaacgagac gtccgaccgc cccctggtgc   1140

acttcacccc caacaagggc tggatgaacg accccaacgg cctgtggtac gacgagaagg   1200

acgccaagtg gcacctgtac ttccagtaca acccgaacga caccgtctgg gggacgccct   1260

tgttctgggg ccacgccacg tccgacgacc tgaccaactg ggaggaccag cccatcgcca   1320

tcgccccgaa gcgcaacgac tccggcgcct tctccggctc catggtggtg gactacaaca   1380

acacctccgg cttcttcaac gacaccatcg acccgcgcca gcgctgcgtg gccatctgga   1440

cctacaacac cccggagtcc gaggagcagt acatctccta cagcctggac ggcggctaca   1500
```

```
ccttcaccga gtaccagaag aaccccgtgc tggccgccaa ctccacccag ttccgcgacc   1560
cgaaggtctt ctggtacgag ccctcccaga agtggatcat gaccgcggcc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtcccca   1740
ccgagcagga ccccagcaag tcctactggg tgatgttcat ctccatcaac cccggcgccc   1800
cggccggcgg ctccttcaac cagtacttcg tcggcagctt caacggcacc cacttcgagg   1860
ccttcgacaa ccagtcccgc gtggtggact tcggcaagga ctactacgcc ctgcagacct   1920
tcttcaacac cgacccgacc tacgggagcg ccctgggcat cgcgtgggcc tccaactggg   1980
agtactccgc cttcgtgccc accaacccct ggcgctcctc catgtccctc gtgcgcaagt   2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accacccaga cgatctccaa gtccgtgttc gcggacctct   2280
ccctctggtt caagggcctg gaggaccccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca accagccctt caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg ggctccgtga   2580
acatgacgac gggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg gaacacaaat ggaggatccc   3060
gcgtctcgaa cagagcgcgc agaggaacgc tgaaggtctc gcctctgtcg cacctcagcg   3120
cggcatacac cacaataacc acctgacgaa tgcgcttggt tcttcgtcca ttagcgaagc   3180
gtccggttca cacacgtgcc acgttggcga ggtggcaggt gacaatgatc ggtggagctg   3240
atggtcgaaa cgttcacagc ctagggatat cgaattcggc cgacaggacg cgcgtcaaag   3300
gtgctggtcg tgtatgccct ggccggcagg tcgttgctgc tgctggttag tgattccgca   3360
accctgattt tggcgtctta ttttggcgtg gcaaacgctg gcgcccgcga gccgggccgg   3420
cggcgatgcg gtgccccacg gctgccggaa tccaagggag gcaagagcgc ccgggtcagt   3480
tgaagggctt tacgcgcaag gtacagccgc tcctgcaagg ctgcgtggtg gaattggacg   3540
tgcaggtcct gctgaagttc ctccaccgcc tcaccagcgg acaaagcacc ggtgtatcag   3600
gtccgtgtca tccactctaa agagctcgac tacgacctac tgatggccct agattcttca   3660
tcaaaaacgc ctgagacact tgcccaggat tgaaactccc tgaagggacc accaggggcc   3720
ctgagttgtt ccttcccccc gtggcgagct gccagccagg ctgtacctgt gatcgaggct   3780
ggcgggaaaa taggcttcgt gtgctcaggt catgggaggt gcaggacagc tcatgaaacg   3840
```

-continued

```
ccaacaatcg cacaattcat gtcaagctaa tcagctattt cctcttcacg agctgtaatt   3900
gtcccaaaat tctggtctac cgggggtgat ccttcgtgta cgggcccttc cctcaaccct   3960
aggtatgcgc gcatgcggtc gccgcgcaac tcgcgcgagg gccgagggtt tgggacgggc   4020
cgtcccgaaa tgcagttgca cccggatgcg tggcaccttt tttgcgataa tttatgcaat   4080
ggactgctct gcaaaattct ggctctgtcg ccaaccctag gatcagcggc gtaggatttc   4140
gtaatcattc gtcctgatgg ggagctaccg actaccctaa tatcagcccg actgcctgac   4200
gccagcgtcc acttttgtgc acacattcca ttcgtgccca agacatttca ttgtggtgcg   4260
aagcgtcccc agttacgctc acctgtttcc cgacctcctt actgttctgt cgacagagcg   4320
ggcccacagg ccggtcgcag ccactagtaa caatggccac cgcatccact ttctcggcgt   4380
tcaatgcccg ctgcggcgac ctgcgtcgct cggcgggctc cgggccccgg cgcccagcga   4440
ggcccctccc cgtgcgcgct gccatcgcca gcgaggtccc cgtggccacc acctcccccc   4500
ggcccgactg gtccatgctg ttcgccgtga tcaccaccat cttcagcgcc gccgagaagc   4560
agtggaccaa cctggagtgg aagcccaagc ccaagctgcc ccagctgctg gacgaccact   4620
tcggcctgca cggcctggtg ttccgccgca ccttcgccat ccgctcctac gaggtgggcc   4680
ccgaccgcag cacctccatc ctggccgtga tgaaccacat gcaggaggcc accctgaacc   4740
acgccaagag cgtgggcatc ctgggcgacg gcttcggcac caccctggag atgtccaagc   4800
gcgacctgat gtgggtggtg cgccgcaccc acgtggccgt ggagcgctac cccacctggg   4860
gcgacaccgt ggaggtggag tgctggatcg gcgccagcgg caacaacggc atgcgccgcg   4920
acttcctggt gcgcgactgc aagaccggcg agatcctgac ccgctgcacc tccctgagcg   4980
tgctgatgaa cacccgcacc cgccgcctga gcaccatccc cgacgaggtg cgcggcgaga   5040
tcggccccgc cttcatcgac aacgtggccg tgaaggacga cgagatcaag aagctgcaga   5100
agctgaacga ctccaccgcc gactacatcc agggcggcct gacccccgc tggaacgacc   5160
tggacgtgaa ccagcacgtg aacaacctga agtacgtggc ctgggtgttc gagaccgtgc   5220
ccgacagcat cttcgagtcc caccacatca gctccttcac cctggagtac cgccgcgagt   5280
gcacccgcga ctccgtgctg cgcagcctga ccaccgtgag cggcggcagc tccgaggccg   5340
gcctggtgtg cgaccacctg ctgcagctgg agggcggcag cgaggtgctg cgcgcccgca   5400
ccgagtggcg ccccaagctg accgactcct tccgcggcat cagcgtgatc cccgccgagc   5460
cccgcgtgat ggactacaag gaccacgacg gcgactacaa ggaccacgac atcgactaca   5520
aggacgacga cgacaagtga ctcgaggcag cagcagctcg gatagtatcg acacactctg   5580
gacgctggtc gtgtgatgga ctgttgccgc cacacttgct gccttgacct gtgaatatcc   5640
ctgccgcttt tatcaaacag cctcagtgtg tttgatcttg tgtgtacgcg cttttgcgag   5700
ttgctagctg cttgtgctat ttgcgaatac cacccccagc atccccttcc ctcgtttcat   5760
atcgcttgca tcccaaccgc aacttatcta cgctgtcctg ctatccctca gcgctgctcc   5820
tgctcctgct cactgcccct cgcacagcct tggtttgggc tccgcctgta ttctcctggt   5880
actgcaacct gtaaaccagc actgcaatgc tgatgcacgg gaagtagtgg gatgggaaca   5940
caaatggaaa gcttgagctc ttgttttcca gaaggagttg ctccttgagc ctttcattct   6000
cagcctcgat aacctccaaa gccgctctaa ttgtggaggg ggttcgaatt taaaagcttg   6060
gaatgttggt tcgtgcgtct ggaacaagcc cagacttgtt gctcactggg aaaaggacca   6120
tcagctccaa aaaacttgcc gctcaaaccg cgtacctctg ctttcgcgca atctgccctg   6180
ttgaaatcgc caccacattc atattgtgac gcttgagcag tctgtaattg cctcagaatg   6240
```

tggaatcatc tgccccctgt gcgagcccat gccaggcatg tcgcgggcga ggacacccgc 6300
cactcgtaca gcagaccatt atgctacctc acaatagttc ataacagtga ccatatttct 6360
cgaagctccc caacgagcac ctccatgctc tgagtggcca ccccccggcc ctggtgcttg 6420
cggagggcag gtcaaccggc atggggctac cgaaatcccc gaccggatcc caccaccccc 6480
gcgatgggaa gaatctctcc ccgggatgtg ggcccaccac cagcacaacc tgctggccca 6540
ggcgagcgtc aaaccatacc acacaaatat ccttggcatc ggccctgaat tccttctgcc 6600
gctctgctac ccggtgcttc tgtccgaagc aggggttgct agggatcgct ccgagtccgc 6660
aaacccttgt cgcgtggcgg ggcttgttcg agcttgaaga gc 6702

<210> SEQ ID NO 17
<211> LENGTH: 1116
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
atggccaccg catccacttt ctcggcgttc aatgcccgct gcggcgacct gcgtcgctcg 60
gcgggctccg ggccccggcg cccagcgagg cccctccccg tgcgcgctgc catcgccagc 120
gaggtccccg tggccaccac ctcccccccgg cccgactggt ccatgctgtt cgccgtgatc 180
accaccatct tcagcgccgc cgagaagcag tggaccaacc tggagtggaa gcccaagccc 240
aagctgcccc agctgctgga cgaccacttc ggcctgcacg gcctggtgtt ccgccgcacc 300
ttcgccatcc gctcctacga ggtgggcccc gaccgcagca cctccatcct ggccgtgatg 360
aaccacatgc aggaggccac cctgaaccac gccaagagcg tgggcatcct gggcgacggc 420
ttcggcacca ccctggagat gtccaagcgc gacctgatgt gggtggtgcg ccgcacccac 480
gtggccgtgg agcgctaccc cacctggggc gacaccgtgg aggtggagtg ctggatcggc 540
gccagcggca acaacggcat gcgccgcgac ttcctggtgc gcgactgcaa gaccggcgag 600
atcctgaccc gctgcacctc cctgagcgtg ctgatgaaca cccgcacccg ccgcctgagc 660
accatccccg acgaggtgcg cggcgagatc ggccccgcct tcatcgacaa cgtggccgtg 720
aaggacgacg agatcaagaa gctgcagaag ctgaacgact ccaccgccga ctacatccag 780
ggcggcctga ccccccgctg gaacgacctg gacgtgaacc agcacgtgaa caacctgaag 840
tacgtggcct gggtgttcga gaccgtgccc gacagcatct tcgagtccca ccacatcagc 900
tccttcaccc tggagtaccg ccgcgagtgc acccgcgact ccgtgctgcg cagcctgacc 960
accgtgagcg gcggcagctc cgaggccggc ctggtgtgcg accacctgct gcagctggag 1020
ggcggcagcg aggtgctgcg cgcccgcacc gagtggcgcc ccaagctgac cgactccttc 1080
cgcggcatca gcgtgatccc cgccgagccc cgcgtg 1116

<210> SEQ ID NO 18
<211> LENGTH: 372
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Met Ala Thr Ala Ser Thr Phe Ser Ala Phe Asn Ala Arg Cys Gly Asp
1 5 10 15

```
Leu Arg Arg Ser Ala Gly Ser Gly Pro Arg Arg Pro Ala Arg Pro Leu
            20                  25                  30

Pro Val Arg Ala Ala Ile Ala Ser Glu Val Pro Val Ala Thr Thr Ser
        35                  40                  45

Pro Arg Pro Asp Trp Ser Met Leu Phe Ala Val Ile Thr Thr Ile Phe
    50                  55                  60

Ser Ala Ala Glu Lys Gln Trp Thr Asn Leu Glu Trp Lys Pro Lys Pro
65                  70                  75                  80

Lys Leu Pro Gln Leu Leu Asp Asp His Phe Gly Leu His Gly Leu Val
                85                  90                  95

Phe Arg Arg Thr Phe Ala Ile Arg Ser Tyr Glu Val Gly Pro Asp Arg
            100                 105                 110

Ser Thr Ser Ile Leu Ala Val Met Asn His Met Gln Glu Ala Thr Leu
        115                 120                 125

Asn His Ala Lys Ser Val Gly Ile Leu Gly Asp Gly Phe Gly Thr Thr
    130                 135                 140

Leu Glu Met Ser Lys Arg Asp Leu Met Trp Val Val Arg Arg Thr His
145                 150                 155                 160

Val Ala Val Glu Arg Tyr Pro Thr Trp Gly Asp Thr Val Glu Val Glu
                165                 170                 175

Cys Trp Ile Gly Ala Ser Gly Asn Asn Gly Met Arg Arg Asp Phe Leu
            180                 185                 190

Val Arg Asp Cys Lys Thr Gly Glu Ile Leu Thr Arg Cys Thr Ser Leu
        195                 200                 205

Ser Val Leu Met Asn Thr Arg Thr Arg Arg Leu Ser Thr Ile Pro Asp
    210                 215                 220

Glu Val Arg Gly Glu Ile Gly Pro Ala Phe Ile Asp Asn Val Ala Val
225                 230                 235                 240

Lys Asp Asp Glu Ile Lys Lys Leu Gln Lys Leu Asn Asp Ser Thr Ala
                245                 250                 255

Asp Tyr Ile Gln Gly Gly Leu Thr Pro Arg Trp Asn Asp Leu Asp Val
            260                 265                 270

Asn Gln His Val Asn Asn Leu Lys Tyr Val Ala Trp Val Phe Glu Thr
        275                 280                 285

Val Pro Asp Ser Ile Phe Glu Ser His His Ile Ser Ser Phe Thr Leu
    290                 295                 300

Glu Tyr Arg Arg Glu Cys Thr Arg Asp Ser Val Leu Arg Ser Leu Thr
305                 310                 315                 320

Thr Val Ser Gly Gly Ser Ser Glu Ala Gly Leu Val Cys Asp His Leu
                325                 330                 335

Leu Gln Leu Glu Gly Gly Ser Glu Val Leu Arg Ala Arg Thr Glu Trp
            340                 345                 350

Arg Pro Lys Leu Thr Asp Ser Phe Arg Gly Ile Ser Val Ile Pro Ala
        355                 360                 365

Glu Pro Arg Val
    370
```

<210> SEQ ID NO 19
<211> LENGTH: 981
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
agcctgaagc gcctgcccga ctggtccatg ctgttcgccg tgatcaccac catcttcagc 60
gccgccgaga agcagtggac caacctggag tggaagccca agcccaagct gccccagctg 120
ctggacgacc acttcggcct gcacggcctg gtgttccgcc gcaccttcgc catccgctcc 180
tacgaggtgg gccccgaccg cagcacctcc atcctggccg tgatgaacca catgcaggag 240
gccaccctga accacgccaa gagcgtgggc atcctgggcg acggcttcgg caccaccctg 300
gagatgtcca agcgcgacct gatgtgggtg gtgcgccgca cccacgtggc cgtggagcgc 360
taccccacct ggggcgacac cgtggaggtg gagtgctgga tcggcgccag cggcaacaac 420
ggcatgcgcc gcgacttcct ggtgcgcgac tgcaagaccg gcgagatcct gacccgctgc 480
acctccctga gcgtgctgat gaacacccgc acccgccgcc tgagcaccat ccccgacgag 540
gtgcgcggcg agatcggccc cgccttcatc gacaacgtgg ccgtgaagga cgacgagatc 600
aagaagctgc agaagctgaa cgactccacc gccgactaca tccagggcgg cctgaccccc 660
cgctggaacg acctggacgt gaaccagcac gtgaacaacc tgaagtacgt ggcctgggtg 720
ttcgagaccg tgcccgacag catcttcgag tcccaccaca tcagctcctt caccctggag 780
taccgccgcg agtgcacccg cgactccgtg ctgcgcagcc tgaccaccgt gagcggcggc 840
agctccgagg ccggcctggt gtgcgaccac ctgctgcagc tggagggcgg cagcgaggtg 900
ctgcgcgccc gcaccgagtg gcgccccaag ctgaccgact ccttccgcgg catcagcgtg 960
atccccgccg agccccgcgt g 981

<210> SEQ ID NO 20
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Ser Leu Lys Arg Leu Pro Asp Trp Ser Met Leu Phe Ala Val Ile Thr
1               5                   10                  15

Thr Ile Phe Ser Ala Ala Glu Lys Gln Trp Thr Asn Leu Glu Trp Lys
            20                  25                  30

Pro Lys Pro Lys Leu Pro Gln Leu Leu Asp Asp His Phe Gly Leu His
        35                  40                  45

Gly Leu Val Phe Arg Arg Thr Phe Ala Ile Arg Ser Tyr Glu Val Gly
    50                  55                  60

Pro Asp Arg Ser Thr Ser Ile Leu Ala Val Met Asn His Met Gln Glu
65                  70                  75                  80

Ala Thr Leu Asn His Ala Lys Ser Val Gly Ile Leu Gly Asp Gly Phe
                85                  90                  95

Gly Thr Thr Leu Glu Met Ser Lys Arg Asp Leu Met Trp Val Val Arg
            100                 105                 110

Arg Thr His Val Ala Val Glu Arg Tyr Pro Thr Trp Gly Asp Thr Val
        115                 120                 125

Glu Val Glu Cys Trp Ile Gly Ala Ser Gly Asn Asn Gly Met Arg Arg
    130                 135                 140

Asp Phe Leu Val Arg Asp Cys Lys Thr Gly Glu Ile Leu Thr Arg Cys
145                 150                 155                 160

Thr Ser Leu Ser Val Leu Met Asn Thr Arg Thr Arg Arg Leu Ser Thr
                165                 170                 175
```

```
Ile Pro Asp Glu Val Arg Gly Glu Ile Gly Pro Ala Phe Ile Asp Asn
            180                 185                 190

Val Ala Val Lys Asp Asp Glu Ile Lys Lys Leu Gln Lys Leu Asn Asp
        195                 200                 205

Ser Thr Ala Asp Tyr Ile Gln Gly Gly Leu Thr Pro Arg Trp Asn Asp
    210                 215                 220

Leu Asp Val Asn Gln His Val Asn Asn Leu Lys Tyr Val Ala Trp Val
225                 230                 235                 240

Phe Glu Thr Val Pro Asp Ser Ile Phe Glu Ser His His Ile Ser Ser
                245                 250                 255

Phe Thr Leu Glu Tyr Arg Arg Glu Cys Thr Arg Asp Ser Val Leu Arg
            260                 265                 270

Ser Leu Thr Thr Val Ser Gly Gly Ser Ser Glu Ala Gly Leu Val Cys
        275                 280                 285

Asp His Leu Leu Gln Leu Glu Gly Gly Ser Glu Val Leu Arg Ala Arg
    290                 295                 300

Thr Glu Trp Arg Pro Lys Leu Thr Asp Ser Phe Arg Gly Ile Ser Val
305                 310                 315                 320

Ile Pro Ala Glu Pro Arg Val
                325
```

<210> SEQ ID NO 21
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atcaacggca ccaagttcag ctacaccgag agcctgaagc gcctgcccga ctggtccatg      60

ctgttcgccg tgatcaccac catcttcagc gccgccgaga agcagtggac caacctggag     120

tggaagccca agcccaagct gccccagctg ctggacgacc acttcggcct gcacggcctg     180

gtgttccgcc gcaccttcgc catccgctcc tacgaggtgg gccccgaccg cagcacctcc     240

atcctggccg tgatgaacca catgcaggag gccaccctga accacgccaa gagcgtgggc     300

atcctgggcg acggcttcgg caccaccctg gagatgtcca agcgcgacct gatgtgggtg     360

gtgcgccgca cccacgtggc cgtggagcgc taccccacct ggggcgacac cgtggaggtg     420

gagtgctgga tcggcgccag cggcaacaac ggcatgcgcc gcgacttcct ggtgcgcgac     480

tgcaagaccg gcgagatcct gacccgctgc acctccctga gcgtgctgat gaacacccgc     540

acccgccgcc tgagcaccat ccccgacgag gtgcgcggcg agatcggccc cgccttcatc     600

gacaacgtgg ccgtgaagga cgacgagatc aagaagctgc agaagctgaa cgactccacc     660

gccgactaca tccagggcgg cctgaccccc cgctggaacg acctggacgt gaaccagcac     720

gtgaacaacc tgaagtacgt ggcctgggtg ttcgagaccg tgcccgacag catcttcgag     780

tcccaccaca tcagctcctt caccctggag taccgccgcg agtgcacccg cgactccgtg     840

ctgcgcagcc tgaccaccgt gagcggcggc agctccgagg ccggcctggt gtgcgaccac     900

ctgctgcagc tggagggcgg cagcgaggtg ctgcgcgccc gcaccgagtg gcgccccaag     960

ctgaccgact ccttccgcgg catcagcgtg atccccgccg agccccgcgt g             1011
```

<210> SEQ ID NO 22
<211> LENGTH: 337

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

```
Ile Asn Gly Thr Lys Phe Ser Tyr Thr Glu Ser Leu Lys Arg Leu Pro
1               5                   10                  15

Asp Trp Ser Met Leu Phe Ala Val Ile Thr Thr Ile Phe Ser Ala Ala
            20                  25                  30

Glu Lys Gln Trp Thr Asn Leu Glu Trp Lys Pro Lys Pro Lys Leu Pro
        35                  40                  45

Gln Leu Leu Asp Asp His Phe Gly Leu His Gly Leu Val Phe Arg Arg
    50                  55                  60

Thr Phe Ala Ile Arg Ser Tyr Glu Val Gly Pro Asp Arg Ser Thr Ser
65                  70                  75                  80

Ile Leu Ala Val Met Asn His Met Gln Glu Ala Thr Leu Asn His Ala
                85                  90                  95

Lys Ser Val Gly Ile Leu Gly Asp Gly Phe Gly Thr Thr Leu Glu Met
            100                 105                 110

Ser Lys Arg Asp Leu Met Trp Val Val Arg Arg Thr His Val Ala Val
        115                 120                 125

Glu Arg Tyr Pro Thr Trp Gly Asp Thr Val Glu Val Glu Cys Trp Ile
    130                 135                 140

Gly Ala Ser Gly Asn Asn Gly Met Arg Arg Asp Phe Leu Val Arg Asp
145                 150                 155                 160

Cys Lys Thr Gly Glu Ile Leu Thr Arg Cys Thr Ser Leu Ser Val Leu
                165                 170                 175

Met Asn Thr Arg Thr Arg Arg Leu Ser Thr Ile Pro Asp Glu Val Arg
            180                 185                 190

Gly Glu Ile Gly Pro Ala Phe Ile Asp Asn Val Ala Val Lys Asp Asp
        195                 200                 205

Glu Ile Lys Lys Leu Gln Lys Leu Asn Asp Ser Thr Ala Asp Tyr Ile
    210                 215                 220

Gln Gly Gly Leu Thr Pro Arg Trp Asn Asp Leu Asp Val Asn Gln His
225                 230                 235                 240

Val Asn Asn Leu Lys Tyr Val Ala Trp Val Phe Glu Thr Val Pro Asp
                245                 250                 255

Ser Ile Phe Glu Ser His His Ile Ser Ser Phe Thr Leu Glu Tyr Arg
            260                 265                 270

Arg Glu Cys Thr Arg Asp Ser Val Leu Arg Ser Leu Thr Thr Val Ser
        275                 280                 285

Gly Gly Ser Ser Glu Ala Gly Leu Val Cys Asp His Leu Leu Gln Leu
    290                 295                 300

Glu Gly Gly Ser Glu Val Leu Arg Ala Arg Thr Glu Trp Arg Pro Lys
305                 310                 315                 320

Leu Thr Asp Ser Phe Arg Gly Ile Ser Val Ile Pro Ala Glu Pro Arg
                325                 330                 335

Val
```

<210> SEQ ID NO 23
<211> LENGTH: 981
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 23

```
agcctgaagc gcctgcccga ctggtccatg ctgttcgccg tgatcaccac catcttctcc     60

gccgccgaga agcagtggac caacctggag tggaagccca agcccaaccc cccccagctg    120

ctggacgacc acttcggccc ccacggcctg gtgttccgcc gcaccttcgc catccgcagc    180

tacgaggtgg gccccgaccg ctccaccagc atcgtggccg tgatgaacca cctgcaggag    240

gccgccctga accacgccaa gtccgtgggc atcctgggcg acggcttcgg caccaccctg    300

gagatgtcca agcgcgacct gatctgggtg gtgaagcgca cccacgtggc cgtggagcgc    360

taccccgcct ggggcgacac cgtggaggtg gagtgctggg tgggcgcctc cggcaacaac    420

ggccgccgcc acgacttcct ggtgcgcgac tgcaagaccg gcgagatcct gacccgctgc    480

acctccctga gcgtgatgat gaacacccgc acccgccgcc tgagcaagat ccccgaggag    540

gtgcgcggcg agatcggccc cgccttcatc gacaacgtgg ccgtgaagga cgaggagatc    600

aagaagcccc agaagctgaa cgactccacc gccgactaca tccagggcgg cctgaccccc    660

cgctggaacg acctggacat caaccagcac gtgaacaaca tcaagtacgt ggactggatc    720

ctggagaccg tgcccgacag catcttcgag agccaccaca tctcctcctt caccatcgag    780

taccgccgcg agtgcaccat ggacagcgtg ctgcagtccc tgaccaccgt gagcggcggc    840

tcctccgagg ccggcctggt gtgcgagcac ctgctgcagc tggagggcgg cagcgaggtg    900

ctgcgcgcca agaccgagtg gcgccccaag ctgaccgact ccttccgcgg catcagcgtg    960

atccccgccg agtccagcgt g                                              981
```

<210> SEQ ID NO 24
<211> LENGTH: 327
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

```
Ser Leu Lys Arg Leu Pro Asp Trp Ser Met Leu Phe Ala Val Ile Thr
1               5                   10                  15

Thr Ile Phe Ser Ala Ala Glu Lys Gln Trp Thr Asn Leu Glu Trp Lys
            20                  25                  30

Pro Lys Pro Asn Pro Pro Gln Leu Leu Asp Asp His Phe Gly Pro His
        35                  40                  45

Gly Leu Val Phe Arg Arg Thr Phe Ala Ile Arg Ser Tyr Glu Val Gly
    50                  55                  60

Pro Asp Arg Ser Thr Ser Ile Val Ala Val Met Asn His Leu Gln Glu
65                  70                  75                  80

Ala Ala Leu Asn His Ala Lys Ser Val Gly Ile Leu Gly Asp Gly Phe
                85                  90                  95

Gly Thr Thr Leu Glu Met Ser Lys Arg Asp Leu Ile Trp Val Val Lys
            100                 105                 110

Arg Thr His Val Ala Val Glu Arg Tyr Pro Ala Trp Gly Asp Thr Val
        115                 120                 125

Glu Val Glu Cys Trp Val Gly Ala Ser Gly Asn Asn Gly Arg Arg His
    130                 135                 140

Asp Phe Leu Val Arg Asp Cys Lys Thr Gly Glu Ile Leu Thr Arg Cys
145                 150                 155                 160
```

-continued

```
Thr Ser Leu Ser Val Met Met Asn Thr Arg Thr Arg Arg Leu Ser Lys
                165                 170                 175

Ile Pro Glu Glu Val Arg Gly Glu Ile Gly Pro Ala Phe Ile Asp Asn
            180                 185                 190

Val Ala Val Lys Asp Glu Glu Ile Lys Lys Pro Gln Lys Leu Asn Asp
        195                 200                 205

Ser Thr Ala Asp Tyr Ile Gln Gly Gly Leu Thr Pro Arg Trp Asn Asp
    210                 215                 220

Leu Asp Ile Asn Gln His Val Asn Asn Ile Lys Tyr Val Asp Trp Ile
225                 230                 235                 240

Leu Glu Thr Val Pro Asp Ser Ile Phe Glu Ser His His Ile Ser Ser
                245                 250                 255

Phe Thr Ile Glu Tyr Arg Arg Glu Cys Thr Met Asp Ser Val Leu Gln
            260                 265                 270

Ser Leu Thr Thr Val Ser Gly Gly Ser Ser Glu Ala Gly Leu Val Cys
        275                 280                 285

Glu His Leu Leu Gln Leu Glu Gly Gly Ser Glu Val Leu Arg Ala Lys
    290                 295                 300

Thr Glu Trp Arg Pro Lys Leu Thr Asp Ser Phe Arg Gly Ile Ser Val
305                 310                 315                 320

Ile Pro Ala Glu Ser Ser Val
                325


<210> SEQ ID NO 25
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

agcctgaaga agctgcccga ctggtccatg ctgttcgccg tgatcaccac catcttctcc      60

gccgccgaga agcagtggac caacctggag tggaagccca agcccaaccc cccccagctg     120

ctggacgacc acttcggccc ccacggcctg gtgttccgcc gcaccttcgc catccgcagc     180

tacgaggtgg gccccgaccg ctccaccagc atcgtggccg tgatgaacca cctgcaggag     240

gccgccctga accacgccaa gtccgtgggc atcctgggcg acggcttcgg caccaccctg     300

gagatgtcca agcgcgacct gatctgggtg gtgaagcgca cccacgtggc cgtggagcgc     360

taccccgcct ggggcgacac cgtggaggtg gagtgctggg tgggcgcctc cggcaacaac     420

ggccgccgcc acgacttcct ggtgcgcgac tgcaagaccg gcgagatcct gacccgctgc     480

acctccctga gcgtgatgat gaacacccgc acccgccgcc tgagcaagat ccccgaggag     540

gtgcgcggcg agatcggccc cgccttcatc gacaacgtgg ccgtgaagga cgaggagatc     600

aagaagcccc agaagctgaa cgactccacc gccgactaca tccagggcgg cctgaccccc     660

cgctggaacg acctggacat caaccagcac gtgaacaaca tcaagtacgt ggactggatc     720

ctggagaccg tgcccgacag catcttcgag agccaccaca tctcctcctt caccatcgag     780

taccgccgcg agtgcaccat ggacagcgtg ctgcagtccc tgaccaccgt gagcggcggc     840

tcctccgagg ccggcctggt gtgcgagcac ctgctgcagc tggagggcgg cagcgaggtg     900

ctgcgcgcca agaccgagtg gcgccccaag ctgaccgact ccttccgcgg catcagcgtg     960

atccccgccg agtccagcgt g                                               981
```

<210> SEQ ID NO 26
<211> LENGTH: 327
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

```
Ser Leu Lys Lys Leu Pro Asp Trp Ser Met Leu Phe Ala Val Ile Thr
1               5                   10                  15

Thr Ile Phe Ser Ala Ala Glu Lys Gln Trp Thr Asn Leu Glu Trp Lys
            20                  25                  30

Pro Lys Pro Asn Pro Pro Gln Leu Leu Asp Asp His Phe Gly Pro His
        35                  40                  45

Gly Leu Val Phe Arg Arg Thr Phe Ala Ile Arg Ser Tyr Glu Val Gly
    50                  55                  60

Pro Asp Arg Ser Thr Ser Ile Val Ala Val Met Asn His Leu Gln Glu
65                  70                  75                  80

Ala Ala Leu Asn His Ala Lys Ser Val Gly Ile Leu Gly Asp Gly Phe
                85                  90                  95

Gly Thr Thr Leu Glu Met Ser Lys Arg Asp Leu Ile Trp Val Val Lys
            100                 105                 110

Arg Thr His Val Ala Val Glu Arg Tyr Pro Ala Trp Gly Asp Thr Val
        115                 120                 125

Glu Val Glu Cys Trp Val Gly Ala Ser Gly Asn Asn Gly Arg Arg His
    130                 135                 140

Asp Phe Leu Val Arg Asp Cys Lys Thr Gly Glu Ile Leu Thr Arg Cys
145                 150                 155                 160

Thr Ser Leu Ser Val Met Met Asn Thr Arg Thr Arg Arg Leu Ser Lys
                165                 170                 175

Ile Pro Glu Glu Val Arg Gly Glu Ile Gly Pro Ala Phe Ile Asp Asn
            180                 185                 190

Val Ala Val Lys Asp Glu Glu Ile Lys Lys Pro Gln Lys Leu Asn Asp
        195                 200                 205

Ser Thr Ala Asp Tyr Ile Gln Gly Gly Leu Thr Pro Arg Trp Asn Asp
    210                 215                 220

Leu Asp Ile Asn Gln His Val Asn Asn Ile Lys Tyr Val Asp Trp Ile
225                 230                 235                 240

Leu Glu Thr Val Pro Asp Ser Ile Phe Glu Ser His His Ile Ser Ser
                245                 250                 255

Phe Thr Ile Glu Tyr Arg Arg Glu Cys Thr Met Asp Ser Val Leu Gln
            260                 265                 270

Ser Leu Thr Thr Val Ser Gly Gly Ser Ser Glu Ala Gly Leu Val Cys
        275                 280                 285

Glu His Leu Leu Gln Leu Glu Gly Gly Ser Glu Val Leu Arg Ala Lys
    290                 295                 300

Thr Glu Trp Arg Pro Lys Leu Thr Asp Ser Phe Arg Gly Ile Ser Val
305                 310                 315                 320

Ile Pro Ala Glu Ser Ser Val
                325
```

<210> SEQ ID NO 27
<211> LENGTH: 1098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
gcgcacccca aggcgaacgg cagcgcggtg tcgctgaagt cgggctccct ggagacccag 60
gaggacaaga cgagcagctc gtcccccccc ccccgcacgt tcatcaacca gctgcccgtg 120
tggagcatgc tgctgtcggc ggtgaccacg gtcttcggcg tggccgagaa gcagtggccc 180
atgctggacc gcaagtccaa gcgccccgac atgctggtcg agcccctggg cgtggaccgc 240
atcgtctacg acggcgtgag cttccgccag tcgttctcca tccgcagcta cgagatcggc 300
gccgaccgca ccgcctcgat cgagacgctg atgaacatgt tccaggagac ctccctgaac 360
cactgcaaga tcatcggcct gctgaacgac ggcttcggcc gcacgcccga gatgtgcaag 420
cgcgacctga tctgggtcgt gaccaagatg cagatcgagg tgaaccgcta ccccacgtgg 480
ggcgacacca tcgaggtcaa cacgtgggtg agcgcctcgg gcaagcacgg catgggccgc 540
gactggctga tctccgactg ccacaccggc gagatcctga tccgcgcgac gagcgtctgg 600
gcgatgatga accagaagac ccgccgcctg tcgaagatcc cctacgaggt gcgccaggag 660
atcgagcccc agttcgtcga ctccgccccc gtgatcgtgg acgaccgcaa gttccacaag 720
ctggacctga agacgggcga cagcatctgc aacggcctga ccccccgctg gacggacctg 780
gacgtgaacc agcacgtcaa caacgtgaag tacatcggct ggatcctgca gtcggtcccc 840
accgaggtgt tcgagacgca ggagctgtgc ggcctgaccc tggagtaccg ccgcgagtgc 900
ggccgcgact ccgtgctgga gagcgtcacg gccatggacc cctcgaagga gggcgaccgc 960
tccctgtacc agcacctgct gcgcctggag gacggcgcgg acatcgtgaa gggccgcacc 1020
gagtggcgcc ccaagaacgc cggcgccaag ggcgccatcc tgacgggcaa gaccagcaac 1080
ggcaactcga tctcctga 1098

<210> SEQ ID NO 28
<211> LENGTH: 365
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val Ala Glu Lys Gln Trp Pro Met Leu Asp Arg
    50                  55                  60

Lys Ser Lys Arg Pro Asp Met Leu Val Glu Pro Leu Gly Val Asp Arg
65                  70                  75                  80

Ile Val Tyr Asp Gly Val Ser Phe Arg Gln Ser Phe Ser Ile Arg Ser
                85                  90                  95

Tyr Glu Ile Gly Ala Asp Arg Thr Ala Ser Ile Glu Thr Leu Met Asn
            100                 105                 110

Met Phe Gln Glu Thr Ser Leu Asn His Cys Lys Ile Ile Gly Leu Leu
        115                 120                 125
```

-continued

```
Asn Asp Gly Phe Gly Arg Thr Pro Glu Met Cys Lys Arg Asp Leu Ile
    130                 135                 140

Trp Val Val Thr Lys Met Gln Ile Glu Val Asn Arg Tyr Pro Thr Trp
145                 150                 155                 160

Gly Asp Thr Ile Glu Val Asn Thr Trp Val Ser Ala Ser Gly Lys His
                165                 170                 175

Gly Met Gly Arg Asp Trp Leu Ile Ser Asp Cys His Thr Gly Glu Ile
            180                 185                 190

Leu Ile Arg Ala Thr Ser Val Trp Ala Met Met Asn Gln Lys Thr Arg
        195                 200                 205

Arg Leu Ser Lys Ile Pro Tyr Glu Val Arg Gln Glu Ile Glu Pro Gln
    210                 215                 220

Phe Val Asp Ser Ala Pro Val Ile Val Asp Asp Arg Lys Phe His Lys
225                 230                 235                 240

Leu Asp Leu Lys Thr Gly Asp Ser Ile Cys Asn Gly Leu Thr Pro Arg
                245                 250                 255

Trp Thr Asp Leu Asp Val Asn Gln His Val Asn Asn Val Lys Tyr Ile
            260                 265                 270

Gly Trp Ile Leu Gln Ser Val Pro Thr Glu Val Phe Glu Thr Gln Glu
        275                 280                 285

Leu Cys Gly Leu Thr Leu Glu Tyr Arg Arg Glu Cys Gly Arg Asp Ser
    290                 295                 300

Val Leu Glu Ser Val Thr Ala Met Asp Pro Ser Lys Glu Gly Asp Arg
305                 310                 315                 320

Ser Leu Tyr Gln His Leu Leu Arg Leu Glu Asp Gly Ala Asp Ile Val
                325                 330                 335

Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser
        355                 360                 365
```

<210> SEQ ID NO 29
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gcgcacccca aggcgaacgg cagcgcggtg tcgctgaagt cgggctccct ggagacccag     60

gaggacaaga cgagcagctc gtcccccccc ccccgcacgt tcatcaacca gctgcccgtg    120

tggagcatgc tgctgtcggc ggtgaccacg gtcttcggcg tggccgagaa gcagtggccc    180

atgctggacc gcaagtccaa gcgccccgac atgctggtcg agcccctggg cgtggaccgc    240

atcgtctacg acggcgtgag cttccgccag tcgttctcca tccgcagcta cgagatcggc    300

gccgaccgca ccgcctcgat cgagacgctg atgaacatgt tccaggagac ctccctgaac    360

cactgcaaga tcatcggcct gctgaacgac ggcttcggcc gcacgcccga gatgtgcaag    420

cgcgacctga tctgggtcgt gaccaagatg cagatcgagg tgaaccgcta ccccacgtgg    480

ggcgacacca tcgaggtcaa cacgtgggtg agcgcctcgg gcaagcacgg catgggccgc    540

gactggctga tctccgactg ccacaccggc gagatcctga tccgcgcgac gagcgtctgg    600

gcgatgatga accagaagac ccgccgcctg tcgaagatcc cctacgaggt gcgccaggag    660

atcgagcccc agttcgtcga ctccgccccc gtgatcgtgg acgaccgcaa gttccacaag    720
```

```
ctggacctga agacgggcga cagcatctgc aacggcctga ccccccgctg gacggacctg    780

gacgtgaacc agcacgtcaa caacgtgaag tacatcggct ggatcctgca gtcggtcccc    840

accgaggtgt tcgagacgca ggagctgtgc ggcctgaccc tggagtaccg ccgcgagtgc    900

ggccgcgact ccgtgctgga gagcgtcacg gccatggacc cctcgaagga gggcgaccgc    960

tccctgtacc agcacctgct gcgcctggag gacggcgcgg acatcgtgaa gggccgcacc   1020

gagtggcgcc ccaagaacgc cggcgccaag ggcgccatcc tgacgggcaa gaccagcaac   1080

ggcaactcga tctccatgga ctacaaggac cacgacggcg actacaagga ccacgacatc   1140

gactacaagg acgacgacga caagtga                                       1167
```

<210> SEQ ID NO 30
<211> LENGTH: 388
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val Ala Glu Lys Gln Trp Pro Met Leu Asp Arg
    50                  55                  60

Lys Ser Lys Arg Pro Asp Met Leu Val Glu Pro Leu Gly Val Asp Arg
65                  70                  75                  80

Ile Val Tyr Asp Gly Val Ser Phe Arg Gln Ser Phe Ser Ile Arg Ser
                85                  90                  95

Tyr Glu Ile Gly Ala Asp Arg Thr Ala Ser Ile Glu Thr Leu Met Asn
            100                 105                 110

Met Phe Gln Glu Thr Ser Leu Asn His Cys Lys Ile Ile Gly Leu Leu
        115                 120                 125

Asn Asp Gly Phe Gly Arg Thr Pro Glu Met Cys Lys Arg Asp Leu Ile
    130                 135                 140

Trp Val Val Thr Lys Met Gln Ile Glu Val Asn Arg Tyr Pro Thr Trp
145                 150                 155                 160

Gly Asp Thr Ile Glu Val Asn Thr Trp Val Ser Ala Ser Gly Lys His
                165                 170                 175

Gly Met Gly Arg Asp Trp Leu Ile Ser Asp Cys His Thr Gly Glu Ile
            180                 185                 190

Leu Ile Arg Ala Thr Ser Val Trp Ala Met Met Asn Gln Lys Thr Arg
        195                 200                 205

Arg Leu Ser Lys Ile Pro Tyr Glu Val Arg Gln Glu Ile Glu Pro Gln
    210                 215                 220

Phe Val Asp Ser Ala Pro Val Ile Val Asp Asp Arg Lys Phe His Lys
225                 230                 235                 240

Leu Asp Leu Lys Thr Gly Asp Ser Ile Cys Asn Gly Leu Thr Pro Arg
                245                 250                 255

Trp Thr Asp Leu Asp Val Asn Gln His Val Asn Asn Val Lys Tyr Ile
            260                 265                 270
```

```
Gly Trp Ile Leu Gln Ser Val Pro Thr Glu Val Phe Glu Thr Gln Glu
        275                 280                 285

Leu Cys Gly Leu Thr Leu Glu Tyr Arg Arg Glu Cys Gly Arg Asp Ser
    290                 295                 300

Val Leu Glu Ser Val Thr Ala Met Asp Pro Ser Lys Glu Gly Asp Arg
305                 310                 315                 320

Ser Leu Tyr Gln His Leu Leu Arg Leu Glu Asp Gly Ala Asp Ile Val
                325                 330                 335

Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser Met Asp Tyr
        355                 360                 365

Lys Asp His Asp Gly Asp Tyr Lys Asp His Asp Ile Asp Tyr Lys Asp
    370                 375                 380

Asp Asp Asp Lys
385
```

<210> SEQ ID NO 31
<211> LENGTH: 1098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ccccccaagc tgaacggctc caacgtgggc ctggtgaagt cctcccagat cgtgaagaag     60

ggcgacgaca ccacctcccc ccccgcccgc accttcatca accagctgcc cgactggagc    120

atgctgctgg ccgcgatcac caccctgttc ctggcggccg agaagcagtg gatgatgctg    180

gactggaagc ccaagcgccc cgacatgctg gtggacccct tcggcctggg ccgcttcgtg    240

caggacggcc tggtgttccg caacaacttc agcatccgca gctacgagat cggcgcggac    300

cgcaccgcca gcatcgagac cctgatgaac cacctgcagg agaccgccct gaaccacgtg    360

aagagtgtgg gcctgctgga ggacggcctg ggcagcaccc gcgagatgag cctgcgcaac    420

ctgatctggg tggtgaccaa gatgcaggtg gcggtggacc gctaccccac ctggggcgac    480

gaggtgcagg tgagcagctg ggcgaccgcc atcggcaaga acggcatgcg ccgcgagtgg    540

atcgtgaccg acttccgcac cggcgagacc ctgctgcgcg ccaccagcgt gtgggtgatg    600

atgaacaagc tgacccgccg catcagcaag atccccgagg aggtgtggca cgagatcggc    660

cccagcttca tcgacgcgcc cccccgcccc accgtggagg acgacggccg caagctgacc    720

cgcttcgacg agagcagcgc cgacttcatc cgcaagggcc tgaccccccg ctggagcgac    780

ctggacatca accagcacgt gaacaacgtg aagtacatcg gctggctgct ggagagcgcg    840

ccccccgaga tccacgagag ccacgagatc gccagcctga ccctggagta ccgccgcgag    900

tgcggccgcg acagcgtgct gaacagcgcc accaaggtga gcgacagcag ccagctgggc    960

aagagcgccg tggagtgcaa ccacctggtg cgcctgcaga acggcggcga gatcgtgaag   1020

ggccgcaccg tgtggcgccc caagcgcccc ctgtacaacg acggcgccgt ggtggacgtg   1080

cccgccaaga ccagctga                                                  1098
```

<210> SEQ ID NO 32
<211> LENGTH: 365
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 32

Pro Pro Lys Leu Asn Gly Ser Asn Val Gly Leu Val Lys Ser Ser Gln
1 5 10 15

Ile Val Lys Lys Gly Asp Asp Thr Thr Ser Pro Pro Ala Arg Thr Phe
20 25 30

Ile Asn Gln Leu Pro Asp Trp Ser Met Leu Leu Ala Ala Ile Thr Thr
35 40 45

Leu Phe Leu Ala Ala Glu Lys Gln Trp Met Met Leu Asp Trp Lys Pro
50 55 60

Lys Arg Pro Asp Met Leu Val Asp Pro Phe Gly Leu Gly Arg Phe Val
65 70 75 80

Gln Asp Gly Leu Val Phe Arg Asn Asn Phe Ser Ile Arg Ser Tyr Glu
85 90 95

Ile Gly Ala Asp Arg Thr Ala Ser Ile Glu Thr Leu Met Asn His Leu
100 105 110

Gln Glu Thr Ala Leu Asn His Val Lys Ser Val Gly Leu Leu Glu Asp
115 120 125

Gly Leu Gly Ser Thr Arg Glu Met Ser Leu Arg Asn Leu Ile Trp Val
130 135 140

Val Thr Lys Met Gln Val Ala Val Asp Arg Tyr Pro Thr Trp Gly Asp
145 150 155 160

Glu Val Gln Val Ser Ser Trp Ala Thr Ala Ile Gly Lys Asn Gly Met
165 170 175

Arg Arg Glu Trp Ile Val Thr Asp Phe Arg Thr Gly Glu Thr Leu Leu
180 185 190

Arg Ala Thr Ser Val Trp Val Met Met Asn Lys Leu Thr Arg Arg Ile
195 200 205

Ser Lys Ile Pro Glu Glu Val Trp His Glu Ile Gly Pro Ser Phe Ile
210 215 220

Asp Ala Pro Pro Leu Pro Thr Val Glu Asp Asp Gly Arg Lys Leu Thr
225 230 235 240

Arg Phe Asp Glu Ser Ser Ala Asp Phe Ile Arg Lys Gly Leu Thr Pro
245 250 255

Arg Trp Ser Asp Leu Asp Ile Asn Gln His Val Asn Asn Val Lys Tyr
260 265 270

Ile Gly Trp Leu Leu Glu Ser Ala Pro Pro Glu Ile His Glu Ser His
275 280 285

Glu Ile Ala Ser Leu Thr Leu Glu Tyr Arg Arg Glu Cys Gly Arg Asp
290 295 300

Ser Val Leu Asn Ser Ala Thr Lys Val Ser Asp Ser Ser Gln Leu Gly
305 310 315 320

Lys Ser Ala Val Glu Cys Asn His Leu Val Arg Leu Gln Asn Gly Gly
325 330 335

Glu Ile Val Lys Gly Arg Thr Val Trp Arg Pro Lys Arg Pro Leu Tyr
340 345 350

Asn Asp Gly Ala Val Val Asp Val Pro Ala Lys Thr Ser
355 360 365

<210> SEQ ID NO 33
<211> LENGTH: 1167
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
cccccaagc tgaacggctc caacgtgggc ctggtgaagt cctcccagat cgtgaagaag     60
ggcgacgaca ccacctcccc ccccgcccgc accttcatca accagctgcc cgactggagc    120
atgctgctgg ccgcgatcac caccctgttc ctggcggccg agaagcagtg gatgatgctg    180
gactggaagc ccaagcgccc cgacatgctg gtggacccct tcggcctggg ccgcttcgtg    240
caggacggcc tggtgttccg caacaacttc agcatccgca gctacgagat cggcgcggac    300
cgcaccgcca gcatcgagac cctgatgaac cacctgcagg agaccgccct gaaccacgtg    360
aagagtgtgg gcctgctgga ggacggcctg ggcagcaccc gcgagatgag cctgcgcaac    420
ctgatctggg tggtgaccaa gatgcaggtg gcggtggacc gctaccccac ctggggcgac    480
gaggtgcagg tgagcagctg ggcgaccgcc atcggcaaga acggcatgcg ccgcgagtgg    540
atcgtgaccg acttccgcac cggcgagacc ctgctgcgcg ccaccagcgt gtgggtgatg    600
atgaacaagc tgacccgccg catcagcaag atccccgagg aggtgtggca cgagatcggc    660
cccagcttca tcgacgcgcc ccccctgccc accgtggagg acgacggccg caagctgacc    720
cgcttcgacg agagcagcgc cgacttcatc cgcaagggcc tgaccccccg ctggagcgac    780
ctggacatca accagcacgt gaacaacgtg aagtacatcg gctggctgct ggagagcgcg    840
ccccccgaga tccacgagag ccacgagatc gccagcctga ccctggagta ccgccgcgag    900
tgcggccgcg acagcgtgct gaacagcgcc accaaggtga gcgacagcag ccagctgggc    960
aagagcgccg tggagtgcaa ccacctggtg cgcctgcaga acggcggcga gatcgtgaag   1020
ggccgcaccg tgtggcgccc caagcgcccc ctgtacaacg acggcgccgt ggtggacgtg   1080
cccgccaaga ccagcatgga ctacaaggac cacgacggcg actacaagga ccacgacatc   1140
gactacaagg acgacgacga caagtga                                       1167
```

<210> SEQ ID NO 34
<211> LENGTH: 388
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Pro Pro Lys Leu Asn Gly Ser Asn Val Gly Leu Val Lys Ser Ser Gln
1               5                   10                  15

Ile Val Lys Lys Gly Asp Asp Thr Thr Ser Pro Pro Ala Arg Thr Phe
            20                  25                  30

Ile Asn Gln Leu Pro Asp Trp Ser Met Leu Leu Ala Ala Ile Thr Thr
        35                  40                  45

Leu Phe Leu Ala Ala Glu Lys Gln Trp Met Met Leu Asp Trp Lys Pro
    50                  55                  60

Lys Arg Pro Asp Met Leu Val Asp Pro Phe Gly Leu Gly Arg Phe Val
65                  70                  75                  80

Gln Asp Gly Leu Val Phe Arg Asn Asn Phe Ser Ile Arg Ser Tyr Glu
                85                  90                  95

Ile Gly Ala Asp Arg Thr Ala Ser Ile Glu Thr Leu Met Asn His Leu
            100                 105                 110

Gln Glu Thr Ala Leu Asn His Val Lys Ser Val Gly Leu Leu Glu Asp
```

```
        115                 120                 125

Gly Leu Gly Ser Thr Arg Glu Met Ser Leu Arg Asn Leu Ile Trp Val
    130                 135                 140

Val Thr Lys Met Gln Val Ala Val Asp Arg Tyr Pro Thr Trp Gly Asp
145                 150                 155                 160

Glu Val Gln Val Ser Ser Trp Ala Thr Ala Ile Gly Lys Asn Gly Met
                165                 170                 175

Arg Arg Glu Trp Ile Val Thr Asp Phe Arg Thr Gly Glu Thr Leu Leu
            180                 185                 190

Arg Ala Thr Ser Val Trp Val Met Met Asn Lys Leu Thr Arg Arg Ile
        195                 200                 205

Ser Lys Ile Pro Glu Glu Val Trp His Glu Ile Gly Pro Ser Phe Ile
    210                 215                 220

Asp Ala Pro Pro Leu Pro Thr Val Glu Asp Asp Gly Arg Lys Leu Thr
225                 230                 235                 240

Arg Phe Asp Glu Ser Ser Ala Asp Phe Ile Arg Lys Gly Leu Thr Pro
                245                 250                 255

Arg Trp Ser Asp Leu Asp Ile Asn Gln His Val Asn Asn Val Lys Tyr
            260                 265                 270

Ile Gly Trp Leu Leu Glu Ser Ala Pro Pro Glu Ile His Glu Ser His
        275                 280                 285

Glu Ile Ala Ser Leu Thr Leu Glu Tyr Arg Arg Glu Cys Gly Arg Asp
    290                 295                 300

Ser Val Leu Asn Ser Ala Thr Lys Val Ser Asp Ser Ser Gln Leu Gly
305                 310                 315                 320

Lys Ser Ala Val Glu Cys Asn His Leu Val Arg Leu Gln Asn Gly Gly
                325                 330                 335

Glu Ile Val Lys Gly Arg Thr Val Trp Arg Pro Lys Arg Pro Leu Tyr
            340                 345                 350

Asn Asp Gly Ala Val Val Asp Val Pro Ala Lys Thr Ser Met Asp Tyr
        355                 360                 365

Lys Asp His Asp Gly Asp Tyr Lys Asp His Asp Ile Asp Tyr Lys Asp
    370                 375                 380

Asp Asp Asp Lys
385
```

<210> SEQ ID NO 35
<211> LENGTH: 1131
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atggccaccg catccacttt ctcggcgttc aatgcccgct gcggcgacct gcgtcgctcg     60

gcgggctccg ggccccggcg cccagcgagg cccctccccg tgcgcgctgc catcgccagc    120

gaggtccccg tggccaccac ctccccccgg agcctgaagc gcctgcccga ctggtccatg    180

ctgttcgccg tgatcaccac catcttctcc gccgccgaga agcagtggac caacctggag    240

tggaagccca agcccaaccc cccccagctg ctggacgacc acttcggccc ccacggcctg    300

gtgttccgcc gcaccttcgc catccgcagc tacgaggtgg gccccgaccg ctccaccagc    360

atcgtggccg tgatgaacca cctgcaggag gccgccctga accacgccaa gtccgtgggc    420

atcctgggcg acggcttcgg caccaccctg gagatgtcca agcgcgacct gatctgggtg    480
```

```
gtgcgccgca cccacgtggc cgtggagcgc taccccacct ggggcgacac cgtggaggtg    540

gagtgctgga tcggcgccag cggcaacaac ggcatgcgcc gcgacttcct ggtgcgcgac    600

tgcaagaccg gcgagatcct gacccgctgc acctccctga gcgtgctgat gaacacccgc    660

acccgccgcc tgagcaccat ccccgacgag gtgcgcggcg agatcggccc cgccttcatc    720

gacaacgtgg ccgtgaagga cgacgagatc aagaagctgc agaagctgaa cgactccacc    780

gccgactaca tccagggcgg cctgaccccc cgctggaacg acctggacgt gaaccagcac    840

gtgaacaacc tgaagtacgt ggcctgggtg ttcgagaccg tgcccgacag catcttcgag    900

tcccaccaca tcagctcctt caccctggag taccgccgcg agtgcacccg cgactccgtg    960

ctgcgcagcc tgaccaccgt gagcggcggc agctccgagg ccggcctggt gtgcgaccac   1020

ctgctgcagc tggagggcgg cagcgaggtg ctgcgcgccc gcaccgagtg gcgccccaag   1080

ctgaccgact ccttccgcgg catcagcgtg atccccgccg agccccgcgt g            1131
```

```
<210> SEQ ID NO 36
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Ala Ser Glu Val Pro Val Ala Thr Thr Ser
        35                  40                  45

Pro Arg Ser Leu Lys Arg Leu Pro Asp Trp Ser Met Leu Phe Ala Val
    50                  55                  60

Ile Thr Thr Ile Phe Ser Ala Ala Glu Lys Gln Trp Thr Asn Leu Glu
65                  70                  75                  80

Trp Lys Pro Lys Pro Asn Pro Pro Gln Leu Leu Asp Asp His Phe Gly
                85                  90                  95

Pro His Gly Leu Val Phe Arg Arg Thr Phe Ala Ile Arg Ser Tyr Glu
            100                 105                 110

Val Gly Pro Asp Arg Ser Thr Ser Ile Val Ala Val Met Asn His Leu
        115                 120                 125

Gln Glu Ala Ala Leu Asn His Ala Lys Ser Val Gly Ile Leu Gly Asp
    130                 135                 140

Gly Phe Gly Thr Thr Leu Glu Met Ser Lys Arg Asp Leu Ile Trp Val
145                 150                 155                 160

Val Arg Arg Thr His Val Ala Val Glu Arg Tyr Pro Thr Trp Gly Asp
                165                 170                 175

Thr Val Glu Val Glu Cys Trp Ile Gly Ala Ser Gly Asn Asn Gly Met
            180                 185                 190

Arg Arg Asp Phe Leu Val Arg Asp Cys Lys Thr Gly Glu Ile Leu Thr
        195                 200                 205

Arg Cys Thr Ser Leu Ser Val Leu Met Asn Thr Arg Thr Arg Arg Leu
    210                 215                 220

Ser Thr Ile Pro Asp Glu Val Arg Gly Glu Ile Gly Pro Ala Phe Ile
225                 230                 235                 240
```

```
Asp Asn Val Ala Val Lys Asp Asp Glu Ile Lys Lys Leu Gln Lys Leu
                245                 250                 255

Asn Asp Ser Thr Ala Asp Tyr Ile Gln Gly Gly Leu Thr Pro Arg Trp
            260                 265                 270

Asn Asp Leu Asp Val Asn Gln His Val Asn Asn Leu Lys Tyr Val Ala
        275                 280                 285

Trp Val Phe Glu Thr Val Pro Asp Ser Ile Phe Glu Ser His His Ile
    290                 295                 300

Ser Ser Phe Thr Leu Glu Tyr Arg Arg Glu Cys Thr Arg Asp Ser Val
305                 310                 315                 320

Leu Arg Ser Leu Thr Thr Val Ser Gly Gly Ser Ser Glu Ala Gly Leu
                325                 330                 335

Val Cys Asp His Leu Leu Gln Leu Glu Gly Gly Ser Glu Val Leu Arg
            340                 345                 350

Ala Arg Thr Glu Trp Arg Pro Lys Leu Thr Asp Ser Phe Arg Gly Ile
        355                 360                 365

Ser Val Ile Pro Ala Glu Pro Arg Val
    370                 375


<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Lys

<400> SEQUENCE: 37

Ser Leu Lys Xaa
1


<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Arg or Lys

<400> SEQUENCE: 38

Ile Asn Gly Thr Lys Phe Ser Tyr Thr Glu Ser Leu Lys Xaa
1               5                   10


<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30
```

Thr Phe Ile Asn Gln
35

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Pro Pro Lys Leu Asn Gly Ser Asn Val Gly Leu Val Lys Ser Ser Gln
1 5 10 15

Ile Val Lys Lys Gly Asp Asp Thr Thr Ser Pro Pro Ala Arg Thr Phe
20 25 30

Ile Asn Gln
35

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ala His Pro Lys Ala Asn Gly Ser Ala Val Asn Leu Lys Ser Gly Ser
1 5 10 15

Leu Glu Thr Pro Pro Arg Ser Phe Ile Asn Gln
20 25

<210> SEQ ID NO 42
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Pro His Pro Lys Ala Asn Gly Ser Ala Val Ser Leu Lys Ser Gly Ser
1 5 10 15

Leu Asn Thr Leu Glu Asp Pro Pro Ser Ser Pro Pro Pro Arg Thr Phe
20 25 30

Leu Asn Gln
35

<210> SEQ ID NO 43
<211> LENGTH: 382
<212> TYPE: PRT
<213> ORGANISM: Umbellularia californica

<400> SEQUENCE: 43

Met Ala Thr Thr Ser Leu Ala Ser Ala Phe Cys Ser Met Lys Ala Val
1 5 10 15

Met Leu Ala Arg Asp Gly Arg Gly Met Lys Pro Arg Ser Ser Asp Leu
20 25 30

Gln Leu Arg Ala Gly Asn Ala Pro Thr Ser Leu Lys Met Ile Asn Gly
35 40 45

Thr Lys Phe Ser Tyr Thr Glu Ser Leu Lys Arg Leu Pro Asp Trp Ser

-continued

```
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380


<210> SEQ ID NO 44
<211> LENGTH: 382
<212> TYPE: PRT
<213> ORGANISM: Cinnamomum camphora

<400> SEQUENCE: 44

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45
```

Thr Lys Phe Ser Tyr Thr Glu Ser Leu Lys Lys Leu Pro Asp Trp Ser
    50              55              60

Met Leu Phe Ala Val Ile Thr Thr Ile Phe Ser Ala Ala Glu Lys Gln
65              70              75              80

Trp Thr Asn Leu Glu Trp Lys Pro Lys Pro Asn Pro Pro Gln Leu Leu
            85              90              95

Asp Asp His Phe Gly Pro His Gly Leu Val Phe Arg Arg Thr Phe Ala
        100             105             110

Ile Arg Ser Tyr Glu Val Gly Pro Asp Arg Ser Thr Ser Ile Val Ala
    115             120             125

Val Met Asn His Leu Gln Glu Ala Ala Leu Asn His Ala Lys Ser Val
    130             135             140

Gly Ile Leu Gly Asp Gly Phe Gly Thr Thr Leu Glu Met Ser Lys Arg
145             150             155             160

Asp Leu Ile Trp Val Val Lys Arg Thr His Val Ala Val Glu Arg Tyr
            165             170             175

Pro Ala Trp Gly Asp Thr Val Glu Val Glu Cys Trp Val Gly Ala Ser
        180             185             190

Gly Asn Asn Gly Arg Arg His Asp Phe Leu Val Arg Asp Cys Lys Thr
    195             200             205

Gly Glu Ile Leu Thr Arg Cys Thr Ser Leu Ser Val Met Met Asn Thr
    210             215             220

Arg Thr Arg Arg Leu Ser Lys Ile Pro Glu Glu Val Arg Gly Glu Ile
225             230             235             240

Gly Pro Ala Phe Ile Asp Asn Val Ala Val Lys Asp Glu Glu Ile Lys
            245             250             255

Lys Pro Gln Lys Leu Asn Asp Ser Thr Ala Asp Tyr Ile Gln Gly Gly
        260             265             270

Leu Thr Pro Arg Trp Asn Asp Leu Asp Ile Asn Gln His Val Asn Asn
    275             280             285

Ile Lys Tyr Val Asp Trp Ile Leu Glu Thr Val Pro Asp Ser Ile Phe
    290             295             300

Glu Ser His His Ile Ser Ser Phe Thr Ile Glu Tyr Arg Arg Glu Cys
305             310             315             320

Thr Met Asp Ser Val Leu Gln Ser Leu Thr Thr Val Ser Gly Gly Ser
            325             330             335

Ser Glu Ala Gly Leu Val Cys Glu His Leu Leu Gln Leu Glu Gly Gly
        340             345             350

Ser Glu Val Leu Arg Ala Lys Thr Glu Trp Arg Pro Lys Leu Thr Asp
    355             360             365

Ser Phe Arg Gly Ile Ser Val Ile Pro Ala Glu Ser Ser Val
    370             375             380

<210> SEQ ID NO 45
<211> LENGTH: 411
<212> TYPE: PRT
<213> ORGANISM: Cuphea palustris

<400> SEQUENCE: 45

Met Val Ala Ala Ala Ala Ser Ala Ala Phe Phe Ser Val Ala Thr Pro
1               5               10              15

Arg Thr Asn Ile Ser Pro Ser Ser Leu Ser Val Pro Phe Lys Pro Lys
            20              25              30

Ser Asn His Asn Gly Gly Phe Gln Val Lys Ala Asn Ala Ser Ala His
        35              40              45

```
Pro Lys Ala Asn Gly Ser Ala Val Ser Leu Lys Ser Gly Ser Leu Glu
    50                  55                  60

Thr Gln Glu Asp Lys Thr Ser Ser Ser Ser Pro Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
            100                 105                 110

Lys Arg Pro Asp Met Leu Val Glu Pro Leu Gly Val Asp Arg Ile Val
        115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
            180                 185                 190

Val Thr Lys Met Gln Ile Glu Val Asn Arg Tyr Pro Thr Trp Gly Asp
        195                 200                 205

Thr Ile Glu Val Asn Thr Trp Val Ser Ala Ser Gly Lys His Gly Met
    210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Asp Arg Lys Phe His Lys Leu Asp
        275                 280                 285

Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
            340                 345                 350

Glu Ser Val Thr Ala Met Asp Pro Ser Lys Glu Gly Asp Arg Ser Leu
        355                 360                 365

Tyr Gln His Leu Leu Arg Leu Glu Asp Gly Ala Asp Ile Val Lys Gly
    370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410
```

<210> SEQ ID NO 46
<211> LENGTH: 398
<212> TYPE: PRT
<213> ORGANISM: Cuphea wrightii

<400> SEQUENCE: 46

```
Met Val Ala Ala Ala Ala Ser Ser Ala Phe Phe Ser Val Pro Thr Pro
```

-continued

```
1               5                   10                  15

Gly Thr Ser Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Met Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Arg Lys Leu His
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Thr Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Ile Ser Ser Gly Lys Thr Ser Asn Gly Asn Ser Val Ser
385                 390                 395
```

<210> SEQ ID NO 47
<211> LENGTH: 378
<212> TYPE: PRT
<213> ORGANISM: Ulmus americana
<220> FEATURE:
<221> NAME/KEY: MOD_RES
<222> LOCATION: (265)..(265)
<223> OTHER INFORMATION: Any amino acid
<220> FEATURE:
<221> NAME/KEY: MOD_RES
<222> LOCATION: (374)..(374)
<223> OTHER INFORMATION: Any amino acid

<400> SEQUENCE: 47

```
Gly Ser Gly Ala Leu Gln Val Lys Ala Ser Ser Gln Ala Pro Pro Lys
1               5                   10                  15

Leu Asn Gly Ser Asn Val Gly Leu Val Lys Ser Ser Gln Ile Val Lys
            20                  25                  30

Lys Gly Asp Asp Thr Thr Ser Pro Pro Ala Arg Thr Phe Ile Asn Gln
        35                  40                  45

Leu Pro Asp Trp Ser Met Leu Leu Ala Ala Ile Thr Thr Leu Phe Leu
    50                  55                  60

Ala Ala Glu Lys Gln Trp Met Met Leu Asp Trp Lys Pro Lys Arg Pro
65                  70                  75                  80

Asp Met Leu Val Asp Pro Phe Gly Leu Gly Arg Phe Val Gln Asp Gly
                85                  90                  95

Leu Val Phe Arg Asn Asn Phe Ser Ile Arg Ser Tyr Glu Ile Gly Ala
            100                 105                 110

Asp Arg Thr Ala Ser Ile Glu Thr Leu Met Asn His Leu Gln Glu Thr
        115                 120                 125

Ala Leu Asn His Val Lys Ser Val Gly Leu Leu Glu Asp Gly Leu Gly
    130                 135                 140

Ser Thr Arg Glu Met Ser Leu Arg Asn Leu Ile Trp Val Val Thr Lys
145                 150                 155                 160

Met Gln Val Ala Val Asp Arg Tyr Pro Thr Trp Gly Asp Glu Val Gln
                165                 170                 175

Val Ser Ser Trp Ala Thr Ala Ile Gly Lys Asn Gly Met Arg Arg Glu
            180                 185                 190

Trp Ile Val Thr Asp Phe Arg Thr Gly Glu Thr Leu Leu Arg Ala Thr
        195                 200                 205

Ser Val Trp Val Met Met Asn Lys Leu Thr Arg Arg Ile Ser Lys Ile
    210                 215                 220

Pro Glu Glu Val Trp His Glu Ile Gly Pro Ser Phe Ile Asp Ala Pro
225                 230                 235                 240

Pro Leu Pro Thr Val Glu Asp Asp Gly Arg Lys Leu Thr Arg Phe Asp
                245                 250                 255

Glu Ser Ser Ala Asp Phe Ile Arg Xaa Gly Leu Thr Pro Arg Trp Ser
            260                 265                 270

Asp Leu Asp Ile Asn Gln His Val Asn Asn Val Lys Tyr Ile Gly Trp
        275                 280                 285

Leu Leu Glu Ser Ala Pro Pro Glu Ile His Glu Ser His Glu Ile Ala
    290                 295                 300

Ser Leu Thr Leu Glu Tyr Arg Arg Glu Cys Gly Arg Asp Ser Val Leu
305                 310                 315                 320

Asn Ser Ala Thr Lys Val Ser Asp Ser Ser Gln Leu Gly Lys Ser Ala
                325                 330                 335

Val Glu Cys Asn His Leu Val Arg Leu Gln Asn Gly Gly Glu Ile Val
            340                 345                 350

Lys Gly Arg Thr Val Trp Arg Pro Lys Arg Pro Leu Tyr Asn Asp Gly
        355                 360                 365
```

Ala Val Val Asp Val Xaa Ala Lys Thr Ser
    370                 375

<210> SEQ ID NO 48
<211> LENGTH: 1302
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggtggtgg ccgccgccgc cagcagcgcc ttcttccccg tgcccgcccc ccgccccacc 60
cccaagcccg gcaagttcgg caactggccc agcagcctga gccagccctt caagcccaag 120
agcaacccca acggccgctt ccaggtgaag gccaacgtga gcccccacgg gcgcgccccc 180
aaggccaacg gcagcgccgt gagcctgaag tccggcagcc tgaacaccct ggaggacccc 240
cccagcagcc cccccccccg caccttcctg aaccagctgc ccgactggag ccgcctgctg 300
accgccatca ccaccgtgtt cgtgaagtcc aagcgccccg acatgcacga ccgcaagtcc 360
aagcgccccg acatgctggt ggacagcttc ggcctggagt ccaccgtgca ggacggcctg 420
gtgttccgcc agtccttctc catccgctcc tacgagatcg gcaccgaccg caccgccagc 480
atcgagaccc tgatgaacca cctgcaggag acctccctga accactgcaa gagcaccggc 540
atcctgctgg acggcttcgg ccgcaccctg gagatgtgca agcgcgacct gatctgggtg 600
gtgattaaga tgcagatcaa ggtgaaccgc taccccacct ggggcgacac cgtggagatc 660
aacagctggt tcagccagag cggcaagatc ggcatgggcc gcgagtggct gatcagcgac 720
tgcaacaccg gcgagatcct ggtgcgcgcc accagcgcct gggccatgat gaaccagaag 780
acccgccgct tcagcaagct gccctgcgag gtgcgccagg agatcgcccc ccacttcgtg 840
gacgcccccc ccgtgatcga ggacaacgac cgcaagctgc acaagttcga cgtgaagacc 900
ggcgacagca tctgcaaggg cctgaccccc ggctggaacg acttcgacgt gaaccagcac 960
gtgagcaacg tgaagtacat cggctggatt ctggagagca tgcccaccga ggtgctggag 1020
acccaggagc tgtgcagcct gaccctggag taccgccgcg agtgcggccg cgagagcgtg 1080
gtggagagcg tgaccagcat gaaccccagc aaggtgggcg accgcagcca gtaccagcac 1140
ctgctgcgcc tggaggacgg cgccgacatc atgaagggcc gcaccgagtg gcgccccaag 1200
aacgccggca ccaaccgcgc catcagcacc atggactaca aggaccacga cggcgactac 1260
aaggaccacg acatcgacta caaggacgac gacgacaagt ga 1302

<210> SEQ ID NO 49
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

```
Val Lys Ala Asn Val Ser Pro His Gly Arg Ala Pro Lys Ala Asn Gly
    50                  55                  60

Ser Ala Val Ser Leu Lys Ser Gly Ser Leu Asn Thr Leu Glu Asp Pro
65                  70                  75                  80

Pro Ser Ser Pro Pro Pro Arg Thr Phe Leu Asn Gln Leu Pro Asp Trp
                85                  90                  95

Ser Arg Leu Leu Thr Ala Ile Thr Thr Val Phe Val Lys Ser Lys Arg
            100                 105                 110

Pro Asp Met His Asp Arg Lys Ser Lys Arg Pro Asp Met Leu Val Asp
        115                 120                 125

Ser Phe Gly Leu Glu Ser Thr Val Gln Asp Gly Leu Val Phe Arg Gln
    130                 135                 140

Ser Phe Ser Ile Arg Ser Tyr Glu Ile Gly Thr Asp Arg Thr Ala Ser
145                 150                 155                 160

Ile Glu Thr Leu Met Asn His Leu Gln Glu Thr Ser Leu Asn His Cys
                165                 170                 175

Lys Ser Thr Gly Ile Leu Leu Asp Gly Phe Gly Arg Thr Leu Glu Met
            180                 185                 190

Cys Lys Arg Asp Leu Ile Trp Val Val Ile Lys Met Gln Ile Lys Val
        195                 200                 205

Asn Arg Tyr Pro Thr Trp Gly Asp Thr Val Glu Ile Asn Ser Trp Phe
    210                 215                 220

Ser Gln Ser Gly Lys Ile Gly Met Gly Arg Glu Trp Leu Ile Ser Asp
225                 230                 235                 240

Cys Asn Thr Gly Glu Ile Leu Val Arg Ala Thr Ser Ala Trp Ala Met
                245                 250                 255

Met Asn Gln Lys Thr Arg Arg Phe Ser Lys Leu Pro Cys Glu Val Arg
            260                 265                 270

Gln Glu Ile Ala Pro His Phe Val Asp Ala Pro Pro Val Ile Glu Asp
        275                 280                 285

Asn Asp Arg Lys Leu His Lys Phe Asp Val Lys Thr Gly Asp Ser Ile
    290                 295                 300

Cys Lys Gly Leu Thr Pro Gly Trp Asn Asp Phe Asp Val Asn Gln His
305                 310                 315                 320

Val Ser Asn Val Lys Tyr Ile Gly Trp Ile Leu Glu Ser Met Pro Thr
                325                 330                 335

Glu Val Leu Glu Thr Gln Glu Leu Cys Ser Leu Thr Leu Glu Tyr Arg
            340                 345                 350

Arg Glu Cys Gly Arg Glu Ser Val Val Glu Ser Val Thr Ser Met Asn
        355                 360                 365

Pro Ser Lys Val Gly Asp Arg Ser Gln Tyr Gln His Leu Leu Arg Leu
    370                 375                 380

Glu Asp Gly Ala Asp Ile Met Lys Gly Arg Thr Glu Trp Arg Pro Lys
385                 390                 395                 400

Asn Ala Gly Thr Asn Arg Ala Ile Ser Thr Met Asp Tyr Lys Asp His
                405                 410                 415

Asp Gly Asp Tyr Lys Asp His Asp Ile Asp Tyr Lys Asp Asp Asp Asp
            420                 425                 430

Lys
```

<210> SEQ ID NO 50
<211> LENGTH: 1305
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50

```
atggtggtgg ccgccgccgc cagcagcgcc ttcttccccg tgcccgcccc ccgccccacc      60

cccaagcccg gcaagttcgg caactggccc agcagcctga gccagccctt caagcccaag     120

agcaacccca acggccgctt ccaggtgaag gccaacgtga gcccccacgg gcgcgccccc     180

aaggccaacg gcagcgccgt gagcctgaag tccggcagcc tgaacaccct ggaggacccc     240

cccagcagcc cccccccccg caccttcctg aaccagctgc ccgactggag ccgcctgcgc     300

accgccatca ccaccgtgtt cgtggccgcc gagaagcagt tcacccgcct ggaccgcaag     360

agcaagcgcc ccgacatgct ggtggactgg ttcggcagcg agaccatcgt gcaggacggc     420

ctggtgttcc gcgagcgctt cagcatccgc agctacgaga tcggcgccga ccgcaccgcc     480

agcatcgaga ccctgatgaa ccacctgcag gagacctccc tgaaccactg caagagcacc     540

ggcatcctgc tggacggctt cggccgcacc ctggagatgt gcaagcgcga cctgatctgg     600

gtggtgatta agatgcagat caaggtgaac cgctacccca cctggggcga caccgtggag     660

atcaacagct ggttcagcca gagcggcaag atcggcatgg gccgcgagtg gctgatcagc     720

gactgcaaca ccggcgagat cctggtgcgc gccaccagcg cctgggccat gatgaaccag     780

aagacccgcc gcttcagcaa gctgccctgc gaggtgcgcc aggagatcgc cccccacttc     840

gtggacgccc cccccgtgat cgaggacaac gaccgcaagc tgcacaagtt cgacgtgaag     900

accggcgaca gcatctgcaa gggcctgacc cccggctgga acgacttcga cgtgaaccag     960

cacgtgagca acgtgaagta catcggctgg attctggaga gcatgcccac cgaggtgctg    1020

gagacccagg agctgtgcag cctgaccctg gagtaccgcc gcgagtgcgg ccgcgagagc    1080

gtggtggaga gcgtgaccag catgaacccc agcaaggtgg gcgaccgcag ccagtaccag    1140

cacctgctgc gcctggagga cggcgccgac atcatgaagg gccgcaccga gtggcgcccc    1200

aagaacgccg gcaccaaccg cgccatcagc accatggact acaaggacca cgacggcgac    1260

tacaaggacc acgacatcga ctacaaggac gacgacgaca agtga                    1305
```

<210> SEQ ID NO 51
<211> LENGTH: 434
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

```
Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

Val Lys Ala Asn Val Ser Pro His Gly Arg Ala Pro Lys Ala Asn Gly
    50                  55                  60

Ser Ala Val Ser Leu Lys Ser Gly Ser Leu Asn Thr Leu Glu Asp Pro
65                  70                  75                  80

Pro Ser Ser Pro Pro Pro Arg Thr Phe Leu Asn Gln Leu Pro Asp Trp
                85                  90                  95
```

```
Ser Arg Leu Arg Thr Ala Ile Thr Thr Val Phe Val Ala Ala Glu Lys
            100                 105                 110

Gln Phe Thr Arg Leu Asp Arg Lys Ser Lys Arg Pro Asp Met Leu Val
        115                 120                 125

Asp Trp Phe Gly Ser Glu Thr Ile Val Gln Asp Gly Leu Val Phe Arg
    130                 135                 140

Glu Arg Phe Ser Ile Arg Ser Tyr Glu Ile Gly Ala Asp Arg Thr Ala
145                 150                 155                 160

Ser Ile Glu Thr Leu Met Asn His Leu Gln Glu Thr Ser Leu Asn His
                165                 170                 175

Cys Lys Ser Thr Gly Ile Leu Leu Asp Gly Phe Gly Arg Thr Leu Glu
            180                 185                 190

Met Cys Lys Arg Asp Leu Ile Trp Val Val Ile Lys Met Gln Ile Lys
        195                 200                 205

Val Asn Arg Tyr Pro Thr Trp Gly Asp Thr Val Glu Ile Asn Ser Trp
    210                 215                 220

Phe Ser Gln Ser Gly Lys Ile Gly Met Gly Arg Glu Trp Leu Ile Ser
225                 230                 235                 240

Asp Cys Asn Thr Gly Glu Ile Leu Val Arg Ala Thr Ser Ala Trp Ala
                245                 250                 255

Met Met Asn Gln Lys Thr Arg Arg Phe Ser Lys Leu Pro Cys Glu Val
            260                 265                 270

Arg Gln Glu Ile Ala Pro His Phe Val Asp Ala Pro Pro Val Ile Glu
        275                 280                 285

Asp Asn Asp Arg Lys Leu His Lys Phe Asp Val Lys Thr Gly Asp Ser
    290                 295                 300

Ile Cys Lys Gly Leu Thr Pro Gly Trp Asn Asp Phe Asp Val Asn Gln
305                 310                 315                 320

His Val Ser Asn Val Lys Tyr Ile Gly Trp Ile Leu Glu Ser Met Pro
                325                 330                 335

Thr Glu Val Leu Glu Thr Gln Glu Leu Cys Ser Leu Thr Leu Glu Tyr
            340                 345                 350

Arg Arg Glu Cys Gly Arg Glu Ser Val Val Glu Ser Val Thr Ser Met
        355                 360                 365

Asn Pro Ser Lys Val Gly Asp Arg Ser Gln Tyr Gln His Leu Leu Arg
    370                 375                 380

Leu Glu Asp Gly Ala Asp Ile Met Lys Gly Arg Thr Glu Trp Arg Pro
385                 390                 395                 400

Lys Asn Ala Gly Thr Asn Arg Ala Ile Ser Thr Met Asp Tyr Lys Asp
                405                 410                 415

His Asp Gly Asp Tyr Lys Asp His Asp Ile Asp Tyr Lys Asp Asp Asp
            420                 425                 430

Asp Lys
```

<210> SEQ ID NO 52
<211> LENGTH: 1302
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
atggtggtgg ccgccgccgc cagcagcgcc ttcttccccg tgcccgcccc ccgccccacc      60

cccaagcccg gcaagttcgg caactggccc agcagcctga gccagccctt caagcccaag     120
```

```
agcaacccca acggccgctt ccaggtgaag gccaacgtga gcccccacgg gcgcgccccc    180

aaggccaacg gcagcgccgt gagcctgaag tccggcagcc tgaacaccct ggaggacccc    240

cccagcagcc ccccccccg caccttcctg aaccagctgc ccgactggag ccgcctgctg    300

accgccatca ccaccgtgtt cgtgaagtcc aagcgccccg acatgcacga ccgcaagtcc    360

aagcgccccg acatgctggt ggacagcttc ggcctggagt ccaccgtgca ggacggcctg    420

gtgttccgcc agtccttctc catccgctcc tacgagatcg gcaccgaccg caccgccagc    480

atcgagaccc tgatgaacca cctgcaggac accagcctga accactgcaa gagcgtgggc    540

ctgctgaacg acggcttcgg ccgcaccccc gagatgtgca cccgcgacct gatctgggtg    600

ctgaccaaga tgcagatcgt ggtgaaccgc taccccacct ggggcgacac cgtggagatc    660

aacagctggt tcagccagag cggcaagatc ggcatgggcc gcgagtggct gatcagcgac    720

tgcaacaccg gcgagatcct ggtgcgcgcc accagcgcct gggccatgat gaaccagaag    780

acccgccgct tcagcaagct gccctgcgag gtgcgccagg agatcgcccc ccacttcgtg    840

gacgcccccc ccgtgatcga ggacaacgac cgcaagctgc acaagttcga cgtgaagacc    900

ggcgacagca tctgcaaggg cctgaccccc ggctggaacg acttcgacgt gaaccagcac    960

gtgagcaacg tgaagtacat cggctggatt ctggagagca tgcccaccga ggtgctggag   1020

acccaggagc tgtgcagcct gaccctggag taccgccgcg agtgcggccg cgagagcgtg   1080

gtggagagcg tgaccagcat gaaccccagc aaggtgggcg accgcagcca gtaccagcac   1140

ctgctgcgcc tggaggacgg cgccgacatc atgaagggcc gcaccgagtg gcgccccaag   1200

aacgccggca ccaaccgcgc catcagcacc atggactaca aggaccacga cggcgactac   1260

aaggaccacg acatcgacta caaggacgac gacgacaagt ga                      1302
```

<210> SEQ ID NO 53
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

Val Lys Ala Asn Val Ser Pro His Gly Arg Ala Pro Lys Ala Asn Gly
    50                  55                  60

Ser Ala Val Ser Leu Lys Ser Gly Ser Leu Asn Thr Leu Glu Asp Pro
65                  70                  75                  80

Pro Ser Ser Pro Pro Pro Arg Thr Phe Leu Asn Gln Leu Pro Asp Trp
                85                  90                  95

Ser Arg Leu Leu Thr Ala Ile Thr Thr Val Phe Val Lys Ser Lys Arg
            100                 105                 110

Pro Asp Met His Asp Arg Lys Ser Lys Arg Pro Asp Met Leu Val Asp
        115                 120                 125

Ser Phe Gly Leu Glu Ser Thr Val Gln Asp Gly Leu Val Phe Arg Gln
    130                 135                 140
```

```
Ser Phe Ser Ile Arg Ser Tyr Glu Ile Gly Thr Asp Arg Thr Ala Ser
145                 150                 155                 160

Ile Glu Thr Leu Met Asn His Leu Gln Asp Thr Ser Leu Asn His Cys
                165                 170                 175

Lys Ser Val Gly Leu Leu Asn Asp Gly Phe Gly Arg Thr Pro Glu Met
            180                 185                 190

Cys Thr Arg Asp Leu Ile Trp Val Leu Thr Lys Met Gln Ile Val Val
        195                 200                 205

Asn Arg Tyr Pro Thr Trp Gly Asp Thr Val Glu Ile Asn Ser Trp Phe
    210                 215                 220

Ser Gln Ser Gly Lys Ile Gly Met Gly Arg Glu Trp Leu Ile Ser Asp
225                 230                 235                 240

Cys Asn Thr Gly Glu Ile Leu Val Arg Ala Thr Ser Ala Trp Ala Met
                245                 250                 255

Met Asn Gln Lys Thr Arg Arg Phe Ser Lys Leu Pro Cys Glu Val Arg
            260                 265                 270

Gln Glu Ile Ala Pro His Phe Val Asp Ala Pro Pro Val Ile Glu Asp
        275                 280                 285

Asn Asp Arg Lys Leu His Lys Phe Asp Val Lys Thr Gly Asp Ser Ile
    290                 295                 300

Cys Lys Gly Leu Thr Pro Gly Trp Asn Asp Phe Asp Val Asn Gln His
305                 310                 315                 320

Val Ser Asn Val Lys Tyr Ile Gly Trp Ile Leu Glu Ser Met Pro Thr
                325                 330                 335

Glu Val Leu Glu Thr Gln Glu Leu Cys Ser Leu Thr Leu Glu Tyr Arg
            340                 345                 350

Arg Glu Cys Gly Arg Glu Ser Val Val Glu Ser Val Thr Ser Met Asn
        355                 360                 365

Pro Ser Lys Val Gly Asp Arg Ser Gln Tyr Gln His Leu Leu Arg Leu
    370                 375                 380

Glu Asp Gly Ala Asp Ile Met Lys Gly Arg Thr Glu Trp Arg Pro Lys
385                 390                 395                 400

Asn Ala Gly Thr Asn Arg Ala Ile Ser Thr Met Asp Tyr Lys Asp His
                405                 410                 415

Asp Gly Asp Tyr Lys Asp His Asp Ile Asp Tyr Lys Asp Asp Asp Asp
            420                 425                 430

Lys


<210> SEQ ID NO 54
<211> LENGTH: 1302
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

atggtggtgg ccgccgccgc cagcagcgcc ttcttccccg tgcccgcccc ccgccccacc     60

cccaagcccg gcaagttcgg caactggccc agcagcctga gccagccctt caagcccaag    120

agcaacccca acggccgctt ccaggtgaag gccaacgtga gcccccacgg gcgcgccccc    180

aaggccaacg gctccgccgt gagcctgaag agcggcagcc tgaacaccca ggaggacacc    240

tcctccagcc cccccccccg caccttcctg caccagctgc ccgactggag ccgcctgctg    300

accgccatca ccaccgtgtt cgtgaagtcc aagcgccccg acatgcacga ccgcaagtcc    360
```

```
aagcgccccg acatgctggt ggacagcttc ggcctggagt ccaccgtgca ggacggcctg    420

gtgttccgcc agtccttctc catccgctcc tacgagatcg gcaccgaccg caccgccagc    480

atcgagaccc tgatgaacca cctgcaggag acctccctga accactgcaa gagcaccggc    540

atcctgctgg acggcttcgg ccgcaccctg gagatgtgca agcgcgacct gatctgggtg    600

gtgattaaga tgcagatcaa ggtgaaccgc taccccacct ggggcgacac cgtggagatc    660

aacagctggt tcagccagag cggcaagatc ggcatgggcc gcgagtggct gatcagcgac    720

tgcaacaccg gcgagatcct ggtgcgcgcc accagcgcct gggccatgat gaaccagaag    780

acccgccgct tcagcaagct gccctgcgag gtgcgccagg agatcgcccc ccacttcgtg    840

gacgcccccc ccgtgatcga ggacaacgac cgcaagctgc acaagttcga cgtgaagacc    900

ggcgacagca tctgcaaggg cctgaccccc ggctggaacg acttcgacgt gaaccagcac    960

gtgagcaacg tgaagtacat cggctggatt ctggagagca tgcccaccga ggtgctggag   1020

acccaggagc tgtgcagcct gaccctggag taccgccgcg agtgcggccg cgagagcgtg   1080

gtggagagcg tgaccagcat gaaccccagc aaggtgggcg accgcagcca gtaccagcac   1140

ctgctgcgcc tggaggacgg cgccgacatc atgaagggcc gcaccgagtg gcgccccaag   1200

aacgccggca ccaaccgcgc catcagcacc atggactaca aggaccacga cggcgactac   1260

aaggaccacg acatcgacta caaggacgac gacgacaagt ga                      1302
```

```
<210> SEQ ID NO 55
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

Val Lys Ala Asn Val Ser Pro His Gly Arg Ala Pro Lys Ala Asn Gly
    50                  55                  60

Ser Ala Val Ser Leu Lys Ser Gly Ser Leu Asn Thr Gln Glu Asp Thr
65                  70                  75                  80

Ser Ser Ser Pro Pro Pro Arg Thr Phe Leu His Gln Leu Pro Asp Trp
                85                  90                  95

Ser Arg Leu Leu Thr Ala Ile Thr Thr Val Phe Val Lys Ser Lys Arg
            100                 105                 110

Pro Asp Met His Asp Arg Lys Ser Lys Arg Pro Asp Met Leu Val Asp
        115                 120                 125

Ser Phe Gly Leu Glu Ser Thr Val Gln Asp Gly Leu Val Phe Arg Gln
    130                 135                 140

Ser Phe Ser Ile Arg Ser Tyr Glu Ile Gly Thr Asp Arg Thr Ala Ser
145                 150                 155                 160

Ile Glu Thr Leu Met Asn His Leu Gln Glu Thr Ser Leu Asn His Cys
                165                 170                 175

Lys Ser Thr Gly Ile Leu Leu Asp Gly Phe Gly Arg Thr Leu Glu Met
            180                 185                 190
```

```
Cys Lys Arg Asp Leu Ile Trp Val Val Ile Lys Met Gln Ile Lys Val
        195                 200                 205

Asn Arg Tyr Pro Thr Trp Gly Asp Thr Val Glu Ile Asn Ser Trp Phe
    210                 215                 220

Ser Gln Ser Gly Lys Ile Gly Met Gly Arg Glu Trp Leu Ile Ser Asp
225                 230                 235                 240

Cys Asn Thr Gly Glu Ile Leu Val Arg Ala Thr Ser Ala Trp Ala Met
                245                 250                 255

Met Asn Gln Lys Thr Arg Arg Phe Ser Lys Leu Pro Cys Glu Val Arg
            260                 265                 270

Gln Glu Ile Ala Pro His Phe Val Asp Ala Pro Pro Val Ile Glu Asp
        275                 280                 285

Asn Asp Arg Lys Leu His Lys Phe Asp Val Lys Thr Gly Asp Ser Ile
    290                 295                 300

Cys Lys Gly Leu Thr Pro Gly Trp Asn Asp Phe Asp Val Asn Gln His
305                 310                 315                 320

Val Ser Asn Val Lys Tyr Ile Gly Trp Ile Leu Glu Ser Met Pro Thr
                325                 330                 335

Glu Val Leu Glu Thr Gln Glu Leu Cys Ser Leu Thr Leu Glu Tyr Arg
            340                 345                 350

Arg Glu Cys Gly Arg Glu Ser Val Val Glu Ser Val Thr Ser Met Asn
        355                 360                 365

Pro Ser Lys Val Gly Asp Arg Ser Gln Tyr Gln His Leu Leu Arg Leu
    370                 375                 380

Glu Asp Gly Ala Asp Ile Met Lys Gly Arg Thr Glu Trp Arg Pro Lys
385                 390                 395                 400

Asn Ala Gly Thr Asn Arg Ala Ile Ser Thr Met Asp Tyr Lys Asp His
                405                 410                 415

Asp Gly Asp Tyr Lys Asp His Asp Ile Asp Tyr Lys Asp Asp Asp Asp
            420                 425                 430

Lys
```

<210> SEQ ID NO 56
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atggtggtgg ccgccgccgc cagcagcgcc ttcttccccg tgcccgcccc ccgccccacc     60

cccaagcccg gcaagttcgg caactggccc agcagcctga gccagccctt caagcccaag    120

agcaacccca acggccgctt ccaggtgaag gccaacgtga gcccccacgg gcgcgccccc    180

aaggccaacg gctccgccgt gagcctgaag agcggcagcc tgaacaccca ggaggacacc    240

tcctccagcc cccccccccg caccttcctg caccagctgc ccgactggag ccgcctgctg    300

accgccatca ccaccgtgtt cgtgaagtcc aagcgccccg acatgcacga ccgcaagtcc    360

aagcgccccg acatgctggt ggacagcttc ggcctggagt ccaccgtgca ggacggcctg    420

gtgttccgcc agtccttctc catccgctcc tacgagatcg gcaccgaccg caccgccagc    480

atcgagaccc tgatgaacca cctgcaggag acctccctga accactgcaa gagcaccggc    540

atcctgctgg acggcttcgg ccgcaccctg gagatgtgca agcgcgacct gatctgggtg    600

gtgatcaaga tgcagatcaa ggtgaaccgc taccccgcct ggggcgacac cgtggagatc    660
```

aacacccgct tcagccgcct gggcaagatc ggcatgggcc gcgactggct gatctccgac 720
tgcaacaccg gcgagatcct ggtgcgcgcc accagcgcct acgccatgat gaaccagaag 780
acccgccgcc tgtccaagct gccctacgag gtgcaccagg agatcgtgcc cctgttcgtg 840
gacagccccg tgatcgagga ctccgacctg aaggtgcaca agttcaaggt gaagaccggc 900
gacagcatcc agaagggcct gacccccggc tggaacgacc tggacgtgaa ccagcacgtg 960
tccaacgtga agtacatcgg ctggatcctg gagagcatgc ccaccgaggt gctggagacc 1020
caggagctgt gctccctggc cctggagtac cgccgcgagt gcggccgcga ctccgtgctg 1080
gagagcgtga ccgccatgga ccccagcaag gtgggcgtgc gctcccagta ccagcacctg 1140
ctgcgcctgg aggacggcac cgccatcgtg aacggcgcca ccgagtggcg ccccaagaac 1200
gccggcgcca acggcgccat ctccaccggc aagaccagca acggcaactc cgtgtccatg 1260
gactacaagg accacgacgg cgactacaag gaccacgaca tcgactacaa ggacgacgac 1320
gacaagtga 1329

<210> SEQ ID NO 57
<211> LENGTH: 442
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Met Val Val Ala Ala Ala Ala Ser Ser Ala Phe Phe Pro Val Pro Ala
1 5 10 15

Pro Arg Pro Thr Pro Lys Pro Gly Lys Phe Gly Asn Trp Pro Ser Ser
20 25 30

Leu Ser Gln Pro Phe Lys Pro Lys Ser Asn Pro Asn Gly Arg Phe Gln
35 40 45

Val Lys Ala Asn Val Ser Pro His Gly Arg Ala Pro Lys Ala Asn Gly
50 55 60

Ser Ala Val Ser Leu Lys Ser Gly Ser Leu Asn Thr Gln Glu Asp Thr
65 70 75 80

Ser Ser Ser Pro Pro Pro Arg Thr Phe Leu His Gln Leu Pro Asp Trp
85 90 95

Ser Arg Leu Leu Thr Ala Ile Thr Thr Val Phe Val Lys Ser Lys Arg
100 105 110

Pro Asp Met His Asp Arg Lys Ser Lys Arg Pro Asp Met Leu Val Asp
115 120 125

Ser Phe Gly Leu Glu Ser Thr Val Gln Asp Gly Leu Val Phe Arg Gln
130 135 140

Ser Phe Ser Ile Arg Ser Tyr Glu Ile Gly Thr Asp Arg Thr Ala Ser
145 150 155 160

Ile Glu Thr Leu Met Asn His Leu Gln Glu Thr Ser Leu Asn His Cys
165 170 175

Lys Ser Thr Gly Ile Leu Leu Asp Gly Phe Gly Arg Thr Leu Glu Met
180 185 190

Cys Lys Arg Asp Leu Ile Trp Val Val Ile Lys Met Gln Ile Lys Val
195 200 205

Asn Arg Tyr Pro Ala Trp Gly Asp Thr Val Glu Ile Asn Thr Arg Phe
210 215 220

Ser Arg Leu Gly Lys Ile Gly Met Gly Arg Asp Trp Leu Ile Ser Asp

```
225                 230                 235                 240

Cys Asn Thr Gly Glu Ile Leu Val Arg Ala Thr Ser Ala Tyr Ala Met
                245                 250                 255

Met Asn Gln Lys Thr Arg Arg Leu Ser Lys Leu Pro Tyr Glu Val His
            260                 265                 270

Gln Glu Ile Val Pro Leu Phe Val Asp Ser Pro Val Ile Glu Asp Ser
        275                 280                 285

Asp Leu Lys Val His Lys Phe Lys Val Lys Thr Gly Asp Ser Ile Gln
    290                 295                 300

Lys Gly Leu Thr Pro Gly Trp Asn Asp Leu Asp Val Asn Gln His Val
305                 310                 315                 320

Ser Asn Val Lys Tyr Ile Gly Trp Ile Leu Glu Ser Met Pro Thr Glu
                325                 330                 335

Val Leu Glu Thr Gln Glu Leu Cys Ser Leu Ala Leu Glu Tyr Arg Arg
            340                 345                 350

Glu Cys Gly Arg Asp Ser Val Leu Glu Ser Val Thr Ala Met Asp Pro
        355                 360                 365

Ser Lys Val Gly Val Arg Ser Gln Tyr Gln His Leu Leu Arg Leu Glu
    370                 375                 380

Asp Gly Thr Ala Ile Val Asn Gly Ala Thr Glu Trp Arg Pro Lys Asn
385                 390                 395                 400

Ala Gly Ala Asn Gly Ala Ile Ser Thr Gly Lys Thr Ser Asn Gly Asn
                405                 410                 415

Ser Val Ser Met Asp Tyr Lys Asp His Asp Gly Asp Tyr Lys Asp His
            420                 425                 430

Asp Ile Asp Tyr Lys Asp Asp Asp Asp Lys
        435                 440
```

```
<210> SEQ ID NO 58
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

atggtggtgg ccgccgccgc cagcagcgcc ttcttccccg tgcccgcccc ccgccccacc      60

cccaagcccg gcaagttcgg caactggccc agcagcctga gccagccctt caagcccaag     120

agcaacccca acggccgctt ccaggtgaag gccaacgtga gcccccacgg gcgcgccccc     180

aaggccaacg gcagcgccgt gagcctgaag tccggcagcc tgaacaccct ggaggacccc     240

cccagcagcc cccccccccg caccttcctg aaccagctgc ccgactggag ccgcctgcgc     300

accgccatca ccaccgtgtt cgtggccgcc gagaagcagt tcacccgcct ggaccgcaag     360

agcaagcgcc ccgacatgct ggtggactgg ttcggcagcg agaccatcgt gcaggacggc     420

ctggtgttcc gcgagcgctt cagcatccgc agctacgaga tcggcgccga ccgcaccgcc     480

agcatcgaga ccctgatgaa ccacctgcag gacaccagcc tgaaccactg caagagcgtg     540

ggcctgctga acgacggctt cggccgcacc cccgagatgt gcacccgcga cctgatctgg     600

gtgctgacca agatgcagat cgtggtgaac cgctacccca cctggggcga caccgtggag     660

atcaacagct ggttcagcca gagcggcaag atcggcatgg gccgcgagtg gctgatcagc     720

gactgcaaca ccggcgagat cctggtgcgc gccaccagcg cctgggccat gatgaaccag     780

aagacccgcc gcttcagcaa gctgccctgc gaggtgcgcc aggagatcgc cccccacttc     840
```

```
gtggacgccc cccccgtgat cgaggacaac gaccgcaagc tgcacaagtt cgacgtgaag    900

accggcgaca gcatctgcaa gggcctgacc cccggctgga acgacttcga cgtgaaccag    960

cacgtgagca acgtgaagta catcggctgg attctggaga gcatgcccac cgaggtgctg   1020

gagacccagg agctgtgcag cctgaccctg gagtaccgcc gcgagtgcgg ccgcgagagc   1080

gtggtggaga gcgtgaccag catgaacccc agcaaggtgg gcgaccgcag ccagtaccag   1140

cacctgctgc gcctggagga cggcgccgac atcatgaagg gccgcaccga gtggcgcccc   1200

aagaacgccg gcaccaaccg cgccatcagc accgactaca aggacgacga cgacaagtga   1260
```

<210> SEQ ID NO 59
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

Val Lys Ala Asn Val Ser Pro His Gly Arg Ala Pro Lys Ala Asn Gly
    50                  55                  60

Ser Ala Val Ser Leu Lys Ser Gly Ser Leu Asn Thr Leu Glu Asp Pro
65                  70                  75                  80

Pro Ser Ser Pro Pro Pro Arg Thr Phe Leu Asn Gln Leu Pro Asp Trp
                85                  90                  95

Ser Arg Leu Arg Thr Ala Ile Thr Thr Val Phe Val Ala Ala Glu Lys
            100                 105                 110

Gln Phe Thr Arg Leu Asp Arg Lys Ser Lys Arg Pro Asp Met Leu Val
        115                 120                 125

Asp Trp Phe Gly Ser Glu Thr Ile Val Gln Asp Gly Leu Val Phe Arg
    130                 135                 140

Glu Arg Phe Ser Ile Arg Ser Tyr Glu Ile Gly Ala Asp Arg Thr Ala
145                 150                 155                 160

Ser Ile Glu Thr Leu Met Asn His Leu Gln Asp Thr Ser Leu Asn His
                165                 170                 175

Cys Lys Ser Val Gly Leu Leu Asn Asp Gly Phe Gly Arg Thr Pro Glu
            180                 185                 190

Met Cys Thr Arg Asp Leu Ile Trp Val Leu Thr Lys Met Gln Ile Val
        195                 200                 205

Val Asn Arg Tyr Pro Thr Trp Gly Asp Thr Val Glu Ile Asn Ser Trp
    210                 215                 220

Phe Ser Gln Ser Gly Lys Ile Gly Met Gly Arg Glu Trp Leu Ile Ser
225                 230                 235                 240

Asp Cys Asn Thr Gly Glu Ile Leu Val Arg Ala Thr Ser Ala Trp Ala
                245                 250                 255

Met Met Asn Gln Lys Thr Arg Arg Phe Ser Lys Leu Pro Cys Glu Val
            260                 265                 270

Arg Gln Glu Ile Ala Pro His Phe Val Asp Ala Pro Pro Val Ile Glu
        275                 280                 285
```

Asp Asn Asp Arg Lys Leu His Lys Phe Asp Val Lys Thr Gly Asp Ser
290 295 300

Ile Cys Lys Gly Leu Thr Pro Gly Trp Asn Asp Phe Asp Val Asn Gln
305 310 315 320

His Val Ser Asn Val Lys Tyr Ile Gly Trp Ile Leu Glu Ser Met Pro
325 330 335

Thr Glu Val Leu Glu Thr Gln Glu Leu Cys Ser Leu Thr Leu Glu Tyr
340 345 350

Arg Arg Glu Cys Gly Arg Glu Ser Val Val Glu Ser Val Thr Ser Met
355 360 365

Asn Pro Ser Lys Val Gly Asp Arg Ser Gln Tyr Gln His Leu Leu Arg
370 375 380

Leu Glu Asp Gly Ala Asp Ile Met Lys Gly Arg Thr Glu Trp Arg Pro
385 390 395 400

Lys Asn Ala Gly Thr Asn Arg Ala Ile Ser Thr Asp Tyr Lys Asp Asp
405 410 415

Asp Asp Lys

<210> SEQ ID NO 60
<211> LENGTH: 408
<212> TYPE: PRT
<213> ORGANISM: Cuphea wrightii

<400> SEQUENCE: 60

Met Val Val Ala Ala Ala Ala Ser Ser Ala Phe Phe Pro Val Pro Ala
1 5 10 15

Pro Arg Pro Thr Pro Lys Pro Gly Lys Phe Gly Asn Trp Pro Ser Ser
20 25 30

Leu Ser Gln Pro Phe Lys Pro Lys Ser Asn Pro Asn Gly Arg Phe Gln
35 40 45

Val Lys Ala Asn Val Ser Pro His Pro Lys Ala Asn Gly Ser Ala Val
50 55 60

Ser Leu Lys Ser Gly Ser Leu Asn Thr Leu Glu Asp Pro Pro Ser Ser
65 70 75 80

Pro Pro Pro Arg Thr Phe Leu Asn Gln Leu Pro Asp Trp Ser Arg Leu
85 90 95

Arg Thr Ala Ile Thr Thr Val Phe Val Ala Ala Glu Lys Gln Phe Thr
100 105 110

Arg Leu Asp Arg Lys Ser Lys Arg Pro Asp Met Leu Val Asp Trp Phe
115 120 125

Gly Ser Glu Thr Ile Val Gln Asp Gly Leu Val Phe Arg Glu Arg Phe
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

Val Gly Leu Leu Asn Asp Gly Phe Gly Arg Thr Pro Glu Met Cys Thr
180 185 190

Arg Asp Leu Ile Trp Val Leu Thr Lys Met Gln Ile Val Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Glu Trp Leu Ile Ser Asp Cys Asn
225 230 235 240

```
Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Phe Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405


<210> SEQ ID NO 61
<211> LENGTH: 415
<212> TYPE: PRT
<213> ORGANISM: Cuphea hookeriana

<400> SEQUENCE: 61

Met Val Ala Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
```

```
        195                 200                 205

Ala Trp Gly Asp Thr Val Glu Ile Asn Thr Arg Phe Ser Arg Leu Gly
    210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

<210> SEQ ID NO 62
<211> LENGTH: 541
<212> TYPE: DNA
<213> ORGANISM: Prototheca kruegani

<400> SEQUENCE: 62

```
tgttgaagaa tgagccggcg agttaaaaag agtggcatgg ttaaagaaaa tactctggag     60

ccatagcgaa agcaagttta gtaagcttag gtcattcttt ttagacccga aaccgagtga    120

tctacccatg atcagggtga agtgttagta aaataacatg gaggcccgaa ccgactaatg    180

ttgaaaaatt agcggatgaa ttgtgggtag gggcgaaaaa ccaatcgaac tcggagttag    240

ctggttctcc ccgaaatgcg tttaggcgca gcagtagcag tacaaataga ggggtaaagc    300

actgtttctt ttgtgggctt cgaaagttgt acctcaaagt ggcaaactct gaatactcta    360

tttagatatc tactagtgag accttggggg ataagctcct tggtcaaaag ggaaacagcc    420

cagatcacca gttaaggccc caaaatgaaa atgatagtga ctaaggatgt gggtatgtca    480

aaacctccag caggttagct tagaagcagc aatcctttca agagtgcgta atagctcact    540

g                                                                    541
```

<210> SEQ ID NO 63
<211> LENGTH: 573
<212> TYPE: DNA
<213> ORGANISM: Prototheca wickerhamii

<400> SEQUENCE: 63

```
tgttgaagaa tgagccggcg acttaaaata aatggcaggc taagagattt aataactcga     60
```

```
aacctaagcg aaagcaagtc ttaatagggc gtcaatttaa caaaacttta aataaattat    120

aaagtcattt attttagacc cgaacctgag tgatctaacc atggtcagga tgaaacttgg    180

gtgacaccaa gtggaagtcc gaaccgaccg atgttgaaaa atcggcggat gaactgtggt    240

tagtggtgaa ataccagtcg aactcagagc tagctggttc tccccgaaat gcgttgaggc    300

gcagcaatat atctcgtcta tctaggggta aagcactgtt tcggtgcggg ctatgaaaat    360

ggtaccaaat cgtggcaaac tctgaatact agaaatgacg atatattagt gagactatgg    420

gggataagct ccatagtcga gagggaaaca gcccagacca ccagttaagg ccccaaaatg    480

ataatgaagt ggtaaaggag gtgaaaatgc aaatacaacc aggaggttgg cttagaagca    540

gccatccttt aaagagtgcg taatagctca ctg                                 573

<210> SEQ ID NO 64
<211> LENGTH: 541
<212> TYPE: DNA
<213> ORGANISM: Prototheca stagnora

<400> SEQUENCE: 64

tgttgaagaa tgagccggcg agttaaaaaa aatggcatgg ttaaagatat ttctctgaag     60

ccatagcgaa agcaagtttt acaagctata gtcattttt ttagacccga aaccgagtga    120

tctacccatg atcagggtga agtgttggtc aaataacatg gaggcccgaa ccgactaatg    180

gtgaaaaatt agcggatgaa ttgtgggtag gggcgaaaaa ccaatcgaac tcggagttag    240

ctggttctcc ccgaaatgcg tttaggcgca gcagtagcaa cacaaataga ggggtaaagc    300

actgtttctt ttgtgggctt cgaaagttgt acctcaaagt ggcaaactct gaatactcta    360

tttagatatc tactagtgag accttggggg ataagctcct tggtcaaaag ggaaacagcc    420

cagatcacca gttaaggccc caaaatgaaa atgatagtga ctaaggacgt gagtatgtca    480

aaacctccag caggttagct tagaagcagc aatcctttca agagtgcgta atagctcact    540

g                                                                   541

<210> SEQ ID NO 65
<211> LENGTH: 541
<212> TYPE: DNA
<213> ORGANISM: Prototheca moriformis

<400> SEQUENCE: 65

tgttgaagaa tgagccggcg agttaaaaag agtggcatgg ttaaagataa ttctctggag     60

ccatagcgaa agcaagttta acaagctaaa gtcacccttt ttagacccga aaccgagtga    120

tctacccatg atcagggtga agtgttggta aaataacatg gaggcccgaa ccgactaatg    180

gtgaaaaatt agcggatgaa ttgtgggtag gggcgaaaaa ccaatcgaac tcggagttag    240

ctggttctcc ccgaaatgcg tttaggcgca gcagtagcaa cacaaataga ggggtaaagc    300

actgtttctt ttgtgggctt cgaaagttgt acctcaaagt ggcaaactct gaatactcta    360

tttagatatc tactagtgag accttggggg ataagctcct tggtcaaaag ggaaacagcc    420

cagatcacca gttaaggccc caaaatgaaa atgatagtga ctaaggatgt gggtatgtta    480

aaacctccag caggttagct tagaagcagc aatcctttca agagtgcgta atagctcact    540

g                                                                   541

<210> SEQ ID NO 66
<211> LENGTH: 573
<212> TYPE: DNA
<213> ORGANISM: Prototheca moriformis
```

<400> SEQUENCE: 66
tgttgaagaa tgagccggcg acttaaaata aatggcaggc taagagaatt aataactcga 60
aacctaagcg aaagcaagtc ttaatagggc gctaatttaa caaaacatta aataaaatct 120
aaagtcattt attttagacc cgaacctgag tgatctaacc atggtcagga tgaaacttgg 180
gtgacaccaa gtggaagtcc gaaccgaccg atgttgaaaa atcggcggat gaactgtggt 240
tagtggtgaa ataccagtcg aactcagagc tagctggttc tccccgaaat gcgttgaggc 300
gcagcaatat atctcgtcta tctaggggta aagcactgtt tcggtgcggg ctatgaaaat 360
ggtaccaaat cgtggcaaac tctgaatact agaaatgacg atatattagt gagactatgg 420
gggataagct ccatagtcga gagggaaaca gcccagacca ccagttaagg ccccaaaatg 480
ataatgaagt ggtaaaggag gtgaaaatgc aaatacaacc aggaggttgg cttagaagca 540
gccatccttt aaagagtgcg taatagctca ctg 573

<210> SEQ ID NO 67
<211> LENGTH: 573
<212> TYPE: DNA
<213> ORGANISM: Prototheca wickerhamii

<400> SEQUENCE: 67
tgttgaagaa tgagccgtcg acttaaaata aatggcaggc taagagaatt aataactcga 60
aacctaagcg aaagcaagtc ttaatagggc gctaatttaa caaaacatta aataaaatct 120
aaagtcattt attttagacc cgaacctgag tgatctaacc atggtcagga tgaaacttgg 180
gtgacaccaa gtggaagtcc gaaccgaccg atgttgaaaa atcggcggat gaactgtggt 240
tagtggtgaa ataccagtcg aactcagagc tagctggttc tccccgaaat gcgttgaggc 300
gcagcaatat atctcgtcta tctaggggta aagcactgtt tcggtgcggg ctatgaaaat 360
ggtaccaaat cgtggcaaac tctgaatact agaaatgacg atatattagt gagactatgg 420
gggataagct ccatagtcga gagggaaaca gcccagacca ccagttaagg ccccaaaatg 480
ataatgaagt ggtaaaggag gtgaaaatgc aaatacaacc aggaggttgg cttagaagca 540
gccatccttt aaagagtgcg taatagctca ctg 573

<210> SEQ ID NO 68
<211> LENGTH: 541
<212> TYPE: DNA
<213> ORGANISM: Prototheca moriformis

<400> SEQUENCE: 68
tgttgaagaa tgagccggcg agttaaaaag agtggcgtgg ttaaagaaaa ttctctggaa 60
ccatagcgaa agcaagttta acaagcttaa gtcacttttt ttagacccga aaccgagtga 120
tctacccatg atcagggtga agtgttggta aaataacatg gaggcccgaa ccgactaatg 180
gtgaaaaatt agcggatgaa ttgtgggtag gggcgaaaaa ccaatcgaac tcggagttag 240
ctggttctcc ccgaaatgcg tttaggcgca gcagtagcaa cacaaataga ggggtaaagc 300
actgtttctt ttgtgggctc cgaaagttgt acctcaaagt ggcaaactct gaatactcta 360
tttagatatc tactagtgag accttggggg ataagctcct tggtcgaaag ggaaacagcc 420
cagatcacca gttaaggccc caaaatgaaa atgatagtga ctaaggatgt gagtatgtca 480
aaacctccag caggttagct tagaagcagc aatcctttca agagtgcgta atagctcact 540
g 541

<210> SEQ ID NO 69
<211> LENGTH: 541
<212> TYPE: DNA
<213> ORGANISM: Prototheca zopfii

<400> SEQUENCE: 69
tgttgaagaa tgagccggcg agttaaaaag agtggcatgg ttaaagaaaa ttctctggag 60
ccatagcgaa agcaagttta acaagcttaa gtcacttttt ttagacccga aaccgagtga 120
tctacccatg atcagggtga agtgttggta aaataacatg gaggcccgaa ccgactaatg 180
gtgaaaaatt agcggatgaa ttgtgggtag gggcgaaaaa ccaatcgaac tcggagttag 240
ctggttctcc ccgaaatgcg tttaggcgca gcagtagcaa cacaaataga ggggtaaagc 300
actgtttctt tcgtgggctt cgaaagttgt acctcaaagt ggcaaactct gaatactcta 360
tttagatatc tactagtgag accttggggg ataagctcct tggtcaaaag ggaaacagcc 420
cagatcacca gttaaggccc caaaatgaaa atgatagtga ctaaggatgt gagtatgtca 480
aaacctccag caggttagct tagaagcagc aatcctttca agagtgcgta atagctcact 540
g 541

<210> SEQ ID NO 70
<211> LENGTH: 565
<212> TYPE: DNA
<213> ORGANISM: Prototheca moriformis

<400> SEQUENCE: 70
tgttgaagaa tgagccggcg acttagaaaa ggtggcatgg ttaaggaaat attccgaagc 60
cgtagcaaaa gcgagtctga atagggcgat aaaatatatt aatatttaga atctagtcat 120
tttttctaga cccgaacccg ggtgatctaa ccatgaccag gatgaagctt gggtgatacc 180
aagtgaaggt ccgaaccgac cgatgttgaa aaatcggcgg atgagttgtg gttagcggtg 240
aaataccagt cgaacccgga gctagctggt tctccccgaa atgcgttgag gcgcagcagt 300
acatctagtc tatctagggg taaagcactg tttcggtgcg ggctgtgaga acggtaccaa 360
atcgtggcaa actctgaata ctagaaatga cgatgtagta gtgagactgt gggggataag 420
ctccattgtc aagagggaaa cagcccagac caccagctaa ggccccaaaa tggtaatgta 480
gtgacaaagg aggtgaaaat gcaaatacaa ccaggaggtt ggcttagaag cagccatcct 540
ttaaagagtg cgtaatagct cactg 565

<210> SEQ ID NO 71
<211> LENGTH: 1344
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
atggccaccg catccacttt ctcggcgttc aatgcccgct gcggcgacct gcgtcgctcg 60
gcgggctccg ggccccggcg cccagcgagg cccctccccg tgcgcgggcg cgcctccagc 120
ctgagcccct ccttcaagcc caagtccatc cccaacggcg gcttccaggt gaaggccaac 180
gacagcgccc accccaaggc caacggctcc gccgtgagcc tgaagagcgg cagcctgaac 240
acccaggagg acacctcctc cagccccccc ccccgcacct tcctgcacca gctgcccgac 300
tggagccgcc tgctgaccgc catcaccacc gtgttcgtga agtccaagcg ccccgacatg 360

```
cacgaccgca agtccaagcg ccccgacatg ctggtggaca gcttcggcct ggagtccacc    420

gtgcaggacg gcctggtgtt ccgccagtcc ttctccatcc gctcctacga gatcggcacc    480

gaccgcaccg ccagcatcga gaccctgatg aaccacctgc aggagacctc cctgaaccac    540

tgcaagagca ccggcatcct gctggacggc ttcggccgca ccctggagat gtgcaagcgc    600

gacctgatct gggtggtgat caagatgcag atcaaggtga accgctaccc cgcctggggc    660

gacaccgtgg agatcaacac ccgcttcagc cgcctgggca agatcggcat gggccgcgac    720

tggctgatct ccgactgcaa caccggcgag atcctggtgc gcgccaccag cgcctacgcc    780

atgatgaacc agaagacccg ccgcctgtcc aagctgccct acgaggtgca ccaggagatc    840

gtgcccctgt tcgtggacag ccccgtgatc gaggactccg acctgaaggt gcacaagttc    900

aaggtgaaga ccggcgacag catccagaag ggcctgaccc ccggctggaa cgacctggac    960

gtgaaccagc acgtgtccaa cgtgaagtac atcggctgga tcctggagag catgcccacc   1020

gaggtgctgg agacccagga gctgtgctcc ctggccctgg agtaccgccg cgagtgcggc   1080

cgcgactccg tgctggagag cgtgaccgcc atggacccca gcaaggtggg cgtgcgctcc   1140

cagtaccagc acctgctgcg cctggaggac ggcaccgcca tcgtgaacgg cgccaccgag   1200

tggcgcccca agaacgccgg cgccaacggc gccatctcca ccggcaagac cagcaacggc   1260

aactccgtgt ccatggacta caaggaccac gacggcgact acaaggacca cgacatcgac   1320

tacaaggacg acgacgacaa gtga                                          1344
```

<210> SEQ ID NO 72
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn His Cys Lys Ser Thr Gly Ile Leu Leu Asp Gly Phe Gly
```

-continued

```
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445
```

<210> SEQ ID NO 73
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
atggccaccg catccacttt ctcggcgttc aatgcccgct gcggcgacct gcgtcgctcg      60

gcgggctccg ggccccggcg cccagcgagg cccctccccg tgcgcgggcg cgcctccagc     120

ctgagcccct ccttcaagcc caagtccatc cccaacggcg gcttccaggt gaaggccaac     180

gacagcgccc accccaaggc caacggctcc gccgtgagcc tgaagagcgg cagcctgaac     240

acccaggagg acacctcctc cagccccccc ccccgcacct tcctgcacca gctgcccgac     300

tggagccgcc tgctgaccgc catcaccacc gtgttcgtga agtccaagcg ccccgacatg     360

cacgaccgca agtccaagcg ccccgacatg ctggtggaca gcttcggcct ggagtccacc     420

gtgcaggacg gcctggtgtt ccgccagtcc ttctccatcc gctcctacga gatcggcacc     480

gaccgcaccg ccagcatcga gaccctgatg aaccacctgc aggacaccag cctgaaccac     540
```

-continued

```
tgcaagagcg tgggcctgct gaacgacggc ttcggccgca cccccgagat gtgcacccgc    600

gacctgatct gggtggtgat caagatgcag atcaaggtga accgctaccc cgcctggggc    660

gacaccgtgg agatcaacac ccgcttcagc cgcctgggca agatcggcat gggccgcgac    720

tggctgatct ccgactgcaa caccggcgag atcctggtgc gcgccaccag cgcctacgcc    780

atgatgaacc agaagacccg ccgcctgtcc aagctgccct acgaggtgca ccaggagatc    840

gtgcccctgt tcgtggacag ccccgtgatc gaggactccg acctgaaggt gcacaagttc    900

aaggtgaaga ccggcgacag catccagaag ggcctgaccc ccggctggaa cgacctggac    960

gtgaaccagc acgtgtccaa cgtgaagtac atcggctgga tcctggagag catgcccacc   1020

gaggtgctgg agacccagga gctgtgctcc ctggccctgg agtaccgccg cgagtgcggc   1080

cgcgactccg tgctggagag cgtgaccgcc atggacccca gcaaggtggg cgtgcgctcc   1140

cagtaccagc acctgctgcg cctggaggac ggcaccgcca tcgtgaacgg cgccaccgag   1200

tggcgcccca agaacgccgg cgccaacggc gccatctcca ccggcaagac cagcaacggc   1260

aactccgtgt ccatggacta caaggaccac gacggcgact acaaggacca cgacatcgac   1320

tacaaggacg acgacgacaa gtga                                          1344


<210> SEQ ID NO 74
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Asp Thr
                165                 170                 175

Ser Leu Asn His Cys Lys Ser Val Gly Leu Leu Asn Asp Gly Phe Gly
            180                 185                 190

Arg Thr Pro Glu Met Cys Thr Arg Asp Leu Ile Trp Val Val Ile Lys
        195                 200                 205

Met Gln Ile Lys Val Asn Arg Tyr Pro Ala Trp Gly Asp Thr Val Glu
```

```
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445
```

<210> SEQ ID NO 75
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
atggccaccg catccacttt ctcggcgttc aatgcccgct gcggcgacct gcgtcgctcg     60

gcgggctccg ggcccggcg cccagcgagg cccctccccg tgcgcgggcg cgcctccagc    120

ctgagcccct ccttcaagcc caagtccatc cccaacggcg gcttccaggt gaaggccaac    180

gacagcgccc accccaaggc caacggctcc gccgtgagcc tgaagagcgg cagcctgaac    240

acccaggagg acacctcctc cagccccccc ccccgcacct tcctgcacca gctgcccgac    300

tggagccgcc tgctgaccgc catcaccacc gtgttcgtga agtccaagcg ccccgacatg    360

cacgaccgca agtccaagcg ccccgacatg ctggtggaca gcttcggcct ggagtccacc    420

gtgcaggacg gcctggtgtt ccgccagtcc ttctccatcc gctcctacga gatcggcacc    480

gaccgcaccg ccagcatcga gaccctgatg aaccacctgc aggagacctc catcaaccac    540

tgcaagtccc tgggcctgct gaacgacggc ttcggccgca cccccggcat gtgcaagaac    600

gacctgatct gggtggtgat caagatgcag atcaaggtga accgctaccc cgcctggggc    660

gacaccgtgg agatcaacac ccgcttcagc cgcctgggca agatcggcat gggccgcgac    720
```

```
tggctgatct ccgactgcaa caccggcgag atcctggtgc gcgccaccag cgcctacgcc    780

atgatgaacc agaagacccg ccgcctgtcc aagctgccct acgaggtgca ccaggagatc    840

gtgcccctgt tcgtggacag ccccgtgatc gaggactccg acctgaaggt gcacaagttc    900

aaggtgaaga ccggcgacag catccagaag ggcctgaccc ccggctggaa cgacctggac    960

gtgaaccagc acgtgtccaa cgtgaagtac atcggctgga tcctggagag catgcccacc   1020

gaggtgctgg agacccagga gctgtgctcc ctggccctgg agtaccgccg cgagtgcggc   1080

cgcgactccg tgctggagag cgtgaccgcc atggacccca gcaaggtggg cgtgcgctcc   1140

cagtaccagc acctgctgcg cctggaggac ggcaccgcca tcgtgaacgg cgccaccgag   1200

tggcgcccca agaacgccgg cgccaacggc gccatctcca ccggcaagac cagcaacggc   1260

aactccgtgt ccatggacta caaggaccac gacggcgact acaaggacca cgacatcgac   1320

tacaaggacg acgacgacaa gtga                                          1344


<210> SEQ ID NO 76
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Ile Asn His Cys Lys Ser Leu Gly Leu Leu Asn Asp Gly Phe Gly
            180                 185                 190

Arg Thr Pro Gly Met Cys Lys Asn Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
```

```
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445


<210> SEQ ID NO 77
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

atggccaccg catccacttt ctcggcgttc aatgcccgct gcggcgacct gcgtcgctcg     60

gcgggctccg ggccccggcg cccagcgagg cccctccccg tgcgcgggcg cgcctccagc    120

ctgagcccct ccttcaagcc caagtccatc cccaacggcg gcttccaggt gaaggccaac    180

gacagcgccc accccaaggc caacggctcc gccgtgagcc tgaagagcgg cagcctgaac    240

acccaggagg acacctcctc cagccccccc ccccgcacct tcctgcacca gctgcccgac    300

tggagccgcc tgctgaccgc catcaccacc gtgttcgtga agtccaagcg ccccgacatg    360

cacgaccgca agtccaagcg ccccgacatg ctggtggaca gcttcggcct ggagtccacc    420

gtgcaggacg gcctggtgtt ccgccagtcc ttctccatcc gctcctacga gatcggcacc    480

gaccgcaccg ccagcatcga gaccgtgatg aaccacgtcc aggagacctc gctgaaccag    540

tgcaagtcca tcggcctgct ggacgacggc ttcggccgca gccccgagat gtgcaagcgc    600

gacctgatct gggtggtgat caagatgcag atcaaggtga accgctaccc cgcctggggc    660

gacaccgtgg agatcaacac ccgcttcagc cgcctgggca agatcggcat gggccgcgac    720

tggctgatct ccgactgcaa caccggcgag atcctggtgc gcgccaccag cgcctacgcc    780

atgatgaacc agaagacccg ccgcctgtcc aagctgccct acgaggtgca ccaggagatc    840

gtgcccctgt tcgtggacag ccccgtgatc gaggactccg acctgaaggt gcacaagttc    900
```

```
aaggtgaaga ccggcgacag catccagaag ggcctgaccc ccggctggaa cgacctggac    960

gtgaaccagc acgtgtccaa cgtgaagtac atcggctgga tcctggagag catgcccacc   1020

gaggtgctgg agacccagga gctgtgctcc ctggccctgg agtaccgccg cgagtgcggc   1080

cgcgactccg tgctggagag cgtgaccgcc atggacccca gcaaggtggg cgtgcgctcc   1140

cagtaccagc acctgctgcg cctggaggac ggcaccgcca tcgtgaacgg cgccaccgag   1200

tggcgcccca agaacgccgg cgccaacggc gccatctcca ccggcaagac cagcaacggc   1260

aactccgtgt ccatggacta caaggaccac gacggcgact acaaggacca cgacatcgac   1320

tacaaggacg acgacgacaa gtga                                          1344
```

<210> SEQ ID NO 78
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Val Met Asn His Val Gln Glu Thr
                165                 170                 175

Ser Leu Asn Gln Cys Lys Ser Ile Gly Leu Leu Asp Asp Gly Phe Gly
            180                 185                 190

Arg Ser Pro Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
```

```
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445


<210> SEQ ID NO 79
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

atggccaccg catccacttt ctcggcgttc aatgcccgct gcggcgacct gcgtcgctcg     60

gcgggctccg ggccccggcg cccagcgagg cccctccccg tgcgcgggcg cgcctccagc    120

ctgagcccct ccttcaagcc caagtccatc cccaacggcg gcttccaggt gaaggccaac    180

gacagcgccc accccaaggc caacggctcc gccgtgagcc tgaagagcgg cagcctgaac    240

acccaggagg acacctcctc cagccccccc ccccgcacct tcctgcacca gctgcccgac    300

tggagccgcc tgctgaccgc catcaccacc gtgttcgtga agtccaagcg ccccgacatg    360

cacgaccgca agtccaagcg ccccgacatg ctggtggaca gcttcggcct ggagtccacc    420

gtgcaggacg gcctggtgtt ccgccagtcc ttctccatcc gctcctacga gatcggcacc    480

gaccgcaccg ccagcatcga gaccctgatg aaccacctgc aggagacctc cctgaaccag    540

tgcaagtccg ccggcatcct gcacgacggc ttcggccgca ccctggagat gtgcaagcgc    600

gacctgatct gggtggtgat caagatgcag atcaaggtga accgctaccc cgcctggggc    660

gacaccgtgg agatcaacac ccgcttcagc cgcctgggca agatcggcat gggccgcgac    720

tggctgatct ccgactgcaa caccggcgag atcctggtgc gcgccaccag cgcctacgcc    780

atgatgaacc agaagacccg ccgcctgtcc aagctgccct acgaggtgca ccaggagatc    840

gtgcccctgt tcgtggacag ccccgtgatc gaggactccg acctgaaggt gcacaagttc    900

aaggtgaaga ccggcgacag catccagaag ggcctgaccc ccggctggaa cgacctggac    960

gtgaaccagc acgtgtccaa cgtgaagtac atcggctgga tcctggagag catgcccacc   1020

gaggtgctgg agacccagga gctgtgctcc ctggccctgg agtaccgccg cgagtgcggc   1080
```

```
cgcgactccg tgctggagag cgtgaccgcc atggacccca gcaaggtggg cgtgcgctcc   1140

cagtaccagc acctgctgcg cctggaggac ggcaccgcca tcgtgaacgg cgccaccgag   1200

tggcgcccca agaacgccgg cgccaacggc gccatctcca ccggcaagac cagcaacggc   1260

aactccgtgt ccatggacta caaggaccac gacggcgact acaaggacca cgacatcgac   1320

tacaaggacg acgacgacaa gtga                                          1344


<210> SEQ ID NO 80
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn Gln Cys Lys Ser Ala Gly Ile Leu His Asp Gly Phe Gly
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
```

305 310 315 320

Val Asn Gln His Val Ser Asn Val Lys Tyr Ile Gly Trp Ile Leu Glu
325 330 335

Ser Met Pro Thr Glu Val Leu Glu Thr Gln Glu Leu Cys Ser Leu Ala
340 345 350

Leu Glu Tyr Arg Arg Glu Cys Gly Arg Asp Ser Val Leu Glu Ser Val
355 360 365

Thr Ala Met Asp Pro Ser Lys Val Gly Val Arg Ser Gln Tyr Gln His
370 375 380

Leu Leu Arg Leu Glu Asp Gly Thr Ala Ile Val Asn Gly Ala Thr Glu
385 390 395 400

Trp Arg Pro Lys Asn Ala Gly Ala Asn Gly Ala Ile Ser Thr Gly Lys
405 410 415

Thr Ser Asn Gly Asn Ser Val Ser Met Asp Tyr Lys Asp His Asp Gly
420 425 430

Asp Tyr Lys Asp His Asp Ile Asp Tyr Lys Asp Asp Asp Asp Lys
435 440 445

<210> SEQ ID NO 81
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
atggccaccg catccacttt ctcggcgttc aatgcccgct gcggcgacct gcgtcgctcg 60
gcgggctccg ggccccggcg cccagcgagg cccctccccg tgcgcgggcg cgcctccagc 120
ctgagcccct ccttcaagcc caagtccatc cccaacggcg gcttccaggt gaaggccaac 180
gacagcgccc accccaaggc caacggctcc gccgtgagcc tgaagagcgg cagcctgaac 240
acccaggagg acacctcctc cagccccccc ccccgcacct tcctgcacca gctgcccgac 300
tggagccgcc tgctgaccgc catcaccacc gtgttcgtga agtccaagcg ccccgacatg 360
cacgaccgca agtccaagcg ccccgacatg ctggtggaca gcttcggcct ggagtccacc 420
gtgcaggacg gcctggtgtt ccgccagtcc ttctccatcc gctcctacga gatcggcacc 480
gaccgcaccg ccagcatcga gaccctgatg aactacctgc aggagacctc cctgaaccac 540
tgcaagtcca ccggcatcct gctggacggc ttcggccgca cccccgagat gtgcaagcgc 600
gacctgatct gggtggtgat caagatgcag atcaaggtga accgctaccc cgcctggggc 660
gacaccgtgg agatcaacac ccgcttcagc cgcctgggca agatcggcat gggccgcgac 720
tggctgatct ccgactgcaa caccggcgag atcctggtgc gcgccaccag cgcctacgcc 780
atgatgaacc agaagacccg ccgcctgtcc aagctgccct acgaggtgca ccaggagatc 840
gtgcccctgt tcgtggacag ccccgtgatc gaggactccg acctgaaggt gcacaagttc 900
aaggtgaaga ccggcgacag catccagaag ggcctgaccc ccggctggaa cgacctggac 960
gtgaaccagc acgtgtccaa cgtgaagtac atcggctgga tcctggagag catgcccacc 1020
gaggtgctgg agacccagga gctgtgctcc ctggccctgg agtaccgccg cgagtgcggc 1080
cgcgactccg tgctggagag cgtgaccgcc atggacccca gcaaggtggg cgtgcgctcc 1140
cagtaccagc acctgctgcg cctggaggac ggcaccgcca tcgtgaacgg cgccaccgag 1200
tggcgcccca agaacgccgg cgccaacggc gccatctcca ccggcaagac cagcaacggc 1260

```
aactccgtgt ccatggacta caaggaccac gacggcgact acaaggacca cgacatcgac   1320

tacaaggacg acgacgacaa gtga                                          1344


<210> SEQ ID NO 82
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Ser Pro Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn Tyr Leu Gln Glu Thr
                165                 170                 175

Ser Leu Asn His Cys Lys Ser Thr Gly Ile Leu Leu Asp Gly Phe Gly
            180                 185                 190

Arg Thr Pro Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
```

```
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445


<210> SEQ ID NO 83
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

atggccaccg catccacttt ctcggcgttc aatgcccgct gcggcgacct gcgtcgctcg      60

gcgggctccg ggcccggcg cccagcgagg cccctccccg tgcgcgggcg cgcctccagc      120

ctgagcccct ccttcaagcc caagtccatc cccaacggcg gcttccaggt gaaggccaac     180

gacagcgccc accccaaggc caacggctcc gccgtgagcc tgaagagcgg cagcctgaac     240

acccaggagg acacctcctc cagccccccc ccccgcacct tcctgcacca gctgcccgac     300

tggagccgcc tgctgaccgc catcaccacc gtgttcgtga agtccaagcg ccccgacatg     360

cacgaccgca agtccaagcg ccccgacatg ctggtggaca gcttcggcct ggagtccacc     420

gtgcaggacg gcctggtgtt ccgccagtcc ttctccatcc gctcctacga gatcggcacc     480

gaccgcaccg ccagcatcat ggccgtgatg aaccacctgc aggaggccgc ccgcaaccac     540

gccgagtccc tgggcctgct gggcgacggc ttcggcgaga ccctggagat gtccaagcgc     600

gacctgatct gggtggtgat caagatgcag atcaaggtga accgctaccc cgcctggggc     660

gacaccgtgg agatcaacac ccgcttcagc cgcctgggca agatcggcat gggccgcgac     720

tggctgatct ccgactgcaa caccggcgag atcctggtgc gcgccaccag cgcctacgcc     780

atgatgaacc agaagacccg ccgcctgtcc aagctgccct acgaggtgca ccaggagatc     840

gtgcccctgt tcgtggacag ccccgtgatc gaggactccg acctgaaggt gcacaagttc     900

aaggtgaaga ccggcgacag catccagaag ggcctgaccc ccggctggaa cgacctggac     960

gtgaaccagc acgtgtccaa cgtgaagtac atcggctgga tcctggagag catgcccacc    1020

gaggtgctgg agacccagga gctgtgctcc ctggccctgg agtaccgccg cgagtgcggc    1080

cgcgactccg tgctggagag cgtgaccgcc atggacccca gcaaggtggg cgtgcgctcc    1140

cagtaccagc acctgctgcg cctggaggac ggcaccgcca tcgtgaacgg cgccaccgag    1200

tggcgcccca agaacgccgg cgccaacggc gccatctcca ccggcaagac cagcaacggc    1260

aactccgtgt ccatggacta caaggaccac gacggcgact acaaggacca cgacatcgac    1320

tacaaggacg acgacgacaa gtga                                           1344


<210> SEQ ID NO 84
```

<211> LENGTH: 447
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Gly Arg Ala Ser Ser Leu Ser Pro Ser Phe Lys Pro Lys
35 40 45

Ser Ile Pro Asn Gly Gly Phe Gln Val Lys Ala Asn Asp Ser Ala His
50 55 60

Pro Lys Ala Asn Gly Ser Ala Val Ser Leu Lys Ser Gly Ser Leu Asn
65 70 75 80

Thr Gln Glu Asp Thr Ser Ser Ser Pro Pro Pro Arg Thr Phe Leu His
85 90 95

Gln Leu Pro Asp Trp Ser Arg Leu Leu Thr Ala Ile Thr Thr Val Phe
100 105 110

Val Lys Ser Lys Arg Pro Asp Met His Asp Arg Lys Ser Lys Arg Pro
115 120 125

Asp Met Leu Val Asp Ser Phe Gly Leu Glu Ser Thr Val Gln Asp Gly
130 135 140

Leu Val Phe Arg Gln Ser Phe Ser Ile Arg Ser Tyr Glu Ile Gly Thr
145 150 155 160

Asp Arg Thr Ala Ser Ile Met Ala Val Met Asn His Leu Gln Glu Ala
165 170 175

Ala Arg Asn His Ala Glu Ser Leu Gly Leu Leu Gly Asp Gly Phe Gly
180 185 190

Glu Thr Leu Glu Met Ser Lys Arg Asp Leu Ile Trp Val Val Ile Lys
195 200 205

Met Gln Ile Lys Val Asn Arg Tyr Pro Ala Trp Gly Asp Thr Val Glu
210 215 220

Ile Asn Thr Arg Phe Ser Arg Leu Gly Lys Ile Gly Met Gly Arg Asp
225 230 235 240

Trp Leu Ile Ser Asp Cys Asn Thr Gly Glu Ile Leu Val Arg Ala Thr
245 250 255

Ser Ala Tyr Ala Met Met Asn Gln Lys Thr Arg Arg Leu Ser Lys Leu
260 265 270

Pro Tyr Glu Val His Gln Glu Ile Val Pro Leu Phe Val Asp Ser Pro
275 280 285

Val Ile Glu Asp Ser Asp Leu Lys Val His Lys Phe Lys Val Lys Thr
290 295 300

Gly Asp Ser Ile Gln Lys Gly Leu Thr Pro Gly Trp Asn Asp Leu Asp
305 310 315 320

Val Asn Gln His Val Ser Asn Val Lys Tyr Ile Gly Trp Ile Leu Glu
325 330 335

Ser Met Pro Thr Glu Val Leu Glu Thr Gln Glu Leu Cys Ser Leu Ala
340 345 350

Leu Glu Tyr Arg Arg Glu Cys Gly Arg Asp Ser Val Leu Glu Ser Val
355 360 365

Thr Ala Met Asp Pro Ser Lys Val Gly Val Arg Ser Gln Tyr Gln His

```
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445
```

<210> SEQ ID NO 85
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (3)..(3)
<223> OTHER INFORMATION: Val, Leu or Glu
<220> FEATURE:
<221> NAME/KEY: MOD_RES
<222> LOCATION: (4)..(4)
<223> OTHER INFORMATION: Ala or Thr
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (8)..(8)
<223> OTHER INFORMATION: His, Tyr, Met or Ile
<220> FEATURE:
<221> NAME/KEY: MOD_RES
<222> LOCATION: (9)..(9)
<223> OTHER INFORMATION: Leu, Met, Val or Phe
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Ala, Ser or Thr
<220> FEATURE:
<221> NAME/KEY: MOD_RES
<222> LOCATION: (14)..(14)
<223> OTHER INFORMATION: Leu or Ile
<220> FEATURE:
<221> NAME/KEY: MOD_RES
<222> LOCATION: (16)..(16)
<223> OTHER INFORMATION: His or Gln
<220> FEATURE:
<221> NAME/KEY: MOD_RES
<222> LOCATION: (17)..(17)
<223> OTHER INFORMATION: Ala, Val or Cys
<220> FEATURE:
<221> NAME/KEY: MOD_RES
<222> LOCATION: (18)..(18)
<223> OTHER INFORMATION: Lys, Glu or Arg
<220> FEATURE:
<221> NAME/KEY: MOD_RES
<222> LOCATION: (19)..(19)
<223> OTHER INFORMATION: Ser, Ile, Thr, Asn or Cys
<220> FEATURE:
<221> NAME/KEY: MOD_RES
<222> LOCATION: (20)..(20)
<223> OTHER INFORMATION: Val, Leu, Ala, Thr, Ile or Asn
<220> FEATURE:
<221> NAME/KEY: MOD_RES
<222> LOCATION: (22)..(22)
<223> OTHER INFORMATION: Leu or Ile
<220> FEATURE:

<221> NAME/KEY: MOD_RES
<222> LOCATION: (23)..(23)
<223> OTHER INFORMATION: Leu, Ser or Met
<220> FEATURE:
<221> NAME/KEY: MOD_RES
<222> LOCATION: (24)..(24)
<223> OTHER INFORMATION: Gly, Leu, Asp, Asn or Glu
<220> FEATURE:
<221> NAME/KEY: MOD_RES
<222> LOCATION: (25)..(25)
<223> OTHER INFORMATION: Asp, Asn or Glu
<220> FEATURE:
<221> NAME/KEY: MOD_RES
<222> LOCATION: (27)..(27)
<223> OTHER INFORMATION: Phe or Leu
<220> FEATURE:
<221> NAME/KEY: MOD_RES
<222> LOCATION: (29)..(29)
<223> OTHER INFORMATION: Thr, Glu, Arg, Ser or Ala
<220> FEATURE:
<221> NAME/KEY: MOD_RES
<222> LOCATION: (30)..(30)
<223> OTHER INFORMATION: Thr or Ser
<220> FEATURE:
<221> NAME/KEY: MOD_RES
<222> LOCATION: (31)..(31)
<223> OTHER INFORMATION: Leu, Pro or Arg
<220> FEATURE:
<221> NAME/KEY: MOD_RES
<222> LOCATION: (32)..(32)
<223> OTHER INFORMATION: Glu or Gly
<220> FEATURE:
<221> NAME/KEY: MOD_RES
<222> LOCATION: (34)..(34)
<223> OTHER INFORMATION: Ser, Tyr, Phe, Cys or Thr
<220> FEATURE:
<221> NAME/KEY: MOD_RES
<222> LOCATION: (35)..(35)
<223> OTHER INFORMATION: Lys, Arg or Leu
<220> FEATURE:
<221> NAME/KEY: MOD_RES
<222> LOCATION: (36)..(36)
<223> OTHER INFORMATION: Arg, Lys, Asn or Met
<220> FEATURE:
<221> NAME/KEY: MOD_RES
<222> LOCATION: (37)..(37)
<223> OTHER INFORMATION: Asp, Gly or Asn
<220> FEATURE:
<221> NAME/KEY: MOD_RES
<222> LOCATION: (39)..(39)
<223> OTHER INFORMATION: Met, Ile or Phe

<400> SEQUENCE: 85

```
Ser Ile Xaa Xaa Xaa Met Asn Xaa Xaa Gln Glu Xaa Xaa Xaa Asn Xaa
1               5                   10                  15

Xaa Xaa Xaa Xaa Gly Xaa Xaa Xaa Xaa Gly Xaa Gly Xaa Xaa Xaa Xaa
            20                  25                  30

Met Xaa Xaa Xaa Xaa Leu Xaa
        35
```

<210> SEQ ID NO 86
<211> LENGTH: 48
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (3)..(3)
<223> OTHER INFORMATION: Val, Leu or Glu
<220> FEATURE:
<221> NAME/KEY: MOD_RES
<222> LOCATION: (4)..(4)
<223> OTHER INFORMATION: Ala or Thr -continued
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (8)..(8)
<223> OTHER INFORMATION: His, Tyr, Met or Ile
<220> FEATURE:
<221> NAME/KEY: MOD_RES
<222> LOCATION: (9)..(9)
<223> OTHER INFORMATION: Leu, Met, Val or Phe
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Ala, Ser or Thr
<220> FEATURE:
<221> NAME/KEY: MOD_RES
<222> LOCATION: (14)..(14)
<223> OTHER INFORMATION: Leu or Ile
<220> FEATURE:
<221> NAME/KEY: MOD_RES
<222> LOCATION: (16)..(16)
<223> OTHER INFORMATION: His or Gln
<220> FEATURE:
<221> NAME/KEY: MOD_RES
<222> LOCATION: (17)..(17)
<223> OTHER INFORMATION: Ala, Val or Cys
<220> FEATURE:
<221> NAME/KEY: MOD_RES
<222> LOCATION: (18)..(18)
<223> OTHER INFORMATION: Lys, Glu or Arg
<220> FEATURE:
<221> NAME/KEY: MOD_RES
<222> LOCATION: (19)..(19)
<223> OTHER INFORMATION: Ser, Ile, Thr, Asn or Cys
<220> FEATURE:
<221> NAME/KEY: MOD_RES
<222> LOCATION: (23)..(23)
<223> OTHER INFORMATION: Leu, Ser or Met
<220> FEATURE:
<221> NAME/KEY: MOD_RES
<222> LOCATION: (25)..(25)
<223> OTHER INFORMATION: Asp, Asn or Glu
<220> FEATURE:
<221> NAME/KEY: MOD_RES
<222> LOCATION: (27)..(27)
<223> OTHER INFORMATION: Phe or Leu
<220> FEATURE:
<221> NAME/KEY: MOD_RES
<222> LOCATION: (29)..(29)
<223> OTHER INFORMATION: Thr, Glu, Arg, Ser or Ala
<220> FEATURE:
<221> NAME/KEY: MOD_RES
<222> LOCATION: (30)..(30)
<223> OTHER INFORMATION: Thr or Ser
<220> FEATURE:
<221> NAME/KEY: MOD_RES
<222> LOCATION: (32)..(32)
<223> OTHER INFORMATION: Glu or Gly
<220> FEATURE:
<221> NAME/KEY: MOD_RES
<222> LOCATION: (34)..(34)
<223> OTHER INFORMATION: Ser, Tyr, Phe, Cys or Thr
<220> FEATURE:
<221> NAME/KEY: MOD_RES
<222> LOCATION: (36)..(36)
<223> OTHER INFORMATION: Arg, Lys, Asn or Met
<220> FEATURE:
<221> NAME/KEY: MOD_RES
<222> LOCATION: (37)..(37)
<223> OTHER INFORMATION: Asp, Gly or Asn
<220> FEATURE:
<221> NAME/KEY: MOD_RES
<222> LOCATION: (39)..(39)

<223> OTHER INFORMATION: Met, Ile or Phe
<220> FEATURE:
<221> NAME/KEY: MOD_RES
<222> LOCATION: (42)..(42)
<223> OTHER INFORMATION: Val or Leu
<220> FEATURE:
<221> NAME/KEY: MOD_RES
<222> LOCATION: (44)..(44)
<223> OTHER INFORMATION: Lys or Arg
<220> FEATURE:
<221> NAME/KEY: MOD_RES
<222> LOCATION: (45)..(45)
<223> OTHER INFORMATION: Met or Thr
<220> FEATURE:
<221> NAME/KEY: MOD_RES
<222> LOCATION: (46)..(46)
<223> OTHER INFORMATION: Gln or His
<220> FEATURE:
<221> NAME/KEY: MOD_RES
<222> LOCATION: (47)..(47)
<223> OTHER INFORMATION: Ile or Val

<400> SEQUENCE: 86

```
Ser Ile Xaa Xaa Xaa Met Asn Xaa Xaa Gln Glu Xaa Xaa Xaa Asn Xaa
1               5                   10                  15

Xaa Xaa Xaa Thr Gly Ile Xaa Leu Xaa Gly Xaa Gly Xaa Xaa Leu Xaa
            20                  25                  30

Met Xaa Lys Xaa Xaa Leu Xaa Trp Val Xaa Ile Xaa Xaa Xaa Xaa Lys
        35                  40                  45
```

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (4)..(4)
<223> OTHER INFORMATION: Ala or Thr
<220> FEATURE:
<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (8)..(8)
<223> OTHER INFORMATION: His, Tyr, Met or Ile
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (14)..(14)
<223> OTHER INFORMATION: Leu or Ile
<220> FEATURE:
<221> NAME/KEY: MOD_RES
<222> LOCATION: (16)..(16)
<223> OTHER INFORMATION: His or Gln
<220> FEATURE:
<221> NAME/KEY: MOD_RES
<222> LOCATION: (17)..(17)
<223> OTHER INFORMATION: Ala, Val or Cys
<220> FEATURE:
<221> NAME/KEY: MOD_RES
<222> LOCATION: (18)..(18)
<223> OTHER INFORMATION: Lys, Glu or Arg
<220> FEATURE:
<221> NAME/KEY: MOD_RES
<222> LOCATION: (19)..(19)
<223> OTHER INFORMATION: Ser, Ile, Thr, Asn or Cys
<220> FEATURE:
<221> NAME/KEY: MOD_RES
<222> LOCATION: (20)..(20)
<223> OTHER INFORMATION: Val, Leu, Ala, Thr, Ile or Asn
<220> FEATURE:
<221> NAME/KEY: MOD_RES
<222> LOCATION: (22)..(22)
<223> OTHER INFORMATION: Leu or Ile
<220> FEATURE:
<221> NAME/KEY: MOD_RES
<222> LOCATION: (23)..(23)
<223> OTHER INFORMATION: Leu, Ser or Met
<220> FEATURE:
<221> NAME/KEY: MOD_RES
<222> LOCATION: (24)..(24)
<223> OTHER INFORMATION: Gly, Leu, Asp, Asn or Glu
<220> FEATURE:
<221> NAME/KEY: MOD_RES
<222> LOCATION: (25)..(25)
<223> OTHER INFORMATION: Asp, Asn or Glu
<220> FEATURE:
<221> NAME/KEY: MOD_RES
<222> LOCATION: (27)..(27)
<223> OTHER INFORMATION: Phe or Leu
<220> FEATURE:
<221> NAME/KEY: MOD_RES
<222> LOCATION: (29)..(29)
<223> OTHER INFORMATION: Thr, Glu, Arg, Ser or Ala
<220> FEATURE:
<221> NAME/KEY: MOD_RES
<222> LOCATION: (30)..(30)
<223> OTHER INFORMATION: Thr or Ser
<220> FEATURE:
<221> NAME/KEY: MOD_RES
<222> LOCATION: (31)..(31)
<223> OTHER INFORMATION: Leu, Pro or Arg
<220> FEATURE:
<221> NAME/KEY: MOD_RES
<222> LOCATION: (32)..(32)
<223> OTHER INFORMATION: Glu or Gly
<220> FEATURE:
<221> NAME/KEY: MOD_RES
<222> LOCATION: (34)..(34)
<223> OTHER INFORMATION: Ser, Tyr, Phe, Cys or Thr
<220> FEATURE:
<221> NAME/KEY: MOD_RES
<222> LOCATION: (35)..(35)
<223> OTHER INFORMATION: Lys, Arg or Leu
<220> FEATURE:
<221> NAME/KEY: MOD_RES
<222> LOCATION: (36)..(36)
<223> OTHER INFORMATION: Arg, Lys, Asn or Met
<220> FEATURE:
<221> NAME/KEY: MOD_RES
<222> LOCATION: (37)..(37)
<223> OTHER INFORMATION: Asp, Gly or Asn

<400> SEQUENCE: 87

```
Ser Ile Leu Xaa Xaa Met Asn Xaa Met Gln Glu Xaa Thr Xaa Asn Xaa
1               5                   10                  15

Xaa Xaa Xaa Xaa Gly Xaa Xaa Xaa Xaa Gly Xaa Gly Xaa Xaa Xaa Xaa
            20                  25                  30

Met Xaa Xaa Xaa Xaa Leu Met
        35
```

<210> SEQ ID NO 88
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Ala or Thr
<220> FEATURE:

<221> NAME/KEY: MOD_RES
<222> LOCATION: (5)..(5)
<223> OTHER INFORMATION: Val or Leu
<220> FEATURE:
<221> NAME/KEY: MOD_RES
<222> LOCATION: (8)..(8)
<223> OTHER INFORMATION: His, Tyr, Met or Ile
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (14)..(14)
<223> OTHER INFORMATION: Leu or Ile
<220> FEATURE:
<221> NAME/KEY: MOD_RES
<222> LOCATION: (16)..(16)
<223> OTHER INFORMATION: His or Gln
<220> FEATURE:
<221> NAME/KEY: MOD_RES
<222> LOCATION: (17)..(17)
<223> OTHER INFORMATION: Ala, Val or Cys
<220> FEATURE:
<221> NAME/KEY: MOD_RES
<222> LOCATION: (18)..(18)
<223> OTHER INFORMATION: Lys, Glu or Arg
<220> FEATURE:
<221> NAME/KEY: MOD_RES
<222> LOCATION: (19)..(19)
<223> OTHER INFORMATION: Ser, Ile, Thr, Asn or Cys
<220> FEATURE:
<221> NAME/KEY: MOD_RES
<222> LOCATION: (20)..(20)
<223> OTHER INFORMATION: Val, Leu, Ala, Thr, Ile or Asn
<220> FEATURE:
<221> NAME/KEY: MOD_RES
<222> LOCATION: (22)..(22)
<223> OTHER INFORMATION: Leu or Ile
<220> FEATURE:
<221> NAME/KEY: MOD_RES
<222> LOCATION: (23)..(23)
<223> OTHER INFORMATION: Leu, Ser or Met
<220> FEATURE:
<221> NAME/KEY: MOD_RES
<222> LOCATION: (24)..(24)
<223> OTHER INFORMATION: Gly, Leu, Asp, Asn or Glu
<220> FEATURE:
<221> NAME/KEY: MOD_RES
<222> LOCATION: (25)..(25)
<223> OTHER INFORMATION: Asp, Asn or Glu
<220> FEATURE:
<221> NAME/KEY: MOD_RES
<222> LOCATION: (27)..(27)
<223> OTHER INFORMATION: Phe or Leu
<220> FEATURE:
<221> NAME/KEY: MOD_RES
<222> LOCATION: (29)..(29)
<223> OTHER INFORMATION: Thr, Glu, Arg, Ser or Ala
<220> FEATURE:
<221> NAME/KEY: MOD_RES
<222> LOCATION: (30)..(30)
<223> OTHER INFORMATION: Thr or Ser
<220> FEATURE:
<221> NAME/KEY: MOD_RES
<222> LOCATION: (31)..(31)
<223> OTHER INFORMATION: Leu, Pro or Arg
<220> FEATURE:
<221> NAME/KEY: MOD_RES
<222> LOCATION: (32)..(32)
<223> OTHER INFORMATION: Glu or Gly
<220> FEATURE:
<221> NAME/KEY: MOD_RES
<222> LOCATION: (34)..(34)
<223> OTHER INFORMATION: Ser, Tyr, Phe, Cys or Thr
<220> FEATURE:
<221> NAME/KEY: MOD_RES
<222> LOCATION: (35)..(35)
<223> OTHER INFORMATION: Lys, Arg or Leu

<220> FEATURE:
<221> NAME/KEY: MOD_RES
<222> LOCATION: (36)..(36)
<223> OTHER INFORMATION: Arg, Lys, Asn or Met
<220> FEATURE:
<221> NAME/KEY: MOD_RES
<222> LOCATION: (37)..(37)
<223> OTHER INFORMATION: Asp, Gly or Asn

<400> SEQUENCE: 88

Ser Ile Val Xaa Xaa Met Asn Xaa Leu Gln Glu Xaa Ala Xaa Asn Xaa
1               5                   10                  15

Xaa Xaa Xaa Xaa Gly Xaa Xaa Xaa Xaa Gly Xaa Gly Xaa Xaa Xaa Xaa
            20                  25                  30

Met Xaa Xaa Xaa Xaa Leu Ile
        35

<210> SEQ ID NO 89
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu or Met
<220> FEATURE:
<221> NAME/KEY: MOD_RES
<222> LOCATION: (4)..(4)
<223> OTHER INFORMATION: Thr or Ala
<220> FEATURE:
<221> NAME/KEY: MOD_RES
<222> LOCATION: (5)..(5)
<223> OTHER INFORMATION: Leu or Val
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (9)..(9)
<223> OTHER INFORMATION: Leu or Val
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Ser or Ala
<220> FEATURE:
<221> NAME/KEY: MOD_RES
<222> LOCATION: (14)..(14)
<223> OTHER INFORMATION: Leu, Ile or Arg
<220> FEATURE:
<221> NAME/KEY: MOD_RES
<222> LOCATION: (16)..(16)
<223> OTHER INFORMATION: His or Gln
<220> FEATURE:
<221> NAME/KEY: MOD_RES
<222> LOCATION: (17)..(17)
<223> OTHER INFORMATION: Cys or Ala
<220> FEATURE:
<221> NAME/KEY: MOD_RES
<222> LOCATION: (18)..(18)
<223> OTHER INFORMATION: Lys or Glu
<220> FEATURE:
<221> NAME/KEY: MOD_RES
<222> LOCATION: (20)..(20)

```
<223> OTHER INFORMATION: Thr, Val, Leu, Ile or Ala
<220> FEATURE:
<221> NAME/KEY: MOD_RES
<222> LOCATION: (22)..(22)
<223> OTHER INFORMATION: Ile or Leu
<220> FEATURE:
<221> NAME/KEY: MOD_RES
<222> LOCATION: (24)..(24)
<223> OTHER INFORMATION: Leu, Asn, Asp, His or Gly
<220> FEATURE:
<221> NAME/KEY: MOD_RES
<222> LOCATION: (29)..(29)
<223> OTHER INFORMATION: Arg or Glu
<220> FEATURE:
<221> NAME/KEY: MOD_RES
<222> LOCATION: (30)..(30)
<223> OTHER INFORMATION: Thr or Ser
<220> FEATURE:
<221> NAME/KEY: MOD_RES
<222> LOCATION: (31)..(31)
<223> OTHER INFORMATION: Leu or Pro
<220> FEATURE:
<221> NAME/KEY: MOD_RES
<222> LOCATION: (32)..(32)
<223> OTHER INFORMATION: Glu or Gly
<220> FEATURE:
<221> NAME/KEY: MOD_RES
<222> LOCATION: (34)..(34)
<223> OTHER INFORMATION: Cys or Ser
<220> FEATURE:
<221> NAME/KEY: MOD_RES
<222> LOCATION: (35)..(35)
<223> OTHER INFORMATION: Lys or Thr
<220> FEATURE:
<221> NAME/KEY: MOD_RES
<222> LOCATION: (36)..(36)
<223> OTHER INFORMATION: Arg or Asn

<400> SEQUENCE: 89

Ser Ile Xaa Xaa Xaa Met Asn Xaa Xaa Gln Xaa Xaa Xaa Xaa Asn Xaa
1               5                   10                  15

Xaa Xaa Ser Xaa Gly Xaa Leu Xaa Asp Gly Phe Gly Xaa Xaa Xaa Xaa
            20                  25                  30

Met Xaa Xaa Xaa Asp Leu
        35


<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or His
<220> FEATURE:
<221> NAME/KEY: MOD_RES
<222> LOCATION: (2)..(2)
<223> OTHER INFORMATION: Gly, Asp or Val
<220> FEATURE:
<221> NAME/KEY: MOD_RES
<222> LOCATION: (3)..(3)
<223> OTHER INFORMATION: Trp or Leu
<220> FEATURE:
<221> NAME/KEY: MOD_RES
<222> LOCATION: (4)..(4)
<223> OTHER INFORMATION: Ser or Asn
<220> FEATURE:
<221> NAME/KEY: MOD_RES
<222> LOCATION: (5)..(5)
<223> OTHER INFORMATION: Met, Arg or Val
<220> FEATURE:
<221> NAME/KEY: MOD_RES
```

<222> LOCATION: (6)..(6)
<223> OTHER INFORMATION: Pro, Leu or Ser
<220> FEATURE:
<221> NAME/KEY: MOD_RES
<222> LOCATION: (7)..(7)
<223> OTHER INFORMATION: Leu or Phe
<220> FEATURE:
<221> NAME/KEY: MOD_RES
<222> LOCATION: (8)..(8)
<223> OTHER INFORMATION: Glu, Ala, Thr or Ser
<220> FEATURE:
<221> NAME/KEY: MOD_RES
<222> LOCATION: (9)..(9)
<223> OTHER INFORMATION: Leu, Ala or Lys
<220> FEATURE:
<221> NAME/KEY: MOD_RES
<222> LOCATION: (10)..(10)
<223> OTHER INFORMATION: Ile or Val
<220> FEATURE:
<221> NAME/KEY: MOD_RES
<222> LOCATION: (13)..(13)
<223> OTHER INFORMATION: Ile or Val
<220> FEATURE:
<221> NAME/KEY: MOD_RES
<222> LOCATION: (15)..(15)
<223> OTHER INFORMATION: Ser, Leu, Val or Gly
<220> FEATURE:
<221> NAME/KEY: MOD_RES
<222> LOCATION: (16)..(16)
<223> OTHER INFORMATION: Ala, Lys or Val
<220> FEATURE:
<221> NAME/KEY: MOD_RES
<222> LOCATION: (17)..(17)
<223> OTHER INFORMATION: Ala or Pro

<400> SEQUENCE: 90

```
Xaa Xaa Xaa Xaa Xaa Xaa Xaa Xaa Xaa Xaa Thr Thr Xaa Phe Xaa Xaa
1               5                   10                  15

Xaa
```

<210> SEQ ID NO 91
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala
        35
```

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Ser Gly Pro Arg Arg Pro Ala Arg Pro Leu Pro Val Arg
1               5                   10
```

<210> SEQ ID NO 93
<211> LENGTH: 28

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ser Gly Pro Arg Arg Pro Ala Arg Pro Leu Pro Val Arg Ala Ala Ile
1 5 10 15

Ala Ser Glu Val Pro Val Ala Thr Thr Ser Pro Arg
20 25

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Arg Pro Ala Arg Pro Leu Pro Val Arg Gly Arg Ala
1 5 10

<210> SEQ ID NO 95
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Arg Pro Ala Arg Pro Leu Pro Val Arg Ala Ala Ile Ala Ser Glu Val
1 5 10 15

Pro Val Ala Thr Thr Ser Pro Arg
20

<210> SEQ ID NO 96
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Arg Cys Gly Asp Leu Arg Arg Ser Ala Gly Ser Gly Pro Arg Arg Pro
1 5 10 15

Ala Arg Pro Leu Pro Val Arg Gly Arg Ala
20 25

<210> SEQ ID NO 97
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

Arg Cys Gly Asp Leu Arg Arg Ser Ala Gly Ser Gly Pro Arg Arg Pro
1 5 10 15

Ala Arg Pro Leu Pro Val Arg Ala Ala Ile Ala Ser Glu Val Pro Val
20 25 30

Ala Thr Thr Ser Pro Arg
35

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Pro Ala Arg Pro Leu Pro Val Arg
1 5

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Pro Ala Arg Pro Leu Pro Val Arg Ala Ala Ile Ala Ser Glu Val Pro
1 5 10 15

Val Ala Thr Thr Ser Pro Arg
20

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Arg Arg Pro Ala Arg Pro Leu Pro Val Arg
1 5 10

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Arg Arg Pro Ala Arg Pro Leu Pro Val Arg Ala Ala Ile Ala Ser Glu
1 5 10 15

Val Pro Val Ala Thr Thr Ser Pro Arg
20 25

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Leu or absent
<220> FEATURE:
<221> NAME/KEY: MOD_RES
<222> LOCATION: (2)..(2)
<223> OTHER INFORMATION: Pro or His
<220> FEATURE:
<221> NAME/KEY: MOD_RES
<222> LOCATION: (3)..(3)
<223> OTHER INFORMATION: Gly, Asp or Val
<220> FEATURE:
<221> NAME/KEY: MOD_RES
<222> LOCATION: (4)..(4)
<223> OTHER INFORMATION: Trp or Leu
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Met, Arg or Val
<220> FEATURE:
<221> NAME/KEY: MOD_RES
<222> LOCATION: (7)..(7)
<223> OTHER INFORMATION: Pro, Leu or Ser
<220> FEATURE:
<221> NAME/KEY: MOD_RES
<222> LOCATION: (8)..(8)
<223> OTHER INFORMATION: Leu or Phe
<220> FEATURE:
<221> NAME/KEY: MOD_RES
<222> LOCATION: (9)..(9)
<223> OTHER INFORMATION: Glu, Ala, Thr or Ser
<220> FEATURE:
<221> NAME/KEY: MOD_RES
<222> LOCATION: (10)..(10)
<223> OTHER INFORMATION: Leu, Ala or Lys
<220> FEATURE:
<221> NAME/KEY: MOD_RES
<222> LOCATION: (11)..(11)
<223> OTHER INFORMATION: Ile or Val
<220> FEATURE:
<221> NAME/KEY: MOD_RES
<222> LOCATION: (14)..(14)
<223> OTHER INFORMATION: Ile or Val
<220> FEATURE:
<221> NAME/KEY: MOD_RES
<222> LOCATION: (16)..(16)
<223> OTHER INFORMATION: Ser, Leu, Val or Gly
<220> FEATURE:
<221> NAME/KEY: MOD_RES
<222> LOCATION: (17)..(17)
<223> OTHER INFORMATION: Ala, Lys or Val
<220> FEATURE:
<221> NAME/KEY: MOD_RES
<222> LOCATION: (18)..(18)
<223> OTHER INFORMATION: Ala or Pro

<400> SEQUENCE: 102

```
Xaa Xaa Xaa Xaa Xaa Xaa Xaa Xaa Xaa Xaa Xaa Thr Thr Xaa Phe Xaa
1               5                   10                  15

Xaa Xaa
```

<210> SEQ ID NO 103
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

```
Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Asn Pro
            20                  25                  30
```

-continued

```
Pro Gln Leu Leu Asp Asp His Phe Gly Pro His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Val Ala Val Met Asn His Leu Gln Glu Ala Ala Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Ile Trp Val Val
            100                 105


<210> SEQ ID NO 104
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Pro Asp Trp Ser Met Leu Phe Ala Val Ile Thr Thr Ile Phe Ser Ala
1               5                   10                  15

Ala Glu Lys Gln Trp Thr Asn Leu Glu Trp Lys Pro Lys Pro Lys Leu
            20                  25                  30

Pro Gln Leu Leu Asp Asp His Phe Gly Leu His Gly Leu Val Phe Arg
        35                  40                  45

Arg Thr Phe Ala Ile Arg Ser Tyr Glu Val Gly Pro Asp Arg Ser Thr
    50                  55                  60

Ser Ile Leu Ala Val Met Asn His Met Gln Glu Ala Thr Leu Asn His
65                  70                  75                  80

Ala Lys Ser Val Gly Ile Leu Gly Asp Gly Phe Gly Thr Thr Leu Glu
                85                  90                  95

Met Ser Lys Arg Asp Leu Met Trp Val Val
            100                 105


<210> SEQ ID NO 105
<211> LENGTH: 93
<212> TYPE: PRT
<213> ORGANISM: Arabidopsis thaliana

<400> SEQUENCE: 105

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr
                85                  90


<210> SEQ ID NO 106
<211> LENGTH: 92
<212> TYPE: PRT
<213> ORGANISM: Arabidopsis thaliana
```

<400> SEQUENCE: 106

Met Leu Lys Leu Ser Cys Asn Val Thr Asp His Ile His Asn Leu Phe
1 5 10 15

Ser Asn Ser Arg Arg Ile Phe Val Pro Val His Arg Gln Thr Arg Pro
20 25 30

Ile Ser Cys Phe Gln Leu Lys Lys Glu Pro Leu Arg Ala Ile Leu Ser
35 40 45

Ala Asp His Gly Asn Ser Ser Val Arg Val Ala Asp Thr Val Ser Gly
50 55 60

Thr Ser Pro Ala Asp Arg Leu Arg Phe Gly Arg Leu Met Glu Asp Gly
65 70 75 80

Phe Ser Tyr Lys Glu Lys Phe Ile Val Arg Ser Tyr
85 90

<210> SEQ ID NO 107
<211> LENGTH: 91
<212> TYPE: PRT
<213> ORGANISM: Brassica juncea

<400> SEQUENCE: 107

Met Leu Lys Leu Ser Cys Asn Val Thr Asn His Leu His Thr Phe Phe
1 5 10 15

Phe Ser Ser Asp Ser Ser Leu Phe Ile Pro Gly Asn Arg Arg Thr Ile
20 25 30

Ala Val Ser Ser Ser Gln Pro Arg Lys Pro Ala Leu Asp Pro Leu Arg
35 40 45

Ala Val Ile Ser Ala Asp Gln Gly Ser Ile Ser Pro Val Asn Ser Tyr
50 55 60

Thr Pro Ala Asp Arg Phe Arg Ala Gly Arg Leu Met Glu Asp Gly Tyr
65 70 75 80

Ser Tyr Lys Glu Lys Phe Ile Val Arg Ser Tyr
85 90

<210> SEQ ID NO 108
<211> LENGTH: 91
<212> TYPE: PRT
<213> ORGANISM: Brassica napus

<400> SEQUENCE: 108

Met Leu Lys Leu Ser Cys Asn Val Thr Asn His Leu His Thr Phe Ser
1 5 10 15

Phe Phe Ser Asp Ser Ser Leu Phe Ile Pro Val Asn Arg Arg Thr Leu
20 25 30

Ala Val Ser Ser Ser Gln Pro Arg Lys Pro Ala Leu Asp Pro Leu Arg
35 40 45

Ala Val Ile Ser Ala Asp Gln Gly Ser Ile Ser Pro Val Asn Ser Cys
50 55 60

Thr Pro Ala Asp Arg Phe Arg Ala Gly Arg Leu Met Glu Asp Gly Tyr
65 70 75 80

Ser Tyr Lys Glu Lys Phe Ile Val Arg Ser Tyr
85 90

<210> SEQ ID NO 109
<211> LENGTH: 99
<212> TYPE: PRT
<213> ORGANISM: Capsicum chinense

<400> SEQUENCE: 109

```
Met Leu Ser Arg Gly Ser Phe Leu Lys Asn Val Ala Ile Gly Asp His
1               5                   10                  15

Asn Gln Cys Thr Lys Arg Phe Phe Asn Ser Asn Ser Val Ser Ile Gly
            20                  25                  30

Cys Arg Lys Pro Val Ile Ser Ser Ser Ser Ser Ser Val Gly Val Arg
        35                  40                  45

Ser Gly Pro Val Leu Ala Val Ala Thr Asn Glu Arg Glu Ser Lys Ser
    50                  55                  60

Lys Gln Gln Val Ser His Glu Pro Ser Leu Ala Asp Arg Leu Arg Leu
65                  70                  75                  80

Gly Thr Met Ser Glu Asp Gly Met Ser Tyr Lys Glu Lys Phe Ile Val
                85                  90                  95

Arg Cys Tyr


<210> SEQ ID NO 110
<211> LENGTH: 91
<212> TYPE: PRT
<213> ORGANISM: Coriandrum sativum

<400> SEQUENCE: 110

Val Tyr Pro His Phe Lys Thr Pro Ile Gln Cys Arg Phe Leu Thr Ser
1               5                   10                  15

Asp Ser Ile Ser Ile Arg Arg Arg Thr Ala Val Ser Arg Trp Arg Ser
            20                  25                  30

Pro Thr Phe Ser Ala Asn Tyr Asn Gly Val Asn Ala Gln Val Leu Gly
        35                  40                  45

Val Leu Lys Gln Glu Gln Lys Glu Ile Glu Glu Glu Lys Arg Ser Ser
    50                  55                  60

Ser Leu Ala Glu Lys Leu Arg Leu Gly Ser Leu Thr Glu Asp Gly Leu
65                  70                  75                  80

Ser Tyr Lys Glu Lys Phe Ile Val Arg Cys Tyr
                85                  90


<210> SEQ ID NO 111
<211> LENGTH: 108
<212> TYPE: PRT
<213> ORGANISM: Carthamus tinctorius

<400> SEQUENCE: 111

Arg Pro Leu Pro Thr Thr Ala Ala Ala Ala Thr Thr Thr Thr Asn Asn
1               5                   10                  15

Cys Asn Gly Val Asn Ser Arg Gly Ala Leu Pro His Ser Arg Ser Val
            20                  25                  30

Gly Phe Ala Ser Ile Arg Lys Arg Ser Thr Gly Ser Leu Cys Asn Ser
        35                  40                  45

Pro Pro Arg Thr Val Ala Pro Val Met Ala Val Arg Thr Gly Glu Gln
    50                  55                  60

Pro Thr Gly Val Ala Val Gly Leu Lys Glu Ala Glu Ala Glu Val Glu
65                  70                  75                  80

Lys Ser Leu Ala Asp Arg Leu Arg Met Gly Ser Leu Thr Glu Asp Gly
                85                  90                  95

Leu Ser Tyr Lys Glu Arg Phe Ile Ile Arg Cys Tyr
            100                 105


<210> SEQ ID NO 112
<211> LENGTH: 88
```

```
<212> TYPE: PRT
<213> ORGANISM: Iris germanica

<400> SEQUENCE: 112

Met Leu Lys Leu Cys Cys Val Ala Ala Val Gly Pro Ala Glu Pro Ser
1               5                   10                  15

Leu Ala Phe Pro Leu Arg Arg Arg Ser Val Pro Ala Ala Phe Arg Ser
            20                  25                  30

Ser Val Val Asn Leu Ser Ser Ser Ala Ser Ala Ala Ala Ala Ser Val
        35                  40                  45

Ser Ala Thr Ala Ala Ala Pro Ala Ala Ala Glu Glu Arg Lys Leu Gly
    50                  55                  60

Glu Arg Met Arg His Gly Arg Leu Val Glu Asp Gly Phe Ser Tyr Lys
65                  70                  75                  80

Glu Ser Phe Val Val Arg Cys Tyr
                85


<210> SEQ ID NO 113
<211> LENGTH: 92
<212> TYPE: PRT
<213> ORGANISM: Iris tectorum

<400> SEQUENCE: 113

Met Leu Lys Leu Cys Ala Ser Pro Ser Leu Gly Pro Ala Glu Gln Pro
1               5                   10                  15

Leu Ala Phe Pro Leu Arg Ser Leu Pro Arg Arg Arg Thr Ser Pro Ala
            20                  25                  30

Ala Phe Trp Tyr Ser Thr Pro Glu Val Arg Cys Ser Ala Val Asn Leu
        35                  40                  45

Ser Ser Ser Ala Gly Ala Ala Ala Ser Ala Val Ala Val Ala Glu Glu
    50                  55                  60

Arg Arg Leu Gly Glu Arg Met Arg His Gly Arg Leu Met Glu Asp Gly
65                  70                  75                  80

Leu Ser Tyr Lys Glu Ser Phe Leu Val Arg Cys Tyr
                85                  90


<210> SEQ ID NO 114
<211> LENGTH: 20
<212> TYPE: PRT
<213> ORGANISM: Triticum aestivum

<400> SEQUENCE: 114

Met Gly Ser Leu Leu Glu Asp Gly Leu Ser Tyr Lys Glu Ser Phe Ile
1               5                   10                  15

Val Arg Cys Tyr
            20


<210> SEQ ID NO 115
<211> LENGTH: 75
<212> TYPE: PRT
<213> ORGANISM: Garcinia mangostana

<400> SEQUENCE: 115

Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45
```

```
Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr
65                  70                  75


<210> SEQ ID NO 116
<211> LENGTH: 84
<212> TYPE: PRT
<213> ORGANISM: Garcinia mangostana

<400> SEQUENCE: 116

Met Phe Lys Ile Ser Ser Ser Leu Ser Pro Val Asp Gln Ile Pro Pro
1               5                   10                  15

Ile Ser Pro Leu Pro Arg Pro Arg Pro Arg Pro Ile Thr Pro Arg Val
            20                  25                  30

Leu Ala Val Ser Ser Ser Ser Gly Lys Ile Val Asn Asn Pro Leu Lys
        35                  40                  45

Ala Glu Thr Thr Glu Ala Val Ser Gly Glu Leu Ala Arg Arg Phe Arg
    50                  55                  60

Leu Gly Arg Leu Ala Glu Asp Gly Phe Ser Tyr Lys Glu Lys Phe Ile
65                  70                  75                  80

Val Arg Cys Tyr


<210> SEQ ID NO 117
<211> LENGTH: 97
<212> TYPE: PRT
<213> ORGANISM: Cuphea hookeriana

<400> SEQUENCE: 117

Met Leu Lys Leu Ser Cys Asn Ala Ala Thr Asp Gln Ile Leu Ser Ser
1               5                   10                  15

Ala Val Ala Gln Thr Ala Leu Trp Gly Gln Pro Arg Asn Arg Ser Phe
            20                  25                  30

Ser Met Ser Ala Arg Arg Arg Gly Ala Val Cys Cys Ala Pro Pro Ala
        35                  40                  45

Ala Gly Lys Pro Pro Ala Met Thr Ala Val Ile Pro Lys Asp Gly Val
    50                  55                  60

Ala Ser Ser Gly Ser Gly Ser Leu Ala Asp Gln Leu Arg Leu Gly Ser
65                  70                  75                  80

Arg Thr Gln Asn Gly Leu Ser Tyr Thr Glu Lys Phe Ile Val Arg Cys
                85                  90                  95

Tyr


<210> SEQ ID NO 118
<211> LENGTH: 85
<212> TYPE: PRT
<213> ORGANISM: Cinnamomum camphora

<400> SEQUENCE: 118

Leu Gln Leu Arg Ala Gly Asn Ala Gln Thr Ser Leu Lys Met Ile Asn
1               5                   10                  15

Gly Thr Lys Phe Ser Tyr Thr Glu Ser Leu Lys Lys Leu Pro Asp Trp
            20                  25                  30

Ser Met Leu Phe Ala Val Ile Thr Thr Ile Phe Ser Ala Ala Glu Lys
        35                  40                  45

Gln Trp Thr Asn Leu Glu Trp Lys Pro Lys Pro Asn Pro Pro Gln Leu
    50                  55                  60
```

Leu Asp Asp His Phe Gly Pro His Gly Leu Val Phe Arg Arg Thr Phe
65 70 75 80

Ala Ile Arg Ser Tyr
85

<210> SEQ ID NO 119
<211> LENGTH: 85
<212> TYPE: PRT
<213> ORGANISM: Umbellularia californica

<400> SEQUENCE: 119

Leu Gln Leu Arg Ala Gly Asn Ala Pro Thr Ser Leu Lys Met Ile Asn
1 5 10 15

Gly Thr Lys Phe Ser Tyr Thr Glu Ser Leu Lys Arg Leu Pro Asp Trp
20 25 30

Ser Met Leu Phe Ala Val Ile Thr Thr Ile Phe Ser Ala Ala Glu Lys
35 40 45

Gln Trp Thr Asn Leu Glu Trp Lys Pro Lys Pro Lys Leu Pro Gln Leu
50 55 60

Leu Asp Asp His Phe Gly Leu His Gly Leu Val Phe Arg Arg Thr Phe
65 70 75 80

Ala Ile Arg Ser Tyr
85

<210> SEQ ID NO 120
<211> LENGTH: 84
<212> TYPE: PRT
<213> ORGANISM: Umbellularia californica

<400> SEQUENCE: 120

Leu Gln Val Arg Ala Gly Lys Glu Gln Asn Ser Cys Lys Met Ile Asn
1 5 10 15

Gly Thr Lys Val Lys Asp Thr Glu Gly Leu Lys Gly Arg Ser Thr Leu
20 25 30

His Gly Trp Ser Met Pro Leu Glu Leu Ile Thr Thr Ile Phe Ser Ala
35 40 45

Ala Glu Lys Gln Trp Thr Asn Leu Val Ser Lys Pro Pro Gln Leu Leu
50 55 60

Asp Asp His Leu Gly Leu His Gly Leu Val Phe Arg Arg Thr Phe Ala
65 70 75 80

Ile Arg Cys Ser

<210> SEQ ID NO 121
<211> LENGTH: 103
<212> TYPE: PRT
<213> ORGANISM: Cuphea hookeriana

<400> SEQUENCE: 121

Leu Gln Val Lys Ala Asn Ala Ser Ala Pro Pro Lys Ile Asn Gly Ser
1 5 10 15

Pro Val Gly Leu Lys Ser Gly Gly Leu Lys Thr Gln Glu Asp Ala His
20 25 30

Ser Ala Pro Pro Pro Arg Thr Phe Ile Asn Gln Leu Pro Asp Trp Ser
35 40 45

Met Leu Leu Ala Ala Ile Thr Thr Val Phe Leu Ala Ala Glu Lys Gln
50 55 60

Trp Met Met Leu Asp Trp Lys Pro Lys Arg Pro Asp Met Leu Val Asp

```
65                  70                  75                  80

Pro Phe Gly Leu Gly Ser Ile Val Gln Asp Gly Leu Val Phe Arg Gln
                85                  90                  95

Asn Phe Ser Ile Arg Ser Tyr
            100


<210> SEQ ID NO 122
<211> LENGTH: 103
<212> TYPE: PRT
<213> ORGANISM: Cuphea hookeriana

<400> SEQUENCE: 122

Leu Gln Val Lys Ala Asn Ala Ser Ala Pro Pro Lys Ile Asn Gly Ser
1               5                   10                  15

Ser Val Gly Leu Lys Ser Cys Ser Leu Lys Thr Gln Glu Asp Thr Pro
            20                  25                  30

Ser Ala Pro Ala Pro Arg Thr Phe Ile Asn Gln Leu Pro Asp Trp Ser
        35                  40                  45

Met Leu Leu Ala Ala Ile Thr Thr Val Phe Leu Ala Ala Glu Lys Gln
    50                  55                  60

Trp Met Met Leu Asp Trp Lys Pro Lys Arg Pro Asp Met Leu Val Asp
65                  70                  75                  80

Pro Phe Gly Leu Gly Ser Ile Val Gln His Gly Leu Val Phe Arg Gln
                85                  90                  95

Asn Phe Ser Ile Arg Ser Tyr
            100


<210> SEQ ID NO 123
<211> LENGTH: 103
<212> TYPE: PRT
<213> ORGANISM: Cuphea lanceolata

<400> SEQUENCE: 123

Leu Lys Val Lys Ala Ser Ala Ser Ala Pro Pro Lys Ile Asn Gly Ser
1               5                   10                  15

Ser Val Gly Leu Lys Ser Gly Ser Leu Lys Thr Gln Glu Asp Thr Pro
            20                  25                  30

Ser Val Pro Pro Pro Arg Thr Phe Ile Asn Gln Leu Pro Asp Trp Ser
        35                  40                  45

Met Leu Leu Ala Ala Ile Thr Thr Val Phe Leu Ala Ala Glu Lys Gln
    50                  55                  60

Trp Met Met Leu Asp Trp Lys Pro Lys Arg Pro Asp Met Leu Val Asp
65                  70                  75                  80

Pro Phe Gly Leu Gly Ser Ile Val Gln Gly Gly Leu Val Phe Arg Gln
                85                  90                  95

Asn Phe Ser Ile Arg Ser Tyr
            100


<210> SEQ ID NO 124
<211> LENGTH: 102
<212> TYPE: PRT
<213> ORGANISM: Cuphea hookeriana

<400> SEQUENCE: 124

Phe Gln Val Lys Ala Asn Asp Ser Ala His Pro Lys Ala Asn Gly Ser
1               5                   10                  15

Ala Val Ser Leu Lys Ser Gly Ser Leu Asn Thr Gln Glu Asp Thr Ser
            20                  25                  30
```

```
Ser Ser Pro Pro Pro Arg Thr Phe Leu His Gln Leu Pro Asp Trp Ser
        35                  40                  45

Arg Leu Leu Thr Ala Ile Thr Thr Val Phe Val Lys Ser Lys Arg Pro
    50                  55                  60

Asp Met His Asp Arg Lys Ser Lys Arg Pro Asp Met Leu Val Asp Ser
65                  70                  75                  80

Phe Gly Leu Glu Ser Thr Val Gln Asp Gly Leu Val Phe Arg Gln Ser
                85                  90                  95

Phe Ser Ile Arg Ser Tyr
            100


<210> SEQ ID NO 125
<211> LENGTH: 104
<212> TYPE: PRT
<213> ORGANISM: Cuphea palustris

<400> SEQUENCE: 125

Phe Gln Val Lys Ala Asn Ala Ser Ala His Pro Lys Ala Asn Gly Ser
1               5                   10                  15

Ala Val Thr Leu Lys Ser Gly Ser Leu Asn Thr Gln Glu Asp Thr Leu
            20                  25                  30

Ser Ser Ser Pro Pro Pro Arg Ala Phe Phe Asn Gln Leu Pro Asp Trp
        35                  40                  45

Ser Met Leu Leu Thr Ala Ile Thr Thr Val Phe Val Ala Pro Glu Lys
    50                  55                  60

Arg Trp Thr Met Phe Asp Arg Lys Ser Lys Arg Pro Asn Met Leu Met
65                  70                  75                  80

Asp Ser Phe Gly Leu Glu Arg Val Val Gln Asp Gly Leu Val Phe Arg
                85                  90                  95

Gln Ser Phe Ser Ile Arg Ser Tyr
            100


<210> SEQ ID NO 126
<211> LENGTH: 103
<212> TYPE: PRT
<213> ORGANISM: Cuphea lanceolata

<400> SEQUENCE: 126

Phe Gln Val Lys Ala Asn Ala Ser Ala His Pro Lys Ala Asn Gly Ser
1               5                   10                  15

Ala Val Asn Leu Lys Ser Gly Ser Leu Asn Thr Gln Glu Asp Thr Ser
            20                  25                  30

Ser Ser Pro Pro Pro Arg Ala Phe Leu Asn Gln Leu Pro Asp Trp Ser
        35                  40                  45

Met Leu Leu Thr Ala Ile Thr Thr Val Phe Val Ala Ala Glu Lys Gln
    50                  55                  60

Trp Thr Met Leu Asp Arg Lys Ser Lys Arg Pro Asp Met Leu Val Asp
65                  70                  75                  80

Ser Val Gly Leu Lys Ser Ile Val Arg Asp Gly Leu Val Ser Arg Gln
                85                  90                  95

Ser Phe Leu Ile Arg Ser Tyr
            100


<210> SEQ ID NO 127
<211> LENGTH: 97
<212> TYPE: PRT
<213> ORGANISM: Cuphea hookeriana
```

<400> SEQUENCE: 127

Phe Gln Val Lys Ala Asn Ala Asn Ala His Pro Ser Leu Lys Ser Gly
1               5                   10                  15

Ser Leu Glu Thr Glu Asp Asp Thr Ser Ser Ser Ser Pro Pro Pro Arg
            20                  25                  30

Thr Phe Ile Asn Gln Leu Pro Asp Trp Ser Met Leu Leu Ser Ala Ile
        35                  40                  45

Thr Thr Ile Phe Gly Ala Ala Glu Lys Gln Trp Met Met Leu Asp Arg
    50                  55                  60

Lys Ser Lys Arg Pro Asp Met Leu Met Glu Pro Phe Gly Val Asp Ser
65                  70                  75                  80

Ile Val Gln Asp Gly Val Phe Phe Arg Gln Ser Phe Ser Ile Arg Ser
                85                  90                  95

Tyr

<210> SEQ ID NO 128
<211> LENGTH: 88
<212> TYPE: PRT
<213> ORGANISM: Cuphea wrightii

<400> SEQUENCE: 128

Phe His Val Lys Ala Asn Ala Ser Ala His Pro Lys Ala Asn Gly Ser
1               5                   10                  15

Ala Val Asn Leu Lys Ser Gly Ser Leu Glu Thr Pro Pro Arg Ser Phe
            20                  25                  30

Ile Asn Gln Leu Pro Asp Leu Ser Met Leu Leu Ser Lys Ile Thr Thr
        35                  40                  45

Val Phe Gly Ala Ala Glu Lys Gln Trp Lys Arg Pro Gly Met Leu Val
    50                  55                  60

Glu Pro Phe Gly Val Asp Arg Ile Phe Gln Asp Gly Val Phe Phe Arg
65                  70                  75                  80

Gln Ser Phe Ser Ile Arg Ser Tyr
                85

<210> SEQ ID NO 129
<211> LENGTH: 99
<212> TYPE: PRT
<213> ORGANISM: Cuphea lanceolata

<400> SEQUENCE: 129

Phe Gln Val Lys Ala Asn Ala Ser Ala His Pro Lys Ala Asn Gly Ser
1               5                   10                  15

Ala Val Ser Leu Lys Ala Gly Ser Leu Glu Thr Gln Glu Asp Thr Ser
            20                  25                  30

Ala Pro Ser Pro Pro Pro Arg Thr Phe Ile Asn Gln Leu Pro Asp Trp
        35                  40                  45

Asn Met Leu Leu Ser Ala Ile Thr Thr Val Phe Val Ala Ala Glu Lys
    50                  55                  60

Gln Trp Thr Met Leu Asp Arg Lys Ser Lys Arg Ser Asp Val Leu Val
65                  70                  75                  80

Glu Pro Tyr Val Gln Asp Gly Val Ser Phe Arg Gln Ser Phe Ser Ile
                85                  90                  95

Arg Ser Tyr

<210> SEQ ID NO 130

<211> LENGTH: 105
<212> TYPE: PRT
<213> ORGANISM: Cuphea palustris

<400> SEQUENCE: 130

```
Phe Gln Val Lys Ala Asn Ala Ser Ala His Pro Lys Ala Asn Gly Ser
1               5                   10                  15

Ala Val Ser Leu Lys Ser Gly Ser Leu Glu Thr Gln Glu Asp Lys Thr
            20                  25                  30

Ser Ser Ser Ser Pro Pro Pro Arg Thr Phe Ile Asn Gln Leu Pro Val
        35                  40                  45

Trp Ser Met Leu Leu Ser Ala Val Thr Thr Val Phe Gly Val Ala Glu
    50                  55                  60

Lys Gln Trp Pro Met Leu Asp Arg Lys Ser Lys Arg Pro Asp Met Leu
65                  70                  75                  80

Val Glu Pro Leu Gly Val Asp Arg Ile Val Tyr Asp Gly Val Ser Phe
                85                  90                  95

Arg Gln Ser Phe Ser Ile Arg Ser Tyr
            100                 105
```

<210> SEQ ID NO 131
<211> LENGTH: 105
<212> TYPE: PRT
<213> ORGANISM: Arabidopsis thaliana

<400> SEQUENCE: 131

```
Met Lys Val Lys Pro Asn Ala Gln Ala Pro Pro Lys Ile Asn Gly Lys
1               5                   10                  15

Arg Val Gly Leu Pro Gly Ser Val Asp Ile Val Arg Thr Asp Thr Glu
            20                  25                  30

Thr Ser Ser His Pro Ala Pro Arg Thr Phe Ile Asn Gln Leu Pro Asp
        35                  40                  45

Trp Ser Met Leu Leu Ala Ala Ile Thr Thr Ile Phe Leu Ala Ala Glu
    50                  55                  60

Lys Gln Trp Met Met Leu Asp Trp Lys Pro Arg Arg Ser Asp Met Leu
65                  70                  75                  80

Val Asp Pro Phe Gly Ile Gly Arg Ile Val Gln Asp Gly Leu Val Phe
                85                  90                  95

Arg Gln Asn Phe Ser Ile Arg Ser Tyr
            100                 105
```

<210> SEQ ID NO 132
<211> LENGTH: 105
<212> TYPE: PRT
<213> ORGANISM: Arabidopsis thaliana

<400> SEQUENCE: 132

```
Met Lys Val Lys Pro Asn Ala Gln Ala Pro Pro Lys Ile Asn Gly Lys
1               5                   10                  15

Arg Val Gly Leu Pro Gly Ser Val Asp Ile Val Arg Thr Asp Thr Glu
            20                  25                  30

Thr Ser Ser His Pro Ala Pro Arg Thr Phe Ile Asn Gln Leu Pro Asp
        35                  40                  45

Trp Ser Met Leu Leu Ala Ala Ile Thr Thr Ile Phe Leu Ala Ala Glu
    50                  55                  60

Lys Gln Trp Met Met Leu Asp Trp Lys Pro Arg Arg Ser Asp Met Leu
65                  70                  75                  80
```

```
Val Asp Pro Phe Gly Ile Gly Arg Ile Val Gln Asp Gly Leu Val Phe
                85                  90                  95

Arg Gln Asn Phe Ser Ile Arg Ser Tyr
            100                 105


<210> SEQ ID NO 133
<211> LENGTH: 91
<212> TYPE: PRT
<213> ORGANISM: Garcinia mangostana

<400> SEQUENCE: 133

Leu Gln Val Lys Ala Asn Ala Gln Ala Pro Thr Lys Ile Asn Gly Ser
1               5                   10                  15

Thr Asp Asp Ala Gln Leu Pro Ala Pro Arg Thr Phe Ile Asn Gln Leu
            20                  25                  30

Pro Asp Trp Ser Met Leu Leu Ala Ala Ile Thr Thr Val Phe Leu Ala
        35                  40                  45

Ala Glu Lys Gln Trp Met Met Leu Asp Trp Lys Pro Arg Arg Pro Asp
    50                  55                  60

Met Leu Ile Asp Thr Phe Gly Leu Gly Arg Ile Val Gln Asp Gly Leu
65                  70                  75                  80

Val Phe Arg Gln Asn Phe Ser Ile Arg Ser Tyr
                85                  90


<210> SEQ ID NO 134
<211> LENGTH: 103
<212> TYPE: PRT
<213> ORGANISM: Gossypium hirsutum

<400> SEQUENCE: 134

Leu Gln Val Lys Ala Asn Ala Gln Ala Pro Pro Lys Ile Asn Gly Thr
1               5                   10                  15

Val Ala Ser Thr Thr Pro Val Glu Gly Ser Lys Asn Asp Asp Gly Ala
            20                  25                  30

Ser Ser Pro Pro Pro Arg Thr Phe Ile Asn Gln Leu Pro Asp Trp Ser
        35                  40                  45

Met Leu Leu Ala Ala Ile Thr Thr Ile Phe Leu Ala Ala Glu Lys Gln
    50                  55                  60

Trp Met Met Leu Asp Trp Lys Pro Arg Arg Pro Asp Met Val Ile Asp
65                  70                  75                  80

Pro Phe Gly Ile Gly Lys Ile Val Gln Asp Gly Leu Val Phe Ser Gln
                85                  90                  95

Asn Phe Ser Ile Arg Ser Tyr
            100


<210> SEQ ID NO 135
<211> LENGTH: 103
<212> TYPE: PRT
<213> ORGANISM: Elaeis guineensis

<400> SEQUENCE: 135

Lys Gln Gly Lys Val Met Ala Gln Ala Val Pro Lys Ile Asn Gly Ala
1               5                   10                  15

Lys Val Gly Leu Lys Ala Glu Ser Gln Lys Ala Glu Glu Asp Ala Ala
            20                  25                  30

Pro Ser Ser Ala Pro Arg Thr Phe Tyr Asn Gln Leu Pro Asp Trp Ser
        35                  40                  45

Val Leu Leu Ala Ala Val Thr Thr Ile Phe Leu Ala Ala Glu Lys Gln
```

```
    50                  55                  60

Trp Thr Leu Leu Asp Trp Lys Pro Arg Arg Pro Asp Met Leu Thr Gly
65                  70                  75                  80

Ala Phe Ser Leu Gly Lys Ile Val Gln Asp Gly Leu Val Phe Arg Gln
                85                  90                  95

Asn Phe Ser Ile Arg Ser Tyr
            100


<210> SEQ ID NO 136
<211> LENGTH: 107
<212> TYPE: PRT
<213> ORGANISM: Iris germanica

<400> SEQUENCE: 136

Arg Leu Ala Ser Glu Gly Gln Cys Pro Glu Ser His Glu Gly Gln Arg
1               5                   10                  15

Val Gln Gly Arg Val Glu Asn Arg Gln Ala Lys Val Glu Asp Gly Arg
            20                  25                  30

Ser Val Leu Pro Ser Ser Ser Ala Pro Arg Thr Phe Tyr Asn Gln Leu
        35                  40                  45

Pro Asp Trp Ser Val Leu Leu Ala Ala Ile Thr Thr Ile Phe Leu Ala
    50                  55                  60

Ala Glu Lys Gln Trp Thr Leu Ile Asp Trp Lys Arg Gly Gly Pro Asp
65                  70                  75                  80

Met Leu Thr Asp Ala Phe Gly Leu Gly Lys Ile Ile Glu Asn Gly Leu
                85                  90                  95

Ile Tyr Arg Gln Asn Phe Ser Ile Arg Ser Tyr
            100                 105


<210> SEQ ID NO 137
<211> LENGTH: 104
<212> TYPE: PRT
<213> ORGANISM: Iris germanica

<400> SEQUENCE: 137

Leu Gln Val Lys Val Asn Ala Gln Ala Ala Thr Arg Val Asn Gly Ser
1               5                   10                  15

Lys Val Gly Leu Lys Thr Asp Thr Asn Lys Leu Glu Asp Ala Pro Phe
            20                  25                  30

Ile Pro Ser Ser Ala Pro Arg Thr Phe Tyr Asn Gln Leu Pro Asp Trp
        35                  40                  45

Ser Val Leu Leu Ala Ala Ile Thr Thr Ile Phe Leu Ala Ala Glu Lys
    50                  55                  60

Gln Trp Thr Leu Ile Asp Trp Lys Arg Gly Gly Pro Asp Met Leu Ser
65                  70                  75                  80

Asp Ala Phe Gly Leu Pro Lys Ile Ile Glu Asn Gly Leu Leu Tyr Arg
                85                  90                  95

Gln Lys Phe Ser Ile Arg Ser Tyr
            100


<210> SEQ ID NO 138
<211> LENGTH: 104
<212> TYPE: PRT
<213> ORGANISM: Iris tectorum

<400> SEQUENCE: 138

Leu Gln Val Lys Val Asn Ala Gln Ala Ala Thr Arg Val Asn Gly Ser
1               5                   10                  15
```

```
Lys Val Gly Leu Lys Thr Asp Thr Asn Lys Leu Glu Asp Ala Pro Phe
            20                  25                  30

Ile Pro Ser Ser Ala Pro Arg Thr Phe Tyr Asn Gln Leu Pro Asp Trp
        35                  40                  45

Ser Val Leu Leu Ala Ala Ile Thr Thr Ile Phe Leu Ala Ala Glu Lys
    50                  55                  60

Gln Trp Thr Leu Ile Asp Trp Lys Ala Glu Ala Pro Asp Met Leu Ser
65                  70                  75                  80

Asp Ala Phe Gly Leu Gly Lys Ile Ile Glu Asn Gly Leu Leu Tyr Arg
                85                  90                  95

Gln Asn Phe Ser Ile Arg Ser Tyr
            100


<210> SEQ ID NO 139
<211> LENGTH: 104
<212> TYPE: PRT
<213> ORGANISM: Iris tectorum

<400> SEQUENCE: 139

Leu Gln Val Lys Val Asn Ala Gln Ala Ala Thr Arg Val Asn Gly Ser
1               5                   10                  15

Lys Val Gly Leu Lys Thr Asp Thr Asn Lys Leu Glu Asp Thr Pro Phe
            20                  25                  30

Phe Pro Ser Ser Ala Pro Arg Thr Phe Tyr Asn Gln Leu Pro Asp Trp
        35                  40                  45

Ser Val Ser Phe Ala Ala Ile Thr Thr Ile Phe Leu Ala Ala Glu Lys
    50                  55                  60

Gln Trp Thr Leu Ile Asp Trp Lys Pro Arg Arg Pro Asp Met Leu Ala
65                  70                  75                  80

Asp Ala Phe Gly Leu Gly Lys Ile Ile Glu Asn Gly Leu Val Tyr Arg
                85                  90                  95

Gln Asn Phe Ser Ile Arg Ser Tyr
            100


<210> SEQ ID NO 140
<211> LENGTH: 109
<212> TYPE: PRT
<213> ORGANISM: Myristica fragrans

<400> SEQUENCE: 140

Leu Gln Val Lys Ala Asn Ala His Thr Val Pro Lys Ile Asn Gly Asn
1               5                   10                  15

Lys Ala Gly Leu Leu Thr Pro Met Glu Ser Thr Lys Asp Glu Asp Ile
            20                  25                  30

Val Ala Ala Pro Thr Val Ala Pro Lys Arg Thr Phe Ile Asn Gln Leu
        35                  40                  45

Pro Asp Trp Ser Met Leu Leu Ala Ala Ile Thr Thr Ile Phe Leu Ala
    50                  55                  60

Ala Glu Lys Gln Trp Thr Asn Leu Asp Trp Lys Pro Arg Arg Pro Asp
65                  70                  75                  80

Met Leu Val Asp Phe Asp Pro Phe Ser Leu Gly Arg Phe Val Gln Asp
                85                  90                  95

Gly Leu Ile Phe Arg Gln Asn Phe Ser Ile Arg Ser Tyr
            100                 105


<210> SEQ ID NO 141
```

<211> LENGTH: 103
<212> TYPE: PRT
<213> ORGANISM: Helianthus annuus

<400> SEQUENCE: 141

Met Lys Val Lys Ala Asn Ala Gln Ala Pro Thr Glu Val Asn Gly Ser
1 5 10 15

Arg Ser Arg Ile Thr His Gly Phe Lys Thr Asp Asp Tyr Ser Thr Ser
20 25 30

Pro Ala Pro Arg Thr Phe Ile Asn Gln Leu Pro Asp Trp Ser Met Leu
35 40 45

Leu Ala Ala Ile Thr Thr Ile Phe Leu Ala Ala Glu Lys Gln Trp Met
50 55 60

Met Leu Glu Trp Lys Thr Lys Arg Pro Asp Met Ile Ala Asp Met Asp
65 70 75 80

Pro Phe Gly Leu Gly Arg Ile Val Gln Asp Gly Leu Val Phe Arg Gln
85 90 95

Asn Phe Ser Ile Arg Ser Tyr
100

<210> SEQ ID NO 142
<211> LENGTH: 104
<212> TYPE: PRT
<213> ORGANISM: Ulmus americana

<400> SEQUENCE: 142

Leu Gln Val Lys Ala Ser Ser Gln Ala Pro Pro Lys Leu Asn Gly Ser
1 5 10 15

Asn Val Gly Leu Val Lys Ser Ser Gln Ile Val Lys Lys Gly Asp Asp
20 25 30

Thr Thr Ser Pro Pro Ala Arg Thr Phe Ile Asn Gln Leu Pro Asp Trp
35 40 45

Ser Met Leu Leu Ala Ala Ile Thr Thr Leu Phe Leu Ala Ala Glu Lys
50 55 60

Gln Trp Met Met Leu Asp Trp Lys Pro Lys Arg Pro Asp Met Leu Val
65 70 75 80

Asp Pro Phe Gly Leu Gly Arg Phe Val Gln Asp Gly Leu Val Phe Arg
85 90 95

Asn Asn Phe Ser Ile Arg Ser Tyr
100

<210> SEQ ID NO 143
<211> LENGTH: 46
<212> TYPE: PRT
<213> ORGANISM: Umbellularia californica

<400> SEQUENCE: 143

Leu Gln Leu Arg Ala Gly Asn Ala Pro Thr Ser Leu Lys Met Ile Asn
1 5 10 15

Gly Thr Lys Phe Ser Tyr Thr Glu Ser Leu Lys Arg Leu Pro Asp Trp
20 25 30

Ser Met Leu Phe Ala Val Ile Thr Thr Ile Phe Ser Ala Ala
35 40 45

<210> SEQ ID NO 144
<211> LENGTH: 49
<212> TYPE: PRT
<213> ORGANISM: Umbellularia californica

<400> SEQUENCE: 144

Leu Gln Val Arg Ala Gly Lys Glu Gln Asn Ser Cys Lys Met Ile Asn
1 5 10 15

Gly Thr Lys Val Lys Asp Thr Glu Gly Leu Lys Gly Arg Ser Thr Leu
20 25 30

His Gly Trp Ser Met Pro Leu Glu Leu Ile Thr Thr Ile Phe Ser Ala
35 40 45

Ala

<210> SEQ ID NO 145
<211> LENGTH: 61
<212> TYPE: PRT
<213> ORGANISM: Cuphea hookeriana

<400> SEQUENCE: 145

Leu Gln Val Lys Ala Asn Ala Ser Ala Pro Pro Lys Ile Asn Gly Ser
1 5 10 15

Pro Val Gly Leu Lys Ser Gly Gly Leu Lys Thr Gln Glu Asp Ala His
20 25 30

Ser Ala Pro Pro Pro Arg Thr Phe Ile Asn Gln Leu Pro Asp Trp Ser
35 40 45

Met Leu Leu Ala Ala Ile Thr Thr Val Phe Leu Ala Ala
50 55 60

<210> SEQ ID NO 146
<211> LENGTH: 61
<212> TYPE: PRT
<213> ORGANISM: Cuphea hookeriana

<400> SEQUENCE: 146

Leu Gln Val Lys Ala Asn Ala Ser Ala Pro Pro Lys Ile Asn Gly Ser
1 5 10 15

Ser Val Gly Leu Lys Ser Cys Ser Leu Lys Thr Gln Glu Asp Thr Pro
20 25 30

Ser Ala Pro Ala Pro Arg Thr Phe Ile Asn Gln Leu Pro Asp Trp Ser
35 40 45

Met Leu Leu Ala Ala Ile Thr Thr Val Phe Leu Ala Ala
50 55 60

<210> SEQ ID NO 147
<211> LENGTH: 61
<212> TYPE: PRT
<213> ORGANISM: Cuphea lanceolata

<400> SEQUENCE: 147

Leu Lys Val Lys Ala Ser Ala Ser Ala Pro Pro Lys Ile Asn Gly Ser
1 5 10 15

Ser Val Gly Leu Lys Ser Gly Ser Leu Lys Thr Gln Glu Asp Thr Pro
20 25 30

Ser Val Pro Pro Pro Arg Thr Phe Ile Asn Gln Leu Pro Asp Trp Ser
35 40 45

Met Leu Leu Ala Ala Ile Thr Thr Val Phe Leu Ala Ala
50 55 60

<210> SEQ ID NO 148
<211> LENGTH: 60
<212> TYPE: PRT
<213> ORGANISM: Cuphea hookeriana

<400> SEQUENCE: 148

```
Phe Gln Val Lys Ala Asn Asp Ser Ala His Pro Lys Ala Asn Gly Ser
1               5                   10                  15

Ala Val Ser Leu Lys Ser Gly Ser Leu Asn Thr Gln Glu Asp Thr Ser
            20                  25                  30

Ser Ser Pro Pro Pro Arg Thr Phe Leu His Gln Leu Pro Asp Trp Ser
        35                  40                  45

Arg Leu Leu Thr Ala Ile Thr Thr Val Phe Val Lys
    50                  55                  60
```

<210> SEQ ID NO 149
<211> LENGTH: 62
<212> TYPE: PRT
<213> ORGANISM: Cuphea palustris

<400> SEQUENCE: 149

```
Phe Gln Val Lys Ala Asn Ala Ser Ala His Pro Lys Ala Asn Gly Ser
1               5                   10                  15

Ala Val Thr Leu Lys Ser Gly Ser Leu Asn Thr Gln Glu Asp Thr Leu
            20                  25                  30

Ser Ser Ser Pro Pro Pro Arg Ala Phe Phe Asn Gln Leu Pro Asp Trp
        35                  40                  45

Ser Met Leu Leu Thr Ala Ile Thr Thr Val Phe Val Ala Pro
    50                  55                  60
```

<210> SEQ ID NO 150
<211> LENGTH: 61
<212> TYPE: PRT
<213> ORGANISM: Cuphea lanceolata

<400> SEQUENCE: 150

```
Phe Gln Val Lys Ala Asn Ala Ser Ala His Pro Lys Ala Asn Gly Ser
1               5                   10                  15

Ala Val Asn Leu Lys Ser Gly Ser Leu Asn Thr Gln Glu Asp Thr Ser
            20                  25                  30

Ser Ser Pro Pro Pro Arg Ala Phe Leu Asn Gln Leu Pro Asp Trp Ser
        35                  40                  45

Met Leu Leu Thr Ala Ile Thr Thr Val Phe Val Ala Ala
    50                  55                  60
```

<210> SEQ ID NO 151
<211> LENGTH: 55
<212> TYPE: PRT
<213> ORGANISM: Cuphea hookeriana

<400> SEQUENCE: 151

```
Phe Gln Val Lys Ala Asn Ala Asn Ala His Pro Ser Leu Lys Ser Gly
1               5                   10                  15

Ser Leu Glu Thr Glu Asp Asp Thr Ser Ser Ser Ser Pro Pro Pro Arg
            20                  25                  30

Thr Phe Ile Asn Gln Leu Pro Asp Trp Ser Met Leu Leu Ser Ala Ile
        35                  40                  45

Thr Thr Ile Phe Gly Ala Ala
    50                  55
```

<210> SEQ ID NO 152
<211> LENGTH: 53
<212> TYPE: PRT
<213> ORGANISM: Cuphea wrightii

<400> SEQUENCE: 152

```
Phe His Val Lys Ala Asn Ala Ser Ala His Pro Lys Ala Asn Gly Ser
1               5                   10                  15

Ala Val Asn Leu Lys Ser Gly Ser Leu Glu Thr Pro Pro Arg Ser Phe
            20                  25                  30

Ile Asn Gln Leu Pro Asp Leu Ser Met Leu Leu Ser Lys Ile Thr Thr
        35                  40                  45

Val Phe Gly Ala Ala
    50
```

<210> SEQ ID NO 153
<211> LENGTH: 62
<212> TYPE: PRT
<213> ORGANISM: Cuphea lanceolata

<400> SEQUENCE: 153

```
Phe Gln Val Lys Ala Asn Ala Ser Ala His Pro Lys Ala Asn Gly Ser
1               5                   10                  15

Ala Val Ser Leu Lys Ala Gly Ser Leu Glu Thr Gln Glu Asp Thr Ser
            20                  25                  30

Ala Pro Ser Pro Pro Pro Arg Thr Phe Ile Asn Gln Leu Pro Asp Trp
        35                  40                  45

Asn Met Leu Leu Ser Ala Ile Thr Thr Val Phe Val Ala Ala
    50                  55                  60
```

<210> SEQ ID NO 154
<211> LENGTH: 63
<212> TYPE: PRT
<213> ORGANISM: Cuphea palustris

<400> SEQUENCE: 154

```
Phe Gln Val Lys Ala Asn Ala Ser Ala His Pro Lys Ala Asn Gly Ser
1               5                   10                  15

Ala Val Ser Leu Lys Ser Gly Ser Leu Glu Thr Gln Glu Asp Lys Thr
            20                  25                  30

Ser Ser Ser Ser Pro Pro Pro Arg Thr Phe Ile Asn Gln Leu Pro Val
        35                  40                  45

Trp Ser Met Leu Leu Ser Ala Val Thr Thr Val Phe Gly Val Ala
    50                  55                  60
```

<210> SEQ ID NO 155
<211> LENGTH: 63
<212> TYPE: PRT
<213> ORGANISM: Arabidopsis thaliana

<400> SEQUENCE: 155

```
Met Lys Val Lys Pro Asn Ala Gln Ala Pro Pro Lys Ile Asn Gly Lys
1               5                   10                  15

Arg Val Gly Leu Pro Gly Ser Val Asp Ile Val Arg Thr Asp Thr Glu
            20                  25                  30

Thr Ser Ser His Pro Ala Pro Arg Thr Phe Ile Asn Gln Leu Pro Asp
        35                  40                  45

Trp Ser Met Leu Leu Ala Ala Ile Thr Thr Ile Phe Leu Ala Ala
    50                  55                  60
```

<210> SEQ ID NO 156
<211> LENGTH: 63
<212> TYPE: PRT

<213> ORGANISM: Arabidopsis thaliana

<400> SEQUENCE: 156

```
Met Lys Val Lys Pro Asn Ala Gln Ala Pro Pro Lys Ile Asn Gly Lys
1               5                   10                  15

Arg Val Gly Leu Pro Gly Ser Val Asp Ile Val Arg Thr Asp Thr Glu
            20                  25                  30

Thr Ser Ser His Pro Ala Pro Arg Thr Phe Ile Asn Gln Leu Pro Asp
        35                  40                  45

Trp Ser Met Leu Leu Ala Ala Ile Thr Thr Ile Phe Leu Ala Ala
    50                  55                  60
```

<210> SEQ ID NO 157
<211> LENGTH: 49
<212> TYPE: PRT
<213> ORGANISM: Garcinia mangostana

<400> SEQUENCE: 157

```
Leu Gln Val Lys Ala Asn Ala Gln Ala Pro Thr Lys Ile Asn Gly Ser
1               5                   10                  15

Thr Asp Asp Ala Gln Leu Pro Ala Pro Arg Thr Phe Ile Asn Gln Leu
            20                  25                  30

Pro Asp Trp Ser Met Leu Leu Ala Ala Ile Thr Thr Val Phe Leu Ala
        35                  40                  45

Ala
```

<210> SEQ ID NO 158
<211> LENGTH: 61
<212> TYPE: PRT
<213> ORGANISM: Gossypium hirsutum

<400> SEQUENCE: 158

```
Leu Gln Val Lys Ala Asn Ala Gln Ala Pro Pro Lys Ile Asn Gly Thr
1               5                   10                  15

Val Ala Ser Thr Thr Pro Val Glu Gly Ser Lys Asn Asp Asp Gly Ala
            20                  25                  30

Ser Ser Pro Pro Pro Arg Thr Phe Ile Asn Gln Leu Pro Asp Trp Ser
        35                  40                  45

Met Leu Leu Ala Ala Ile Thr Thr Ile Phe Leu Ala Ala
    50                  55                  60
```

<210> SEQ ID NO 159
<211> LENGTH: 61
<212> TYPE: PRT
<213> ORGANISM: Elaeis guineensis

<400> SEQUENCE: 159

```
Lys Gln Gly Lys Val Met Ala Gln Ala Val Pro Lys Ile Asn Gly Ala
1               5                   10                  15

Lys Val Gly Leu Lys Ala Glu Ser Gln Lys Ala Glu Glu Asp Ala Ala
            20                  25                  30

Pro Ser Ser Ala Pro Arg Thr Phe Tyr Asn Gln Leu Pro Asp Trp Ser
        35                  40                  45

Val Leu Leu Ala Ala Val Thr Thr Ile Phe Leu Ala Ala
    50                  55                  60
```

<210> SEQ ID NO 160
<211> LENGTH: 65
<212> TYPE: PRT

<213> ORGANISM: Iris germanica

<400> SEQUENCE: 160

```
Arg Leu Ala Ser Glu Gly Gln Cys Pro Glu Ser His Glu Gly Gln Arg
1               5                   10                  15

Val Gln Gly Arg Val Glu Asn Arg Gln Ala Lys Val Glu Asp Gly Arg
            20                  25                  30

Ser Val Leu Pro Ser Ser Ser Ala Pro Arg Thr Phe Tyr Asn Gln Leu
        35                  40                  45

Pro Asp Trp Ser Val Leu Leu Ala Ala Ile Thr Thr Ile Phe Leu Ala
    50                  55                  60

Ala
65
```

<210> SEQ ID NO 161
<211> LENGTH: 62
<212> TYPE: PRT
<213> ORGANISM: Iris germanica

<400> SEQUENCE: 161

```
Leu Gln Val Lys Val Asn Ala Gln Ala Ala Thr Arg Val Asn Gly Ser
1               5                   10                  15

Lys Val Gly Leu Lys Thr Asp Thr Asn Lys Leu Glu Asp Ala Pro Phe
            20                  25                  30

Ile Pro Ser Ser Ala Pro Arg Thr Phe Tyr Asn Gln Leu Pro Asp Trp
        35                  40                  45

Ser Val Leu Leu Ala Ala Ile Thr Thr Ile Phe Leu Ala Ala
    50                  55                  60
```

<210> SEQ ID NO 162
<211> LENGTH: 62
<212> TYPE: PRT
<213> ORGANISM: Iris tectorum

<400> SEQUENCE: 162

```
Leu Gln Val Lys Val Asn Ala Gln Ala Ala Thr Arg Val Asn Gly Ser
1               5                   10                  15

Lys Val Gly Leu Lys Thr Asp Thr Asn Lys Leu Glu Asp Ala Pro Phe
            20                  25                  30

Ile Pro Ser Ser Ala Pro Arg Thr Phe Tyr Asn Gln Leu Pro Asp Trp
        35                  40                  45

Ser Val Leu Leu Ala Ala Ile Thr Thr Ile Phe Leu Ala Ala
    50                  55                  60
```

<210> SEQ ID NO 163
<211> LENGTH: 62
<212> TYPE: PRT
<213> ORGANISM: Iris tectorum

<400> SEQUENCE: 163

```
Leu Gln Val Lys Val Asn Ala Gln Ala Ala Thr Arg Val Asn Gly Ser
1               5                   10                  15

Lys Val Gly Leu Lys Thr Asp Thr Asn Lys Leu Glu Asp Thr Pro Phe
            20                  25                  30

Phe Pro Ser Ser Ala Pro Arg Thr Phe Tyr Asn Gln Leu Pro Asp Trp
        35                  40                  45

Ser Val Ser Phe Ala Ala Ile Thr Thr Ile Phe Leu Ala Ala
    50                  55                  60
```

<210> SEQ ID NO 164
<211> LENGTH: 65
<212> TYPE: PRT
<213> ORGANISM: Myristica fragrans

<400> SEQUENCE: 164

```
Leu Gln Val Lys Ala Asn Ala His Thr Val Pro Lys Ile Asn Gly Asn
1               5                   10                  15

Lys Ala Gly Leu Leu Thr Pro Met Glu Ser Thr Lys Asp Glu Asp Ile
            20                  25                  30

Val Ala Ala Pro Thr Val Ala Pro Lys Arg Thr Phe Ile Asn Gln Leu
        35                  40                  45

Pro Asp Trp Ser Met Leu Leu Ala Ala Ile Thr Thr Ile Phe Leu Ala
    50                  55                  60

Ala
65
```

<210> SEQ ID NO 165
<211> LENGTH: 59
<212> TYPE: PRT
<213> ORGANISM: Helianthus annuus

<400> SEQUENCE: 165

```
Met Lys Val Lys Ala Asn Ala Gln Ala Pro Thr Glu Val Asn Gly Ser
1               5                   10                  15

Arg Ser Arg Ile Thr His Gly Phe Lys Thr Asp Asp Tyr Ser Thr Ser
            20                  25                  30

Pro Ala Pro Arg Thr Phe Ile Asn Gln Leu Pro Asp Trp Ser Met Leu
        35                  40                  45

Leu Ala Ala Ile Thr Thr Ile Phe Leu Ala Ala
    50                  55
```

<210> SEQ ID NO 166
<211> LENGTH: 62
<212> TYPE: PRT
<213> ORGANISM: Ulmus americana

<400> SEQUENCE: 166

```
Leu Gln Val Lys Ala Ser Ser Gln Ala Pro Pro Lys Leu Asn Gly Ser
1               5                   10                  15

Asn Val Gly Leu Val Lys Ser Ser Gln Ile Val Lys Lys Gly Asp Asp
            20                  25                  30

Thr Thr Ser Pro Pro Ala Arg Thr Phe Ile Asn Gln Leu Pro Asp Trp
        35                  40                  45

Ser Met Leu Leu Ala Ala Ile Thr Thr Leu Phe Leu Ala Ala
    50                  55                  60
```

<210> SEQ ID NO 167
<211> LENGTH: 40
<212> TYPE: PRT
<213> ORGANISM: Umbellularia californica

<400> SEQUENCE: 167

```
Lys Pro Arg Ser Ser Asp Leu Gln Leu Arg Ala Gly Asn Ala Pro Thr
1               5                   10                  15

Ser Leu Lys Met Ile Asn Gly Thr Lys Phe Ser Tyr Thr Glu Ser Leu
            20                  25                  30

Lys Arg Leu Pro Asp Trp Ser Met
        35                  40
```

```
<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Arg Pro Ala Arg Pro Leu Pro Val Arg Gly Arg Ala Pro Asp Trp
1               5                   10                  15

Ser Met


<210> SEQ ID NO 169
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Arg Arg Pro Ala Arg Pro Leu Pro Val Arg Ala Ala Ile Ala Ser Glu
1               5                   10                  15

Val Pro Val Ala Thr Thr Ser Pro Arg Pro Asp Trp Ser Met
            20                  25                  30


<210> SEQ ID NO 170
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Arg Arg Pro Ala Arg Pro Leu Pro Val Arg Ala Ala Ile Ala Ser Glu
1               5                   10                  15

Val Pro Val Ala Thr Thr Ser Pro Arg Ser Leu Lys Arg Leu Pro Asp
            20                  25                  30

Trp Ser Met
        35


<210> SEQ ID NO 171
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Arg Arg Pro Ala Arg Pro Leu Pro Val Arg Ala Ala Ile Ala Ser Glu
1               5                   10                  15

Val Pro Val Ala Thr Thr Ser Pro Arg Ile Asn Gly Thr Lys Phe Ser
            20                  25                  30

Tyr Thr Glu Ser Leu Lys Arg Leu Pro Asp Trp Ser Met
        35                  40                  45


<210> SEQ ID NO 172
<211> LENGTH: 56
<212> TYPE: PRT
<213> ORGANISM: Cinnamomum camphora
```

<400> SEQUENCE: 172

Arg Gly Met Lys Pro Arg Ser Ser Asp Leu Gln Leu Arg Ala Gly Asn
1               5                   10                  15

Ala Gln Thr Ser Leu Lys Met Ile Asn Gly Thr Lys Phe Ser Tyr Thr
            20                  25                  30

Glu Ser Leu Lys Lys Leu Pro Asp Trp Ser Met Leu Phe Ala Val Ile
        35                  40                  45

Thr Thr Ile Phe Ser Ala Ala Glu
    50                  55

<210> SEQ ID NO 173
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Ser Gly Pro Arg Arg Pro Ala Arg Pro Leu Pro Val Arg Gly Arg Ala
1               5                   10                  15

Pro Asp Trp Ser Met Leu Phe Ala Val Ile Thr Thr Ile Phe Ser Ala
            20                  25                  30

Ala Glu

<210> SEQ ID NO 174
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ser Gly Pro Arg Arg Pro Ala Arg Pro Leu Pro Val Arg Ala Ala Ile
1               5                   10                  15

Ala Ser Glu Val Pro Val Ala Thr Thr Ser Pro Arg Ser Leu Lys Arg
            20                  25                  30

Leu Pro Asp Trp Ser Met Leu Phe Ala Val Ile Thr Thr Ile Phe Ser
        35                  40                  45

Ala Ala Glu
    50

<210> SEQ ID NO 175
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Ser Gly Pro Arg Arg Pro Ala Arg Pro Leu Pro Val Arg Ala Ala Ile
1               5                   10                  15

Ala Ser Glu Val Pro Val Ala Thr Thr Ser Pro Arg Ser Leu Lys Lys
            20                  25                  30

Leu Pro Asp Trp Ser Met Leu Phe Ala Val Ile Thr Thr Ile Phe Ser
        35                  40                  45

Ala Ala Glu
    50

<210> SEQ ID NO 176
<211> LENGTH: 83
<212> TYPE: PRT
<213> ORGANISM: Cuphea palustris

<400> SEQUENCE: 176

```
Ser Ser Leu Ser Val Pro Phe Lys Pro Lys Ser Asn His Asn Gly Gly
1               5                   10                  15

Phe Gln Val Lys Ala Asn Ala Ser Ala His Pro Lys Ala Asn Gly Ser
            20                  25                  30

Ala Val Ser Leu Lys Ser Gly Ser Leu Glu Thr Gln Glu Asp Lys Thr
        35                  40                  45

Ser Ser Ser Ser Pro Pro Pro Arg Thr Phe Ile Asn Gln Leu Pro Val
    50                  55                  60

Trp Ser Met Leu Leu Ser Ala Val Thr Thr Val Phe Gly Val Ala Glu
65                  70                  75                  80

Lys Gln Trp
```

<210> SEQ ID NO 177
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Arg Pro Ala Arg Pro Leu Pro Val Arg Gly Arg Ala Ser Met Leu Leu
1               5                   10                  15

Ser Ala Val Thr Thr Val Phe Gly Val Ala Glu Lys Gln Trp
            20                  25                  30
```

<210> SEQ ID NO 178
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Arg Pro Ala Arg Pro Leu Pro Val Arg Ala Ala Ile Ala Ser Glu Val
1               5                   10                  15

Pro Val Ala Thr Thr Ser Pro Arg Ala His Pro Lys Ala Asn Gly Ser
            20                  25                  30

Ala Val Ser Leu Lys Ser Gly Ser Leu Glu Thr Gln Glu Asp Lys Thr
        35                  40                  45

Ser Ser Ser Ser Pro Pro Pro Arg Thr Phe Ile Asn Gln Leu Pro Val
    50                  55                  60

Trp Ser Met Leu Leu Ser Ala Val Thr Thr Val Phe Gly Val Ala Glu
65                  70                  75                  80

Lys Gln Trp
```

<210> SEQ ID NO 179
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Arg Pro Ala Arg Pro Leu Pro Val Arg Ala Ala Ile Ala Ser Glu Val
1 5 10 15

Pro Val Ala Thr Thr Ser Pro Arg Ala His Pro Lys Ala Asn Gly Ser
20 25 30

Ala Val Ser Leu Lys Ser Gly Ser Leu Glu Thr Gln Glu Asp Lys Thr
35 40 45

Ser Ser Ser Ser Pro Pro Pro Arg Thr Phe Ile Asn Gln Leu Pro Val
50 55 60

Trp Ser Met Leu Leu Ser Ala Val Thr Thr Val Phe Gly Val Ala Glu
65 70 75 80

Lys Gln Trp

<210> SEQ ID NO 180
<211> LENGTH: 73
<212> TYPE: PRT
<213> ORGANISM: Ulmus americana

<400> SEQUENCE: 180

Gly Ser Gly Ala Leu Gln Val Lys Ala Ser Ser Gln Ala Pro Pro Lys
1 5 10 15

Leu Asn Gly Ser Asn Val Gly Leu Val Lys Ser Ser Gln Ile Val Lys
20 25 30

Lys Gly Asp Asp Thr Thr Ser Pro Pro Ala Arg Thr Phe Ile Asn Gln
35 40 45

Leu Pro Asp Trp Ser Met Leu Leu Ala Ala Ile Thr Thr Leu Phe Leu
50 55 60

Ala Ala Glu Lys Gln Trp Met Met Leu
65 70

<210> SEQ ID NO 181
<211> LENGTH: 52
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 181

Arg Cys Gly Asp Leu Arg Arg Ser Ala Gly Ser Gly Pro Arg Arg Pro
1 5 10 15

Ala Arg Pro Leu Pro Val Arg Gly Arg Ala Gln Leu Pro Asp Trp Ser
20 25 30

Met Leu Leu Ala Ala Ile Thr Thr Leu Phe Leu Ala Ala Glu Lys Gln
35 40 45

Trp Met Met Leu
50

<210> SEQ ID NO 182
<211> LENGTH: 98
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 182

Arg Cys Gly Asp Leu Arg Arg Ser Ala Gly Ser Gly Pro Arg Arg Pro
1 5 10 15

```
Ala Arg Pro Leu Pro Val Arg Ala Ala Ile Ala Ser Glu Val Pro Val
            20                  25                  30

Ala Thr Thr Ser Pro Arg Pro Pro Lys Leu Asn Gly Ser Asn Val Gly
        35                  40                  45

Leu Val Lys Ser Ser Gln Ile Val Lys Lys Gly Asp Asp Thr Thr Ser
    50                  55                  60

Pro Pro Ala Arg Thr Phe Ile Asn Gln Leu Pro Asp Trp Ser Met Leu
65                  70                  75                  80

Leu Ala Ala Ile Thr Thr Leu Phe Leu Ala Ala Glu Lys Gln Trp Met
                85                  90                  95

Met Leu


<210> SEQ ID NO 183
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Arg Cys Gly Asp Leu Arg Arg Ser Ala Gly Ser Gly Pro Arg Arg Pro
1               5                   10                  15

Ala Arg Pro Leu Pro Val Arg Ala Ala Ile Ala Ser Glu Val Pro Val
            20                  25                  30

Ala Thr Thr Ser Pro Arg Pro Pro Lys Leu Asn Gly Ser Asn Val Gly
        35                  40                  45

Leu Val Lys Ser Ser Gln Ile Val Lys Lys Gly Asp Asp Thr Thr Ser
    50                  55                  60

Pro Pro Ala Arg Thr Phe Ile Asn Gln Leu Pro Asp Trp Ser Met Leu
65                  70                  75                  80

Leu Ala Ala Ile Thr Thr Leu Phe Leu Ala Ala Glu Lys Gln Trp Met
                85                  90                  95

Met Leu


<210> SEQ ID NO 184
<211> LENGTH: 60
<212> TYPE: PRT
<213> ORGANISM: Umbellularia californica

<400> SEQUENCE: 184

Arg Ser Ser Asp Leu Gln Leu Arg Ala Gly Asn Ala Pro Thr Ser Leu
1               5                   10                  15

Lys Met Ile Asn Gly Thr Lys Phe Ser Tyr Thr Glu Ser Leu Lys Arg
            20                  25                  30

Leu Pro Asp Trp Ser Met Leu Phe Ala Val Ile Thr Thr Ile Phe Ser
        35                  40                  45

Ala Ala Glu Lys Gln Trp Thr Asn Leu Glu Trp Lys
    50                  55                  60


<210> SEQ ID NO 185
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185
```

```
Pro Ala Arg Pro Leu Pro Val Arg Gly Arg Ala Pro Asp Trp Ser Met
1               5                   10                  15

Leu Phe Ala Val Ile Thr Thr Ile Phe Ser Ala Ala Glu Lys Gln Trp
            20                  25                  30

Thr Asn Leu Glu Trp Lys
        35


<210> SEQ ID NO 186
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Pro Ala Arg Pro Leu Pro Val Arg Ala Ala Ile Ala Ser Glu Val Pro
1               5                   10                  15

Val Ala Thr Thr Ser Pro Arg Ser Leu Lys Arg Leu Pro Asp Trp Ser
            20                  25                  30

Met Leu Phe Ala Val Ile Thr Thr Ile Phe Ser Ala Ala Glu Lys Gln
        35                  40                  45

Trp Thr Asn Leu Glu Trp Lys
    50                  55


<210> SEQ ID NO 187
<211> LENGTH: 55
<212> TYPE: PRT
<213> ORGANISM: Umbellularia californica

<400> SEQUENCE: 187

Pro Arg Ser Ser Asp Leu Gln Leu Arg Ala Gly Asn Ala Pro Thr Ser
1               5                   10                  15

Leu Lys Met Ile Asn Gly Thr Lys Phe Ser Tyr Thr Glu Ser Leu Lys
            20                  25                  30

Arg Leu Pro Asp Trp Ser Met Leu Phe Ala Val Ile Thr Thr Ile Phe
        35                  40                  45

Ser Ala Ala Glu Lys Gln Trp
    50                  55


<210> SEQ ID NO 188
<211> LENGTH: 58
<212> TYPE: PRT
<213> ORGANISM: Umbellularia californica

<400> SEQUENCE: 188

Pro Arg Ser Ser Gly Leu Gln Val Arg Ala Gly Lys Glu Gln Asn Ser
1               5                   10                  15

Cys Lys Met Ile Asn Gly Thr Lys Val Lys Asp Thr Glu Gly Leu Lys
            20                  25                  30

Gly Arg Ser Thr Leu His Gly Trp Ser Met Pro Leu Glu Leu Ile Thr
        35                  40                  45

Thr Ile Phe Ser Ala Ala Glu Lys Gln Trp
    50                  55


<210> SEQ ID NO 189
<211> LENGTH: 73
<212> TYPE: PRT
<213> ORGANISM: Cuphea hookeriana
```

<400> SEQUENCE: 189

Pro Lys Ser Thr Pro Asn Gly Gly Leu Gln Val Lys Ala Asn Ala Ser
1 5 10 15

Ala Pro Pro Lys Ile Asn Gly Ser Pro Val Gly Leu Lys Ser Gly Gly
20 25 30

Leu Lys Thr Gln Glu Asp Ala His Ser Ala Pro Pro Pro Arg Thr Phe
35 40 45

Ile Asn Gln Leu Pro Asp Trp Ser Met Leu Leu Ala Ala Ile Thr Thr
50 55 60

Val Phe Leu Ala Ala Glu Lys Gln Trp
65 70

<210> SEQ ID NO 190
<211> LENGTH: 73
<212> TYPE: PRT
<213> ORGANISM: Cuphea hookeriana

<400> SEQUENCE: 190

Pro Lys Phe Val Ala Asn Gly Gly Leu Gln Val Lys Ala Asn Ala Ser
1 5 10 15

Ala Pro Pro Lys Ile Asn Gly Ser Ser Val Gly Leu Lys Ser Cys Ser
20 25 30

Leu Lys Thr Gln Glu Asp Thr Pro Ser Ala Pro Ala Pro Arg Thr Phe
35 40 45

Ile Asn Gln Leu Pro Asp Trp Ser Met Leu Leu Ala Ala Ile Thr Thr
50 55 60

Val Phe Leu Ala Ala Glu Lys Gln Trp
65 70

<210> SEQ ID NO 191
<211> LENGTH: 73
<212> TYPE: PRT
<213> ORGANISM: Cuphea lanceolata

<400> SEQUENCE: 191

Pro Lys Phe Val Ala Asn Ala Gly Leu Lys Val Lys Ala Ser Ala Ser
1 5 10 15

Ala Pro Pro Lys Ile Asn Gly Ser Ser Val Gly Leu Lys Ser Gly Ser
20 25 30

Leu Lys Thr Gln Glu Asp Thr Pro Ser Val Pro Pro Pro Arg Thr Phe
35 40 45

Ile Asn Gln Leu Pro Asp Trp Ser Met Leu Leu Ala Ala Ile Thr Thr
50 55 60

Val Phe Leu Ala Ala Glu Lys Gln Trp
65 70

<210> SEQ ID NO 192
<211> LENGTH: 72
<212> TYPE: PRT
<213> ORGANISM: Cuphea hookeriana

<400> SEQUENCE: 192

Pro Lys Ser Ile Pro Asn Gly Gly Phe Gln Val Lys Ala Asn Asp Ser
1 5 10 15

Ala His Pro Lys Ala Asn Gly Ser Ala Val Ser Leu Lys Ser Gly Ser
20 25 30

Leu Asn Thr Gln Glu Asp Thr Ser Ser Ser Pro Pro Pro Arg Thr Phe
35 40 45

```
Leu His Gln Leu Pro Asp Trp Ser Arg Leu Leu Thr Ala Ile Thr Thr
    50                  55                  60

Val Phe Val Lys Ser Lys Arg Pro
65                  70


<210> SEQ ID NO 193
<211> LENGTH: 74
<212> TYPE: PRT
<213> ORGANISM: Cuphea palustris

<400> SEQUENCE: 193

Pro Lys Ser Ile Pro Asn Gly Gly Phe Gln Val Lys Ala Asn Ala Ser
1               5                   10                  15

Ala His Pro Lys Ala Asn Gly Ser Ala Val Thr Leu Lys Ser Gly Ser
            20                  25                  30

Leu Asn Thr Gln Glu Asp Thr Leu Ser Ser Ser Pro Pro Pro Arg Ala
        35                  40                  45

Phe Phe Asn Gln Leu Pro Asp Trp Ser Met Leu Leu Thr Ala Ile Thr
    50                  55                  60

Thr Val Phe Val Ala Pro Glu Lys Arg Trp
65                  70


<210> SEQ ID NO 194
<211> LENGTH: 73
<212> TYPE: PRT
<213> ORGANISM: Cuphea lanceolata

<400> SEQUENCE: 194

Pro Lys Ser Ile Pro Asn Ala Gly Phe Gln Val Lys Ala Asn Ala Ser
1               5                   10                  15

Ala His Pro Lys Ala Asn Gly Ser Ala Val Asn Leu Lys Ser Gly Ser
            20                  25                  30

Leu Asn Thr Gln Glu Asp Thr Ser Ser Ser Pro Pro Pro Arg Ala Phe
        35                  40                  45

Leu Asn Gln Leu Pro Asp Trp Ser Met Leu Leu Thr Ala Ile Thr Thr
    50                  55                  60

Val Phe Val Ala Ala Glu Lys Gln Trp
65                  70


<210> SEQ ID NO 195
<211> LENGTH: 62
<212> TYPE: PRT
<213> ORGANISM: Cuphea hookeriana

<400> SEQUENCE: 195

Asn Gly Gly Phe Gln Val Lys Ala Asn Ala Asn Ala His Pro Ser Leu
1               5                   10                  15

Lys Ser Gly Ser Leu Glu Thr Glu Asp Asp Thr Ser Ser Ser Ser Pro
            20                  25                  30

Pro Pro Arg Thr Phe Ile Asn Gln Leu Pro Asp Trp Ser Met Leu Leu
        35                  40                  45

Ser Ala Ile Thr Thr Ile Phe Gly Ala Ala Glu Lys Gln Trp
    50                  55                  60


<210> SEQ ID NO 196
<211> LENGTH: 62
<212> TYPE: PRT
<213> ORGANISM: Cuphea wrightii
```

<400> SEQUENCE: 196

Pro Asp Asn Gly Gly Phe His Val Lys Ala Asn Ala Ser Ala His Pro
1 5 10 15

Lys Ala Asn Gly Ser Ala Val Asn Leu Lys Ser Gly Ser Leu Glu Thr
20 25 30

Pro Pro Arg Ser Phe Ile Asn Gln Leu Pro Asp Leu Ser Met Leu Leu
35 40 45

Ser Lys Ile Thr Thr Val Phe Gly Ala Ala Glu Lys Gln Trp
50 55 60

<210> SEQ ID NO 197
<211> LENGTH: 74
<212> TYPE: PRT
<213> ORGANISM: Cuphea lanceolata

<400> SEQUENCE: 197

Leu Lys Ser Asn His Asn Gly Gly Phe Gln Val Lys Ala Asn Ala Ser
1 5 10 15

Ala His Pro Lys Ala Asn Gly Ser Ala Val Ser Leu Lys Ala Gly Ser
20 25 30

Leu Glu Thr Gln Glu Asp Thr Ser Ala Pro Ser Pro Pro Pro Arg Thr
35 40 45

Phe Ile Asn Gln Leu Pro Asp Trp Asn Met Leu Leu Ser Ala Ile Thr
50 55 60

Thr Val Phe Val Ala Ala Glu Lys Gln Trp
65 70

<210> SEQ ID NO 198
<211> LENGTH: 75
<212> TYPE: PRT
<213> ORGANISM: Cuphea palustris

<400> SEQUENCE: 198

Pro Lys Ser Asn His Asn Gly Gly Phe Gln Val Lys Ala Asn Ala Ser
1 5 10 15

Ala His Pro Lys Ala Asn Gly Ser Ala Val Ser Leu Lys Ser Gly Ser
20 25 30

Leu Glu Thr Gln Glu Asp Lys Thr Ser Ser Ser Ser Pro Pro Pro Arg
35 40 45

Thr Phe Ile Asn Gln Leu Pro Val Trp Ser Met Leu Leu Ser Ala Val
50 55 60

Thr Thr Val Phe Gly Val Ala Glu Lys Gln Trp
65 70 75

<210> SEQ ID NO 199
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (23)..(23)
<223> OTHER INFORMATION: Any amino acid

<400> SEQUENCE: 199

Pro Phe Thr Ile Gly Thr Leu Arg Lys Ala Ile Pro Ala His Cys Phe
1 5 10 15

Glu Arg Ser Ala Leu Arg Xaa Arg Ala Ser Met Leu Leu Ser Ala Val

```
            20                  25                  30

Thr Thr Val Phe Gly Val Ala Glu Lys Gln Trp
        35                  40


<210> SEQ ID NO 200
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Any amino acid

<400> SEQUENCE: 200

Leu Arg Arg Ser Ala Gly Ser Gly Pro Arg Arg Pro Ala Arg Pro Leu
1               5                   10                  15

Pro Val Arg Gly Xaa Ala Ser Met Leu Leu Ser Ala Val Thr Thr Val
            20                  25                  30

Phe Gly Val Ala Glu Lys Gln Trp
        35                  40


<210> SEQ ID NO 201
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any amino acid

<400> SEQUENCE: 201

Pro Phe Thr Ile Gly Thr Leu Arg Lys Ala Ile Pro Ala His Cys Phe
1               5                   10                  15

Glu Arg Ser Ala Leu Arg Xaa Arg Ala Pro Ala Asn Gly Ser Ala Val
            20                  25                  30

Thr Leu Lys Ser Gly Ser Leu Asn Thr Gln Glu Asp Thr Leu Ser Ser
        35                  40                  45

Ser Pro Pro Pro Arg Ala Phe Phe Asn Gln Leu Pro Asp Trp Ser Met
    50                  55                  60

Leu Leu Thr Ala Ile Thr Thr Val Phe Val Ala Pro Glu Lys Arg Trp
65                  70                  75                  80


<210> SEQ ID NO 202
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any amino acid

<400> SEQUENCE: 202

Cys Gly Asp Leu Arg Arg Ser Ala Gly Ser Gly Pro Arg Arg Pro Ala
1               5                   10                  15

Arg Pro Leu Pro Val Arg Xaa Arg Ala Pro Ala Asn Gly Ser Ala Val
            20                  25                  30
```

```
Thr Leu Lys Ser Gly Ser Leu Asn Thr Gln Glu Asp Thr Leu Ser Ser
        35                  40                  45

Ser Pro Pro Pro Arg Ala Phe Phe Asn Gln Leu Pro Asp Trp Ser Met
    50                  55                  60

Leu Leu Thr Ala Ile Thr Thr Val Phe Val Ala Pro Glu Lys Arg Trp
65                  70                  75                  80


<210> SEQ ID NO 203
<211> LENGTH: 44
<212> TYPE: PRT
<213> ORGANISM: Cuphea wrightii

<400> SEQUENCE: 203

Ala His Pro Lys Ala Asn Gly Ser Ala Val Asn Leu Lys Ser Gly Ser
1               5                   10                  15

Leu Glu Thr Pro Pro Arg Ser Phe Ile Asn Gln Leu Pro Asp Leu Ser
            20                  25                  30

Met Leu Leu Ser Lys Ile Thr Thr Val Phe Gly Ala
        35                  40


<210> SEQ ID NO 204
<211> LENGTH: 53
<212> TYPE: PRT
<213> ORGANISM: Cuphea lanceolata

<400> SEQUENCE: 204

Ala His Pro Lys Ala Asn Gly Ser Ala Val Ser Leu Lys Ala Gly Ser
1               5                   10                  15

Leu Glu Thr Gln Glu Asp Thr Ser Ala Pro Ser Pro Pro Pro Arg Thr
            20                  25                  30

Phe Ile Asn Gln Leu Pro Asp Trp Asn Met Leu Leu Ser Ala Ile Thr
        35                  40                  45

Thr Val Phe Val Ala
    50


<210> SEQ ID NO 205
<211> LENGTH: 54
<212> TYPE: PRT
<213> ORGANISM: Cuphea palustris

<400> SEQUENCE: 205

Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val
    50


<210> SEQ ID NO 206
<211> LENGTH: 54
<212> TYPE: PRT
<213> ORGANISM: Arabidopsis thaliana

<400> SEQUENCE: 206

Ala Pro Pro Lys Ile Asn Gly Lys Arg Val Gly Leu Pro Gly Ser Val
1               5                   10                  15

Asp Ile Val Arg Thr Asp Thr Glu Thr Ser Ser His Pro Ala Pro Arg
```

```
            20                  25                  30

Thr Phe Ile Asn Gln Leu Pro Asp Trp Ser Met Leu Leu Ala Ala Ile
        35                  40                  45

Thr Thr Ile Phe Leu Ala
    50
```

<210> SEQ ID NO 207
<211> LENGTH: 54
<212> TYPE: PRT
<213> ORGANISM: Arabidopsis thaliana

<400> SEQUENCE: 207

```
Ala Pro Pro Lys Ile Asn Gly Lys Arg Val Gly Leu Pro Gly Ser Val
1               5                   10                  15

Asp Ile Val Arg Thr Asp Thr Glu Thr Ser Ser His Pro Ala Pro Arg
            20                  25                  30

Thr Phe Ile Asn Gln Leu Pro Asp Trp Ser Met Leu Leu Ala Ala Ile
        35                  40                  45

Thr Thr Ile Phe Leu Ala
    50
```

<210> SEQ ID NO 208
<211> LENGTH: 40
<212> TYPE: PRT
<213> ORGANISM: Garcinia mangostana

<400> SEQUENCE: 208

```
Ala Pro Thr Lys Ile Asn Gly Ser Thr Asp Asp Ala Gln Leu Pro Ala
1               5                   10                  15

Pro Arg Thr Phe Ile Asn Gln Leu Pro Asp Trp Ser Met Leu Leu Ala
            20                  25                  30

Ala Ile Thr Thr Val Phe Leu Ala
        35                  40
```

<210> SEQ ID NO 209
<211> LENGTH: 52
<212> TYPE: PRT
<213> ORGANISM: Gossypium hirsutum

<400> SEQUENCE: 209

```
Ala Pro Pro Lys Ile Asn Gly Thr Val Ala Ser Thr Thr Pro Val Glu
1               5                   10                  15

Gly Ser Lys Asn Asp Asp Gly Ala Ser Ser Pro Pro Pro Arg Thr Phe
            20                  25                  30

Ile Asn Gln Leu Pro Asp Trp Ser Met Leu Leu Ala Ala Ile Thr Thr
        35                  40                  45

Ile Phe Leu Ala
    50
```

<210> SEQ ID NO 210
<211> LENGTH: 52
<212> TYPE: PRT
<213> ORGANISM: Elaeis guineensis

<400> SEQUENCE: 210

```
Ala Val Pro Lys Ile Asn Gly Ala Lys Val Gly Leu Lys Ala Glu Ser
1               5                   10                  15

Gln Lys Ala Glu Glu Asp Ala Ala Pro Ser Ser Ala Pro Arg Thr Phe
            20                  25                  30
```

Tyr Asn Gln Leu Pro Asp Trp Ser Val Leu Leu Ala Ala Val Thr Thr
35 40 45

Ile Phe Leu Ala
50

<210> SEQ ID NO 211
<211> LENGTH: 57
<212> TYPE: PRT
<213> ORGANISM: Iris germanica

<400> SEQUENCE: 211

Cys Pro Glu Ser His Glu Gly Gln Arg Val Gln Gly Arg Val Glu Asn
1 5 10 15

Arg Gln Ala Lys Val Glu Asp Gly Arg Ser Val Leu Pro Ser Ser Ser
20 25 30

Ala Pro Arg Thr Phe Tyr Asn Gln Leu Pro Asp Trp Ser Val Leu Leu
35 40 45

Ala Ala Ile Thr Thr Ile Phe Leu Ala
50 55

<210> SEQ ID NO 212
<211> LENGTH: 53
<212> TYPE: PRT
<213> ORGANISM: Iris germanica

<400> SEQUENCE: 212

Ala Ala Thr Arg Val Asn Gly Ser Lys Val Gly Leu Lys Thr Asp Thr
1 5 10 15

Asn Lys Leu Glu Asp Ala Pro Phe Ile Pro Ser Ser Ala Pro Arg Thr
20 25 30

Phe Tyr Asn Gln Leu Pro Asp Trp Ser Val Leu Leu Ala Ala Ile Thr
35 40 45

Thr Ile Phe Leu Ala
50

<210> SEQ ID NO 213
<211> LENGTH: 53
<212> TYPE: PRT
<213> ORGANISM: Iris tectorum

<400> SEQUENCE: 213

Ala Ala Thr Arg Val Asn Gly Ser Lys Val Gly Leu Lys Thr Asp Thr
1 5 10 15

Asn Lys Leu Glu Asp Ala Pro Phe Ile Pro Ser Ser Ala Pro Arg Thr
20 25 30

Phe Tyr Asn Gln Leu Pro Asp Trp Ser Val Leu Leu Ala Ala Ile Thr
35 40 45

Thr Ile Phe Leu Ala
50

<210> SEQ ID NO 214
<211> LENGTH: 53
<212> TYPE: PRT
<213> ORGANISM: Iris tectorum

<400> SEQUENCE: 214

Ala Ala Thr Arg Val Asn Gly Ser Lys Val Gly Leu Lys Thr Asp Thr
1 5 10 15

Asn Lys Leu Glu Asp Thr Pro Phe Phe Pro Ser Ser Ala Pro Arg Thr
20 25 30

```
Phe Tyr Asn Gln Leu Pro Asp Trp Ser Val Ser Phe Ala Ala Ile Thr
        35                  40                  45

Thr Ile Phe Leu Ala
    50


<210> SEQ ID NO 215
<211> LENGTH: 56
<212> TYPE: PRT
<213> ORGANISM: Myristica fragrans

<400> SEQUENCE: 215

Thr Val Pro Lys Ile Asn Gly Asn Lys Ala Gly Leu Leu Thr Pro Met
1               5                   10                  15

Glu Ser Thr Lys Asp Glu Asp Ile Val Ala Ala Pro Thr Val Ala Pro
            20                  25                  30

Lys Arg Thr Phe Ile Asn Gln Leu Pro Asp Trp Ser Met Leu Leu Ala
        35                  40                  45

Ala Ile Thr Thr Ile Phe Leu Ala
    50                  55


<210> SEQ ID NO 216
<211> LENGTH: 50
<212> TYPE: PRT
<213> ORGANISM: Helianthus annuus

<400> SEQUENCE: 216

Ala Pro Thr Glu Val Asn Gly Ser Arg Ser Arg Ile Thr His Gly Phe
1               5                   10                  15

Lys Thr Asp Asp Tyr Ser Thr Ser Pro Ala Pro Arg Thr Phe Ile Asn
            20                  25                  30

Gln Leu Pro Asp Trp Ser Met Leu Leu Ala Ala Ile Thr Thr Ile Phe
        35                  40                  45

Leu Ala
    50


<210> SEQ ID NO 217
<211> LENGTH: 53
<212> TYPE: PRT
<213> ORGANISM: Ulmus americana

<400> SEQUENCE: 217

Ala Pro Pro Lys Leu Asn Gly Ser Asn Val Gly Leu Val Lys Ser Ser
1               5                   10                  15

Gln Ile Val Lys Lys Gly Asp Asp Thr Thr Ser Pro Pro Ala Arg Thr
            20                  25                  30

Phe Ile Asn Gln Leu Pro Asp Trp Ser Met Leu Leu Ala Ala Ile Thr
        35                  40                  45

Thr Leu Phe Leu Ala
    50


<210> SEQ ID NO 218
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
```

<400> SEQUENCE: 218

Met Xaa Ile Lys Thr Asn Arg Gln Pro Val Glu Lys Pro Pro Phe Thr
1 5 10 15

Ile Gly Thr Leu Arg Lys Ala Ile Pro Ala His Cys Phe Glu Arg Ser
20 25 30

Ala Leu Arg Gly Arg Ala Gln Leu Pro Asp Trp Ser Met Leu Leu Ala
35 40 45

Ala Ile Thr Thr Leu Phe Leu Ala
50 55

<210> SEQ ID NO 219
<211> LENGTH: 56
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Any amino acid

<400> SEQUENCE: 219

Met Xaa Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Gly Arg Ala Gln Leu Pro Asp Trp Ser Met Leu Leu Ala
35 40 45

Ala Ile Thr Thr Leu Phe Leu Ala
50 55

<210> SEQ ID NO 220
<211> LENGTH: 197
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

Pro Phe Lys Pro Lys Ser Asn Pro Asn Gly Arg Phe Gln Val Lys Ala
1 5 10 15

Asn Val Ser Pro His Gly Arg Ala Pro Lys Ala Asn Gly Ser Ala Val
20 25 30

Ser Leu Lys Ser Gly Ser Leu Asn Thr Leu Glu Asp Pro Pro Ser Ser
35 40 45

Pro Pro Pro Arg Thr Phe Leu Asn Gln Leu Pro Asp Trp Ser Arg Leu
50 55 60

Arg Thr Ala Ile Thr Thr Val Phe Val Ala Ala Glu Lys Gln Phe Thr
65 70 75 80

Arg Leu Asp Arg Lys Ser Lys Arg Pro Asp Met Leu Val Asp Trp Phe
85 90 95

Gly Ser Glu Thr Ile Val Gln Asp Gly Leu Val Phe Arg Glu Arg Phe
100 105 110

Ser Ile Arg Ser Tyr Glu Ile Gly Ala Asp Arg Thr Ala Ser Ile Glu
115 120 125

Thr Leu Met Asn His Leu Gln Asp Thr Ser Leu Asn His Cys Lys Ser
130 135 140

```
Val Gly Leu Leu Asn Asp Gly Phe Gly Arg Thr Pro Glu Met Cys Thr
145                 150                 155                 160

Arg Asp Leu Ile Trp Val Leu Thr Lys Met Gln Ile Val Val Asn Arg
                165                 170                 175

Tyr Pro Thr Trp Gly Asp Thr Val Glu Ile Asn Ser Trp Phe Ser Gln
        180                 185                 190

Ser Gly Lys Ile Gly
    195
```

<210> SEQ ID NO 221
<211> LENGTH: 196
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 221

```
Pro Phe Lys Pro Lys Ser Asn Pro Asn Gly Arg Phe Gln Val Lys Ala
1               5                   10                  15

Asn Val Ser Pro His Gly Arg Ala Pro Lys Ala Asn Gly Ser Ala Val
            20                  25                  30

Ser Leu Lys Ser Gly Ser Leu Asn Thr Leu Glu Asp Pro Pro Ser Ser
        35                  40                  45

Pro Pro Pro Arg Thr Phe Leu Asn Gln Leu Pro Asp Trp Ser Arg Leu
    50                  55                  60

Leu Thr Ala Ile Thr Thr Val Phe Val Lys Ser Lys Arg Pro Asp Met
65                  70                  75                  80

His Asp Arg Lys Ser Lys Arg Pro Asp Met Leu Val Asp Ser Phe Gly
                85                  90                  95

Leu Glu Ser Thr Val Gln Asp Gly Leu Val Phe Arg Gln Ser Phe Ser
            100                 105                 110

Ile Arg Ser Tyr Glu Ile Gly Thr Asp Arg Thr Ala Ser Ile Glu Thr
        115                 120                 125

Leu Met Asn His Leu Gln Glu Thr Ser Leu Asn His Cys Lys Ser Thr
    130                 135                 140

Gly Ile Leu Leu Asp Gly Phe Gly Arg Thr Leu Glu Met Cys Lys Arg
145                 150                 155                 160

Asp Leu Ile Trp Val Val Ile Lys Met Gln Ile Lys Val Asn Arg Tyr
                165                 170                 175

Pro Thr Trp Gly Asp Thr Val Glu Ile Asn Ser Trp Phe Ser Gln Ser
            180                 185                 190

Gly Lys Ile Gly
        195
```

<210> SEQ ID NO 222
<211> LENGTH: 197
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 222

```
Pro Phe Lys Pro Lys Ser Asn Pro Asn Gly Arg Phe Gln Val Lys Ala
1               5                   10                  15

Asn Val Ser Pro His Gly Arg Ala Pro Lys Ala Asn Gly Ser Ala Val
            20                  25                  30
```

```
Ser Leu Lys Ser Gly Ser Leu Asn Thr Leu Glu Asp Pro Pro Ser Ser
        35                  40                  45

Pro Pro Pro Arg Thr Phe Leu Asn Gln Leu Pro Asp Trp Ser Arg Leu
    50                  55                  60

Arg Thr Ala Ile Thr Thr Val Phe Val Ala Ala Glu Lys Gln Phe Thr
65                  70                  75                  80

Arg Leu Asp Arg Lys Ser Lys Arg Pro Asp Met Leu Val Asp Trp Phe
                85                  90                  95

Gly Ser Glu Thr Ile Val Gln Asp Gly Leu Val Phe Arg Glu Arg Phe
            100                 105                 110

Ser Ile Arg Ser Tyr Glu Ile Gly Ala Asp Arg Thr Ala Ser Ile Glu
        115                 120                 125

Thr Leu Met Asn His Leu Gln Glu Thr Ser Leu Asn His Cys Lys Ser
    130                 135                 140

Thr Gly Ile Leu Leu Asp Gly Phe Gly Arg Thr Leu Glu Met Cys Lys
145                 150                 155                 160

Arg Asp Leu Ile Trp Val Val Ile Lys Met Gln Ile Lys Val Asn Arg
                165                 170                 175

Tyr Pro Thr Trp Gly Asp Thr Val Glu Ile Asn Ser Trp Phe Ser Gln
            180                 185                 190

Ser Gly Lys Ile Gly
        195


<210> SEQ ID NO 223
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Pro Phe Lys Pro Lys Ser Asn Pro Asn Gly Arg Phe Gln Val Lys Ala
1               5                   10                  15

Asn Val Ser Pro His Gly Arg Ala Pro Lys Ala Asn Gly Ser Ala Val
            20                  25                  30

Ser Leu Lys Ser Gly Ser Leu Asn Thr Leu Glu Asp Pro Pro Ser Ser
        35                  40                  45

Pro Pro Pro Arg Thr Phe Leu Asn Gln Leu Pro Asp Trp Ser Arg Leu
    50                  55                  60

Leu Thr Ala Ile Thr Thr Val Phe Val Lys Ser Lys Arg Pro Asp Met
65                  70                  75                  80

His Asp Arg Lys Ser Lys Arg Pro Asp Met Leu Val Asp Ser Phe Gly
                85                  90                  95

Leu Glu Ser Thr Val Gln Asp Gly Leu Val Phe Arg Gln Ser Phe Ser
            100                 105                 110

Ile Arg Ser Tyr Glu Ile Gly Thr Asp Arg Thr Ala Ser Ile Glu Thr
        115                 120                 125

Leu Met Asn His Leu Gln Asp Thr Ser Leu Asn His Cys Lys Ser Val
    130                 135                 140

Gly Leu Leu Asn Asp Gly Phe Gly Arg Thr Pro Glu Met Cys Thr Arg
145                 150                 155                 160

Asp Leu Ile Trp Val Leu Thr Lys Met Gln Ile Val Val Asn Arg Tyr
                165                 170                 175

Pro Thr Trp Gly Asp Thr Val Glu Ile Asn Ser Trp Phe Ser Gln Ser
```

```
            180                 185                 190

Gly Lys Ile Gly
        195


<210> SEQ ID NO 224
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Pro Phe Lys Pro Lys Ser Asn Pro Asn Gly Arg Phe Gln Val Lys Ala
1               5                   10                  15

Asn Val Ser Pro His Gly Arg Ala Pro Lys Ala Asn Gly Ser Ala Val
            20                  25                  30

Ser Leu Lys Ser Gly Ser Leu Asn Thr Gln Glu Asp Thr Ser Ser Ser
        35                  40                  45

Pro Pro Pro Arg Thr Phe Leu His Gln Leu Pro Asp Trp Ser Arg Leu
    50                  55                  60

Leu Thr Ala Ile Thr Thr Val Phe Val Lys Ser Lys Arg Pro Asp Met
65                  70                  75                  80

His Asp Arg Lys Ser Lys Arg Pro Asp Met Leu Val Asp Ser Phe Gly
                85                  90                  95

Leu Glu Ser Thr Val Gln Asp Gly Leu Val Phe Arg Gln Ser Phe Ser
            100                 105                 110

Ile Arg Ser Tyr Glu Ile Gly Thr Asp Arg Thr Ala Ser Ile Glu Thr
        115                 120                 125

Leu Met Asn His Leu Gln Glu Thr Ser Leu Asn His Cys Lys Ser Thr
    130                 135                 140

Gly Ile Leu Leu Asp Gly Phe Gly Arg Thr Leu Glu Met Cys Lys Arg
145                 150                 155                 160

Asp Leu Ile Trp Val Val Ile Lys Met Gln Ile Lys Val Asn Arg Tyr
                165                 170                 175

Pro Thr Trp Gly Asp Thr Val Glu Ile Asn Ser Trp Phe Ser Gln Ser
            180                 185                 190

Gly Lys Ile Gly
        195


<210> SEQ ID NO 225
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Phe Lys Pro Lys Ser Asn Pro Asn Gly Arg Phe Gln Val Lys Ala Asn
1               5                   10                  15

Val Ser Pro His Gly Arg Ala Pro Lys Ala Asn Gly Ser Ala Val Ser
            20                  25                  30

Leu Lys Ser Gly Ser Leu Asn Thr Gln Glu Asp Thr Ser Ser Ser Pro
        35                  40                  45

Pro Pro Arg Thr Phe Leu His Gln Leu Pro Asp Trp Ser Arg Leu Leu
    50                  55                  60

Thr Ala Ile Thr Thr Val Phe Val Lys Ser Lys Arg Pro Asp Met His
```

```
65                  70                  75                  80

Asp Arg Lys Ser Lys Arg Pro Asp Met Leu Val Asp Ser Phe Gly Leu
                85                  90                  95

Glu Ser Thr Val Gln Asp Gly Leu Val Phe Arg Gln Ser Phe Ser Ile
            100                 105                 110

Arg Ser Tyr Glu Ile Gly Thr Asp Arg Thr Ala Ser Ile Glu Thr Leu
        115                 120                 125

Met Asn His Leu Gln Glu Thr Ser Leu Asn His Cys Lys Ser Thr Gly
    130                 135                 140

Ile Leu Leu Asp Gly Phe Gly Arg Thr Leu Glu Met Cys Lys Arg Asp
145                 150                 155                 160

Leu Ile Trp Val Val Ile Lys Met Gln Ile Lys Val Asn Arg Tyr Pro
                165                 170                 175

Ala Trp Gly Asp Thr Val Glu Ile Asn Thr Arg Phe Ser Arg Leu Gly
            180                 185                 190

Lys Ile Gly
        195


<210> SEQ ID NO 226
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Lys Ala Ile Pro Ala His Cys Phe Glu Arg Ser Ala Leu Arg Gly Arg
1               5                   10                  15

Ala Gln Leu Pro Asp Trp Ser Arg Leu Leu Thr Ala Ile Thr Thr Val
            20                  25                  30

Phe Val Lys Ser Lys Arg Pro Asp Met His Asp Arg Lys Ser Lys Arg
        35                  40                  45

Pro Asp Met Leu Val Asp Ser Phe Gly Leu Glu Ser Thr Val Gln Asp
    50                  55                  60

Gly Leu Val Phe Arg Gln Ser Phe Ser Ile Arg Ser Tyr Glu Ile Gly
65                  70                  75                  80

Thr Asp Arg Thr Ala Ser Ile Glu Thr Leu Met Asn His Leu Gln Glu
                85                  90                  95

Thr Ser Leu Asn His Cys Lys Ser Thr Gly Ile Leu Leu Asp Gly Phe
            100                 105                 110

Gly Arg Thr Leu Glu Met Cys Lys Arg Asp Leu Ile Trp Val Val Ile
        115                 120                 125

Lys Met Gln Ile Lys Val Asn Arg Tyr Pro Ala Trp Gly Asp Thr Val
    130                 135                 140

Glu Ile Asn Thr Arg Phe Ser Arg Leu Gly Lys Ile Gly
145                 150                 155


<210> SEQ ID NO 227
<211> LENGTH: 48
<212> TYPE: PRT
<213> ORGANISM: Cuphea hookeriana

<400> SEQUENCE: 227

Ser Ile Glu Thr Leu Met Asn His Leu Gln Glu Thr Ser Leu Asn His
1               5                   10                  15

Cys Lys Ser Thr Gly Ile Leu Leu Asp Gly Phe Gly Arg Thr Leu Glu
```

```
            20                  25                  30

Met Cys Lys Arg Asp Leu Ile Trp Val Val Ile Lys Met Gln Ile Lys
        35                  40                  45


<210> SEQ ID NO 228
<211> LENGTH: 48
<212> TYPE: PRT
<213> ORGANISM: Cuphea wrightii

<400> SEQUENCE: 228

Ser Ile Glu Thr Leu Met Asn His Leu Gln Asp Thr Ser Leu Asn His
1               5                   10                  15

Cys Lys Ser Val Gly Leu Leu Asn Asp Gly Phe Gly Arg Thr Pro Glu
            20                  25                  30

Met Cys Thr Arg Asp Leu Ile Trp Val Leu Thr Lys Met Gln Ile Val
        35                  40                  45


<210> SEQ ID NO 229
<211> LENGTH: 48
<212> TYPE: PRT
<213> ORGANISM: Umbellularia californica

<400> SEQUENCE: 229

Ser Ile Leu Ala Val Met Asn His Met Gln Glu Ala Thr Leu Asn His
1               5                   10                  15

Ala Lys Ser Val Gly Ile Leu Gly Asp Gly Phe Gly Thr Thr Leu Glu
            20                  25                  30

Met Ser Lys Arg Asp Leu Met Trp Val Val Arg Arg Thr His Val Ala
        35                  40                  45


<210> SEQ ID NO 230
<211> LENGTH: 48
<212> TYPE: PRT
<213> ORGANISM: Cinnamomum camphora

<400> SEQUENCE: 230

Ser Ile Val Ala Val Met Asn His Leu Gln Glu Ala Ala Leu Asn His
1               5                   10                  15

Ala Lys Ser Val Gly Ile Leu Gly Asp Gly Phe Gly Thr Thr Leu Glu
            20                  25                  30

Met Ser Lys Arg Asp Leu Ile Trp Val Val Lys Arg Thr His Val Ala
        35                  40                  45


<210> SEQ ID NO 231
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Ser Ile Glu Thr Leu Met Asn His Leu Gln Glu Thr Ser Leu Asn His
1               5                   10                  15

Cys Lys Ser Thr Gly Ile Leu Leu Asp Gly Phe Gly Arg Thr Leu Glu
            20                  25                  30

Met Cys Lys Arg Asp Leu Ile
        35


<210> SEQ ID NO 232
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Ser Ile Leu Ala Val Met Asn His Met Gln Glu Ala Thr Leu Asn His
1               5                   10                  15

Ala Lys Ser Val Gly Ile Leu Gly Asp Gly Phe Gly Thr Thr Leu Glu
            20                  25                  30

Met Ser Lys Arg Asp Leu Met
        35


<210> SEQ ID NO 233
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Ser Ile Val Ala Val Met Asn His Leu Gln Glu Ala Ala Leu Asn His
1               5                   10                  15

Ala Lys Ser Val Gly Ile Leu Gly Asp Gly Phe Gly Thr Thr Leu Glu
            20                  25                  30

Met Ser Lys Arg Asp Leu Ile
        35


<210> SEQ ID NO 234
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Ser Ile Glu Thr Leu Met Asn His Leu Gln Glu Thr Ser Leu Asn His
1               5                   10                  15

Cys Lys Ser Thr Gly Ile Leu Leu Asp Gly Phe Gly Arg Thr Leu Glu
            20                  25                  30

Met Cys Lys Arg Asp Leu
        35


<210> SEQ ID NO 235
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Ser Ile Glu Thr Leu Met Asn His Leu Gln Asp Thr Ser Leu Asn His
1               5                   10                  15

Cys Lys Ser Val Gly Leu Leu Asn Asp Gly Phe Gly Arg Thr Pro Glu
            20                  25                  30

Met Cys Thr Arg Asp Leu
        35


<210> SEQ ID NO 236
```

<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 236

Ser Ile Glu Thr Leu Met Asn His Leu Gln Glu Thr Ser Ile Asn His
1 5 10 15

Cys Lys Ser Leu Gly Leu Leu Asn Asp Gly Phe Gly Arg Thr Pro Gly
20 25 30

Met Cys Lys Asn Asp Leu
35

<210> SEQ ID NO 237
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 237

Ser Ile Glu Thr Val Met Asn His Val Gln Glu Thr Ser Leu Asn Gln
1 5 10 15

Cys Lys Ser Ile Gly Leu Leu Asp Asp Gly Phe Gly Arg Ser Pro Glu
20 25 30

Met Cys Lys Arg Asp Leu
35

<210> SEQ ID NO 238
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

Ser Ile Glu Thr Leu Met Asn His Leu Gln Glu Thr Ser Leu Asn Gln
1 5 10 15

Cys Lys Ser Ala Gly Ile Leu His Asp Gly Phe Gly Arg Thr Leu Glu
20 25 30

Met Cys Lys Arg Asp Leu
35

<210> SEQ ID NO 239
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 239

Ser Ile Glu Thr Leu Met Asn Tyr Leu Gln Glu Thr Ser Leu Asn His
1 5 10 15

Cys Lys Ser Thr Gly Ile Leu Leu Asp Gly Phe Gly Arg Thr Pro Glu
20 25 30

Met Cys Lys Arg Asp Leu
35

```
<210> SEQ ID NO 240
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Ser Ile Met Ala Val Met Asn His Leu Gln Glu Ala Ala Arg Asn His
1               5                   10                  15

Ala Glu Ser Leu Gly Leu Leu Gly Asp Gly Phe Gly Glu Thr Leu Glu
            20                  25                  30

Met Ser Lys Arg Asp Leu
        35


<210> SEQ ID NO 241
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Ser Ile Glu Thr Leu Met Asn His Leu Gln Asp Thr Ser Leu Asn His
1               5                   10                  15

Cys Lys Ser Val Gly Leu Leu Asn Asp Gly Phe Gly Arg Thr Pro Glu
            20                  25                  30

Met Cys Thr Arg Asp Leu Ile
        35


<210> SEQ ID NO 242
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Ser Ile Glu Thr Leu Met Asn His Leu Gln Glu Thr Ser Ile Asn His
1               5                   10                  15

Cys Lys Ser Leu Gly Leu Leu Asn Asp Gly Phe Gly Arg Thr Pro Gly
            20                  25                  30

Met Cys Lys Asn Asp Leu Ile
        35


<210> SEQ ID NO 243
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Ser Ile Glu Thr Val Met Asn His Val Gln Glu Thr Ser Leu Asn Gln
1               5                   10                  15

Cys Lys Ser Ile Gly Leu Leu Asp Asp Gly Phe Gly Arg Ser Pro Glu
            20                  25                  30

Met Cys Lys Arg Asp Leu Ile
        35
```

-continued

```
<210> SEQ ID NO 244
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Ser Ile Glu Thr Leu Met Asn His Leu Gln Glu Thr Ser Leu Asn Gln
1               5                   10                  15

Cys Lys Ser Ala Gly Ile Leu His Asp Gly Phe Gly Arg Thr Leu Glu
            20                  25                  30

Met Cys Lys Arg Asp Leu Ile
        35


<210> SEQ ID NO 245
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Ser Ile Glu Thr Leu Met Asn Tyr Leu Gln Glu Thr Ser Leu Asn His
1               5                   10                  15

Cys Lys Ser Thr Gly Ile Leu Leu Asp Gly Phe Gly Arg Thr Pro Glu
            20                  25                  30

Met Cys Lys Arg Asp Leu Ile
        35


<210> SEQ ID NO 246
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ser Ile Met Ala Val Met Asn His Leu Gln Glu Ala Ala Arg Asn His
1               5                   10                  15

Ala Glu Ser Leu Gly Leu Leu Gly Asp Gly Phe Gly Glu Thr Leu Glu
            20                  25                  30

Met Ser Lys Arg Asp Leu Ile
        35
```

VARIANT THIOESTERASES AND METHODS OF USE

CROSS-REFERENCE TO RELATED APPLICATIONS

This application claims the benefit under 35 U.S.C.§119 (e) of U.S. Provisional Application No. 61/758,223, filed on Jan. 29, 2013, and is a continuation-in-part of U.S. application Ser. No. 13/797,733, filed on Mar. 12, 2013, both of which are hereby incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Mar. 10, 2014, is named SOLAP015X1US_SL.txt and is 327,441 bytes in size.

FIELD

The present invention relates to variant acyl-ACP thioesterases and their use in oil-producing cells, e.g., to increase enzymatic activity toward certain acyl-ACP substrates and to promote increased production of oils with desired fatty acid profiles.

BACKGROUND

Today, fats and fatty acids primarily come from vegetable and animal sources, with the notable exception of commercial production of omega-3 fatty acids by fermentation of microbes for use in baby formula and nutritional supplements. Progress is being made however toward the commercial production of tailored oils using recombinant microalgae. See PCT Publications WO2008/151149, WO2010/06032, WO2011/150410, WO2011/150411, and international patent application PCT/US12/23696.

One method for producing a desired fatty acid profile in an oleaginous organism is to introduce an acyl-ACP thioesterase transgene; e.g., a transgene from a plant that produces a desired fatty acid.

By terminating fatty acid biosynthesis, the acyl-acyl carrier protein (ACP) thioesterase (TE) functionally determines the length and identity of the fatty acid end product (Salas et al., (2002) *Archives of Biochemistry and Biophysics* 403: 25-34). Based on amino acid sequence alignments, the plant TEs have been shown to cluster into two families, FatAs, which show marked preference for 18:1-ACP with minor activity towards 18:0- and 16:0-ACPs; and FatBs, which hydrolyze primarily saturated acyl-ACPs with chain lengths that vary between 8-16 carbons (Voelker, In Genetic Engineering Volume 18. Edited by: Setlow J K. New York, Plenum Press; 1996:111-133; Ginalski, et al., *Nucl Acids Res* (2003) 31:3291-3292; and Jones, et al., (1995) *Plant Cell* 7: 359-371). FatB TEs have a conserved hydrophobic 18-amino acid domain (Facciotti and Yuan (1998) *European Journal of Lipid Science and Technology* 100:167-172), and a conserved Asn-His-Cys catalytic triad in the C-terminal catalytic domain (Blatti, et al., PLoS ONE (2012) 7(9): e42949. doi:10.1371 and Mayer and Shanklin, *BMC Plant Biology* (2007) 7:1-11). Mayer and Shanklin, *BMC Plant Biology* (2007) 7:1-11, identify a C-terminal conserved acyl-ACP thioesterase catalytic domain characterized by a C-terminal hot dog fold encompassing the Cys-His-Asn catalytic triad. The conserved acyl-ACP TE catalytic domain is well-characterized and has been assigned conserved domain accession number pfam01643. The hot dog fold is also well-characterized and has been assigned conserved domain accession number cd03440 and is part of the hotdog superfamily assigned conserved domain accession number c100509.

SUMMARY

In one aspect, provided are nucleic acid molecules encoding a variant acyl-ACP thioesterase comprising a C-terminal catalytic domain, and an N-terminal hydrophobic domain and specificity domain, wherein one or more of the hydrophobic domain and/or the specificity domain are heterologous to the catalytic domain. Generally, reading in the 5' to 3' direction, the N-terminal hydrophobic domain, the specificity domain and the catalytic domain are operably linked. In varying embodiments, one or more of the domains may abut one another.

In some embodiments, the nucleic acid molecule encodes a variant acyl-acyl carrier protein (ACP) thioesterase (TE) comprising:

i) the specificity domain from a C10:0 acyl-ACP preferring TE and a catalytic domain from a C12:0 acyl-ACP preferring TE;

ii) the specificity domain from a C12:0 acyl-ACP preferring TE and a catalytic domain from a C14:0 acyl-ACP preferring TE;

iii) the specificity domain from a C14:0 acyl-ACP preferring TE and a catalytic domain from a C12:0 acyl-ACP preferring TE;

iv) the specificity domain from a C12:0 acyl-ACP preferring TE and a catalytic domain from a C10:0 acyl-ACP preferring TE;

v) the specificity domain from a C10:0 acyl-ACP preferring TE and a catalytic domain from a C8:0 acyl-ACP preferring TE; and/or vi) the specificity domain from a C8:0 acyl-ACP preferring TE and a catalytic domain from a C10:0 acyl-ACP preferring TE.

In some embodiments, the nucleic acid encodes a specificity domain that comprises:

a) amino acid residues of an acyl-ACP-TE corresponding to an amino acid sequence selected from the group consisting of amino acid residues 125-163 of SEQ ID NO:43; amino acid residues 125-163 of SEQ ID NO:44; amino acid residues 152-190 of SEQ ID NO:45; amino acid residues 139-177 of SEQ ID NO:46; amino acid residues 117-155 of SEQ ID NO:47; amino acid residues 158-196 of SEQ ID NO:60; and amino acid residues 156-194 of SEQ ID NO:61;

b) a motif comprising the amino acid sequence (SEQ ID NO: 85)
SI(V/L/E)(A/T)(V/L)MN(H/Y/M/I)(L/M/V/F)QE(T/A)(A/S/T)(L/I)N(H/Q)(A/V/C)(K/E/R)(S/I/T/N/C)(V/L/A/T/I/N)G(L/I)(L/S/M)(G/L/D/N/E)(D/N/E)G(F/L)G(T/E/R/S/A)(T/S)(L/P/R)(E/G)M(S/Y/F/C/T)(K/R/L)(R/K/N/M)(D/G/N)L(M/I/F);
and/or and/or c) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 125-163 of SEQ ID NO:43; amino acid residues 125-163 of SEQ ID NO:44; amino acid residues 152-190 of SEQ ID NO:45; amino acid residues 139-177 of SEQ ID NO:46; amino acid residues 117-155 of SEQ ID NO:47; amino acid residues 158-196 of SEQ ID NO:60; and amino acid residues 156-194 of SEQ ID NO:61.

In some embodiments, the nucleic acid encodes a specificity domain that promotes, increases and/or prefers the production of triglycerides with an altered fatty acid profile and comprises:

a) a motif comprising the amino acid sequence (SEQ ID NO: 86)
SI(V/L/E)(A/T)(V/L)MN(H/Y/M/I)(L/M/V/F)QE(T/A)(A/S/T)(L/I)N(H/Q)(A/V/C)(K/E/R)(S/I/T/N/C)TGI(L/S/M)L(D/N/E)G(F/L)G(T/E/R/S/A)(T/S)L(E/G)M(S/Y/F/C/T)K(R/K/N/M)(D/G/N)L(M/I/F)WV(V/L)I(K/R)(M/T)(Q/H)(I/V)K;

b) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to amino acid residues 156-203 of SEQ ID NO:61, wherein the amino acid residue at or corresponding to position 166 is Glutamine; the amino acid residue at or corresponding to position 175 is Threonine; the amino acid residue at or corresponding to position 177 is Isoleucine; the amino acid residue at or corresponding to position 179 is Leucine; the amino acid residue at or corresponding to position 186 is Leucine; the amino acid residue at or corresponding to position 190 is Lysine; the amino acid at or corresponding to position 198 is Isoleucine and the amino acid at or corresponding to position 203 is Lysine; and/or c) SEQ ID NO:61.

In some embodiments, the nucleic acid encodes a specificity domain that promotes, increases and/or prefers the production of C12:0 fatty acids and comprises:

a) a motif comprising the amino acid sequence (SEQ ID NO: 87)
SIL(A/T)(V/L)MN(H/Y/M/I)MQE(T/A)T(L/I)N(H/Q)(A/V/C)(K/E/R)(S/I/T/N/C)(V/L/A/T/I/N)G(L/I)(L/S/M)(G/L/D/N/E)(D/N/E)G(F/L)G(T/E/R/S/A)(T/S)(L/P/R)(E/G)M(S/Y/F/C/T)(K/R/L)(R/K/N/M)(D/G/N)LM;

b) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 125-163 of SEQ ID NO:43 and amino acid residues 125-163 of SEQ ID NO:44; wherein the amino acid residue at or corresponding to position 127 is Leucine, the amino acid residue at or corresponding to position 133 is Methionine, the amino acid residue at or corresponding to position 137 is Threonine and the amino acid residue at or corresponding to position 163 is Methionine; and/or c) SEQ ID NO:43.

In some embodiments, the nucleic acid encodes a specificity domain that promotes, increases and/or prefers the production of C14:0 fatty acids and comprises:

a) a motif comprising the amino acid sequence (SEQ ID NO: 88)
SIV(A/T)(V/L)MN(H/Y/M/I)LQE(T/A)A(L/I)N(H/Q)(A/V/C)(K/E/R)(S/I/T/N/C)(V/L/A/T/I/N)G(L/I)(L/S/M)(G/L/D/N/E)(D/N/E)G(F/L)G(T/E/R/S/A)(T/S)(L/P/R)(E/G)M(S/Y/F/C/T)(K/R/L)(R/K/N/M)(D/G/N)LI;

b) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 125-163 of SEQ ID NO:43 and amino acid residues 125-163 of SEQ ID NO:44; wherein the amino acid residue at or corresponding to position 127 is Valine, the amino acid residue at or corresponding to position 133 is Leucine, the amino acid residue at or corresponding to position 137 is Alanine and the amino acid residue at or corresponding to position 163 is Isoleucine; and/or c) SEQ ID NO:44.

In some embodiments, the nucleic acid encodes a specificity domain that promotes, increases and/or prefers the production of C8:0-C:10 fatty acids and comprises:

a) a motif comprising the amino acid sequence (SEQ ID NO: 89)
SI(E/M)(T/A)(L/V)MN(H/Y)(L/V)Q(E/D)(T/A)(S/A)(L/I/R)N(H/Q)(C/A)(K/E)S(T/V/L/I/A)G(I/L)L(L/N/D/H/G)DGFG(R/E)(T/S)(L/P)(E/G)M(C/S)(K/T)(R/N)DL;

b) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 156-193 SEQ ID NO:61; wherein the amino acid residue at or corresponding to position 163 is Tyrosine, or the amino acid residue at or corresponding to position 186 is Proline; and/or c) SEQ ID NO:84.

In some embodiments, the nucleic acid encodes a specificity domain that comprises at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 91-163 of SEQ ID NO:43 and amino acid residues 91-163 of SEQ ID NO:44 and wherein the amino acid residue at or corresponding to position 91 is Asparagine, the amino acid at or corresponding to position 92 is Proline, the amino acid position 102 is Proline, the amino acid residue at or corresponding to position 127 is Valine, the amino acid residue at or corresponding to position 133 is Leucine, the amino acid residue at or corresponding to position 137 is Alanine and the amino acid residue at or corresponding to position 163 is Isoleucine.

In some embodiments, the nucleic acid encodes a specificity domain that comprises at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 91-163 of SEQ ID NO:43 and amino acid residues 91-163 of SEQ ID NO:44 and wherein the amino acid residue at or corresponding to position 91 is Asparagine, the amino acid at or corresponding to position 92 is Proline, the amino acid position 102 is Proline, the amino acid residue at or corresponding to position 127 is Leucine, the amino acid residue at or corresponding to position 133 is Methionine, the amino acid residue at or corresponding to position 137 is Threonine and the amino acid residue at or corresponding to position 163 is Methionine.

In some embodiments, the nucleic acid encodes a hydrophobic domain that comprises:

a) amino acid residues of an acyl-ACP-TE corresponding to an amino acid sequence selected from the group consisting of amino acid residues 61-77 of SEQ ID NO:43; amino acid residues 61-77 of SEQ ID NO:44; amino acid residues 85-101 of SEQ ID NO:45; amino acid residues 78-95 of SEQ ID NO:46; amino acid residues 50-66 of SEQ ID NO:47; amino acid residues 91-107 of SEQ ID NO:60; and amino acid residues 90-106 of SEQ ID NO:61;

b) a motif comprising the amino acid sequence (SEQ ID NO: 90)
(P/H)(G/D/V)(W/L)(S/N)(M/R/V)(P/L/S)(L/F)(E/A/T/S)

(L/A/K)(I/V)TT(I/V)F(S/L/V/G)(A/K/V)(A/P);

c) at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 61-77 of SEQ ID NO:43; amino acid residues 61-77 of SEQ ID NO:44; amino acid residues 85-101 of SEQ ID NO:45; amino acid residues 78-95 of SEQ ID NO:46; amino acid residues 50-66 of SEQ ID NO:47; amino acid residues 91-107 of SEQ ID NO:60; and amino acid residues 90-106 of SEQ ID NO:61; and/or d) amino acid residues 61-77 of SEQ ID NO:43; amino acid residues 61-77 of SEQ ID NO:44; amino acid residues 85-101 of SEQ ID NO:45; amino acid residues 78-95 of SEQ ID NO:46; amino acid residues 50-66 of SEQ ID NO:47; amino acid residues 91-107 of SEQ ID NO:60; and/or amino acid residues 90-106 of SEQ ID NO:61. In some embodiments, the nucleic acid encodes a hydrophobic domain that comprises an N-terminal Leucine residue.

In some embodiments, the nucleic acid further encodes an N-terminal sequence encoding a plastid transit peptide. In some embodiments, the plastid transit peptide comprises a transit peptide subsequence from *Chlorella protothecoides* Stearoyl ACP Desaturase (SAD) protein. In some embodiments, the plastid transit peptide comprises an amino acid sequence having at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of MATASTFSAFNARCGDLRRSAGSGPRRPARPLPVR-GRA (SEQ ID NO: 91), SGPRRPARPLPVR (SEQ ID NO: 92), SGPRRPARPLPVRAAIASEVPVATTSPR (SEQ ID NO: 93), RPARPLPVRGRA (SEQ ID NO: 94), RPAR-PLPVRAAIASEVPVATTSPR (SEQ ID NO: 95), RCGDL-RRSAGSGPRRPARPLPVRGRA (SEQ ID NO: 96), RCGDLRRSAGSGPRRPARPLPVRAAIASEVP-VATTSPR (SEQ ID NO: 97), PARPLPVR (SEQ ID NO: 98) PARPLPVRAAIASEVPVATTSPR (SEQ ID NO: 99), RRPARPLPVR (SEQ ID NO: 100), and RRPAR-PLPVRAAIASEVPVATTSPR (SEQ ID NO: 101). In some embodiments, the plastid transit peptide comprises an amino acid sequence selected from the group consisting of MATASTFSAFNARCGDLRRSAGSGPRRPARPLPVR-GRA (SEQ ID NO: 91), SGPRRPARPLPVR (SEQ ID NO: 92), SGPRRPARPLPVRAAIASEVPVATTSPR (SEQ ID NO: 93), RPARPLPVRGRA (SEQ ID NO: 94), RPAR-PLPVRAAIASEVPVATTSPR (SEQ ID NO: 95), RCGDL-RRSAGSGPRRPARPLPVRGRA (SEQ ID NO: 96), RCGDLRRSAGSGPRRPARPLPVRAAIASEVP-VATTSPR (SEQ ID NO: 97), PARPLPVR (SEQ ID NO: 98), PARPLPVRAAIASEVPVATTSPR (SEQ ID NO: 99), RRPARPLPVR (SEQ ID NO: 100), and RRPAR-PLPVRAAIASEVPVATTSPR (SEQ ID NO: 101).

In some embodiments, the nucleic acid further encodes a linker domain positioned N-terminal to the hydrophobic domain.

In some embodiments, the nucleic acid encodes a linker domain that comprises:

a) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence corresponding to residues selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61;

b) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61;

c) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61; and/or d) an amino acid sequence selected from the group consisting of SEQ ID NO:37, SEQ ID NO:38, SEQ ID NO:39, SEQ ID NO:40; SEQ ID NO:41 and SEQ ID NO:42.

In some embodiments, the nucleic acid encodes a variant acyl-ACP-TE comprising an amino acid sequence having at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15; SEQ ID NO:18, SEQ ID NO:20, SEQ ID NO:22, SEQ ID NO:24, SEQ ID NO:26; SEQ ID NO:28; SEQ ID NO:30, SEQ ID NO:32; SEQ ID NO:34; SEQ ID NO:36; SEQ ID NO:49, SEQ ID NO:51; SEQ ID NO:53; SEQ ID NO:55; SEQ ID NO:57 and SEQ ID NO:59. In some embodiments, the nucleic acid encodes a variant acyl-ACP-TE comprising an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15; SEQ ID NO:18, SEQ ID NO:20, SEQ ID NO:22, SEQ ID NO:24, SEQ ID NO:26; SEQ ID NO:28; SEQ ID NO:30, SEQ ID NO:32, SEQ ID NO:34; SEQ ID NO:36; SEQ ID NO:49, SEQ ID NO:51; SEQ ID NO:53; SEQ ID NO:55; SEQ ID NO:57 and SEQ ID NO:59.

In varying embodiments, the nucleic acid sequence comprises codon bias for improved expression in an algal host cell.

In a further aspect, expression cassettes comprising a nucleic acid as described above and herein are provided.

In another aspect, vectors comprising a nucleic acid (e.g., a polynucleotide) and/or an expression cassette as described above and herein are provided.

In another aspect, a variant acyl-acyl carrier protein (ACP) thioesterase (TE) encoded by a nucleic acid as described above and herein is provided.

In a further aspect, host cells are provided that comprise a nucleic acid, an expression cassette, and/or a variant acyl-ACP-TE as described above and herein. In varying embodiments, the host cell is an oleaginous cell (e.g., a plant cell, an algae cell, a microalgae cell). In some embodiments, the algae cell is of the genus *Prototheca*, or a cell having a 23S rRNA sequence with at least 70% nucleic acid sequence identity to one or more of SEQ ID NOs: 62-70. In some embodiments, algae cell is selected from the group consisting of *Prototheca moriformis, Prototheca krugani, Prototheca stagnora* and *Prototheca zopfii*. In some embodiments, the host cell further comprises an exogenous lysophosphatidic acid acyltransferase gene encoding an active lysophosphatidic acid acyltransferase (LPAAT) that catalyzes the transfer of a mid-chain fatty-acyl group to the sn-2 position of a substituted acylglyceroester. In varying embodiments, the host cell produces an oil having at least 1% increased levels, e.g., at least about 1%, 2%, 3%, 4%, 5%, 6%, 7%, 8%, 9%, 10%, 15%, 20%, 30%, 40%, 50%, 60%, 70%, from 75-85%, from 70-90%, from 90-200%, from 200-300%, from 300-400%, from 400-500%, or greater than 500%, increased levels of C8:0, C10:0, C12:0 or C14:0 fatty acids in comparison to an untransformed host cell or a host cell transformed with a wild-type acyl-ACP TE.

In a further aspect, an oleaginous cell or organism (e.g, a plant, an algae, a microalgae) is provided comprising a nucleic acid, an expression cassette, a vector, and/or a variant acyl-ACP-TE, as described above and herein. In some embodiments, the algae is of the genus *Prototheca*. In some embodiments, the algae is selected from the group consisting of *Prototheca moriformis, Prototheca krugani, Prototheca stagnora* and *Prototheca zopfii*. In another aspect, an oil product produced by the plant, algae or microalgae is provided, or a chemical, material, or food product produced from that oil.

In another aspect, methods of producing a plant, algae or microalgae that produces an oil having a desired fatty acid profile are provided. In some embodiments, the methods comprise transforming the plant, algae or microalgae with a nucleic acid sequence as described above and herein, and cultivating the plant, algae or microalgae so as to produce the oil. In some embodiments, the plant, algae or microalgae produces at least about 1% increased levels of C8:0, C10:0, C12:0 and/or C14:0 fatty acids, e.g., at least about 1%, 2%, 3%, 4%, 5%, 6%, 7%, 8%, 9%, 10%, 15%, 20%, 30%, 40%, 50%, 60%, 70%, from 75-85%, from 70-90%, from 90-200%, from 200-300%, from 300-400%, from 400-500%, or greater than 500%, increased levels of C8:0, C10:0, C12:0 and/or C14:0 fatty acids in comparison to an untransformed plant, algae or microalgae or a plant, algae or microalgae transformed with a wild-type acyl-ACP TE.

In another aspect, methods of producing an oil are provided. In some embodiments the methods comprise transforming the plant, algae or microalgae with a nucleic acid molecule encoding a variant acyl-ACP TE as described above and herein, expressing the variant acyl-ACP TE to produce fatty acids, and recovering the oil produced by the plant, algae or microalgae comprising the fatty acids.

In another aspect, methods of producing an oil are provided. In some embodiments, the methods comprise culturing a plant, algae or microalgae comprising a nucleic acid molecule encoding a variant acyl-ACP TE as described above and herein, expressing the variant acyl-ACP TE to produce fatty acids, and recovering the oil produced by the plant, algae or microalgae comprising the fatty acids.

Definitions

An "acyl-ACP thioesterase" or "acyl-ACP TE" interchangeably refer to an enzyme that catalyzes the cleavage of a fatty acid from an acyl carrier protein (ACP) during lipid synthesis. Acyl-acyl carrier protein (ACP) thioesterases (TEs) hydrolyze acyl-ACP thioester bonds, releasing free fatty acids and ACP. By terminating fatty acid biosynthesis, the TE functionally determines the length and identity of the fatty acid end product. See, Salas, et al., *Archives of Biochemistry and Biophysics* (2002) 403: 25-34.

The term "catalytic domain" refers to the C-terminal portion of an acyl-ACP TE comprising the Cys-His-Asn catalytic triad and which catalyzes the reaction of hydrolyzing an acyl group on a fatty acid. Acyl-ACP TE catalytic domains are known in the art, and have been described, e.g., in Blatti, et al., *PLoS ONE* (2012) 7(9): e42949 and Mayer and Shanklin, *BMC Plant Biology* (2007) 7:1-11.

The term "hydrophobic domain" refers to a conserved hydrophobic 18-amino acid domain or subsequence thereof in an acyl-ACP TE. Hydrophobic domains have been described in the art and are believed to anchor a FatB acyl-ACP TE in a plastid membrane. See, e.g., Facciotti and Yuan *Eur J Lipid Sci Tech* (1998) 100:167-172; Blatti, et al., *PLoS ONE* (2012) 7(9): e42949; and Mayer and Shanklin, *BMC Plant Biology* (2007) 7:1-11.

The term "linker domain" refers to an amino acid subsequence of an acyl-ACP TE that is positioned N-terminal to the hydrophobic domain, and can link the hydrophobic domain to a transit peptide. Wild-type FatB acyl-ACP TEs contain a linker domain.

The term "heterologous" with respect to the N-terminus and N-terminal domains of an acyl-ACP TE (e.g., a transit peptide, a linker domain, a hydrophobic domain, a specificity domain), refers to amino acid subsequences that are not encoded by the naturally occurring gene encoding an acyl-ACP TE C-terminus and/or catalytic domain. With relation to the C-terminal region and/or catalytic domain of an acyl-ACP TE, a heterologous N-terminal region of an acyl-ACP TE can arise from exchanging or altering an N-terminal region of the acyl-ACP TE for an N-terminal region that is not encoded by the naturally occurring gene encoding an acyl-ACP TE C-terminus and/or C-terminal catalytic domain. This can be accomplished in any way known in the art, including, e.g., swapping of individual domains with an altered and/or non-naturally occurring domain, introduction of point mutations, introduction of altered or non-naturally occurring subsequences, or deletion of single amino acid residues, subsequences and/or domains.

The term "acyl-ACP preferring TE" refers to the fatty acyl-ACP substrate specificity of a TE. An acyl-ACP preferring TE preferentially liberates a particular fatty acid from an acyl-ACP substrate. For example, the acyl-ACP preferring TE can preferentially liberate a given fatty acid over all other fatty acids in the set of C8:0, C10:0, C12:0, C14:0, C16:0, C18:0, C18:1, and C18:2 fatty acids. The preference of the acyl-ACP preferring TE can be detected as a higher $V_{max}$ (a higher $k_{cat}$, or a higher V/K) in comparison to other non-preferred fatty acid-ACP substrates. In the absence of a kinetic assay using purified protein, the preference can be inferred from changes in fatty acid profile of a cell genetically engineered to overexpress the acyl-ACP preferring TE relative to a control cell that does not overexpress the acyl-ACP preferring TE.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence which differs in one or more amino acid position(s) from that of a parent polypeptide sequence (e.g., by substitution, deletion, or insertion). A variant may comprise a sequence which differs from the parent polypeptides sequence in up to 40% of the total number of residues of the parent polypeptide sequence, such as in up to 40%, 35%, 30%, 25%, 20%, 15%, 10%, 9%, 8%, 7%, 6%, 5%, 4%, 3% 2% or 1% of the total number of residues of the parent polypeptide sequence. For example, a variant of a 400 amino acid polypeptide sequence comprises a sequence which differs in up to 40% of the total number of residues of the parent polypeptide sequence, that is, in up to 160 amino acid positions within the 400 amino acid polypeptide sequence (such as in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 85, 90, 95, 100, 105, 110, 115, 120, 125, 130, 135, 140, 145, 150, 155, or 160 amino acid positions within the reference sequence (e.g., SEQ ID NO:3, SEQ ID NO:5, SEQ ID NO:7, SEQ ID NO:9, SEQ ID NO:11, SEQ ID NO:13, SEQ ID NO:15; SEQ ID NO:18, SEQ ID NO:20, SEQ ID NO:22, SEQ ID NO:24, SEQ ID NO:26; SEQ ID NO:28; SEQ ID NO:30, SEQ ID NO:32; SEQ ID NO:34; SEQ ID NO:36; SEQ ID NO:49, SEQ ID NO:51; SEQ ID NO:53; SEQ ID NO:55; SEQ ID NO:57 and SEQ ID NO:59).

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "natural oil" or "natural fat" refers to a predominantly triglyceride oil obtained from an organism, where the oil has not undergone blending with another natural or synthetic oil, or fractionation, or other process, so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. A natural oil encompasses such an oil obtained from an organism, where the oil has undergone minimal processing, including refining, bleaching and/or degumming, that does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Fatty acid profile" refers to the distribution of fatty acids in a cell or oil derived from a cell in terms of chain length and/or saturation pattern. In this context the saturation pattern can comprise a measure of saturated versus unsaturated acid or a more detailed analysis of the distribution of the positions of double bonds in the various fatty acids of a cell, and in particular cell triglycerides. A "fatty acid" in a fatty acid profile of a cell or oil triglyceride refers to a fatty acyl group of the cell or oil triglycerides.

In connection with an oil, a "profile" is the distribution of particular species or triglycerides or fatty acyl groups within the oil. A "fatty acid profile" is the distribution of fatty acyl groups in the triglycerides of the oil without reference to attachment to a glycerol backbone. An "sn-2 profile" is the distribution of fatty acids found at the sn-2 position of the triacylglycerides in the oil. A "regiospecific profile" is the distribution of triglycerides with reference to the positioning of acyl group attachment to the glycerol backbone without reference to stereospecificity. In other words, a regiospecific profile describes acyl group attachment at sn-1/3 vs. sn-2. Thus, in a regiospecific profile, POS and SOP are treated identically. A "stereospecific profile" describes the attachment of acyl groups at sn-1, sn-2 and sn-3. Unless otherwise indicated, triglycerides such as SOP and POS are to be considered equivalent. A "TAG profile" refers to the distribution of fatty acids found in the triglycerides with reference to connection to the glycerol backbone, but without reference to the regiospecific nature of the connections. Thus, in a TAG profile, the percent of SSO in the oil is the sum of SSO and SOS, while in a regiospecific profile, the percent of SSO is calculated without inclusion of SOS species in the oil.

"Microalgae" are microbial organisms that contain a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a non-human cell capable of producing at least 20% lipid by dry cell weight, naturally or through recombinant or classical strain improvement. An "oleaginous microbe" or "oleaginous microorganism is a microbe, including a microalga that is oleaginous.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "polypeptide" and "protein" are used interchangeably herein to refer a polymer of amino acids, and unless otherwise limited, include atypical amino acids that can function in a similar manner to naturally occurring amino acids.

The terms "amino acid" or "amino acid residue," include naturally occurring L-amino acids or residues, unless otherwise specifically indicated. The commonly used one- and three-letter abbreviations for amino acids are used herein (Lehninger, A. L. (1975) Biochemistry, 2d ed., pp. 71-92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Exemplary atypical amino acids, include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and H is; N-ethylglycine (EtGly) for Gly, Pro, and Ala; N-ethylasparagine (EtAsn), for Asn and Gln; hydroxyllysine (Hyl), for Lys; allohydroxyllysine (Rhyl), for Lys; 3-(and 4-) hydroxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Orn), for Lys, Arg, and H is; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

The term "sequence", as used in connection with a polypeptide or nucleic acid polymer refers to the order of monomers making up the polymer or the sub-polymer or fragment having that sequence.

A "subsequence" of an amino acid or nucleotide sequence is a portion of a larger sequence or the peptide or nucleic acid sub-polymer or fragment characterized by the portion of the larger sequence.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using BLAST set to default parameters.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "mutation" shall mean a change in a protein, polypeptide, or peptide sequence or subsequence produced by altering one or more nucleotides in a nucleotide coding for the protein, polypeptide, or peptide, however the alteration is obtained. For example, a mutation can be produced randomly, by PCR mutation, by synthesis of entire gene, or any other method.

The term "conservative amino acid substitution" is used herein to refer to the replacement of an amino acid with a functionally equivalent amino acid. Functionally equivalent amino acids are generally similar in size and/or character (e.g., charge or hydrophobicity) to the amino acids they replace. Amino acids of similar character can be grouped as follows:

(1) hydrophobic: H is, Tip, Tyr, Phe, Met, Leu, Ile, Val, Ala;

(2) neutral hydrophobic: Cys, Ser, Thr;

(3) polar: Ser, Thr, Asn, Gln;

(4) acidic/negatively charged: Asp, Glu;

(5) charged: Asp, Glu, Arg, Lys, H is;

(6) basic/positively charged: Arg, Lys, H is;

(7) basic: Asn, Gln, H is, Lys, Arg;

(8) residues that influence chain orientation: Gly, Pro; and (9) aromatic: Trp, Tyr, Phe, His.

The following table shows exemplary and preferred conservative amino acid substitutions.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Asn |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the terms "expression vector" or "expression construct" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Exogenous gene" refers to a nucleic acid transformed into a cell. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

"Exogenously provided" describes a molecule provided to the culture media of a cell culture.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, recombinant cells express genes that are not found within the native (non-recombinant) form of the cell or express native genes that are otherwise abnormally expressed, over-expressed, under-expressed or not expressed at all. "Recombinant nucleic acid" as used herein refers to nucleic acid molecules that are initially synthesized through the use of laboratory methods, thereby creating nucleic acid sequences that are not normally found in nature. By using laboratory methods, recombinant nucleic acid molecules in operable linkage with different sequences (e.g., promoter, targeting sequence, etc.) is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

A "transit peptide" is an amino acid sequence that directs the trafficking of a polypeptide fused to the signal sequence. In connection with plastidic cells expressing the polypeptide, the transit peptide may direct trafficking of the polypeptide to the plastid.

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

The term "host cell" refers to a cell capable of maintaining a vector either transiently or stably. Host cells include, without limitation, bacterial cells, yeast cells, insect cells, algal cells (e.g., microalgal cells), plant cells and mammalian cells. Other host cells known in the art, or which become known, are also suitable for use in the invention.

As used herein, the term "complementary" refers to the capacity for precise pairing between two nucleotides. For example, if a nucleotide at a given position of a nucleic acid molecule is capable of hybridizing with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions.

The phrase "stringent hybridization conditions" generally refers to a temperature about 5° C. lower than the melting temperature (Tm) for a specific sequence at a defined ionic strength and pH. Exemplary stringent conditions suitable for achieving specific hybridization of most sequences are a temperature of at least about 60° C. and a salt concentration of about 0.2 molar at pH 7.0.

"Cellulosic material" means the products of digestion of cellulose, including glucose and xylose, and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

BRIEF DESCRIPTION OF THE DRAWINGS

FIGS. 3A-C illustrate the nucleotide sequence (SEQ ID NO: 1) of transforming DNA contained in plasmid pSZ2037. Construct D1022 [pSZ2037] was used to express the Cc-Uc TE chimera A within *P. moriformis* (UTEX 1435 strain A). Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlorella vulgaris* nitrate reductase (NR) gene 3' UTR is indicated by lowercase text followed by a spacer segment (dotted underlined, lowercase) and a *P. moriformis* AMT3 promoter (indicated by boxed italicized text) driving the expression of the *C. camphorum* and *U. californica* chimeric fusion thioesterase. The *C. protothecoides* SAD1 transit peptide is indicated with uppercase, boxed text, while the *C. camphorum* and *U. californica* derived sequences with underlined italic and bold uppercase, respectively. The C-terminal FLAG epitope tag is noted with underlined lowercase. The *C. vulgaris* nitrate reductase 3' UTR is again indicated by lowercase text followed by the A 6S genomic region indicated by bold, lowercase text.

FIG. 4 illustrates the nucleotide sequence (SEQ ID NO: 6) of transforming DNA contained in plasmid pSZ2038. Construct D1023 [pSZ2038] was used to express the Uc-Cc TE chimera within *P. moriformis* (UTEX 1435 strain A). Cc TE derived sequence is noted with underlined italic while the Uc TE derived sequence is noted with bold uppercase text.

FIG. 5 illustrates the nucleotide sequence (SEQ ID NO: 8) of transforming DNA contained in plasmid pSZ2231. Construct D1210 [pSZ2231] was used to express the Cc-Uc TE chimera B within *P. moriformis* (UTEX 1435 strain A). Cc TE derived sequence is noted with underlined italic while the Uc TE derived sequence is noted with bold uppercase text.

FIG. 6 illustrates the nucleotide sequence (SEQ ID NO: 10) of transforming DNA contained in plasmid pSZ2232. Construct D1211 [pSZ2232] was used to express the Cc-Uc TE chimera C within *P. moriformis* (UTEX 1435 strain A). Cc TE derived sequence is noted with underlined italic while the Uc TE derived sequence is noted with bold uppercase text.

FIG. 7 illustrates the nucleotide sequence (SEQ ID NO: 12) of transforming DNA contained in plasmid pSZ2233. Construct D1212 [pSZ2233] was used to express the Cc-Uc TE chimera D within *P. moriformis* (UTEX 1435 strain A). Cc TE derived sequence is noted with underlined italic while the Uc TE derived sequence is noted with bold uppercase text.

FIG. 8 illustrates the nucleotide sequence (SEQ ID NO: 14) of transforming DNA contained in plasmid pSZ2234. Construct D1213 [pSZ2234] was used to express the Cc-Uc TE chimera E within *P. moriformis* (UTEX 1435 strain A). Cc TE derived sequence is noted with underlined italic while the Uc TE derived sequence is noted with bold uppercase text.

FIG. 12 discloses SEQ ID NOS 103-104, respectively, in order of appearance.

FIG. 13 discloses SEQ ID NOS 105-166, respectively, in order of appearance.

FIGS. 14A-C illustrate the nucleotide sequence (SEQ ID NO: 16) of construct D1056 [pSZ2084] . Construct D1056 [pSZ2084] was used to express the Uc TE containing an extended heterologous transit peptide from *C. protothecoides* within *P. moriformis* (UTEX 1435 strain A). Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlo-*

*rella vulgaris* nitrate reductase (NR) gene 3' UTR is indicated by lowercase text followed by a spacer segment (dotted underlined, lowercase) and a *P. moriformis* AMT3 promoter (indicated by boxed italicized text) driving the expression of the *U. californica* chimeric fusion thioesterase. The extended *C. protothecoides* SAD1 transit peptide is indicated with underlined uppercase, while the *U. californica* FATB2 derived sequence is noted with bold uppercase. The C-terminal FLAG epitope tag is noted with underlined lowercase. The *C. vulgaris* nitrate reductase 3' UTR is again indicated by lowercase text followed by the A 6S genomic region indicated by bold, lowercase text.

FIG. 15 illustrates the nucleotide sequence (SEQ ID NO: 19) of transforming DNA contained in plasmid pSZ2085. Construct D1057 [pSZ2085] was used to express the Uc FATB2ExtA within *P. moriformis* (UTEX 1435 strain A). The Uc FATB2 thioesterase extension is noted with underlined italic while the remaining Uc FATB2 sequence found in pSZ2084 is noted with bold uppercase text.

FIG. 16 illustrates the nucleotide sequence (SEQ ID NO: 21) of transforming DNA contained in plasmid pSZ2086. Construct D1058 [pSZ2086] was used to express the Uc FATB2ExtB within *P. moriformis* (UTEX 1435 strain A). The Uc FATB2 thioesterase extension is noted with underlined italic while the remaining Uc FATB2 sequence found in pSZ2084 is noted with bold uppercase text.

Figure 17A:
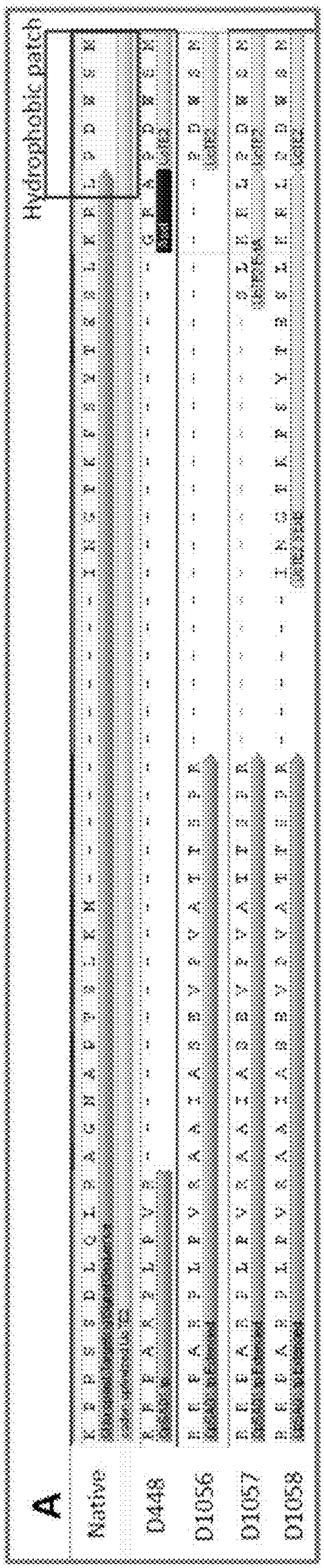
Figure 17B:
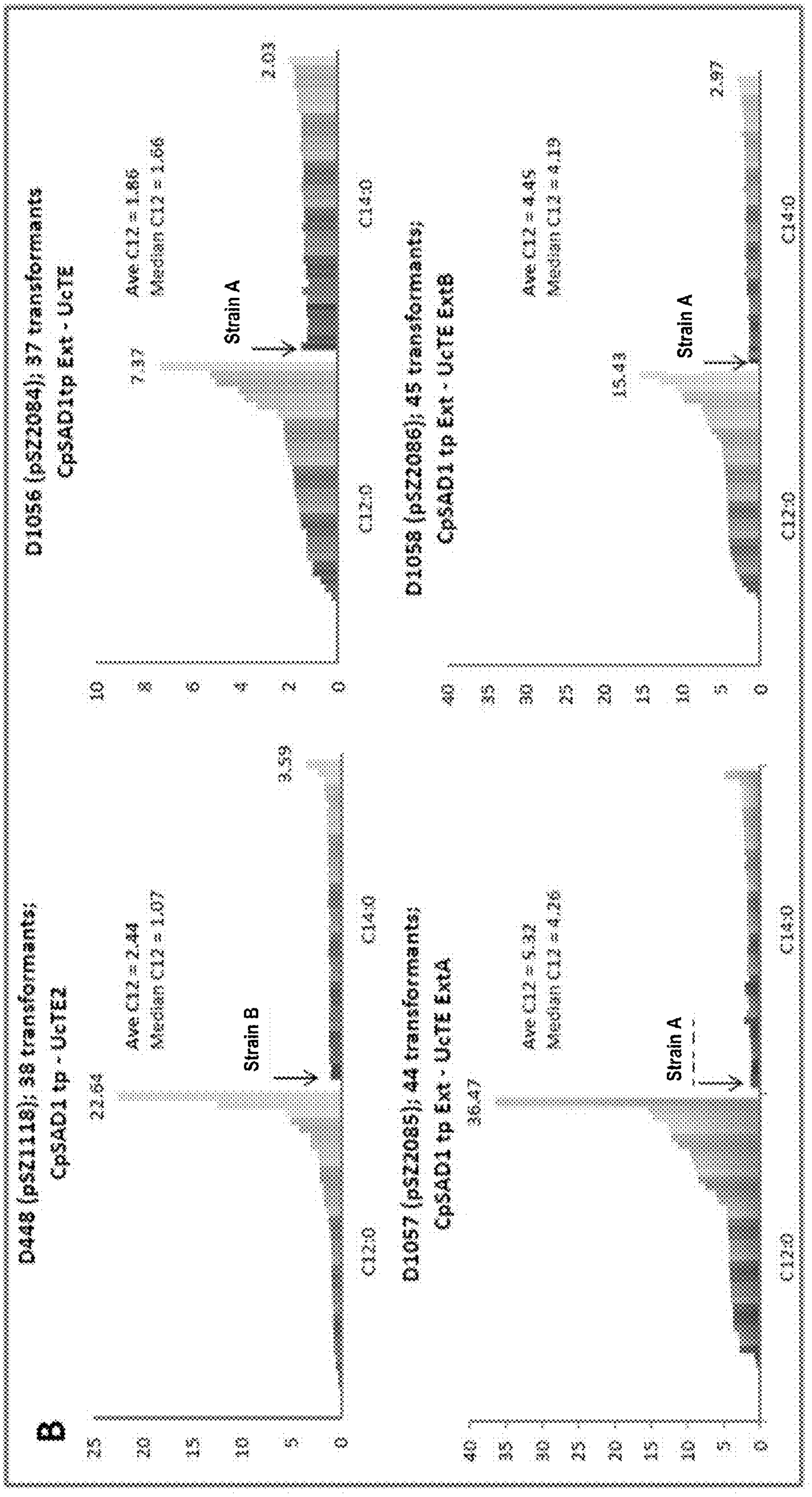

FIGS. 17A-B illustrate that the N-terminus of the 12:0-ACP thioesterase Uc FATB2 impacts the enzyme activity when expressed in *P. moriformis*. Panel A illustrates the sequence differences between D448 (SEQ ID NO: 168), D1056 (SEQ ID NO: 169), D1057 (SEQ ID NO: 170) and D1058 (SEQ ID NO: 171) relative to the native protein (SEQ ID NO: 167). Panel B compares the fatty acid profiles between the four constructs upon transformation of *P. moriformis*. D1057 and D1058 exhibit an approximate two-fold increase in the average C12 fatty acid profiles relative to D448 and D1056. The fatty acid profiles for the wild-type strains (strain B and strain A) are indicated.

FIG. 18 illustrates the nucleotide sequence (SEQ ID NO: 23) of transforming DNA contained in plasmid pSZ2450. Construct D1431 [pSZ2450] was used to express the Cc FATB1ExtA within *P. moriformis* (UTEX 1435 strain C). The Cc FATB1 thioesterase extension is noted with underlined italic while the remaining Cc FATB1 sequence is noted with bold uppercase text.

FIG. 19 illustrates the nucleotide sequence (SEQ ID NO: 25) of transforming DNA contained in plasmid pSZ2451. Construct D1432 [pSZ2451] was used to express the Cc FATB1ExtB within *P. moriformis* (UTEX 1435 strain C). The Cc FATB1 thioesterase extension is noted with underlined italic while the remaining Cc FATB1 sequence is noted with bold uppercase text.

Figure 20A:
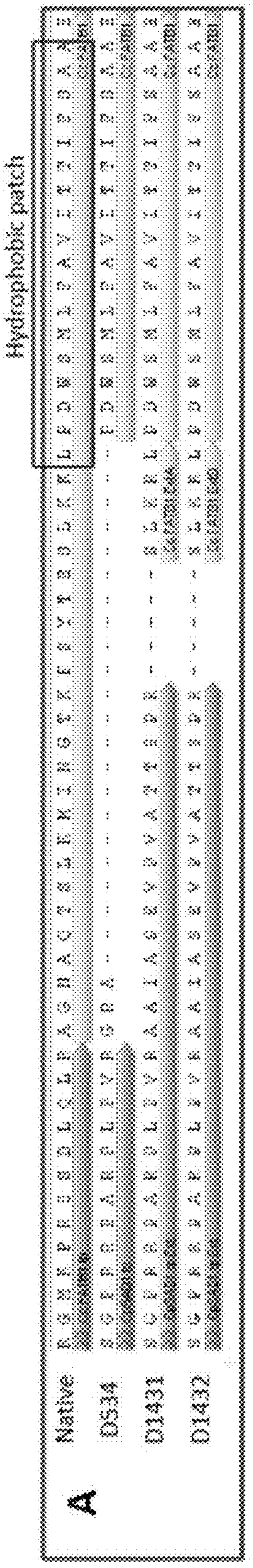
Figure 20B:
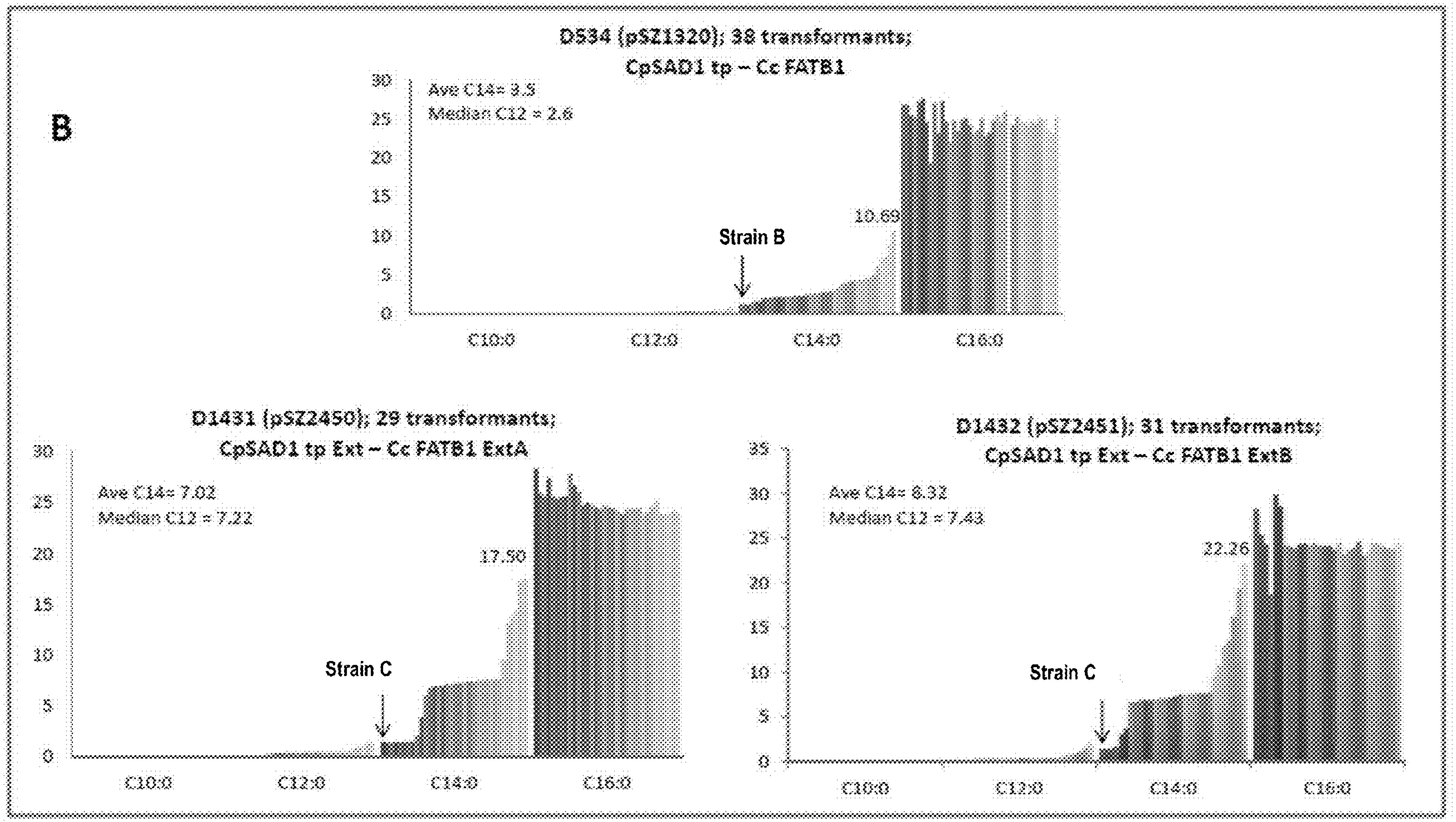

FIGS. 20A-B illustrate that the N-terminus of the 14:0-ACP thioesterase Cc FATB1 impacts the enzyme activity when expressed in *P. moriformis*. Panel A illustrates the sequence differences between D534 (SEQ ID NO: 173), D1431 (SEQ ID NO: 174), D1432 (SEQ ID NO: 175) relative to the native protein (SEQ ID NO: 172). Panel B compares the fatty acid profiles between the three constructs upon transformation of *P. moriformis*. D1431 and D1432 exhibit an approximate two-fold increase in the average C12 fatty acid profiles relative to D534. The fatty acid profiles for the wild-type strain C is indicated.

FIG. 21 illustrates the nucleotide sequence (SEQ ID NO: 27) of transforming DNA contained in plasmid pSZ2479. Construct D1481 [pSZ2479] was used to express the *Cuphea palustris* (Cpal) FATB2 ExtA within *P. moriformis* (UTEX 1435 strain C). The Cpal FATB2 thioesterase extension is noted with underlined italic while the remaining Cpal FATB2 sequence is noted with bold uppercase text and the FLAG epitope (pSZ2480) noted in lowercase text.

FIG. 22 illustrates the nucleotide sequence (SEQ ID NO: 29) of transforming DNA contained in plasmid pSZ2480. Construct D1482 [pSZ2480] was used to express the Cpal FATB2 ExtA containing a C-terminal FLAG epitope tag within *P. moriformis* (UTEX 1435 strain C). The Cpal FATB2 thioesterase extension is noted with underlined italic while the remaining Cpal FATB2 sequence is noted with bold uppercase text and the FLAG epitope (pSZ2480) noted in lowercase text.

Figure 23A:
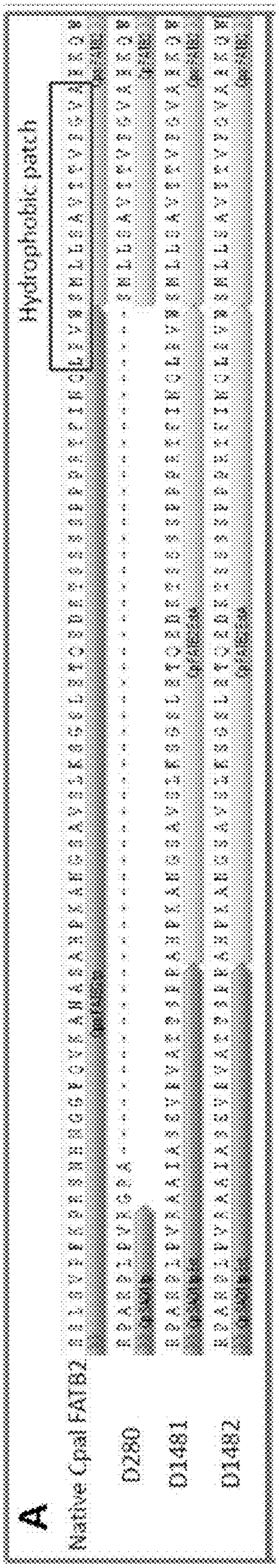
Figure 23B:
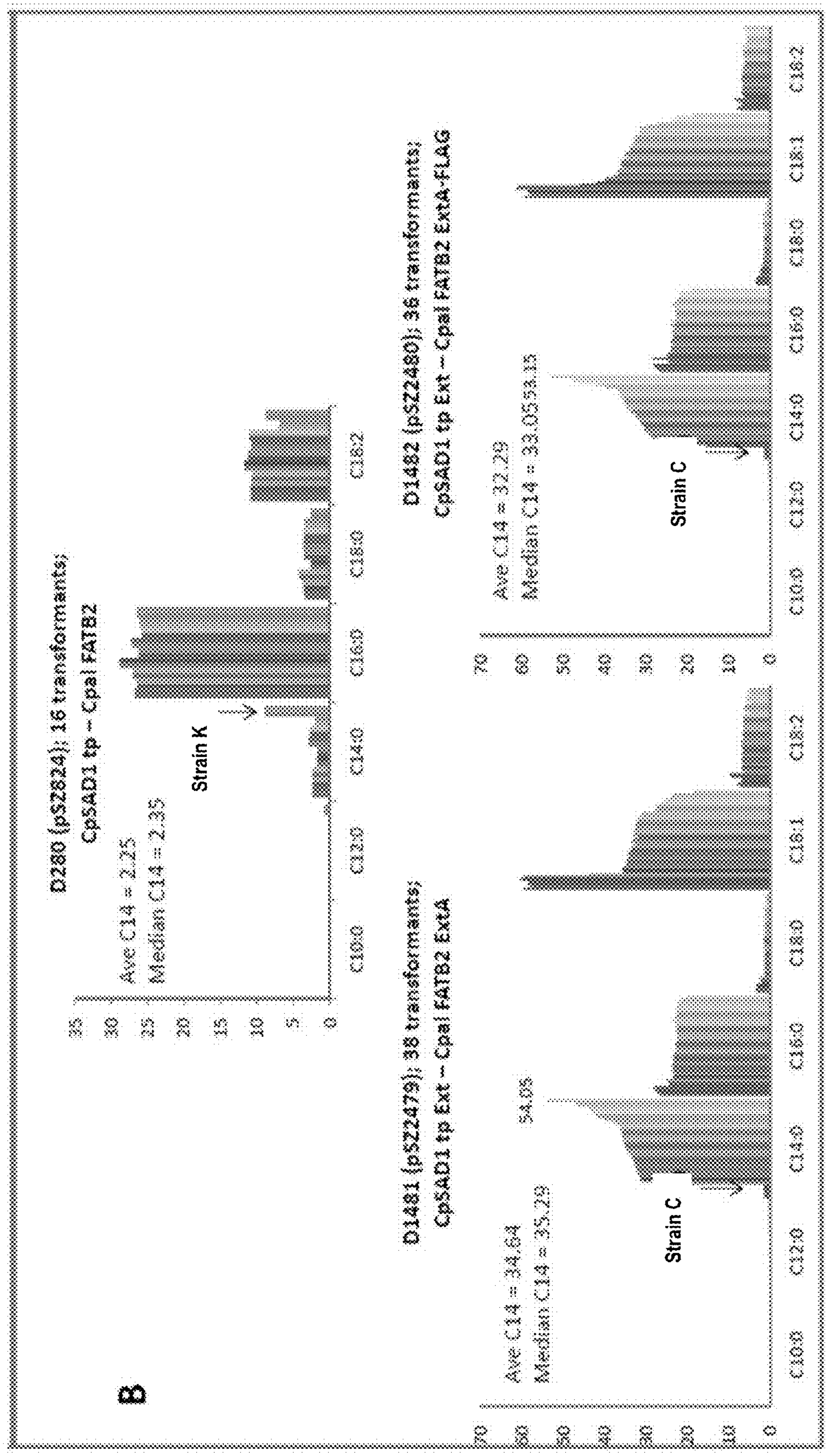

FIGS. 23A-B illustrate that the N-terminus of the 14:0-ACP thioesterase Cpal FATB2 impacts the enzyme activity when expressed in *P. moriformis*. Panel A illustrates the sequence differences between D280 (SEQ ID NO: 177), D1481 (SEQ ID NO: 178) and D1482 (SEQ ID NO: 179) relative to the native protein (SEQ ID NO: 176). Panel B compares the fatty acid profiles between the three constructs upon transformation of *P. moriformis*. D1481 and D1482 exhibit an average C14 value of approximately 33%. The fatty acid profiles for the wild-type strain C and a Cc FATB2 expressing strain (Strain K) are indicated with arrows.

FIG. 24 illustrates the nucleotide sequence (SEQ ID NO: 31) of transforming DNA contained in plasmid pSZ2477. Construct D1479 [pSZ2477] was used to express the Ulmus Americana (Ua) FATB1 ExtA within *P. moriformis* (UTEX 1435 strain C). The Ua FATB1 thioesterase sequence extension is noted with underlined italic while the remaining Ua FATB1 sequence is noted with bold uppercase text. The FLAG epitope in pSZ2478 is noted in lowercase text.

FIG. 25 illustrates the nucleotide sequence (SEQ ID NO: 33) of transforming DNA contained in plasmid pSZ2478. Construct D1480 [pSZ2478] was used to express the Ua FATB1 ExtA containing a C-terminal FLAG epitope tag within *P. moriformis* (UTEX 1435 strain C). The Ua FATB1 thioesterase sequence extension is noted with underlined italic while the remaining Ua FATB1 sequence is noted with bold uppercase text. The FLAG epitope in pSZ2478 is noted in lowercase text.

Figure 26A:
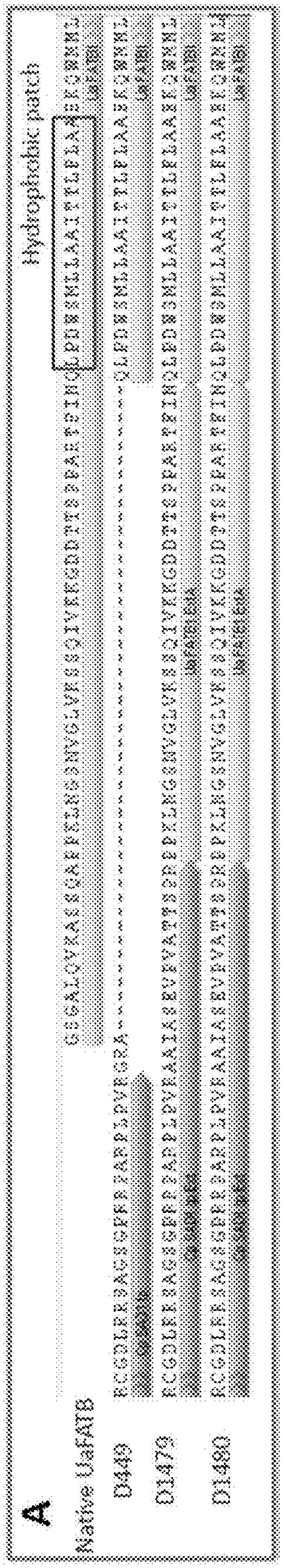
Figure 26B:
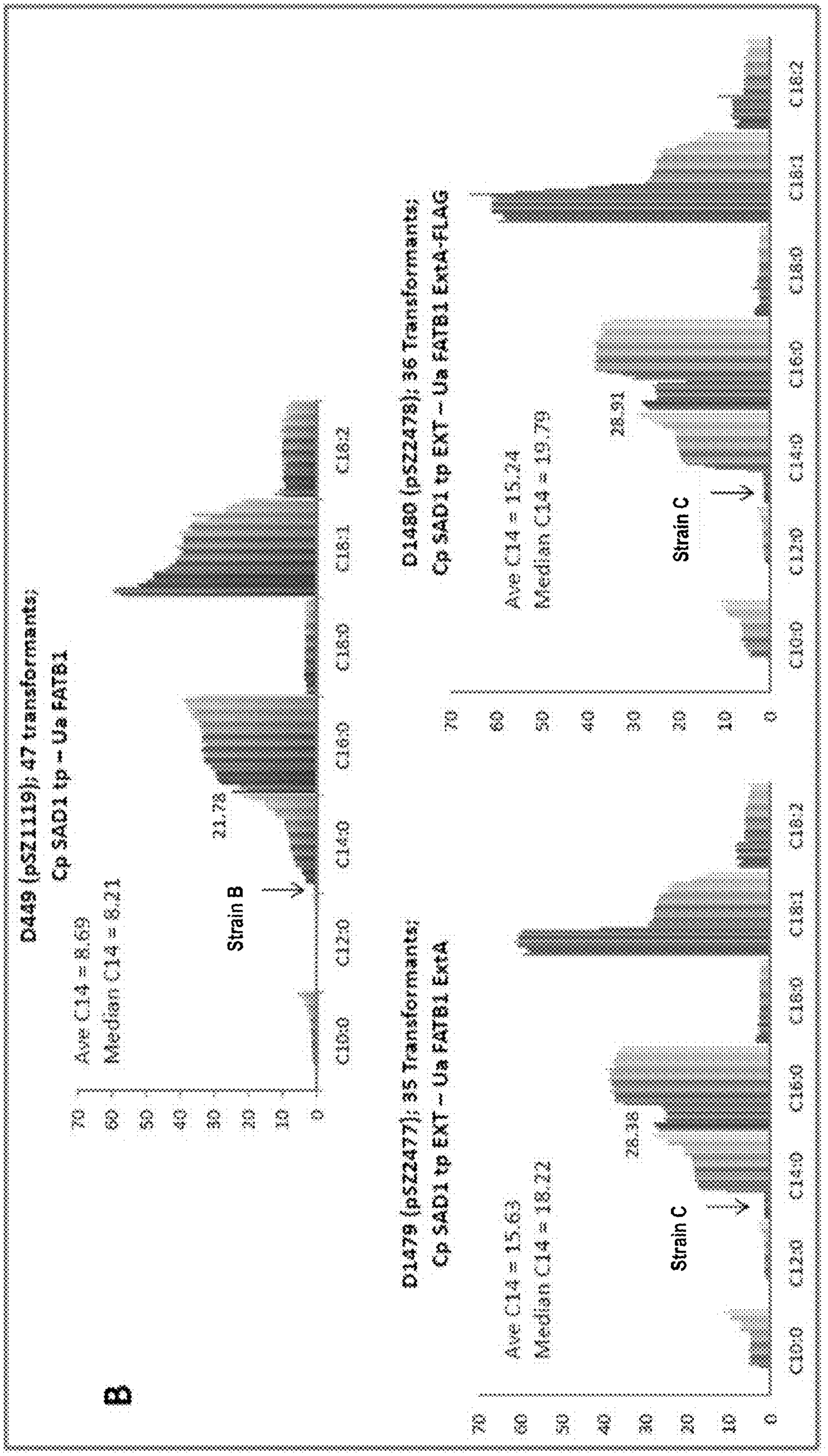

FIGS. 26A-B illustrate that the N-terminus of the 10:0-14:0-16:0-ACP thioesterase Ua FATB1 impacts the enzyme activity when expressed in *P. moriformis*. Panel A illustrates the sequence differences between D449 (SEQ ID NO: 181), D1479 (SEQ ID NO: 182), D1480 (SEQ ID NO: 183) relative to the native protein (SEQ ID NO: 180). Panel B compares the fatty acid profiles between the three constructs upon transformation of *P. moriformis*. D1479 and D1480 exhibit an approximate two-fold increase in the average C12 fatty acid profiles relative to D449. The fatty acid profiles for the wild-type strains B and C are indicated.

FIG. 27 illustrates the nucleotide sequence (SEQ ID NO: 2) of transforming DNA contained in plasmid pSZ2231. Construct D1210 [pSZ2231] was used to express the Cc-Uc FATB2 ChimeraB within *P. moriformis* (UTEX 1435 strain A). The Cc-Uc FATB2 thioesterase sequence is indicated by bold uppercase text; the trimmed or extended *C. protothecoides* SAD1 transit peptide is indicated with underlined uppercase and the Uc FATB2 extension within D1429 is noted with underlined lowercase italic.

FIG. 28 illustrates the nucleotide sequence (SEQ ID NO: 35) of transforming DNA contained in plasmid pSZ2448. Construct D1429 [pSZ2448] used to express the Cc-Uc FATB2 ExtA containing the extended *C. protothecoides* SAD1 transit peptide and a five amino acid N-terminal extension derived from the native Uc FATB2 sequence within *P. moriformis* (UTEX 1435 strain C). The Cc-Uc FATB2 thioesterase sequence is indicated by bold uppercase text; the trimmed or extended *C. protothecoides* SAD1 transit peptide is indicated with underlined uppercase and the Uc FATB2 extension within D1429 is noted with underlined lowercase italic.

FIGS. 29A-B illustrate that the N-terminus of the 12:0-ACP thioesterase Uc FATB2 improves the enzyme activity of the Cc-Uc FATB2 chimera B when expressed in *P. moriformis*. Panel A illustrates the sequence differences between D1210 (SEQ ID NO: 185) and D1429 (SEQ ID NO: 186) relative to the native protein (SEQ ID NO: 184). Panel B compares the fatty acid profiles between the two constructs upon transformation of *P. moriformis*. D1429 exhibits an approximate two-fold increase in the average C12 fatty acid profiles relative to D1210. The fatty acid profiles for the wild-type strains A and C are indicated. The relative C12:C14 activity within these chimeric TEs, is strikingly lowered, with a significant increase in C14:0 activity relative to the native UcTE enzyme (compare for example FIG. 18, D448 lines, with FIGS. 30, D1210 and D1429 lines).

Figure 30A:
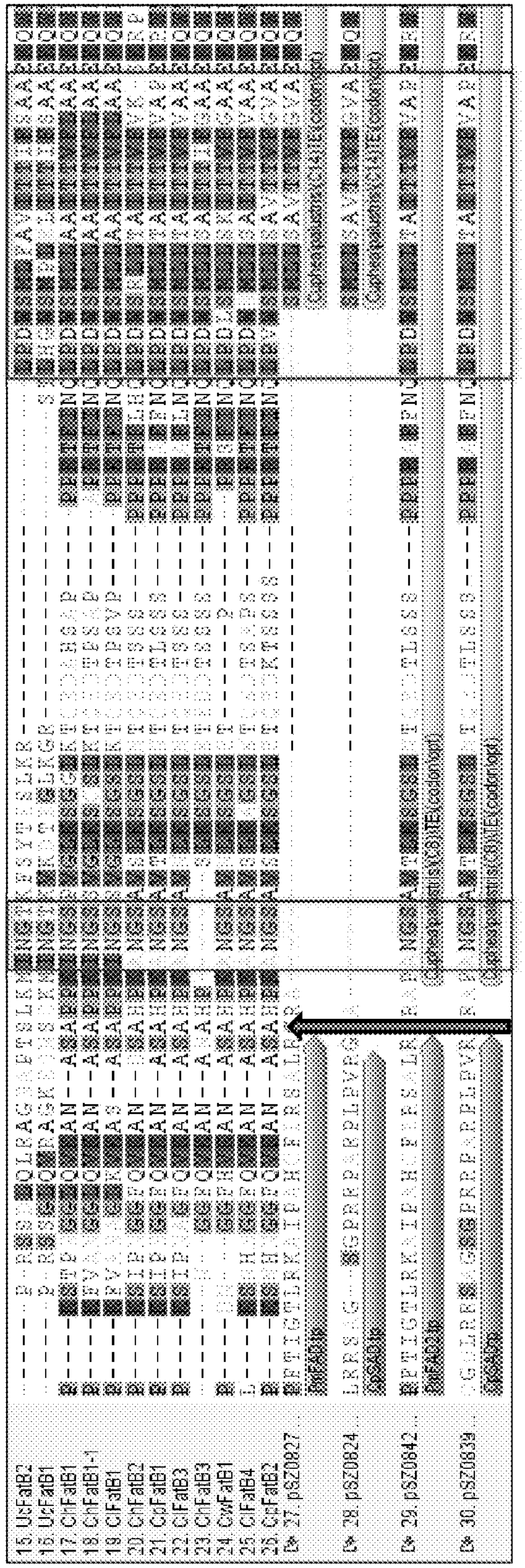
Figure 30B:
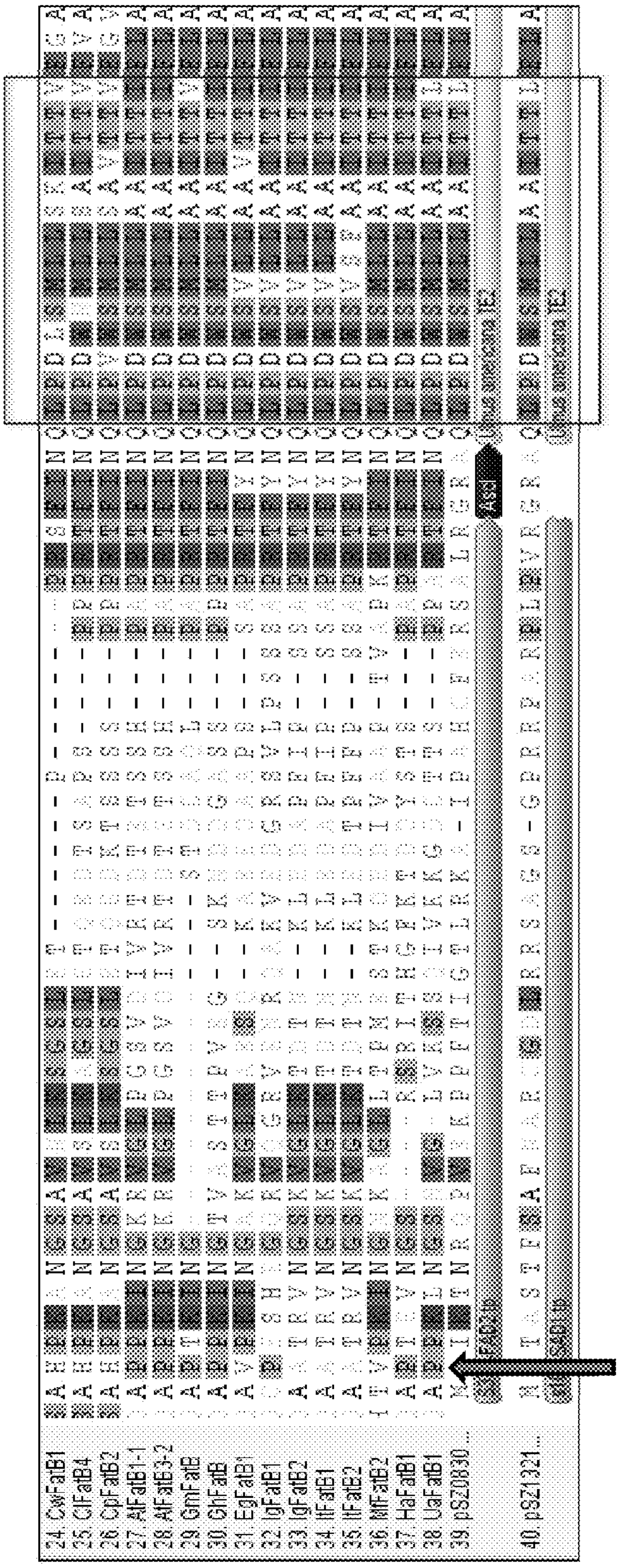

FIGS. 30A-B illustrate extensions of Cpal FATB2 and UaFATB1. A. CpalFATB2 (C14) extended to AHPK −/+FLAG Tag (psZ2479 (D1481) and psZ2480 (D1482)). B. UaFATB1 (C10-C16) extended to PPKL −/+FLAG Tag (psZ2477 (D1479) and psZ2478 (D1480)). FIG. 30A-B discloses SEQ ID NOS 187-219, respectively, in order of appearance.

FIG. 31 illustrates the nucleic acid sequence (SEQ ID NO: 48) of pSZ2609 (D1558) *Cuphea hookeriana* (Chook) and *Cuphea wrightii* (Cw) Chook-CwFATB ChimeraA. CwFATB transit peptide (underlined text), Ascl linker (lowercase), CwFATB sequence (italic), Chook FATB sequence (bold), FLAG epitope tag (underlined lowercase).

FIG. 32 illustrates the nucleic acid sequence (SEQ ID NO: 50) of pSZ2610 (D1559) Chook- CwFATB ChimeraB. CwFATB transit peptide (underlined text), Ascl linker (lowercase), CwFATB sequence (italic), Chook FATB sequence (bold), FLAG epitope tag (underlined lowercase).

FIG. 33 illustrates the nucleic acid sequence (SEQ ID NO: 52) of pSZ2611 (D1560) Chook- CwFATB ChimeraC. CwFATB transit peptide (underlined text), Ascl linker (lowercase), CwFATB sequence (italic), Chook FATB sequence (bold), FLAG epitope tag (underlined lowercase).

FIG. 34 illustrates the nucleic acid sequence (SEQ ID NO: 54) of pSZ2612 (D1561) Chook- CwFATB ChimeraD. CwFATB transit peptide (underlined text), Ascl linker (lowercase), CwFATB sequence (italic), Chook FATB sequence (bold), FLAG epitope tag (underlined lowercase).

FIG. 35 illustrates the nucleic acid sequence (SEQ ID NO: 56) of pSZ2613 (D1562) ChookF ATB. CwFATB transit peptide (underlined text), Ascl linker (lowercase), Chook FATB sequence (bold), FLAG epitope tag (underlined lowercase).

FIG. 36 illustrates the nucleic acid sequence (SEQ ID NO: 58) of pSZ1954 (D965) CwFATB. CwFATB transit peptide (underlined text), Ascl linker (lowercase), CwFATB sequence (italic), FLAG epitope tag (underlined lowercase).

Figure 37:
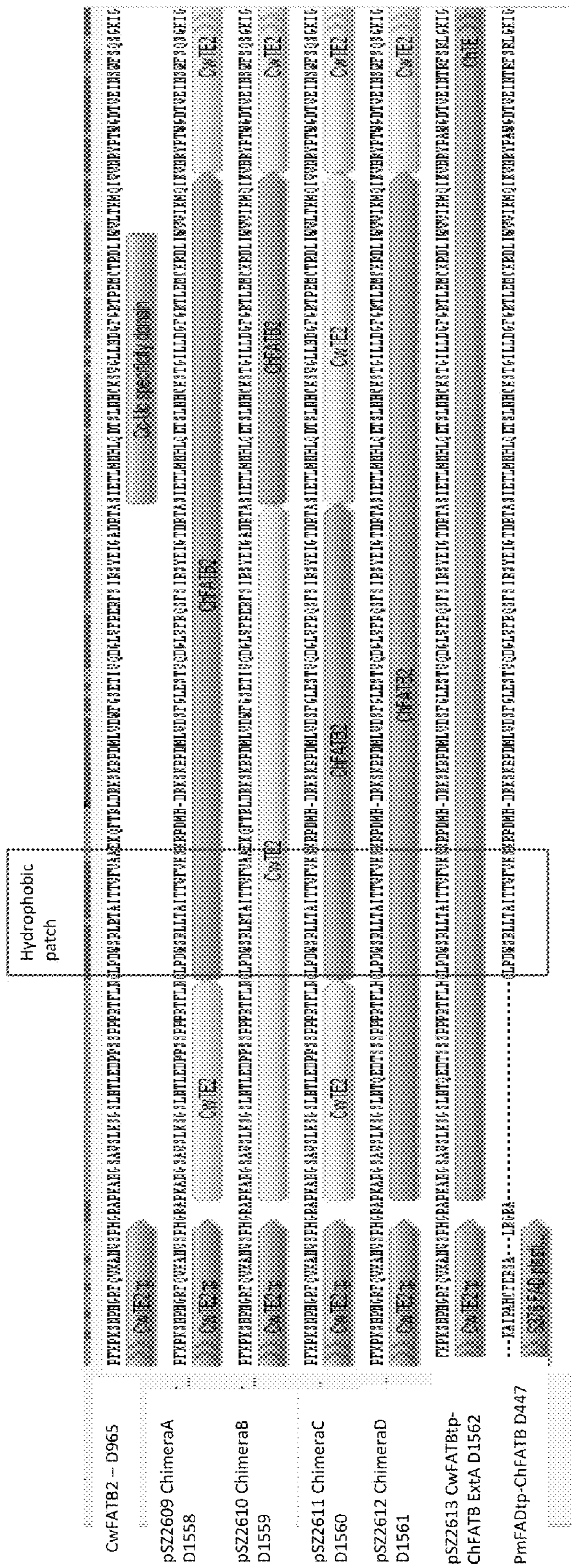

FIG. 37 illustrates acyl-ACP TE FATB chimeras of *Cuphea hookeriana* (Chook) and *Cuphea wrightii* (Cw) ("Chook-CwFATB chimeras"). FIG. 37 discloses SEQ ID NOS 220-226, respectively, in order of appearance.

Figure 38A:
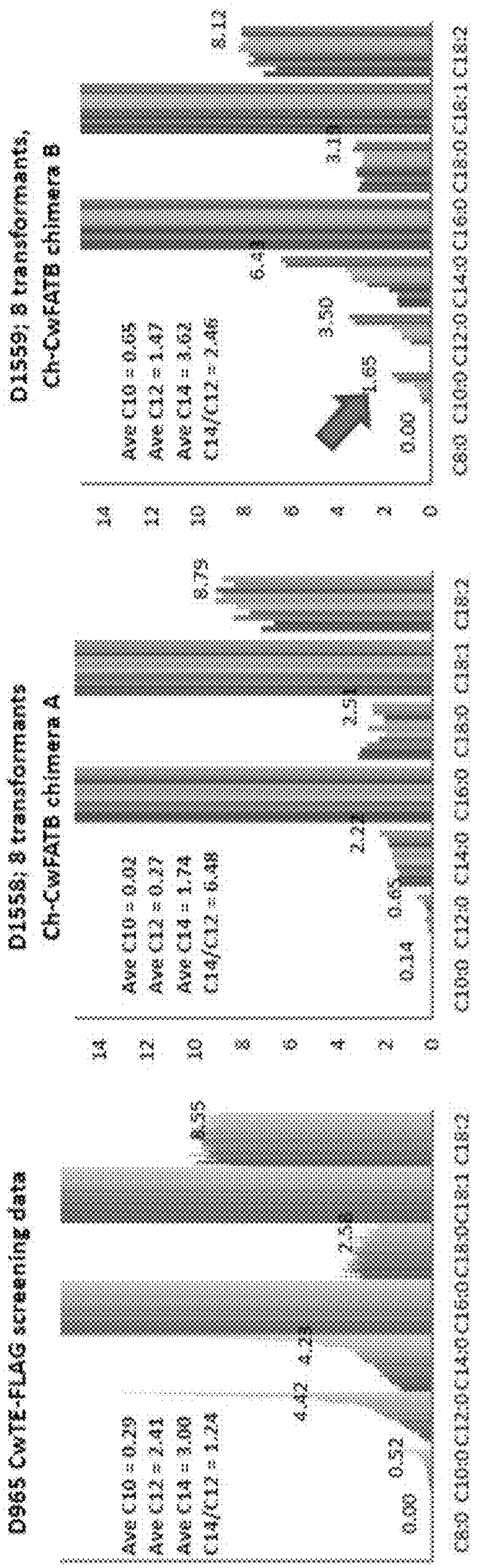
Figure 38B:
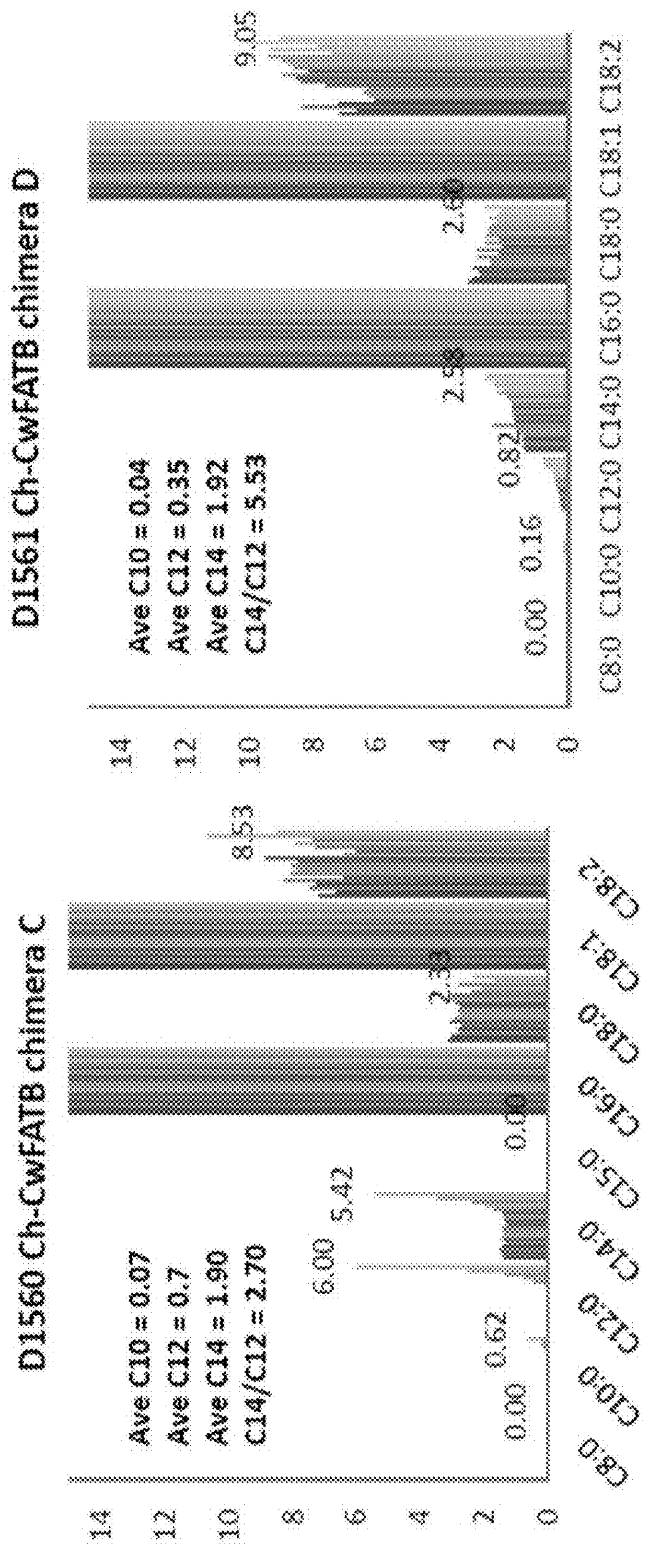

FIGS. 38A-B illustrate primary lipid profiles of Chook-CwFATB chimeras.

Figure 39A:
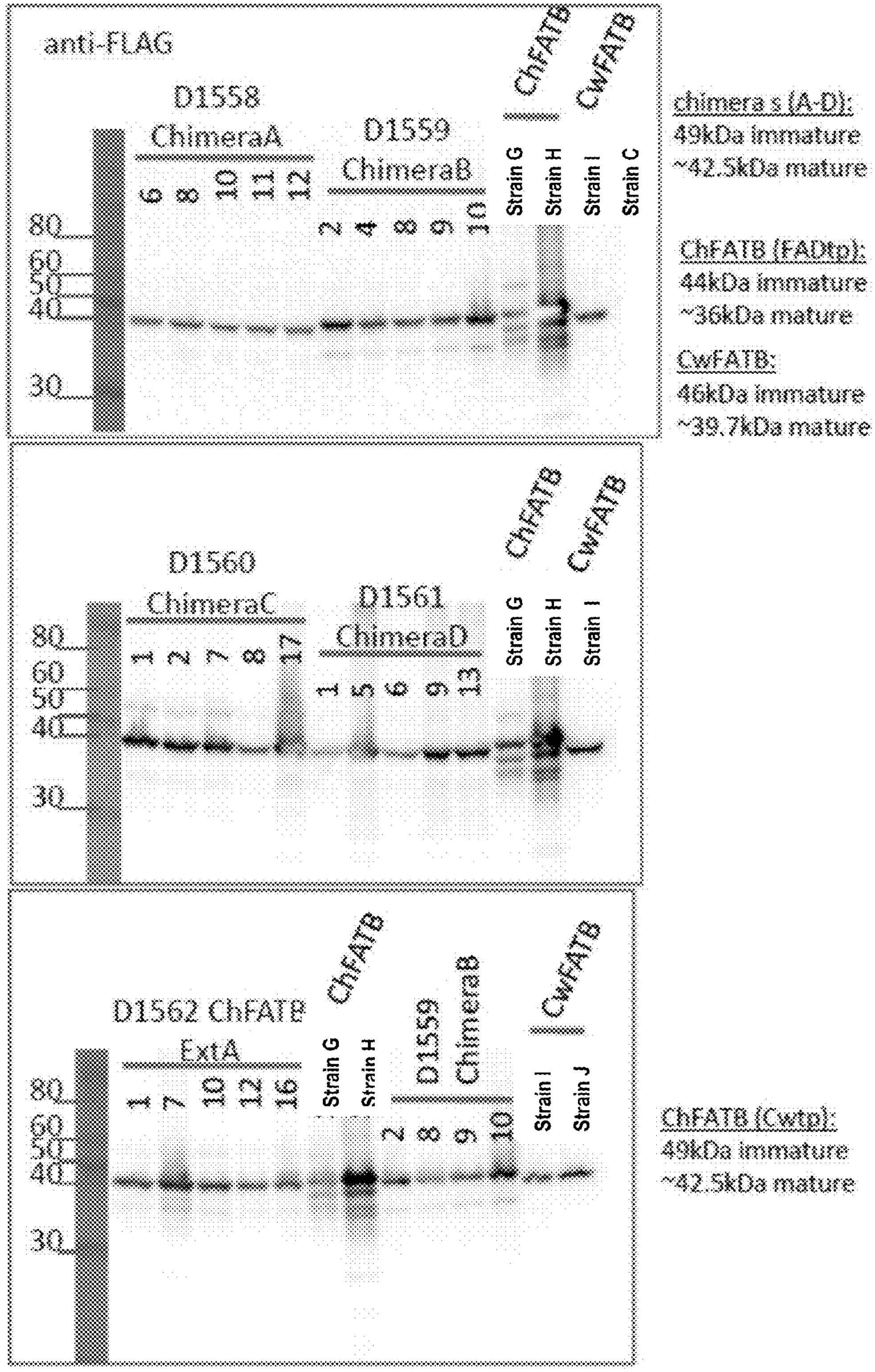

FIGS. 39A-B illustrate a Western analysis of expression and summary of fatty acid profiles of Chook-CwFATB chimeras.

Figure 40:
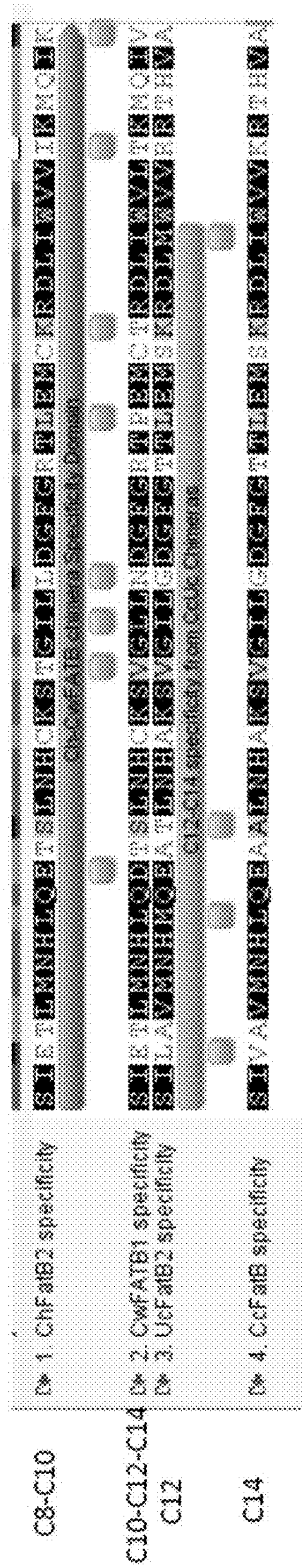

FIG. 40 illustrates residues within the specificity domains of ChookFATB2, CwFATB1, UcFATB2 and CcFATB that influence fatty acid-ACP substrate specificity of the TE. Residues influencing the fatty acid-ACP substrate specificity of ChookFATB2 include, e.g., E166, T175, I177, L179, L186, K190, I198 and K203 (residue numbering with reference to SEQ ID NO:61). Residues influencing the fatty acid-ACP substrate specificities of UcFATB2 and CcFATB include, e.g., L/V127, M/L133, T/A137, M/I163 and (residue numbering with reference to SEQ ID NO:43 and SEQ ID NO:44). FIG. 40 discloses SEQ ID NOS 227-230, respectively, in order of appearance.

Figure 41A:
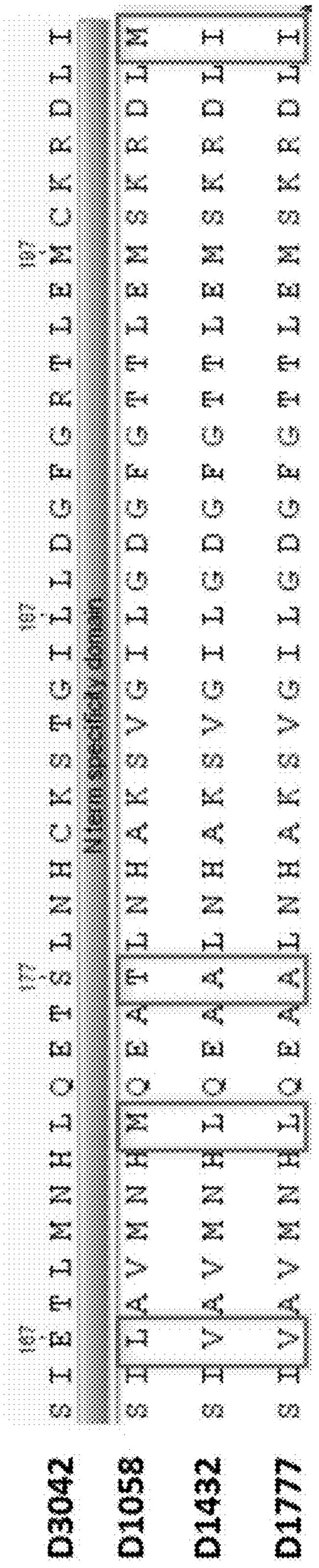
Figure 41B:
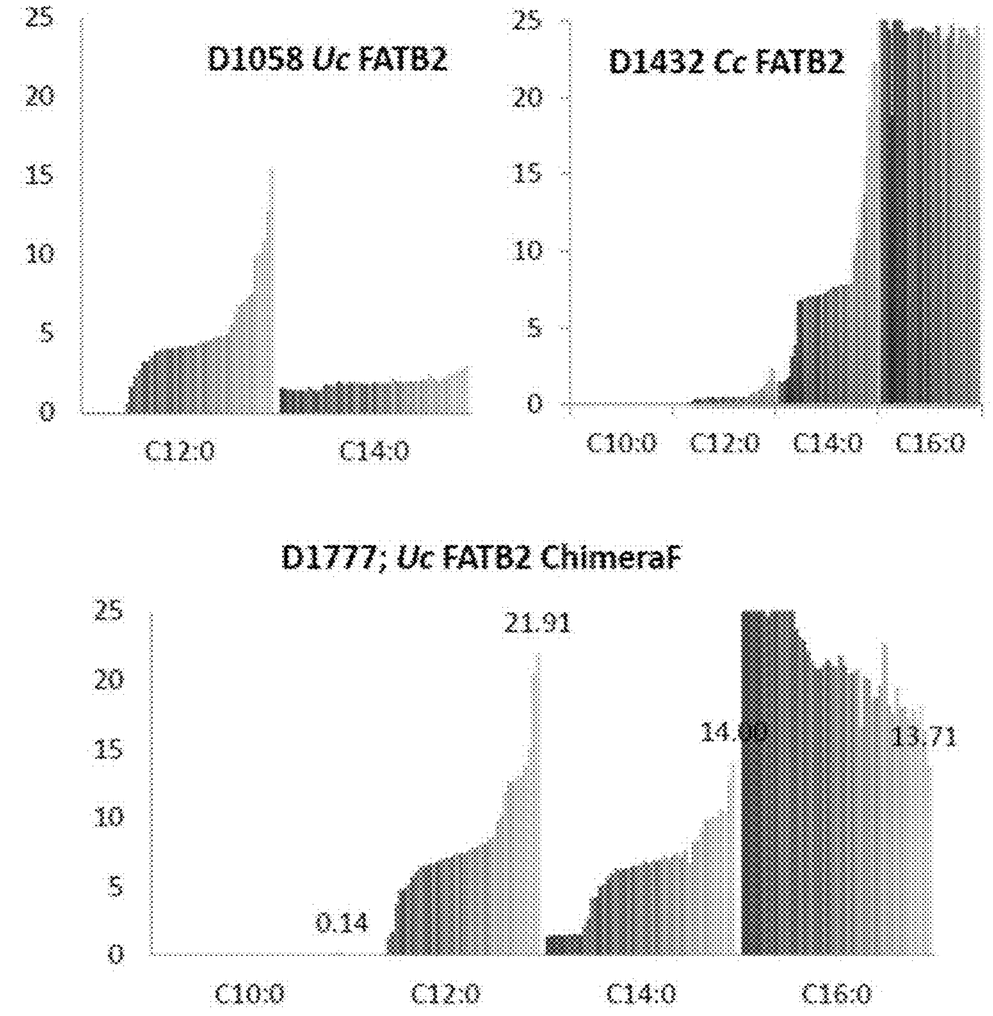
Figure 41C:
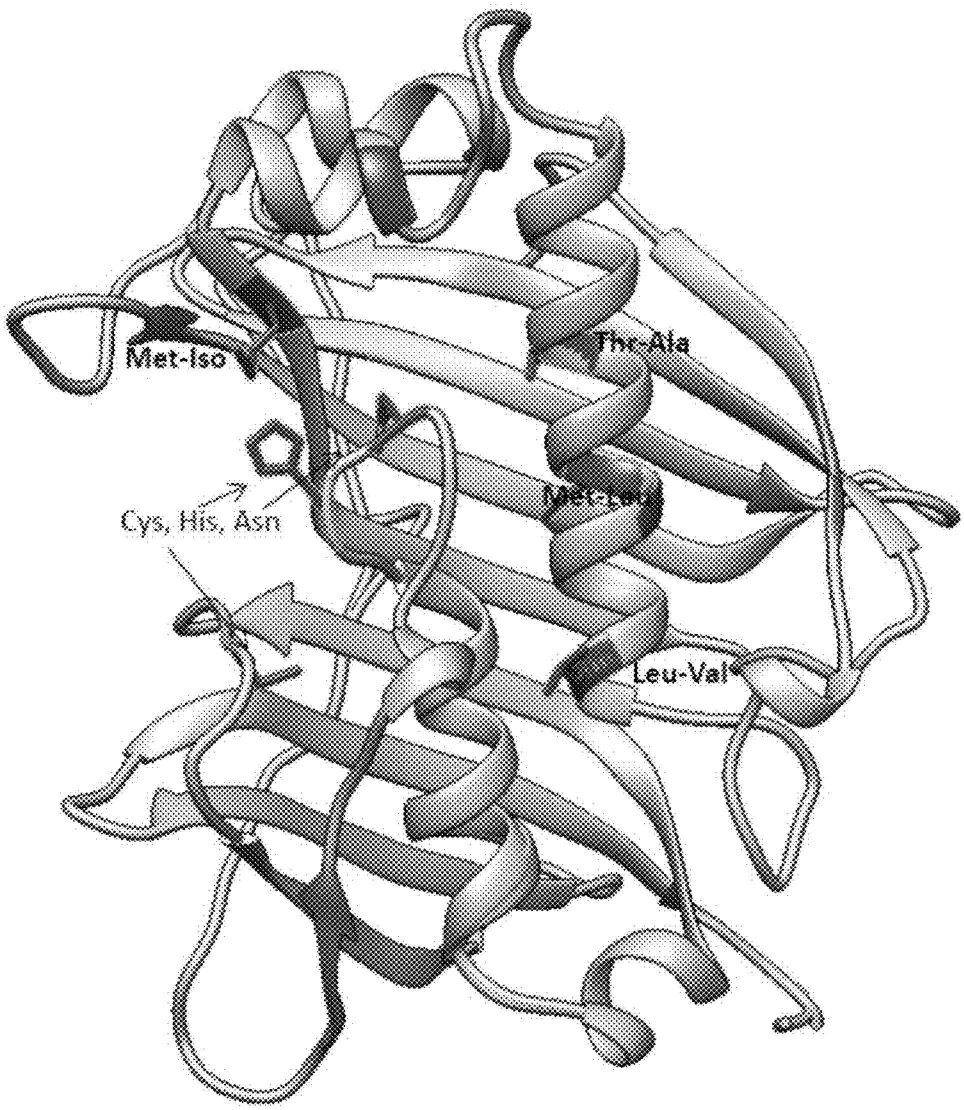

FIGS. 41A-C. FIG. 41A. Sequence alignment of the previously described N-terminal specificity domain derived from the Ch FATB2 (D3042), *Umbellularia californica* (Uc FatB2 accession M94159; D1058), *Cinnamomum camphorum* FATB1 (Cc FATB2, accession U31813; D1432) and the Uc FATB2 Chimera F (D1777). Boxes highlight the four amino acids that were altered within the N-terminal specificity domain of the Uc FATB2 to generate the Uc FATB2 Chimera F. FIG. 41A discloses SEQ ID NOS 231-233 and 233, respectively, in order of appearance. FIG. 41B illustrates the C12:0 preferring fatty acid profile for D1058, the C14:0 fatty acid profile for D1432 and a novel hybrid C12:0-C14:0 profile for D1777. FIG. 41C. The four amino acid alterations which yielded D1777 are highlighted on a homology model of the native Uc FATB2. Also shown are the catalytic triad (Cys, His, and Asn) comprising the enzymatic core.

Figure 42A:
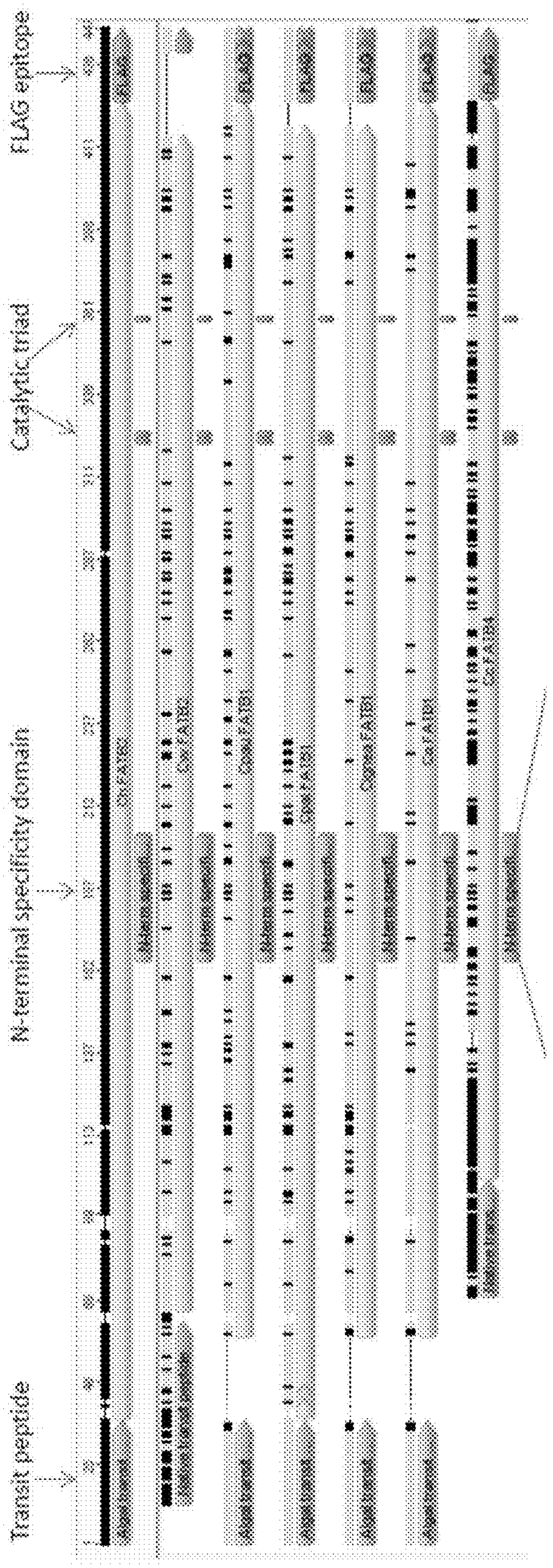
Figure 42B:
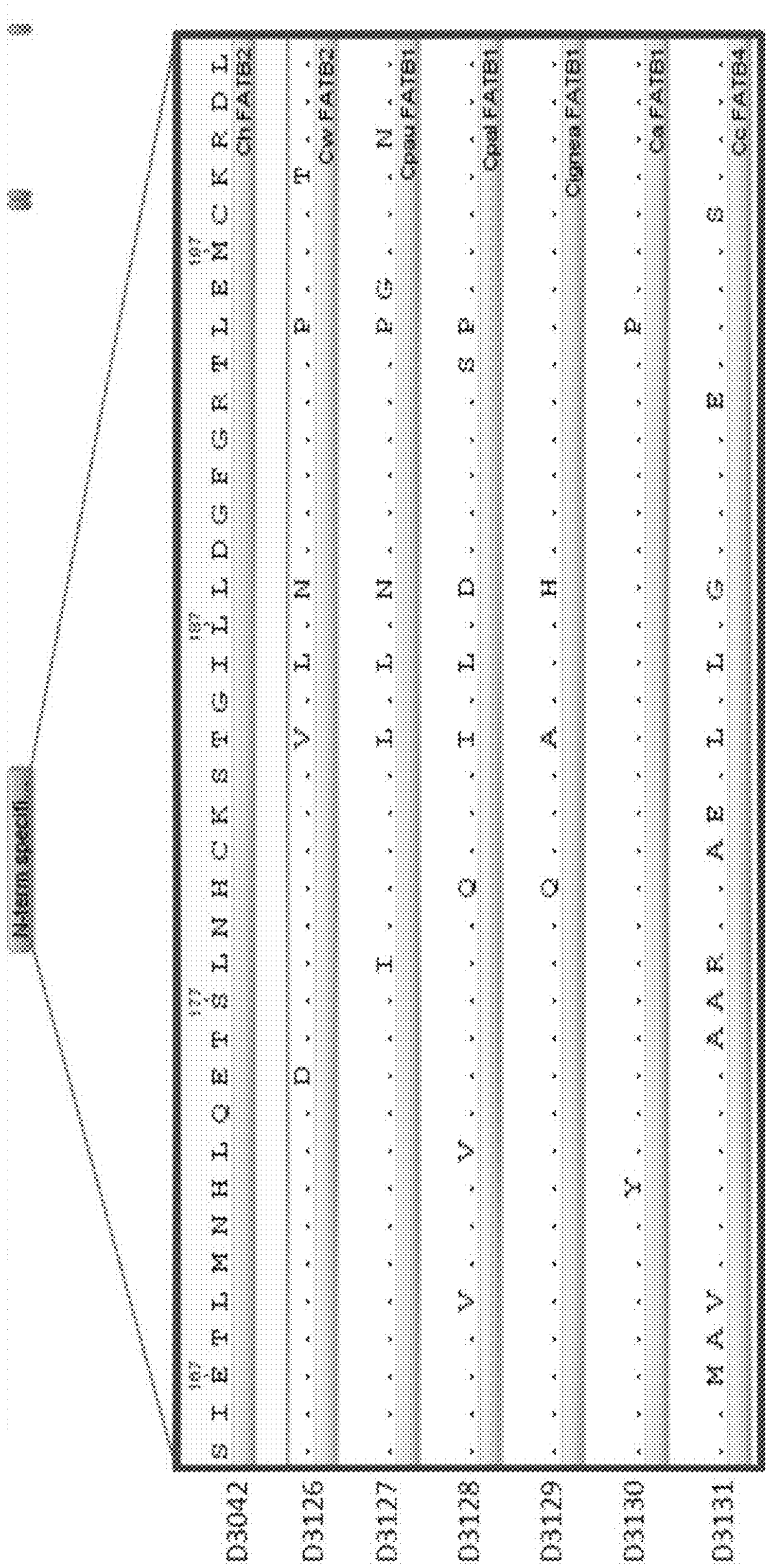

FIGS. 42A-B. FIG. 42A. Sequence alignment between Ch FATB2, *Cuphea wrightii* (Cw FATB2, accession U56103), *Cuphea paucipetala* (Cpau FATB1), *Cuphea palustris* (Cpal FATB1, accession AAC49179), *Cuphea ignea* (Cignea FATB1), *Cuphea avigera* (Ca FATB1), and *Cinnamomum camphorum* (Cc FATB4). The N-terminal specificity domain is highlighted relative to the transit peptide, catalytic triad and C-terminal FLAG epitope tag. FIG. 42B. Sequence alignment of the N-terminal specificity domain derived from the wild-type Ch FATB2 and the six Ch FATB2 chimeras. Residues identical the wild-type Ch FATB2 (D3042) are noted with dots, while alterations are noted with the amino acid letter. The FATB gene from which the substitutions were derived are the following: D3126 Cw FATB2; D3127 Cpau FATB1; D3128 Cpal FATB1; D3129 Cignea FATB1; D3130 Ca FATB1; and D3131 Cc FATB4. FIG. 42B discloses SEQ ID NOS 234-240, respectively, in order of appearance.

Figure 43A:
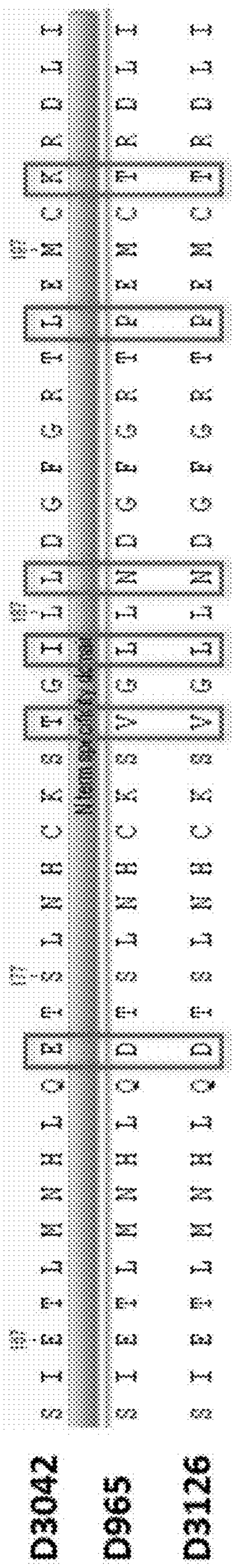
Figure 43B:
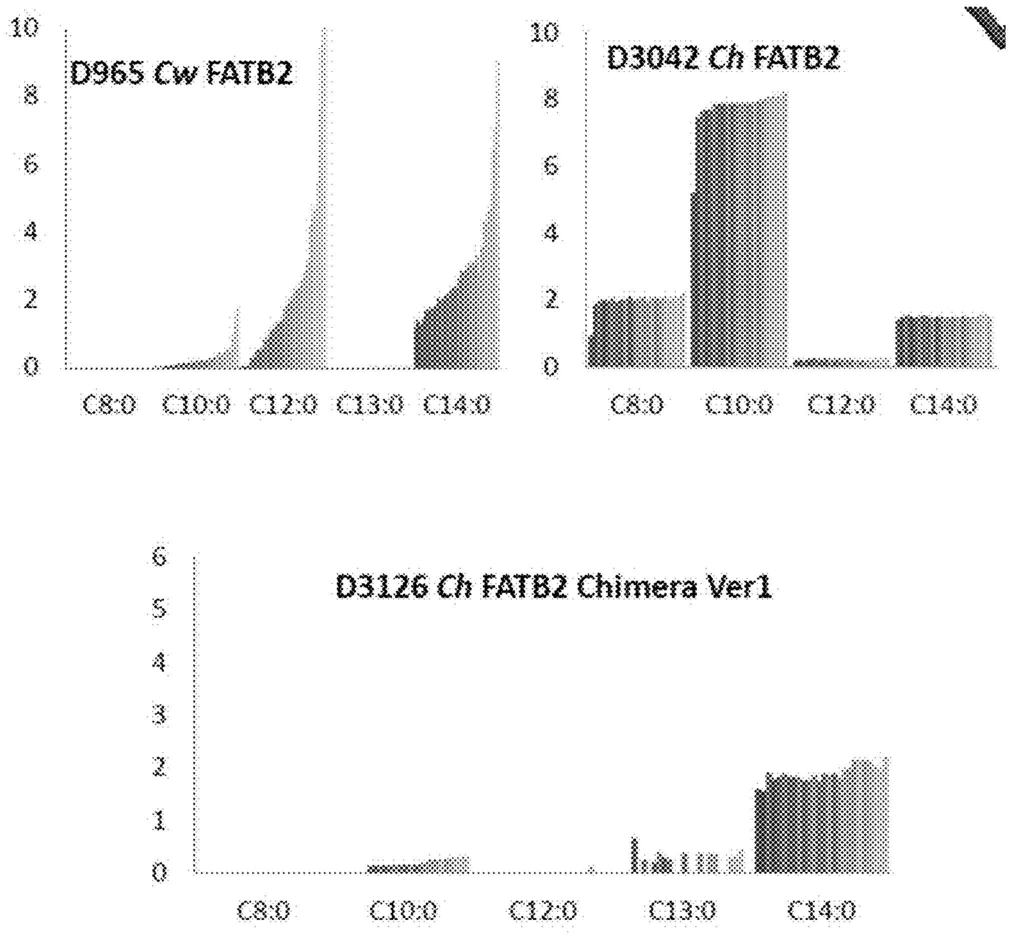
Figure 43C:
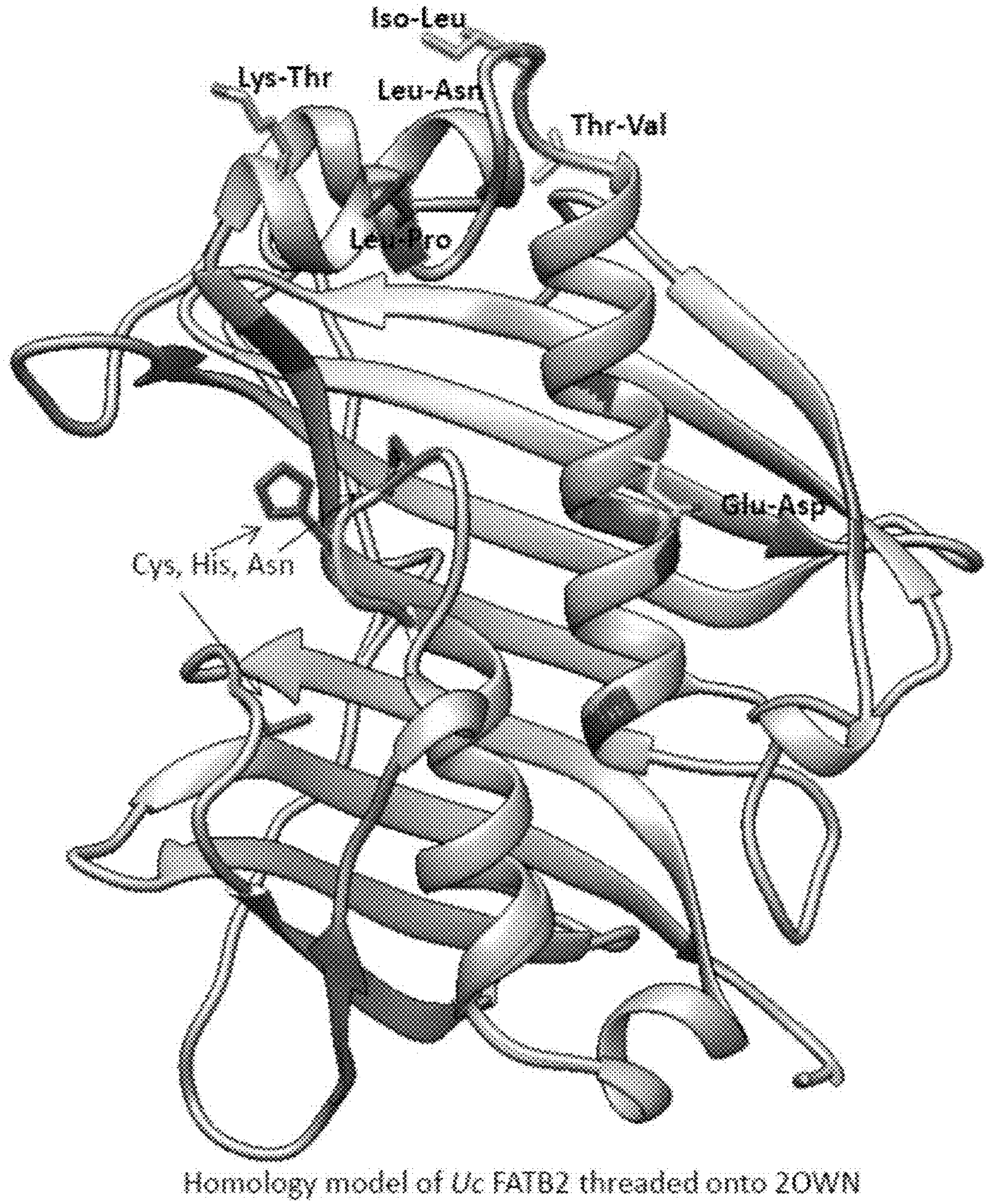

FIGS. 43A-C. FIG. 43A. Sequence alignment of the N-terminal specificity domain derived from the Ch FATB2 (D3042), the Cw FATB2 (D965) and the Ch FATB2 Chimera Ver1 (D3126). Boxes highlight the six amino acids that were altered within the N-terminal specificity domain of the Ch FATB2 to generate the Ch FATB2 Chimera Ver1. FIG. 43A discloses SEQ ID NOS 231, 241 and 241, respectively, in order of appearance. FIG. 43B illustrates the C12:0-C14:0 preferring fatty acid profile for D965, the C8:0-C10:0 fatty acid profile for D3042 and the barely detectable C10:0 accumulation in strains expressing D3126. FIG. 43C. The six amino acid alterations which generated D3126 are highlighted on a homology model of the native Uc FATB2. Also shown are the catalytic triad (Cys, His, and Asn) comprising the enzymatic core.

Figure 44A:
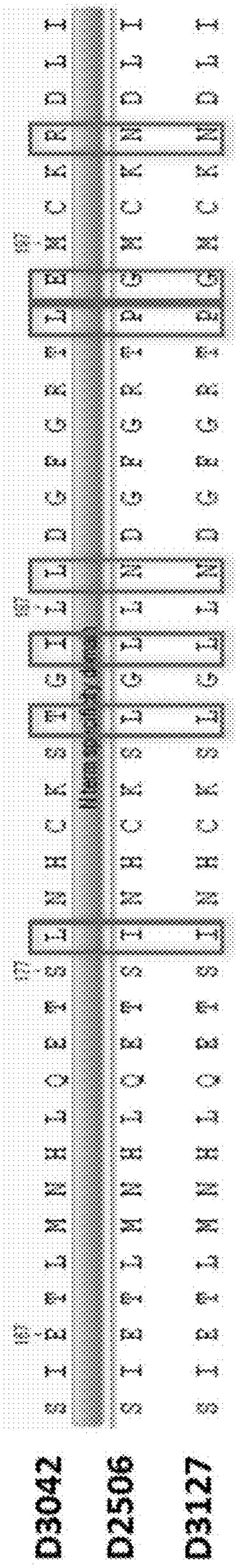
Figure 44B:
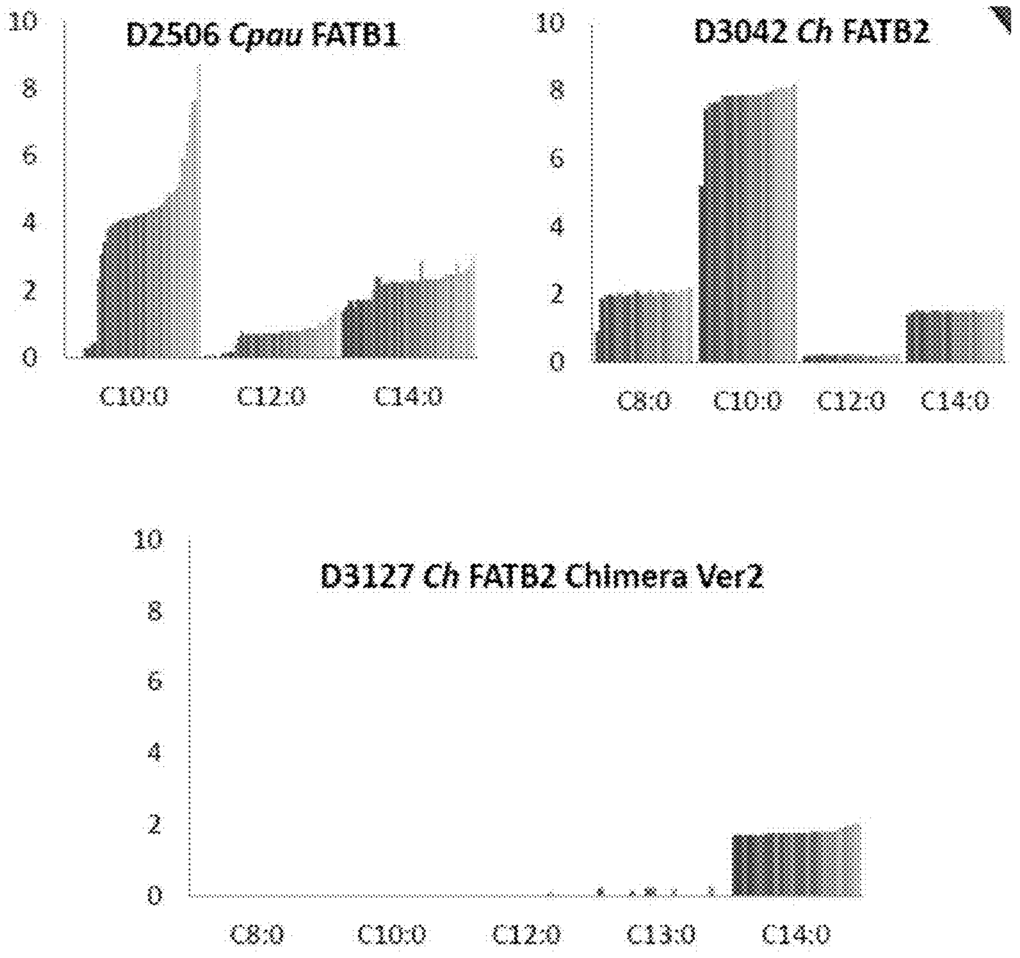
Figure 44C:
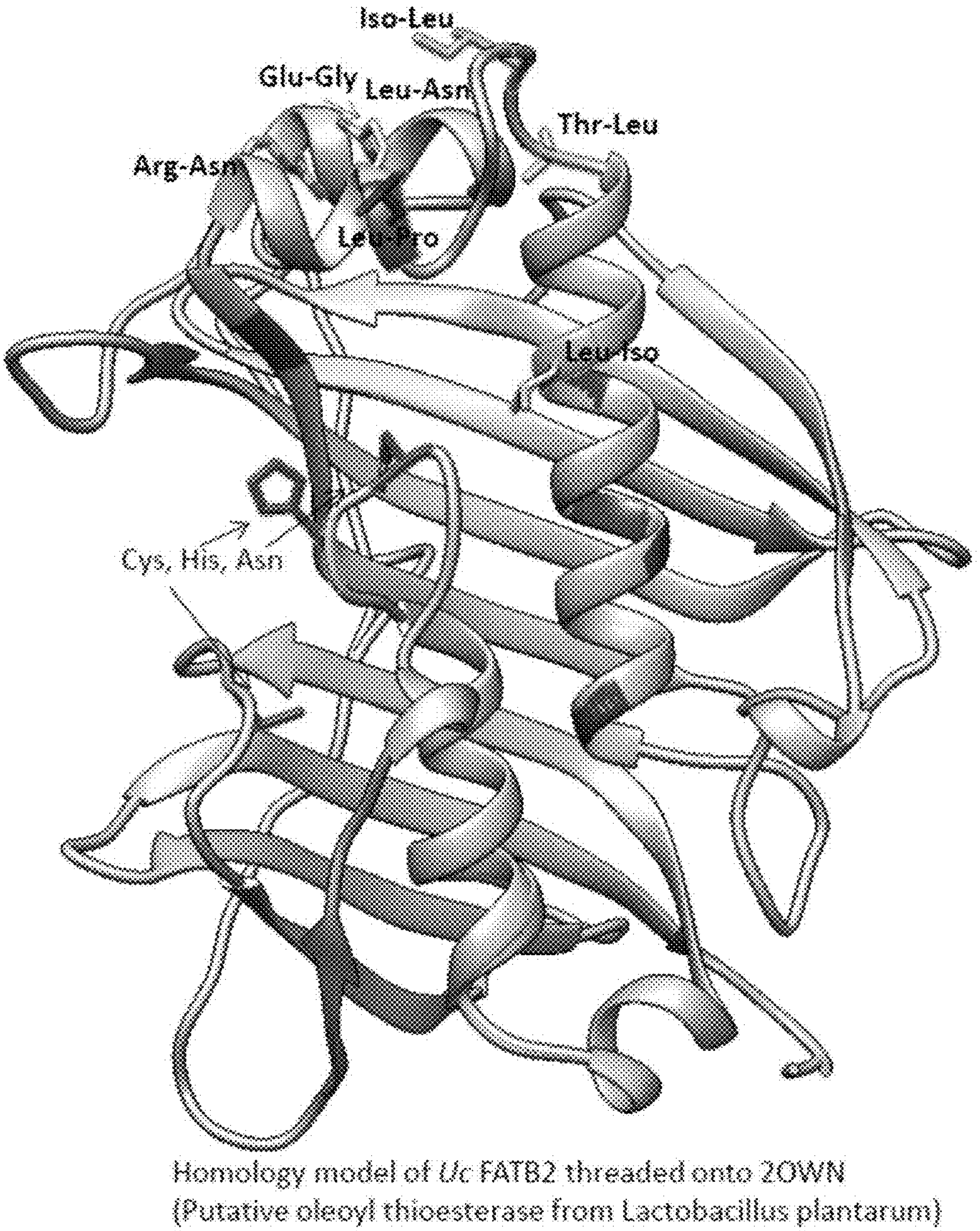

FIGS. 44A-C. FIG. 44A. Sequence alignment of the N-terminal specificity domain derived from the Ch FATB2

(D3042), the Cpau FATB1 (D2506) and the Ch FATB2 Chimera Ver2 (D3127). Boxes highlight the seven amino acids that were altered within the N-terminal specificity domain of the Ch FATB2 to generate the Ch FATB2 Chimera Ver2. FIG. 44A discloses SEQ ID NOS 231, 242 and 242, respectively, in order of appearance. FIG. 44B illustrates the C10:0-C14:0 preferring fatty acid profile for D2506, the C8:0-C10:0 fatty acid profile for D3042 and the loss of all detectable C8:0-C10:0 accumulation in strains expressing D3127. FIG. 44C. The seven amino acid alterations which generated D3127 are highlighted on a homology model of the native Uc FATB2. Also shown are the catalytic triad (Cys, His, and Asn) comprising the enzymatic core.

Figure 45A:
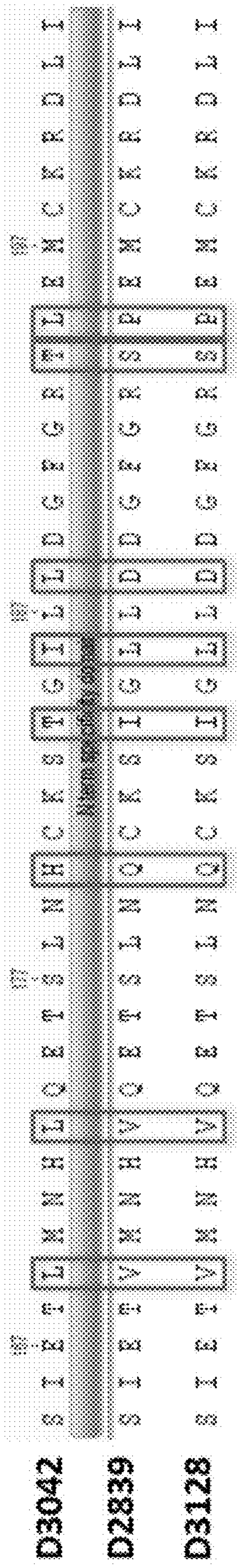
Figure 45B:
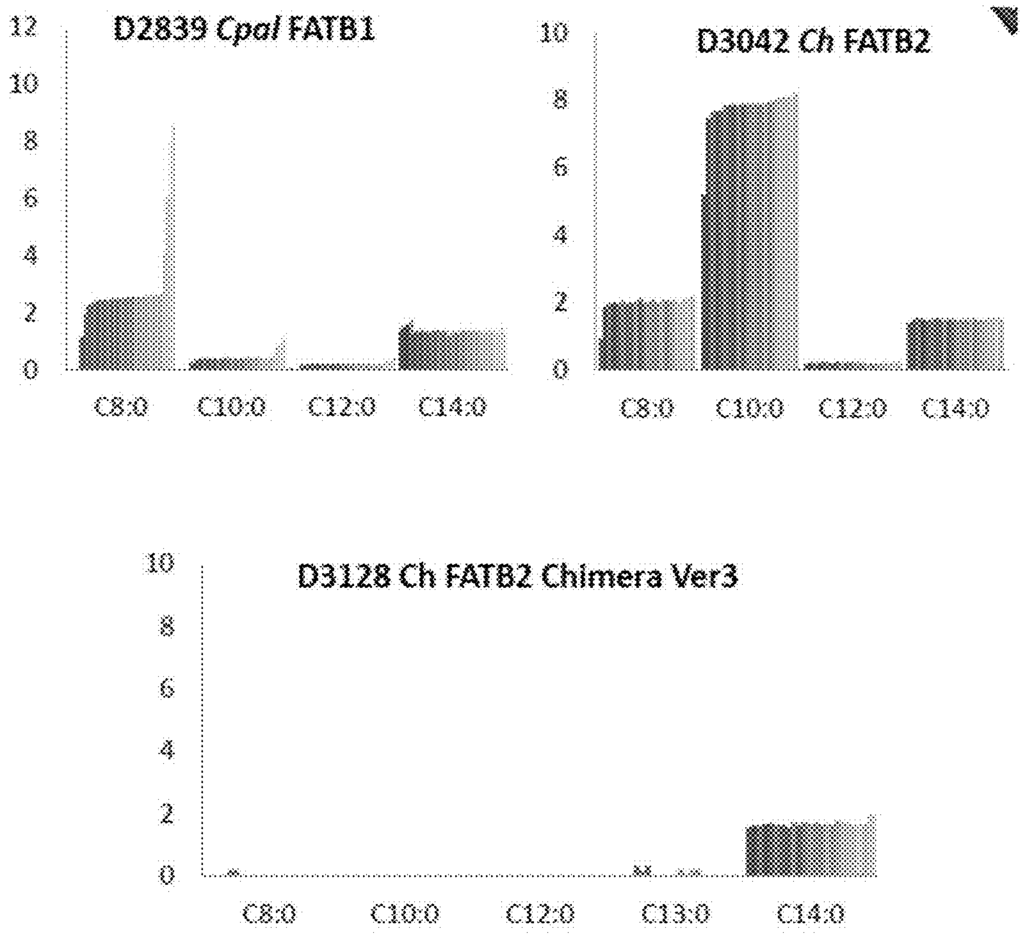
Figure 45C:
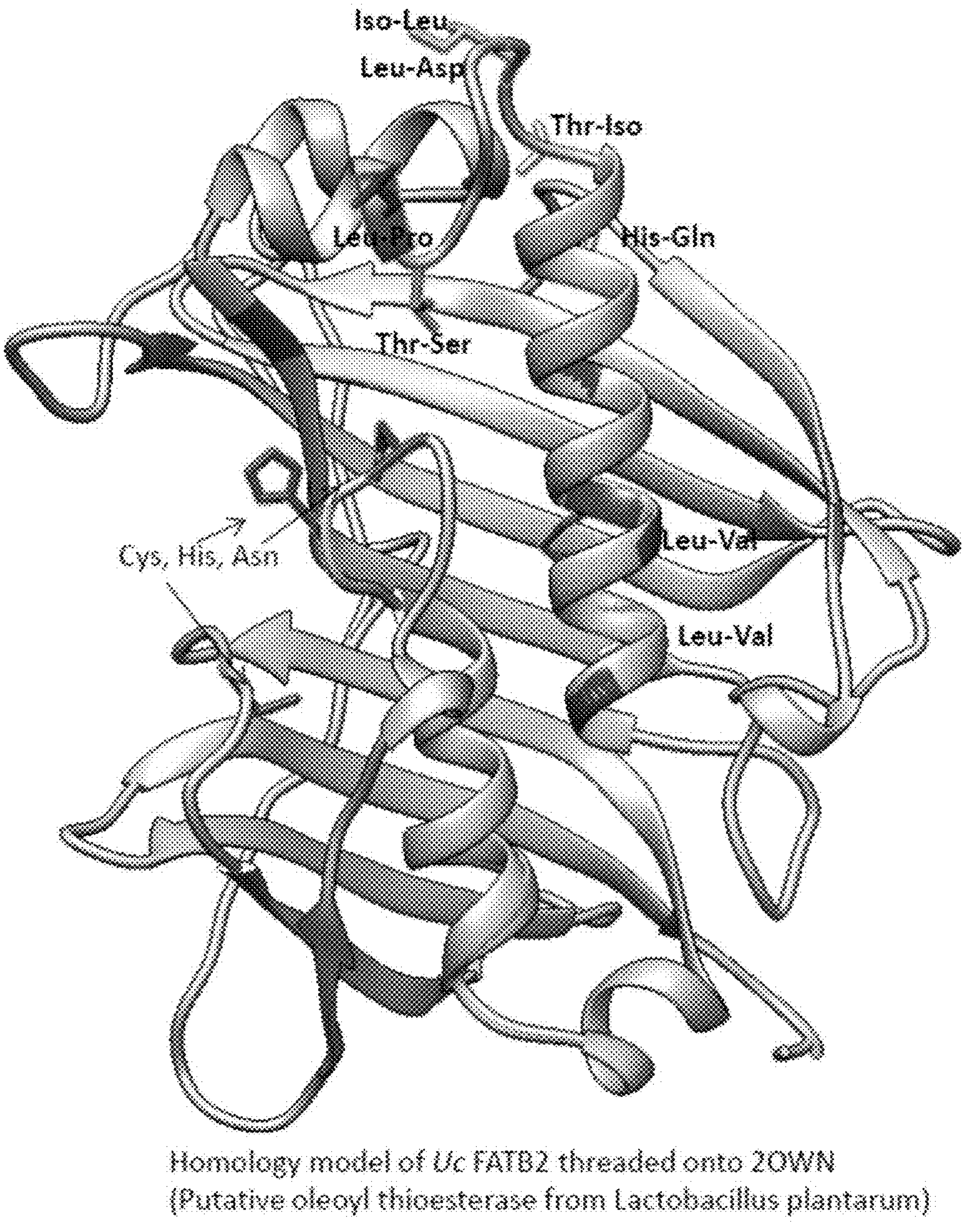

FIGS. 45A-C. FIG. 45A. Sequence alignment of the N-terminal specificity domain derived from the Ch FATB2 (D3042), the Cpal FATB1 (D2839) and the Ch FATB2 Chimera Ver3 (D3128). Boxes highlight the eight amino acids that were altered within the N-terminal specificity domain of the Ch FATB2 to generate the Ch FATB2 Chimera Ver3. FIG. 45A discloses SEQ ID NOS 231, 243 and 243, respectively, in order of appearance. FIG. 45B illustrates the C8:0-C10:0 preferring fatty acid profile for D2839, the C8:0-C10:0 fatty acid profile for D3042 and the loss of all detectable C8:0-C10:0 accumulation in strains expressing D3128. FIG. 45C. The eight amino acid alterations which generated D3128 are highlighted on a homology model of the native Uc FATB2. Also shown are the catalytic triad (Cys, His, and Asn) comprising the enzymatic core.

Figure 46A:
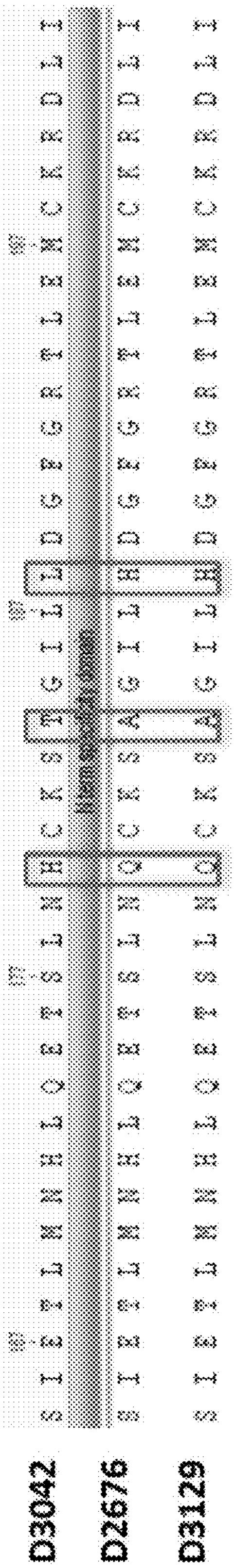
Figure 46B:
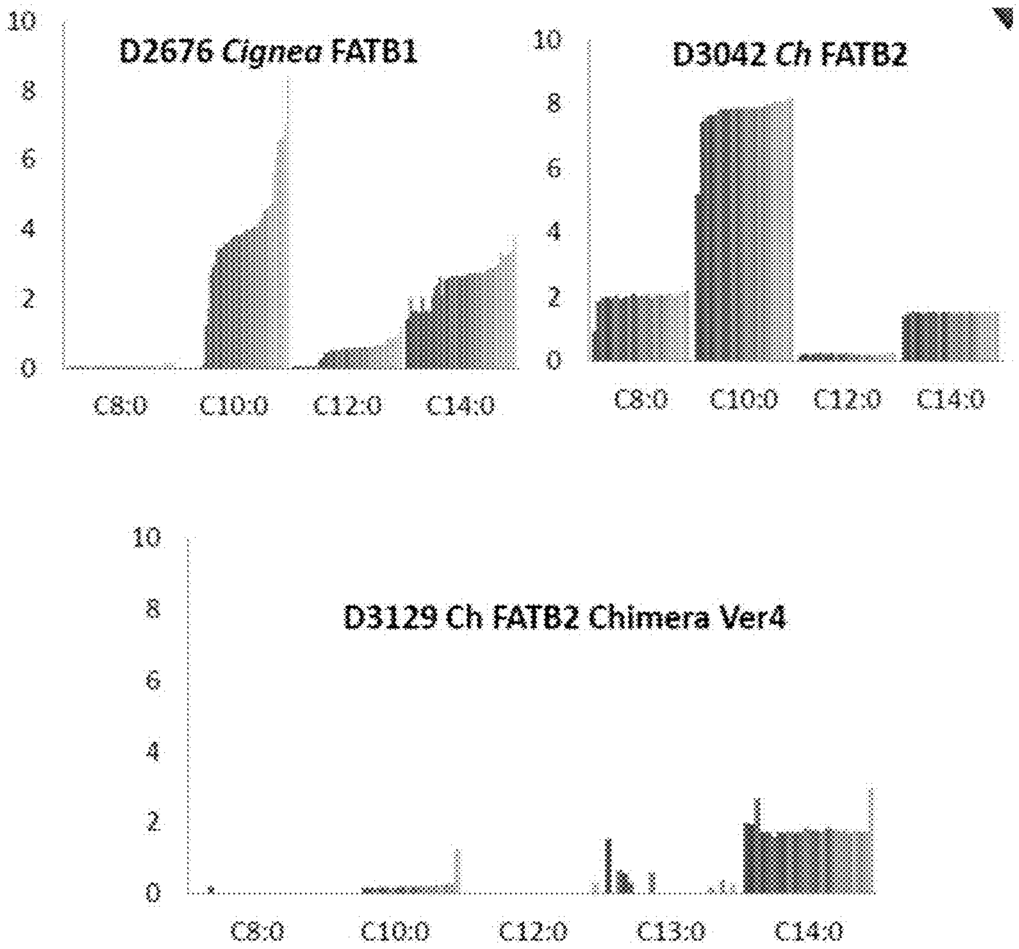
Figure 46C:
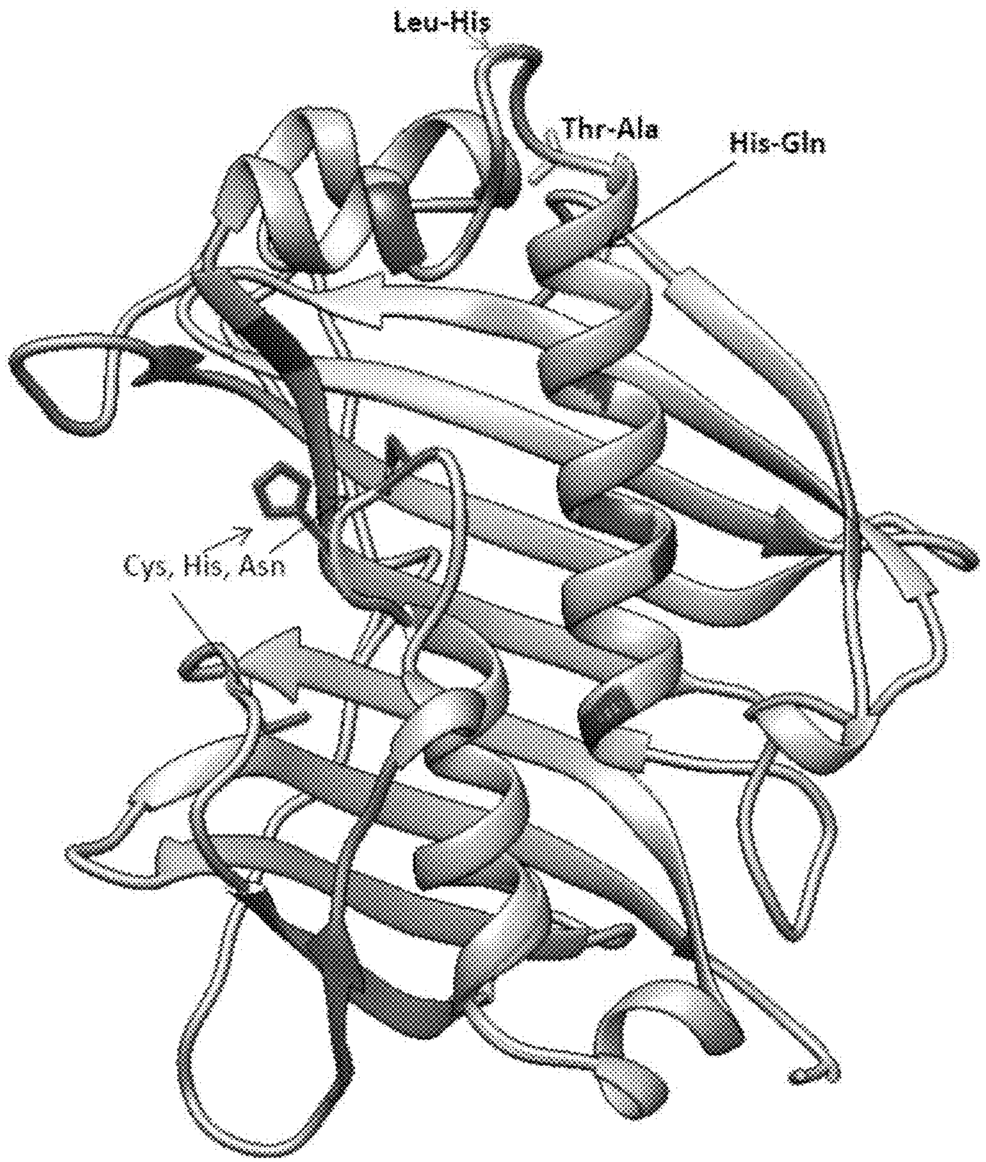

FIGS. 46A-C. FIG. 46A. Sequence alignment of the N-terminal specificity domain derived from the Ch FATB2 (D3042), the Cignea FATB1 (D2676) and the Ch FATB2 Chimera Ver4 (D3129). Boxes highlight the three amino acids that were altered within the N-terminal specificity domain of the Ch FATB2 to generate the Ch FATB2 Chimera Ver4. FIG. 46A discloses SEQ ID NOS 231, 244 and 244, respectively, in order of appearance. FIG. 46B illustrates the C10:0-C14:0 preferring fatty acid profile for D2676, the C8:0-C10:0 fatty acid profile for D3042 and the barely detectable C10:0 accumulation in strains expressing D3129. FIG. 46C. The three amino acid alterations which generated D3129 are highlighted on a homology model of the native Uc FATB2. Also shown are the catalytic triad (Cys, His, and Asn) comprising the enzymatic core.

Figure 47A:
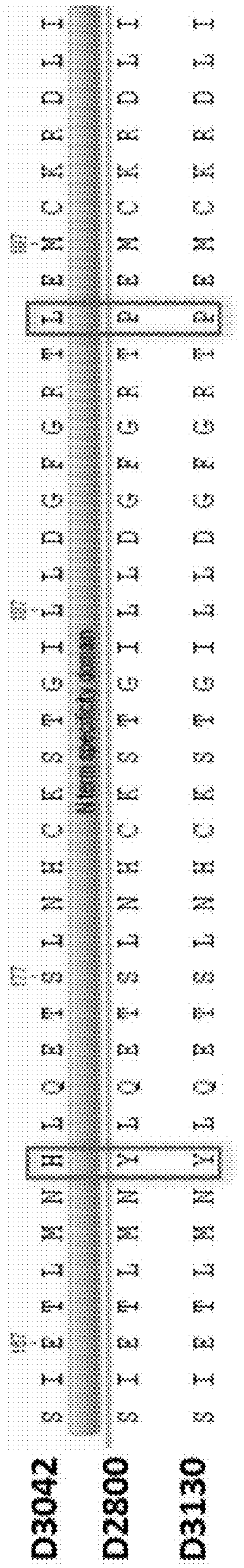
Figure 47B:
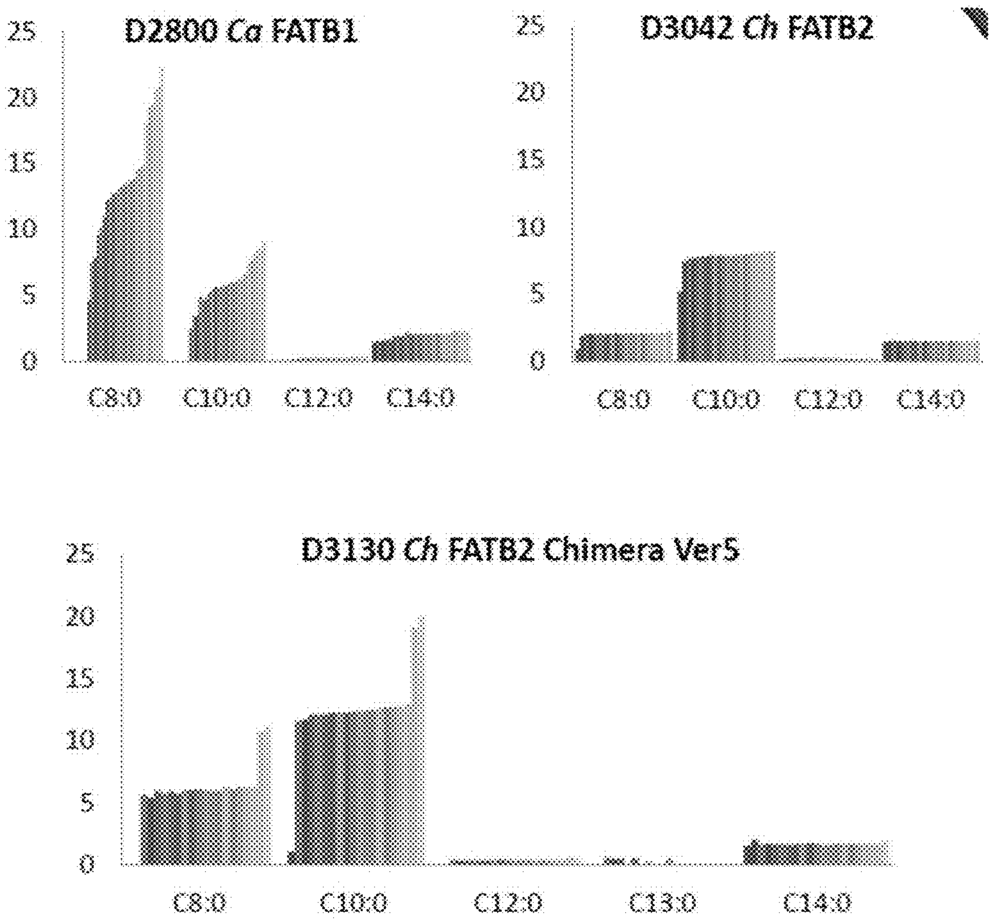
Figure 47C:
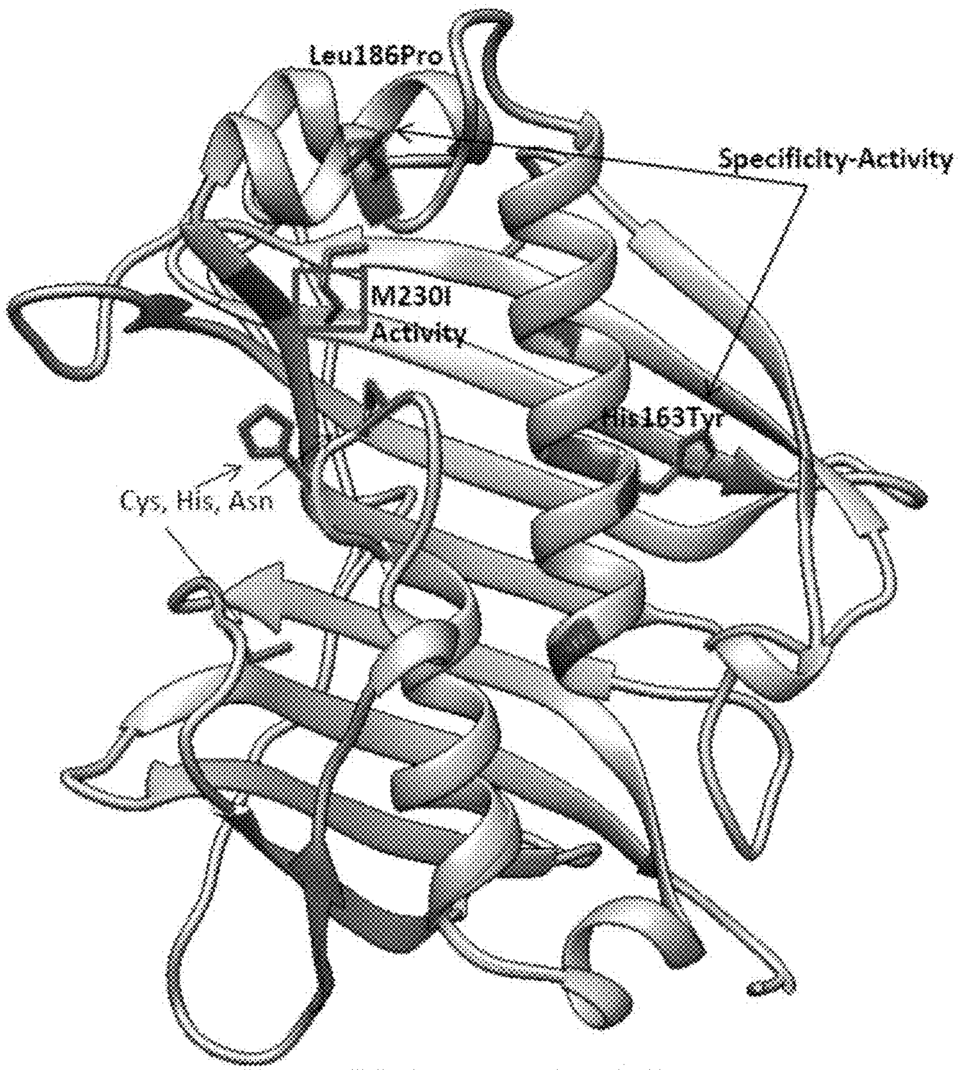

FIGS. 47A-C. FIG. 47A. Sequence alignment of the N-terminal specificity domain derived from the Ch FATB2 (D3042), the Ca FATB1 (D2800) and the Ch FATB2 Chimera Ver5 (D3130). Boxes highlight the two amino acids that were altered within the N-terminal specificity domain of the Ch FATB2 to generate the Ch FATB2 Chimera Ver5. FIG. 47A discloses SEQ ID NOS 231, 245 and 245, respectively, in order of appearance. FIG. 47B illustrates the C8:0-C12:0 preferring fatty acid profile for D2800, the C8:0-C10:0 fatty acid profile for D3042 and robust C8:0-C10:0 accumulation in strains expressing D3130. FIG. 47C. The two amino acid alterations which generated D3130 are highlighted on a homology model of the native Uc FATB2. Also shown are the catalytic triad (Cys, His, and Asn) comprising the enzymatic core as well as the published M230I substitution that has been shown to enhance the enzymatic activity of the Cpal FATB1.

Figure 48A:
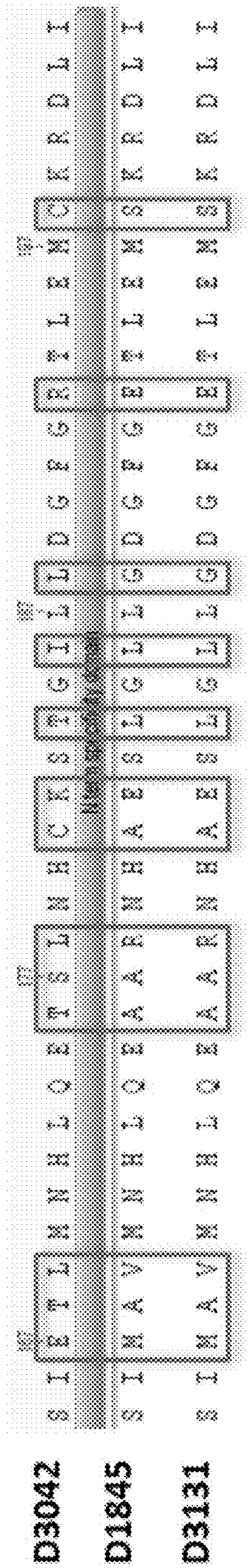
Figure 48B:
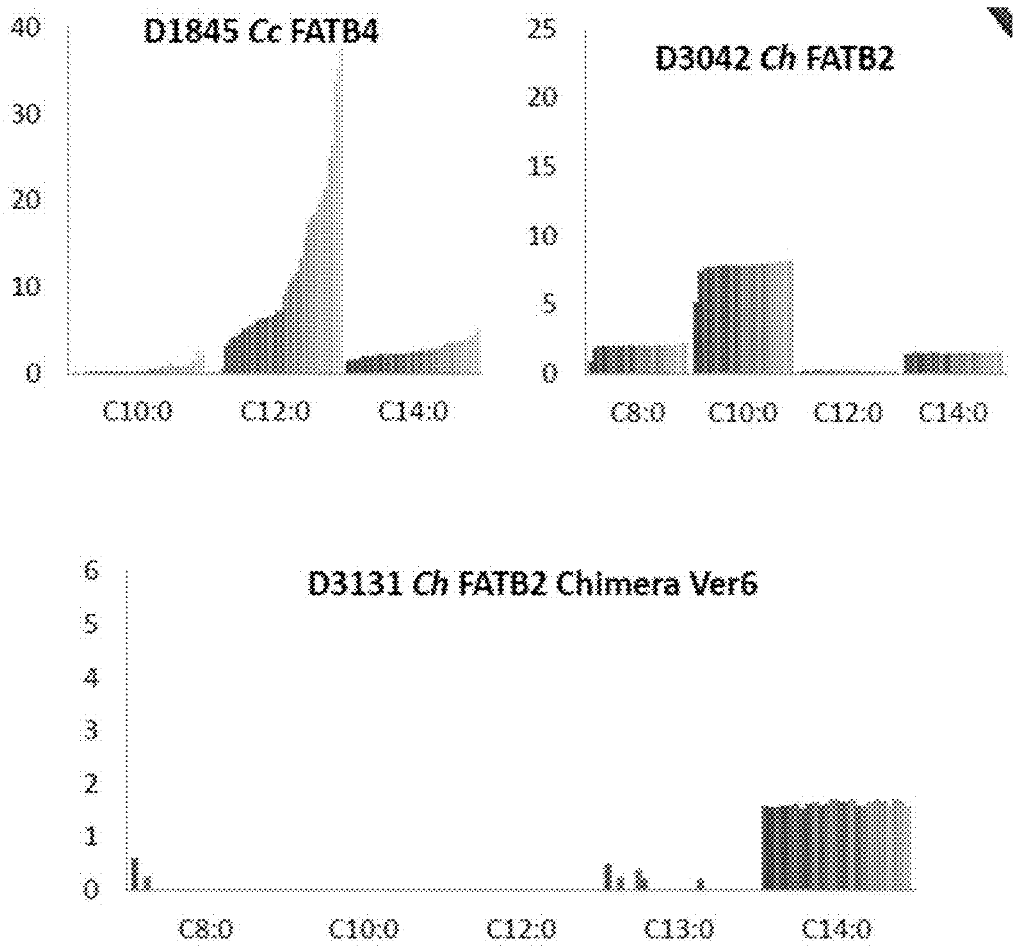
Figure 48C:
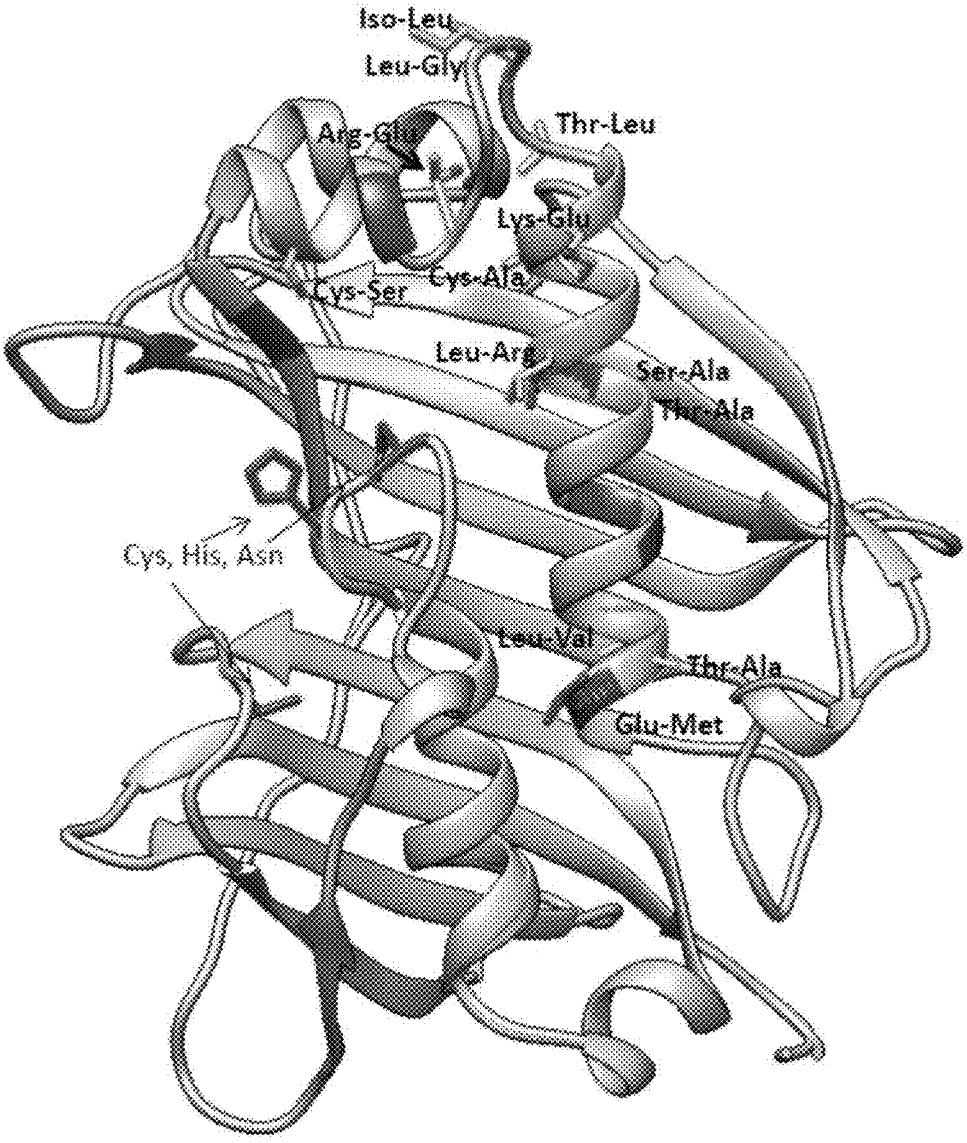

FIGS. 48A-C. FIG. 48A. Sequence alignment of the N-terminal specificity domain derived from the Ch FATB2 (D3042), the Cc FATB4 (D1845) and the Ch FATB2 Chimera Ver6 (D3131). Boxes highlight the thirteen amino acids that were altered within the N-terminal specificity domain of the Ch FATB2 to generate the Ch FATB2 Chimera Ver6. FIG. 48A discloses SEQ ID NOS 231, 246 and 246, respectively, in order of appearance. FIG. 48B illustrates the C12:0-C14:0 preferring fatty acid profile for D1845, the C8:0-C10:0 fatty acid profile for D3042 and the lack of detectable C10:0 accumulation in strains expressing D3131. FIG. 48C. The thirteen amino acid alterations which generated D3131 are highlighted on a homology model of the native Uc FATB2. Also shown are the catalytic triad (Cys, His, and Asn) comprising the enzymatic core.

FIG. 49 illustrates the amino acid sequence (SEQ ID NO: 72) of the Ch FATB2 (D3042; pSZ4243). The algal transit peptide from *C. protothecoides* is noted with lower case and the C-terminal FLAG epitope tag is highlighted with underlined uppercase. The Ch FATB2 is represented with bold uppercase and the N-terminal specificity domain is boxed.

DETAILED DESCRIPTION

I. Introduction

Provided are variant thioesterases that allow for finer control over acyl-ACP thioesterase substrate specificity in order to obtain more precisely defined fatty acid profiles in a lipid production organism.

Certain embodiments are based on the discoveries that a N-terminal hydrophobic domain of acyl-ACP thioesterase from plants is important in maturation and cell-activity of the thioesterases. Inclusion of this region has been found to increase activity and swapping of domains between plant thioesterases can be used to increase activity in less active thioesterases. Accordingly, certain embodiments comprise fusion proteins incorporating a more active hydrophobic domain into a thioesterase to increase its activity in a cell and thereby alter the fatty acid profile of the cell. It has also been found that in FATB thioesterases, certain amino acids play a role in increasing TE catalytic activity. In particular, the inclusion of one or more amino acid residues corresponding to Asn91, Pro92 and Pro102 of SEQ ID NO:43 or SEQ ID NO:44 can increase thioesterase activity.

In some embodiments, the hydrophobic domain can be linked to a transit peptide using a linker domain. Selection of the linker domain is described below, including the advantageous inclusion of proline residues.

In addition, inclusion of certain amino acid substitutions N-terminal to the catalytic domain of FATB can alter the fatty acid preference of the FATB enzyme and thereby shift the fatty acid profile of a cell expressing a gene with these amino acid substitutions. In particular, the inclusion of one or more amino acid residues corresponding to Val127, Leu133, Ala137, and Ile163 of SEQ ID NO:43 or SEQ ID NO:44 can shift the fatty acid preference of a FATB thioesterase.

These discoveries may be combined to create a variant acyl-ACP thioesterase having both increased activity due to domain swapping and/or mutation of the hydrophobic domain and also incorporating mutations at the newly discovered specificity-altering positions. Optionally, a variant linker domain is included in a variant acyl-ACP thioesterase having one or both of the variant hydrophobic domain and novel variant specificity mutations disclosed herein. The result is a thioesterase having improved activity or altered specificity.

When incorporated into an oleaginous cell (e.g., of an oilseed plant, algae (e.g., microalgae)) the variant thioesterases can alter the fatty acid profiles of the cell to produce novel or more economical high-value commercial products.

The embodiments also encompass the residual biomass from such cells after oil extraction, oleochemicals, fuels and food products made from the oils and methods of cultivating the cells. In varying embodiments, the cells are microalgal cells, including heterotrophic or obligate heterotrophic cells, and cells classified as *Chlorophyta, Trebouxiophyceae, Chlorellales, Chlorellaceae*, or *Chlorophyceae*. The cells can also be plant cells or cells of macroalgae. Host cells having a type II fatty acid synthesis pathway are preferred. Although the examples given below use the Trebouxiophyte *Prototheca moriformis* as a host cell, the genes, constructs and methods disclosed may also find use in oilseed crops. Methods for introducing these genes into such crops are known in the art; see, for example, U.S. Pat. Nos. 6,331,664, 5,512,482, 5,455,167, 5,667,997.

II. Variant Acyl-ACP Thioesterases

The variant TEs can be used in genetic constructs and genetically engineered oleaginous cells (e.g., plants, algae, microalgae) with one or more exogenous genes to produce fatty acids, acylglycerides, or derivatives thereof. For example, microalgae or oilseed crops that would naturally, or through genetic modification, produce high levels of lipids can be engineered (or further engineered) to express an exogenous variant fatty acyl-ACP thioesterase, which can facilitate the cleavage of fatty acids from acyl carrier protein (ACP) during fatty acid synthesis. The fatty acids synthesized may be incorporated into acyl glycerides including triacylglycerides (TAGs, triglycerides). The TAGs can be recovered or, through further enzymatic processing within the cell, or in vitro, yield other useful compounds.

In an embodiment, the variant fatty acyl-ACP thioesterases are designed based on the desired specificity for a growing (during fatty acid synthesis) fatty acyl group having a particular carbon chain length. A specificity domain is selected based on its preference for a particular fatty acyl ACP substrate and/or for its ability to influence, increase and/or promote the production of fatty acids of a desired carbon chain length. Generally, the variant fatty acyl-ACP thioesterases have preferential substrate specificity for mid-chain ACP-fatty acyl substrates (e.g., to liberate C8, C10, C12, and/or C14 fatty acids). In varying embodiments, the specificity domain in the N-terminus of the acyl-ACP thioesterase is heterologous (e.g., due to point mutations and/or domain swapping) to the C-terminal catalytic domain. In certain embodiments, the fatty acid chain length substrate specificity and/or preference of the specificity domain and the catalytic domain is the same or within 1-2 carbons. For example, in varying embodiments, the variant acyl-acyl carrier protein (ACP) thioesterase (TE) comprises:

i) the specificity domain from a C10:0 acyl-ACP preferring TE and a catalytic domain from a C12:0 acyl-ACP preferring TE;

ii) the specificity domain from a C12:0 acyl-ACP preferring TE and a catalytic domain from a C14:0 acyl-ACP preferring TE;

iii) the specificity domain from a C14:0 acyl-ACP preferring TE and a catalytic domain from a C12:0 acyl-ACP preferring TE;

iv) the specificity domain from a C12:0 acyl-ACP preferring TE and a catalytic domain from a C10:0 acyl-ACP preferring TE;

v) the specificity domain from a C10:0 acyl-ACP preferring TE and a catalytic domain from a C8:0 acyl-ACP preferring TE; and/or vi) the specificity domain from a C8:0 acyl-ACP preferring TE and a catalytic domain from a C10:0 acyl-ACP preferring TE.

In varying embodiments, the variant acyl-acyl carrier protein (ACP) thioesterase (TE) comprises:

i) the specificity domain from *C. hookeriana* acyl-ACP TE and a catalytic domain from a *C. wrightii* acyl-ACP TE preferring TE;

ii) the specificity domain from a *Cinnamomum camphora* acyl-ACP TE and a catalytic domain from a *Umbellularia californica* acyl-ACP preferring TE; and/or iii) the specificity domain from a *Umbellularia californica* acyl-ACP preferring TE and a catalytic domain from a *innamomum camphora* acyl-ACP TE preferring TE.

In varying embodiments, the specificity domain encompasses an amino acid subsequence within the N-terminal hot dog fold domain of an acyl-ACP TE, e.g., corresponding to amino acid residues 125-163 of SEQ ID NO:43; amino acid residues 125-163 of SEQ ID NO:44; amino acid residues 152-190 of SEQ ID NO:45; amino acid residues 139-177 of SEQ ID NO:46; amino acid residues 117-155 of SEQ ID NO:47; amino acid residues 158-196 of SEQ ID NO:60; or amino acid residues 156-194 of SEQ ID NO:61. In varying embodiments, the specificity domain comprises a motif comprising the amino acid sequence

```
                                    (SEQ ID NO: 85)
SI(V/L/E)(A/T)(V/L)MN(H/Y/M/I)(L/M/V/F)QE(T/A)(A/
S/T)(L/I)N(H/Q)(A/V/C)(K/E/R)(S/I/T/N/C)(V/L/A/T/
I/N)G(L/I)(L/S/M)(G/L/D/N/E)(D/N/E)G(F/L)G(T/E/R/
S/A)(T/S)(L/P/R)(E/G)M(S/Y/F/C/T)(K/R/L)(R/K/N/M)
(D/G/N)L(M/I/F).
```

In varying embodiments, the variant acyl-acyl carrier protein (ACP) thioesterase (TE) comprises:

iv) a specificity domain comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity to an amino acid sequence selected from the group consisting of amino acid residues 125-163 of SEQ ID NO:43 and amino acid residues 125-163 of SEQ ID NO:44; wherein the amino acid residue at or corresponding to position 127 is Valine, the amino acid residue at or corresponding to position 133 is Leucine, the amino acid residue at or corresponding to position 137 is Alanine and the amino acid residue at or corresponding to position 163 is Isoleucine, and a catalytic domain from a C10:0 acyl-ACP preferring TE or from a C12:0 acyl-ACP preferring TE;

v) a specificity domain comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity to an amino acid sequence selected from the group consisting of amino acid residues 125-163 of SEQ ID NO:43 and amino acid residues 125-163 of SEQ ID NO:44; wherein the amino acid residue at or corresponding to position 127 is Leucine, the amino acid residue at or corresponding to position 133 is Methionine, the amino acid residue at or corresponding to position 137 is Threonine and the amino acid residue at or corresponding to position 163 is Methionine, and a catalytic domain from a C10:0 acyl-ACP preferring TE or from a C14:0 acyl-ACP preferring TE; and/or vi) a specificity domain comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to amino acid residues 156-203 of SEQ ID NO:61, wherein the amino acid residue at or corresponding to position 166 is Glutamine; the amino acid residue at or corresponding to position 175 is Threonine; the amino acid residue at or corresponding to position 177 is Isoleucine; the amino acid residue at or corresponding to position 179 is Leucine; the amino acid residue at or corresponding to position 186 is Leucine; the amino acid residue at or corresponding to position 190 is Lysine; the amino acid at or corresponding to position 198 is Isoleucine and the amino acid at or corresponding to position 203 is Lysine, and a catalytic domain from a C8:0 acyl-ACP preferring TE or from a C12:0 acyl-ACP preferring TE.

vii) a specificity domain comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to amino acid residues 156-193 SEQ ID NO:61; wherein the amino acid residue at or corresponding to position 163 is Tyrosine, or the amino acid residue at or corresponding to position 186 is Proline; and a catalytic domain from a C8:0 acyl-ACP preferring TE, from a C10:0 acyl-ACP preferring TE or from a C12:0 acyl-ACP preferring TE.

In embodiments where the specificity domain comprises at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 125-163 of SEQ ID NO:43 and amino acid residues 125-163 of SEQ ID NO:44, cleavage to the mature form of the variant acyl-ACP thioesterase can be increased, promoted and/or facilitated when the amino acid residue at or corresponding to position 91 is Asparagine, the amino acid at or corresponding to position 92 is Proline and the amino acid position 102 is Proline.

Alternately, or in addition, to increase expression levels and/or increase enzymatic activity of the variant acyl-ACP thioesterase in a host cell, the variant acyl-ACP thioesterases can be expressed with a hydrophobic domain N-terminally positioned in relation to the specificity domain. In varying embodiments, the N-terminal amino acid residue of the hydrophobic domain is a Leucine. In varying embodiments, the N-terminal amino acid residue of the hydrophobic domain is a Proline. In one embodiment, the subsequence comprising the hydrophobic domain can be 15, 16, 17, or 18 amino acids in length as appropriate. In varying embodiments, the hydrophobic domain is an amino acid subsequence within the N-terminal half of an acyl-ACP TE corresponding to amino acid residues 61-77 of SEQ ID NO:43; amino acid residues 61-77 of SEQ ID NO:44; amino acid residues 85-101 of SEQ ID NO:45; amino acid residues 78-95 of SEQ ID NO:46; amino acid residues 50-66 of SEQ ID NO:47; amino acid residues 91-107 of SEQ ID NO:60; or amino acid residues 90-106 of SEQ ID NO:61. In varying embodiments, the hydrophobic domain comprises a motif comprising the amino acid sequence (L/-)(P/H)(G/D/V)(W/L)(S/N)(M/R/V)(P/L/S)(L/F)(E/A/T/S)(L/A/K)(I/V)TT(I/V)F(S/L/V/G)(A/K/V) (A/P) (SEQ ID NO: 102). As described and demonstrated herein, the hydrophobic domain can, but need not, comprise an N-terminal Leucine residue.

Yet another way has been found to increase the impact of a thioesterase on the fatty acid profile of a host cell. A variant acyl-ACP thioesterase can be expressed with a linker domain N-terminally positioned in relation to the hydrophobic domain. The linker domain can be rich in proline. The linker domain can be used alone or in combination with either or both of the variant hydrophobic domain and specificity-imparting variations discussed above. In embodiments where the variant acyl-ACP comprises a transit or signal peptide, e.g., a plastid transit peptide, the linker domain is C-terminally positioned in relation to the transit peptide (e.g., from N— to C-terminus, the linker domain is positioned between a transit peptide, when present and a hydrophobic domain). In varying embodiments, the acyl-ACP linker domains are proline rich and comprise 3, 4, 5, 6 or more proline residues. In varying embodiments, the linker domain encompasses an amino acid subsequence within the N-terminal half of an acyl-ACP TE corresponding to at least 5 amino acid residues, e.g, at least 6, 7, 8, 9, 10, 11, 12, 13, 14, 15, 20, 21, 22, 23, 24, 25, 26, 27, 28, 29, 30, 31, 32, 33, 34, 35 or 36 residues, extending N-terminally from the C-terminus from an acyl-ACP-TE subsequence and corresponding to residues selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61.

In varying embodiments, subsequence comprising the linker domain comprises:

a) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence corresponding to residues selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61;

b) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence comprising at least 60% sequence identity, e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity, to an amino acid sequence selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61;

c) at least 5 amino acid residues, e.g., at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 residues, extending from the C-terminus from an acyl-ACP-TE subsequence selected from the group consisting of amino acid residues 43-59 of SEQ ID NO:43; amino acid residues 43-59 of SEQ ID NO:44; amino acid residues 49-83 of SEQ ID NO:45; amino acid residues 53-77 of SEQ ID NO:46; amino acid residues 15-48 of SEQ ID NO:47; amino acid residues 57-89 of SEQ ID NO:60; and amino acid residues 56-88 of SEQ ID NO:61; and/or d) an amino acid sequence selected from the group consisting of SEQ ID NO:37, SEQ ID NO:38, SEQ ID NO:39, SEQ ID NO:40; SEQ ID NO:41 and SEQ ID NO:42.

In varying embodiments, the variant acyl-ACP thioesterases may further comprise a signal peptide or a transit peptide. In varying embodiments, the transit peptide directs the variant acyl-ACP thioesterase to a plastid, e.g., the chloroplast. In varying embodiments, the plastid transit peptide comprises an amino acid sequence selected from the group consisting of MATASTFSAFNARCGDLRRSAGSGPRRPARPLPVRGRA (SEQ ID NO: 91), SGPRRPARPLPVR (SEQ ID NO: 92), SGPRRPARPLPVRAAIASEVPVATTSPR (SEQ ID NO: 93), RPARPLPVRGRA (SEQ ID NO: 94), RPARPLPVRAAIASEVPVATTSPR (SEQ ID NO: 95), RCGDLRRSAGSGPRRPARPLPVRGRA (SEQ ID NO: 96), RCGDLRRSAGSGPRRPARPLPVRAAIASEVPVATTSPR (SEQ ID NO: 97), PARPLPVR (SEQ ID NO: 98), PARPLPVRAAIASEVPVATTSPR (SEQ ID NO: 99), RRPARPLPVR (SEQ ID NO: 100), and RRPARPLPVRAAIASEVPVATTSPR (SEQ ID NO: 101). Other plastid transit sequences are known in the art and described in further detail below.

In varying embodiments, the polynucleotide encodes a variant acyl-ACP thioesterase having an N-terminal region that is heterologous to the C-terminal region or to the catalytic domain and comprising a hydrophobic domain and/or a specificity domain from an acyl-ACP TE selected from the group consisting of *Umbellularia californica* fatty acyl-ACP thioesterase (e.g., GenBank Acc. Nos. AAC49001, Q41635, M94159), *Cinnamomum camphora* fatty acyl-ACP thioesterase (e.g., GenBank Acc. Nos. Q39473; U31813), *Myristica fragrans* fatty acyl-ACP thioesterase (e.g., GenBank Acc. Nos. AAB71729, AAB71730, AAB717291.1), *Elaeis guineensis* fatty acyl-ACP thioesterase (e.g., GenBank Acc. Nos. ABD83939, AAD42220, AAL15645), *Populus tomentosa* fatty acyl-ACP thioesterase (e.g., GenBank Acc. No. ABC47311), *Arabidopsis thaliana* fatty acyl-ACP thioesterase (e.g., GenBank Acc. Nos. NP_172327, CAA85387, CAA85388), *Arabidopsis thaliana* fatty acyl-ACP thioesterase (e.g., GenBank Acc. No.), *Gossypium hirsutum* fatty acyl-ACP thioesterase (e.g., GenBank Acc. Nos. AAD01982, Q9SQI3), *Cuphea wrightii* fatty acyl-ACP thioesterase (e.g., GenBank Acc. Nos. U56103, Q39663), *Cuphea lanceolata* fatty acyl-ACP thioesterase (e.g., GenBank Acc. Nos. CAA54060, CAB60830, CAC19933), *Cuphea hookeriana* fatty acyl-ACP thioesterase (e.g., GenBank Acc. Nos. AAC72882, U39834, Q39513, Q39514, AAC49269), *Cuphea calophylla* subsp. *mesostemon* fatty acyl-ACP thioesterase (e.g., GenBank Acc. No. ABB71581), *Cuphea palustris* fatty acyl-ACP thioesterase (e.g., GenBank Acc. Nos. AAC49180; AAC49179), *Vitis vinifera* fatty acyl-ACP thioesterase (e.g., GenBank Acc. No. CAN81819), *Garcinia mangostana* fatty acyl-ACP thioesterase (e.g., GenBank Acc. No. AAB51525), *Brassica juncea* fatty acyl-ACP thioesterase (e.g., GenBank Acc. No. ABI18986), *Madhuca longifolia* fatty acyl-ACP thioesterase (e.g., GenBank Acc. No. AAX51637), *Brassica napus* fatty acyl-ACP thioesterase (e.g., GenBank Acc. Nos. ABH11710; CAA52070.1), *Oryza sativa* (indica cultivar-group) fatty acyl-ACP thioesterase (e.g., GenBank Acc. No. EAY86877), *Oryza sativa* (japonica cultivar-group) fatty acyl-ACP thioesterase (e.g., GenBank Acc. No. NP_001068400), *Oryza sativa* (indica cultivar-group) fatty acyl-ACP thioesterase (e.g., GenBank Acc. No. EAY99617), *Ulmus Americana* fatty acyl-ACP thioesterase (e.g., GenBank Acc. No. AAB71731, 024420), *Iris germanica* fatty acyl-ACP thioesterase (e.g., GenBank Acc. Nos. AAG43858, AAG43858.1), *Ricinus communis* fatty acyl-ACP thioesterase (e.g., GenBank Acc. No. ABS30422.1), *Helianthus annuus* acyl-ACP thioesterase (e.g., GenBank Accession No. AAL79361.1), *Jatropha curcas* acyl-ACP thioesterase (e.g., GenBank Accession No. ABX82799.3), *Zea mays* oleoyl-acyl carrier protein thioesterase, (e.g., GenBank Accession No. ACG40089.1), and *Haematococcus pluvialis* fatty acyl-ACP thioesterase (e.g., GenBank Accession No. HM560034.1).

In particular embodiments, the variant acyl-ACP thioesterase comprises an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15; SEQ ID NO:18, SEQ ID NO:20, SEQ ID NO:22, SEQ ID NO:24, SEQ ID NO:26; SEQ ID NO:28; SEQ ID NO:30, SEQ ID NO:32; SEQ ID NO:34; SEQ ID NO:36; SEQ ID NO:49, SEQ ID NO:51; SEQ ID NO:53; SEQ ID NO:55; SEQ ID NO:57 and SEQ ID NO:59.

In particular embodiments, the variant acyl-ACP thioesterase is encoded by a nucleic acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14; SEQ ID N0:17, SEQ ID NO:19, SEQ ID NO:21, SEQ ID NO:23, SEQ ID NO:25; SEQ ID NO:27; SEQ ID NO:29, SEQ ID NO:31; SEQ ID NO:33; SEQ ID NO:35; SEQ ID NO:48, SEQ ID NO:50; SEQ ID NO:52; SEQ ID NO:54; SEQ ID NO:56 and SEQ ID NO:58.

III. Microbe Engineering—Expression Cassettes and Vectors

Promoters, cDNAs, and 3'UTRs, as well as other elements of the vectors, can be generated through cloning techniques using fragments isolated from native sources (see for example Green and Sambrook, Molecular Cloning: A Laboratory Manual, $4^{th}$ Edition, 2012, Cold Spring Harbor Press; and U.S. Pat. No. 4,683,202). Alternatively, elements can be generated synthetically using known methods (see for example Gene. 1995 Oct. 16; 164(1):49-53).

A. Codon-Optimization for Expression

DNA encoding a polypeptide to be expressed in a microorganism, e.g., a variant acyl-ACP thioesterase and selectable marker can be codon-optimized cDNA. Methods of recoding genes for expression in microalgae are described in U.S. Pat. No. 7,135,290. Additional information for codon optimization is available, e.g., at the Codon Usage Database at kazusa.or.jp/codon/. The table for *Prototheca* preferred codon usage is also provided in U.S. Patent Publ. No. 2012/0283460, hereby incorporated herein by reference in its entirety for all purposes.

B. Promoters

Many promoters are active in microalgae, including promoters that are endogenous to the microalgae being transformed, as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are described by e.g., Curr Microbiol. 1997 December; 35(6):356-62 (*Chlorella vulgaris*); Mar Biotechnol (NY). 2002 January; 4(1):63-73 (*Chlorella ellipsoidea*); Mol Gen Genet. 1996 Oct. 16; 252(5):572-9 (*Phaeodactylum tricornutum*); Plant Mol. Biol. 1996 April; 31(1):1-12 (*Volvox carteri*); Proc Natl Acad Sci USA. 1994 Nov. 22; 91(24):11562-6 (*Volvox carteri*); Falciatore A, Casotti R, Leblanc C, Abrescia C, Bowler C, PMID: 10383998, 1999 May; 1(3):239-251 (Laboratory of Molecular Plant Biology, Stazione Zoologica, VIIIa Comunale, 1-80121 Naples, Italy) (*Phaeodactylum tricornutum* and *Thalassiosira weissflogii*); Plant Physiol. 2002 May; 129(1):7-12. (*Porphyridium* sp.); Proc Natl Acad Sci USA. 2003 Jan. 21; 100(2):438-42. (*Chlamydomonas reinhardtii*); Proc Natl Acad Sci USA. 1990 February; 87(3):1228-32. (*Chlamydomonas reinhardtii*);

Nucleic Acids Res. 1992 Jun. 25; 20(12):2959-65; Mar Biotechnol (NY). 2002 January; 4(1):63-73 (*Chlorella*); Biochem Mol Biol Int. 1995 August; 36(5):1025-35 (*Chlamydomonas reinhardtii*); J. Microbiol. 2005 August; 43(4): 361-5 (*Dunaliella*); Yi Chuan Xue Bao. 2005 April; 32(4): 424-33 (*Dunaliella*); Mar Biotechnol (NY). 1999 May; 1(3):239-251. (*Thalassiosira* and *Phaedactylum*); Koksharova, Appl Microbiol Biotechnol 2002 February; 58(2): 123-37 (various species); Mol Genet Genomics. 2004 February; 271(1):50-9 (*Thermosynechococcus elongates*); J. Bacteriol. (2000), 182, 211-215; FEMS Microbiol Lett. 2003 Apr. 25; 221(2):155-9; Plant Physiol. 1994 June; 105(2):635-41; Plant Mol. Biol. 1995 December; 29(5):897-907 (Synechococcus PCC 7942); Mar Pollut Bull. 2002; 45(1-12):163-7 (Anabaena PCC 7120); Proc Natl Acad Sci USA. 1984 March; 81(5):1561-5 (*Anabaena* (various strains)); Proc Natl Acad Sci USA. 2001 Mar. 27; 98(7): 4243-8 (*Synechocystis*); Wirth, Mol Gen Genet. 1989 March; 216(1):175-7 (various species); Mol Microbiol, 2002 June; 44(6):1517-31 and Plasmid, 1993 September; 30(2):90-105 (*Fremyella diplosiphon*); Hall et al. (1993) Gene 124: 75-81 (*Chlamydomonas reinhardtii*); Gruber et al. (1991). Current Micro. 22: 15-20; Jarvis et al. (1991) Current Genet. 19: 317-322 (*Chlorella*); for additional promoters see also table 1 from U.S. Pat. No. 6,027,900).

The promoter used to express an exogenous gene can be the promoter naturally linked to that gene or can be a heterologous gene. Some promoters are active in more than one species of microalgae. Other promoters are species-specific. Illustrative promoters include promoters such as RBCS2 from *Chlamydomonas reinhardtii* and viral promoters, such as cauliflower mosaic virus (CMV) and *Chlorella* virus, which have been shown to be active in multiple species of microalgae (see for example Plant Cell Rep. 2005 March; 23(10-11):727-35; J. Microbiol. 2005 August; 43(4): 361-5; Mar Biotechnol (NY). 2002 January; 4(1):63-73). In other embodiments, the *Botryococcus* malate dehydrogenase promoter, or the *Chlamydomonas reinhardtii* RBCS2 promoter can be used. Optionally, at least 10, 20, 30, 40, 50, or 60 nucleotides or more of these sequences containing a promoter are used. In varying embodiments, the promoters used in the expression cassettes are endogenous to species of the genus *Chlorella.*

Promoters useful for expression of exogenous genes in *Chlorella* include the promoter of the *Chlorella* HUP 1 gene and the *Chlorella ellipsoidea* nitrate reductase promoter *Chlorella* virus promoters can also be used to express genes in *Chlorella*, described in U.S. Pat. No. 6,395,965. Additional promoters active in *Chlorella* can be found, for example, in Biochem Biophys Res Commun. 1994 Oct. 14; 204(1):187-94; Plant Mol. Biol. 1994 October; 26(1):85-93; Virology. 2004 Aug. 15; 326(1):150-9; and Virology. 2004 Jan. 5; 318(1):214-23.

C. Selectable Markers

Any of a wide variety of selectable markers can be employed in a transgene construct useful for transforming microalgae. Examples of suitable selectable markers include the sucrose invertase gene, nitrate reductase gene, the hygromycin phosphotransferase gene (HPT), the neomycin phosphotransferase gene, and the ble gene, which confers resistance to phleomycin. Methods of determining sensitivity of microalgae to antibiotics are well known. For example, Mol Gen Genet. 1996 Oct. 16; 252(5):572-9. Examples below illustrate the use of sucrose invertase as a selectable marker in strains of *Prototheca.*

D. Inducible Expression

The present invention also provides for the use of an inducible promoter to express a gene of interest. In particular, the use of an inducible promoter to express a variant acyl-ACP thioesterase gene permits production of the variant acyl-ACP thioesterase after growth of the microorganism when conditions have been adjusted.

Inducible promoters useful include those that mediate transcription of an operably linked gene in response to a stimulus, such as an exogenously provided small molecule (e.g., glucose), temperature (heat or cold), light, etc. Suitable promoters can activate transcription of an essentially silent gene or upregulate, e.g., substantially, transcription of an operably linked gene that is transcribed at a low level. In the latter case, the level of transcription of the acyl-ACP thioesterase does not significantly interfere with the growth of the microorganism in which it is expressed.

E. Expression of Two or More Exogenous Genes

Further, a genetically engineered microorganism, such as a microalgae, may comprise and express two or more exogenous genes, such as, for example, a variant fatty acyl-ACP thioesterase and a gene encoding a lysophosphatidic acid acyltransferase (LPAAT). One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second exogenous gene can be induced for a second period of time (during which expression of a first exogenous gene may or may not be induced). Provided herein are vectors and methods for engineering lipid-producing microbes to metabolize sucrose, which is an advantageous trait because it allows the engineered cells to convert sugar cane feedstocks into lipids.

Examples of further modifications suitable for use in the present invention are include genetically engineering strains of microalgae to express two or more exogenous genes, one encoding a transporter of a fixed carbon source (such as sucrose) and a second encoding a sucrose invertase enzyme. The resulting fermentable organisms produce hydrocarbons at lower manufacturing cost than what has been obtainable by previously known methods of biological hydrocarbon production. Insertion of the two exogenous genes described above can be combined with the disruption of polysaccharide biosynthesis through directed and/or random mutagenesis, which steers ever greater carbon flux into hydrocarbon production. Individually and in combination, trophic conversion, engineering to alter hydrocarbon production and treatment with exogenous enzymes alter the hydrocarbon composition produced by a microorganism. The alteration can be a change in the amount of hydrocarbons produced, the amount of one or more hydrocarbon species produced relative to other hydrocarbons, and/or the types of hydrocarbon species produced in the microorganism. For example, microalgae can be engineered to produce a higher amount and/or percentage of TAGs.

F. Compartmentalized Expression

The present invention also provides for compartmentalized expression of a gene of interest. In some embodiments, it may be desirable to target expression of the acyl-ACP thioesterase to one or more cellular compartments. Illustrative organelles for targeting are lipid bodies, plastids (including chloroplasts), mitochondria, and endoplasmic reticulum.

1. Expression and Targeting to Plastids

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors of the present invention to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecodies* cells and are described in the Examples of U.S. Patent Publ. No. 2012/0283460 and in PCT Application No. PCT/US2009/066142. Amino acid sequences of the algal plastid targeting sequences identified from the cDNA libraries useful plastid targeting of recombinantly expressed variant acyl-ACP thioesterases are provided in U.S. Patent Publ. No. 2012/0283460 and herein. In varying embodiments, the plastid transit peptide comprises an amino acid sequence selected from the group consisting of

```
                                    (SEQ ID NO: 91)
MATASTFSAFNARCGDLRRSAG
SGPRRPARPLPVRGRA,

                                    (SEQ ID NO: 92)
SGPRRPARPLPVR,

                                    (SEQ ID NO: 93)
SGPRRPARPLPVRAAIASEVPVATTSPR,

                                    (SEQ ID NO: 94)
RPARPLPVRGRA,

                                    (SEQ ID NO: 95)
RPARPLPVRAAIASEVPVATTSPR,

                                    (SEQ ID NO: 96)
RCGDLRRSAGSGPRRPARPLPVRGRA,

                                    (SEQ ID NO: 97)
RCGDLRRSAGSGPRRPARPLPVR
AAIASEVPVATTSPR,

                                    (SEQ ID NO: 98)
PARPLPVR,

                                    (SEQ ID NO: 99)
PARPLPVRAAIASEVPVATTSPR,

                                   (SEQ ID NO: 100)
RRPARPLPVR, and

                                   (SEQ ID NO: 101)
RRPARPLPVRAAIASEVPVATTSPR.
```

In one embodiment of the present invention, the expression of a polypeptide in a microorganism is targeted to chloroplasts. Methods for targeting expression of a heterologous gene to the chloroplast are known and can be employed in the present invention. Methods for targeting gene products into chloroplasts are described in Shrier et al., EMBO J. (1985) 4:25 32. See also Tomai et al. Gen. Biol. Chem. (1988) 263:15104 15109 and U.S. Pat. No. 4,940,835 for the use of transit peptides for translocating nuclear gene products into the chloroplast. Methods for directing the transport of proteins to the chloroplast are also reviewed in Kenauf TIBTECH (1987) 5:40 47. Chloroplast targeting sequences endogenous to *Chlorella* are known, such as genes in the *Chlorella* nuclear genome that encode proteins that are targeted to the chloroplast; see for example GenBank Accession numbers AY646197 and AF499684.

Wageningen UR-Plant Research International sells an IMPACTVECTOR1.4 vector, which uses the secretion signal of the *Chrysanthemum morifolium* small subunit protein to deliver a heterologous protein into the chloroplast stroma (cytoplasmic) environment, shuttling across a double membrane system. The protein is fused to the first 11 amino acids of the mature rubisco protein in order to allow proper processing of the signal peptide (Wong et al., Plant Molecular Biology 20: 81-93 (1992)). The signal peptide contains a natural intron from the RbcS gene.

In another approach, the chloroplast genome is genetically engineered to express the heterologous protein. Stable transformation of chloroplasts of *Chlamydomonas reinhardtii* (a green alga) using bombardment of recipient cells with high-velocity tungsten microprojectiles coated with foreign DNA has been described. See, for example, Boynton et al., Science (1988) 240: 1534 1538; Blowers et al. Plant Cell (1989) 1:123 132 and Debuchy et al., EMBO J. (1989) 8: 2803 2809. The transformation technique, using tungsten microprojectiles, is described by Klein et al., Nature (London) (1987) 7:70 73. Other methods of chloroplast transformation for both plants and microalgae are known. See for example U.S. Pat. Nos. 5,693,507; 6,680,426; and Plant Physiol. 2002 May; 129(1):7-12; and Plant Biotechnol J. 2007 May; 5(3):402-12.

As described in U.S. Pat. No. 6,320,101 (issued Nov. 20, 2001 to Kaplan et al.; which is incorporated herein by reference), cells can be chemically treated so as to reduce the number of chloroplasts per cell to about one. Then, the heterologous nucleic acid can be introduced into the cells via particle bombardment with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid sequence that is derived from the chloroplast's genome. In addition, the heterologous nucleic acid typically includes a selectable marker. Further details relating to this technique are found in U.S. Pat. Nos. 4,945,050 and 5,693,507 which are incorporated herein by reference. A polypeptide can thus be produced by the protein expression system of the chloroplast.

U.S. Pat. No. 7,135,620 (issued Nov. 14, 2006 to Daniell et al.; incorporated herein by reference) describes chloroplast expression vectors and related methods. Typical expression cassettes include the following components: the 5' untranslated region from a microorganism gene or chloroplast gene such as psbA which will provide for transcription and translation of a DNA sequence encoding a polypeptide of interest in the chloroplast; a DNA sequence encoding a polypeptide of interest; and a translational and transcriptional termination region, such as a 3' inverted repeat region of a chloroplast gene that can stabilize RNA of introduced genes, thereby enhancing foreign gene expression. The cassette can optionally include an antibiotic resistance gene.

Typically, the expression cassette is flanked by convenient restriction sites for insertion into an appropriate genome. The expression cassette can be flanked by DNA sequences from chloroplast DNA to facilitate stable integration of the expression cassette into the chloroplast genome, particularly by homologous recombination. Alternatively, the expression cassette may remain unintegrated, in which case, the expression cassette typically includes a chloroplast origin of replication, which is capable of providing for replication of the heterologous DNA in the chloroplast.

The expression cassette generally includes a promoter region from a gene capable of expression in the chloroplast. The promoter region may include promoters obtainable from chloroplast genes, such as the psbA gene from spinach or pea, or the rbcL and atpB promoter region from maize and Rma promoters. Examples of promoters are described in Hanley-Bowdoin and Chua, TIBS (1987) 12:67 70; Mullet et al., Plant Molec Biol. (1985) 4: 39 54; Hanley-Bowdoin (1986) PhD. Dissertation, the Rockefeller University; Krebbers et al., Nucleic Acids Res. (1982) 10: 4985 5002; Zurawaki et al., Nucleic Acids Res. (1981) 9:3251 3270; and Zurawski et al., Proc. Nat'l Acad. Sci. U.S.A. (1982) 79: 7699 7703. Other promoters can be identified and the relative strength of promoters so identified evaluated, by placing a promoter of interest 5' to a promoterless marker gene and observing its effectiveness relative to transcription obtained from, for example, the promoter from the psbA gene, a relatively strong chloroplast promoter. The efficiency of heterologus gene expression additionally can be enhanced by any of a variety of techniques. These include the use of multiple promoters inserted in tandem 5' to the heterologous gente, for example a double psbA promoter, the addition of enhancer sequences and the like.

Numerous promoters active in the *Chlorella* chloroplast can be used for expression of exogenous genes in the *Chlorella* chloroplast, such as those found in GenBank accession number NC001865 (*Chlorella vulgaris* chloroplast, complete genome), Where it is desired to provide for inducible expression of the heterologous gene, an inducible promoter and/or a 5' untranslated region containing sequences which provide for regulation at the level of transcription and/or translation (at the 3' end) may be included in the expression cassette. For example, the 5' untranslated region can be from a gene wherein expression is regulatable by light. Similarly, 3' inverted repeat regions could be used to stabilize RNA of heterologous genes. Inducible genes may be identified by enhanced expression in response to a particular stimulus of interest and low or absent expression in the absence of the stimulus. For example, a light-inducible gene can be identified where enhanced expression occurs during irradiation with light, while substantially reduced expression or no expression occurs in low or no light. Light regulated promoters from green microalgae are known (see for example Mol Genet Genomics. 2005 December; 274(6):625-36).

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. See, for example, Chen and Orozco, Nucleic Acids Res. (1988) 16:8411.

The expression cassettes may be transformed into a plant cell of interest by any of a number of methods. These methods include, for example, biolistic methods (See, for example, Sanford, Trends In Biotech. (1988) 6:299 302, U.S. Pat. No. 4,945,050; electroporation (Fromm et al., Proc. Nat'l. Acad. Sci. (USA) (1985) 82:5824 5828); use of a laser beam, microinjection or any other method capable of introducing DNA into a chloroplast.

Additional descriptions of chloroplast expression vectors suitable for use in microorganisms such as microalgae are found in U.S. Pat. No. 7,081,567 (issued Jul. 25, 2006 to Xue et al.); U.S. Pat. No. 6,680,426 (issued Jan. 20, 2004 to Daniell et al.); and U.S. Pat. No. 5,693,507 (issued Dec. 2, 1997 to Daniell et al.).

Proteins expressed in the nuclear genome of *Chlorella* can be targeted to the chloroplast using chloroplast targeting signals. Chloroplast targeting sequences endogenous to *Chlorella* are known, such as genes in the *Chlorella* nuclear genome that encode proteins that are targeted to the chloroplast; see for example GenBank Accession numbers AY646197 and AF499684. Proteins can also be expressed in the *Chlorella* chloroplast by insertion of genes directly into the chloroplast genome. Chloroplast transformation typically occurs through homologous recombination, and can be performed if chloroplast genome sequences are known for creation of targeting vectors (see for example the complete genome sequence of a *Chlorella* chloroplast; Genbank accession number NC001865).

G. Transformation

Cells can be transformed by any suitable technique including, e.g., biolistics, electroporation, glass bead transformation and silicon carbide whisker transformation.

Vectors for transformation of microorganisms in accordance with the present invention can be prepared by known techniques familiar to those skilled in the art. In one embodiment, an exemplary vector design for expression of an acyl-ACP thioesterase gene in a microorganism such as a microalgae contains a gene encoding an acyl-ACP thioesterase in operable linkage with a promoter active in microalgae. Alternatively, if the vector does not contain a promoter in operable linkage with the gene of interest, the gene can be transformed into the cells such that it becomes operably linked to an endogenous promoter at the point of vector integration. The promoterless method of transformation has been proven to work in microalgae (see for example Plant Journal 14:4, (1998), pp. 441-447). The vector can also contain a second gene that encodes a protein that, e.g., imparts resistance to an antibiotic or herbicide, i.e., a selectable marker. Optionally, one or both gene(s) is/are followed by a 3' untranslated sequence containing a polyadenylation signal. Expression cassettes encoding the two genes can be physically linked in the vector or on separate vectors. Co-transformation of microalgae can also be used, in which distinct vector molecules are simultaneously used to transform cells (see for example Protist 2004 December; 155(4): 381-93). The transformed cells can be optionally selected based upon the ability to grow in the presence of the antibiotic or other selectable marker under conditions in which cells lacking the resistance cassette would not grow.

IV. Host Cells—Oil- or Lipid-Producing Microorganisms

Any species of organism that produces suitable lipid and/or hydrocarbon can be used, although microorganisms that naturally produce high levels of suitable lipid and/or hydrocarbon are preferred. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREUTP-580-24190, John Sheehan, Terri Dunahay, John Benemann and Paul Roessler (1998).

Considerations for the selection of microorganisms include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wildtype or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light) or can be engineered to do so using, for example, methods disclosed herein. The ease of transformation and availability of selectable markers and promoters, constitutive or inducible, that are functional in the microorganism affect the ease of genetic engineering. Processing considerations can include, for example, the availability of effective means for lysing the cells.

A. Algae

In one embodiment of the present invention, the microorganism is a microalgae. Nonlimiting examples of microalgae that can be used for expression of variant acyl-ACP thioestesterases include, e.g., *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides* (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* f. *tertia, Chlorella vulgaris* var. *autotrophica, Chlorella vulgaris* var. *viridis, Chlorella vulgaris* var. *vulgaris, Chlorella vulgaris* var. *vulgaris f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., Euglena, *Franceia* sp., *Fragilaria crotonensis, Fragilaria* sp., *Gleocapsa* sp., *Gloeothamnion* sp., *Hymenomonas* sp., *Isochrysis aff. galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, ParaChlorella kessleri, Pascheria acidophila, Pavlova* sp., *Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, PseudoChlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii*, and *Viridiella fridericiana.*

Illustrative host cells feature oleaginous cells that produce altered fatty acid profiles and/or altered regiospecific distribution of fatty acids in glycerolipids, and products produced from the cells. Examples of oleaginous cells include microbial cells having a type II lipid biosynthesis pathway, including plastidic oleaginous cells such as those of oleaginous algae. Specific examples of cells include heterotrophic or obligate heterotophic microalgae of the phylum *Chlorpophya*, the class *Trebouxiophytae*, the order *Chlorellales*, or the family *Chlorellacae*. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. The above mentioned publications also disclose methods for cultivating such cells and extracting oil, especially from microalgal cells; such methods are applicable to the cells disclosed herein. In any of the embodiments described herein, the cells can be heterotrophic cells comprising an exogenous invertase gene so as to allow the cells to produce oil from a sucrose feedstock.

1. *Prototheca*

In one embodiment, the microorganism is of the genus *Prototheca*. Naturally occurring and recombinant *Prototheca* strains find use for the production of lipid.

*Prototheca* is a remarkable microorganism for use in the production of lipid, because it can produce high levels of lipid, particularly lipids suitable for fuel and oleochemical production. The lipid produced by *Prototheca* has hydrocarbon chains of shorter chain length and a higher degree of saturation than that produced by other microalgae. Moreover, *Prototheca* lipid is generally free of pigment (low to undetectable levels of chlorophyll and certain carotenoids) and in any event contains much less pigment than lipid from other microalgae. Moreover, recombinant *Prototheca* cells provided by the invention can be used to produce lipid in greater yield and efficiency, and with reduced cost, relative to the production of lipid from other microorganisms. In addition, this microalgae grows heterotrophically and can be genetically engineered as*Prototheca wickerhamii, Prototheca stagnora* (including UTEX 327), *Prototheca portoricensis, Prototheca moriformis* (including UTEX strains 1441, 1435), and *Prototheca zopfii*. Species of the genus *Prototheca* are obligate heterotrophs.

Species of *Prototheca* for use in the invention can be identified by amplification of certain target regions of the genome. For example, identification of a specific *Prototheca* species or strain can be achieved through amplification and sequencing of nuclear and/or chloroplast DNA using primers and methodology using any region of the genome, for example using the methods described in Wu et al., Bot. Bull. Acad. Sin. (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid profiles and production capability. For examples of methods of identification and classification of algae also see for example Genetics, 2005 August; 170(4):1601-10 and RNA, 2005 April; 11(4):361-4.

Thus, genomic DNA comparison can be used to identify suitable species of microalgae to be used in the present invention. Regions of conserved genomic DNA, such as but not limited to DNA encoding for 23S rRNA, can be amplified from microalgal species and compared to consensus sequences in order to screen for microalgal species that are taxonomically related to the preferred microalgae used in the present invention. Examples of such DNA sequence comparison for species within the *Prototheca* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

Microalgae for use in the present invention typically have genomic DNA sequences encoding for 23S rRNA that have at least 99%, least 95%, at least 90%, or at least 85% nucleotide identity to at least one of the sequences listed in SEQ ID NOs: 62-70.

2. *Chlorella*

In one embodiment, the microorganism is of the genus *Chlorella*, for example, *Chlorella protothecoides, Chlorella ellipsoidea, Chlorella minutissima*, or *Chlorella emersonii.*

*Chlorella* is a genus of single-celled green algae, belonging to the phylum *Chlorophyta*. It is spherical in shape, about 2 to 10 μm in diameter, and is without flagella. Some species of *Chlorella* are naturally heterotrophic.

*Chlorella*, particularly *Chlorella protothecoides*, is one microorganism for use in expressing the variant acyl-ACP thioesterases because of its high composition of lipid, particularly long-chain lipid suitable for biodiesel. In addition, this microalgae grows heterotrophically and can be genetically engineered.

In one embodiment, the microorganism used for expression of a transgene is of the genus *Chlorella*, preferably, *Chlorella protothecoides, Chlorella minutissima*, or *Chlorella emersonii*. Examples of expression of transgenes in, e.g., *Chlorella*, can be found in the literature (see for example Current Microbiology Vol. 35 (1997), pp. 356-362; Sheng Wu Gong Cheng Xue Bao. 2000 July; 16(4):443-6; Current Microbiology Vol. 38 (1999), pp. 335-341; Appl Microbiol Biotechnol (2006) 72: 197-205; Marine Biotechnology 4, 63-73, 2002; Current Genetics 39:5, 365-370 (2001); Plant Cell Reports 18:9, 778-780, (1999); Biologia Plantarium 42(2): 209-216, (1999); Plant Pathol. J 21(1): 13-20, (2005)). Other lipid-producing microalgae can be engineered as well, including prokaryotic Microalgae (see Kalscheuer et al., Applied Microbiology and Biotechnology, Volume 52, Number 4/October, 1999).

3. Identification of *Chlorella* Species

Species of *Chlorella* for use in expressing variant acyl-ACP thioesterases can be identified by amplification of certain target regions of the genome. For example, identification of a specific *Chlorella* species or strain can be achieved through amplification and sequencing of nuclear and/or chloroplast DNA using primers and methodology using any region of the genome, for example using the methods described in Wu et al., Bot. Bull. Acad. Sin. (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 18S rRNA, and other conserved genomic regions can be used by those skilled in the art to identify species of not only *Chlorella*, but other hydrocarbon and lipid producing organisms capable of using the methods disclosed herein. For examples of methods of identification and classification of algae also see for example Genetics, 2005 August; 170(4):1601-10 and RNA, 2005 April; 11(4):361-4.

Illustrative embodiments of host cells include recombinant oleaginous cells expressing one or more exogenous genes encoding fatty acid biosynthesis enzymes. As a result, some embodiments feature natural oils never before obtainable in a natural oil. In some cases, the natural oils were not obtainable from a non-plant or non-seed oil, or not obtainable at all.

The oleaginous cells produce a storage oil, which may be stored in storage vesicles of the cell. A raw oil may be obtained from the cells by disrupting the cells and isolating the oil. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride cell oil is given, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). Because the cells are oleaginous, in some cases the storage oil will constitute the bulk of all the TAGs in the cell.

In varying embodiments, the host cell is a plastidic cell, e.g., a heterotrophic microalgae of the phylum *Chlorpophya*, the class *Trebouxiophytae*, the order *Chlorellales*, or the family *Chlorellacae*. In varying embodiments, the cell is oleaginous and capable of accumulating at least 40% oil by dry cell weight. The cell can be an obligate heterotroph, such as a species of *Prototheca*, including *Prototheca moriformis* or *Prototheca zopfii*. The nucleic acid encoding the variant acyl-ACP TEs described herein can also be expressed in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase may be codon optimized and integrated into a chromosome of the cell, as may all of the genes mentioned here. Codon usage for different algal and plant species of interest is known in the art and can be found, e.g., on the internet at the Codon Usage Database at kazusa.or.jp/codon/.

The polynucleotides encoding the variant acyl-ACP TEs described herein further can be expressed in a wide variety of plant host cells. Of particular interest are plant cells of plants involved in the production of vegetable oils for edible and industrial uses, including e.g., temperate oilseed crops. Plants of interest include, but are not limited to, grapeseed (Canola and High Erucic Acid varieties), sunflower, safflower, cotton, *Cuphea*, soybean, peanut, coconut and oil palms, and corn.

V. Methods of Culturing Microorganisms

Microorganisms are cultured both for purposes of conducting genetic manipulations and for subsequent production of hydrocarbons (e.g., lipids, fatty acids, aldehydes, alcohols, and alkanes). The former type of culture is conducted on a small scale and initially, at least, under conditions in which the starting microorganism can grow. For example, if the starting microorganism is a photoautotroph the initial culture is conducted in the presence of light. The culture conditions can be changed if the microorganism is evolved or engineered to grow independently of light. Culture for purposes of hydrocarbon production is usually conducted on a large scale. Preferably a fixed carbon source is present. The culture can also be exposed to light some or all of the time.

Microalgae can be cultured in liquid media. The culture can be contained within a bioreactor. Optionally, the bioreactor does not allow light to enter. Alternatively, microalgae can also be cultured in photobioreactors that contain a fixed carbon source and allow light to strike the cells. Exposure of microalgae cells to light, even in the presence of a fixed carbon source that the cells transport and utilize (i.e., mixotrophic growth), nonetheless accelerates growth compared to culturing cells in the dark. Culture condition parameters can be manipulated to optimize total hydrocarbon production, the combination of hydrocarbon species produced, and/or production of a hydrocarbon species. In some instances it is preferable to culture cells in the dark, such as, for example, when using extremely large (e.g., 10,000 L, 40,000 L, 100,000 L 500,000 L, or larger, bioreactors) fermentors that do not allow light to strike the culture.

Microalgal culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_26H_2O$, $CuCl_2H_2O$, $MnCl_24H_2O$ and $(NH_4)_6MO_7O_{24}.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Some microalgae species can grow by utilizing a fixed carbon source such as glucose or acetate in the absence of light. Such growth is known as heterotrophic growth. For *Chlorella* and/or *Prototheca*, for example, heterotrophic growth results in high production of biomass and accumulation of high lipid content in cells.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of hydrocarbons, and the culture provides an inexpensive source of hydrocarbons.

Other culture parameters can also be manipulated, such as the pH of the culture media, the identity and concentration of trace elements and other media constituents.

A. Photosynthetic Growth

Certain microalgae can be grown in the presence of light. The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, certain species microalgae of the genus *Chlorella* and/or *Prototheca* can be cultured under natural light during daylight hours and under artificial light during night hours.

The gas content of a photobioreactor to grow microorganisms like microalgae can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and others. The rate of entry of gas into a photobioreactor can also be manipulated. Increasing gas flow into a photobioreactor increases the turbidity of a culture of microalgae. Placement of ports conveying gases into a photobioreactor can also affect the turbidity of a culture at a given gas flow rate. Air/$CO_2$ mixtures can be modulated to generate optimal amounts of $CO_2$ for maximal growth by a particular organism. Microalgae grow significantly faster in the light under, for example, 3% $CO_2$/97% air than in 100% air. 3% $CO_2$/97% air is approximately 100-fold more $CO_2$ than found in air. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a bioreactor or photobioreactor.

Microalgae cultures can also be subjected to mixing using devices such as spinning blades and impellers, rocking of a culture, stir bars, infusion of pressurized gas, and other instruments.

Photobioreactors can have ports allowing entry of gases, solids, semisolids and liquids into the chamber containing the microalgae. Ports are usually attached to tubing or other means of conveying substances. Gas ports, for example, convey gases into the culture. Pumping gases into a photobioreactor can serve to both feed cells $CO_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $CO_2$ is added to air and bubbled into a photobioreactor. For example, a 5% $CO_2$:95% air mixture is infused into a photobioreactor containing *Botryococcus* cells (see for example J Agric Food Chem. 2006 Jun. 28; 54(13):4593-9; J Biosci Bioeng. 1999; 87(6):811-5; and J Nat. Prod. 2003 June; 66(6):772-8).

Photobioreactors can be exposed to one or more light sources to provide microalgae with light as an energy source via light directed to a surface of the photobioreactor. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range is used. Photobioreactors can be placed outdoors or in a greenhouse or other facility that allows sunlight to strike the surface. Preferred photon intensities for species of the genus *Botryococcus* are between 25 and 500 $\mu E\ m^{-2}\ s^{-1}$ (see for example Photosynth Res. 2005 June; 84(1-3):21-7).

Photobioreactors preferably have one or more ports that allow media entry. It is not necessary that only one substance enter or leave a port. For example, a port can be used to flow culture media into the photobioreactor and then later can be used for sampling, gas entry, gas exit, or other purposes. In some instances a photobioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the photobioreactor throughout the time period. Thus in some embodiments, aqueous culture medium is not flowed through the photobioreactor after inoculation.

In other instances culture media can be flowed through the photobioreactor throughout the time period during which the microalgae reproduce and increase in number. In some embodiments media is infused into the photobioreactor after inoculation but before the cells reach a desired density. In other words, a turbulent flow regime of gas entry and media entry is not maintained for reproduction of microalgae until a desired increase in number of said microalgae has been achieved.

Photobioreactors preferably have one or more ports that allow gas entry. Gas can serve to both provide nutrients such as $CO_2$ as well as to provide turbulence in the culture media. Turbulence can be achieved by placing a gas entry port below the level of the aqueous culture media so that gas entering the photobioreactor bubbles to the surface of the culture. One or more gas exit ports allow gas to escape, thereby preventing pressure buildup in the photobioreactor. Preferably a gas exit port leads to a "one-way" valve that prevents contaminating microorganisms from entering the photobioreactor. In some instances cells are cultured in a photobioreactor for a period of time during which the microalgae reproduce and increase in number, however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the photobioreactor and the scale of eddies is not maintained for the period of time during which the microalgae reproduce and increase in number. In other instances such a range can be maintained.

Photobioreactors preferably have at least one port that can be used for sampling the culture. Preferably a sampling port can be used repeatedly without altering compromising the axenic nature of the culture. A sampling port can be configured with a valve or other device that allows the flow of sample to be stopped and started. Alternatively a sampling port can allow continuous sampling. Photobioreactors preferably have at least one port that allows inoculation of a culture. Such a port can also be used for other purposes such as media or gas entry.

B. Heterotrophic Growth

As an alternative to photosynthetic growth of microorganisms, as described above, some microorganisms can be cultured under heterotrophic growth conditions in which a fixed carbon source provides energy for growth and lipid accumulation.

In one heterotrophic culture method in accordance with the invention, the cost of biodiesel production, crude, partially purified, or purified glycerol produced as a byproduct of lipid transesterification can be employed as a feedstock for fermenting, for example, lipid-producing microbial cultures. Thus, the invention encompasses culturing a microbe (e.g., a microalgae) in a first microbial culture; recovering microbial lipid from the culture; subjecting the microbial lipid to transesterification to produce fatty acid ester(s) and glycerol, as described above; and adding the glycerol to a second microbial culture as a feedstock. The first and second microbial cultures can, but need not, be cultures of the same microbe. If desired, a continuous system can be devised whereby glycerol produced from the lipid recovered from a culture can be fed back into the same culture.

The invention provides significantly improved culture parameters incorporating the use of glycerol for fermentation of multiple genera of both eukaryotic and prokaryotic microbes, including microbes of the genera *Prototheca, Chlorella, Navicula, Scenedesmus*, and *Spirulina*. As the Examples demonstrate, microbes of extremely divergent evolutionary lineages, including *Prototheca, Chlorella, Navicula, Scenedesmus*, and *Spirulina* as well as cultures of multiple distinct *Prototheca* and/or *Chlorella* species and strains grow very well on not only purified reagent-grade glycerol, but also on acidulated and non-acidulated glycerol byproduct from biodiesel transesterification. In some instances microalgae, such as *Chlorella* and/or *Prototheca* strains, undergo cell division faster in the presence of glycerol than in the presence of glucose. In these instances, two-stage growth processes in which cells are first fed glycerol to rapidly increase cell density, and are then fed glucose to accumulate lipids can improve the efficiency with which lipids are produced. The use of the glycerol byproduct of the transesterification process provides significant economic advantages when put back into the production process. Other feeding methods are provided as well, such as mixtures of glycerol and glucose. Feeding such mixtures also captures the same economic benefits. In addition, the invention provides methods of feeding alternative sugars to microalgae such as sucrose in various combinations with glycerol. These benefits provided by the invention have been demonstrated herein on microbes from extremely divergent evolutionary lineages, including both prokaryotes and eukaryotes, demonstrating the utility of the invention for microbial fermentation.

Standard methods for the growth and propagation of *Chlorella* and/or *Prototheca* are known (see for example Miao and Wu, J. Biotechnology, 2004, 11:85-93 and Miao and Wu, Biosource Technology (2006) 97:841-846). In addition, multiple species of *Chlorella* and/or *Prototheca* and multiple strains within a species can be grown in the presence of glycerol, including glycerol byproduct from biodiesel transesterification.

For hydrocarbon production, cells, including recombinant cells described herein, are preferably cultured or fermented in large quantities. The culturing may be in large liquid volumes, such as in suspension cultures as an example. Other examples include starting with a small culture of cells which expand into a large biomass in combination with cell growth and propagation as well as hydrocarbon production. Bioreactors or steel fermentors can be used to accommodate large culture volumes. A fermentor similar those used in the production of beer and/or wine is suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other starch (polymerized glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of hydrocarbon-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Hydrocarbon production by cells disclosed herein can occur during the log phase or thereafter, including the stationary phase wherein nutrients are supplied, or still available, to allow the continuation of hydrocarbon production in the absence of cell division.

In varying embodiments, microorganisms grown using conditions described herein and comprise at least about 20% by weight of lipid, preferably at least about 40% by weight, at least about 50% by weight, and more preferably at least about 60% by weight, even more preferably at least about 70%, 75%, 80% or 85% by weight.

Multiple species, and multiple strains within a species of *Chlorella* and/or *Prototheca* perform better in the presence of glycerol byproduct from transesterification than in an equivalent amount of reagent grade glycerol. Glycerol byproduct from transesterification usually contains residual methanol and other contaminants in addition to glycerol. For example, strains of *Chlorella* and/or *Prototheca* species can exhibit better productivity on acidulated and non-acidulated glycerol byproduct from lipid transesterification reactions than when grown on pure reagent grade glycerol. Other microbes, such as *Scenedesmus* and *Navicula* microalgae can also perform better in the presence of glycerol byproduct from transesterification than in an equivalent amount of reagent grade glycerol. In varying embodiments, dry cell weight is higher on biodiesel glycerol byproduct than on pure glycerol. For example, dry cell weight per liter of *Scenedesmus armatus* and *Navicula pelliculosa* is higher on acidulated and non-acidulated biodiesel byproducts glycerol than on pure reagent grade glycerol. Furthermore, for multiple species of *Chlorella* and/or *Prototheca* and multiple strains within a species of *Chlorella* and/or *Prototheca*, lipid levels per liter are higher when the cells are cultured in the presence of biodiesel glycerol byproduct than when cultured in the presence of equivalent concentrations of pure reagent grade glycerol. Multiple species of *Chlorella* and/or *Prototheca* and multiple strains within a species of *Chlorella* and/or *Prototheca*, as well as *Spirulina platensis, Navicula pelliculosa* and *Scenedesmus armatus* accumulate a higher percentage of dry cell weight as lipid when cultured in the presence of biodiesel glycerol byproduct than when cultured in the presence of equivalent concentrations of pure reagent grade glycerol.

Another surprising result is that multiple species of microbes, including microalgae such as *Chlorella* and/or *Prototheca* and multiple strains within a species of *Chlorella* and/or *Prototheca*, and other microalgae such as *Scenedesmus, Navicula*, and *Spirulina* exhibit better characteristics as biodiesel producers in the presence of mixtures of glycerol and glucose than in the presence of only glucose.

Three different markers of productivity (dry cell weight per liter, grams per liter of lipid, and percentage of dry cell weight as lipid) in microbial lipid production are improved by the use of biodiesel byproduct and temporal separation of carbon sources. The invention therefore provides novel methods of generating higher quantities of lipid per unit time in multiple species of microbes from highly divergent areas of the evolutionary tree, including both prokaryotes and eukaryotes. The methods of manufacturing lipids and hydrocarbons disclosed herein using glycerol are not limited to microalgae, but can be used with any microbe capable of utilizing glycerol as an energy source.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock has been found to be inhibitory to yeast growth, and yeast cannot use the 5-carbon sugars produced from cellulosic materials (e.g., xylose from hemicellulose). By contrast, microalgae can grow on processed cellulosic material. Accordingly, the invention provides a method of culturing a microalgae in the presence of a cellulosic material and/or a 5-carbon sugar. Cellulosic materials generally include as component percent dry weight 40-60% cellulose, 20-40% hemicellulose, and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste.

Additional cellulosics include dedicated cellulosic crops such as switchgrass, hybrid poplar wood, and miscanthus, fiber cane, and fiber sorghum. Five-carbon sugars that are produced from such materials include xylose.

Some species of *Chlorella* and/or *Prototheca* have been shown herein to exhibit higher levels of productivity when cultured on a combination of glucose and xylose than when cultured on either glucose or xylose alone. This synergistic effect provides a significant advantage in that it allows cultivation of *Chlorella* and/or *Prototheca* on combinations of xylose and glucose, such as cellulosic material.

In still another alternative heterotrophic growth method, which itself may optionally be used in combination with the methods described above, sucrose, produced by example from sugar cane or sugar beet, is used as a feedstock. As described in greater detail in the section entitled "Microbe Engineering" below, lipid production can be facilitated or made more efficient through the engineering of microbes such as *Chlorella* and/or *Prototheca*, to utilize sucrose as a carbon source. For example, expression of a sucrose transporter and a sucrose invertase allows *Chlorella* and/or *Prototheca* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are Genbank accession numbers CAD91334, CAB92307, and CAA53390. Examples of suitable sucrose invertases are Genbank accession numbers CAB95010, NP012104 and CAA06839. Examples of suitable fructokinases are Genbank accession numbers P26984, P26420 and CAA43322. Vectors for transformation of microalgae, including *Chlorella* and/or *Prototheca*, encoding one or more of such genes can be designed as described herein.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. For example, expression of a sucrose invertase with a secretion signal generates invertase activity outside the cell. See Hawkins et al., Current Microbiology Vol. 38 (1999), pp. 335-341 for examples of secretion signals active in *Chlorella* and/or *Prototheca*. Expression of such a protein, as enabled by the genetic engineering methodology disclosed herein, allows cells already capable of utilizing extracellular glucose as an energy source to utilize sucrose as an extracellular energy source. *Chlorella* and/or *Prototheca* cells can use both extracellular fructose and extracellular glucose as an energy source, secretion of an invertase can provide the sole catalytic activity necessary for use of sucrose as an efficient, inexpensive energy source.

For example, *Chlorella* and/or *Prototheca* cells can be engineered with a sucrose invertase gene under the regulatory control of one of three promoters (Cauliflower mosaic virus 35S promoter (CMV), *Chlorella* virus promoter (CV), or *Chlorella* HUP1 promoter (HUP 1)). The sucrose invertase gene used in this example comprises a modification to the *S. cerevisiae* SUC2 gene to optimize for *C. protothecoides* codon usage. Expression of a secretable sucrose invertase, such as that described herein, permits the use of molasses, sugar cane juice, and other sucrose-containing feedstocks for cell fermentation.

The growth potential of microorganisms expressing an exogenous secretable sucrose invertase is illustrated by the addition of an invertase to the culture medium of *Chlorella* and/or *Prototheca*. *Chlorella* and/or *Prototheca* cells can grow as well on waste molasses from sugar cane processing as they do on pure reagent-grade glucose; the use of this low-value waste product of sugar cane processing can provide significant cost savings in the production of hydrocarbons and other oils. Molasses contains lignin and other cellulosic waste products that poison many microorganisms and retard their growth, however it was discovered that *Chlorella* and/or *Prototheca* cells thrive in the presence of such poisons.

Alternatively, a sucrose invertase can also be expressed intracellularly in cells that express a sucrose transporter, as well as in cells that express any carbohydrate transporter that allows sucrose to enter the cell.

Bioreactors can be employed for use in heterotrophic growth methods. As will be appreciated, provisions made to make light available to the cells in photosynthetic growth methods are unnecessary when using a fixed-carbon source in the heterotrophic growth methods described herein.

The specific examples of process conditions and heterotrophic growth methods described herein can be combined in any suitable manner to improve efficiencies of microbial growth and/or lipid production. In addition, the invention includes the selection and/or genetic engineering of microbes, such as microalgae, to produce microbes that are even more suitable for use in the above-described methods. For example, the microbes having a greater ability to utilize any of the above-described feedstocks for increased proliferation and/or lipid (e.g., fatty acid) production are within the scope of the invention.

C. Mixotrophic Growth

Mixotrophic growth is the use of both light and fixed carbon source(s) as energy sources for cells to grow and produce hydrocarbons. Mixotrophic growth can be conducted in a photobioreactor. Microalgae can be grown and maintained in closed photobioreactors made of different types of transparent or semitransparent material. Such material can include Plexiglas™ enclosures, glass enclosures, bags made from substances such as polyethylene, transparent or semitransparent pipes, and other materials. Microalgae can be grown and maintained in open photobioreactors such as raceway ponds, settling ponds, and other non-enclosed containers.

D. Growth Media

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at utex.org/, a site maintained by the University of Texas at Austin for its culture collection of algae (UTEX). For example, various fresh water and salt water media are provided in U.S. Patent Publ. No. 2012/0288930, hereby incorporated herein by reference in its entirety for all purposes.

In a particular example, a medium suitable for culturing *Chlorella* and/or *Prototheca* cells comprises Proteose Medium. This medium is suitable for axenic cultures, and a 1 L volume of the medium (pH .about.6.8) can be prepared by addition of 1 g of proteose peptone to 1 liter of Bristol Medium. Bristol medium comprises 2.94 mM $NaNO_3$, 0.17 mM $CaCl_22H_2O$, 0.3 mM $MgSO_47H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use.

Other suitable media for use with the methods described herein can be readily identified by consulting the URL identified above, or by consulting other organizations that maintain cultures of microorganisms, such as SAG, CCAP, or CCALA. SAG refers to the Culture Collection of Algae at the University of Gottingen (Gottingen, Germany), CCAP refers to the culture collection of algae and protozoa managed by the Scottish Association for Marine Science (Scotland, United Kingdom), and CCALA refers to the culture collection of algal laboratory at the Institute of Botany (T {hacek over (r)}ebo{hacek over (n)}, Czech Republic).

E. Increasing Yield of Lipids

Process conditions can be adjusted to increase the yield of lipids suitable for a particular use and/or to reduce production cost. For example, in certain embodiments, an oleaginous cell (e.g., a plant, an algae, a microalgae) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 20%, 30%, 40%, 50%, 75%, 100%, 200%, 300%, 400%, or 500%. The oleaginous cells (e.g., plant cells, algae cells, microalgae cells) can be cultured in the presence of a limiting amount of a nutrient for a portion of the total culture period or for the entire period. In particular embodiments, the nutrient concentration is cycled between a limiting concentration and a non-limiting concentration at least twice during the total culture period.

To increase lipid yield, acetic acid can be employed in the feedstock for a lipid-producing oleaginous cells or organism (e.g., plants, algae, microalgae). Acetic acid feeds directly into the point of metabolism that initiates fatty acid synthesis (i.e., acetyl-CoA); thus providing acetic acid in the culture can increase fatty acid production. Generally, the oleaginous cells or organism is cultured in the presence of a sufficient amount of acetic acid to increase microbial lipid yield, and/or microbial fatty acid yield, specifically, over microbial lipid (e.g., fatty acid) yield in the absence of acetic acid.

In another embodiment, lipid yield is increased by culturing a lipid-producing oleaginous cells or organism (e.g., plants, algae, microalgae) in the presence of one or more cofactor(s) for a lipid pathway enzyme (e.g., a fatty acid synthetic enzyme). Generally, the concentration of the cofactor(s) is sufficient to increase microbial lipid (e.g., fatty acid) yield over microbial lipid yield in the absence of the cofactor(s). In a particular embodiment, the cofactor(s) are provided to the culture by including in the culture oleaginous cells (e.g., plant cells, algae cells, microalgae cells) containing an exogenous gene encoding the cofactor(s). Alternatively, cofactor(s) may be provided to a culture by including an oleaginous cell (e.g., a plant, an algae, a microalgae) containing an exogenous gene that encodes a protein that participates in the synthesis of the cofactor. In certain embodiments, suitable cofactors include any vitamin required by a lipid pathway enzyme, such as, for example: biotin, pantothenate. Genes encoding cofactors suitable for use in the invention or that participate in the synthesis of such cofactors are well known and can be introduced into oleaginous cells (e.g., plant cells, algae cells, microalgae cells), using constructs and techniques such as those described above and herein.

In varying embodiments, the cells can be fully auxotrophic or partially auxotrophic (i.e., synthetic sickness or lethality) with respect to one or more types of fatty acid. The cells are cultured with supplementation of the fatty acid(s) so as to increase the cell number, then allowing the cells to accumulate oil (e.g., to at least 40% by dry cell weight). Alternatively, the cells comprise a regulatable fatty acid synthesis gene that can be switched in activity based on environmental conditions and the environmental conditions during a first, cell division, phase favor production of the fatty acid and the environmental conditions during a second, oil accumulation, phase disfavor production of the fatty acid.

As a result of applying either of these supplementation or regulation methods, a cell oil may be obtained from the cell that has low amounts of one or more fatty acids essential for optimal cell propagation. Specific examples of oils that can be obtained include those low in stearic, linoleic and/or linolenic acids. Optionally, the cells are oleaginous plastidic microbes such as those of the division *Chlorphyta.*

Accordingly, in some embodiments, provided are methods for producing an oil or fat. The method comprises cultivating a recombinant oleaginous cell in a growth phase under a first set of conditions that is permissive to cell division so as to increase the number of cells due to the presence of a fatty acid, cultivating the cell in an oil production phase under a second set of conditions that is restrictive to cell division but permissive to production of an oil that is depleted in the fatty acid, and extracting the oil from the cell, wherein the cell has a mutation or exogenous nucleic acids operable to suppress the activity of a fatty acid synthesis enzyme, the enzyme optionally being a stearoyl-ACP desaturase, delta 12 fatty acid desaturase, or a ketoacyl-ACP synthase. The fatty acid can be depleted in the oil by at least than 50, 60, 70, 80, or 90. The cell can be cultivated heterotrophically.

In varying embodiments, the cell can be a microalgal cell and may produce at least 40, 50, 60, 70, 80, or 90% oil by dry cell weight.

VI. Methods of Recovering Lipids and Hydrocarbons

Hydrocarbons (e.g., lipids, fatty acids, aldehydes, alcohols, and alkanes) produced by cells described herein can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate in after centrifugation. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins. Proteases can be added to hydrocarbon preparations containing proteins to degrade proteins (for example, the protease from *Streptomyces griseus* can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

Extracellular hydrocarbons can also be extracted in vivo from living microalgae cells which are then returned to a bioreactor by exposure of the cells, in an otherwise sterile environment, to a non-toxic extraction solvent, followed by separation of the living cells and the hydrophobic fraction of extraction solvent and hydrocarbons, wherein the separated living cells are then returned to a culture container such as a stainless steel fermentor or photobioreactor (see Biotechnol Bioeng. 2004 Dec. 5; 88(5):593-600 and Biotechnol Bioeng. 2004 Mar. 5; 85(5):475-81).

Hydrocarbons can also be isolated by whole cell extraction. The cells are first disrupted, as described in the section entitled "Lysing Cells", and then intracellular and cell membrane/cell wall-associated hydrocarbons as well as extracellular hydrocarbons can be collected from the whole cell mass, such as by use of centrifugation as described above.

Various methods are available for separating hydrocarbons and lipids from cellular lysates produced by the above methods. For example, hydrocarbons can be extracted with a hydrophobic solvent such as hexane (see Frenz et al. 1989, Enzyme Microb. Technol., 11:717). Hydrocarbons can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334).

A. Lysing Cells

Intracellular lipids and hydrocarbons produced in microorganisms are, in some embodiments, extracted after lysing the cells of the microorganism. Once extracted, the lipids or hydrocarbons can be further refined to produce oils, fuels, or oleochemicals.

After completion of culturing, the microorganisms can be separated from the fermentation broth. Optionally, the separation is effected by centrifugation to generate a concentrated paste. Centrifugation does not remove significant amounts of intracellular water from the microorganisms and is not a drying step. The biomass can then be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid and/or hydrocarbon can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially.

The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of cellular lipid and/or hydrocarbon for extraction or further processing. The timing of acyl-ACP thioesterase expression (e.g., via an inducible promoter) or cell lysis can be adjusted to optimize the yield of lipids and/or hydrocarbons. Below are described a number of lysis techniques. These techniques can be used individually or in combination.

1. Heat-Induced Lysis

In some embodiments, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50° C. Higher temperatures, such as, at least 30° C., at least 60° C., at least 70° C., at least 80° C., at least 90° C., at least 100° C., at least 110° C., at least 120° C., at least 130° C. or higher are used for more efficient cell lysis.

Lysing cells by heat treatment can be performed by boiling the microorganism. Alternatively, heat treatment (without boiling) can be performed in an autoclave. The heat treated lysate may be cooled for further treatment.

Cell disruption can also be performed by steam treatment, i.e., through addition of pressurized steam. Steam treatment of microalgae for cell disruption is described, for example, in U.S. Pat. No. 6,750,048.

2. Lysis Using a Base

In some embodiments, the step of lysing a microorganism comprises adding a base to a cellular suspension containing the microorganism.

The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

3. Acidic Lysis

In some embodiments, the step of lysing a microorganism comprises adding an acid to a cellular suspension containing the microorganism. Acid lysis can be effected using an acid at a concentration of 10-500 nM or preferably 40-160 nM. Acid lysis is preferably performed at above room temperature (e.g., at 40-160° C., and preferably a temperature of 50-130° C. For moderate temperatures (e.g., room temperature to 100° C. and particularly room temperature to 65° C., acid treatment can usefully be combined with sonication or other cell disruption methods.

4. Lysing Cells Using Enzymes

In some embodiments, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.;

#C9422), and driselase (e.g., driselase from *Basidiomycetes* sp.; Sigma Aldrich, St. Louis, Mo.; #D9515.

a) Cellulases

In an embodiment of the present invention, a cellulase for lysing a microorganism is a polysaccharide-degrading enzyme, optionally from *Chlorella* and/or *Prototheca* or a *Chlorella* and/or *Prototheca* virus.

b) Proteases

Proteases such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), and other proteases can be used to lyse microorganisms. Other proteases that can be used include Alcalase 2.4 FG (Novozymes) and Flavourzyme 100 L (Novozymes).

c) Combinations

Any combination of a protease and a polysaccharide-degrading enzyme can also be used, including any combination of the preceding proteases and polysaccharide-degrading enzymes.

5. Lysing Cells Using Ultrasound

In another embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

6. Mechanical Lysis

In another embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

B. Extraction of Lipids and Hydrocarbons

Lipids and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid and/or hydrocarbon components. Hexane extraction methods are well known in the art.

Various methods are available for separating lipids from cellular lysates produced by the above methods. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334). Miao and Wu describe a protocol of the recovery of microalgal lipid from a culture of *Chlorella* prototheocoides in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Thus, lipids, lipid derivatives and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid and/or hydrocarbon components. Hexane extraction methods are well known in the art.

Lipids and lipid derivatives such as fatty aldehydes, fatty alcohols, and hydrocarbons such as alkanes produced by cells as described herein can be modified by the use of one or more enzymes, including a lipase, as described above. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

Thus, lipids and hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

VII. Oils with Non-Naturally Occurring Fatty Acid Profiles

Oils disclosed herein are distinct from other naturally occurring oils that are high in mid-chain fatty acids, such as palm oil, palm kernel oil, and coconut oil. For example, levels of contaminants such as carotenoids are far higher in palm oil and palm kernel oil than in the oils described herein. Palm and palm kernel oils in particular contain alpha and beta carotenes and lycopene in much higher amounts than is in the oils described herein. In addition, over 20 different carotenoids are found in palm and palm kernel oil, whereas the Examples demonstrate that the oils described herein contain very few carotenoids species and very low levels. In addition, the levels of vitamin E compounds such as tocotrienols are far higher in palm, palm kernel, and coconut oil than in the oils described herein.

Generally, *Prototheca* strains have very little or no fatty acids with the chain length C8-C14. For example, *Prototheca* strains *Prototheca moriformis* (UTEX 1435), *Prototheca krugani* (UTEX 329), *Prototheca stagnora* (UTEX 1442) and *Prototheca zopfii* (UTEX 1438) produce no (or undetectable amounts) C8 fatty acids, between 0-0.01% C10 fatty acids, between 0.03-2.1% C12 fatty acids and between 1.0-1.7% C14 fatty acids.

In some cases, the oleaginous cells (e.g, *Prototheca* strains) containing a transgene encoding a variant fatty acyl-ACP thioesterase has a fatty acid profile characterized by 5-10, 10-20, 20-30, 30-40, 40-50, 50-60, 60-70, 70-80, 80-90, or 90-99% C8, C10, C12, or C14 fatty acids. In other cases, the *Prototheca* strains containing a transgene encoding a fatty acyl-ACP thioesterase that has activity towards fatty acyl-ACP substrates of chain length C12 and C14 and produces fatty acids of the chain length C12 and the chain length C14 at a ratio of 1:1+/−20%.

In some instances, keeping the transgenic *Prototheca* strains under constant and high selective pressure to retain exogenous genes is advantageous due to the increase in the desired fatty acid of a specific chain length. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are also contemplated.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds.

In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

Oils produced from host cells expressing a variant acyl-ACP thioesterase will have an isotopic profile that distinguishes it, e.g., from blended oils from other sources. The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments the oils are derived from oleaginous organisms heterotrophically grown on sugar derived from a C4 plant such as corn or sugarcane. In some embodiments, the δ13C (0/00) of the oil is from 10 to −17 0/00 or from 13 to −16 0/00.

In varying embodiments, a host cell expressing a variant acyl-ACP thioesterase comprising all or specificity-determining residues of a specificity domain from a C10-preferring acyl-ACP thioesterase (e.g., an acyl-ACP thioesterase from *Cuphea hookeriana*), and a catalytic domain from a C12-preferring acyl-ACP thioesterase (e.g., an acyl-ACP thioesterase from *Cuphea wrightii* or *Umbellularia californica*) produces an oil comprising at least about 10% C12:0 fatty acids, and at least about 10% C14:0 fatty acids.

In varying embodiments, a host cell expressing a variant acyl-ACP thioesterase comprising all or specificity-determining residues of a modified specificity domain of a first acyl-ACP thioesterase having one or both His163→Tyr or Leu186→Pro substitutions (or at positions corresponding to His163→Tyr or Leu186→Pro of SEQ ID NO:61), and a catalytic domain of a second acyl-ACP thioesterase produces an oil comprising at least about 5%, e.g., at least about 6%, 7%, 8%, 9%, 10%, 12%, 15%, or more, C8:0 fatty acids or at least about 5%, e.g., at least about 6%, 7%, 8%, 9%, 10%, 12%, 15%, or more, C10:0 fatty acids or a C8:0/C10:0 ratio that is at least about 5%, e.g., at least about 6%, 7%, 8%, 9%, 10%, 12%, 15%, or more. As appropriate, the specificity domain can be derived from a C8:0-, C10:0- or a C12:0- preferring acyl-ACP thioesterase and independently the catalytic domain can be derived from a C8:0-, C10:0- or a C12:0-preferring acyl-ACP thioesterase. The specificity domain and the catalytic domain can be from the same or different acyl-ACP thioesterases. In varying embodiments, a host cell expressing a variant acyl-ACP thioesterase comprising all or specificity-determining residues of a modified specificity domain from a C10-preferring acyl-ACP thioesterase (e.g., an acyl-ACP thioesterase from *Cuphea hookeriana* having one or both His163→Tyr or Leu186→Pro substitutions), and a catalytic domain from a C10-preferring acyl-ACP thioesterase (e.g., an acyl-ACP thioesterase from *Cuphea hookeriana*) produces an oil comprising at least about 5%, e.g., at least about 6%, 7%, 8%, 9%, 10%, 12%, 15%, or more, C8:0 fatty acids or at least about 5%, e.g., at least about 6%, 7%, 8%, 9%, 10%, 12%, 15%, or more, C10:0 fatty acids or a C8:0/C10:0 ratio that is at least about 5%, e.g., at least about 6%, 7%, 8%, 9%, 10%, 12%, 15%, or more.

In varying embodiments, a host cell expressing a variant acyl-ACP thioesterase comprising all or specificity-determining residues of a specificity domain from a C14-preferring acyl-ACP thioesterase (e.g., an acyl-ACP thioesterase from *Cinnamomum camphorum*), and a catalytic domain from a C12-preferring acyl-ACP thioesterase (e.g., an acyl-ACP thioesterase from *Cuphea wrightii* or *Umbellularia californica*) produces an oil comprising C12:0 fatty acids and C14:0 fatty acid at an approximate 1:1 ratio; e.g, a ratio of 1:1+/−20%.

Further, host cells expressing a variant acyl-ACP thioesterase comprising or more amino acid residues extending from the C-terminus of a linker domain positioned N-terminal to the hydrophobic domain, produce an oil comprising relatively elevated mid-chain length fatty acids (e.g., C8:0, C10:0, C12:0, C14:0) in comparison to host cells expressing the same acyl-ACP thioesterase without a linker domain. In varying embodiments, host cells expressing a variant acyl-ACP thioesterase comprising 5 or more amino acid residues extending from the C-terminus of a linker domain positioned N-terminal to the hydrophobic domain, produce an oil comprising mid-chain length fatty acids increased by at least 1-fold, 2-fold, 3-fold, or more, in comparison to host cells expressing the same acyl-ACP thioesterase without a linker domain.

In a specific embodiment, a recombinant cell comprises nucleic acids operable to express a product of an exogenous gene encoding a variant acyl-ACP thioesterase exogenous gene encoding an active acyl-ACP thioesterase that catalyzes the cleavage of mid-chain fatty acids from ACP. As a result, in one embodiment, the oil produced can be characterized by a fatty acid profile elevated in C8, C10, C12, and/or C14 fatty acids and reduced in C16, C18, and C18:1 fatty acids as a result of expression of the recombinant nucleic acids. In varying embodiments, the increase in C8, C10, C12, and/or C14 fatty acids is greater than 1%, 2%, 3%, 4%, 5%, 6%, 7%, 8%, 9%, 10%, 20%, 30%, 40%, 50%, 60%, 70%, from 75-85%, from 70-90%, from 90-200%, from 200-300%, from 300-400%, from 400-500%, or greater than 500%.

In some embodiments, an additional genetic modification to increase the level of mid-chain fatty acids in the cell or oil of the cell includes the expression of an exogenous lysophosphatidic acid acyltransferase gene encoding an active lysophosphatidic acid acyltransferase (LPAAT) that catalyzes the transfer of a mid-chain fatty-acyl group to the sn-2 position of a substituted acylglyceroester. In a specific related embodiment, both an exogenous acyl-ACP thioesterase and LPAAT are stably expressed in the cell. As a result of introducing recombinant nucleic acids into an oleaginous cell (and especially into a plastidic microbial cell) an exogenous mid-chain-specific thioesterase and an exogenous LPAAT that catalyzes the transfer of a mid-chain fatty-acyl group to the sn-2 position of a substituted acylglyceroester, the cell can be made to increase the percent of a particular mid-chain fatty acid in the triacylglycerides (TAGs) that it produces by 10, 20 30, 40, 50, 60, 70, 80, 90-fold, or more. Introduction of the exogenous LPAAT can increase mid-chain fatty acids at the sn-2 position by 1, 2, 3, 4 fold or more compared to introducing an exogenous mid-chain preferring acyl-ACP thioesterase alone. In an embodiment, the mid-chain fatty acid is greater than 30, 40, 50 60, 70, 80, or 90% of the TAG fatty acids produced by the cell. In various embodiments, the mid-chain fatty acid is capric, caprylic, lauric, myristic, and/or palmitic.

In varying embodiments, the gene encoding an lysophosphatidic acid acyltransferase (LPAAT) is selected from the group consisting of *Arabidopsis thaliana* 1-acyl-sn-glycerol-3-phosphate acyltransferase (GenBank Accession No. AEE85783), *Brassica juncea* 1-acyl-sn-glycerol-3-phosphate acyltransferase (GenBank Accession No. ABQ42862), *Brassica juncea* 1-acyl-sn-glycerol-3-phosphate acyltransferase (GenBank Accession No. ABM92334), *Brassica napus* 1-acyl-sn-glycerol-3-phosphate acyltransferase (GenBank Accession No. CAB09138), *Chlamydomonas reinhardtii* lysophosphatidic acid acyltransferase (GenBank Accession No. EDP02300), *Cocos nucifera* lysophosphatidic acid acyltransferase (GenBank Acc. No. AAC49119), *Limnanthes alba* lysophosphatidic acid acyltransferase (GenBank Accession No. EDP02300), *Limnanthes douglasii* 1-acyl-sn-glycerol-3-phosphate acyltransferase (putative) (GenBank Accession No. CAA88620), *Limnanthes douglasii* acyl-CoA:sn-1-acylglycerol-3-phosphate acyltransferase (GenBank Accession No. ABD62751), *Limnanthes douglasii* 1-acylglycerol-3-phosphate O-acyltransferase (GenBank Accession No. CAA58239), *Ricinus communis* 1-acyl-sn-glycerol-3-phosphate acyltransferase (GenBank Accession No. EEF39377).

Alternately, or in addition to expression of an exogenous LPAAT, the cell may comprise recombinant nucleic acids that are operable to express an exogenous KASI or KASIV enzyme and optionally to decrease or eliminate the activity of a KASII, which is particularly advantageous when a mid-chain-preferring acyl-ACP thioesterase is expressed. Engineering of *Prototheca* cells to overexpress KASI and/or KASIV enzymes in conjunction with a mid-chain preferring acyl-ACP thioesterase can generate strains in which production of C10-C12 fatty acids is at least about 40% of total fatty acids, e.g., at least about 45%, 50%, 55%, 60% or more, of total fatty acids. Mid-chain production can also be increased by suppressing the activity of KASI and/or KASII (e.g., using a knockout or knockdown). Chromosomal knockout of different alleles of *Prototheca moriformis* (UTEX 1435) KASI in conjunction with overexpression of a mid-chain preferring acyl-ACP thioesterase can achieve fatty acid profiles that are at least about 60% C10-C14 fatty acids, e.g., at least about 65%, 70%, 75%, 80%, 85% or more C10-C14 fatty acids. Elevated mid-chain fatty acids can also be achieved as a result of expression of KASI RNA hairpin polynucleotides. In addition to any of these modifications, unsaturated or polyunsaturated fatty acid production can be suppressed (e.g., by knockout or knockdown) of a SAD or FAD enzyme.

In an embodiment, one of the above described high mid-chain producing cells is further engineered to produce a low polyunsaturated oil by knocking out or knocking down one or more fatty acyl desaturases. Accordingly, the oil produced has high stability.

The high mid-chain oils or fatty acids derived from hydrolysis of these oils may be particularly useful in food, fuel and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

VIII. Fuels and Chemicals Production

Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. The present invention provides methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers may contain rubber parts and may require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers. Biodiesel can be used as an additive in formulations of diesel to increase the lubricity of pure Ultra-Low Sulfur Diesel (ULSD) fuel, which is advantageous because it has virtually no sulfur content. Biodiesel is a better solvent than petrodiesel and can be used to break down deposits of residues in the fuel lines of vehicles that have previously been run on petrodiesel.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

The lipid profile of the biodiesel is usually highly similar to the lipid profile of the feedstock oil. Other oils provided by the methods and compositions described herein can be subjected to transesterification to yield biodiesel with lipid profiles including (a) at least 4% C8-C14; (b) at least 0.3% C8; (c) at least 2% C10; (d) at least 2% C12; and (3) at least 30% C8-C14.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol.

In this reaction, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base can be used to help the reaction proceed more quickly. The acid or base are not consumed by the transesterification reaction, thus they are not reactants but catalysts. Almost all biodiesel has been produced using the base-catalyzed technique as it requires only low temperatures and pressures and produces over 98% conversion yield (provided the starting oil is low in moisture and free fatty acids).

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 7. Other examples of lipases useful for transesterification are found in, e.g. U.S. Pat. Nos. 4,798,793; 4,940,845 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida*, and *Humicola* and pancreas lipase.

Lipases suitable for use in transesterification include without limitation *Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus* japonicas lipase (Lilipase A-10FG) Q7M4U7_1, *Rhizomucor miehei* lipase B34959, *Rhizopus oryzae* lipase (Lipase F) AAF32408, *Serratia marcescens* lipase (SM Enzyme) ABI13521, *Thermomyces lanuginosa* lipase CAB58509, Lipase P (Nagase ChemteX Corporation), and Lipase QLM (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity. Some suitable methods include immersing an immobilized lipase in an alcohol having a carbon atom number not less than 3 for a period of time, preferably from 0.5-48 hours, and more preferably from 0.5-1.5 hours. Some suitable methods also include washing a deactivated immobilized lipase with an alcohol having a carbon atom number not less than 3 and then immersing the deactivated immobilized lipase in a vegetable oil for 0.5-48 hours.

In particular embodiments, a recombinant lipase is expressed in the same microorganisms that produce the lipid on which the lipase acts. Suitable recombinant lipases include those listed above and/or having GenBank Accession numbers listed above, or a polypeptide that has at least 70% amino acid identity with one of the lipases listed above and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference as if fully set forth. DNA encoding the lipase and selectable marker is preferably codon-optimized cDNA. Methods of recoding genes for expression in microalgae are described in U.S. Pat. No. 7,135,290.

The common international standard for biodiesel is EN 14214. ASTM D6751 is the most common biodiesel standard referenced in the United States and Canada. Germany uses DIN EN 14214 and the UK requires compliance with BS EN 14214. Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

Although biodiesel that meets the ASTM standards has to be non-toxic, there can be contaminants which tend to crystallize and/or precipitate and fall out of solution as sediment. Sediment formation is particularly a problem when biodiesel is used at lower temperatures. The sediment or precipitates may cause problems such as decreasing fuel flow, clogging fuel lines, clogging filters, etc. Processes are well-known in the art that specifically deal with the removal of these contaminants and sediments in biodiesel in order to produce a higher quality product. Examples for such processes include, but are not limited to, pretreatment of the oil to remove contaminants such as phospholipids and free fatty acids (e.g., degumming, caustic refining and silica adsorbent filtration) and cold filtration. Cold filtration is a process that was developed specifically to remove any particulates and sediments that are present in the biodiesel after production. This process cools the biodiesel and filters out any sediments or precipitates that might form when the fuel is used at a lower temperature. Such a process is well known in the art and is described in US Patent Application Publication No. 2007-0175091. Suitable methods may include cooling the biodiesel to a temperature of less than about 38° C. so that the impurities and contaminants precipitate out as particulates in the biodiesel liquid. Diatomaceous earth or other filtering material may then added to the cooled biodiesel to form a slurry, which may then filtered through a pressure leaf or other type of filter to remove the particulates. The filtered biodiesel may then be run through a polish filter to remove any remaining sediments and diatomaceous earth, so as to produce the final biodiesel product.

U.S. Patent Publ. No. 2012/0283460 the production of biodiesel using triglyceride oil from *Prototheca moriformis*. The Cold Soak Filterability by the ASTM D6751 A1 method of the biodiesel produced was 120 seconds for a volume of 300 ml. This test involves filtration of 300 ml of B100, chilled to 40° F. for 16 hours, allowed to warm to room temp, and filtered under vacuum using 0.7 micron glass fiber filter with stainless steel support. Oils described herein can be transesterified to generate biodiesel with a cold soak time of less than 120 seconds, less than 100 seconds, and less than 90 seconds.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging.

In some methods, the microbial lipid is first cracked in conjunction with hydrotreating to reduce carbon chain length and saturate double bonds, respectively. The material is then isomerized, also in conjunction with hydrotreating. The naphtha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 $hr^{-1}$ to about 5 $hr^{-1}$. One skilled in the art will recognize that the time period required for reaction will vary according to the temperature used, the molar ratio of hydrogen to triglyceride, and the partial pressure of hydrogen. The products produced by the such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization includes using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions described herein is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). Renewable diesel was produced from *Prototheca* moriformis triglyceride oil. The T10-T90 of the material produced in Example 14 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

The T10 of the material produced was 242.1° C. Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

The T90 of the material produced was 300° C. Methods of hydrotreating, isomerization, and other covalent modification of oils disclosed herein, as well as methods of distillation and fractionation (such as cold filtration) disclosed herein can be employed to generate renewable diesel compositions with other T90 values, such as T90 between 280 and 380, between 290 and 360, between 300 and 350, between 310 and 340, and at least 290.

The FBP of the material produced was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions described herein can be subjected to combinations of hydrotreating, isomerization, and other covalent modification including oils with lipid profiles including (a) at least 4% C8-C14; (b) at least 0.3% C8; (c) at least 2% C10; (d) at least 2% C12; and (3) at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Aeroplane fuel (including Jet A and Jet A-1) has a carbon number distribution between about 8 and 16 carbon numbers. Wide-cut or naphta-type Aeroplane fuel (including Jet B) typically has a carbon number distribution between about 5 and 15 carbons.

Both Aeroplanes (Jet A and Jet B) may contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A is used for civilian and military fuels and DCI-6A is used for military fuels. FSII agents, include, e.g., Di-EGME.

In some embodiments, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as “coked catalyst”, is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

Suitable FCC catalysts generally comprise at least two components that may or may not be on the same matrix. In some embodiments, both two components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may be preferred over amorphous catalysts because of their much-improved selectivity to desired products. In some preferred embodiments, zeolites may be used as the molecular sieve in the FCC processes. Preferably, the first catalyst component comprises a large pore zeolite, such as an Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as “coked catalyst.” In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo and/or a CoMo catalysts, the support being alumina and/or silica. Typically, NiMo/$Al_2O_3$ and CoMo/$Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50 400° C. and at hydrogen pressures of 1 200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo and/or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed and/or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerzation step, the pressure varies in the range of 20 150 bar, preferably in the range of 20 100 bar, the temperature being between 200 and 500° C., preferably between 300 and 400° C. In the isomerization step, isomerization catalysts known in the art may be used. Suitable isomerization catalysts contain molecular sieve or a metal from Group VII and/or a carrier. Preferably, the isomerization catalyst contains SAPO-11 or SAPO41 or ZSM-22 or ZSM-23 and/or ferrierite and Pt, Pd or Ni and $Al_2O_3$ and/or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of the one or more chemical reactions is an alkane mixture that comprises ASTM D1655 jet fuel. In some embodiments, the composition conforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between 775K/$M^3$ and 840 K/$M^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., that is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty acid methyl esters, and glycerol. Examples of derivative oleochemicals include, but are not limited to, fatty nitriles, esters, dimer acids, quats, surfactants, fatty alkanolamides, fatty alcohol sulfates, resins, emulsifiers, fatty alcohols, olefins, and higher alkanes.

Hydrolysis of the fatty acid constituents from the glycerolipids produced by the methods described herein yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173 (Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

With regard to hydrolysis, in some embodiments, a triglyceride oil is optionally first hydrolyzed in a liquid medium such as water or sodium hydroxide so as to obtain glycerol and soaps. There are various suitable triglyceride hydrolysis methods, including, but not limited to, saponification, acid hydrolysis, alkaline hydrolysis, enzymatic hydrolysis (referred herein as splitting), and hydrolysis using hot-compressed water. One skilled in the art will recognize that a triglyceride oil need not be hydrolyzed in order to produce an oleochemical; rather, the oil may be converted directly to the desired oleochemical by other known process. For example, the triglyceride oil may be directly converted to a methyl ester fatty acid through esterification.

In some embodiments, catalytic hydrolysis of the oil produced by methods disclosed herein occurs by splitting the oil into glycerol and fatty acids. As discussed above, the fatty acids may then be further processed through several other modifications to obtained derivative oleochemicals. For example, in one embodiment the fatty acids may undergo an amination reaction to produce fatty nitrogen compounds. In another embodiment, the fatty acids may undergo ozonolysis to produce mono- and dibasic-acids.

In other embodiments hydrolysis may occur via the, splitting of oils produced herein to create oleochemicals. In some embodiments, a triglyceride oil may be split before other processes is performed. One skilled in the art will recognize that there are many suitable triglyceride splitting methods, including, but not limited to, enzymatic splitting and pressure splitting.

Generally, enzymatic oil splitting methods use enzymes, lipases, as biocatalysts acting on a water/oil mixture. Enzymatic splitting then splits the oil or fat, respectively, is into glycerol and free fatty acids. The glycerol may then migrates into the water phase whereas the organic phase enriches with free fatty acids.

The enzymatic splitting reactions generally take place at the phase boundary between organic and aqueous phase, where the enzyme is present only at the phase boundary. Triglycerides that meet the phase boundary then contribute to or participate in the splitting reaction. As the reaction proceeds, the occupation density or concentration of fatty acids still chemically bonded as glycerides, in comparison to free fatty acids, decreases at the phase boundary so that the reaction is slowed down. In certain embodiments, enzymatic splitting may occur at room temperature. One of ordinary skill in the art would know the suitable conditions for splitting oil into the desired fatty acids.

By way of example, the reaction speed can be accelerated by increasing the interface boundary surface. Once the reaction is complete, free fatty acids are then separated from the organic phase freed from enzyme, and the residue which still contains fatty acids chemically bonded as glycerides is fed back or recycled and mixed with fresh oil or fat to be subjected to splitting. In this manner, recycled glycerides are then subjected to a further enzymatic splitting process. In some embodiments, the free fatty acids are extracted from an oil or fat partially split in such a manner. In that way, if the chemically bound fatty acids (triglycerides) are returned or fed back into the splitting process, the enzyme consumption can be drastically reduced.

The splitting degree is determined as the ratio of the measured acid value divided by the theoretically possible acid value which can be computed for a given oil or fat. Preferably, the acid value is measured by means of titration according to standard common methods. Alternatively, the density of the aqueous glycerol phase can be taken as a measure for the splitting degree.

In one embodiment, the slitting process as described herein is also suitable for splitting the mono-, di- and triglyceride that are contained in the so-called soap-stock from the alkali refining processes of the produced oils. In this manner, the soap-stock can be quantitatively converted without prior saponification of the neutral oils into the fatty acids. For this purpose, the fatty acids being chemically bonded in the soaps are released, preferably before splitting, through an addition of acid. In certain embodiments, a buffer solution is used in addition to water and enzyme for the splitting process.

In one embodiment, oils produced in accordance with the methods described herein can also be subjected to saponification as a method of hydrolysis Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. In this scheme, the carboxylic acid constituents are cleaved from the glycerol moiety and replaced with hydroxyl groups. The quantity of base (e.g., KOH) that is used in the reaction is determined by the desired degree of saponification. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some cases, these alternatives may be preferred to produce a clear soap product.

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation.

Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. No. 5,233,099 and U.S. Pat. No. 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate carbohydrates. One suitable method includes contacting the carbohydrate with hydrogen or hydrogen mixed with a suitable gas and a catalyst under conditions sufficient in a hydrogenation reactor to form a hydrogenated product. The hydrogenation catalyst generally can include Cu, Re Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for a hydrogenation reaction is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term "external hydrogen" refers to hydrogen that does not originate from the biomass reaction itself, but rather is added to the system from another source.

In some embodiments, it is desirable to convert the starting carbohydrate to a smaller molecule that will be more readily converted to desired higher hydrocarbons. One suitable method for this conversion is through a hydrogenolysis reaction. Various processes are known for performing hydrogenolysis of carbohydrates. One suitable method includes contacting a carbohydrate with hydrogen or hydrogen mixed with a suitable gas and a hydrogenolysis catalyst in a hydrogenolysis reactor under conditions sufficient to form a reaction product comprising smaller molecules or polyols. As used herein, the term "smaller molecules or polyols" includes any molecule that has a smaller molecular weight, which can include a smaller number of carbon atoms or oxygen atoms than the starting carbohydrate. In an embodiment, the reaction products include smaller molecules that include polyols and alcohols. Someone of ordinary skill in the art would be able to choose the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdemum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

Figure 1:
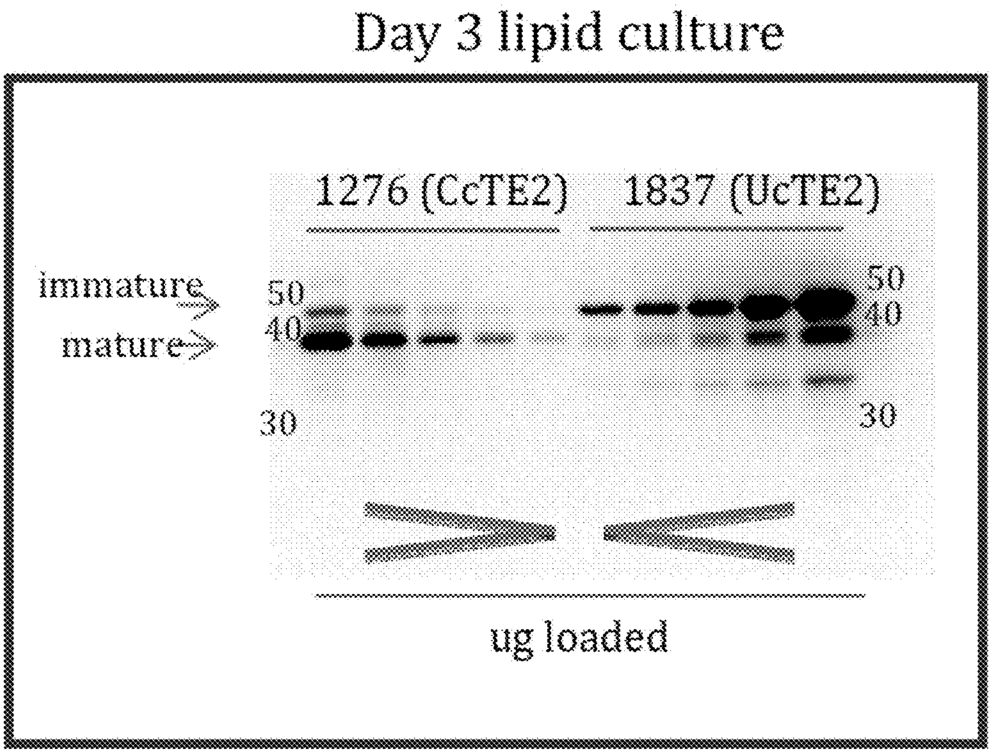
FIG. 1 illustrates Western blotting of whole cell lysates from *P. moriformis* strains engineered to express the C-terminally FLAG epitope tagged Uc TE (F) or Cc TE (E) acyl-ACP thioesterase.
Figure 2:
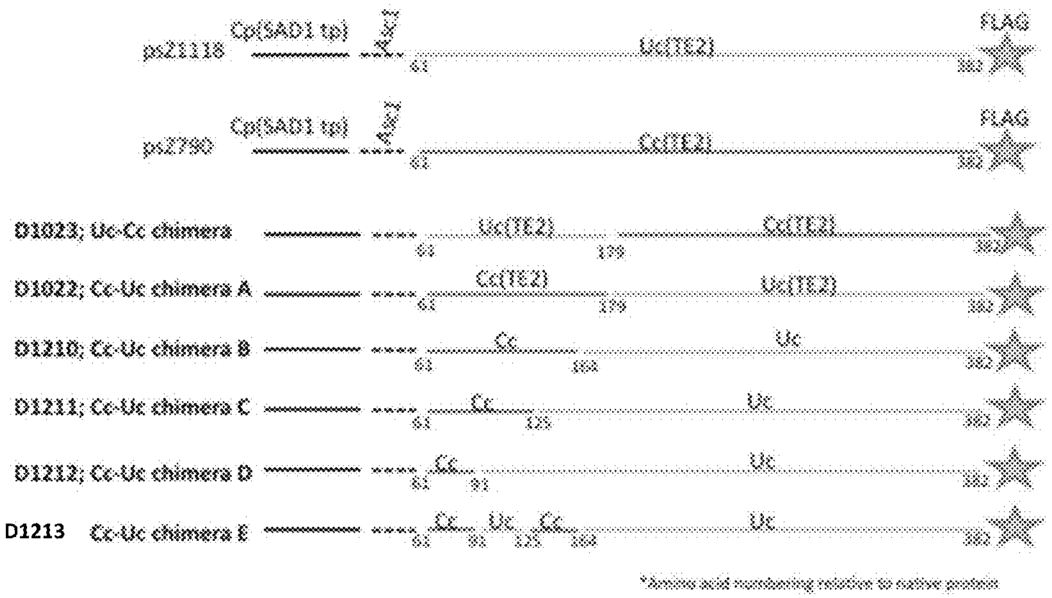
FIG. 2 illustrates a schematic cartoon of *Umbellularia californica* (Uc) TE, *Cinnamomum camphora* (Cc) TE and chimeric expression constructs. All constructs contained the same *C. protothecoides* SAD1 transit peptide, AscI linker and C-terminal FLAG epitope tag.
Figure 9:
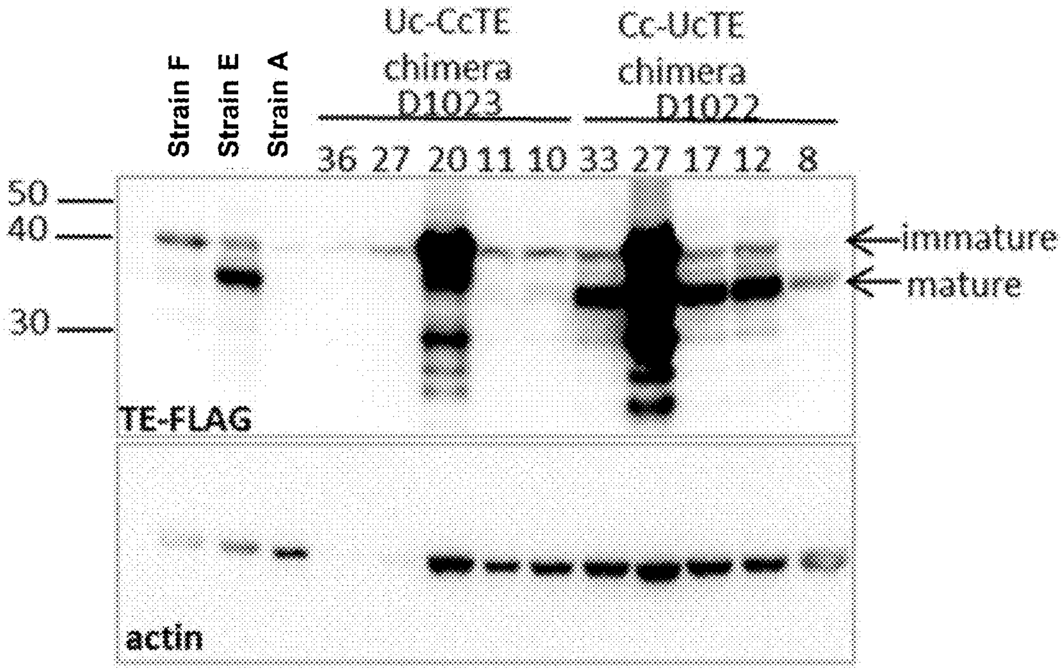
FIG. 9 illustrates a Western Blot comparing Strain A, Strain E and Strain F and representative derivative transgenic lines transformed with pSZ2037 (D1022, Cc-Uc TE chimera A) and pSZ2038 (D1023, Uc-Cc TE chimera) DNAs.

In some embodiments, the reaction products discussed above may be converted into higher hydrocarbons through a condensation reaction in a condensation reactor (shown schematically as condensation reactor 110 in FIG. 1). In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 Kpa to 9000 KPa, and preferably in a range between 0 KPa and 7000 KPa, and even more preferably between 0 KPa and 5000 KPa.

The higher alkanes formed by the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2,-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another such chemical modification is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Nondigestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C. combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., JAOCS 71(2): 169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

EXAMPLES

The following examples are offered to illustrate, but not to limit the claimed invention.

Example 1

Altering the Specificity of a 12:0-Acyl-Acyl Carrier Protein (ACP) Thioesterase This example demonstrates altering the specificity of a 12:0-Acyl ACP Thioesterase (TE), using *Prototheca moriformis* as a host.

In the present example, we demonstrate the ability to alter the substrate specificity as well as enhance the maturation of the 12:0-acyl-acyl carrier protein (ACP) thioesterase from California bay tree (*Umbellularia californica*,"Uc") (Uc FatB2/Uc TE, accession M94159). This was achieved by replacing the N-terminal portion of Uc TE with the corresponding region from the closely related 14:0-ACP thioesterase from camphor tree (Cinnamomum camphorum, "Cc") (Cc FATB1/Cc TE, accession U31813).

Both Uc TE and Cc TE are nuclear encoded proteins, which must be trafficked to the plastid to perform their respective activities in microalgae. This transport occurs through the recognition of a transit peptide located at the N-terminus of the nascent thioesterase by the plastid transporter complex. Once inside the plastid, the transit peptide is cleaved, liberating the mature thioesterase. This maturation process can be tracked by Western blotting of total cell lysates due to a discernible difference in mobility between the nascent and the mature protein. As shown in FIG. 1, we found a significant difference in the overall efficiency of maturation between Uc TE and Cc TE within *P. moriformis*. This finding is surprising, as both proteins contain the same heterologous transit peptide from the *Chlorella protothecoides* Stearoyl ACP Desaturase (SAD) protein and exhibit greater than 90% amino acid identity between the mature proteins.

We then investigated whether one or more of the nine non-overlapping amino acids within the N-terminus of the Cc TE (as compared to the corresponding aligned Uc TE sequence) was critical for the efficient maturation observed for this thioesterase. Therefore, we decided to test the impact of replacing the N-terminus of the Uc TE with the corresponding region from Cc TE. Yuan et al. (*Proc Natl Acad Sci USA*. (1995) 92(23):10639-43), concluded that acyl-ACP thioesterase specificity was not impacted by the N-terminal 178 amino acids of Uc TE or Cc TE as assessed in *E. coli*. In Yuan, et al., Leu84 was the start of the mature protein for expression in *E. coli*. In contrast, Pro61 is the first residue after the *C. protothecoides* SAD transit peptide for the present Cc TE and Uc TE expression constructs. Trp179 was the fusion point for the Uc TE and Cc TE thioesterase chimeras of Yuan, et al.

We used Trp179 as the fusion point for the construction of six Cc-Uc TE chimeras in which different segments of the Cc TE gene were used to replace the corresponding region of the Uc TE (FIG. 3). The constructs were transformed into a classically mutagenized derivative of *Prototheca moriformis* strain UTEX 1435 that we term strain A. Transformations, cell culture, lipid production and quantification were all carried out as previously described, e.g., in PCT Publications WO2008/151149, WO2010/06032, WO2011/150410, and WO2011/150411. The impact on maturation of each chimeric thioesterase was compared to the wild-type Cc TE and Uc TE via Western blotting of total cell lysates.

As described below, we discovered three amino acids (Asn91, Pro92 and Pro102) unique to Cc TE that enabled efficient maturation when grafted onto Uc TE. The more efficient maturation may allow for greater shifts in the fatty acid profile of an oil produced by a cell expressing an exogenous acyl-ACP TE having variant amino acids at those positions. Moreover, we discovered four Cc TE specific amino acids (Val127, Leu133, Ala137, and Ile163) that imparted a novel, dual 12:0 and 14:0 ACP activities when grafted onto Uc TE. When acyl-ACP TEs variants in these amino acid positions are expressed in an oleaginous cell, the cell may produce triglycerides with desirable or even novel fatty acid profiles.

Example 2

Cc-Uc Thioesterase Chimera Constructs

Construct D1022 [pSZ2037] used to Express the Cc-Uc FATB TE Chimera A within *P. moriformis* (UTEX 1435 strain A).

In this example, A strains, transformed with the construct pSZ2037, were generated which express sucrose invertase (allowing for their selection and growth on medium containing sucrose) and a chimeric fusion between Cc TE and Uc TE. Construct pSZ2037 introduced for expression in strain A can be written as 6SA::Cr(btub)-syn(yINV)-Cv(nr):Pm(amt03)-Cp(SAD1tp)-Cc(TE2)-Uc(TE2)-chimeraA-Cv(nr)::6sB.

The sequence of the transforming DNA is provided in FIG. 4. Relevant restriction sites in the construct are indicated with underlined lowercase, and are from 5'-3' BspQI, KpnI, Ascl, Mfel, EcoRI, SpeI, Ascl, XhoI, SacI, BspQI, respectively. BspQI sites delimit the 5' and 3' ends of the transforming DNA. Bold, lowercase sequences represent genomic DNA from A that permit targeted integration at the 6S locus via homologous recombination. Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlorella vulgaris* nitrate reductase (NR) gene 3'-UTR is indicated by lowercase text followed by a spacer segment (dotted underlined, lowercase) and a *P. moriformis* AMT3 promoter (indicated by boxed italicized text) driving the expression of the *C. camphorum* and *U. californica* chimeric fusion thioesterase. The *C. protothecoides* SAD 1 transit peptide is indicated with uppercase, boxed text, while the *C. camphorum* and *U. californica* derived sequences with underlined italic and bold uppercase, respectively. The C-terminal FLAG epitope tag is noted with underlined lowercase. The *C. vulgaris* nitrate reductase 3'-UTR is again indicated by lowercase text followed by the A 6S genomic region indicated by bold, lowercase text. The final construct was sequenced to ensure correct reading frames and targeting sequences.

Constructs used for the Expression of an Uc-Cc TE Chimera and Four Additional Cc-Uc TE Chimeras (Chimeras B-E) in A In addition to the Cc-UC TE chimera A, five additional chimeric thioesterase expression constructs were designed. These constructs can be described as:

pSZ2038-6SA::Cr(btub)-syn(INV)-Cv(nr):Pm(amt03)-Cp(SAD1tp)-Uc(TE2)-Cc(TE2)-Cv(nr)::6sB pSZ2231-6SA::Cr(btub)-syn(yINV)-Cv(nr):Pm(amt03)-Cp(SAD1tp)-Cc(TE2)-Uc(TE2)-chimeraB-Cv(nr)::6sB pSZ2232-6SA:: Cr(btub)-syn(yINV)-Cv(nr):Pm(amt03)-Cp(SAD1tp)-Cc(TE2)-Uc(TE2)-chimeraC-Cv(nr)::6sB pSZ2233-6SA::Cr(btub)-syn(yINV)-Cv(nr):Pm(amt03)-Cp(SAD1tp)-Cc(TE2)-Uc(TE2)-chimeraD-Cv(nr)::6sB pSZ2234-6SA::Cr(btub)-syn(yINV)-Cv(nr):Pm(amt03)-Cp(SAD1tp)-Cc(TE2)-Uc(TE2)-chimeraE-Cv(nr)::6sB All of these constructs have the same vector backbone; selectable marker, promoter, plastid transit peptide, FLAG epitope tag and 3'-UTR as pSZ2037, differing only in the respective Cc-Uc chimeric thioesterase. Relevant restriction sites in these constructs are also the same as in pSZ2037. FIGS. 5-9 indicate the appropriate chimeric thioesterase sequence wherein the Cc TE derived sequence is noted with underlined italic while the Uc TE derived sequence is noted with bold uppercase text.

Expression of heterologous thioesterase variants in *P. moriformis* resulted in unique specific fatty acid profiles of interest. Strain D, which expresses a *Cuphea wrightii* thioesterase (accession U56103) with its endogenous plastid transit peptide, gave elevated levels of C10:0, C12:0 and C14:0 fatty acids with approximately a 1:6:3 ratio (C10:C12:C14). Expression of the Cc TE (accession U31813) in strain E with the *Chlorella protothecoides* SAD transit peptide, resulted in elevated C12:0 and C14:0 fatty acids at a 1:10 ratio of C12:C14. Expression of the Uc TE (accession M94159) in strain F, also containing the *Chlorella* protothecoides SAD transit peptide, resulted in elevated C12:0 and C14:0 fatty acids at a 7:1 ratio of C12:C14. Strain A represents the base strain of *P. moriformis*. Data is shown in Table 1 in biological replicates (A and B) for each strain.

TABLE 1

| Sample ID | C8:0 | C10:0 | C12:0 | C14:0 | C16:0 | C18:0 | C18:1 | C18:2 |
|---|---|---|---|---|---|---|---|---|
| Strain D-A | 0.03 | 5.59 | 32.11 | 15.59 | 12.73 | 1.14 | 24.59 | 6.98 |
| Strain D-C | 0.03 | 5.89 | 32.79 | 15.61 | 12.58 | 1.16 | 24.01 | 6.63 |
| Strain E-A | 0.00 | 0.03 | 2.47 | 23.90 | 23.95 | 1.72 | 35.93 | 10.32 |
| Strain E-B | 0.00 | 0.04 | 2.50 | 25.02 | 23.06 | 1.69 | 36.91 | 9.28 |
| Strain F-A | 0.00 | 0.25 | 29.59 | 4.00 | 11.51 | 0.84 | 36.86 | 14.91 |
| Strain F-B | 0.00 | 0.22 | 27.16 | 4.20 | 13.50 | 1.06 | 37.30 | 14.42 |
| Strain A-A | 0.00 | 0.00 | 0.03 | 1.28 | 28.88 | 2.92 | 59.91 | 5.32 |
| Strain A-A | 0.00 | 0.01 | 0.04 | 1.35 | 30.23 | 2.89 | 58.38 | 5.44 |

Figure 10:
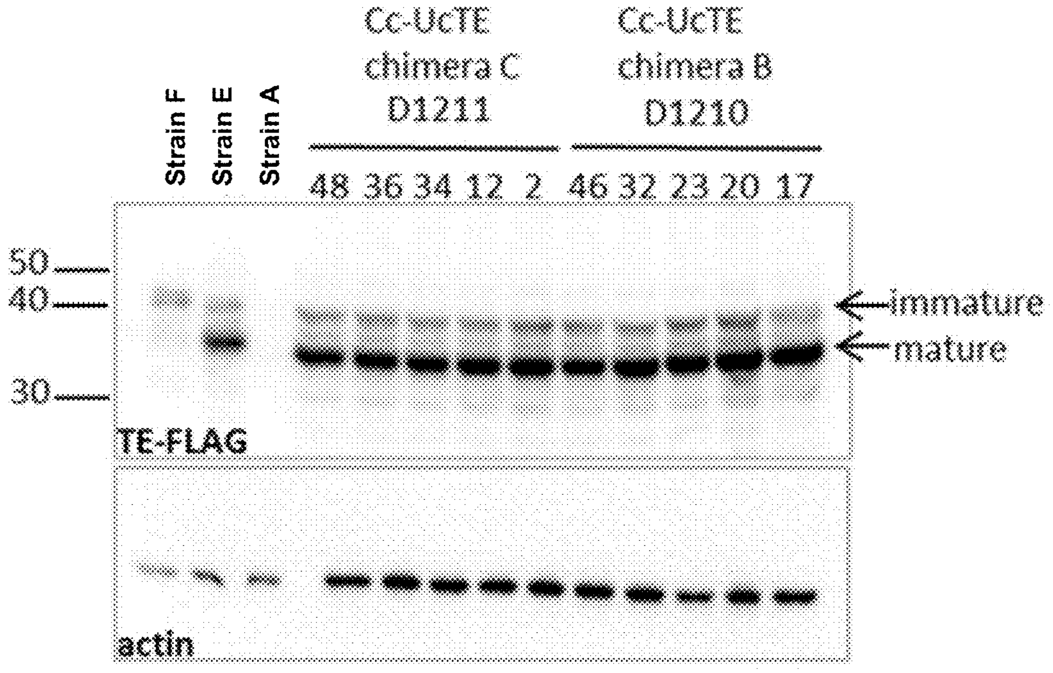
FIG. 10 illustrates a Western Blot comparing Strain A, Strain E and Strain F and representative derivative transgenic lines transformed with pSZ2231 (D1210, Cc-Uc TE chimera B) or pSZ2232 (D1211, Cc-Uc TE chimera C) DNAs.

Table 2 and FIG. 10 illustrate a comparison of fatty acid (FA) profiles for representative derivative transgenic lines transformed with pSZ2037 (D1022, Cc-Uc TE chimera A) and pSZ2038 (D1023, Uc-Cc TE chimera) DNAs (see FIG.

3), and, as a reference, expression in Strain A. Replacing the N-terminus of Uc TE with the corresponding region from Cc TE (pSZ2037; D1022) resulted in a novel FA profile exhibiting elevated C12:0 and C14:0 at an approximate 1:1 ratio. Moreover, these strains exhibit increased steady state levels of mature protein as compared to the wild-type Uc TE (represented in strain F). In contrast, replacing the N-terminus of Cc TE with the corresponding region from Uc TE (pSZ2038; D1023) resulted in poor expression and limited processing of the nascent protein into the mature form.

TABLE 2

| Sample ID | C10:0 | C12:0 | C14:0 | C16:0 |
|---|---|---|---|---|
| ctrl A | 0.01 | 0.04 | 1.37 | 29.62 |
| T289; D1023-36 | 0.01 | 0.04 | 1.52 | 29.98 |
| T289; D1023-27 | 0.01 | 0.04 | 1.39 | 26.97 |
| T289; D1023-20 | 0.01 | 0.04 | 1.43 | 27.18 |
| T289; D1023-11 | 0.01 | 0.04 | 1.45 | 29.11 |
| T289; D1023-10 | 0.01 | 0.04 | 1.40 | 28.38 |
| T289; D1022-33 | 0.02 | 2.34 | 3.09 | 24.81 |
| T289; D1022-27 | 0.08 | 14.43 | 10.92 | 20.21 |
| T289; D1022-17 | 0.02 | 1.8 | 2.7 | 25.07 |
| T289; D1022-12 | 0.03 | 3.27 | 3.72 | 23.75 |
| T289; D1022-8 | 0.02 | 1.54 | 2.47 | 25.92 |

Figure 11:
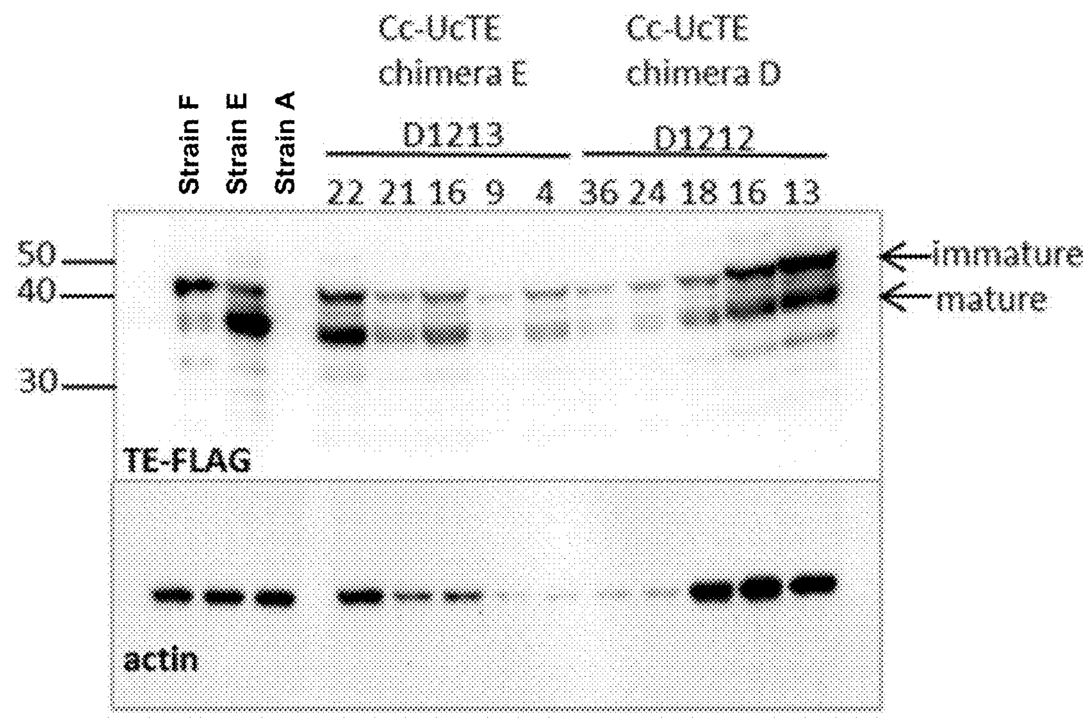
FIG. 11 illustrates a Western Blot comparing Strain A, Strain E and Strain F and representative derivative transgenic lines transformed with pSZ2233 (D1212, Cc-Uc TE chimera D) or pSZ2234 (D1213, Cc-Uc TE chimera E) DNAs.

Table 3 and FIG. 11 illustrate a comparison of FA profiles for expression in Strain A versus representative derivative transgenic lines transformed with pSZ2231 (D1210, Cc-Uc TE chimera B) or pSZ2232 (D1211, Cc-Uc TE chimera C) DNAs. While strains expressing the Cc-Uc TE chimera B (pSZ2231; D1210) exhibited FA profiles with C12:0 and C14:0 levels at an approximate 1:1 ratio; the Cc-Uc TE chimera C (pSZ2232; D1211) results in an approximate 4:1 ratio of C12:0 to C14:0.

TABLE 3

| Sample ID | C8:0 | C10:0 | C12:0 | C14:0 | C16:0 |
|---|---|---|---|---|---|
| ctrl A | 0.00 | 0.01 | 0.04 | 1.48 | 28.70 |
| T326; D1211-48 | 0.00 | 0.03 | 5.73 | 1.88 | 22.07 |
| T326; D1211-36 | 0.00 | 0.05 | 8.22 | 2.19 | 20.16 |
| T326; D1211-34 | 0.00 | 0.04 | 6.75 | 2.00 | 21.85 |
| T326; D1211-12 | 0.00 | 0.06 | 10.89 | 2.48 | 20.12 |
| T326; D1211-2 | 0.00 | 0.06 | 11.24 | 2.50 | 18.90 |
| T326; D1210-46 | 0.00 | 0.05 | 7.85 | 6.65 | 19.71 |
| T326; D1210-32 | 0.00 | 0.05 | 7.35 | 6.36 | 19.92 |
| T326; D1210-23 | 0.00 | 0.08 | 12.48 | 8.91 | 19.24 |
| T326; D1210-20 | 0.00 | 0.08 | 12.58 | 9.12 | 18.12 |
| T326; D1210-17 | 0.00 | 0.05 | 8.12 | 6.70 | 20.43 |

Importantly, strains expressing either construct exhibited increased steady state levels of mature protein as compared to the wild-type Uc TE (represented in strain F).

Figure 12:
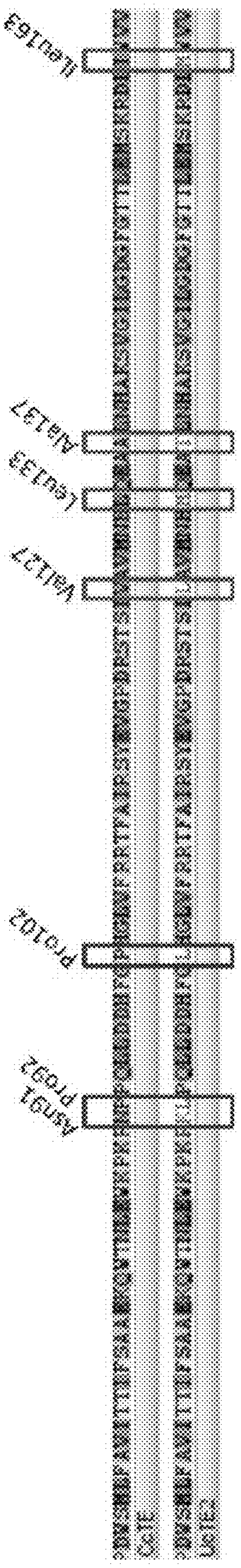
FIG. 12 illustrates amino acids identified from chimeric fusions between Cc TE and Uc TE required for efficient maturation of the nascent protein (Asn91, Pro92 and Pro102) and four Cc TE specific amino acids (Val127, Leu133, Ala137, and Ile163) which impart a novel 1:1 ratio of C12:0 to C14:0 when inserted into the context of an Uc TE backbone.

Table 4 and FIG. 12 illustrate a comparison of FA profiles for expression in Strain A versus representative derivative transgenic lines transformed with pSZ2233 (D1212, Cc-Uc TE chimera D) or pSZ2234 (D1213, Cc-Uc TE chimera E) DNAs (see FIG. 3). Strains expressing the Cc-Uc TE chimera D (pSZ2233; D1212) exhibited FA profiles with C12:0 and C14:0 levels at an approximate 4:1 ratio, similar to that for the native Uc TE enzyme. In contrast, strains expressing the Cc-Uc TE chimera E (pSZ2234; D1213) exhibited FA profiles in an approximate 1:1 ratio of C12:0 to C14:0. Furthermore, strains expressing either construct exhibited a moderate increase in steady state levels of mature protein as compared to the wild-type Uc TE (represented in strain F).

TABLE 4

| Sample ID | C8:0 | C10:0 | C12:0 | C14:0 | C16:0 |
|---|---|---|---|---|---|
| ctrl A | 0.00 | 0.01 | 0.04 | 1.48 | 28.70 |
| T326; D1213-22 | 0.00 | 0.04 | 5.05 | 5.02 | 21.32 |
| T326; D1213-21 | 0.00 | 0.05 | 6.84 | 6.28 | 20.23 |
| T326; D1213-16 | 0.00 | 0.05 | 7.98 | 6.82 | 19.88 |
| T326; D1213-9 | 0.00 | 0.04 | 4.66 | 4.72 | 21.55 |
| T326; D1213-4 | 0.00 | 0.07 | 10.62 | 8.34 | 18.39 |
| T326; D1212-36 | 0.00 | 0.03 | 5.09 | 1.82 | 21.31 |
| T326; D1212-24 | 0.00 | 0.05 | 7.34 | 2.21 | 15.83 |
| T326; D1212-18 | 0.00 | 0.05 | 8.96 | 2.32 | 23.03 |
| T326; D1212-16 | 0.00 | 0.04 | 4.84 | 1.82 | 21.95 |
| T326; D1212-13 | 0.00 | 0.06 | 11.43 | 2.44 | 20.36 |

Figure 13A:
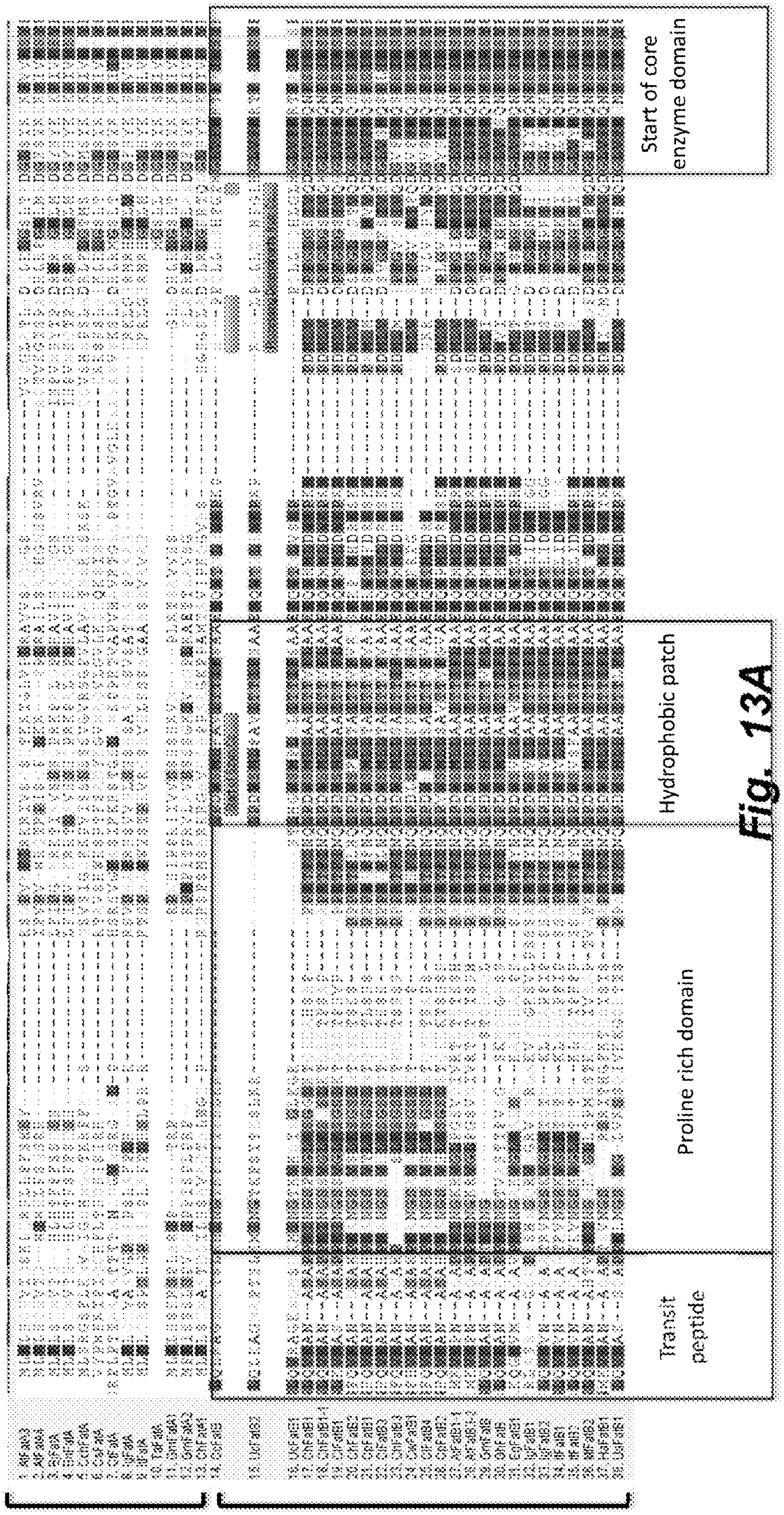
FIGS. 13A-B illustrate a sequence alignment of FATA and FATB thioesterase proteins. The N-terminus of FATBs exhibit a high degree of sequence conservation. The approximate regions for the transit peptide, a proline-rich domain and hydrophobic patch are boxed. Three amino acids shown to be important for the efficient processing of the Uc FATB2 (e.g., N91, P92 and P102) are noted with an underscore below row 14 and are located between the hydrophobic patch and start of the core enzyme domain.
Figure 13B:
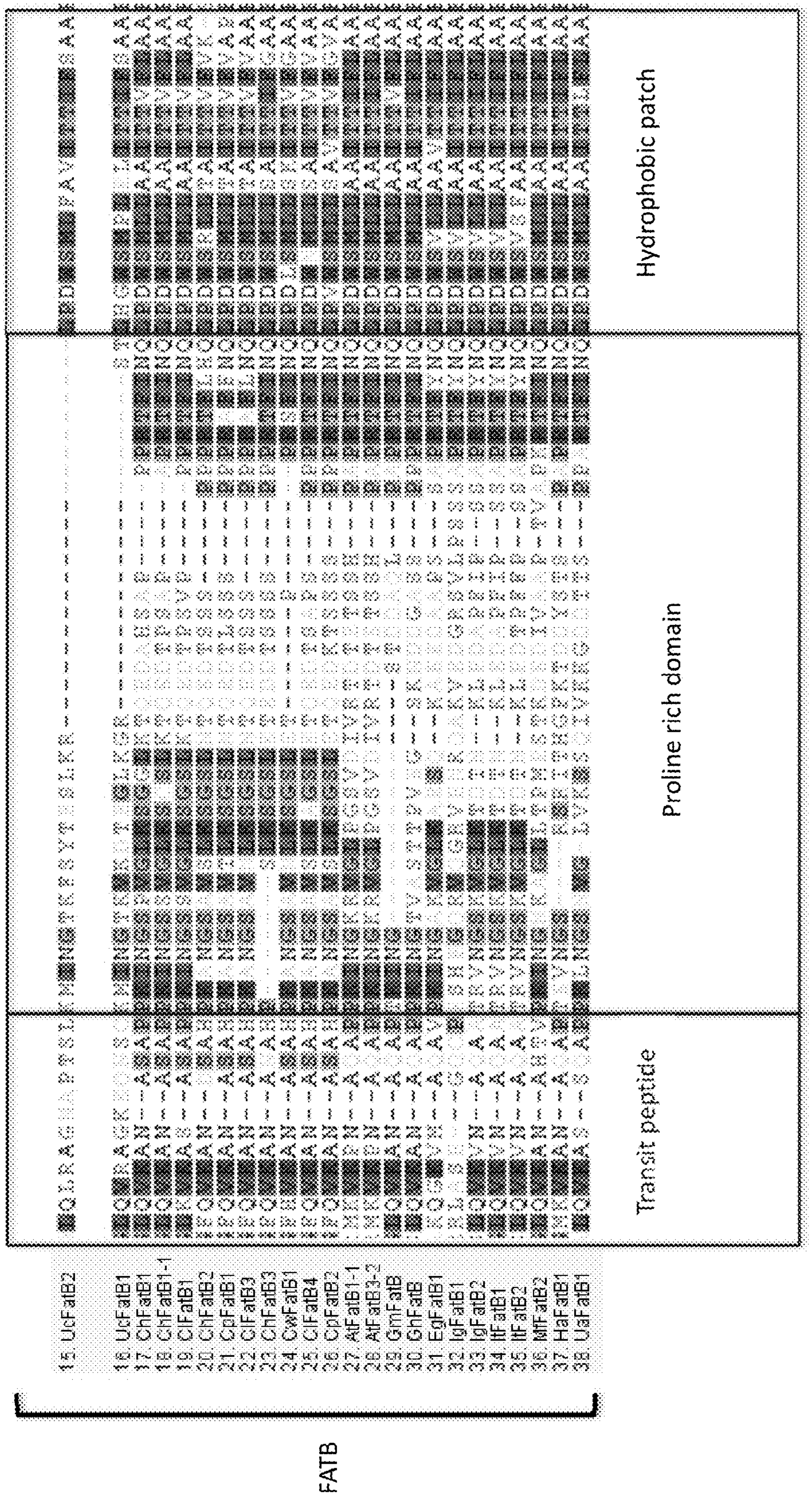

Amino acids identified from chimeric fusions between Cc TE and Uc TE required for efficient maturation of the nascent protein (Asn91, Pro92 and Pro 102) and the four Cc TE specific amino acids (Val127, Leu133, Ala137, and Ile163) which impart a novel 1:1 ratio of C12:0 to C14:0 when inserted into the context of an Uc TE backbone are depicted in FIG. 13. Accordingly, mutation of a FATB2 gene to have one or more or Asn91, Pro92 and Pro102 can increase the activity of the gene product encoded by the gene when expressed in an oleaginous cell, and especially a microalgal algal or plant cell having a type 2 fatty acid synthesis pathway. Likewise, mutation of a FATB2 gene to have one or more or Val127, Leu133, Ala137, and Ile163 can increase the activity of the gene product encoded by the gene when expressed in an oleaginous cell, and especially a microalgal algal or plant cell having a type 2 fatty acid synthesis pathway.

Example 3

Conserved Domains Immediately Downstream of the Predicted Plastid Transit Peptide Enhance the Activity of FATB Thioesterases In the present example, we demonstrate the ability to enhance the activity of FATB thioesterases by including conserved domains immediately downstream of the predicted plastid transit peptide. No function for these domains was previously known and so they may have been thought of as merely linkers between the enzyme and its plastid transit peptide. We show that including these domains with a native or heterologous transit peptide significantly improves the overall enzyme activity of a FATB acyl-ACP thioesterase overexpressed in *Prototheca moriformis*, as manifested in shifted fatty acid profiles. Moreover, we determined that fusing this region from a highly active thioesterase such as the 14:0-acyl-acyl carrier protein (ACP) thioesterase from *Cuphea palustris* (Cpal FATB2, accession AAC49180) or *Cuphea wrightii* (Cw FATB2, accession U56103) enhanced the activity of less functional thioesterases such as the FATB2 protein from *Umbellularia californica* (Uc FatB2/Uc TE, accession M94159).

We observed that several FATB proteins consistently exhibited an elevated specific activity when expressed in *P. moriformis*. As part of an effort to determine the reason for this difference, we investigated whether the N-terminal region of the FATB thioesterase contributed to the enzyme activity. Sequence alignment of plant thioesterases illustrates a striking degree of conservation at the extreme N-termini of FATB proteins (FIG. 14). This region overlaps the predicted plastid transit peptide and includes a Proline rich domain and a hydrophobic patch. Based on the assumption that the major function of the N-terminal region was to provide proper targeting of the nascent protein into the plastid, this portion of the thioesterase was generally replaced with a heterologous transit peptide for expression within *P. moriformis*.

Surprisingly, we noted the FATB thioesterase expression constructs with the highest degree of activity included most or all of the native N-termini, and that activity could be improved by varying the hydrophobic patch or proline-rich domain. As described below, we improved the specific activity of several thioesterases (e.g., Uc FATB2, accession M94159; *Cinnamomum camphorum* FATB1, accession U31813; Cpal FATB2, accession AAC49180; *Ulmus Americana* FATB1, accession 024420 and the herein-described Cc-Uc FATB chimera B (construct D1210)) by extending their N-termini to include the hydrophobic patch as well as all or part of the Proline-rich domain. These results demonstrate the importance of the N-terminal region for maximal FATB thioesterase activity. Moreover, these results demonstrate the ability to improve the activity of an under-performing FATB thioesterase by replacing its N-terminus with that of a highly active thioesterase.

Construct D1056

Construct D1056 [pSZ2084] was used to express the Uc FATB2 containing an extended heterologous transit peptide from *C. protothecoides* within *P. moriformis* (UTEX 1435 strain A).

A strains, transformed with the construct pSZ2084, were generated which express sucrose invertase (allowing for their selection and growth on medium containing sucrose) and an Uc FATB2 expression construct derived from pSZ1118 in which the heterologous transit peptide from *C. protothecoides* is extended to include 15 additional amino acids from the SAD1 transit peptide and flanking region. Construct pSZ2084 introduced for expression in Strain A can be written as 6SA::CrTUB2-ScSUC2-CvNR:PmAMT3-CpSAD1tpExt-UcFATB2-CvNR::6SB.

The sequence of the transforming DNA is provided in FIGS. 15A-C. Relevant restriction sites in the construct are indicated with underlined lowercase, and are from 5'-3' BspQI, KpnI, Ascl, MfeI, EcoRI, SpeI, XhoI, SacI, BspQI, respectively. BspQI sites delimit the 5' and 3' ends of the transforming DNA. Bold, lowercase sequences represent genomic DNA from A that permit targeted integration at the 6S locus via homologous recombination. Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlorella vulgaris* nitrate reductase (NR) gene 3'-UTR is indicated by lowercase text followed by a spacer segment (dotted underlined, lowercase) and a *P. moriformis* AMT3 promoter (indicated by boxed italicized text) driving the expression of the *U. califormica* chimeric fusion thioesterase. The extended *C. protothecoides* SAD1 transit peptide is indicated with underlined uppercase, while the *U. californica* FATB2 derived sequence is noted with bold uppercase. The C-terminal FLAG epitope tag is noted with underlined lowercase. The *C. vulgaris* nitrate reductase 3'-UTR is again indicated by lowercase text followed by the A 6S genomic region indicated by bold, lowercase text. The final construct was sequenced to ensure correct reading frames and targeting sequences.

Constructs D1057 and D1058

Constructs D1057 and D1058 were used for the expression of Uc FATB2 with 5 or 15 amino acid N-terminal extension (Uc FATB2 Ext A and Uc FATB2 Ext B, respectively) in Strain A.

In addition to the pSZ2084, two additional Uc FATB2 thioesterase expression constructs were designed. These constructs can be described as:

pSZ2085-6SA::CrTUB2-ScSUC2-CvNR:PmAMT3-CpSAD1 tpExt-UcFATB2ExtA-CvNR::6SB pSZ2086-6SA::CrTUB2-ScSUC2-CvNR:PmAMT3-CpSAD1 tpExt-UcFATB2ExtB-CvNR::6SB

These constructs have the same vector backbone; selectable marker, promoter, plastid transit peptide, FLAG epitope tag and 3'-UTR as pSZ2084, differing only in the respective Uc FATB2 thioesterase coding sequence. Relevant restriction sites in these constructs are also the same as in pSZ2084. FIGS. 16-17 indicate the appropriate extended Uc FATB2 thioesterase sequence wherein the extension is noted with underlined italic while the remaining Uc FATB2 sequence found in pSZ2084 is noted with bold uppercase text.

Constructs D1431 and D1432

Constructs D1431 and D1432 [pSZ2450 and pSZ2451] were used to express the 14:0-ACP thioesterase, *Cinnamomum camphorum* (Cc FATB1/Cc TE, accession U31813) containing an extended heterologous transit peptide from *C. protothecoides* and a five amino acid N-terminal extension derived from Uc FATB2 or Cc FATB 1 (D1431 or D1432, respectively) within *P. moriformis* (UTEX 1435 strain C). These constructs can be described as:

pSZ2450-6SA::CrTUB2-ScSUC2-CvNR:PmAMT3-CpSAD1 tpExt-CcFATB1ExtA-CvNR::6SB pSZ2451-6SA:: CrTUB2-S cSUC2-CvNR:PmAMT3-Cp SAD1tpExt-CcFATB1ExtB-CvNR::6SB

Both of these constructs have the same vector backbone; selectable marker, promoter, plastid transit peptide, FLAG epitope tag and 3'-UTR as pSZ2084, differing only in the respective Cc FATB1 thioesterase coding sequence. Relevant restriction sites in these constructs are also the same as in pSZ2084. FIGS. 19-20 indicate the appropriate extended Cc FATB 1 thioesterase sequence wherein the extension is noted with underlined italic while the remaining Cc FATB 1 sequence is noted with bold uppercase text.

Constructs D1481 and D1482

Constructs D1481 and D1482 [pSZ2479 and pSZ2480] were used to express the 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence within *P. moriformis* (UTEX 1435 strain C). These constructs can be described as:

pSZ2479-6SA::CrTUB2-ScSUC2-CvNR:PmAMT3-CpSAD1 tpExt-CpalFATB2ExtA-CvNR::6SB pSZ2480-6SA::CrTUB2-ScSUC2-CvNR:PmAMT3-CpSAD1 tpExt-CpalFATB2ExtA3xFLAG-CvNR::6SB Both of these constructs have the same vector backbone; selectable marker, promoter, plastid transit peptide, and 3' UTR as pSZ2084, differing only in the respective Cpal FATB2 thioesterase coding sequence and the presence or absence of a FLAG epitope tag. Relevant restriction sites in these constructs are also the same as in pSZ2084. FIGS. 22-23 indicate the appropriate extended Cpal FATB2 thioesterase sequence wherein the extension is noted with underlined italic while the remaining Cpal FATB2 sequence is noted with bold uppercase text and the FLAG epitope (pSZ2480) noted in lowercase text.

Constructs D1479 and D1480

Constructs D1479 and D1480 [pSZ2477 and pSZ2478] were used to express the Ulmus Americana 10:0-16:0-ACP thioesterase (Ua FATB1, accession 024420) containing an extended heterologous transit peptide from *C. protothecoides* and a 34 amino acid N-terminal extension derived from the native Ua FATB 1 sequence within *P. moriformis* (UTEX 1435 strain C). These constructs can be described as:

pSZ2477-6SA::CrTUB2-ScSUC2-CvNR:PmAMT3-CpSAD1 tpExt-UaFATB1ExtA-CvNR::6SB pSZ2478-6SA::CrTUB2-ScSUC2-CvNR:PmAMT3-CpSAD1 tpExt-UaFATB1ExtA3xFLAG-CvNR::6SB

Both of these constructs have the same vector backbone; selectable marker, promoter, plastid transit peptide, and 3' UTR as pSZ2084, differing only in the respective Ua FATB1 thioesterase and the presence or absence of a C-terminal FLAG epitope tag. Relevant restriction sites in these constructs are also the same as in pSZ2084. FIGS. 25-26 indicate the appropriate extended Ua FATB1 thioesterase sequence wherein the extension is noted with underlined italic while the remaining Ua FATB 1 sequence is noted with bold uppercase text. The FLAG epitope in pSZ2478 is noted in lowercase text.

Constructs D1210 and D1429

Figure 29:
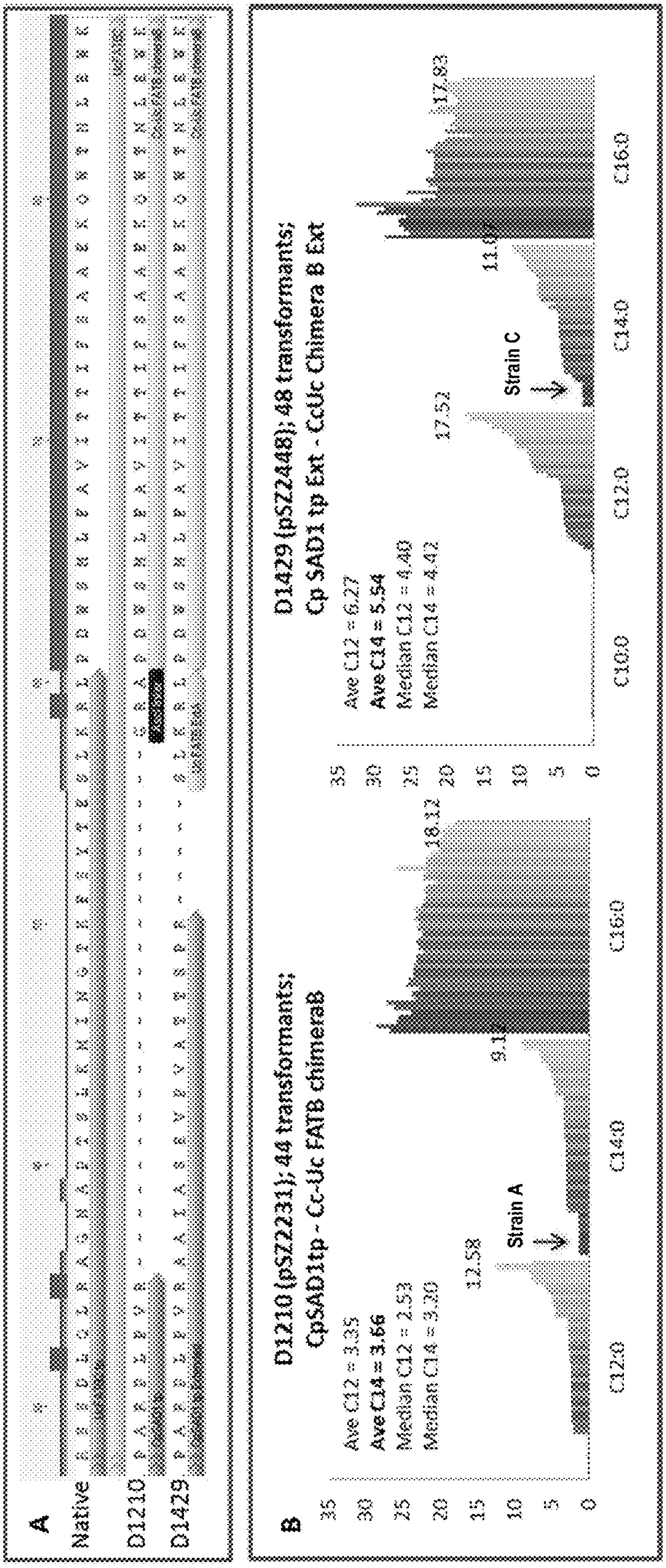

Constructs D1210 and D1429 [pSZ2231 and pSZ2448] were used to express the Cc-Uc FATB chimera B 12:0-14:0-ACP thioesterase within *P. moriformis* (UTEX 1435 strain C). The Cc-Uc chimera B (construct D1210, previously described) was generated by replacing the N-terminal portion of the *Umbellularia californica* (Uc FatB2/Uc TE, accession M94159) with the corresponding region from the closely related 14:0-ACP thioesterase, *Cinnamomum camphorum* (Cc FATB1/Cc TE, accession U31813). Construct D1429 contained an extended heterologous transit peptide from *C. protothecoides* and a five amino acid N-terminal extension derived from the native Uc FATB2 sequence. These constructs can be described as:

pSZ2231-6SA::CrTUB2-ScSUC2-CvNR:PmAMT3-CpSAD1tp-CcFATB1-UcFATB2-ChimeraB-CvNR::6SB pSZ2448-6SA::CrTUB2-ScSUC2-CvNR:PmAMT3-CpSAD1 tpExt-CcFATB1-UcFATB2-ChimeraB-ExtA-CvNR::6SB Both of these constructs have the same vector backbone; selectable marker, promoter, C-terminal FLAG epitope and 3' UTR as pSZ2084, differing only in the respective Cc-Uc FATB2 chimeric thioesterase and plastid transit peptide. Relevant restriction sites in these constructs are also the same as in pSZ2084. FIGS. 28-29 indicate the appropriate Cc-Uc FATB2 thioesterase sequence (bold uppercase text) wherein the trimmed or extended *C. protothecoides* SAD1 transit peptide is indicated with underlined uppercase and the Uc FATB2 extension within D1429 is noted with underlined lowercase italic.

Example 4

Modifying Activity and Specificity of the *Cuphea Hookeriana* FATB Thioesterase In this example, we demonstrate the ability to modify the activity and specificity of the *Cuphea hookeriana* FATB thioesterase (Ch FATB2, accession U39834) through mutagenesis of specific amino acids. Certain variant FATB are modified in the N-terminal specificity domain, which we described above as influencing the enzymatic fatty acid specificity (FIG. 41). Certain of these mutations are useful in generating natural oils enriched in C8 or C10 fatty acids (e.g. having a fatty acid profile with at least 10% C8, 10% C10, or 10% C8/C10). For example, use of the variants can at least double the C8, C10 percentage or C8/C10 ratio in a natural oil produced by a cell population, as compared to a wildtype FATB.

Based on the ability to generate a novel C12:0-C14:0 thioesterase through mutagenesis of the N-terminal specificity domain, a similar approach was followed to alter the activity of the C8:0-C10 Ch FATB2 thioesterase. Variant FATB genes were cloned into *P. moriformis* via homologous recombination as described in previous examples. FIG. 42A illustrates the sequence alignment of six unique FATB thioesterases relative to the Ch FATB2. Six chimeric FATBs were generated in which the highlighted N-terminal specificity domain of the Ch FATB2 was mutated to match the same region from each of the six alternative FATB sequences. This resulted in Ch FATB2 chimeras with as few as two, to as many 13 amino acid substitutions (FIG. 42B). The activity of each Ch FATB2 chimera was tested by expression within *Prototheca moriformis*. The fatty acid profiles of each chimera were compared to the expression of the wild-type FATB thioesterases (FIGS. 43-48).

Interestingly, *P. moriformis* strains expressing D3126-D3129, or D3131 had little or no C8:0-C10:0 fatty acid accumulation above non-transformed strains. However, *P. moriformis* strains expressing D3130 exhibited significant accumulation of C8:0-C10:0 fatty acids. In fact, the degree of C8:0-C10:0 accumulation for the D3130 chimera was greater than what was observed in strains expressing the wild-type D3042 Ch FATB2 (19.6% versus 9.7% C8:0-C10:0 sum, respectively). Moreover, the ratio of C8:0-C10:0 within D3130 strains was higher than what was observed in wild-type D3042 Ch FATB2 (0.49 versus 0.26 C8:0/C10:0, respectively) strains. These results suggest the D3130 Ch FATB2 chimera exhibits improved enzymatic activity as well as an altered specificity relative to the wild-type D3042 Ch FATB2.

The D3130 chimera contains two amino acid substitutions relative to the wild-type D3042 Ch FATB2. Both amino acid substitutions are located on helixes within the model structure. The His163-Tyr substitution is found within the same helix which contained three of the four amino acid substitutions present in the D1777 Uc FATB2 Chimera F. The Leu186-Pro substitution appears to be across from a published Met230-Iso substitution that improves the enzymatic activity of the *C. palustris* FATB1. Therefore, it is possible that the His163-Tyr substitution is responsible for the altered C8:0-C10 ratio while the Leu186-Pro substitution improves the accumulation of total C8:0-C10:0 fatty acids. These variations can be used synergistically. For example, a strain with both H163Y and L186P variations increased C8 from 1.8% to 6.5%, increased C10 from 7.44% to 13.11% and increased the C8/C10 ratio from 0.23 to 0.51.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

Sequence ID No: 1 - Construct D1022 [pSZ2037], also written as
6SA::Cr(btub)-syn(yINV)-Cv(nr):Pm(amt03)-Cp(SAD1tp)-Cc(TE2)-
Uc(TE2)-chimeraA-Cv(nr)::6sB.
gctcttcgccgccgccactcctgctcgagcgcgcccgcgcgtgcgccgccagcgccttggccttttc
gccgcgctcgtgcgcgtcgctgatgtccatcaccaggtccatgaggtctgccttgcgccggctgagc
cactgcttcgtccgggcggccaagaggagcatgagggaggactcctggtccagggtcctgacgtggt
cgcggctctgggagcgggccagcatcatctggctctgccgcaccgaggccgcctccaactggtcctc
cagcagccgcagtcgccgccgaccctggcagaggaagacaggtgaggggtgtatgaattgtacagaa
caaccacgagccttgtctaggcagaatccctaccagtcatggctttacctggatgacggcctgcgaa
cagctgtccagcgaccctcgctgccgccgcttctcccgcacgcttctttccagcaccgtgatggcgc
gagccagcgccgcacgctggcgctgcgcttcgccgatctgaggacagtcggggaactctgatcagtc
taaacccccttgcgcgttagtgttgccatcctttgcagaccggtgagagccgacttgttgtgcgcca
ccccccacaccacctcctcccagaccaattctgtcacctttttggcgaaggcatcggcctcggcctg
cagagaggacagcagtgcccagccgctggggggttggcggatgcacgctcaggtaccctttcttgcgc
tatgacacttccagcaaaaggtagggcgggctgcgagacggcttcccggcgctgcatgcaacaccga
tgatgcttcgacccccccgaagctccttcggggctgcatgggcgctccgatgccgctccagggcgagc
gctgtttaaatagccaggcccccgattgcaaagacattatagcgagctaccaaagccatattcaaac
acctagatcactaccacttctacacaggccactcgagcttgtgatcgcactccgctaagggggcgcc
tcttcctcttcgtttcagtcacaacccgcaaacggcgcgccATGctgctgcaggccttcctgttcct
gctggccggcttcgccgccaagatcagcgcctccatgacgaacgagacgtccgaccgccccctggtg
cacttcacccccaacaagggctggatgaacgaccccaacggcctgtggtacgacgagaaggacgcca
agtggcacctgtacttccagtacaacccgaacgacaccgtctgggggacgcccttgttctggggcca
cgccacgtccgacgacctgaccaactgggaggaccagcccatcgccatcgccccgaagcgcaacgac
tccggcgccttctccggctccatggtggtggactacaacaacacctccggcttcttcaacgacacca
tcgacccgcgccagcgctgcgtggccatctggacctacaacaccccggagtccgaggagcagtacat
ctcctacagcctggacggcggctacaccttcaccgagtaccagaagaaccccgtgctggccgccaac
tccacccagttccgcgacccgaaggtcttctggtacgagccctcccagaagtggatcatgaccgcgg
ccaagtcccaggactacaagatcgagatctactcctccgacgacctgaagtcctggaagctggagtc
cgcgttcgccaacgagggcttcctcggctaccagtacgagtgccccggcctgatcgaggtccccacc
gagcaggaccccagcaagtcctactgggtgatgttcatctccatcaaccccggcgccccggccggcg
gctccttcaaccagtacttcgtcggcagcttcaacggcacccacttcgaggccttcgacaaccagtc
ccgcgtggtggacttcggcaaggactactacgccctgcagaccttcttcaacaccgacccgacctac
gggagcgccctgggcatcgcgtgggcctccaactgggagtactccgccttcgtgcccaccaacccct
ggcgctcctccatgtccctcgtgcgcaagttctccctcaacaccgagtaccaggccaacccggagac
ggagctgatcaacctgaaggccgagccgatcctgaacatcagcaacgccggcccctggagccggttc
gccaccaacaccacgttgacgaaggccaacagctacaacgtcgacctgtccaacagcaccggcaccc
tggagttcgagctggtgtacgccgtcaacaccacccagacgatctccaagtccgtgttcgcggacct
ctccctctggttcaagggcctggaggaccccgaggagtacctccgcatgggcttcgaggtgtccgcg
tcctccttcttcctggaccgcgggaacagcaaggtgaagttcgtgaaggagaacccctacttcacca
accgcatgagcgtgaacaaccagcccttcaagagcgagaacgacctgtcctactacaaggtgtacgg
cttgctggaccagaacatcctggagctgtacttcaacgacggcgacgtcgtgtccaccaacacctac
ttcatgaccaccgggaacgccctgggctccgtgaacatgacgacgggggtggacaacctgttctaca
tcgacaagttccaggtgcgcgaggtcaagTGAcaattggcagcagcagctcggatagtatcgacaca
ctctggacgctggtcgtgtgatggactgttgccgccacacttgctgccttgacctgtgaatatccct
gccgcttttatcaaacagcctcagtgtgtttgatcttgtgtgtacgcgcttttgcgagttgctagct
gcttgtgctatttgcgaataccacccccagcatccccttccctcgtttcatatcgcttgcatcccaa
ccgcaacttatctacgctgtcctgctatccctcagcgctgctcctgctcctgctcactgcccctcgc
acagccttggtttgggctccgcctgtattctcctggtactgcaacctgtaaaccagcactgcaatgc
tgatgcacgggaagtagtgggatgggaacacaaatggaggatcccgcgtctcgaacagagcgcgcag
aggaacgctgaaggtctcgcctctgtcgcacctcagcgcggcatacaccacaataaccacctgacga
atgcgcttggttcttcgtccattagcgaagcgtccggttcacacacgtgccacgttggcgaggtggc
aggtgacaatgatcggtggagctgatggtcgaaacgttcacagcctagggatatcgaattcGGCCGA
CAGGACGCGCGTCAAAGGTGCTGGTCGTGTATGCCCTGGCCGGCAGGTCGTTGCTGCTGCTGGTTAG
TGATTCCGCAACCCTGATTTTGGCGTCTTATTTTGGCGTGGCAAACGCTGGCGCCCGCGAGCCGGGC
CGGCGGCGATGCGGTGCCCCACGGCTGCCGGAATCCAAGGGAGGCAAGAGCGCCCGGGTCAGTTGAA
GGGCTTTACGCGCAAGGTACAGCCGCTCCTGCAAGGCTGCGTGGTGGAATTGGACGTGCAGGTCCTG
CTGAAGTTCCTCCACCGCCTCACCAGCGGACAAAGCACCGGTGTATCAGGTCCGTGTCATCCACTCT
AAAGAGCTCGACTACGACCTACTGATGGCCCTAGATTCTTCATCAAAAACGCCTGAGACACTTGCCC
AGGATTGAAACTCCCTGAAGGGACCACCAGGGGCCCTGAGTTGTTCCTTCCCCCCGTGGCGAGCTGC
CAGCCAGGCTGTACCTGTGATCGAGGCTGGCGGGAAAATAGGCTTCGTGTGCTCAGGTCATGGGAGG
TGCAGGACAGCTCATGAAACGCCAACAATCGCACAATTCATGTCAAGCTAATCAGCTATTTCCTCTT
CACGAGCTGTAATTGTCCCAAAATTCTGGTCTACCGGGGGTGATCCTTCGTGTACGGGCCCTTCCCT
CAACCCTAGGTATGCGCGCATGCGGTCGCCGCGCAACTCGCGCGAGGGCCGAGGGTTTGGGACGGGC
CGTCCCGAAATGCAGTTGCACCCGGATGCGTGGCACCTTTTTTGCGATAATTTATGCAATGGACTGC
TCTGCAAAATTCTGGCTCTGTCGCCAACCCTAGGATCAGCGGCGTAGGATTTCGTAATCATTCGTCC
TGATGGGGAGCTACCGACTACCCTAATATCAGCCCGACTGCCTGACGCCAGCGTCCACTTTTGTGCA
CACATTCCATTCGTGCCCAAGACATTTCATTGTGGTGCGAAGCGTCCCCAGTTACGCTCACCTGTTT
CCCGACCTCCTTACTGTTCTGTCGACAGAGCGGGCCCACAGGCCGGTCGCAGCCactagtAACAATG
GCCACCGCATCCACTTTCTCGGCGTTCAATGCCCGCTGCGGCGACCTGCGTCGCTCGGCGGGCTCCG
GGCCCCGGCGCCCAGCGAGGCCCCTCCCCGTGCGCGggcgcgccCCCGACTGGTCCATGCTGTTCGC
CGTGATCACCACCATCTTCTCCGCCGCCGAGAAGCAGTGGACCAACCTGGAGTGGAAGCCCAAGCCC
AACCCCCCCCAGCTGCTGGACGACCACTTCGGCCCCCACGGCCTGGTGTTCCGCCGCACCTTCGCCA
TCCGCAGCTACGAGGTGGGCCCCGACCGCTCCACCAGCATCGTGGCCGTGATGAACCACCTGCAGGA
GGCCGCCCTGAACCACGCCAAGTCCGTGGGCATCCTGGGCGACGGCTTCGGCACCACCCTGGAGATG
TCCAAGCGCGACCTGATCTGGGTGGTGAAGCGCACCCACGTGGCCGTGGAGCGCTACCCCGCCTGGG
GCGACACCGTGGAGGTGGAGTGCTGGATCGGCGCCAGCGGCAACAACGGCATGCGCCGCGACTTCCT
GGTGCGCGACTGCAAGACCGGCGAGATCCTGACCCGCTGCACCTCCCTGAGCGTGCTGATGAACACC
CGCACCCGCCGCCTGAGCACCATCCCCGACGAGGTGCGCGGCGAGATCGGCCCCGCCTTCATCGACA
ACGTGGCCGTGAAGGACGACGAGATCAAGAAGCTGCAGAAGCTGAACGACTCCACCGCCGACTACAT -continued

INFORMAL SEQUENCE LISTING

CCAGGGCGGCCTGACCCCCCGCTGGAACGACCTGGACGTGAACCAGCACGTGAACAACCTGAAGTAC
GTGGCCTGGGTGTTCGAGACCGTGCCCGACAGCATCTTCGAGTCCCACCACATCAGCTCCTTCACCC
TGGAGTACCGCCGCGAGTGCACCCGCGACTCCGTGCTGCGCAGCCTGACCACCGTGAGCGGCGGCAG
CTCCGAGGCCGGCCTGGTGTGCGACCACCTGCTGCAGCTGGAGGGCGGCAGCGAGGTGCTGCGCGCC
CGCACCGAGTGGCGCCCCAAGCTGACCGACTCCTTCCGCGGCATCAGCGTGATCCCCGCCGAGCCCC
GCGTGatggactacaaggaccacgacggcgactacaaggaccacgacatcgactacaaggacgacga
cgacaagtgactcgaggcagcagcagctcggatagtatcgacacactctggacgctggtcgtgtgat
ggactgttgccgccacacttgctgccttgacctgtgaatatccctgccgcttttatcaaacagcctc
agtgtgtttgatcttgtgtgtacgcgcttttgcgagttgctagctgcttgtgctatttgcgaatacc
acccccagcatccccttccctcgtttcatatcgcttgcatcccaaccgcaacttatctacgctgtcc
tgctatccctcagcgctgctcctgctcctgctcactgcccctcgcacagccttggtttgggctccgc
ctgtattctcctggtactgcaacctgtaaaccagcactgcaatgctgatgcacgggaagtagtggga
tgggaacacaaatggaaagcttgagctcttgttttccagaaggagttgctccttgagcctttcattc
tcagcctcgataacctccaaagccgctctaattgtggagggggttcgaatttaaaagcttggaatgt
tggttcgtgcgtctggaacaagcccagacttgttgctcactgggaaaaggaccatcagctccaaaaa
acttgccgctcaaaccgcgtacctctgctttcgcgcaatctgccctgttgaaatcgccaccacattc
atattgtgacgcttgagcagtctgtaattgcctcagaatgtggaatcatctgcccccctgtgcgagcc
catgccaggcatgtcgcgggcgaggacacccgccactcgtacagcagaccattatgctacctcacaa
tagttcataacagtgaccatatttctcgaagctccccaacgagcacctccatgctctgagtggccac
cccccggccctggtgcttgcggagggcaggtcaaccggcatggggctaccgaaatccccgaccggat
cccaccacccccgcgatgggaagaatctctccccgggatgtgggcccaccaccagcacaacctgctg
gcccaggcgagcgtcaaaccataccacacaaatatccttggcatcggccctgaattccttctgccgc
tctgctacccggtgcttctgtccgaagcaggggttgctagggatcgctccgagtccgcaaacccttg
tcgcgtggcggggcttgttcgagcttgaagagc Sequence ID No: 2 - nucleic acid sequence of *C. protothecoides* SAD1 transit peptide followed by *C. camphorum* and *U. californica* chimeric thioesterase in Construct D1022 [pSZ2037].

ATGGCCACCGCATCCACTTTCTCGGCGTTCAATGCCCGCTGCGGCGACCTGCGTCGCTCGGCGGGCT
CCGGGCCCCGGCGCCCAGCGAGGCCCCTCCCCGTGCGCGggcgcgccCCCGACTGGTCCATGCTGTT
CGCCGTGATCACCACCATCTTCTCCGCCGCCGAGAAGCAGTGGACCAACCTGGAGTGGAAGCCCAAG
CCCAACCCCCCCCAGCTGCTGGACGACCACTTCGGCCCCCACGGCCTGGTGTTCCGCCGCACCTTCG
CCATCCGCAGCTACGAGGTGGGCCCCGACCGCTCCACCAGCATCGTGGCCGTGATGAACCACCTGCA
GGAGGCCGCCCTGAACCACGCCAAGTCCGTGGGCATCCTGGGCGACGGCTTCGGCACCACCCTGGAG
ATGTCCAAGCGCGACCTGATCTGGGTGGTGAAGCGCACCCACGTGGCCGTGGAGCGCTACCCCGCCT
GGGGCGACACCGTGGAGGTGGAGTGCTGGATCGGCGCCAGCGGCAACAACGGCATGCGCCGCGACTT
CCTGGTGCGCGACTGCAAGACCGGCGAGATCCTGACCCGCTGCACCTCCCTGAGCGTGCTGATGAAC
ACCCGCACCCGCCGCCTGAGCACCATCCCCGACGAGGTGCGCGGCGAGATCGGCCCCGCCTTCATCG
ACAACGTGGCCGTGAAGGACGACGAGATCAAGAAGCTGCAGAAGCTGAACGACTCCACCGCCGACTA
CATCCAGGGCGGCCTGACCCCCCGCTGGAACGACCTGGACGTGAACCAGCACGTGAACAACCTGAAG
TACGTGGCCTGGGTGTTCGAGACCGTGCCCGACAGCATCTTCGAGTCCCACCACATCAGCTCCTTCA
CCCTGGAGTACCGCCGCGAGTGCACCCGCGACTCCGTGCTGCGCAGCCTGACCACCGTGAGCGGCGG
CAGCTCCGAGGCCGGCCTGGTGTGCGACCACCTGCTGCAGCTGGAGGGCGGCAGCGAGGTGCTGCGC
GCCCGCACCGAGTGGCGCCCCAAGCTGACCGACTCCTTCCGCGGCATCAGCGTGATCCCCGCCGAGC
CCCGCGTG Sequence ID No: 3 - amino acid sequence of *C. protothecoides* SAD1 transit peptide followed by *C. camphorum* and *U. californica* chimeric thioesterase encoded by Construct D1022 [pSZ2037].

MATASTFSAFNARCGDLRRSAGSGPRRPARPLPVRGRAPDWSMLFAVITTIFSAAEKQWTNLEWKPK
PNPPQLLDDHFGPHGLVFRRTFAIRSYEVGPDRSTSIVAVMNHLQEAALNHAKSVGILGDGFGTTLE
MSKRDLIWVVKRTHVAVERYPAWGDTVEVECWIGASGNNGMRRDFLVRDCKTGEILTRCTSLSVLMN
TRTRRLSTIPDEVRGEIGPAFIDNVAVKDDEIKKLQKLNDSTADYIQGGLTPRWNDLDVNQHVNNLK
YVAWVFETVPDSIFESHHISSFTLEYRRECTRDSVLRSLTTVSGGSSEAGLVCDHLLQLEGGSEVLR
ARTEWRPKLTDSFRGISVIPAEPRV

Sequence ID No: 4 - nucleic acid sequence of *C. camphorum* and *U. californica* chimeric thioesterase in Construct D1022 [pSZ2037].

CCCGACTGGTCCATGCTGTTCGCCGTGATCACCACCATCTTCTCCGCCGCCGAGAAGCAGTGGACCA
ACCTGGAGTGGAAGCCCAAGCCCAACCCCCCCCAGCTGCTGGACGACCACTTCGGCCCCCACGGCCT
GGTGTTCCGCCGCACCTTCGCCATCCGCAGCTACGAGGTGGGCCCCGACCGCTCCACCAGCATCGTG
GCCGTGATGAACCACCTGCAGGAGGCCGCCCTGAACCACGCCAAGTCCGTGGGCATCCTGGGCGACG
GCTTCGGCACCACCCTGGAGATGTCCAAGCGCGACCTGATCTGGGTGGTGAAGCGCACCCACGTGGC
CGTGGAGCGCTACCCCGCCTGGGGCGACACCGTGGAGGTGGAGTGCTGGATCGGCGCCAGCGGCAAC
AACGGCATGCGCCGCGACTTCCTGGTGCGCGACTGCAAGACCGGCGAGATCCTGACCCGCTGCACCT
CCCTGAGCGTGCTGATGAACACCCGCACCCGCCGCCTGAGCACCATCCCCGACGAGGTGCGCGGCGA
GATCGGCCCCGCCTTCATCGACAACGTGGCCGTGAAGGACGACGAGATCAAGAAGCTGCAGAAGCTG
AACGACTCCACCGCCGACTACATCCAGGGCGGCCTGACCCCCCGCTGGAACGACCTGGACGTGAACC
AGCACGTGAACAACCTGAAGTACGTGGCCTGGGTGTTCGAGACCGTGCCCGACAGCATCTTCGAGTC
CCACCACATCAGCTCCTTCACCCTGGAGTACCGCCGCGAGTGCACCCGCGACTCCGTGCTGCGCAGC
CTGACCACCGTGAGCGGCGGCAGCTCCGAGGCCGGCCTGGTGTGCGACCACCTGCTGCAGCTGGAGG
GCGGCAGCGAGGTGCTGCGCGCCCGCACCGAGTGGCGCCCCAAGCTGACCGACTCCTTCCGCGGCAT
CAGCGTGATCCCCGCCGAGCCCCGCGTG

-continued

INFORMAL SEQUENCE LISTING

Sequence ID No: 5 - amino acid sequence of *C. camphorum* and *U. californica* chimeric thioesterase encoded by Construct D1022 [pSZ2037].
PDWSMLFAVITTIFSAAEKQWTNLEWKPKPNPPQLLDDHFGPHGLVFRRTFAIRSYEVGP
DRSTSIVAVMNHLQEAALNHAKSVGILGDGFGTTLEMSKRDLIWVVKRTHVAVERYPAWG
DTVEVECWIGASGNNGMRRDFLVRDCKTGEILTRCTSLSVLMNTRTRRLSTIPDEVRGEI
GPAFIDNVAVKDDEIKKLQKLNDSTADYIQGGLTPRWNDLDVNQHVNNLKYVAWVFETVP
DSIFESHHISSFTLEYRRECTRDSVLRSLTTVSGGSSEAGLVCDHLLQLEGGSEVLRART
EWRPKLTDSFRGISVIPAEPRV Sequence ID No: 6 - nucleic acid sequence of *C. camphorum* and *U. californica* chimeric thioesterase in Construct D1023 [pSZ2038]
CCCGACTGGTCCATGCTGTTCGCCGTGATCACCACCATCTTCAGCGCCGCCGAGAAGCAGTGGACCA
ACCTGGAGTGGAAGCCCAAGCCCAAGCTGCCCCAGCTGCTGGACGACCACTTCGGCCTGCACGGCCT
GGTGTTCCGCCGCACCTTCGCCATCCGCTCCTACGAGGTGGGCCCCGACCGCAGCACCTCCATCCTG
GCCGTGATGAACCACATGCAGGAGGCCACCCTGAACCACGCCAAGAGCGTGGGCATCCTGGGCGACG
GCTTCGGCACCACCCTGGAGATGTCCAAGCGCGACCTGATGTGGGTGGTGCGCCGCACCCACGTGGC
CGTGGAGCGCTACCCCACCTGGGGCGACACCGTGGAGGTGGAGTGCTGGGTGGGCGCCTCCGGCAAC
AACGGCCGCCGCCACGACTTCCTGGTGCGCGACTGCAAGACCGGCGAGATCCTGACCCGCTGCACCT
CCCTGAGCGTGATGATGAACACCCGCACCCGCCGCCTGAGCAAGATCCCCGAGGAGGTGCGCGGCGA
GATCGGCCCCGCCTTCATCGACAACGTGGCCGTGAAGGACGAGGAGATCAAGAAGCCCCAGAAGCTG
AACGACTCCACCGCCGACTACATCCAGGGCGGCCTGACCCCCCGCTGGAACGACCTGGACATCAACC
AGCACGTGAACAACATCAAGTACGTGGACTGGATCCTGGAGACCGTGCCCGACAGCATCTTCGAGAG
CCACCACATCTCCTCCTTCACCATCGAGTACCGCCGCGAGTGCACCATGGACAGCGTGCTGCAGTCC
CTGACCACCGTGAGCGGCGGCTCCTCCGAGGCCGGCCTGGTGTGCGAGCACCTGCTGCAGCTGGAGG
GCGGCAGCGAGGTGCTGCGCGCCAAGACCGAGTGGCGCCCCAAGCTGACCGACTCCTTCCGCGGCAT
CAGCGTGATCCCCGCCGAGTCCAGCGTG Sequence ID No: 7 - amino acid sequence of *C. camphorum* and *U. californica* chimeric thioesterase encoded by Construct D1023 [pSZ2038]
PDWSMLFAVITTIFSAAEKQWTNLEWKPKPKLPQLLDDHFGLHGLVFRRTFAIRSYEVGP
DRSTSILAVMNHMQEATLNHAKSVGILGDGFGTTLEMSKRDLMWVVRRTHVAVERYPTWG
DTVEVECWVGASGNNGRRHDFLVRDCKTGEILTRCTSLSVMMNTRTRRLSKIPEEVRGEI
GPAFIDNVAVKDEEIKKPQKLNDSTADYIQGGLTPRWNDLDINQHVNNIKYVDWILETVP
DSIFESHHISSFTIEYRRECTMDSVLQSLTTVSGGSSEAGLVCEHLLQLEGGSEVLRAKT
EWRPKLTDSFRGISVIPAESSV Sequence ID No: 8 - nucleic acid sequence of *C. camphorum* and *U. californica* chimeric thioesterase B in Construct D1210 [pSZ2231]
CCCGACTGGTCCATGCTGTTCGCCGTGATCACCACCATCTTCTCCGCCGCCGAGAAGCAGTGGACCA
ACCTGGAGTGGAAGCCCAAGCCCAACCCCCCCCAGCTGCTGGACGACCACTTCGGCCCCCACGGCCT
GGTGTTCCGCCGCACCTTCGCCATCCGCAGCTACGAGGTGGGCCCCGACCGCTCCACCAGCATCGTG
GCCGTGATGAACCACCTGCAGGAGGCCGCCCTGAACCACGCCAAGTCCGTGGGCATCCTGGGCGACG
GCTTCGGCACCACCCTGGAGATGTCCAAGCGCGACCTGATCTGGGTGGTGCGCCGCACCCACGTGGC
CGTGGAGCGCTACCCCACCTGGGGCGACACCGTGGAGGTGGAGTGCTGGATCGGCGCCAGCGGCAAC
AACGGCATGCGCCGCGACTTCCTGGTGCGCGACTGCAAGACCGGCGAGATCCTGACCCGCTGCACCT
CCCTGAGCGTGCTGATGAACACCCGCACCCGCCGCCTGAGCACCATCCCCGACGAGGTGCGCGGCGA
GATCGGCCCCGCCTTCATCGACAACGTGGCCGTGAAGGACGACGAGATCAAGAAGCTGCAGAAGCTG
AACGACTCCACCGCCGACTACATCCAGGGCGGCCTGACCCCCCGCTGGAACGACCTGGACGTGAACC
AGCACGTGAACAACCTGAAGTACGTGGCCTGGGTGTTCGAGACCGTGCCCGACAGCATCTTCGAGTC
CCACCACATCAGCTCCTTCACCCTGGAGTACCGCCGCGAGTGCACCCGCGACTCCGTGCTGCGCAGC
CTGACCACCGTGAGCGGCGGCAGCTCCGAGGCCGGCCTGGTGTGCGACCACCTGCTGCAGCTGGAGG
GCGGCAGCGAGGTGCTGCGCGCCCGCACCGAGTGGCGCCCCAAGCTGACCGACTCCTTCCGCGGCAT
CAGCGTGATCCCCGCCGAGCCCCGCGTG Sequence ID No: 9 - amino acid sequence of *C. camphorum* and *U. californica* chimeric thioesterase B encoded by Construct D1210 [pSZ2231]
PDWSMLFAVITTIFSAAEKQWTNLEWKPKPNPPQLLDDHFGPHGLVFRRTFAIRSYEVGP
DRSTSIVAVMNHLQEAALNHAKSVGILGDGFGTTLEMSKRDLIWVVRRTHVAVERYPTWG
DTVEVECWIGASGNNGMRRDFLVRDCKTGEILTRCTSLSVLMNTRTRRLSTIPDEVRGEI
GPAFIDNVAVKDDEIKKLQKLNDSTADYIQGGLTPRWNDLDVNQHVNNLKYVAWVFETVP
DSIFESHHISSFTLEYRRECTRDSVLRSLTTVSGGSSEAGLVCDHLLQLEGGSEVLRART
EWRPKLTDSFRGISVIPAEPRV Sequence ID No: 10 - nucleic acid sequence of *C. camphorum* and *U. californica* chimeric thioesterase C in Construct D1211 [pSZ2232]
CCCGACTGGTCCATGCTGTTCGCCGTGATCACCACCATCTTCTCCGCCGCCGAGAAGCAGTGGACCA
ACCTGGAGTGGAAGCCCAAGCCCAACCCCCCCCAGCTGCTGGACGACCACTTCGGCCCCCACGGCCT
GGTGTTCCGCCGCACCTTCGCCATCCGCAGCTACGAGGTGGGCCCCGACCGCTCCACCTCCATCCTG
GCCGTGATGAACCACATGCAGGAGGCCACCCTGAACCACGCCAAGAGCGTGGGCATCCTGGGCGACG
GCTTCGGCACCACCCTGGAGATGTCCAAGCGCGACCTGATGTGGGTGGTGCGCCGCACCCACGTGGC
CGTGGAGCGCTACCCCACCTGGGGCGACACCGTGGAGGTGGAGTGCTGGATCGGCGCCAGCGGCAAC
AACGGCATGCGCCGCGACTTCCTGGTGCGCGACTGCAAGACCGGCGAGATCCTGACCCGCTGCACCT
CCCTGAGCGTGCTGATGAACACCCGCACCCGCCGCCTGAGCACCATCCCCGACGAGGTGCGCGGCGA -continued

| INFORMAL SEQUENCE LISTING |
|---|
| GATCGGCCCCGCCTTCATCGACAACGTGGCCGTGAAGGACGACGAGATCAAGAAGCTGCAGAAGCTG<br>AACGACTCCACCGCCGACTACATCCAGGGCGGCCTGACCCCCCGCTGGAACGACCTGGACGTGAACC<br>AGCACGTGAACAACCTGAAGTACGTGGCCTGGGTGTTCGAGACCGTGCCCGACAGCATCTTCGAGTC<br>CCACCACATCAGCTCCTTCACCCTGGAGTACCGCCGCGAGTGCACCCGCGACTCCGTGCTGCGCAGC<br>CTGACCACCGTGAGCGGCGGCAGCTCCGAGGCCGGCCTGGTGTGCGACCACCTGCTGCAGCTGGAGG<br>GCGGCAGCGAGGTGCTGCGCGCCCGCACCGAGTGGCGCCCCAAGCTGACCGACTCCTTCCGCGGCAT<br>CAGCGTGATCCCCGCCGAGCCCCGCGTG |
| Sequence ID No: 11 - amino acid sequence of *C. camphorum* and *U. californica* chimeric thioesterase C encoded by Construct D1211 [pSZ2232]<br>PDWSMLFAVITTIFSAAEKQWTNLEWKPKPNPPQLLDDHFGPHGLVFRRTFAIRSYEVGP<br>DRSTSILAVMNHMQEATLNHAKSVGILGDGFGTTLEMSKRDLMWVVRRTHVAVERYPTWG<br>DTVEVECWIGASGNNGMRRDFLVRDCKTGEILTRCTSLSVLMNTRTRRLSTIPDEVRGEI<br>GPAFIDNVAVKDDEIKKLQKLNDSTADYIQGGLTPRWNDLDVNQHVNNLKYVAWVFETVP<br>DSIFESHHISSFTLEYRRECTRDSVLRSLTTVSGGSSEAGLVCDHLLQLEGGSEVLRART<br>EWRPKLTDSFRGISVIPAEPRV |
| Sequence ID No: 12 - nucleic acid sequence of *C. camphorum* and *U. californica* chimeric thioesterase D in Construct D1212 [pSZ2233]<br>CCCGACTGGTCCATGCTGTTCGCCGTGATCACCACCATCTTCTCCGCCGCCGAGAAGCAGTGGACCA<br>ACCTGGAGTGGAAGCCCAAGCCCAAGCTGCCCCAGCTGCTGGACGACCACTTCGGCCTGCACGGCCT<br>GGTGTTCCGCCGCACCTTCGCCATCCGCTCCTACGAGGTGGGCCCCGACCGCAGCACCTCCATCCTG<br>GCCGTGATGAACCACATGCAGGAGGCCACCCTGAACCACGCCAAGAGCGTGGGCATCCTGGGCGACG<br>GCTTCGGCACCACCCTGGAGATGTCCAAGCGCGACCTGATGTGGGTGGTGCGCCGCACCCACGTGGC<br>CGTGGAGCGCTACCCCACCTGGGGCGACACCGTGGAGGTGGAGTGCTGGATCGGCGCCAGCGGCAAC<br>AACGGCATGCGCCGCGACTTCCTGGTGCGCGACTGCAAGACCGGCGAGATCCTGACCCGCTGCACCT<br>CCCTGAGCGTGCTGATGAACACCCGCACCCGCCGCCTGAGCACCATCCCCGACGAGGTGCGCGGCGA<br>GATCGGCCCCGCCTTCATCGACAACGTGGCCGTGAAGGACGACGAGATCAAGAAGCTGCAGAAGCTG<br>AACGACTCCACCGCCGACTACATCCAGGGCGGCCTGACCCCCCGCTGGAACGACCTGGACGTGAACC<br>AGCACGTGAACAACCTGAAGTACGTGGCCTGGGTGTTCGAGACCGTGCCCGACAGCATCTTCGAGTC<br>CCACCACATCAGCTCCTTCACCCTGGAGTACCGCCGCGAGTGCACCCGCGACTCCGTGCTGCGCAGC<br>CTGACCACCGTGAGCGGCGGCAGCTCCGAGGCCGGCCTGGTGTGCGACCACCTGCTGCAGCTGGAGG<br>GCGGCAGCGAGGTGCTGCGCGCCCGCACCGAGTGGCGCCCCAAGCTGACCGACTCCTTCCGCGGCAT<br>CAGCGTGATCCCCGCCGAGCCCCGCGTG |
| Sequence ID No: 13 - amino acid sequence of *C. camphorum* and *U. californica* chimeric thioesterase D encoded by Construct D1212 [pSZ2233]<br>PDWSMLFAVITTIFSAAEKQWTNLEWKPKPKLPQLLDDHFGLHGLVFRRTFAIRSYEVGP<br>DRSTSILAVMNHMQEATLNHAKSVGILGDGFGTTLEMSKRDLMWVVRRTHVAVERYPTWG<br>DTVEVECWIGASGNNGMRRDFLVRDCKTGEILTRCTSLSVLMNTRTRRLSTIPDEVRGEI<br>GPAFIDNVAVKDDEIKKLQKLNDSTADYIQGGLTPRWNDLDVNQHVNNLKYVAWVFETVP<br>DSIFESHHISSFTLEYRRECTRDSVLRSLTTVSGGSSEAGLVCDHLLQLEGGSEVLRART<br>EWRPKLTDSFRGISVIPAEPRV |
| Sequence ID No: 14 - nucleic acid sequence of *C. camphorum* and *U. californica* chimeric thioesterase E in Construct D1213 [pSZ2234]<br>CCCGACTGGTCCATGCTGTTCGCCGTGATCACCACCATCTTCTCCGCCGCCGAGAAGCAGTGGACCA<br>ACCTGGAGTGGAAGCCCAAGCCCAAGCTGCCCCAGCTGCTGGACGACCACTTCGGCCTGCACGGCCT<br>GGTGTTCCGCCGCACCTTCGCCATCCGCTCCTACGAGGTGGGCCCCGACCGCAGCACCAGCATCGTG<br>GCCGTGATGAACCACCTGCAGGAGGCCGCCCTGAACCACGCCAAGTCCGTGGGCATCCTGGGCGACG<br>GCTTCGGCACCACCCTGGAGATGTCCAAGCGCGACCTGATCTGGGTGGTGCGCCGCACCCACGTGGC<br>CGTGGAGCGCTACCCCACCTGGGGCGACACCGTGGAGGTGGAGTGCTGGATCGGCGCCAGCGGCAAC<br>AACGGCATGCGCCGCGACTTCCTGGTGCGCGACTGCAAGACCGGCGAGATCCTGACCCGCTGCACCT<br>CCCTGAGCGTGCTGATGAACACCCGCACCCGCCGCCTGAGCACCATCCCCGACGAGGTGCGCGGCGA<br>GATCGGCCCCGCCTTCATCGACAACGTGGCCGTGAAGGACGACGAGATCAAGAAGCTGCAGAAGCTG<br>AACGACTCCACCGCCGACTACATCCAGGGCGGCCTGACCCCCCGCTGGAACGACCTGGACGTGAACC<br>AGCACGTGAACAACCTGAAGTACGTGGCCTGGGTGTTCGAGACCGTGCCCGACAGCATCTTCGAGTC<br>CCACCACATCAGCTCCTTCACCCTGGAGTACCGCCGCGAGTGCACCCGCGACTCCGTGCTGCGCAGC<br>CTGACCACCGTGAGCGGCGGCAGCTCCGAGGCCGGCCTGGTGTGCGACCACCTGCTGCAGCTGGAGG<br>GCGGCAGCGAGGTGCTGCGCGCCCGCACCGAGTGGCGCCCCAAGCTGACCGACTCCTTCCGCGGCAT<br>CAGCGTGATCCCCGCCGAGCCCCGCGTG |
| Sequence ID No: 15 - amino acid sequence of *C. camphorum* and *U. californica* chimeric thioesterase E encoded by Construct D1213 [pSZ2234]<br>PDWSMLFAVITTIFSAAEKQWTNLEWKPKPKLPQLLDDHFGLHGLVFRRTFAIRSYEVGP<br>DRSTSIVAVMNHLQEAALNHAKSVGILGDGFGTTLEMSKRDLIWVVRRTHVAVERYPTWG<br>DTVEVECWIGASGNNGMRRDFLVRDCKTGEILTRCTSLSVLMNTRTRRLSTIPDEVRGEI<br>GPAFIDNVAVKDDEIKKLQKLNDSTADYIQGGLTPRWNDLDVNQHVNNLKYVAWVFETVP<br>DSIFESHHISSFTLEYRRECTRDSVLRSLTTVSGGSSEAGLVCDHLLQLEGGSEVLRART<br>EWRPKLTDSFRGISVIPAEPRV |

-continued

INFORMAL SEQUENCE LISTING

Sequence ID No: 16 - Construct pSZ2084, also written as
6SA::CrTUB2-ScSUC2-CvNR:PmAMT3-CpSAD1tpExt-UcFATB2-CvNR::6SB,
comprising an extended heterologous transit peptide from *C. protothecoides*
extended to include 15 additional amino acids from
the SAD1 transit peptide and flanking region
gctcttcgccgccgccactcctgctcgagcgcgcccgcgcgtgcgccgccagcgccttggccttttc
gccgcgctcgtgcgcgtcgctgatgtccatcaccaggtccatgaggtctgccttgcgccggctgagc
cactgcttcgtccgggcggccaagaggagcatgagggaggactcctggtccagggtcctgacgtggt
cgcggctctgggagcgggccagcatcatctggctctgccgcaccgaggccgcctccaactggtcctc
cagcagccgcagtcgccgccgaccctggcagaggaagacaggtgaggggtgtatgaattgtacagaa
caaccacgagccttgtctaggcagaatccctaccagtcatggctttacctggatgacggcctgcgaa
cagctgtccagcgaccctcgctgccgccgcttctcccgcacgcttctttccagcaccgtgatggcgc
gagccagcgccgcacgctggcgctgcgcttcgccgatctgaggacagtcggggaactctgatcagtc
taaacccccttgcgcgttagtgttgccatcctttgcagaccggtgagagccgacttgttgtgcgcca
cccccacaccacctcctcccagaccaattctgtcacctttttggcgaaggcatcggcctcggcctg
cagagaggacagcagtgcccagccgctggggggttggcggatgcacgctcaggtaccctttcttgcgc
tatgacacttccagcaaaaggtagggcgggctgcgagacggcttcccggcgctgcatgcaacaccga
tgatgcttcgacccccccgaagctccttcggggctgcatgggcgctccgatgccgctccagggcgagc
gctgtttaaatagccaggcccccgattgcaaagacattatagcgagctaccaaagccatattcaaac
acctagatcactaccacttctacacaggccactcgagcttgtgatcgcactccgctaagggggcgcc
tcttcctcttcgtttcagtcacaacccgcaaacggcgcgccATGctgctgcaggccttcctgttcct
gctggccggcttcgccgccaagatcagcgcctccatgacgaacgagacgtccgaccgccccctggtg
cacttcacccccaacaagggctggatgaacgaccccaacggcctgtggtacgacgagaaggacgcca
agtggcacctgtacttccagtacaacccgaacgacaccgtctgggggacgcccttgttctggggcca
cgccacgtccgacgacctgaccaactgggaggaccagcccatcgccatcgccccgaagcgcaacgac
tccggcgccttctccggctccatggtggtggactacaacaacacctccggcttcttcaacgacacca
tcgacccgcgccagcgctgcgtggccatctggacctacaacaccccggagtccgaggagcagtacat
ctcctacagcctggacggcggctacaccttcaccgagtaccagaagaaccccgtgctggccgccaac
tccacccagttccgcgacccgaaggtcttctggtacgagccctcccagaagtggatcatgaccgcgg
ccaagtcccaggactacaagatcgagatctactcctccgacgacctgaagtcctggaagctggagtc
cgcgttcgccaacgagggcttcctcggctaccagtacgagtgccccggcctgatcgaggtccccacc
gagcaggaccccagcaagtcctactgggtgatgttcatctccatcaaccccggcgccccggccggcg
gctccttcaaccagtacttcgtcggcagcttcaacggcacccacttcgaggccttcgacaaccagtc
ccgcgtggtggacttcggcaaggactactacgccctgcagaccttcttcaacaccgacccgacctac
gggagcgccctgggcatcgcgtgggcctccaactgggagtactccgccttcgtgcccaccaacccct
ggcgctcctccatgtccctcgtgcgcaagttctccctcaacaccgagtaccaggccaacccggagac
ggagctgatcaacctgaaggccgagccgatcctgaacatcagcaacgccggcccctggagccggttc
gccaccaacaccacgttgacgaaggccaacagctacaacgtcgacctgtccaacagcaccggcaccc
tggagttcgagctggtgtacgccgtcaacaccacccagacgatctccaagtccgtgttcgcggacct
ctccctctggttcaagggcctggaggaccccgaggagtacctccgcatgggcttcgaggtgtccgcg
tcctccttcttcctggaccgcgggaacagcaaggtgaagttcgtgaaggagaacccctacttcacca
accgcatgagcgtgaacaaccagcccttcaagagcgagaacgacctgtcctactacaaggtgtacgg
cttgctggaccagaacatcctggagctgtacttcaacgacggcgacgtcgtgtccaccaacacctac
ttcatgaccaccgggaacgccctgggctccgtgaacatgacgacgggggtggacaacctgttctaca
tcgacaagttccaggtgcgcgaggtcaagTGAcaattggcagcagcagctcggatagtatcgacaca
ctctggacgctggtcgtgtgatggactgttgccgccacacttgctgccttgacctgtgaatatccct
gccgcttttatcaaacagcctcagtgtgtttgatcttgtgtgtacgcgcttttgcgagttgctagct
gcttgtgctatttgcgaataccacccccagcatccccttccctcgtttcatatcgcttgcatcccaa
ccgcaacttatctacgctgtcctgctatccctcagcgctgctcctgctcctgctcactgcccctcgc
acagccttggtttgggctccgcctgtattctcctggtactgcaacctgtaaaccagcactgcaatgc
tgatgcacgggaagtagtgggatgggaacacaaatggaggatcccgcgtctcgaacagagcgcgcag
aggaacgctgaaggtctcgcctctgtcgcacctcagcgcggcatacaccacaataaccacctgacga
atgcgcttggttcttcgtccattagcgaagcgtccggttcacacacgtgccacgttggcgaggtggc
aggtgacaatgatcggtggagctgatggtcgaaacgttcacagcctagggatatcgaattcGGCCGA
CAGGACGCGCGTCAAAGGTGCTGGTCGTGTATGCCCTGGCCGGCAGGTCGTTGCTGCTGCTGGTTAG
TGATTCCGCAACCCTGATTTTGGCGTCTTATTTTGGCGTGGCAAACGCTGGCGCCCGCGAGCCGGGC
CGGCGGCGATGCGGTGCCCCACGGCTGCCGGAATCCAAGGGAGGCAAGAGCGCCCGGGTCAGTTGAA
GGGCTTTACGCGCAAGGTACAGCCGCTCCTGCAAGGCTGCGTGGTGGAATTGGACGTGCAGGTCCTG
CTGAAGTTCCTCCACCGCCTCACCAGCGGACAAAGCACCGGTGTATCAGGTCCGTGTCATCCACTCT
AAAGAGCTCGACTACGACCTACTGATGGCCCTAGATTCTTCATCAAAAACGCCTGAGACACTTGCCC
AGGATTGAAACTCCCTGAAGGGACCACCAGGGGCCCTGAGTTGTTCCTTCCCCCCGTGGCGAGCTGC
CAGCCAGGCTGTACCTGTGATCGAGGCTGGCGGGAAAATAGGCTTCGTGTGCTCAGGTCATGGGAGG
TGCAGGACAGCTCATGAAACGCCAACAATCGCACAATTCATGTCAAGCTAATCAGCTATTTCCTCTT
CACGAGCTGTAATTGTCCCAAAATTCTGGTCTACCGGGGGTGATCCTTCGTGTACGGGCCCTTCCCT
CAACCCTAGGTATGCGCGCATGCGGTCGCCGCGCAACTCGCGCGAGGGCCGAGGGTTTGGGACGGGC
CGTCCCGAAATGCAGTTGCACCCGGATGCGTGGCACCTTTTTTGCGATAATTTATGCAATGGACTGC
TCTGCAAAATTCTGGCTCTGTCGCCAACCCTAGGATCAGCGGCGTAGGATTTCGTAATCATTCGTCC
TGATGGGGAGCTACCGACTACCCTAATATCAGCCCGACTGCCTGACGCCAGCGTCCACTTTTGTGCA
CACATTCCATTCGTGCCCAAGACATTTCATTGTGGTGCGAAGCGTCCCCAGTTACGCTCACCTGTTT
CCCGACCTCCTTACTGTTCTGTCGACAGAGCGGGCCCACAGGCCGGTCGCAGCCactagtAACAATG
GCCACCGCATCCACTTTCTCGGCGTTCAATGCCCGCTGCGGCGACCTGCGTCGCTCGGCGGGCTCCG
GGCCCCGGCGCCCAGCGAGGCCCCTCCCCGTGCGCGCTGCCATCGCCAGCGAGGTCCCCGTGGCCAC
CACCTCCCCCCGGCCCGACTGGTCCATGCTGTTCGCCGTGATCACCACCATCTTCAGCGCCGCCGAG
AAGCAGTGGACCAACCTGGAGTGGAAGCCCAAGCCCAAGCTGCCCCAGCTGCTGGACGACCACTTCG
GCCTGCACGGCCTGGTGTTCCGCCGCACCTTCGCCATCCGCTCCTACGAGGTGGGCCCCGACCGCAG
CACCTCCATCCTGGCCGTGATGAACCACATGCAGGAGGCCACCCTGAACCACGCCAAGAGCGTGGGC -continued

INFORMAL SEQUENCE LISTING

ATCCTGGGCGACGGCTTCGGCACCACCCTGGAGATGTCCAAGCGCGACCTGATGTGGGTGGTGCGCC
GCACCCACGTGGCCGTGGAGCGCTACCCCACCTGGGGCGACACCGTGGAGGTGGAGTGCTGGATCGG
CGCCAGCGGCAACAACGGCATGCGCCGCGACTTCCTGGTGCGCGACTGCAAGACCGGCGAGATCCTG
ACCCGCTGCACCTCCCTGAGCGTGCTGATGAACACCCGCACCCGCCGCCTGAGCACCATCCCCGACG
AGGTGCGCGGCGAGATCGGCCCCGCCTTCATCGACAACGTGGCCGTGAAGGACGACGAGATCAAGAA
GCTGCAGAAGCTGAACGACTCCACCGCCGACTACATCCAGGGCGGCCTGACCCCCCGCTGGAACGAC
CTGGACGTGAACCAGCACGTGAACAACCTGAAGTACGTGGCCTGGGTGTTCGAGACCGTGCCCGACA
GCATCTTCGAGTCCCACCACATCAGCTCCTTCACCCTGGAGTACCGCCGCGAGTGCACCCGCGACTC
CGTGCTGCGCAGCCTGACCACCGTGAGCGGCGGCAGCTCCGAGGCCGGCCTGGTGTGCGACCACCTG
CTGCAGCTGGAGGGCGGCAGCGAGGTGCTGCGCGCCCGCACCGAGTGGCGCCCCAAGCTGACCGACT
CCTTCCGCGGCATCAGCGTGATCCCCGCCGAGCCCCGCGTGatggactacaaggaccacgacggcga
ctacaaggaccacgacatcgactacaaggacgacgacgacaagtgactcgaggcagcagcagctcgg
atagtatcgacacactctggacgctggtcgtgtgatggactgttgccgccacacttgctgccttgac
ctgtgaatatccctgccgcttttatcaaacagcctcagtgtgtttgatcttgtgtgtacgcgctttt
gcgagttgctagctgcttgtgctatttgcgaataccacccccagcatccccttccctcgtttcatat
cgcttgcatcccaaccgcaacttatctacgctgtcctgctatccctcagcgctgctcctgctcctgc
tcactgcccctcgcacagccttggtttgggctccgcctgtattctcctggtactgcaacctgtaaac
cagcactgcaatgctgatgcacgggaagtagtgggatgggaacacaaatggaaagcttgagctcttg
ttttccagaaggagttgctccttgagcctttcattctcagcctcgataacctccaaagccgctctaa
ttgtggagggggttcgaatttaaaagcttggaatgttggttcgtgcgtctggaacaagcccagactt
gttgctcactgggaaaaggaccatcagctccaaaaaacttgccgctcaaaccgcgtacctctgcttt
cgcgcaatctgccctgttgaaatcgccaccacattcatattgtgacgcttgagcagtctgtaattgc
ctcagaatgtggaatcatctgcccccctgtgcgagcccatgccaggcatgtcgcgggcgaggacaccc
gccactcgtacagcagaccattatgctacctcacaatagttcataacagtgaccatatttctcgaag
ctccccaacgagcacctccatgctctgagtggccaccccccggccctggtgcttgcggagggcaggt
caaccggcatggggctaccgaaatccccgaccggatcccaccacccccgcgatgggaagaatctctc
cccgggatgtgggcccaccaccagcacaacctgctggcccaggcgagcgtcaaaccataccacacaa
atatccttggcatcggccctgaattccttctgccgctctgctacccggtgcttctgtccgaagcagg
ggttgctagggatcgctccgagtccgcaaacccttgtcgcgtggcggggcttgttcgagcttgaaga
gc Sequence ID No: 17 - nucleic acid sequence of extended *C. protothecoides* SAD1 transit peptide fused to *U. californica* FATB2 derived sequence in construct D1056 [pSZ2084].
ATGGCCACCGCATCCACTTTCTCGGCGTTCAATGCCCGCTGCGGCGACCTGCGTCGCTCGGCGGGCT
CCGGGCCCCGGCGCCCAGCGAGGCCCCTCCCCGTGCGCGCTGCCATCGCCAGCGAGGTCCCCGTGGC
CACCACCTCCCCCGGCCCGACTGGTCCATGCTGTTCGCCGTGATCACCACCATCTTCAGCGCCGCC
GAGAAGCAGTGGACCAACCTGGAGTGGAAGCCCAAGCCCAAGCTGCCCCAGCTGCTGGACGACCACT
TCGGCCTGCACGGCCTGGTGTTCCGCCGCACCTTCGCCATCCGCTCCTACGAGGTGGGCCCCGACCG
CAGCACCTCCATCCTGGCCGTGATGAACCACATGCAGGAGGCCACCCTGAACCACGCCAAGAGCGTG
GGCATCCTGGGCGACGGCTTCGGCACCACCCTGGAGATGTCCAAGCGCGACCTGATGTGGGTGGTGC
GCCGCACCCACGTGGCCGTGGAGCGCTACCCCACCTGGGGCGACACCGTGGAGGTGGAGTGCTGGAT
CGGCGCCAGCGGCAACAACGGCATGCGCCGCGACTTCCTGGTGCGCGACTGCAAGACCGGCGAGATC
CTGACCCGCTGCACCTCCCTGAGCGTGCTGATGAACACCCGCACCCGCCGCCTGAGCACCATCCCCG
ACGAGGTGCGCGGCGAGATCGGCCCCGCCTTCATCGACAACGTGGCCGTGAAGGACGACGAGATCAA
GAAGCTGCAGAAGCTGAACGACTCCACCGCCGACTACATCCAGGGCGGCCTGACCCCCCGCTGGAAC
GACCTGGACGTGAACCAGCACGTGAACAACCTGAAGTACGTGGCCTGGGTGTTCGAGACCGTGCCCG
ACAGCATCTTCGAGTCCCACCACATCAGCTCCTTCACCCTGGAGTACCGCCGCGAGTGCACCCGCGA
CTCCGTGCTGCGCAGCCTGACCACCGTGAGCGGCGGCAGCTCCGAGGCCGGCCTGGTGTGCGACCAC
CTGCTGCAGCTGGAGGGCGGCAGCGAGGTGCTGCGCGCCCGCACCGAGTGGCGCCCCAAGCTGACCG
ACTCCTTCCGCGGCATCAGCGTGATCCCCGCCGAGCCCCGCGTG Sequence ID No: 18 - amino acid sequence of extended *C. protothecoides* SAD1 transit peptide fused to *U. californica* FATB2 derived sequence encoded by construct D1056 [pSZ2084].
MATASTFSAFNARCGDLRRSAGSGPRRPARPLPVRAAIASEVPVATTSPRPDWSMLFAVI
TTIFSAAEKQWTNLEWKPKPKLPQLLDDHFGLHGLVFRRTFAIRSYEVGPDRSTSILAVM
NHMQEATLNHAKSVGILGDGFGTTLEMSKRDLMWVVRRTHVAVERYPTWGDTVEVECWIG
ASGNNGMRRDFLVRDCKTGEILTRCTSLSVLMNTRTRRLSTIPDEVRGEIGPAFIDNVAV
KDDEIKKLQKLNDSTADYIQGGLTPRWNDLDVNQHVNNLKYVAWVFETVPDSIFESHHIS
SFTLEYRRECTRDSVLRSLTTVSGGSSEAGLVCDHLLQLEGGSEVLRARTEWRPKLTDSF
RGISVIPAEPRV Sequence ID No: 19 - nucleic acid sequence encoding Uc FATB2 with 5 amino acid N-terminal extension in Construct D1057 [pSZ2085]
AGCCTGAAGCGCCTGCCCGACTGGTCCATGCTGTTCGCCGTGATCACCACCATCTTCAGCGCCGCCG
AGAAGCAGTGGACCAACCTGGAGTGGAAGCCCAAGCCCAAGCTGCCCCAGCTGCTGGACGACCACTT
CGGCCTGCACGGCCTGGTGTTCCGCCGCACCTTCGCCATCCGCTCCTACGAGGTGGGCCCCGACCGC
AGCACCTCCATCCTGGCCGTGATGAACCACATGCAGGAGGCCACCCTGAACCACGCCAAGAGCGTGG
GCATCCTGGGCGACGGCTTCGGCACCACCCTGGAGATGTCCAAGCGCGACCTGATGTGGGTGGTGCG
CCGCACCCACGTGGCCGTGGAGCGCTACCCCACCTGGGGCGACACCGTGGAGGTGGAGTGCTGGATC
GGCGCCAGCGGCAACAACGGCATGCGCCGCGACTTCCTGGTGCGCGACTGCAAGACCGGCGAGATCC
TGACCCGCTGCACCTCCCTGAGCGTGCTGATGAACACCCGCACCCGCCGCCTGAGCACCATCCCCGA
CGAGGTGCGCGGCGAGATCGGCCCCGCCTTCATCGACAACGTGGCCGTGAAGGACGACGAGATCAAG
AAGCTGCAGAAGCTGAACGACTCCACCGCCGACTACATCCAGGGCGGCCTGACCCCCCGCTGGAACG
ACCTGGACGTGAACCAGCACGTGAACAACCTGAAGTACGTGGCCTGGGTGTTCGAGACCGTGCCCGA
CAGCATCTTCGAGTCCCACCACATCAGCTCCTTCACCCTGGAGTACCGCCGCGAGTGCACCCGCGAC -continued

| INFORMAL SEQUENCE LISTING |
|---|

TCCGTGCTGCGCAGCCTGACCACCGTGAGCGGCGGCAGCTCCGAGGCCGGCCTGGTGTGCGACCACC
TGCTGCAGCTGGAGGGCGGCAGCGAGGTGCTGCGCGCCCGCACCGAGTGGCGCCCCAAGCTGACCGA
CTCCTTCCGCGGCATCAGCGTGATCCCCGCCGAGCCCCGCGTG

Sequence ID No: 20 - amino acid sequence of Uc FATB2 with 5 amino acid N-terminal extension encoded by Construct D1057 [pSZ2085]
SLKRLPDWSMLFAVITTIFSAAEKQWTNLEWKPKPKLPQLLDDHFGLHGLVFRRTFAIRS
YEVGPDRSTSILAVMNHMQEATLNHAKSVGILGDGFGTTLEMSKRDLMWVVRRTHVAVER
YPTWGDTVEVECWIGASGNNGMRRDFLVRDCKTGEILTRCTSLSVLMNTRTRRLSTIPDE
VRGEIGPAFIDNVAVKDDEIKKLQKLNDSTADYIQGGLTPRWNDLDVNQHVNNLKYVAWV
FETVPDSIFESHHISSFTLEYRRECTRDSVLRSLTTVSGGSSEAGLVCDHLLQLEGGSEV
LRARTEWRPKLTDSFRGISVIPAEPRV Sequence ID No: 21 - nucleic acid sequence encoding Uc FATB2 with 15 amino acid N-terminal extension in Construct D1058 [pSZ2086]
ATCAACGGCACCAAGTTCAGCTACACCGAGAGCCTGAAGCGCCTGCCCGACTGGTCCATGCTGTTCG
CCGTGATCACCACCATCTTCAGCGCCGCCGAGAAGCAGTGGACCAACCTGGAGTGGAAGCCCAAGCC
CAAGCTGCCCCAGCTGCTGGACGACCACTTCGGCCTGCACGGCCTGGTGTTCCGCCGCACCTTCGCC
ATCCGCTCCTACGAGGTGGGCCCCGACCGCAGCACCTCCATCCTGGCCGTGATGAACCACATGCAGG
AGGCCACCCTGAACCACGCCAAGAGCGTGGGCATCCTGGGCGACGGCTTCGGCACCACCCTGGAGAT
GTCCAAGCGCGACCTGATGTGGGTGGTGCGCCGCACCCACGTGGCCGTGGAGCGCTACCCCACCTGG
GGCGACACCGTGGAGGTGGAGTGCTGGATCGGCGCCAGCGGCAACAACGGCATGCGCCGCGACTTCC
TGGTGCGCGACTGCAAGACCGGCGAGATCCTGACCCGCTGCACCTCCCTGAGCGTGCTGATGAACAC
CCGCACCCGCCGCCTGAGCACCATCCCCGACGAGGTGCGCGGCGAGATCGGCCCCGCCTTCATCGAC
AACGTGGCCGTGAAGGACGACGAGATCAAGAAGCTGCAGAAGCTGAACGACTCCACCGCCGACTACA
TCCAGGGCGGCCTGACCCCCCGCTGGAACGACCTGGACGTGAACCAGCACGTGAACAACCTGAAGTA
CGTGGCCTGGGTGTTCGAGACCGTGCCCGACAGCATCTTCGAGTCCCACCACATCAGCTCCTTCACC
CTGGAGTACCGCCGCGAGTGCACCCGCGACTCCGTGCTGCGCAGCCTGACCACCGTGAGCGGCGGCA
GCTCCGAGGCCGGCCTGGTGTGCGACCACCTGCTGCAGCTGGAGGGCGGCAGCGAGGTGCTGCGCGC
CCGCACCGAGTGGCGCCCCAAGCTGACCGACTCCTTCCGCGGCATCAGCGTGATCCCCGCCGAGCCC
CGCGTG Sequence ID No: 22 - amino acid sequence of Uc FATB2 with 15 amino acid N-terminal extension encoded by Construct D1058 [pSZ2086]
INGTKFSYTESLKRLPDWSMLFAVITTIFSAAEKQWTNLEWKPKPKLPQLLDDHFGLHGL
VFRRTFAIRSYEVGPDRSTSILAVMNHMQEATLNHAKSVGILGDGFGTTLEMSKRDLMWV
VRRTHVAVERYPTWGDTVEVECWIGASGNNGMRRDFLVRDCKTGEILTRCTSLSVLMNTR
TRRLSTIPDEVRGEIGPAFIDNVAVKDDEIKKLQKLNDSTADYIQGGLTPRWNDLDVNQH
VNNLKYVAWVFETVPDSIFESHHISSFTLEYRRECTRDSVLRSLTTVSGGSSEAGLVCDH
LLQLEGGSEVLRARTEWRPKLTDSFRGISVIPAEPRV Sequence ID No: 23 - nucleic acid sequence of *Cinnamomum camphorum* 14:0-ACP thioesterase (Cc FATB1/Cc TE, accession U31813) containing a five amino acid N-terminal extension derived from Uc FATB2 in Construct D1431 [pSZ2450]
AGCCTGAAGCGCCTGCCCGACTGGTCCATGCTGTTCGCCGTGATCACCACCATCTTCTCCGCCGCCG
AGAAGCAGTGGACCAACCTGGAGTGGAAGCCCAAGCCCAACCCCCCCCAGCTGCTGGACGACCACTT
CGGCCCCCACGGCCTGGTGTTCCGCCGCACCTTCGCCATCCGCAGCTACGAGGTGGGCCCCGACCGC
TCCACCAGCATCGTGGCCGTGATGAACCACCTGCAGGAGGCCGCCCTGAACCACGCCAAGTCCGTGG
GCATCCTGGGCGACGGCTTCGGCACCACCCTGGAGATGTCCAAGCGCGACCTGATCTGGGTGGTGAA
GCGCACCCACGTGGCCGTGGAGCGCTACCCCGCCTGGGGCGACACCGTGGAGGTGGAGTGCTGGGTG
GGCGCCTCCGGCAACAACGGCCGCCGCCACGACTTCCTGGTGCGCGACTGCAAGACCGGCGAGATCC
TGACCCGCTGCACCTCCCTGAGCGTGATGATGAACACCCGCACCCGCCGCCTGAGCAAGATCCCCGA
GGAGGTGCGCGGCGAGATCGGCCCCGCCTTCATCGACAACGTGGCCGTGAAGGACGAGGAGATCAAG
AAGCCCCAGAAGCTGAACGACTCCACCGCCGACTACATCCAGGGCGGCCTGACCCCCCGCTGGAACG
ACCTGGACATCAACCAGCACGTGAACAACATCAAGTACGTGGACTGGATCCTGGAGACCGTGCCCGA
CAGCATCTTCGAGAGCCACCACATCTCCTCCTTCACCATCGAGTACCGCCGCGAGTGCACCATGGAC
AGCGTGCTGCAGTCCCTGACCACCGTGAGCGGCGGCTCCTCCGAGGCCGGCCTGGTGTGCGAGCACC
TGCTGCAGCTGGAGGGCGGCAGCGAGGTGCTGCGCGCCAAGACCGAGTGGCGCCCCAAGCTGACCGA
CTCCTTCCGCGGCATCAGCGTGATCCCCGCCGAGTCCAGCGTG Sequence ID No: 24 - amino acid sequence of *Cinnamomum camphorum* 14:0-ACP thioesterase (Cc FATB1/Cc TE, accession U31813) containing a five amino acid N-terminal extension derived from Uc FATB2 encoded by Construct D1431 [pSZ2450]
SLKRLPDWSMLFAVITTIFSAAEKQWTNLEWKPKPNPPQLLDDHFGPHGLVFRRTFAIRS
YEVGPDRSTSIVAVMNHLQEAALNHAKSVGILGDGFGTTLEMSKRDLIWVVKRTHVAVER
YPAWGDTVEVECWVGASGNNGRRHDFLVRDCKTGEILTRCTSLSVMMNTRTRRLSKIPEE
VRGEIGPAFIDNVAVKDEEIKKPQKLNDSTADYIQGGLTPRWNDLDINQHVNNIKYVDWI
LETVPDSIFESHHISSFTIEYRRECTMDSVLQSLTTVSGGSSEAGLVCEHLLQLEGGSEV
LRAKTEWRPKLTDSFRGISVIPAESSV -continued

INFORMAL SEQUENCE LISTING

Sequence ID No: 25 - nucleic acid sequence of *Cinnamomum camphorum* 14:0-ACP thioesterase (Cc FATB1/Cc TE, accession U31813) containing a five amino acid N-terminal extension derived from Cc FATB1 in Construct D1432 [pSZ2451]
AGCCTGAAGAAGCTGCCCGACTGGTCCATGCTGTTCGCCGTGATCACCACCATCTTCTCCGCCGCCG
AGAAGCAGTGGACCAACCTGGAGTGGAAGCCCAAGCCCAACCCCCCCCAGCTGCTGGACGACCACTT
CGGCCCCCACGGCCTGGTGTTCCGCCGCACCTTCGCCATCCGCAGCTACGAGGTGGGCCCCGACCGC
TCCACCAGCATCGTGGCCGTGATGAACCACCTGCAGGAGGCCGCCCTGAACCACGCCAAGTCCGTGG
GCATCCTGGGCGACGGCTTCGGCACCACCCTGGAGATGTCCAAGCGCGACCTGATCTGGGTGGTGAA
GCGCACCCACGTGGCCGTGGAGCGCTACCCCGCCTGGGGCGACACCGTGGAGGTGGAGTGCTGGGTG
GGCGCCTCCGGCAACAACGGCCGCCGCCACGACTTCCTGGTGCGCGACTGCAAGACCGGCGAGATCC
TGACCCGCTGCACCTCCCTGAGCGTGATGATGAACACCCGCACCCGCCGCCTGAGCAAGATCCCCGA
GGAGGTGCGCGGCGAGATCGGCCCCGCCTTCATCGACAACGTGGCCGTGAAGGACGAGGAGATCAAG
AAGCCCCAGAAGCTGAACGACTCCACCGCCGACTACATCCAGGGCGGCCTGACCCCCCGCTGGAACG
ACCTGGACATCAACCAGCACGTGAACAACATCAAGTACGTGGACTGGATCCTGGAGACCGTGCCCGA
CAGCATCTTCGAGAGCCACCACATCTCCTCCTTCACCATCGAGTACCGCCGCGAGTGCACCATGGAC
AGCGTGCTGCAGTCCCTGACCACCGTGAGCGGCGGCTCCTCCGAGGCCGGCCTGGTGTGCGAGCACC
TGCTGCAGCTGGAGGGCGGCAGCGAGGTGCTGCGCGCCAAGACCGAGTGGCGCCCCAAGCTGACCGA
CTCCTTCCGCGGCATCAGCGTGATCCCCGCCGAGTCCAGCGTG Sequence ID No: 26 - amino acid sequence of *Cinnamomum camphorum* 14:0-ACP thioesterase (Cc FATB1/Cc TE, accession U31813) containing a five amino acid N-terminal extension derived from Cc FATB1 encoded by Construct D1432 [pSZ2451]
SLKKLPDWSMLFAVITTIFSAAEKQWTNLEWKPKPNPPQLLDDHFGPHGLVFRRTFAIRS
YEVGPDRSTSIVAVMNHLQEAALNHAKSVGILGDGFGTTLEMSKRDLIWVVKRTHVAVER
YPAWGDTVEVECWVGASGNNGRRHDFLVRDCKTGEILTRCTSLSVMMNTRTRRLSKIPEE
VRGEIGPAFIDNVAVKDEEIKKPQKLNDSTADYIQGGLTPRWNDLDINQHVNNIKYVDWI
LETVPDSIFESHHISSFTIEYRRECTMDSVLQSLTTVSGGSSEAGLVCEHLLQLEGGSEV
LRAKTEWRPKLTDSFRGISVIPAESSV Sequence ID No: 27 - nucleic acid sequence encoding 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence in construct D1481 [pSZ2479]
GCGCACCCCAAGGCGAACGGCAGCGCGGTGTCGCTGAAGTCGGGCTCCCTGGAGACCCAGGAGGACA
AGACGAGCAGCTCGTCCCCCCCCCCCCGCACGTTCATCAACCAGCTGCCCGTGTGGAGCATGCTGCT
GTCGGCGGTGACCACGGTCTTCGGCGTGGCCGAGAAGCAGTGGCCCATGCTGGACCGCAAGTCCAAG
CGCCCCGACATGCTGGTCGAGCCCCTGGGCGTGGACCGCATCGTCTACGACGGCGTGAGCTTCCGCC
AGTCGTTCTCCATCCGCAGCTACGAGATCGGCGCCGACCGCACCGCCTCGATCGAGACGCTGATGAA
CATGTTCCAGGAGACCTCCCTGAACCACTGCAAGATCATCGGCCTGCTGAACGACGGCTTCGGCCGC
ACGCCCGAGATGTGCAAGCGCGACCTGATCTGGGTCGTGACCAAGATGCAGATCGAGGTGAACCGCT
ACCCCACGTGGGGCGACACCATCGAGGTCAACACGTGGGTGAGCGCCTCGGGCAAGCACGGCATGGG
CCGCGACTGGCTGATCTCCGACTGCCACACCGGCGAGATCCTGATCCGCGCGACGAGCGTCTGGGCG
ATGATGAACCAGAAGACCCGCCGCCTGTCGAAGATCCCCTACGAGGTGCGCCAGGAGATCGAGCCCC
AGTTCGTCGACTCCGCCCCCGTGATCGTGGACGACCGCAAGTTCCACAAGCTGGACCTGAAGACGGG
CGACAGCATCTGCAACGGCCTGACCCCCCGCTGGACGGACCTGGACGTGAACCAGCACGTCAACAAC
GTGAAGTACATCGGCTGGATCCTGCAGTCGGTCCCCACCGAGGTGTTCGAGACGCAGGAGCTGTGCG
GCCTGACCCTGGAGTACCGCCGCGAGTGCGGCCGCGACTCCGTGCTGGAGAGCGTCACGGCCATGGA
CCCCTCGAAGGAGGGCGACCGCTCCCTGTACCAGCACCTGCTGCGCCTGGAGGACGGCGCGGACATC
GTGAAGGGCCGCACCGAGTGGCGCCCCAAGAACGCCGGCGCCAAGGGCGCCATCCTGACGGGCAAGA
CCAGCAACGGCAACTCGATCTCCTGA Sequence ID No: 28 - amino acid sequence of 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence encoded by construct D1481 [pSZ2479]
AHPKANGSAVSLKSGSLETQEDKTSSSSPPPRTFINQLPVWSMLLSAVTTVFGVAEKQWP
MLDRKSKRPDMLVEPLGVDRIVYDGVSFRQSFSIRSYEIGADRTASIETLMNMFQETSLN
HCKIIGLLNDGFGRTPEMCKRDLIWVVTKMQIEVNRYPTWGDTIEVNTWVSASGKHGMGR
DWLISDCHTGEILIRATSVWAMMNQKTRRLSKIPYEVRQEIEPQFVDSAPVIVDDRKFHK
LDLKTGDSICNGLTPRWTDLDVNQHVNNVKYIGWILQSVPTEVFETQELCGLTLEYRREC
GRDSVLESVTAMDPSKEGDRSLYQHLLRLEDGADIVKGRTEWRPKNAGAKGAILTGKTSN
GNSIS Sequence ID No: 29 - nucleic acid sequence encoding 14:0-ACP thioesterase, *Cuphea palustris* (Cpal FATB2, accession AAC49180) containing an extended heterologous transit peptide from *C. protothecoides,* a 41 amino acid N-terminal extension derived from the native Cpal FATB2 sequence, and a C-terminal FLAG epitope tag in construct D1482 [pSZ2480]
GCGCACCCCAAGGCGAACGGCAGCGCGGTGTCGCTGAAGTCGGGCTCCCTGGAGACCCAGGAGGACA
AGACGAGCAGCTCGTCCCCCCCCCCCCGCACGTTCATCAACCAGCTGCCCGTGTGGAGCATGCTGCT
GTCGGCGGTGACCACGGTCTTCGGCGTGGCCGAGAAGCAGTGGCCCATGCTGGACCGCAAGTCCAAG -continued

INFORMAL SEQUENCE LISTING

CGCCCCGACATGCTGGTCGAGCCCCTGGGCGTGGACCGCATCGTCTACGACGGCGTGAGCTTCCGCC
AGTCGTTCTCCATCCGCAGCTACGAGATCGGCGCCGACCGCACCGCCTCGATCGAGACGCTGATGAA
CATGTTCCAGGAGACCTCCCTGAACCACTGCAAGATCATCGGCCTGCTGAACGACGGCTTCGGCCGC
ACGCCCGAGATGTGCAAGCGCGACCTGATCTGGGTCGTGACCAAGATGCAGATCGAGGTGAACCGCT
ACCCCACGTGGGGCGACACCATCGAGGTCAACACGTGGGTGAGCGCCTCGGGCAAGCACGGCATGGG
CCGCGACTGGCTGATCTCCGACTGCCACACCGGCGAGATCCTGATCCGCGCGACGAGCGTCTGGGCG
ATGATGAACCAGAAGACCCGCCGCCTGTCGAAGATCCCCTACGAGGTGCGCCAGGAGATCGAGCCCC
AGTTCGTCGACTCCGCCCCCGTGATCGTGGACGACCGCAAGTTCCACAAGCTGGACCTGAAGACGGG
CGACAGCATCTGCAACGGCCTGACCCCCCGCTGGACGGACCTGGACGTGAACCAGCACGTCAACAAC
GTGAAGTACATCGGCTGGATCCTGCAGTCGGTCCCCACCGAGGTGTTCGAGACGCAGGAGCTGTGCG
GCCTGACCCTGGAGTACCGCCGCGAGTGCGGCCGCGACTCCGTGCTGGAGAGCGTCACGGCCATGGA
CCCCTCGAAGGAGGGCGACCGCTCCCTGTACCAGCACCTGCTGCGCCTGGAGGACGGCGCGGACATC
GTGAAGGGCCGCACCGAGTGGCGCCCCAAGAACGCCGGCGCCAAGGGCGCCATCCTGACGGGCAAGA
CCAGCAACGGCAACTCGATCTCCatggactacaaggaccacgacggcgactacaaggaccacgacat
cgactacaaggacgacgacgacaagtga Sequence ID No: 30 - amino acid sequence of 14:0-ACP thioesterase, *Cuphea palustris* (Cpal FATB2, accession AAC49180) containing an extended heterologous transit peptide from *C. protothecoides*, a 41 amino acid N-terminal extension derived from the native Cpal FATB2 sequence, and a C-terminal FLAG epitope tag encoded by construct D1482 [pSZ2480]

AHPKANGSAVSLKSGSLETQEDKTSSSSPPPRTFINQLPVWSMLLSAVTTVFGVAEKQWP
MLDRKSKRPDMLVEPLGVDRIVYDGVSFRQSFSIRSYEIGADRTASIETLMNMFQETSLN
HCKIIGLLNDGFGRTPEMCKRDLIWVVTKMQIEVNRYPTWGDTIEVNTWVSASGKHGMGR
DWLISDCHTGEILIRATSVWAMMNQKTRRLSKIPYEVRQEIEPQFVDSAPVIVDDRKFHK
LDLKTGDSICNGLTPRWTDLDVNQHVNNVKYIGWILQSVPTEVFETQELCGLTLEYRREC
GRDSVLESVTAMDPSKEGDRSLYQHLLRLEDGADIVKGRTEWRPKNAGAKGAILTGKTSN
GNSISMDYKDHDGDYKDHDIDYKDDDDK

Sequence ID No: 31 - nucleic acid sequence encoding *Ulmus Americana* 10:0-16:0-ACP thioesterase (Ua FATB1, accession 024420) containing an extended heterologous transit peptide from *C. protothecoides* and a 34 amino acid N-terminal extension derived from the native Ua FATB1 sequence in construct D1479 [pSZ2477]

CCCCCCAAGCTGAACGGCTCCAACGTGGGCCTGGTGAAGTCCTCCCAGATCGTGAAGAAGGGCGACG
ACACCACCTCCCCCCCCGCCCGCACCTTCATCAACCAGCTGCCCGACTGGAGCATGCTGCTGGCCGC
GATCACCACCCTGTTCCTGGCGGCCGAGAAGCAGTGGATGATGCTGGACTGGAAGCCCAAGCGCCCC
GACATGCTGGTGGACCCCTTCGGCCTGGGCCGCTTCGTGCAGGACGGCCTGGTGTTCCGCAACAACT
TCAGCATCCGCAGCTACGAGATCGGCGCGGACCGCACCGCCAGCATCGAGACCCTGATGAACCACCT
GCAGGAGACCGCCCTGAACCACGTGAAGAGTGTGGGCCTGCTGGAGGACGGCCTGGGCAGCACCCGC
GAGATGAGCCTGCGCAACCTGATCTGGGTGGTGACCAAGATGCAGGTGGCGGTGGACCGCTACCCCA
CCTGGGGCGACGAGGTGCAGGTGAGCAGCTGGGCGACCGCCATCGGCAAGAACGGCATGCGCCGCGA
GTGGATCGTGACCGACTTCCGCACCGGCGAGACCCTGCTGCGCGCCACCAGCGTGTGGGTGATGATG
AACAAGCTGACCCGCCGCATCAGCAAGATCCCCGAGGAGGTGTGGCACGAGATCGGCCCCAGCTTCA
TCGACGCGCCCCCCCTGCCCACCGTGGAGGACGACGGCCGCAAGCTGACCCGCTTCGACGAGAGCAG
CGCCGACTTCATCCGCAAGGGCCTGACCCCCCGCTGGAGCGACCTGGACATCAACCAGCACGTGAAC
AACGTGAAGTACATCGGCTGGCTGCTGGAGAGCGCGCCCCCCGAGATCCACGAGAGCCACGAGATCG
CCAGCCTGACCCTGGAGTACCGCCGCGAGTGCGGCCGCGACAGCGTGCTGAACAGCGCCACCAAGGT
GAGCGACAGCAGCCAGCTGGGCAAGAGCGCCGTGGAGTGCAACCACCTGGTGCGCCTGCAGAACGGC
GGCGAGATCGTGAAGGGCCGCACCGTGTGGCGCCCCAAGCGCCCCCTGTACAACGACGGCGCCGTGG
TGGACGTGCCCGCCAAGACCAGCTGA

Sequence ID No: 32 - amino acid sequence of *Ulmus Americana 10:0*-16:0-ACP thioesterase (Ua FATB1, accession O24420) containing an extended heterologous transit peptide from *C. protothecoides* and a 34 amino acid N-terminal extension derived from the native Ua FATB1 sequence encoded by construct D1479 [pSZ2477]

PPKLNGSNVGLVKSSQIVKKGDDTTSPPARTFINQLPDWSMLLAAITTLFLAAEKQWMML
DWKPKRPDMLVDPFGLGRFVQDGLVFRNNFSIRSYEIGADRTASIETLMNHLQETALNHV
KSVGLLEDGLGSTREMSLRNLIWVVTKMQVAVDRYPTWGDEVQVSSWATAIGKNGMRREW
IVTDFRTGETLLRATSVWVMMNKLTRRISKIPEEVWHEIGPSFIDAPPLPTVEDDGRKLT
RFDESSADFIRKGLTPRWSDLDINQHVNNVKYIGWLLESAPPEIHESHEIASLTLEYRRE
CGRDSVLNSATKVSDSSQLGKSAVECNHLVRLQNGGEIVKGRTVWRPKRPLYNDGAVVDV
PAKTS

Sequence ID No: 33 - nucleic acid sequence encoding *Ulmus Americana* 10:0-16:0-ACP thioesterase (Ua FATB1, accession O24420) containing an extended heterologous transit peptide from *C. protothecoides*, a 34 amino acid N-terminal extension derived from the native Ua FATB1 sequence, and a C-terminal FLAG epitope tag in construct D1480 [pSZ2478]

CCCCCCAAGCTGAACGGCTCCAACGTGGGCCTGGTGAAGTCCTCCCAGATCGTGAAGAAGGGCGACG
ACACCACCTCCCCCCCCGCCCGCACCTTCATCAACCAGCTGCCCGACTGGAGCATGCTGCTGGCCGC
GATCACCACCCTGTTCCTGGCGGCCGAGAAGCAGTGGATGATGCTGGACTGGAAGCCCAAGCGCCCC
GACATGCTGGTGGACCCCTTCGGCCTGGGCCGCTTCGTGCAGGACGGCCTGGTGTTCCGCAACAACT
TCAGCATCCGCAGCTACGAGATCGGCGCGGACCGCACCGCCAGCATCGAGACCCTGATGAACCACCT

-continued

INFORMAL SEQUENCE LISTING

GCAGGAGACCGCCCTGAACCACGTGAAGAGTGTGGGCCTGCTGGAGGACGGCCTGGGCAGCACCCGC
GAGATGAGCCTGCGCAACCTGATCTGGGTGGTGACCAAGATGCAGGTGGCGGTGGACCGCTACCCCA
CCTGGGGCGACGAGGTGCAGGTGAGCAGCTGGGCGACCGCCATCGGCAAGAACGGCATGCGCCGCGA
GTGGATCGTGACCGACTTCCGCACCGGCGAGACCCTGCTGCGCGCCACCAGCGTGTGGGTGATGATG
AACAAGCTGACCCGCCGCATCAGCAAGATCCCCGAGGAGGTGTGGCACGAGATCGGCCCCAGCTTCA
TCGACGCGCCCCCCCTGCCCACCGTGGAGGACGACGGCCGCAAGCTGACCCGCTTCGACGAGAGCAG
CGCCGACTTCATCCGCAAGGGCCTGACCCCCCGCTGGAGCGACCTGGACATCAACCAGCACGTGAAC
AACGTGAAGTACATCGGCTGGCTGCTGGAGAGCGCGCCCCCCGAGATCCACGAGAGCCACGAGATCG
CCAGCCTGACCCTGGAGTACCGCCGCGAGTGCGGCCGCGACAGCGTGCTGAACAGCGCCACCAAGGT
GAGCGACAGCAGCCAGCTGGGCAAGAGCGCCGTGGAGTGCAACCACCTGGTGCGCCTGCAGAACGGC
GGCGAGATCGTGAAGGGCCGCACCGTGTGGCGCCCCAAGCGCCCCCTGTACAACGACGGCGCCGTGG
TGGACGTGCCCGCCAAGACCAGCatggactacaaggaccacgacggcgactacaaggaccacgacat
cgactacaaggacgacgacgacaagtga Sequence ID No: 34 - amino acid sequence of *Ulmus Americana* 10:0-16:0-ACP thioesterase (Ua FATB1, accession O24420) containing an extended heterologous transit peptide from *C. protothecoides*, a 34 amino acid N-terminal extension derived from the native Ua FATB1 sequence, and a C-terminal FLAG epitope tag encoded by construct D1480 [pSZ2478]
PPKLNGSNVGLVKSSQIVKKGDDTTSPPARTFINQLPDWSMLLAAITTLFLAAEKQWMML
DWKPKRPDMLVDPFGLGRFVQDGLVFRNNFSIRSYEIGADRTASIETLMNHLQETALNHV
KSVGLLEDGLGSTREMSLRNLIWVVTKMQVAVDRYPTWGDEVQVSSWATAIGKNGMRREW
IVTDFRTGETLLRATSVWVMMNKLTRRISKIPEEVWHEIGPSFIDAPPLPTVEDDGRKLT
RFDESSADFIRKGLTPRWSDLDINQHVNNVKYIGWLLESAPPEIHESHEIASLTLEYRRE
CGRDSVLNSATKVSDSSQLGKSAVECNHLVRLQNGGEIVKGRTVWRPKRPLYNDGAVVDV
PAKTSMDYKDHDGDYKDHDIDYKDDDDK Sequence ID No: 35 - nucleic acid sequence encoding Cc-Uc FATB chimera B 12:0-14:0-ACP thioesterase containing an extended heterologous transit peptide from *C. protothecoides* and a five amino acid N-terminal extension derived from the native Uc FATB2 sequence in construct D1429 [pSZ2448[
ATGGCCACCGCATCCACTTTCTCGGCGTTCAATGCCCGCTGCGGCGACCTGCGTCGCTCGGCGGGCT
CCGGGCCCCGGCGCCCAGCGAGGCCCCTCCCCGTGCGCGCTGCCATCGCCAGCGAGGTCCCCGTGGC
CACCACCTCCCCCCGGagcctgaagcgcctgCCCGACTGGTCCATGCTGTTCGCCGTGATCACCACC
ATCTTCTCCGCCGCCGAGAAGCAGTGGACCAACCTGGAGTGGAAGCCCAAGCCCAACCCCCCCCAGC
TGCTGGACGACCACTTCGGCCCCCACGGCCTGGTGTTCCGCCGCACCTTCGCCATCCGCAGCTACGA
GGTGGGCCCCGACCGCTCCACCAGCATCGTGGCCGTGATGAACCACCTGCAGGAGGCCGCCCTGAAC
CACGCCAAGTCCGTGGGCATCCTGGGCGACGGCTTCGGCACCACCCTGGAGATGTCCAAGCGCGACC
TGATCTGGGTGGTGCGCCGCACCCACGTGGCCGTGGAGCGCTACCCCACCTGGGGCGACACCGTGGA
GGTGGAGTGCTGGATCGGCGCCAGCGGCAACAACGGCATGCGCCGCGACTTCCTGGTGCGCGACTGC
AAGACCGGCGAGATCCTGACCCGCTGCACCTCCCTGAGCGTGCTGATGAACACCCGCACCCGCCGCC
TGAGCACCATCCCCGACGAGGTGCGCGGCGAGATCGGCCCCGCCTTCATCGACAACGTGGCCGTGAA
GGACGACGAGATCAAGAAGCTGCAGAAGCTGAACGACTCCACCGCCGACTACATCCAGGGCGGCCTG
ACCCCCCGCTGGAACGACCTGGACGTGAACCAGCACGTGAACAACCTGAAGTACGTGGCCTGGGTGT
TCGAGACCGTGCCCGACAGCATCTTCGAGTCCCACCACATCAGCTCCTTCACCCTGGAGTACCGCCG
CGAGTGCACCCGCGACTCCGTGCTGCGCAGCCTGACCACCGTGAGCGGCGGCAGCTCCGAGGCCGGC
CTGGTGTGCGACCACCTGCTGCAGCTGGAGGGCGGCAGCGAGGTGCTGCGCGCCCGCACCGAGTGGC
GCCCCAAGCTGACCGACTCCTTCCGCGGCATCAGCGTGATCCCCGCCGAGCCCCGCGTG Sequence ID No: 36 - amino acid sequence of Cc-Uc FATB chimera B 12:0-14:0-ACP thioesterase containing an extended heterologous transit peptide from *C. protothecoides* and a five amino acid N-terminal extension derived from the native Uc FATB2 sequence encoded by construct D1429 [pSZ2448]
MATASTFSAFNARCGDLRRSAGSGPRRPARPLPVRAAIASEVPVATTSPRSLKRLPDWSM
LFAVITTIFSAAEKQWTNLEWKPKPNPPQLLDDHFGPHGLVFRRTFAIRSYEVGPDRSTS
IVAVMNHLQEAALNHAKSVGILGDGFGTTLEMSKRDLIWVVRRTHVAVERYPTWGDTVEV
ECWIGASGNNGMRRDFLVRDCKTGEILTRCTSLSVLMNTRTRRLSTIPDEVRGEIGPAFI
DNVAVKDDEIKKLQKLNDSTADYIQGGLTPRWNDLDVNQHVNNLKYVAWVFETVPDSIFE
SHHISSFTLEYRRECTRDSVLRSLTTVSGGSSEAGLVCDHLLQLEGGSEVLRARTEWRPK
LTDSFRGISVIPAEPRV Sequence ID No: 37 - 5 amino acid Uc/Cc FATB N-terminal extension
SLK (R/K)

Sequence ID No: 38 - 15 amino acid Uc/Cc FATB N-terminal extension
INGTKFSYTESLK(R/K)

Sequence ID No: 39 - N-terminal extension derived from the native Cpal FATB2 sequence
AHPKANGSAVSLKSGSLETQEDKTSSSSPPPRTFINQ Sequence ID No: 40 - N-terminal extension derived from the native Ua FATB1 sequence
PPKLNGSNVGLVKSSQIVKKGDDTTSPPARTFINQ -continued

INFORMAL SEQUENCE LISTING

Sequence ID No: 41 - N-terminal extension derived from the native Cw FATB1 sequence
AHPKANGSAVNLKSGSLETPPRSFINQ Sequence ID No: 42 - N-terminal extension derived from the native Cw FATB2 sequence (GenBank accession Q39663)
PHPKANGSAVSLKSGSLNTLEDPPSSPPPRTFLNQ Sequence ID No: 43 - wild-type California Bay Tree acyl-ACP thioesterase (GenBank Accession No. M94159.1)
MATTSLASAFCSMKAVMLARDGRGMKPRSSDLQLRAGNAPTSLKMINGTKFSYTESLKRLPDWSMLF
AVITTIFSAAEKQWTNLEWKPKPKLPQLLDDHFGLHGLVFRRTFAIRSYEVGPDRSTSILAVMNHMQ
EATLNHAKSVGILGDGFGTTLEMSKRDLMWVVRRTHVAVERYPTWGDTVEVECWIGASGNNGMRRDF
LVRDCKTGEILTRCTSLSVLMNTRTRRLSTIPDEVRGEIGPAFIDNVAVKDDEIKKLQKLNDSTADY
IQGGLTPRWNDLDVNQHVNNLKYVAWVFETVPDSIFESHHISSFTLEYRRECTRDSVLRSLTTVSGG
SSEAGLVCDHLLQLEGGSEVLRARTEWRPKLTDSFRGISVIPAEPRV Sequence ID No: 44 - wild-type *Cinnamomum camphora* acyl-ACP thioesterase (GenBank Accession No. U31813.1)
MATTSLASAFCSMKAVMLARDGRGMKPRSSDLQLRAGNAQTSLKMINGTKFSYTESLKKLPDWSMLF
AVITTIFSAAEKQWTNLEWKPKPNPPQLLDDHFGPHGLVFRRTFAIRSYEVGPDRSTSIVAVMNHLQ
EAALNHAKSVGILGDGFGTTLEMSKRDLIWVVKRTHVAVERYPAWGDTVEVECWVGASGNNGRRHDF
LVRDCKTGEILTRCTSLSVMMNTRTRRLSKIPEEVRGEIGPAFIDNVAVKDEEIKKPQKLNDSTADY
IQGGLTPRWNDLDINQHVNNIKYVDWILETVPDSIFESHHISSFTIEYRRECTMDSVLQSLTTVSGG
SSEAGLVCEHLLQLEGGSEVLRAKTEWRPKLTDSFRGISVIPAESSV Sequence ID No: 45 - wild-type *Cuphea palustris* (Cpal) acyl-ACP thioesterase (GenBank Accession No. AAC49180)
MVAAAASAAFFSVATPRTNISPSSLSVPFKPKSNHNGGFQVKANASAHPKANGSAVSLKSGSLETQE
DKTSSSSPPPRTFINQLPVWSMLLSAVTTVFGVAEKQWPMLDRKSKRPDMLVEPLGVDRIVYDGVSF
RQSFSIRSYEIGADRTASIETLMNMFQETSLNHCKIIGLLNDGFGRTPEMCKRDLIWVVTKMQIEVN
RYPTWGDTIEVNTWVSASGKHGMGRDWLISDCHTGEILIRATSVWAMMNQKTRRLSKIPYEVRQEIE
PQFVDSAPVIVDDRKFHKLDLKTGDSICNGLTPRWTDLDVNQHVNNVKYIGWILQSVPTEVFETQEL
CGLTLEYRRECGRDSVLESVTAMDPSKEGDRSLYQHLLRLEDGADIVKGRTEWRPKNAGAKGAILTG
KTSNGNSIS Sequence ID No: 46 - wild-type *Cuphea wrightii* (Cw) acyl-ACP thioesterase FATB1 (GenBank Accession No. U56103)
MVAAAASSAFFSVPTPGTSPKPGKFGNWPSSLSVPFKPDNGGFHVKANASAHPKANGSAVNLKSGSL
ETPPRSFINQLPDLSMLLSKITTVFGAAEKQWKRPGMLVEPFGVDRIFQDGVFFRQSFSIRSYEIGV
DRTASIETLMNIFQETSLNHCKSIGLLNDGFGRTPEMCKRDLIWVVTKIQVEVNRYPTWGDTIEVNT
WVSESGKNGMGRDWLISDCRTGEILIRATSVWAMMNQNTRRLSKFPYEVRQEIAPHFVDSAPVIEDD
RKLHKLDVKTGDSIRDGLTPRWNDLDVNQHVNNVKYIGWILKSVPIEVFETQELCGVTLEYRRECGR
DSVLESVTTMDPAKEGDRCVYQHLLRLEDGADITIGRTEWRPKNAGANGAISSGKTSNGNSVS Sequence ID No: 47 - wild-type *Ulmus Americana* acyl-ACP thioesterase (GenBank Accession No. O24420)
GSGALQVKASSQAPPKLNGSNVGLVKSSQIVKKGDDTTSPPARTFINQLPDWSMLLAAITTLFLAAE
KQWMMLDWKPKRPDMLVDPFGLGRFVQDGLVFRNNFSIRSYEIGADRTASIETLMNHLQETALNHVK
SVGLLEDGLGSTREMSLRNLIWVVTKMQVAVDRYPTWGDEVQVSSWATAIGKNGMRREWIVTDFRTG
ETLLRATSVWVMMNKLTRRISKIPEEVWHEIGPSFIDAPPLPTVEDDGRKLTRFDESSADFIRXGLT
PRWSDLDINQHVNNVKYIGWLLESAPPEIHESHEIASLTLEYRRECGRDSVLNSATKVSDSSQLGKS
AVECNHLVRLQNGGEIVKGRTVWRPKRPLYNDGAVVDVXAKTS Sequence ID No: 48 - nucleic acid sequence of pSZ2609 (D1558) Chook-CwFATB ChimeraA
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCAGCGCCGTG
AGCCTGAAGTCCGGCAGCCTGAACACCCTGGAGGACCCCCCCAGCAGCCCCCCCCCCCGCACCTTCC
TGAACCAGCTGCCCGACTGGAGCCGCCTGCTGACCGCCATCACCACCGTGTTCGTGAAGTCCAAGCG
CCCCGACATGCACGACCGCAAGTCCAAGCGCCCCGACATGCTGGTGGACAGCTTCGGCCTGGAGTCC
ACCGTGCAGGACGGCCTGGTGTTCCGCCAGTCCTTCTCCATCCGCTCCTACGAGATCGGCACCGACC
GCACCGCCAGCATCGAGACCCTGATGAACCACCTGCAGGAGACCTCCCTGAACCACTGCAAGAGCAC
CGGCATCCTGCTGGACGGCTTCGGCCGCACCCTGGAGATGTGCAAGCGCGACCTGATCTGGGTGGTG
ATTAAGATGCAGATCAAGGTGAACCGCTACCCCACCTGGGGCGACACCGTGGAGATCAACAGCTGGT
TCAGCCAGAGCGGCAAGATCGGCATGGGCCGCGAGTGGCTGATCAGCGACTGCAACACCGGCGAGAT
CCTGGTGCGCGCCACCAGCGCCTGGGCCATGATGAACCAGAAGACCCGCCGCTTCAGCAAGCTGCCC
TGCGAGGTGCGCCAGGAGATCGCCCCCCACTTCGTGGACGCCCCCCCCGTGATCGAGGACAACGACC
GCAAGCTGCACAAGTTCGACGTGAAGACCGGCGACAGCATCTGCAAGGGCCTGACCCCCGGCTGGAA
CGACTTCGACGTGAACCAGCACGTGAGCAACGTGAAGTACATCGGCTGGATTCTGGAGAGCATGCCC
ACCGAGGTGCTGGAGACCCAGGAGCTGTGCAGCCTGACCCTGGAGTACCGCCGCGAGTGCGGCCGCG
AGAGCGTGGTGGAGAGCGTGACCAGCATGAACCCCAGCAAGGTGGGCGACCGCAGCCAGTACCAGCA
CCTGCTGCGCCTGGAGGACGGCGCCGACATCATGAAGGGCCGCACCGAGTGGCGCCCCAAGAACGCC
GGCACCAACCGCGCCATCAGCACCatggactacaaggaccacgacggcgactacaaggaccacgaca
tcgactacaaggacgacgacgacaagtga -continued

INFORMAL SEQUENCE LISTING

Sequence ID No: 49 - amino acid sequence encoded by pSZ2609 (D1558)
Chook-CwFATB ChimeraA
MVVAAAASSAFFPVPAPRPTPKPGKFGNWPSSLSQPFKPKSNPNGRFQVKANVSPHGRAP
KANGSAVSLKSGSLNTLEDPPSSPPPRTFLNQLPDWSRLLTAITTVFVKSKRPDMHDRKS
KRPDMLVDSFGLESTVQDGLVFRQSFSIRSYEIGTDRTASIETLMNHLQETSLNHCKSTG
ILLDGFGRTLEMCKRDLIWVVIKMQIKVNRYPTWGDTVEINSWFSQSGKIGMGREWLISD
CNTGEILVRATSAWAMMNQKTRRFSKLPCEVRQEIAPHFVDAPPVIEDNDRKLHKFDVKT
GDSICKGLTPGWNDFDVNQHVSNVKYIGWILESMPTEVLETQELCSLTLEYRRECGRESV
VESVTSMNPSKVGDRSQYQHLLRLEDGADIMKGRTEWRPKNAGTNRAISTMDYKDHDGDY
KDHDIDYKDDDDK Sequence ID No: 50 - nucleic acid sequence of pSZ2610 (D1559)
Chook-CwFATB ChimeraB
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCAGCGCCGTG
AGCCTGAAGTCCGGCAGCCTGAACACCCTGGAGGACCCCCCCAGCAGCCCCCCCCCCCGCACCTTCC
TGAACCAGCTGCCCGACTGGAGCCGCCTGCGCACCGCCATCACCACCGTGTTCGTGGCCGCCGAGAA
GCAGTTCACCCGCCTGGACCGCAAGAGCAAGCGCCCCGACATGCTGGTGGACTGGTTCGGCAGCGAG
ACCATCGTGCAGGACGGCCTGGTGTTCCGCGAGCGCTTCAGCATCCGCAGCTACGAGATCGGCGCCG
ACCGCACCGCCAGCATCGAGACCCTGATGAACCACCTGCAGGAGACCTCCCTGAACCACTGCAAGAG
CACCGGCATCCTGCTGGACGGCTTCGGCCGCACCCTGGAGATGTGCAAGCGCGACCTGATCTGGGTG
GTGATTAAGATGCAGATCAAGGTGAACCGCTACCCCACCTGGGGCGACACCGTGGAGATCAACAGCT
GGTTCAGCCAGAGCGGCAAGATCGGCATGGGCCGCGAGTGGCTGATCAGCGACTGCAACACCGGCGA
GATCCTGGTGCGCGCCACCAGCGCCTGGGCCATGATGAACCAGAAGACCCGCCGCTTCAGCAAGCTG
CCCTGCGAGGTGCGCCAGGAGATCGCCCCCCACTTCGTGGACGCCCCCCCCGTGATCGAGGACAACG
ACCGCAAGCTGCACAAGTTCGACGTGAAGACCGGCGACAGCATCTGCAAGGGCCTGACCCCCGGCTG
GAACGACTTCGACGTGAACCAGCACGTGAGCAACGTGAAGTACATCGGCTGGATTCTGGAGAGCATG
CCCACCGAGGTGCTGGAGACCCAGGAGCTGTGCAGCCTGACCCTGGAGTACCGCCGCGAGTGCGGCC
GCGAGAGCGTGGTGGAGAGCGTGACCAGCATGAACCCCAGCAAGGTGGGCGACCGCAGCCAGTACCA
GCACCTGCTGCGCCTGGAGGACGGCGCCGACATCATGAAGGGCCGCACCGAGTGGCGCCCCAAGAAC
GCCGGCACCAACCGCGCCATCAGCACCatggactacaaggaccacgacggcgactacaaggaccacg
acatcgactacaaggacgacgacgacaagtga Sequence ID No: 51 - amino acid sequence encoded by pSZ2610 (D1559)
Chook-CwFATB ChimeraB
MVVAAAASSAFFPVPAPRPTPKPGKFGNWPSSLSQPFKPKSNPNGRFQVKANVSPHGRAP
KANGSAVSLKSGSLNTLEDPPSSPPPRTFLNQLPDWSRLRTAITTVFVAAEKQFTRLDRK
SKRPDMLVDWFGSETIVQDGLVFRERFSIRSYEIGADRTASIETLMNHLQETSLNHCKST
GILLDGFGRTLEMCKRDLIWVVIKMQIKVNRYPTWGDTVEINSWFSQSGKIGMGREWLIS
DCNTGEILVRATSAWAMMNQKTRRFSKLPCEVRQEIAPHFVDAPPVIEDNDRKLHKFDVK
TGDSICKGLTPGWNDFDVNQHVSNVKYIGWILESMPTEVLETQELCSLTLEYRRECGRES
VVESVTSMNPSKVGDRSQYQHLLRLEDGADIMKGRTEWRPKNAGTNRAISTMDYKDHDGD
YKDHDIDYKDDDDK Sequence ID No: 52 - nucleic acid sequence of pSZ2611 (D1560)
Chook-CwFATB ChimeraC
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCAGCGCCGTG
AGCCTGAAGTCCGGCAGCCTGAACACCCTGGAGGACCCCCCCAGCAGCCCCCCCCCCCGCACCTTCC
TGAACCAGCTGCCCGACTGGAGCCGCCTGCTGACCGCCATCACCACCGTGTTCGTGAAGTCCAAGCG
CCCCGACATGCACGACCGCAAGTCCAAGCGCCCCGACATGCTGGTGGACAGCTTCGGCCTGGAGTCC
ACCGTGCAGGACGGCCTGGTGTTCCGCCAGTCCTTCTCCATCCGCTCCTACGAGATCGGCACCGACC
GCACCGCCAGCATCGAGACCCTGATGAACCACCTGCAGGACACCAGCCTGAACCACTGCAAGAGCGT
GGGCCTGCTGAACGACGGCTTCGGCCGCACCCCCGAGATGTGCACCCGCGACCTGATCTGGGTGCTG
ACCAAGATGCAGATCGTGGTGAACCGCTACCCCACCTGGGGCGACACCGTGGAGATCAACAGCTGGT
TCAGCCAGAGCGGCAAGATCGGCATGGGCCGCGAGTGGCTGATCAGCGACTGCAACACCGGCGAGAT
CCTGGTGCGCGCCACCAGCGCCTGGGCCATGATGAACCAGAAGACCCGCCGCTTCAGCAAGCTGCCC
TGCGAGGTGCGCCAGGAGATCGCCCCCCACTTCGTGGACGCCCCCCCCGTGATCGAGGACAACGACC
GCAAGCTGCACAAGTTCGACGTGAAGACCGGCGACAGCATCTGCAAGGGCCTGACCCCCGGCTGGAA
CGACTTCGACGTGAACCAGCACGTGAGCAACGTGAAGTACATCGGCTGGATTCTGGAGAGCATGCCC
ACCGAGGTGCTGGAGACCCAGGAGCTGTGCAGCCTGACCCTGGAGTACCGCCGCGAGTGCGGCCGCG
AGAGCGTGGTGGAGAGCGTGACCAGCATGAACCCCAGCAAGGTGGGCGACCGCAGCCAGTACCAGCA
CCTGCTGCGCCTGGAGGACGGCGCCGACATCATGAAGGGCCGCACCGAGTGGCGCCCCAAGAACGCC
GGCACCAACCGCGCCATCAGCACCatggactacaaggaccacgacggcgactacaaggaccacgaca
tcgactacaaggacgacgacgacaagtga Sequence ID No: 53 - amino acid sequence encoded by pSZ2611 (D1560)
Chook-CwFATB ChimeraC
MVVAAAASSAFFPVPAPRPTPKPGKFGNWPSSLSQPFKPKSNPNGRFQVKANVSPHGRAP
KANGSAVSLKSGSLNTLEDPPSSPPPRTFLNQLPDWSRLLTAITTVFVKSKRPDMHDRKS
KRPDMLVDSFGLESTVQDGLVFRQSFSIRSYEIGTDRTASIETLMNHLQDTSLNHCKSVG
LLNDGFGRTPEMCTRDLIWVLTKMQIVVNRYPTWGDTVEINSWFSQSGKIGMGREWLISD
CNTGEILVRATSAWAMMNQKTRRFSKLPCEVRQEIAPHFVDAPPVIEDNDRKLHKFDVKT
GDSICKGLTPGWNDFDVNQHVSNVKYIGWILESMPTEVLETQELCSLTLEYRRECGRESV -continued

INFORMAL SEQUENCE LISTING

VESVTSMNPSKVGDRSQYQHLLRLEDGADIMKGRTEWRPKNAGTNRAISTMDYKDHDGDY
KDHDIDYKDDDDK

Sequence ID No: 54 - nucleic acid sequence of pSZ2612 (D1561)
Chook-CwFATB ChimeraD
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCTCCGCCGTG
AGCCTGAAGAGCGGCAGCCTGAACACCCAGGAGGACACCTCCTCCAGCCCCCCCCCCCGCACCTTCC
TGCACCAGCTGCCCGACTGGAGCCGCCTGCTGACCGCCATCACCACCGTGTTCGTGAAGTCCAAGCG
CCCCGACATGCACGACCGCAAGTCCAAGCGCCCCGACATGCTGGTGGACAGCTTCGGCCTGGAGTCC
ACCGTGCAGGACGGCCTGGTGTTCCGCCAGTCCTTCTCCATCCGCTCCTACGAGATCGGCACCGACC
GCACCGCCAGCATCGAGACCCTGATGAACCACCTGCAGGAGACCTCCCTGAACCACTGCAAGAGCAC
CGGCATCCTGCTGGACGGCTTCGGCCGCACCCTGGAGATGTGCAAGCGCGACCTGATCTGGGTGGTG
ATTAAGATGCAGATCAAGGTGAACCGCTACCCCACCTGGGGCGACACCGTGGAGATCAACAGCTGGT
TCAGCCAGAGCGGCAAGATCGGCATGGGCCGCGAGTGGCTGATCAGCGACTGCAACACCGGCGAGAT
CCTGGTGCGCGCCACCAGCGCCTGGGCCATGATGAACCAGAAGACCCGCCGCTTCAGCAAGCTGCCC
TGCGAGGTGCGCCAGGAGATCGCCCCCCACTTCGTGGACGCCCCCCCCGTGATCGAGGACAACGACC
GCAAGCTGCACAAGTTCGACGTGAAGACCGGCGACAGCATCTGCAAGGGCCTGACCCCCGGCTGGAA
CGACTTCGACGTGAACCAGCACGTGAGCAACGTGAAGTACATCGGCTGGATTCTGGAGAGCATGCCC
ACCGAGGTGCTGGAGACCCAGGAGCTGTGCAGCCTGACCCTGGAGTACCGCCGCGAGTGCGGCCGCG
AGAGCGTGGTGGAGAGCGTGACCAGCATGAACCCCAGCAAGGTGGGCGACCGCAGCCAGTACCAGCA
CCTGCTGCGCCTGGAGGACGGCGCCGACATCATGAAGGGCCGCACCGAGTGGCGCCCCAAGAACGCC
GGCACCAACCGCGCCATCAGCACCatggactacaaggaccacgacggcgactacaaggaccacgaca
tcgactacaaggacgacgacgacaagtga Sequence ID No: 55 - amino acid sequence encoded by pSZ2612 (D1561)
Chook-CwFATB ChimeraD
MVVAAAASSAFFPVPAPRPTPKPGKFGNWPSSLSQPFKPKSNPNGRFQVKANVSPHGRAP
KANGSAVSLKSGSLNTQEDTSSSPPPRTFLHQLPDWSRLLTAITTVFVKSKRPDMHDRKS
KRPDMLVDSFGLESTVQDGLVFRQSFSIRSYEIGTDRTASIETLMNHLQETSLNHCKSTG
ILLDGFGRTLEMCKRDLIWVVIKMQIKVNRYPTWGDTVEINSWFSQSGKIGMGREWLISD
CNTGEILVRATSAWAMMNQKTRRFSKLPCEVRQEIAPHFVDAPPVIEDNDRKLHKFDVKT
GDSICKGLTPGWNDFDVNQHVSNVKYIGWILESMPTEVLETQELCSLTLEYRRECGRESV
VESVTSMNPSKVGDRSQYQHLLRLEDGADIMKGRTEWRPKNAGTNRAISTMDYKDHDGDY
KDHDIDYKDDDDK Sequence ID No: 56 - nucleic acid sequence of pSZ2613 (D1562)
ChookFATB
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCTCCGCCGTG
AGCCTGAAGAGCGGCAGCCTGAACACCCAGGAGGACACCTCCTCCAGCCCCCCCCCCCGCACCTTCC
TGCACCAGCTGCCCGACTGGAGCCGCCTGCTGACCGCCATCACCACCGTGTTCGTGAAGTCCAAGCG
CCCCGACATGCACGACCGCAAGTCCAAGCGCCCCGACATGCTGGTGGACAGCTTCGGCCTGGAGTCC
ACCGTGCAGGACGGCCTGGTGTTCCGCCAGTCCTTCTCCATCCGCTCCTACGAGATCGGCACCGACC
GCACCGCCAGCATCGAGACCCTGATGAACCACCTGCAGGAGACCTCCCTGAACCACTGCAAGAGCAC
CGGCATCCTGCTGGACGGCTTCGGCCGCACCCTGGAGATGTGCAAGCGCGACCTGATCTGGGTGGTG
ATCAAGATGCAGATCAAGGTGAACCGCTACCCCGCCTGGGGCGACACCGTGGAGATCAACACCCGCT
TCAGCCGCCTGGGCAAGATCGGCATGGGCCGCGACTGGCTGATCTCCGACTGCAACACCGGCGAGAT
CCTGGTGCGCGCCACCAGCGCCTACGCCATGATGAACCAGAAGACCCGCCGCCTGTCCAAGCTGCCC
TACGAGGTGCACCAGGAGATCGTGCCCCTGTTCGTGGACAGCCCCGTGATCGAGGACTCCGACCTGA
AGGTGCACAAGTTCAAGGTGAAGACCGGCGACAGCATCCAGAAGGGCCTGACCCCCGGCTGGAACGA
CCTGGACGTGAACCAGCACGTGTCCAACGTGAAGTACATCGGCTGGATCCTGGAGAGCATGCCCACC
GAGGTGCTGGAGACCCAGGAGCTGTGCTCCCTGGCCCTGGAGTACCGCCGCGAGTGCGGCCGCGACT
CCGTGCTGGAGAGCGTGACCGCCATGGACCCCAGCAAGGTGGGCGTGCGCTCCCAGTACCAGCACCT
GCTGCGCCTGGAGGACGGCACCGCCATCGTGAACGGCGCCACCGAGTGGCGCCCCAAGAACGCCGGC
GCCAACGGCGCCATCTCCACCGGCAAGACCAGCAACGGCAACTCCGTGTCCatggactacaaggacc
acgacggcgactacaaggaccacgacatcgactacaaggacgacgacgacaagtga Sequence ID No: 57 - amino acid sequence encoding pSZ2613 (D1562)
ChookFATB
MVVAAAASSAFFPVPAPRPTPKPGKFGNWPSSLSQPFKPKSNPNGRFQVKANVSPHGRAP
KANGSAVSLKSGSLNTQEDTSSSPPPRTFLHQLPDWSRLLTAITTVFVKSKRPDMHDRKS
KRPDMLVDSFGLESTVQDGLVFRQSFSIRSYEIGTDRTASIETLMNHLQETSLNHCKSTG
ILLDGFGRTLEMCKRDLIWVVIKMQIKVNRYPAWGDTVEINTRFSRLGKIGMGRDWLISD
CNTGEILVRATSAYAMMNQKTRRLSKLPYEVHQEIVPLFVDSPVIEDSDLKVHKFKVKTG
DSIQKGLTPGWNDLDVNQHVSNVKYIGWILESMPTEVLETQELCSLALEYRRECGRDSVL
ESVTAMDPSKVGVRSQYQHLLRLEDGTAIVNGATEWRPKNAGANGAISTGKTSNGNSVSM
DYKDHDGDYKDHDIDYKDDDDK Sequence ID No: 58 - nucleic acid sequence of pSZ1954 (D965) CwFATB
ATGGTGGTGGCCGCCGCCGCCAGCAGCGCCTTCTTCCCCGTGCCCGCCCCCCGCCCCACCCCCAAGC
CCGGCAAGTTCGGCAACTGGCCCAGCAGCCTGAGCCAGCCCTTCAAGCCCAAGAGCAACCCCAACGG
CCGCTTCCAGGTGAAGGCCAACGTGAGCCCCCACgggcgcgccCCCAAGGCCAACGGCAGCGCCGTG
AGCCTGAAGTCCGGCAGCCTGAACACCCTGGAGGACCCCCCCAGCAGCCCCCCCCCCCGCACCTTCC
TGAACCAGCTGCCCGACTGGAGCCGCCTGCGCACCGCCATCACCACCGTGTTCGTGGCCGCCGAGAA -continued

INFORMAL SEQUENCE LISTING

GCAGTTCACCCGCCTGGACCGCAAGAGCAAGCGCCCCGACATGCTGGTGGACTGGTTCGGCAGCGAG
ACCATCGTGCAGGACGGCCTGGTGTTCCGCGAGCGCTTCAGCATCCGCAGCTACGAGATCGGCGCCG
ACCGCACCGCCAGCATCGAGACCCTGATGAACCACCTGCAGGACACCAGCCTGAACCACTGCAAGAG
CGTGGGCCTGCTGAACGACGGCTTCGGCCGCACCCCCGAGATGTGCACCCGCGACCTGATCTGGGTG
CTGACCAAGATGCAGATCGTGGTGAACCGCTACCCCACCTGGGGCGACACCGTGGAGATCAACAGCT
GGTTCAGCCAGAGCGGCAAGATCGGCATGGGCCGCGAGTGGCTGATCAGCGACTGCAACACCGGCGA
GATCCTGGTGCGCGCCACCAGCGCCTGGGCCATGATGAACCAGAAGACCCGCCGCTTCAGCAAGCTG
CCCTGCGAGGTGCGCCAGGAGATCGCCCCCCACTTCGTGGACGCCCCCCCCGTGATCGAGGACAACG
ACCGCAAGCTGCACAAGTTCGACGTGAAGACCGGCGACAGCATCTGCAAGGGCCTGACCCCCGGCTG
GAACGACTTCGACGTGAACCAGCACGTGAGCAACGTGAAGTACATCGGCTGGATTCTGGAGAGCATG
CCCACCGAGGTGCTGGAGACCCAGGAGCTGTGCAGCCTGACCCTGGAGTACCGCCGCGAGTGCGGCC
GCGAGAGCGTGGTGGAGAGCGTGACCAGCATGAACCCCAGCAAGGTGGGCGACCGCAGCCAGTACCA
GCACCTGCTGCGCCTGGAGGACGGCGCCGACATCATGAAGGGCCGCACCGAGTGGCGCCCCAAGAAC
GCCGGCACCAACCGCGCCATCAGCACCgactacaaggacgacgacgacaagtga Sequence ID No: 59 - amino acid sequence encoded by pSZ1954 (D965) CwFATB
MVVAAAASSAFFPVPAPRPTPKPGKFGNWPSSLSQPFKPKSNPNGRFQVKANVSPHGRAP
KANGSAVSLKSGSLNTLEDPPSSPPPRTFLNQLPDWSRLRTAITTVFVAAEKQFTRLDRK
SKRPDMLVDWFGSETIVQDGLVFRERFSIRSYEIGADRTASIETLMNHLQDTSLNHCKSV
GLLNDGFGRTPEMCTRDLIWVLTKMQIVVNRYPTWGDTVEINSWFSQSGKIGMGREWLIS
DCNTGEILVRATSAWAMMNQKTRRFSKLPCEVRQEIAPHFVDAPPVIEDNDRKLHKFDVK
TGDSICKGLTPGWNDFDVNQHVSNVKYIGWILESMPTEVLETQELCSLTLEYRRECGRES
VVESVTSMNPSKVGDRSQYQHLLRLEDGADIMKGRTEWRPKNAGTNRAISTDYKDDDDK Sequence ID No: 60 - wild-type *Cuphea wrightii* (Cw) acyl-ACP thioesterase FATB2 (GenBank Accession Nos. U56104.1 (RNA); Q39663 (Protein))
MVVAAAASSAFFPVPAPRPTPKPGKFGNWPSSLSQPFKPKSNPNGRFQVKANVSPHPKANGSAVSLK
SGSLNTLEDPPSSPPPRTFLNQLPDWSRLRTAITTVFVAAEKQFTRLDRKSKRPDMLVDWFGSETIV
QDGLVFRERFSIRSYEIGADRTASIETLMNHLQDTSLNHCKSVGLLNDGFGRTPEMCTRDLIWVLTK
MQIVVNRYPTWGDTVEINSWFSQSGKIGMGREWLISDCNTGEILVRATSAWAMMNQKTRRFSKLPCE
VRQEIAPHFVDAPPVIEDNDRKLHKFDVKTGDSICKGLTPGWNDFDVNQHVSNVKYIGWILESMPTE
VLETQELCSLTLEYRRECGRESVVESVTSMNPSKVGDRSQYQHLLRLEDGADIMKGRTEWRPKNAGT
NRAIST Sequence ID No: 61 - wild-type *Cuphea hookeriana* (Chook) acyl-ACP thioesterase (GenBank Accession Nos. U39834.1 (RNA); Q39514 (Protein))
MVAAAASSAFFPVPAPGASPKPGKFGNWPSSLSPSFKPKSIPNGGFQVKANDSAHPKANGSAVSLKS
GSLNTQEDTSSSPPPRTFLHQLPDWSRLLTAITTVFVKSKRPDMHDRKSKRPDMLVDSFGLESTVQD
GLVFRQSFSIRSYEIGTDRTASIETLMNHLQETSLNHCKSTGILLDGFGRTLEMCKRDLIWVVIKMQ
IKVNRYPAWGDTVEINTRFSRLGKIGMGRDWLISDCNTGEILVRATSAYAMMNQKTRRLSKLPYEVH
QEIVPLFVDSPVIEDSDLKVHKFKVKTGDSIQKGLTPGWNDLDVNQHVSNVKYIGWILESMPTEVL
ETQELCSLALEYRRECGRDSVLESVTAMDPSKVGVRSQYQHLLRLEDGTAIVNGATEWRPKNAGANG
AISTGKTSNGNSVS SEQ ID NO: 62 - *Prototheca kruegani* 23S rRNA
tgttgaagaa tgagccggcg agttaaaaag agtggcatgg ttaaagaaaa tactctggag
ccatagcgaa agcaagttta gtaagcttag gtcattcttt ttagacccga aaccgagtga
tctacccatg atcagggtga agtgttagta aaataacatg gaggcccgaa ccgactaatg
ttgaaaaatt agcggatgaa ttgtgggtag gggcgaaaaa ccaatcgaac tcggagttag
ctggttctcc ccgaaatgcg tttaggcgca gcagtagcag tacaaataga ggggtaaagc
actgtttctt ttgtgggctt cgaaagttgt acctcaaagt ggcaaactct gaatactcta
tttagatatc tactagtgag accttggggg ataagctcct tggtcaaaag ggaaacagcc
cagatcacca gttaaggccc caaaatgaaa atgatagtga ctaaggatgt gggtatgtca
aaacctccag caggttagct tagaagcagc aatcctttca agagtgcgta atagctcact
g SEQ ID NO: 63 - *Prototheca wickerhamii* 23S rRNA
tgttgaagaa tgagccggcg acttaaaata aatggcaggc taagagattt aataactcga
aacctaagcg aaagcaagtc ttaatagggc gtcaatttaa caaaacttta aataaattat
aaagtcattt attttagacc cgaacctgag tgatctaacc atggtcagga tgaaacttgg
gtgacaccaa gtggaagtcc gaaccgaccg atgttgaaaa atcggcggat gaactgtggt
tagtggtgaa ataccagtcg aactcagagc tagctggttc tccccgaaat gcgttgaggc
gcagcaatat atctcgtcta tctaggggta aagcactgtt tcggtgcggg ctatgaaaat
ggtaccaaat cgtggcaaac tctgaatact agaaatgacg atatattagt gagactatgg
gggataagct ccatagtcga gagggaaaca gcccagacca ccagttaagg ccccaaaatg
ataatgaagt ggtaaaggag gtgaaaatgc aaatacaacc aggaggttgg cttagaagca
gccatccttt aaagagtgcg taatagctca ctg SEQ ID NO: 64 - *Prototheca stagnora* 23S rRNA
tgttgaagaa tgagccggcg agttaaaaaa aatggcatgg ttaaagatat ttctctgaag
ccatagcgaa agcaagtttt acaagctata gtcatttttt ttagacccga aaccgagtga
tctacccatg atcagggtga agtgttggtc aaataacatg gaggcccgaa ccgactaatg
gtgaaaaatt agcggatgaa ttgtgggtag gggcgaaaaa ccaatcgaac tcggagttag
ctggttctcc ccgaaatgcg tttaggcgca gcagtagcaa cacaaataga ggggtaaagc -continued

INFORMAL SEQUENCE LISTING actgtttctt ttgtgggctt cgaaagttgt acctcaaagt ggcaaactct gaatactcta
tttagatatc tactagtgag accttggggg ataagctcct tggtcaaaag ggaaacagcc
cagatcacca gttaaggccc caaaatgaaa atgatagtga ctaaggacgt gagtatgtca
aaacctccag caggttagct tagaagcagc aatcctttca agagtgcgta atagctcact
g SEQ ID NO: 65 - *Prototheca moriformis* 23S rRNA
tgttgaagaa tgagccggcg agttaaaaag agtggcatgg ttaaagataa ttctctggag
ccatagcgaa agcaagttta acaagctaaa gtcacccttt ttagacccga aaccgagtga
tctacccatg atcagggtga agtgttggta aaataacatg gaggcccgaa ccgactaatg
gtgaaaaatt agcggatgaa ttgtgggtag gggcgaaaaa ccaatcgaac tcggagttag
ctggttctcc ccgaaatgcg tttaggcgca gcagtagcaa cacaaataga ggggtaaagc
actgtttctt ttgtgggctt cgaaagttgt acctcaaagt ggcaaactct gaatactcta
tttagatatc tactagtgag accttggggg ataagctcct tggtcaaaag ggaaacagcc
cagatcacca gttaaggccc caaaatgaaa atgatagtga ctaaggatgt gggtatgtta
aaacctccag caggttagct tagaagcagc aatcctttca agagtgcgta atagctcact
g SEQ ID NO: 66 - *Prototheca moriformis* 23S rRNA
tgttgaagaa tgagccggcg acttaaaata aatggcaggc taagagaatt aataactcga
aacctaagcg aaagcaagtc ttaatagggc gctaatttaa caaaacatta aataaaatct
aaagtcattt attttagacc cgaacctgag tgatctaacc atggtcagga tgaaacttgg
gtgacaccaa gtggaagtcc gaaccgaccg atgttgaaaa atcggcggat gaactgtggt
tagtggtgaa ataccagtcg aactcagagc tagctggttc tccccgaaat gcgttgaggc
gcagcaatat atctcgtcta tctaggggta aagcactgtt tcggtgcggg ctatgaaaat
ggtaccaaat cgtggcaaac tctgaatact agaaatgacg atatattagt gagactatgg
gggataagct ccatagtcga gagggaaaca gcccagacca ccagttaagg ccccaaaatg
ataatgaagt ggtaaaggag gtgaaaatgc aaatacaacc aggaggttgg cttagaagca
gccatccttt aaagagtgcg taatagctca ctg SEQ ID NO: 67 - *Prototheca wickerhamii* 23S rRNA
tgttgaagaa tgagccgtcg acttaaaata aatggcaggc taagagaatt aataactcga
aacctaagcg aaagcaagtc ttaatagggc gctaatttaa caaaacatta aataaaatct
aaagtcattt attttagacc cgaacctgag tgatctaacc atggtcagga tgaaacttgg
gtgacaccaa gtggaagtcc gaaccgaccg atgttgaaaa atcggcggat gaactgtggt
tagtggtgaa ataccagtcg aactcagagc tagctggttc tccccgaaat gcgttgaggc
gcagcaatat atctcgtcta tctaggggta aagcactgtt tcggtgcggg ctatgaaaat
ggtaccaaat cgtggcaaac tctgaatact agaaatgacg atatattagt gagactatgg
gggataagct ccatagtcga gagggaaaca gcccagacca ccagttaagg ccccaaaatg
ataatgaagt ggtaaaggag gtgaaaatgc aaatacaacc aggaggttgg cttagaagca
gccatccttt aaagagtgcg taatagctca ctg SEQ ID NO: 68 - *Prototheca moriformis* 23S rRNA
tgttgaagaa tgagccggcg agttaaaaag agtggcgtgg ttaaagaaaa ttctctggaa
ccatagcgaa agcaagttta acaagcttaa gtcacttttt ttagacccga aaccgagtga
tctacccatg atcagggtga agtgttggta aaataacatg gaggcccgaa ccgactaatg
gtgaaaaatt agcggatgaa ttgtgggtag gggcgaaaaa ccaatcgaac tcggagttag
ctggttctcc ccgaaatgcg tttaggcgca gcagtagcaa cacaaataga ggggtaaagc
actgtttctt ttgtgggctc cgaaagttgt acctcaaagt ggcaaactct gaatactcta
tttagatatc tactagtgag accttggggg ataagctcct tggtcgaaag ggaaacagcc
cagatcacca gttaaggccc caaaatgaaa atgatagtga ctaaggatgt gagtatgtca
aaacctccag caggttagct tagaagcagc aatcctttca agagtgcgta atagctcact
g SEQ ID NO: 69 - *Prototheca zopfii* 23S rRNA
tgttgaagaa tgagccggcg agttaaaaag agtggcatgg ttaaagaaaa ttctctggag
ccatagcgaa agcaagttta acaagcttaa gtcacttttt ttagacccga aaccgagtga
tctacccatg atcagggtga agtgttggta aaataacatg gaggcccgaa ccgactaatg
gtgaaaaatt agcggatgaa ttgtgggtag gggcgaaaaa ccaatcgaac tcggagttag
ctggttctcc ccgaaatgcg tttaggcgca gcagtagcaa cacaaataga ggggtaaagc
actgtttctt tcgtgggctt cgaaagttgt acctcaaagt ggcaaactct gaatactcta
tttagatatc tactagtgag accttggggg ataagctcct tggtcaaaag ggaaacagcc
cagatcacca gttaaggccc caaaatgaaa atgatagtga ctaaggatgt gagtatgtca
aaacctccag caggttagct tagaagcagc aatcctttca agagtgcgta atagctcact
g SEQ ID NO: 70 - *Prototheca moriformis* rRNA
tgttgaagaa tgagccggcg acttagaaaa ggtggcatgg ttaaggaaat attccgaagc
cgtagcaaaa gcgagtctga atagggcgat aaaatatatt aatatttaga atctagtcat
tttttctaga cccgaacccg ggtgatctaa ccatgaccag gatgaagctt gggtgatacc
aagtgaaggt ccgaaccgac cgatgttgaa aaatcggcgg atgagttgtg gttagcggtg
aaataccagt cgaacccgga gctagctggt tctccccgaa atgcgttgag gcgcagcagt
acatctagtc tatctagggg taaagcactg tttcggtgcg ggctgtgaga acggtaccaa
atcgtggcaa actctgaata ctagaaatga cgatgtagta gtgagactgt gggggataag
ctccattgtc aagagggaaa cagcccagac caccagctaa ggccccaaaa tggtaatgta
gtgacaaagg aggtgaaaat gcaaatacaa ccaggaggtt ggcttagaag cagccatcct
ttaaagagtg cgtaatagct cactg -continued

| INFORMAL SEQUENCE LISTING |
|---|

SEQ ID NO: 71 - nucleic acid sequence for D3042 (pSZ4243) (wild-type); Algal transit peptide represented with lower case, FLAG epitope tag with underline
atggccaccgcatccactttctcggcgttcaatgcccgctgcggcgacctgcgtcgctcggcgggct
ccgggccccggcgcccagcgaggcccctccccgtgcgcgggcgcgccTCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCCTGATGAACCACCTGCAGGAGACCTCCCTGAA
CCACTGCAAGAGCACCGGCATCCTGCTGGACGGCTTCGGCCGCACCCTGGAGATGTGCAAGCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 72 - amino acid sequence for D3042; pSZ4243 (wild-type); Algal transit peptide represented with lower case, FLAG epitope tag with underline
matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIETLMNHLQETSLNHCKSTGILLDGFGRTLEMCKRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK SEQ ID NO: 73 - nucleic acid sequence for D3126 (pSZ4331); Algal transit peptide represented with lower case, FLAG epitope tag with underline and the portion of N-terminal specificity domain that was mutated relative to the wild-type ChFATB2 (D3042, pSZ4243) highlighted with bolded text
atggccaccgcatccactttctcggcgttcaatgcccgctgcggcgacctgcgtcgctcggcgggct
ccgggccccggcgcccagcgaggcccctccccgtgcgcgggcgcgccTCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCCTGATGAACCACCTGCAGGACACCAGCCTGAA
CCACTGCAAGAGCGTGGGCCTGCTGAACGACGGCTTCGGCCGCACCCCCGAGATGTGCACCCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 74 - amino acid sequence for for D3126 (pSZ4331); Algal transit peptide represented with lower case, FLAG epitope tag with underline and the portion of N-terminal specificity domain that was mutated relative to the wild-type ChFATB2 (D3042, pSZ4243) highlighted with bolded text
matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIETLMNHLQDTSLNHCKSVGLLNDGFGRTPEMCTRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK -continued

| INFORMAL SEQUENCE LISTING |
| --- |

SEQ ID NO: 75 - nucleic acid sequence for D3127 (pSZ4332); Algal transit peptide represented with lower case, FLAG epitope tag with underline and the portion of N-terminal specificity domain that was mutated relative to the wild-type ChFATB2 (D3042, pSZ4243) highlighted with bolded text atggccaccgcatccactttctcggcgttcaatgcccgctgcggcgacctgcgtcgctcggcgggct
ccgggccccggcgcccagcgaggcccctccccgtgcgcgggcgcgccTCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCCTGATGAACCACCTGCAGGAGACCTCCATCAA
CCACTGCAAGTCCCTGGGCCTGCTGAACGACGGCTTCGGCCGCACCCCCGGCATGTGCAAGAACGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 76 - amino acid sequence for D3127 (pSZ4332); Algal transit peptide represented with lower case, FLAG epitope tag with underline and the portion of N-terminal specificity domain that was mutated relative to the wild-type ChFATB2 (D3042, pSZ4243) highlighted with bolded text matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIETLMNHLQETSINHCKSLGLLNDGFGRTPGMCKND
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK SEQ ID NO: 77 - nucleic acid sequence for D3128 (pSZ4333); Algal transit peptide represented with lower case, FLAG epitope tag with underline and the portion of N-terminal specificity domain that was mutated relative to the wild-type ChFATB2 (D3042, pSZ4243) highlighted with bolded text atggccaccgcatccactttctcggcgttcaatgcccgctgcggcgacctgcgtcgctcggcgggct
ccgggccccggcgcccagcgaggcccctccccgtgcgcgggcgcgccTCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCGTGATGAACCACGTCCAGGAGACCTCGCTGAA
CCAGTGCAAGTCCATCGGCCTGCTGGACGACGGCTTCGGCCGCAGCCCCGAGATGTGCAAGCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 78 - amino acid sequence for D3128 (pSZ4333); Algal transit peptide represented with lower case, FLAG epitope tag with underline and the portion of N-terminal specificity domain that was mutated relative to the wild-type ChFATB2 (D3042, pSZ4243) highlighted with bolded text matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIETVMNHVQETSLNQCKSIGLLDDGFGRSPEMCKRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL -continued

INFORMAL SEQUENCE LISTING

ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK

SEQ ID NO: 79 - nucleic acid sequence for D3129 (pSZ4334); Algal transit peptide represented with lower case, FLAG epitope tag with underline and the portion of N-terminal specificity domain that was mutated relative to the wild-type ChFATB2 (D3042, pSZ4243) highlighted with bolded text atggccaccgcatccactttctcggcgttcaatgcccgctgcggcgacctgcgtcgctcggcgggct
ccgggccccggcgcccagcgaggcccctccccgtgcgcgggcgcgcctCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCCTGATGAACCACCTGCAGGAGACCTCCCTGAA
CCAGTGCAAGTCCGCCGGCATCCTGCACGACGGCTTCGGCCGCACCCTGGAGATGTGCAAGCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 80 - amino acid sequence for D3129 (pSZ4334); Algal transit peptide represented with lower case, FLAG epitope tag with underline and the portion of N-terminal specificity domain that was mutated relative to the wild-type ChFATB2 (D3042, pSZ4243) highlighted with bolded text matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIETLMNHLQETSLNQCKSAGILHDGFGRTLEMCKRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK SEQ ID NO: 81 - nucleic acid sequence for D3130 (pSZ4335); Algal transit peptide represented with lower case, FLAG epitope tag with underline and the portion of N-terminal specificity domain that was mutated relative to the wild-type ChFATB2 (D3042, pSZ4243) highlighted with bolded text atggccaccgcatccactttctcggcgttcaatgcccgctgcggcgacctgcgtcgctcggcgggct
ccgggccccggcgcccagcgaggcccctccccgtgcgcgggcgcgcctCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCGAGACCCTGATGAACTACCTGCAGGAGACCTCCCTGAA
CCACTGCAAGTCCACCGGCATCCTGCTGGACGGCTTCGGCCGCACCCCCGAGATGTGCAAGCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 82 - nucleic acid sequence for D3130 (pSZ4335); Algal transit peptide represented with lower case, FLAG epitope tag with underline and the portion of N-terminal specificity domain that was mutated relative to the wild-type ChFATB2 (D3042, pSZ4243) highlighted with bolded text matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS -continued

INFORMAL SEQUENCE LISTING

FGLESTVQDGLVFRQSFSIRSYEIGTDRTASIETLMNYLQETSLNHCKSTGILLDGFGRTPEMCKRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK

SEQ ID NO: 83 - amino acid sequence for D3131 (pSZ4336); Algal transit peptide represented with lower case, FLAG epitope tag with underline and the portion of N-terminal specificity domain that was mutated relative to the wild-type ChFATB2 (D3042, pSZ4243) highlighted with bolded text atggccaccgcatccactttctcggcgttcaatgcccgctgcggcgacctgcgtcgctcggcgggct
ccgggccccggcgcccagcgaggcccctccccgtgcgcgggcgcgccTCCAGCCTGAGCCCCTCCTT
CAAGCCCAAGTCCATCCCCAACGGCGGCTTCCAGGTGAAGGCCAACGACAGCGCCCACCCCAAGGCC
AACGGCTCCGCCGTGAGCCTGAAGAGCGGCAGCCTGAACACCCAGGAGGACACCTCCTCCAGCCCCC
CCCCCCGCACCTTCCTGCACCAGCTGCCCGACTGGAGCCGCCTGCTGACCGCCATCACCACCGTGTT
CGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACG
AGATCGGCACCGACCGCACCGCCAGCATCATGGCCGTGATGAACCACCTGCAGGAGGCCGCCCGCAA
CCACGCCGAGTCCCTGGGCCTGCTGGGCGACGGCTTCGGCGAGACCCTGGAGATGTCCAAGCGCGAC
CTGATCTGGGTGGTGATCAAGATGCAGATCAAGGTGAACCGCTACCCCGCCTGGGGCGACACCGTGG
AGATCAACACCCGCTTCAGCCGCCTGGGCAAGATCGGCATGGGCCGCGACTGGCTGATCTCCGACTG
CAACACCGGCGAGATCCTGGTGCGCGCCACCAGCGCCTACGCCATGATGAACCAGAAGACCCGCCGC
CTGTCCAAGCTGCCCTACGAGGTGCACCAGGAGATCGTGCCCCTGTTCGTGGACAGCCCCGTGATCG
AGGACTCCGACCTGAAGGTGCACAAGTTCAAGGTGAAGACCGGCGACAGCATCCAGAAGGGCCTGAC
CCCCGGCTGGAACGACCTGGACGTGAACCAGCACGTGTCCAACGTGAAGTACATCGGCTGGATCCTG
GAGAGCATGCCCACCGAGGTGCTGGAGACCCAGGAGCTGTGCTCCCTGGCCCTGGAGTACCGCCGCG
AGTGCGGCCGCGACTCCGTGCTGGAGAGCGTGACCGCCATGGACCCCAGCAAGGTGGGCGTGCGCTC
CCAGTACCAGCACCTGCTGCGCCTGGAGGACGGCACCGCCATCGTGAACGGCGCCACCGAGTGGCGC
CCCAAGAACGCCGGCGCCAACGGCGCCATCTCCACCGGCAAGACCAGCAACGGCAACTCCGTGTCCA
TGGACTACAAGGACCACGACGGCGACTACAAGGACCACGACATCGACTACAAGGACGACGACGACAA
GTGA SEQ ID NO: 84 - amino acid sequence for D3131 (pSZ4336); Algal transit peptide represented with lower case, FLAG epitope tag with underline and the portion of N-terminal specificity domain that was mutated relative to the wild-type ChFATB2 (D3042, pSZ4243) highlighted with bolded text matastfsafnarcgdlrrsagsgprrparplpvrgraSSLSPSFKPKSIPNGGFQVKANDSAHPKA
NGSAVSLKSGSLNTQEDTSSSPPPRTFLHQLPDWSRLLTAITTVFVKSKRPDMHDRKSKRPDMLVDS
FGLESTVQDGLVFRQSFSIRSYEIGTDRTASIMAVMNHLQEAARNHAESLGLLGDGFGETLEMSKRD
LIWVVIKMQIKVNRYPAWGDTVEINTRFSRLGKIGMGRDWLISDCNTGEILVRATSAYAMMNQKTRR
LSKLPYEVHQEIVPLFVDSPVIEDSDLKVHKFKVKTGDSIQKGLTPGWNDLDVNQHVSNVKYIGWIL
ESMPTEVLETQELCSLALEYRRECGRDSVLESVTAMDPSKVGVRSQYQHLLRLEDGTAIVNGATEWR
PKNAGANGAISTGKTSNGNSVSMDYKDHDGDYKDHDIDYKDDDDK

What is claimed is:

1. A nucleic acid molecule encoding a variant acyl-acyl carrier protein (ACP) thioesterase comprising at least 90% sequence identity to SEQ ID NO:61; wherein the amino acid residue at position 163 is Tyrosine, and the amino acid residue at position 186 is Proline, wherein the thioesterase has thioesterase activity and comprises a specificity domain that promotes or increases C8:0-C10:0 fatty acids in a microalgal host cell.

2. A nucleic acid of claim 1, comprising codon bias for improved expression in a microalgal host cell.

3. An expression cassette comprising the nucleic acid of claim 1.

4. A vector comprising the nucleic acid of claim 1, and/or the expression cassette of claim 3.

5. A variant acyl-acyl carrier protein (ACP) thioesterase (TE) encoded by the nucleic acid of claim 1.

6. A microalgal host cell comprising the nucleic acid claim 1, the expression cassette of claim 3, and/or the vector of claim 4.

7. The host cell of claim 6, wherein the microalgal host cell is an oleaginous microalgal cell.

8. The host cell of claim 6, wherein the host cell is a microalgae cell of the genus *Prototheca*.

9. The host cell of claim 6, wherein the microalgae cell is selected from the group consisting of *Prototheca moriformis, Prototheca krugani, Prototheca stagnora*and *Prototheca zopfii*.

10. The host cell of claim 6, wherein the host cell has a fatty acid profile comprising at least 10% C8:0, 10% C10:0, or 10% C8:0/C10:0.

11. The host cell of claim 6, wherein the host cell produces an oil having at least 5% increased levels of C8:0 and/or C10:0 fatty acids in comparison to an untransformed host cell or a host cell transformed with a wild-type acyl-ACP TE.

12. A method of producing a microalgae that produces an oil having a desired fatty acid profile, comprising transforming the microalgae with a nucleic acid sequence of claim 1, and cultivating the microalgae so as to produce the oil.

13. The method of claim 12, wherein the microalgae produces at least 5% increased levels of C8:0 and/or C10:0 fatty acids in comparison to an untransformed microalgae or a microalgae transformed with a wild-type acyl-ACP TE.

14. The method of claim 12, wherein the plant, algae or microalgae produces an oil comprising at least 5% C8:0 fatty acids.

15. The method of claim 12, wherein the plant, algae or microalgae produces an oil comprising at least 5% C10:0 fatty acids.

16. The method of claim 12, wherein the plant, algae or microalgae produces an oil comprising a C8:0/C10:0 ratio that is at least 5%.

17. A method of producing an oil, comprising transforming the microalgae with a nucleic acid molecule of claim 1, expressing the variant acyl-ACP TE to produce fatty acids, and recovering the oil produced by the microalgae comprising the fatty acids.

18. A nucleic acid molecule encoding a variant acyl-acyl carrier protein (ACP) thioesterase comprising SEQ ID NO:82.

* * * * *